(12) United States Patent
Hirst et al.

(10) Patent No.: US 6,660,744 B1
(45) Date of Patent: Dec. 9, 2003

(54) PYRAZOLOPYRIMIDINES AS THERAPEUTIC AGENTS

(75) Inventors: Gavin C. Hirst, Marlborough, MA (US); Paul Rafferty, Westborough, MA (US); Kurt Ritter, Newton, MA (US); David Calderwood, Framingham, MA (US); Neil Wishart, Jefferson, MA (US); Lee D. Arnold, Westborough, MA (US); Michael M. Friedman, Newton, MA (US)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/663,780

(22) Filed: Sep. 15, 2000

Related U.S. Application Data

(60) Provisional application No. 60/154,620, filed on Sep. 17, 1999.

(51) Int. Cl.[7] .................. C07D 487/04; A61K 31/519; A61P 3/10; A61P 9/10; A61P 35/02
(52) U.S. Cl. ........................ 514/258; 544/262
(58) Field of Search ............. 544/262; 514/258

(56) References Cited

U.S. PATENT DOCUMENTS

| | | | |
|---|---|---|---|
| 4,140,851 A | 2/1979 | Townsend | 536/24 |
| 4,229,453 A | 10/1980 | Roth et al. | 424/251 |
| 4,892,865 A | 1/1990 | Townsend et al. | 514/43 |
| 4,927,830 A | 5/1990 | Townsend et al. | 514/258 |
| 4,968,686 A | 11/1990 | Townsend et al. | 514/258 |
| 4,996,206 A | 2/1991 | Taylor et al. | 514/258 |
| 5,028,608 A | 7/1991 | Taylor et al. | 514/258 |
| 5,248,775 A | 9/1993 | Taylor et al. | 544/280 |
| 5,254,687 A | 10/1993 | Taylor et al. | 544/280 |
| 5,344,932 A | 9/1994 | Taylor | 544/280 |
| 5,349,064 A | 9/1994 | Akimoto et al. | 544/280 |

FOREIGN PATENT DOCUMENTS

| | | |
|---|---|---|
| DE | 3036390 A1 | 5/1982 |
| EP | 0 496 617 A1 | 7/1992 |
| WO | WO 94/17803 | 8/1994 |
| WO | WO 96/10028 | 4/1996 |
| WO | WO 96/31510 | 10/1996 |
| WO | WO 96/40705 | 12/1996 |
| WO | WO 96/40706 | 12/1996 |
| WO | WO 96/40707 | 12/1996 |
| WO | WO 97/03069 | 1/1997 |
| WO | WO 97/13771 | 4/1997 |
| WO | WO 97/28161 | 8/1997 |
| WO | WO 98/41525 | 9/1998 |

OTHER PUBLICATIONS

Traxler, P.M., et al., "4–(Phenylamino)pyrrolopyrimidines: Potent and Selective, ATP Site Directed Inhibitors of the EGF–Receptor Protein Tyrosine Kinase," *J. Med. Chem.*, 39(12):2285–2292 (1996).

Showalter, H.D.H., et al., "Synthesis and SAR for a series of 4–substituted 1H–pyrimido[4,5–b] and 5H–pyrimido[5,4–b] indoles as EGF receptor tyrosine kinase inhibitors," *Proceedings of the American Assoc. for Cancer Research*, 37, p. 425 (1996).

Traxler, P.M., "Protein tyrosine kinase inhibitors in cancer treatment," *Exp. Opin. Ther. Patents* 7(6):571–588 (1997).

*Primary Examiner*—Mark L. Berch
*Assistant Examiner*—Kahsay Habte
(74) *Attorney, Agent, or Firm*—John D. Conway; Gayle B. O'Brien

(57) ABSTRACT

The present invention is directed to pyrazolopyrimidine derivatives which are useful as kinase inhibitors and as such are useful for affecting angiogenesis and diseases and conditions associated with angiogenesis.

86 Claims, No Drawings

PYRAZOLOPYRIMIDINES AS THERAPEUTIC AGENTS

RELATED APPLICATION

This application claims the benefit of United States Provisional Application No.: 60/154,620, filed Sep. 17, 1999, the entire teachings of which are incorporated herein by reference.

BACKGROUND OF THE INVENTION

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in countless cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383–391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990).

The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1–20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413–423; Songyang et al., 1994, *Mol. Cell. Biol.* 14:2777–2785; Songyang et al., 1993, *Cell* 72:767–778; and Koch et al., 1991, *Science* 252:668–678; Shoelson, *Curr. Opin. Chem. Biol.* (1997), 1(2), 227–234; Cowburn, *Curr. Opin. Struct. Biol.* (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767–778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, TIE-2 and c-Met, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman et al., *Oncogene* 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1):11–15, 1993). DNAs encoding mouse, rat and human FLK-1 have been isolated, and the nucleotide and encoded amino acid sequences reported (Matthews et al., *Proc. Natl.*

Acad. Sci. USA, 88:9026–30, 1991; Terman et al., 1991, supra; Terman et al., Biochem. Biophys. Res. Comm. 187:1579–86, 1992; Sarzani et al., supra; and Millauer et al., Cell 72:835–846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fins-like tyrosine kinase-1" (Flt-1) is related to FLK-1/KDR (DeVries et al. Science 255;989–991, 1992; Shibuya et al., Oncogene 5:519–524, 1990). An alternative designation for Flt-1 is "vascular endothelial cell growth factor receptor 1" (VEGFR-1). To date, members of the FLK-1/KDR/ NVEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, Cytokine & Growth Factor Reviews 7: 259–270, 1996). Vascular endothelial cell growth factor (VEGF) binds to Flt-I with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., Endocrinology 133: 848–859, 1993; Kolch et al., Breast Cancer Research and Treatment 36: 139–155, 1995; Ferrara et al., Endocrine Reviews 18(1); 4–25, 1997; Ferrara et al., Regulation of Angiogenesis (ed. L. D. Goldberg and E. M. Rosen), 209–232, 1997). In addition, VEGF has been implicated in the control and enhancement of vascular permeability (Connolly, et al., J. Biol. Chem. 264: 20017–20024, 1989; Brown et al., Regulation of Angiogenesis (ed. L. D. Goldberg and E. M. Rosen), 233–269, 1997).

Different forms of VEGF arising from alternative splicing of mRNA have been reported, including the four species described by Ferrara et al. (J. Cell. Biochem. 47:211–218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, Curr. Opin. Cell Biol., 159–164, 1998 and references cited therein).

Placenta growth factor (PlGF) has an amino acid sequence that exhibits significant homology to the VEGF sequence (Park et al., J. Biol. Chem. 269:25646–54, 1994; Maglione et al. Oncogene 8:925–31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, J. Biol. Chem. 273 (35): 22272–22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor I (Pepper et al, Proc. Natl. Acad. Sci. U.S.A. (1998), 95(20): 11709–11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, Am. J. Pathol. (1998), 153(2): 395–403; Witzenbichler et al, Am. J. Pathol. (1998), 153(2), 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, J. Biol. Chem. (1998), 273(14),8413–8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, Proc. Natl. Acad. Sci. U.S.A. (1998), 95(2), 548–553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, EMBO J. (1999), 18(2), 363–374; Ogawa et al, J. Biol. Chem. (1998), 273(47), 31273–31282.). VEGF-E sequences possess 25% homology to mammalian VEGF and are encoded by the parapoxvirus Orf virus (OV). This parapoxvirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular Ca2+ concentrations, while in contrast to VEGF165, VEGF-E did not bind to VEGF receptor-1 (Flt-1).

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., "Angiogenesis and Cancer" Conference, Amer. Assoc. Cancer Res., January 1998, Orlando, Fla.; Williams, *Diabetelogia* 40: S118–120 (1997)).

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietinl ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Angl ligand is directly involved in the branching, sprouting and outgrowth of new vessels, and recruitment and interaction of periendothelial support cells important in maintaining vessel integrity and inducing quiescence. The absence of Angl stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7–10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a nonproductive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, thereful, useful in treating such disorders, and in other situations of inappropriate neovascularization.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, *Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. application Ser. No. 4,966,849), soluble receptors and antibodies (Application No. WO 94/10202; Kendall & Thomas, 1994, *Proc. Natl. Acad. Sci* 90:10705–09; Kim et al., 1993, *Nature* 362:841–844), RNA ligands (Jellinek, et al., *Biochemistry* 33:10450–56; Takano, et al., 1993, *Mol. Bio. Cell* 4:358A; Kinsella, et al. 1992, *Exp. Cell Res*. 199:56–62; Wright, et al., 1992, *J. Cellular Phys*. 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res*. 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475–478), selenoindoles and selenides (PCTWO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is also known as cdk1)

Cdc2/cyclin B is another serine/threonine kinase enzyme which belongs to the cyclin-dependent kinase (cdks) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors could suppress proliferation and may restore the normal control of cell cycle progression.

The regulation of CDK activation is complex, but requires the association of the CDK with a member of the cyclin family of regulatory subunits (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992)). A further level of regulation occurs through both activating and inactivating phosphorylations of the CDK subunit (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992); Ducommun et al., *EMBO Journal*, 10:3311–3319 (1991); Gautier et al., *Nature* 339:626–629 (1989); Gould and Nurse, *Nature*, 342:39–45 (1989); Krek and Nigg, *EMBO Journal*, 10:3331–3341 (1991); Solomon et al., *Cell*, 63:1013–1024 (1990)). The coordinate activation and inactivation of different cyclin/CDK complexes is necessary for normal progression through the cell cycle (Pines, *Trends in Biochemical Sciences*, 18:195–197 (1993); Sherr, *Cell*, 73:1059–1065 (1993)). Both the critical G1-S and G2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066–2076 (1994); Ohtsubo and Roberts, *Science*, 259:1908–1912 (1993); Quelle et al., *Genes & Development*, 7:1559–1571 (1993); Resnitzky et al., *Molecular & Cellular Biology*, 14:1669–1679 (1994)). Progression through S-phase requires the activity of cyclin A/CDK2 (Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)) whereas the activation of cyclin A/cdc2 (CDK1) and cyclin B/cdc2 are required for the onset of metaphase (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992); Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)). It is not surprising, therefore, that the loss of control of CDK regulation is a frequent event in hyperproliferative diseases and cancer. (Pines, *Current Opinion in Cell Biology*, 4:144–148 (1992); Lees, *Current Opinion in Cell Biology*, 7:773–780 (1995); Hunter and Pines, *Cell*, 79:573–582 (1994)).

Inhibitors of kinases involved in mediating or maintaining disease states represent novel therapies for these disorders. Examples of such kinases include, but are not limited to: (1) inhibition of c-Src (Brickell, *Critical Reviews in Oncogenesis*, 3:401–406 (1992); Courtneidge, *Seminars in Cancer Biology*, 5:236–246 (1994), raf (Powis, *Pharmacology & Therapeutics*, 62:57–95 (1994)) and the cyclin-dependent kinases (CDKs) 1, 2 and 4 in cancer (Pines, *Current Opinion in Cell Biology*, 4:144–148 (1992); Lees, *Current Opinion in Cell Biology*, 7:773–780 (1995); Hunter and Pines, *Cell*, 79:573–582 (1994)), (2) inhibition of CDK2 or PDGF-R kinase in restenosis (Buchdunger et al., *Proceedings of the National Academy of Science USA*, 92:2258–2262 (1995)), (3) inhibition of CDK5 and GSK3 kinase in Alzheimers (Hosoi et al., *Journal of Biochemistry* (Tokyo), 117:741–749 (1995); Aplin et al., *Journal of Neurochemistry*, 67:699–707 (1996), (4) inhibition of c-Src kinase in osteoporosis (Tanaka et al., *Nature*, 383:528–531 (1996), (5) inhibition of GSK-3 kinase in type-2 diabetes (Borthwick et al., *Biochemical & Biophysical Research Communications*, 210:738–745 (1995), (6) inhibition of the p38 kinase in inflammation (Badger et al., *The Journal of Pharmacology and Experimental Therapeutics*, 279:1453–1461 (1996)), (7) inhibition of VEGF-R 1-3 and TIE-1 and -2 kinases in diseases which involve angiogenesis (Shawver et al., *Drug Discovery Today*, 2:50–63 (1997)), (8) inhibition of UL97 kinase in viral infections (He et al., *Journal of Virology*, 71:405–411 (1997)), (9) inhibition of CSF-1R kinase in bone and hematopoetic diseases (Myers et al., *Bioorganic & Medicinal Chemistry Letters*, 7:421–424 (1997), and (10) inhibition of Lck kinase in autoimmune diseases and transplant rejection (Myers et al., *Bioorganic & Medicinal Chemistry Letters*, 7:417–420(1997)).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199–3202 (1996); Kohn et al., *Journal of Cellular Biochemistry*, 54:44–452 (1994)). Inhibition of CDKs 2 or 4 will prevent progression into the cycle in normal cells and limit the toxicity of cytotoxics which act in S-phase, G2 or mitosis. Furthermore, CDK2/cyclin E activity has also been shown to regulate NF-kB. Inhibition of CDK2 activity stimulates NF-kB-dependent gene expression, an event mediated through interactions with the p300 coactivator (Perkins et al., *Science*, 275:523–527 (1997)). NF-KB regulates genes involved in inflammatory responses (such as hematopoetic growth factors, chemokines and leukocyte adhesion molecules) (Baeuerle and Henkel, *Annual Review ofImmunology*, 12:141–179 (1994)) and may be involved in the suppression of apoptotic signals within the cell (Beg and Baltimore, Science, 274:782–784 (1996); Wang et al., Science, 274:784–787 (1996); Van Antwerp et al., Science, 274:787–789 (1996)). Thus, inhibition of CDK2 may suppress apoptosis induced by cytotoxic drugs via a mechanism which involves NF-KB. This therefore suggests that inhibition of CDK2 activity may also have utility in other cases where regulation of NF-kB plays a role in etiology of disease. A further example may be take from fungal infections: Aspergillosis is a common infection in immune-compromised patients (Armstrong, *Clinical Infectious Diseases*, 16:1–7 (1993)). Inhibition of the Aspergillus kinases Cdc2/CDC28 or Nim A (Osmani et al., *EMBO Journal*, 10:2669–2679 (1991); Osmani et al., *Cell*, 67:283–291 (1991)) may cause arrest or death in the fungi, improving the therapeutic outcome for patients with these infections.

The identification of effective small compounds which specifically inhibit signal transduction and cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for antiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention provides compounds of Formula I,

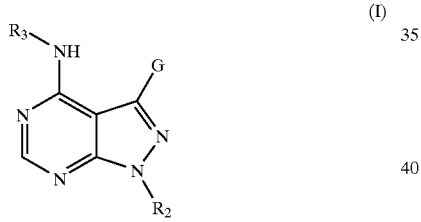

the racemic-diastereomeric mixtures, optical isomers, pharmaceutically-acceptable salts, prodrugs or biologically active metabolites thereof wherein:

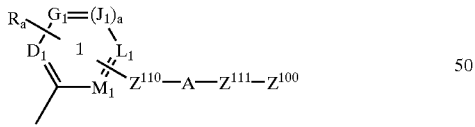

G is
where $Z^{100}$ is

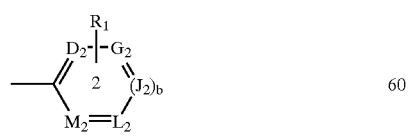

or a group optionally substituted with $R_1$ selected from the group consisting of cycloalkyl, naphthyl, tetrahydronaphthyl, benzothienyl, furanyl, thienyl, benzoxazolyt, benzothiazolyl,

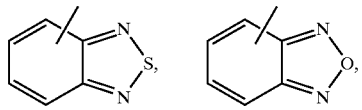

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, oxazolyl, isothiazolyl, oxadiazolyl, thiadiazolyl, indolinyl, indazolyl, benzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted ($C_1$–$C_6$) which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted ($C_1$–$C_6$) or an optionally substituted —$(CH_2)_n$-cycloalkyl-$(CH_2)_n$—; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, substituted or unsubstituted carboxamido, tetrazolyl, trifluoromethylcarbonylamino, trifluoromethylsulfonamido, substituted or unsubstituted alkyl, substituted or unsubstituted alkoxy, substituted or unsubstituted aryl, substituted or unsubstituted alkenyl, substituted or unsubstituted aryloxy, substituted or unsubstituted heteroaryloxy, substituted or unsubstituted arylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, $R_c$ and $CH_2OR_c$;

where $R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$-Oalkyl, —W—$(CH_2)_t$—S-alkyl, or —W—$(CH_2)_t$—OH;

$Z^{105}$ for each occurrence is independently a covalent bond or ($C_1$–$C_6$);

$Z^{200}$ for each occurrence is independently a substituted or unsubstituted ($C_1$–$C_6$), substituted or unsubstituted phenyl or substituted or unsubstituted —($C_1$–$C_6$)-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring; t for each occurrence is independently an integer from 2 to 6; W for each occurrence is independently a direct bond or O, S, S(O), S(O)$_2$, or $NR_f$, wherein $R_f$ for each occurrence is independently H or alkyl;

or $R_1$ is a substituted or unsubstituted carbocyclic or heterocyclic ring fused with ring 2;

$R_3$ is hydrogen, hydroxy, substituted or unsubstituted alkyl or substituted or unsubstituted alkoxy;

A is —O—; —S—; —S(O)$_p$—; —N(R)—; —N(C(O)OR)—; —N(C(O)R)—; —N(SO$_2$R)—; —CH$_2$O—; —CH$_2$S—; —CH$_2$N(R)—; —CH(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)$_p$—; —OC(O)N(R)—; —N(R)—C(O)—(CH$_2$)$_n$—N(R)—, —N(R)C(O)O—; —N(R)—(CH$_2$)$_{n+1}$—C(O)—, —S(O)$_p$N(R)—; —O—(CR$_2$)$_{n+1}$—C(O)—, —O—(CR$_2$)$_{n+1}$—O—, —N(C(O)R)S(O)$_p$—; —N(R)S(O)$_p$N(R)—; —N(R)—C(O)—(CH$_2$)$_n$—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_b$)O—; —N(R)P(OR$_b$)—; —N(R)P(O)(OR$_b$)O—; —N(R)P(O)(OR$_b$)—; —N(C(O)R)P(OR$_b$)O—; —N(C(O)R)P(OR$_b$)—; —N(C(O)R)P(O)(OR$_b$)O—, or —N(C(O)R)P(OR$_b$)—;

where R for each occurrence is independently H, substituted or unsubstituted alkyl, substituted or unsubstituted arylalkyl or substituted or unsubstituted aryl;

$R_b$ for each occurrence is independently H, substituted or unsubstituted alkyl, substituted or unsubstituted arylalkyl, substituted or unsubstituted cycloalkyl or substituted or unsubstituted aryl;

p is 1 or 2;

or in a phosphorus containing group, the nitrogen atom, the phosphorus atom, R and $R_b$ together form a five- or six-membered heterocyclic ring; or A is NRSO$_2$ and R, $R_a$ and the nitrogen atom together form a substituted or unsubstituted five or-six-membered heterocyclic ring fused to ring 1;

$R_2$ is —Z$^{101}$—Z$^{102}$;

Z$^{101}$ is a covalent bond, —(C$_1$-C$_6$)—, —(C$_1$-C$_6$)—O—, —(C$_1$-C$_6$)—C(O)—, —(C$_1$-C$_6$)—C(O)O—, —(C$_1$-C$_6$)—C(O)—NH—, —(C$_1$-C$_6$)—C(O)—N((C$_1$-C$_6$))— or a substituted or unsubstituted phenyl group;

Z$^{102}$ is hydrogen, a substituted or unsubstituted alkyl group, a substituted or unsubstituted cycloalkyl group, a substituted or unsubstituted, saturated or unsaturated heterocyclic group, or a substituted or unsubstituted, saturated or unsaturated heterobicyclic group;

said substituted heterocyclic or substituted heterobicyclic group having one or more substituents each independently selected from the group consisting of hydroxyl, cyano, substituted or unsubstituted alkoxy, substituted or unsubstituted sulfonamido, substituted or unsubstituted ureido, substituted or unsubstituted carboxamido; substituted or unsubstituted amino, oxo, a saturated, unsaturated or aromatic, substituted or unsubstituted heterocyclic group comprising one or more nitrogen atoms, one or more oxygen atoms or a combination thereof;

wherein said nitrogen atoms are independently optionally substituted by a substituted or unsubstituted alkyl, substituted or unsubstituted aryl or substituted or unsubstituted arylalkyl group; or $R_2$ is of the formula B–E, wherein B is a substituted or unsubstituted cycloalkyl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalklylcarbonyl, hydroxy, substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted azacycloalkyl, substituted or unsubstituted azacycloalkylcarbonyl, substituted or unsubstituted azacycloalkylsulfonyl, substituted or unsubstituted azacycloalkylalkyl, substituted or unsubstituted heteroaryl, substituted or unsubstituted heteroarylcarbonyl, substituted or unsubstituted heteroarylsulfonyl, substituted or unsubstituted heteroarylalkyl, substituted or unsubstituted azacycloalkylcarbonylamino, substituted or unsubstituted heteroarylcarbonylamino or substituted or unsubstituted aryl;

a is 1 and $D_1$, $G_1$, $J_1$, $L_1$ and $M_1$ are each independently selected from the group consisting of CR$_a$ and N, provided that at least two of $D_1$, $G_1$, $J_1$, $L_1$ and $M_1$ are CR$_a$; or a is 0, and one of $D_1$, $G_1$, $L_1$ and $M_1$ is NR$_a$, one of $D_1$, $G_1$, $L_1$ and $M_1$ is CR$_a$ and the remainder are independently selected from the group consisting of CR$_a$ and N, wherein R$_a$ is as defined above;

b is 1 and $D_2$, $G_2$, $J_2$, $L_2$ and $M_2$ are each independently selected from the group consisting of CR$_a$ and N, provided that at least two of $D_2$, $G_2$, $J_2$, $L_2$ and $M_2$ are CR$_a$; or b is 0, and one of $D_2$, $G_2$, $L_2$ and $M_2$ is NR$_a$, one of $D_2$, $G_2$, $L_2$ and $M_2$ is CR$_a$ and the remainder are independently selected from the group consisting of CR$_a$ and N, wherein R$_a$ is as defined above; and n for each occurrence is independently an integer from 0 to 6.

A preferred compound of Formula (1) is wherein $R_3$ is H; $R_1$ for each occurrence is independently selected from the group consisting of F, Cl, Br, I, CH$_3$, NO$_2$, OCF$_3$, OCH$_3$, CN, CO$_2$CH$_3$, CF$_3$, —CH$_2$NR$_d$R$_e$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

Another preferred compound of Formula (I) is wherein $R_3$ is H; $R_a$ for each occurrence is independently selected from the group consisting of F, Cl, Br, I, CH$_3$, NO$_2$, OCF$_3$, OCH$_3$, CN, CO$_2$CH$_3$, CF$_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

Another preferred compound of Formula (I) is wherein $R_3$ is H; $R_2$ is of the formula

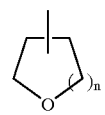

wherein n is 1, 2 or 3.

Another preferred compound of Formula (I) is wherein $R_3$ is H; $R_2$ is of the formula

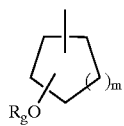

wherein m is 0, 1, 2 or 3 and $R_g$ is H or —$(CH_2)_pN(R_4)R_5$, wherein p is an integer from 2 to 6 and $R_4$ and $R_5$ are each, independently, H, azabicycloalkyl or Y—Z, wherein Y is selected from the group consisting of —C(O)—, —$(CH_2)_q$—, —$S(O)_2$—, —C(O)O—, —$SO_2NH$—, —CONH—, —$(CH_2)_qO$—, —$(CH_2)_qNH$—, and —$(CH_2)_qS(O)_r$—; wherein q is an integer from 0 to 6; and r is 0, 1 or 2; and Z is a substituted or unsubstituted moiety selected from the group consisting of alkyl, alkoxy, amino, aryl, heteroaryl and heterocycloalkyl group or $R_4$, $R_5$ and the nitrogen atom to which they are attached together form a 3, 4, 5, 6 or 7-membered, substituted or unsubstituted heterocyclic or heterobicyclic group.

Another preferred compound of Formula (I) is wherein $R_3$ is H; $R_2$ is of the formula

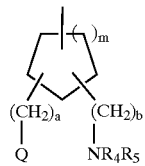

wherein m is 0, 1, 2 or 3
a and b are each, independently, an integer from 0 to 6;
Q is —$OR_6$ or —$NR_4R_5$;
each $R_4$ and $R_5$ is, independently, H, azabicycloalkyl or Y—Z, wherein Y is selected from the group consisting of —C(O)—, —$(CH_2)_q$—, —$S(O)_2$—, —C(O)O—, —$SO_2NH$—, —CONH—, —$(CH_2)_qO$—, —$(CH_2)_qNH$—, and —$(CH_2)_qS(O)_r$—; wherein q is an integer from 0 to 6; and r is 0, 1 or 2; and Z is a substituted or unsubstituted alkyl, substituted or unsubstituted alkoxy, amino, aryl, heteroaryl or heterocycloalkyl group or
$R_4$, $R_5$ and the nitrogen atom to which they are attached together form a 3, 4, 5, 6 or 7-membered, substituted or unsubstituted heterocyclic or heterobicyclic group; and
$R_6$ is hydrogen or a substituted or unsubstituted alkyl group.

Another preferred compound of Formula (I) is wherein $R_3$ is H; $R_2$ is of the formula

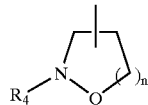

wherein n is 1, 2 or 3; and
$R_4$ is H, azabicycloalkyl or Y—Z, wherein Y is selected from the group consisting of —C(O)—, —$(CH_2)_q$—, —$S(O)_2$—, —C(O)O—, —$SO_2NH$—, —CONH—, —$(CH_2)_qO$—, —$(CH_2)_qNH$—, and —$(CH_2)_qS(O)_r$—; wherein q is an integer 0 to 6; and r is 0, 1 or 2;
and Z is a substituted or unsubstituted alkyl, substituted or unsubstituted amino, aryl, substituted or unsubstituted heteroaryl or substituted or unsubstituted heterocycloalkyl group.

Another preferred compound of Formula (I) is wherein $R_3$ is H; $R_2$ is of the formula

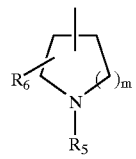

wherein is 0, 1, 2 or 3;

$R_5$ is H, azabicycloalkyl or Y—Z, wherein Y is selected from the group consisting of a covalent bond, —C(O)—, —$(CH_2)_q$—, —$S(O)_2$—, —C(O)O—, —$SO_2NH$—, —CONH—, —$(CH_2)_qO$—, —$(CH_2)_qNH$—, —$(CH_2)_qC(O)$—, —$C(O)(CH_2)_q$— and —$(CH_2)_qS(O)_r$—, where the alkyl portion of —$(CH_2)_q$—, —$(CH_2)_qO$—, —$(CH_2)_qNH$—, —$(CH_2)_qC(O)$—, —$C(O)(CH_2)_q$— and —$(CH_2)_qS(O)_r$ is optionally substituted by a halogen, hydroxy or an alkyl group; wherein q is an integer from 0 to 6;

and r is 0, 1 or 2; and Z is a substituted or unsubstituted alkyl, substituted or unsubstituted amino, substituted or unsubstituted alkoxy, substituted or unsubstituted aryl, substituted or unsubstituted heteroaryl or substituted or unsubstituted heterocycloalkyl group;

or Y and Z together are a natural or unnatural amino acid, which may be mono- or di-alkylated at the amine nitrogen; and $R_6$ represents one or more substituents each independently selected from the group consisting of hydrogen, hydroxy, oxo, substituted or unsubstituted alkyl, substituted or unsubstituted aryl, substituted or unsubstituted heterocyclyl, substituted or unsubstituted alkoxycarbonyl, substituted or unsubstituted alkoxyalkyl, substituted or unsubstituted aminocarbonyl, substituted or unsubstituted alkylcarbonyl, substituted or unsubstituted arylcarbonyl, substituted or unsubstituted heterocyclylcarbonyl, substituted or unsubstituted aminoalkyl and substituted or unsubstituted arylalkyl; provided that the carbon atoms adjacent to the nitrogen atom are not substituted by a hydroxy group.

Another preferred compound of Formula (I) is wherein $R_3$ is H; $R_2$ is of the formula

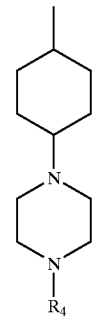

wherein $R_4$ is H, substituted or unsubstituted alkyl, substituted or unsubstituted azabicycloalkyl or Y—Z, wherein Y is selected from the group consisting of —C(O)—, —$(CH_2)_q$—, —$S(O)_2$—, —C(O)O—, —$SO_2NH$—, —CONH—, —$(CH_2)_qO$—, —$(CH_2)_qNH$—, and —$(CH_2)_qS(O)_r$—;

wherein q is an integer from 0 to 6, and r is 0, 1 or 2; and
Z is hydrogen, substituted or unsubstituted alkyl, substituted or unsubstituted amino, substituted or unsubstituted aryl, substituted or unsubstituted heteroaryl or substituted or unsubstituted heterocycloalkyl.

Another preferred compound of Formula (I) is wherein $R_3$ is H; $R_2$ is of the formula

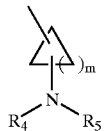

wherein
m is an integer from 1 to 6; and
$R_4$ and $R_5$ are each, independently, H, substituted or unsubstituted azabicycloalkyl or Y—Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6; and r is 0, 1 or 2; and Z is a substituted or unsubstituted alkyl, substituted or unsubstituted amino, substituted or unsubstituted aryl, substituted or unsubstituted heteroaryl or substituted or unsubstituted heterocycloalkyl group; or
$R_4$, $R_5$ and the nitrogen atom to which they are attached together form a 3, 4, 5, 6 or 7-membered, substituted or unsubstituted heterocyclic or substituted or unsubstituted heterobicyclic group.

Another preferred compound of Formula (I) is wherein $R_3$ is H; $R_2$ is of the formula

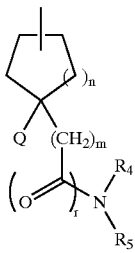

where
n is an integer from 0 to 4;
r is 0 and m is an integer from 1 to 6; or
r is 1 and m is an integer from 0 to 6;
Q is —OR$_6$ or —NR$_4$R$_5$;
each $R_4$ and $R_5$ is, independently, H, substituted or unsubstituted azabicycloalkyl or Y—Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; q is an integer from 0 to 6; and r is 0, 1 or 2; and Z is a substituted or unsubstituted alkyl, substituted or unsubstituted alkoxy, substituted or unsubstituted amino, substituted or unsubstituted aryl, substituted or unsubstituted heteroaryl or substituted or unsubstituted heterocycloalkyl group; or
$R_4$, $R_5$ and the nitrogen atom to which they are attached together form a 3, 4, 5 or 6-membered, substituted or unsubstituted heterocyclic group; and
$R_6$ is hydrogen or a substituted or unsubstituted alkyl group.

Another preferred compound of Formula (I) is wherein $R_3$ is H; $R_2$ is of the formula

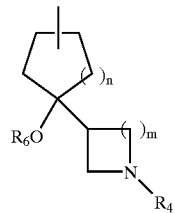

n is an integer from 0 to 4;
m is an integer from 0 to 6;
$R_4$ is H, substituted or unsubstituted azabicycloalkyl or Y—Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6; and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl; and
$R_6$ is hydrogen or a substituted or unsubstituted alkyl group.

A more preferred compound of Formula (I) is where in any of the applicable foregoing preferred compounds $R_4$, $R_5$ and the nitrogen atom together form a heterocyclic group of the formula

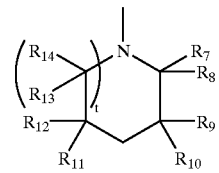

wherein
$R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$ and $R_{12}$; or $R_{13}$ and $R_{14}$ together are an oxygen atom; or at least one of $R_7$ and $R_9$ is cyano, CONHR$_{15}$, COOR$_{15}$, CH$_2$OR$_{15}$ or CH$_2$NR$_{15}$(R$_{16}$), wherein $R_{15}$ and $R_{16}$ are each, independently, H, azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or $R_{15}$, $R_{16}$ and the nitrogen atom together form a 3, 4, 5, 6 or 7-membered, substituted or unsubstituted heterocyclic or a substituted or unsubstituted heterobicyclic group;
X is O, S, SO, SO$_2$, CH$_2$, CHOR$_{17}$ or NR$_{17}$, wherein $R_{17}$ is hydrogen, substituted or unsubstituted alkyl, substituted or unsubstituted aryl, substituted or unsubstituted arylalkyl, —C(NH)NH$_2$, —C(O)R$_{17}$, or —C(O)OR$_{18}$, wherein $R_{18}$ is hydrogen, substituted or unsubstituted alkyl, substituted or unsubstituted aryl or substituted or unsubstituted arylalkyl; and
t is 0 or 1.

A more preferred compound of Formula (I) is where in any of the applicable foregoing preferred compounds $R_4$, $R_5$ and the nitrogen atom together form a heterocycle of the formula

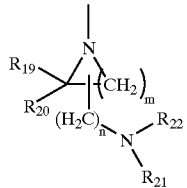

wherein $R_{19}$ and $R_{20}$ are each, independently, hydrogen or lower alkyl; or $R_{19}$ and $R_{20}$ together are an oxygen atom;

$R_{21}$ and $R_{22}$ are each, independently, H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or $R_{21}$, $R_{22}$ and the nitrogen atom together form a 3, 4, 5 or 6-membered, substituted or unsubstituted heterocyclic group;

m is an integer from 1 to 6; and n is an integer from 0 to 6.

A more preferred compound of Formula (I) is where in any of the applicable foregoing preferred compounds $R_4$, $R_5$ and the nitrogen atom together form a heterocyclic group of the formula

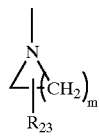

wherein m is an integer from 1 to 6; and $R_{23}$ is CH$_2$OH, NRR', C(O)NRR' or COOR, wherein R and R' are each, independently, hydrogen or substituted or unsubstituted alkyl, substituted or unsubstituted aryl or substituted or unsubstituted arylalkyl.

A more preferred compound of Formula (I) is where in any of the applicable foregoing preferred compounds $R_4$, $R_5$ and the nitrogen atom together form a heterocyclic group of the formula

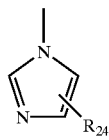

wherein $R_{24}$ is substituted or unsubstituted alkyl, substituted or unsubstituted aryl or substituted or unsubstituted arylalkyl, carboxyl, cyano, C(O)OR$_{25}$, CH$_2$OR$_{25}$, CH$_2$NR$_{26}$R$_{27}$ or C(O)NHR$_{26}$, wherein $R_{25}$ is substituted or unsubstituted alkyl, substituted or unsubstituted aryl, substituted or unsubstituted arylalkyl, substituted or unsubstituted heterocyclic or substituted or unsubstituted heterocycloaryl; and $R_{26}$ and $R_{27}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or $R_{26}$, $R_{27}$ and the nitrogen atom together form a 3, 4, 5 or 6-membered, substituted or unsubstituted heterocyclic group.

A more preferred compound of Formula (I) is where in any of the applicable foregoing preferred compounds at least one of $R_4$ and $R_5$ is of the formula Y—Z, wherein Z is of the formula

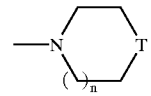

wherein

T is C(O), S, SO, SO$_2$, CHOR or NR, wherein R is hydrogen or a substituted or unsubstituted alkyl, substituted or unsubstituted aryl or substituted or unsubstituted arylalkyl group; and n is 0, 1 or 2.

A more preferred compound of Formula (I) is where in any of the applicable foregoing preferred compounds at least one of $R_4$ and $R_5$ is of the formula Y—Z, wherein Z is of the formula —N(R$_{28}$)R$_{29}$, wherein $R_{28}$ and $R_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or $R_{28}$ and $R_{29}$, together with the nitrogen atom, form a five- or six-membered substituted or unsubstituted heterocyclic group.

A more preferred compound of Formula (I) is where in any of the applicable foregoing preferred compounds $R_4$, $R_5$ and the nitrogen atom together form a heterocycle of the formula

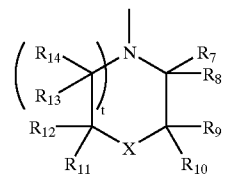

wherein $R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$ and $R_{12}$; or $R_{13}$ and $R_{14}$ together are an oxygen atom; or at least one of $R_7$ and $R_9$ is cyano, CONHR$_{15}$, COOR$_{15}$, CH$_2$OR$_{15}$ or CH$_2$NR$_{15}$(R$_{16}$), wherein $R_{15}$ and $R_{16}$ are each, independently, H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or R$_{15}$, R$_{16}$ and the nitrogen atom together form a 3, 4, 5, 6 or 7-membered, substituted or unsubstituted heterocyclic or heterobicyclic group;

X is O, S, SO, SO$_2$, CH$_2$, CHOR$_{17}$ or NR$_{17}$, wherein R$_{17}$ is hydrogen, substituted or unsubstituted alkyl, substituted or unsubstituted aryl, substituted or unsubstituted arylalkyl, —C(NH)NH$_2$, —C(O)R$_{18}$, or —C(O)OR$_{18}$, wherein R$_{18}$ is hydrogen, substituted or unsubstituted alkyl, substituted or unsubstituted aryl or substituted or unsubstituted arylalkyl; and t is 0 or 1.

A more preferred compound of Formula (I) is where in any of the applicable foregoing preferred compounds R$_4$, R$_5$ and the nitrogen atom together form a heterocycle of the formula

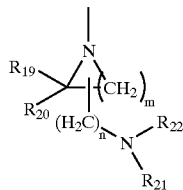

wherein
R$_{19}$ and R$_{20}$ are each, independently, hydrogen or lower alkyl; or R$_{19}$ and R$_{20}$ together are an oxygen atom;
R$_{21}$ and R$_{22}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or
R$_{21}$, R$_{22}$ and the nitrogen atom together form a 3, 4, 5 or 6-membered, substituted or unsubstituted heterocyclic group;
m is an integer from 1 to 6; and
n is an integer from 0 to 6.

A more preferred compound of Formula (I) is where in any of the applicable foregoing preferred compounds R$_4$, R$_5$ and the nitrogen atom together form a heterocyclic group of the formula

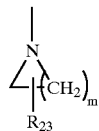

wherein
m is an integer from 1 to 6; and

R$_{23}$ is CH$_2$OH, NRR', C(O)NRR' or COOR, wherein R is hydrogen or a substituted or unsubstituted alkyl, substituted or unsubstituted aryl or substituted or unsubstituted arylalkyl group.

A more preferred compound of Formula (I) is where in any of the applicable foregoing preferred compounds R$_4$, R$_5$ and the nitrogen atom together form a heterocyclic group of the formula

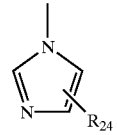

wherein R$_{24}$ is substituted or unsubstituted alkyl, substituted or unsubstituted aryl or substituted or unsubstituted arylalkyl, carboxyl, cyano, C(O)OR$_{25}$, CH$_2$OR$_{25}$, CH$_2$NR$_{26}$R$_{27}$ or C(O)NHR$_{26}$, wherein R$_{25}$ is substituted or unsubstituted alkyl, substituted or unsubstituted aryl, substituted or unsubstituted arylalkyl, substituted or unsubstituted heterocyclic or substituted or unsubstituted heterocycloaryl group; and R$_{26}$ and R$_{27}$ are each, independently, H, substituted or unsubstituted azabicycloalkyl or V-L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or R$_{26}$, R$_{27}$ and the nitrogen atom together form a 3, 4, 5 or 6-membered, substituted or unsubstituted heterocyclic group.

A more preferred compound of Formula (I) is where in any of the applicable foregoing preferred compounds at least one of R$_4$ and R$_5$ is of the formula Y—Z, wherein Z is of the formula

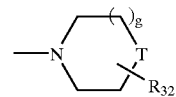

wherein
g is 0 or 1;
T is C(O), O, S, SO, SO$_2$, CH$_2$, CHOR$_{17}$ or NR$_{17}$, wherein R$_{17}$ is hydrogen, substituted or unsubstituted alkyl, substituted or unsubstituted aryl, substituted or unsubstituted arylalkyl, —C(NH)NH$_2$, —C(O)R$_{18}$, or —C(O)OR$_{18}$, wherein R$_{18}$ is hydrogen, substituted or unsubstituted alkyl, substituted or unsubstituted aryl or substituted or unsubstituted arylalkyl; and
R$_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl.

A more preferred compound of Formula (I) is where in any of the applicable foregoing preferred compounds at least one of R$_4$ and R$_5$ is of the formula Y—Z, wherein Z is of the formula —N(R$_{28}$)R$_{29}$, wherein R$_{28}$ and R$_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or $R_{28}$ and $R_{29}$, together with the nitrogen atom, form a five- or six-membered substituted or unsubstituted heterocyclic group.

A more preferred compound of Formula (I) is where in any of the applicable foregoing preferred compounds $R_5$ is Y—Z, wherein Z is of the formula $N(R_{30})R_{31}$, wherein $R_{30}$ and $R_{31}$ are each, independently, hydrogen, alkyl, alkoxycarbonyl, alkoxyalkyl, hydroxyalkyl, aminocarbonyl, cyano, alkylcarbonyl or arylalkyl.

A more preferred compound of Formula (I) is where in any of the applicable foregoing preferred compounds $R_5$ is Y—Z, wherein Z is of the formula

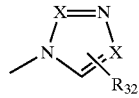

wherein
  each X is, independently, CH or N; and
  $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds $R_5$ is Y—Z, wherein Z is of the formula

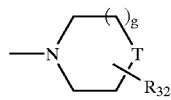

wherein
  g is 0 or 1;
  T is O, S, SO, $SO_2$, $CH_2$, $CHOR_{17}$ or $NR_{17}$, wherein $R_{17}$ is hydrogen, substituted or unsubstituted alkyl, substituted or unsubstituted aryl, substituted or unsubstituted arylalkyl, $C(O)NH_2$, —$C(NH)NH_2$, —$C(O)R_{17}$, or —$C(O)OR_{18}$, wherein $R_{18}$ is hydrogen, substituted or unsubstituted alkyl, substituted or unsubstituted aryl or substituted or unsubstituted arylalkyl; and
  $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds $R_5$ is Y—Z, wherein Z is of the formula

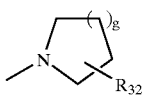

wherein
  g is 0, 1 or 2; and
  $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds $R_5$ is Y—Z, wherein Z is of the formula

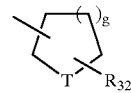

wherein
  T is C(O), O, S, SO, $SO_2$, $CH_2$, $CHOR_{17}$ or $NR_{17}$, wherein $R_{17}$ is hydrogen, substituted or unsubstituted alkyl, aryl, arylalkyl, —$C(O)NH_2$, —$C(O)R_{18}$, or —$C(O)OR_{18}$, wherein $R_{18}$ is hydrogen, substituted or unsubstituted alkyl, substituted or unsubstituted aryl or substituted or unsubstituted arylalkyl;
  g is 0 or 1; and
  $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

A more preferred compound of Formula (I) is where in any of the applicable foregoing preferred compounds $R_5$ is Y—Z, wherein Z is of the formula

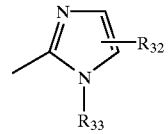

wherein
  $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, alkylcarbonyl, substituted or unsubstituted thioalkoxy or substituted or unsubstituted arylalkyl; and
  $R_{33}$ is hydrogen, substituted or unsubstituted alkyl, substituted or unsubstituted alkoxycarbonyl, substituted or unsubstituted alkoxyalkyl, substituted or unsubstituted aminocarbonyl, perhaloalkyl, substituted or unsubstituted alkenyl, substituted or unsubstituted alkylcarbonyl or substituted or unsubstituted arylalkyl.

A preferred compound of Formula (I) is where $R_3$ is H; $R_2$ is of the formula

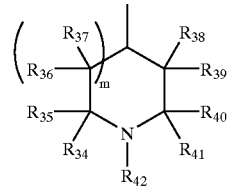

wherein m is 0 or 1;

$R_{34}$, $R_{35}$, $R_{36}$, $R_{37}$, $R_{38}$, $R_{39}$, $R_{40}$ and $R_{41}$ are each, independently, methyl or hydrogen; or at least one pair of substituents $R_{34}$ and $R_{35}$; $R_{36}$ and $R_{37}$; $R_{38}$ and $R_{39}$; or $R_{40}$ and $R_{41}$ together are an oxygen atom; and $R_{42}$ is H, substituted or unsubstituted azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl group; or $R_{42}$ is of the formula

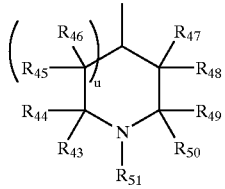

wherein u is 0 or 1;

$R_{43}$, $R_{44}$, $R_{45}$, $R_{46}$, $R_{47}$, $R_{48}$, $R_{49}$ and $R_{50}$ are each, independently, methyl or hydrogen; or at least one pair of substituents $R_{43}$ and $R_{44}$; $R_{45}$ and $R_{46}$; $R_{47}$ and $R_{48}$; or $R_{49}$ and $R_{50}$ together are an oxygen atom; and $R_{51}$ is H, substituted or unsubstituted azabicycloalkyl or V-L, wherein V is selected from the group consisting of —C(O)—, —(CH$_2$)p—, —S(O)$_2$—, —C(O)O—, —SO$_2$NH—, —CONH—, (CH$_2$)$_q$O$_{13}$, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl.

A preferred compound of Formula (1) is where $R_3$ is H; $R_2$ is of the formula

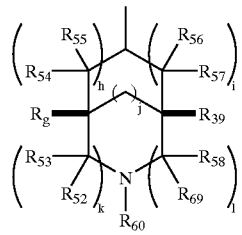

wherein h, i, j, k and l are independently 0 or 1;

$R_{52}$, $R_{53}$, $R_{54}$, $R_{55}$, $R_{56}$, $R_{57}$, $R_{58}$, $R_{59}$, $R_g$ and $R_h$ are each, independently, methyl or hydrogen; or at least one pair of substituents $R_{52}$ and $R_{53}$; $R_{54}$ and $R_{55}$; $R_{56}$ and $R_{57}$; or $R_{58}$ and $R_{59}$ together are an oxygen atom; and $R_{60}$ is H, substituted or unsubstituted azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl; or $R_{60}$ is of the formula

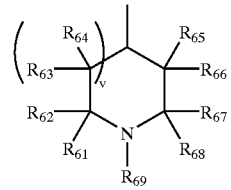

wherein v is 0 or 1;

$R_{61}$, $R_{62}$, $R_{63}$, $R_{64}$, $R_{65}$, $R_{66}$, $R_{67}$ and $R_{68}$ are each, independently, lower alkyl or hydrogen; or at least one pair of substituents $R_{61}$ and $R_{62}$; $R_{63}$ and $R_{64}$; $R_{65}$ and $R_{66}$; and $R_{67}$ and $R_{68}$ together are an oxygen atom; and $R_{69}$ is H, substituted or unsubstituted azabicycloalkyl or V-1, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl.

Another preferred compound of Formula (I) is where $R_3$ is H; $R_2$ is —$Z^{101}$-$Z^{102}$ where $Z^{101}$ is a covalent bond, —(C$_1$-C$_6$)—, —(C$_1$-C$_6$)—O—, —(C$_1$-C$_6$)—C(O)—, —(C$_1$-C$_6$)—C(O)O—, —(C$_1$-C$_6$)—C(O)—NH—, —(C$_1$-C$_6$)—C(O)—N((C$_1$-C$_6$))— or a substituted phenyl group; and $Z^{102}$ is hydrogen, a substituted or unsubstituted alkyl group or a substituted or unsubstituted, saturated or unsaturated heterocyclic group.

Another more preferred compound of Formula (I) is where in any of the applicable foregoing preferred compounds $Z^{101}$ is selected from the group consisting of —CH$_2$—C(O)O—, —CH$_2$—C(O)—, —CH$_2$—C(O)—NH—, —CH$_2$—C(O)—N(Me)—, —CH(Me)—C(O)O—, —(CH$_2$)$_3$—C(O)O—, —CH(Me)—C(O)—NH—, and —(CH$_2$)$_3$—C(O)—NH—; and $Z^{102}$ is selected from the group consisting of hydrogen, methyl, ethyl, N,N-dimethylaminoethyl, N,N-diethylaminoethyl, 2-phenyl-2-hydroxyethyl, morpholino, piperazinyl, N-methylpiperazinyl and 2-hydroxymethylpyrrolidinyl.

Another more preferred compound of Formula (I) is where in any of the applicable foregoing preferred compounds G is

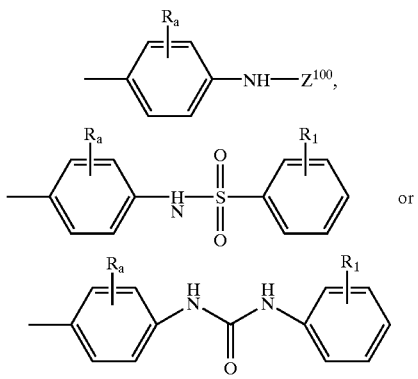

where $Z^{100}$ is a substituted or unsubstituted benzoxazolyl or a substituted or unsubstituted benzthiazolyl.

Another more preferred compound of Formula (I) is where in any of the applicable foregoing preferred compounds G is

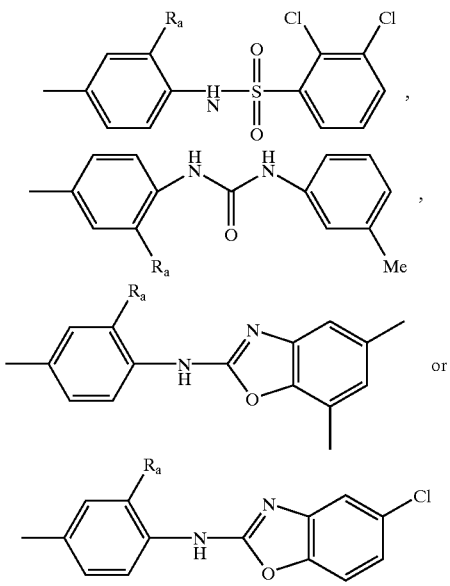

where there is only one $R_a$ and it is H or F.

Another more preferred compound of Formula (I) is where in any of the applicable foregoing preferred compounds $Z^{101}$ is a covalent bond; and $Z^{102}$ is an optionally substituted pyridyl.

Another more preferred compound of Formula (I) is where in any of the applicable foregoing preferred compounds G is

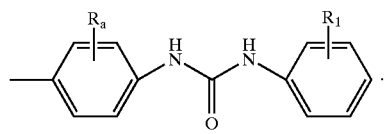

Another preferred compound of Formula (I) is where $R_3$ is H;

$R_2$ is cyclopentyl; and

G is

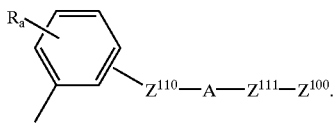

Another more preferred compound of Formula (I) is where in any of the applicable foregoing preferred compounds $Z^{110}$ is hydrogen; A is O; and $Z^{100}$ is optionally substituted phenyl, furanyl or thienyl, where $Z^{100}$ is optionally substituted with one or more substituents each independently selected from the group consisting of F, COOH, $NO_2$, OMe, —COOMe, $OCF_3$ and $CF_3$.

Another more preferred compound of Formula (I) is where in any of the applicable foregoing preferred compounds $Z^{110}$ is hydrogen; A is —O—, —O—$(CR_2)_n$—C(O)— or —O—$(CR_2)_n$—O—; n for each occurrence is 0 to 3;

$Z^{100}$ is an optionally substituted group selected from the group consisting of cyclohexyl, phenyl, tetrahydropyranyl, tetrahydrofuranyl, isoxazolyl and piperidinyl; where $Z^{100}$ is optionally substituted with one or more substituents selected from the group consisting of alkyl, alkoxy, halo, hydroxy and alkoxycarbonyl.

Another more preferred compound of Formula (I) is where in any of the applicable foregoing preferred compounds $R^2$ is an optionally substituted group selected from the group consisting of cyclobutyl and cyclohexyl.

Another more preferred compound of Formula (I) is where in any of the applicable foregoing preferred compounds $R^2$ is optionally substituted with one or more substituents selected from the group consisting of hydroxy, alkyl, hydroxyalkyl, carboxyalkyl and phenylalkoxyalkyl.

Another more preferred compound of Formula (I) is where in any of the applicable foregoing preferred compounds G is 4-phenoxyphenyl.

Another more preferred compound of Formula (I) is where in any of the applicable foregoing preferred compounds m is 2; a is 0; $R_6$ is H; b is 1 or 2; and $R_4$ and $R_5$ are each hydrogen.

Another more preferred compound of Formula (I) is where in any of the applicable foregoing preferred compounds m is 0, 1 or 2; $R_6$ is hydrogen; $R_5$ is H or Y—Z; where Y is a covalent bond, —C(O)—, —$(CH_2)_qO$—, —$(CH_2)_q$—, —$(CH_2)_qC(O)$— or —$C(O)(CH_2)_q$—, where the alkyl portion of —$(CH_2)_qO$—, —$(CH_2)_p$—, —$(CH_2)_qC(O)$— and —$C(O)(CH_2)_q$— is optionally substituted by a halogen, hydroxy or an alkyl group; and Z is hydrogen, alkyl, optionally substituted alkyl, alkoxyalkyl, optionally substituted heterocycloalkyl, optionally substituted heteroaryl, or optionally substituted amino.

Another more preferred compound of Formula (I) is where in any of the applicable foregoing preferred compounds Z is hydrogen, methyl, ethyl, hydroxymethyl, methoxyethyl, N-methyl-piperidinyl, (t-butoxycarbonyl)(hydroxy)-piperidinyl, hydroxypiperidinyl, (hydroxymethyl)piperdinyl, (hydroxy)(methyl)-piperidinyl, morpholino, (methoxyethyl)piperizinyl, methylpiperizinyl, 4-piperidinylpiperidinyl, imidazolyl, methylimidazolyl, N-methylamino, N,N-dimethylamino, N-isopropylamino, N,N-diethylamino, 2,3-dihydroxypropylamino, 2-hydroxyethylamino, 3-hydroxypropylamino, methoxyethylamino, ethoxycarbonylmethylamino, phenylmethylamino, N-methyl-N-methoxyamino,

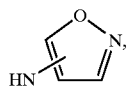

furanylmethylamino, piperidinylethylamino, N-(2-N,N-dimethylaminoethyl)-N-methylamino, 2-N,N-dimethylaminoethylamino, N-methyl-N-(N-methylpiperidin-4-yl)amino, 2-morpholino-ethylamino, 3-morpholino-propylamino, 3-imidazolylpropylamino, or 3-(2-oxopyrrolidinyl)propylamino.

Another more preferred compound of Formula (I) is where in any of the applicable foregoing preferred compounds m is 2; $R_5$ is Y—Z; Y is —C(O)—; and Z is

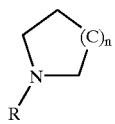

where n is 0, 1, 2 or 3.

Another more preferred compound of Formula (I) is where in any of the applicable foregoing preferred compounds $R_4$ is hydrogen or methyl;

G is

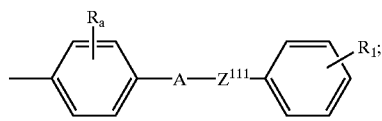

A is selected from the group consisting of O, —N(R)— and —N(R)C(O)—;

$Z^{111}$ is —(CH$_2$)$_n$-cycloalkyl-(CH$_2$)$_n$—; R is hydrogen or alkyl; n is 0 to 5;

$R_a$ is one or more substituents each independently selected from the group consisting of H, OH, F, Cl, methyl and methoxy;

$R_1$ is one or more substituents each independently selected from the group consisting of H, CN, F, CF$_3$, OCF$_3$, methyl, methoxy and an optionally substituted amino group; and where said amino group is optionally substituted with one or two groups each independently selected from the group consisting of alkyl, alkoxyalkyl, phenyl, substituted phenyl, and optionally substituted heteroaryl.

Another more preferred compound of Formula (I) is where in any of the applicable foregoing preferred compounds $R_1$ is 4-methylphenylthio or 2-pyridinylthio.

Another more preferred compound of Formula (I) is where in any of the applicable foregoing preferred compounds G is

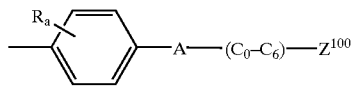

where $Z^{100}$ is selected from the group consisting of benzo[b]thiophene, furanyl and thiophene.

Another more preferred compound of Formula (I) is where in any of the applicable foregoing preferred compounds $R_a$ is alkoxy; A is —NH—C(O)—; and there is a covalent bond between A and $Z^{100}$.

Another more preferred compound of Formula (I) is where in any of the applicable foregoing preferred compounds G is

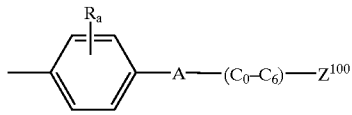

A is selected from the group consisting of —N(R)—C(O)—N(R)—, —(CH$_2$)$_n$—N(R)C(O)N(R)—, —N(R)— and —N(R)—SO$_2$—; R is hydrogen or alkyl;

$Z^{100}$ is

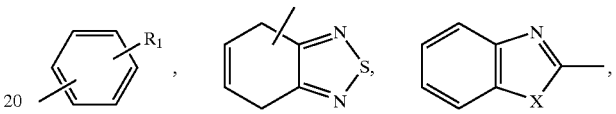

pyridinyl, thiazolyl, furanyl, benzofuranyl or oxazolyl;

X is S, O or NR$^1$ where R$^1$ for each occurrence is independently H or Me;

$R_a$ is one or more substituents each independently selected from the group consisting of H and F; and $R_1$ is one or more substituents each independently selected from the group consisting of H, F, Cl, Br, NO$_2$, CF$_3$, alkyl, alkoxy and alkoxycarbonyl.

Another more preferred compound of Formula (I) is where in any of the applicable foregoing preferred compounds $R_4$ is methyl; m is 1, 2 or 3; $R_5$ is Y—Z, where Y is —C(O)O—, —C(O)— or —C(O)—(CH$_2$)$_p$—; and Z is aminoalkyl, N-alkylamino, N,N-dialkylamino or hydroxyalkylaminoalkyl.

Another more preferred compound of Formula (I) is where in any of the applicable foregoing preferred compounds $R_4$ is methyl; G is

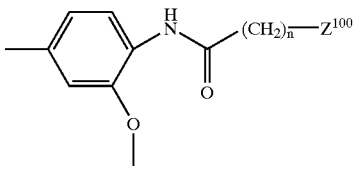

where n is 0 to 3; $Z^{100}$ is an optionally substituted group selected from the group consisting of indolyl, indenyl, methylindenyl, methylindolyl, dimethylaminophenyl, phenyl, cyclohexyl and benzofuranyl.

Another more preferred compound of Formula (I) is where in any of the applicable foregoing preferred compounds G is

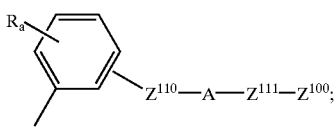

$Z^{100}$ is an optionally substituted group selected from the group consisting of phenyl, imidazolyl, indolyl, furanyl, benzofuranyl and 2,3-dihydrobenzofuranyl; where $Z^{100}$ is optionally substituted with one or more substituents each independently selected from the group consisting of F, Cl, CN, optionally substituted alkyl, —O-(optionally substituted alkyl), —COOH, —Z$^{105}$—C(O)N(R)$_2$, —Z$^{105}$—N(R)—C(O)—Z$^{200}$, —Z$^{105}$—N(R)—S(O)$_2$—Z$^{200}$, and —Z$^{105}$—N(R)—C(O)—N(R)—Z$^{200}$;

Z$^{105}$ is a covalent bond or (C$_1$–C$_6$);

Z$^{200}$ is an optionally substituted group selected from group consisting of (C$_1$–C$_6$), phenyl and —(C$_1$–C$_6$)-phenyl;

Z$^{110}$ and Z$^{111}$ are each independently a covalent bond or (C$_1$–C$_3$) group optionally substituted with alkyl, hydroxy, COOH, CN or phenyl; and A is O, —N(R)—C(O)—N(R)—, —N(R)—C(O)—O—, —N(R)— or —N(R)—C(O)—, where R is H or alkyl.

Another more preferred compound of Formula (I) is where in any of the applicable foregoing preferred compounds R$_4$ is methyl.

Another more preferred compound of Formula (I) is where in any of the applicable foregoing preferred compounds G is

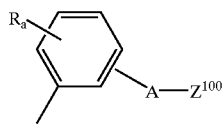

where Z$^{100}$ is an optionally substituted group selected from the group consisting of benzoxazolyl, benzothiazolyl and benzimidazolyl.

Another more preferred compound of Formula (I) is where in any of the applicable foregoing preferred compounds R$_4$ is methyl; A is —NH—; there is only one R$_a$ and it is H or F; and Z$^{100}$ is optionally substituted with one or more substituents each independently selected from the group consisting of alkyl, halo, CF$_3$, and alkoxy.

Another more preferred compound of Formula (I) is where in any of the applicable foregoing preferred compounds G is

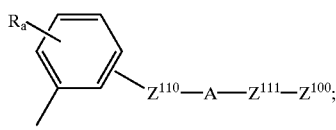

Z$^{100}$ is an optionally substituted group selected from the group consisting of phenyl, pyrrolyl, pyridyl, benzimidazolyl, naphthyl and

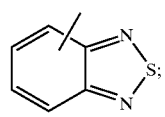

where Z$^{100}$ is optionally substituted with one or more substituents each independently selected from the group consisting of F, Cl, Br, NO$_2$, amino, N-alkylamino, N,N-dialkylamino, CN, optionally substituted alkyl, —O-(optionally substituted alkyl) and phenyl;

Z$^{110}$ and Z$^{111}$ for each occurrence is independently (C$_0$–C$_3$) optionally substituted with optionally substituted phenyl; and A is —N(R)—C(O)—N(R)—, —N(R)—S(O)$_2$—, —N(R)—C(O)—, —N(R)— or —N(R)—C(O)—O—.

Another more preferred compound of Formula (I) is where in any of the applicable foregoing preferred compounds R$_4$ is methyl and there is only one R$_a$ and it is F.

Another more preferred compound of Formula (I) is where in any of the applicable foregoing preferred compounds G is

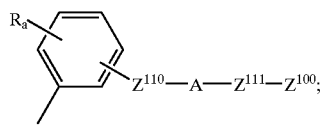

Z$^{100}$ is an optionally substituted group selected from the group consisting of phenyl, isoxazolyl, tetrahydronaphthyl, furanyl, benzofuranyl, pyridyl and indolyl; where Z$^{100}$ is optionally substituted with one or more substituents each independently selected from the group consisting of F, CN, NO$_2$, —C(O)H, —CONH$_2$, —NHSO$_2$CF$_3$, optionally substituted alkyl, optionally substituted heteroaryl and —O-(optionally substituted alkyl);

Z$^{110}$ and Z$^{111}$ are each independently optionally substituted (C$_0$–C$_3$); and A is O, —N(R)—C(O)—(CH$_2$)n—N(R)—, —C(O)—N(R)—, —N(R)—C(O)—O—, —N(R)—C(O)— or —N(R)—.

Another more preferred compound of Formula (I) is where in any of the applicable foregoing preferred compounds R$_4$ is methyl; R$_a$ is H or methoxy; and Z$^{110}$ and Z$^{111}$ are each unsubstituted.

Another more preferred compound of Formula (I) is where in any of the applicable foregoing preferred compounds G is

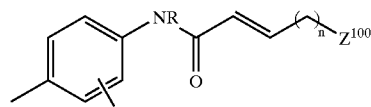

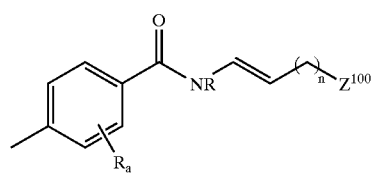

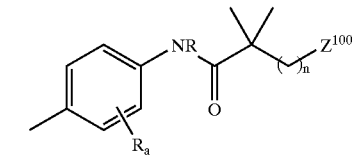

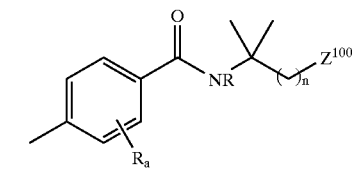

-continued

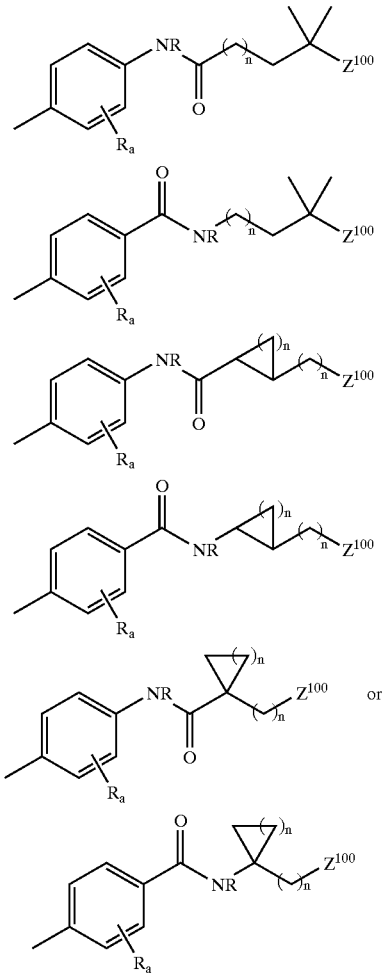

where R is H or lower alkyl and n is for each occurrence is independently 1 to 6.

Another more preferred compound of Formula (I) is where in any of the applicable foregoing preferred compounds G is

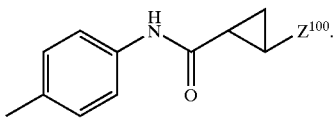

Another more preferred compound of Formula (I) is where in any of the applicable foregoing preferred compounds wherein $Z^{100}$ is substituted or unsubstituted phenyl.

Another more preferred compound of Formula (I) is where in any of the applicable foregoing preferred compounds G is

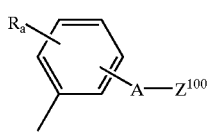

where $Z^{100}$ is an optionally substituted group selected from the group consisting of benzoxazolyl, benzothiazolyl and benzimidazolyl.

Another more preferred compound of Formula (I) is where in any of the applicable foregoing preferred compounds n is 2; $R_6$ is H; m is 1; r is 1; and $R_4$ and $R_5$ are each hydrogen.

Another more preferred compound of Formula (I) is where in any of the applicable foregoing preferred compounds wherein G is 4-phenoxyphenyl.

In another aspect the present invention is directed to a method of inhibiting one or more protein kinase activity in a patient comprising administering a therapeutically effective amount of a compound of Formula (I) or a physiologically acceptable salt, prodrug or biologically active metabolites thereof to said patient. A preferred method is where said protein kinase is selected from the group consisting of KDR, FGFR-1, PDGFRβ, PDGFRα, IGF-1R, c-Met, Flt-1, Flt-4, TIE-2, TIE-1, Lck, Src, fyn, Lyn, Blk, hck, fgr and yes. Another preferred method is where the protein kinase is a protein serine/threonine kinase or a protein tyrosine kinase. A more preferred method is where the protein kinase is TIE-2 and another more preferred method is where the protein kinase activity is involved in T cell activation, B cell activation, mast cell degranulation, monocyte activation, the potentiation of an inflammatory response or a combination thereof.

In another aspect the present invention is directed to a method of affecting hyperproliferative disorders in a patient comprising administering a therapeutically effective amount of a compound of Formula (I) or a physiologically acceptable salt, prodrug or biologically active metabolites thereof to said patient.

In another aspect the present invention is directed to a method of affecting angiogenesis in a patient comprising administering a therapeutically effective amount of a compound of Formula (I) or a physiologically acceptable salt, prodrug or biologically active metabolites thereof to said patient. A preferred method is where the compound or a physiologically acceptable salt, prodrug or biologically active metabolite thereof is administered in an amount effective to promote angiogenesis or vasculogenesis. A more preferred method is where the patient is suffering from anemia, ischemia, infarct, transplant rejection, a wound, gangrene or necrosis.

In another aspect the present invention is directed to a method of treating one or more ulcers in a patient comprising administering a therapeutically effective amount of a compound of Formula (I) or a physiologically acceptable salt, prodrug or biologically active metabolites thereof to said patient. A preferred method is where the ulcer or ulcers are caused by a bacterial or fungal infection; or the ulcer or ulcers are Mooren ulcers; or the ulcer or ulcers are a symptom of ulcerative colitis.

In another aspect the present invention is directed to a method of treating a condition in a patient comprising administering a therapeutically effective amount of a compound of Formula (I) or a physiologically acceptable salt, prodrug or biologically active metabolites thereof to said patient, wherein said condition is an ocular condition, a cardiovascular condition, a cancer, Crow-Fukase (POEMS) syndrome, a diabetic condition, sickle cell anaemia, chronic inflammation, systemic lupus, glomerulonephritis, synovitis, inflammatory bowel disease, Crohn's disease, glomerulonephritis, rheumatoid arthritis, osteoarthritis, multiple sclerosis, graft rejection, Lyme disease, sepsis, von Hippel Lindau disease, pemphigoid, psoriasis, Paget's disease, polycystic kidney disease, fibrosis, sarcoidosis, cirrhosis, thyroiditis, hyperviscosity syndrome, Osler-Weber-Rendu disease, chronic occlusive pulmonary disease, asthma or edema following bums, trauma, radiation, stroke, hypoxia, ischemia, ovarian hyperstimulation syndrome, preeclampsia, menometrorrhagia, endometriosis, or infection by Herpes simplex, Herpes Zoster, human immunodeficiency virus, parapoxvirus, protozoa or toxoplasmosis.

A preferred method is where the ocular condition is:

ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy or macular degeneration;

the cardiovascular condition is:

atherosclerosis, restenosis, ischemia/reperfusion injury, vascular occlusion or carotid obstructive disease;

the cancer is:

a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, Kaposi's sarcoma, Hodgkin's disease, lymphoma, myeloma, leukemia or malignant ascites; and the diabetic condition is:

insulin-dependent diabetes mellitus glaucoma, diabetic retinopathy or microangiopathy.

In another aspect the present invention is directed to a method of decreasing fertility in a patient, said method comprising the step of administering to the patient an effective amount of a compound of Formula (I) or a physiologically acceptable salt, prodrug or biologically active metabolite thereof.

In another aspect the present invention is directed to a method wherein the compound of Formula I, or physiologically acceptable salt, prodrug or biologically active metabolite thereof, is administered in combination with a pro-angiogenic growth factor. A preferred method is where the pro-angiogenic growth factor is selected from the group consisting of VEGF, VEGF-B, VEGF-C, VEGF-D, VEGF-E, HGF, FGF-1, FGF-2, derivatives thereof and antiiodotypic antibodies.

DETAILED DESCRIPTION OF THE INVENTION

In one embodiment, the present invention provides compounds of Formula I as described above. The values of substituents in preferred groups of compounds of Formula I are given below.

Preferably, $R_1$ is selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted and unsubstituted tetrazolyl, substituted and usubstituted styryl, substituted and unsubstituted arylthio, substituted or unsubstituted thioalkoxy, substituted and unsubstituted heteroarylthio; $CH_2OR_c$, wherein $R_c$ is hydrogen or substituted or unsubstituted alkyl or aryl; and $-W-(CH_2)_t-NR_dR_e$, wherein t is an integer from about 1 to about 6; W is a direct bond, O, S, S(O), $S(O)_2$, or $NR_f$, wherein $R_f$ is H or alkyl and Rd and Re are independently H, alkyl, alkanoyl or $SO_2$-alkyl; or $R_d$, $R_e$ and the nitrogen atom to which they are attached together form a five- or six-membered heterocyclic ring.

Preferably $R_a$ is selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, substituted or unsubstituted thioalkoxy, carboxyl, substituted and unsubstituted tetrazolyl, substituted and usubstituted styryl, substituted and unsubstituted arylthio, substituted and unsubstituted heteroarylthio; $CH_2OR_c$, wherein $R_c$ is hydrogen or substituted or unsubstituted alkyl or aryl; and $-W-(CH_2)_t-NR_dR_e$, wherein t is an integer from about 1 to about 6; W is a direct bond, O, S, S(O), $S(O)_2$, or $NR_f$, wherein $R_f$ is H or alkyl and $R_d$ and $R_e$ are independently H, alkyl, alkanoyl or $SO_2$-alkyl; or $R_d$, $R_e$ and the nitrogen atom to which they are attached together form a five- or six-membered heterocyclic ring.

Compounds of Formula (I) may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. These salts may be prepared by methods known to those skilled in the art.

Certain compounds of Formula (I) which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centres, and exist in different optically active forms. When compounds of formula I contain one chiral centre, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral centre it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formula I and mixtures thereof.

Certain compounds of Formula (I) may exist in different tautomeric forms or as different geometric isomers, and the present invention includes each tautomer and/or geometric isomer of compounds of formula I and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof. Certain compounds of Formula (I) may exist in zwitterionic form and the present invention includes each zwitterionic form of compounds of Formula (I) and mixtures thereof.

Heteroaromatic groups, as used herein, include heteroayl ng systems (e.g., for purposes of exemplification, which should not be construed as limiting the scope of this invention: thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isothiazoles, oxazolyl or tetrazoles) and heteroaryl ring systems in which a carbocyclic aromatic ring, carbocyclic non-aromatic ring or heteroaryl ring is fused to one or more other heteroaryl rings (e.g., for purposes of exemplification, which should not be construed as limiting the scope of this invention: benzo(b)thienyl, benzimidazolyl, benzoxazolyl, benzothiazolyl, benzothiadiazolyl, benzoxadiazolyl, indole, tetrahydroindole, azaindole, indazole, quinoline, imidazopyridine, quinazoline purine, pyrrolo[2,3-d]pyrimidine, pyrazolo[3,4-d]pyrimidine) and their N-oxides. Substituted heteroaryl groups are preferably substituted with one or more substituents each independently selected from the group consisting of a halogen, hydroxy, alkyl, alkoxy, alkyl-O—C(O)—, alkoxyalkyl, a heterocycloalkyl group, optionally substituted phenyl, nitro, amino, mono-substituted amino or di-substituted amino.

A heterocyclic (heterocyclyl) group, as used herein, refers to both heteroaryl groups and heterocycloalkyl groups.

A heterobicyclic group, as used herein, refers to a bicyclic group having one or more heteroatoms, which is saturated, partially unsaturated or unsaturated.

An arylalkyl group, as used herein, is an aromatic substituent that is linked to a compound by an aliphatic group having from one to about six carbon atoms. A preferred arylalkyl group is a benzyl group.

An heteroaralkyl group, as used herein, is a heteroaromatic substituent that is linked to a compound by an aliphatic group having from one to about six carbon atoms.

A heterocycloalkyl group, as used herein, is a non-aromatic ring system that has 3 to 8 atoms and includes at least one heteroatom, such as nitrogen, oxygen, or sulfur.

As used herein, aliphatic groups or notations such as "$C_0$–$C_6$" include straight chained, branched or cyclic hydrocarbons which are completely saturated or which contain one or more units of unsaturation. When the group is a $C_0$ it means that the moiety is not present or in other words is a bond.

As used herein, aromatic groups (or aryl groups) include aromatic carbocyclic ring systems (e.g. phenyl) and fused polycyclic aromatic ring systems (e.g. naphthyl and 1,2,3,4-tetrahydronaphthyl).

As used herein, the term "natural amino acid" refers to the twenty-three natural amino acids known in the art, which are as follows (denoted by their three letter acronym): Ala, Arg, Asn, Asp, Cys, Cys-Cys, Glu, Gln, Gly, His, Hyl, Hyp, Ile, Leu, Lys, Met, Phe, Pro, Ser, Thr, Trp, Tyr, and Val. The term non-natural amino acid refers to compounds of the formula $NH_2$—$(C(X)_2)_n$—COOH, which are alpha- (when n is 1) or beta- (when n is 2) amino acids where X for each occurrence is independently any side chain moiety recognized by those skilled in the art; examples of non-natural amino acids include, but are not limited to: hydroxyproline, homoproline, 4-amino-phenylalanine, β-(2-naphthyl)alanine, norleucine, cyclohexylalanine, β-(3-pyridinyl)alanine, β-(4-pyridinyl)alanine, α-aminoisobutyric acid, urocanic acid, N,N-tetramethylamidino-histidine, N-methyl-alanine, N-methyl-glycine, N-methyl-glutamic acid, tert-butylglycine, α-aminobutyric acid, tert-butylalanine, ornithine, α-aminoisobutyric acid, β-alanine, γ-aminobutyric acid, 5-aminovaleric acid, 12-aminododecanoic acid, 2-aminoindane-2-carboxylic acid, etc. and the derivatives thereof, especially where the amine nitrogen has been mono- or di-alkylated.

As used herein, many moieties or substituents are termed as being either "substituted or unsubstituted" or "optionally substituted". When a moiety is modified by one of these terms, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkyl groups (which itself can also be substituted, such as $CF_3$), alkoxy group (which itself can be substituted, such as $OCF_3$), a halogen or halo group (F, Cl, Br, I), hydroxy, nitro, oxo, CN, COH, COOH, amino, N-alkylamino or N,N-dialkylamino (in which the alkyl groups can also be substituted), esters (—C(O)—OR, where R is groups such as alkyl, aryl, etc., which can be substituted), aryl (most preferred is phenyl, which can be substituted) and arylalkyl (which can be substituted).

Suitable synthetic routes to compounds of Formula I are outlined in Schemes I–XII. Scheme I shows the conversion of 3-halo-4-chloropyrazolopyrimidine, to an N1-substituted 3-aryl-4-aminopyrazolopyrimidine. Scheme II illustrates substitution at N-1 of a 3-halo-4-aminopyrazolopyrimidine, followed by replacement of halo with an aryl group. Scheme III illustrates substitution at N-1 of a 3-aryl-4-aminopyrazolopyrimidine. Scheme IV shows the conversion of 4-hydroxypyrazolopyrimidine to a 1-substituted 3-bromo-4-chloropyrazolopyrimidine. Scheme V illustrates the formation of the pyrazolopyrimidine core. Scheme VI shows the formation of a 3-aryl-4-aminopyrazolopyrimidine. Scheme VII shows further elaboration of the N-1 substituent. P represents a suitable amino protecting group. Scheme VIII illustrates the preparation of the aryl boronates utilized in Scheme I. Schemes IX and X show the modification of the N-1 substituent. Scheme XI illustrates functionalization of the 3-aryl group. In Schemes I–XI, certain reactions may require suitable protection/deprotection of non-participating functional groups, as is known in the art.

The compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, restenosis, psoriasis, hemangiomas, myocardial angiogenesis, coronary and cerebral collaterals, ischemic limb angiogenesis, ischemia/reperfusion injury, wound healing, peptic ulcer Helicobacter related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, von Hippel Lindau disease, hematopoietic cancers and hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease.

Further, some of these compounds can be used as active agents against burns, chronic lung disease, stroke, polyps, anaphylaxis, chronic and allergic inflammation, delayed-type hypersensitivity, ovarian hyperstimulation syndrome, brain tumor-associated cerebral edema, high-altitude, trauma or hypoxia induced cerebral or pulmonary edema, ocular and macular edema, ascites, glomerulonephritis and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

Scheme I

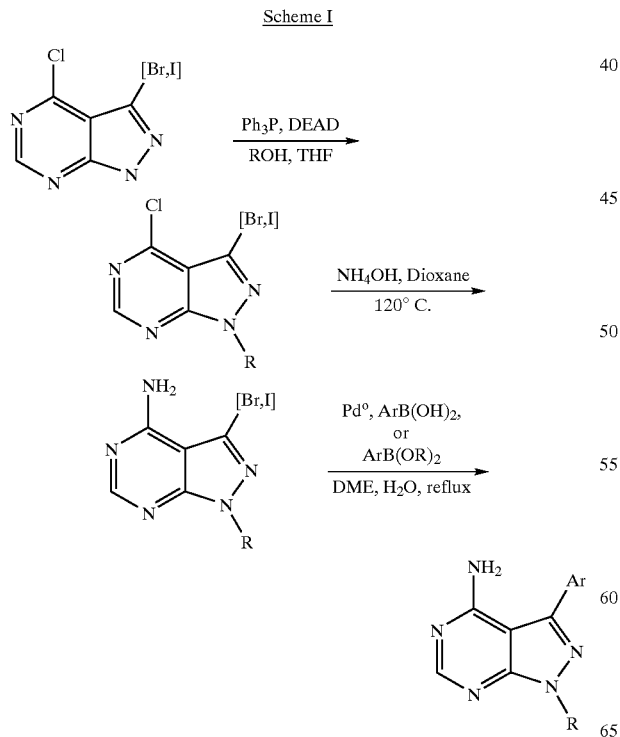

Scheme II

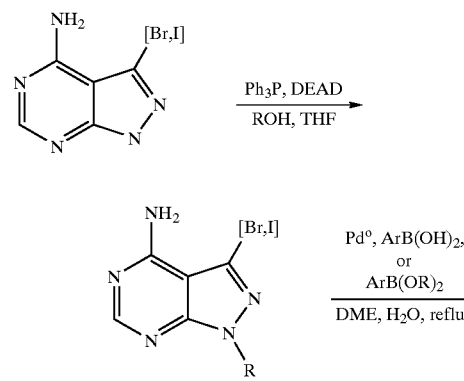

Scheme III

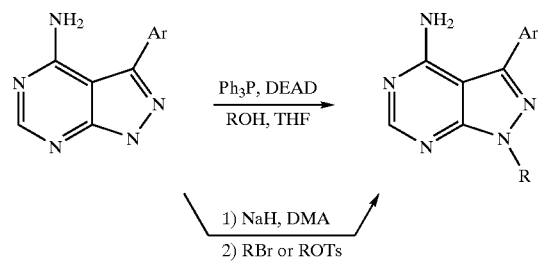

Scheme IV

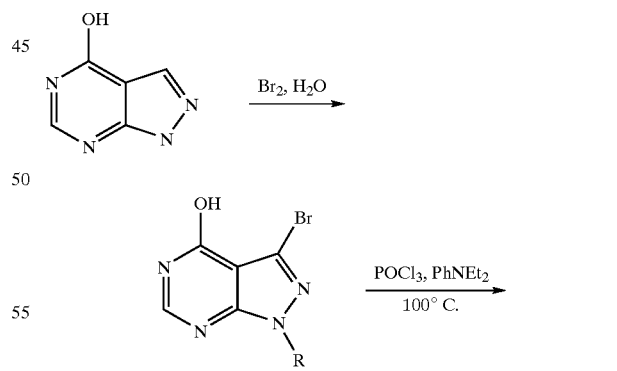

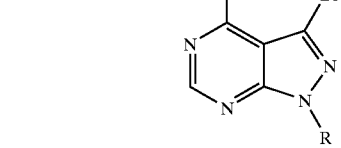

Scheme V
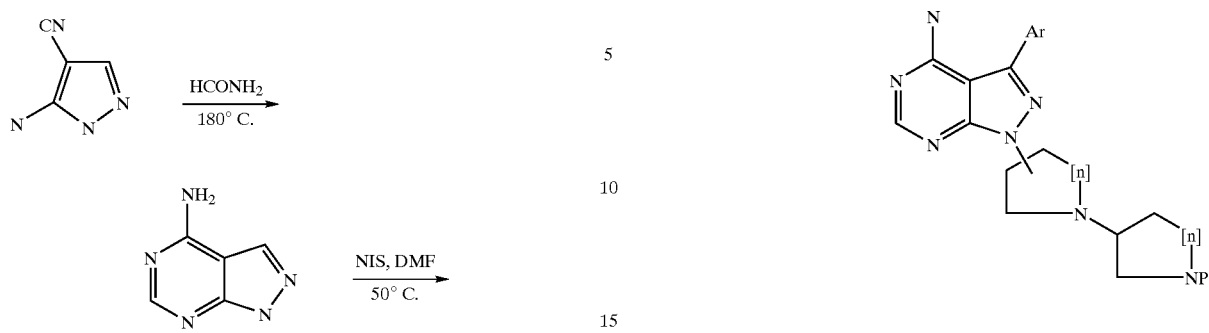
Scheme VI
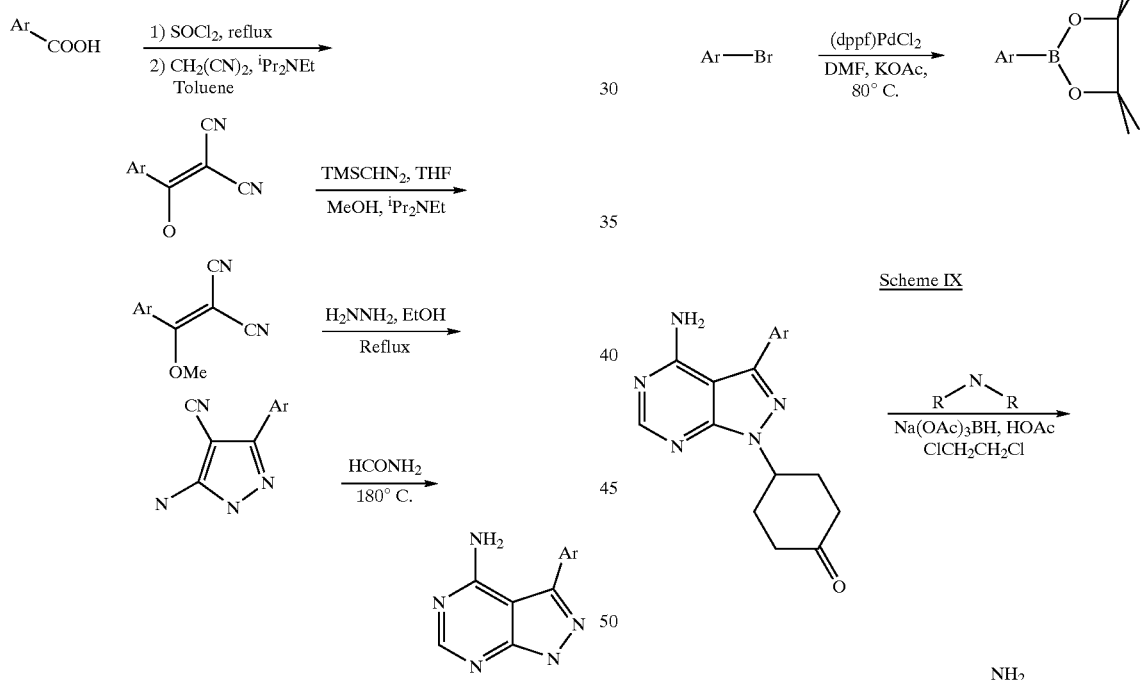
Scheme VII
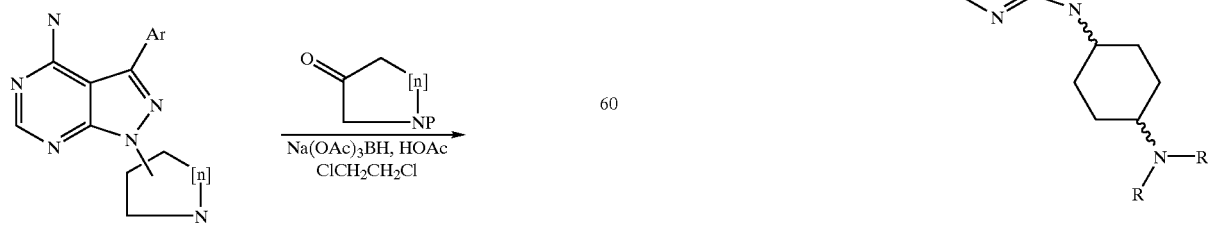
Scheme VIII
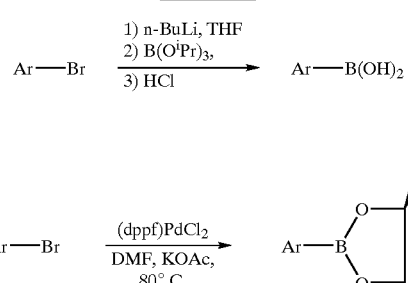
Scheme IX
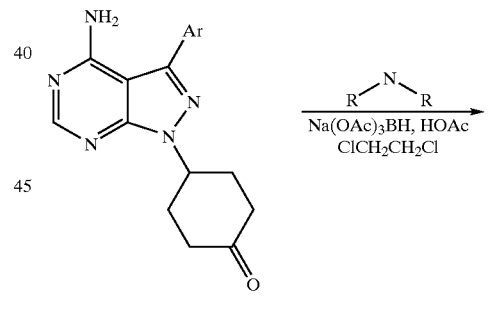

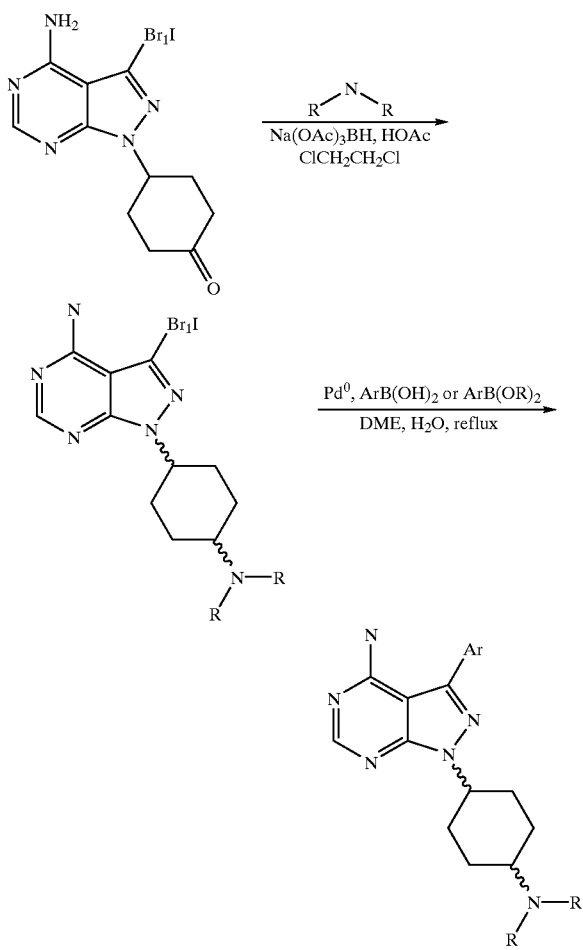

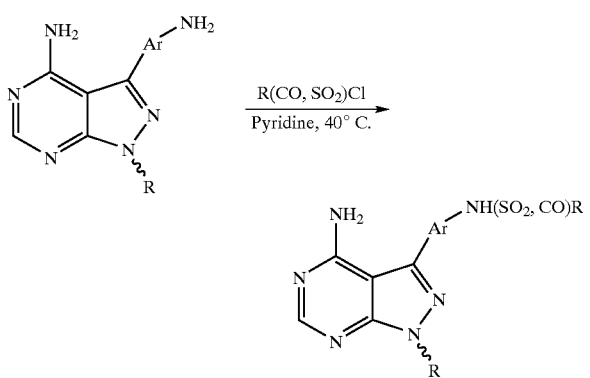

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

Because blastocyst implantation, placental development and embryogenesis are angiogenesis dependent, certain compounds of the invention areuseful as contraceptive agents and antifertility agents.

It is envisaged that the disorders listed above are mediated to a significant extent by protein tyrosine kinase activity involving the KDR/VEGFR-2 and/or the Flt-1/VEGFR-1 and/or TIE-2 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R. These receptor kinases can directly or indirectly potentiate angiogenic and hyperproliferative responses in various disorders, hence their inhibition can impede disease progression.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 tyrosine kinases. Certain compounds of this invention also inhibit the activity of additional tyrosine kinases such as Flt-1/VEGFR-1, Flt-4, Tie-1, Tie-2, FGFR, PDGFR, IGF-1R, c-Met, Src-subfamily kinases such as Lck, Src, hck, fgr, fyn, yes, etc. Additionally, some compounds of this invention significantly inhibit serine/threonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., $R_1$, $R_2$, $R_3$, A and ring 1) and conformational restrictions. In addition the metabolites of certain compounds may also possess significant protein kinase inhibitory activity.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., Cancer Res. 58:1278–1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. In this manner, certain preferred compounds of this invention are, therefore, selective in their tyrosine kinase inhibitory activity.

In one embodiment, the present invention provides a method of treating a protein kinase-mediated condition in a patient, comprising adiminstering to the patient a therapeutically or prophylactically effective amount of one or more compounds of Formula I.

A "protein kinase-mediated condition" or a "condition mediated by protein kinase activity" is a medical condition, such as a disease or other undesirable physical condition, the genesis or progression of which depends, at least in part, on the activity of at least one protein kinase. The protein kinase can be, for example, a protein tyrosine kinase or a protein serine/threonine kinase.

The patient to be treated can be any animal, and is preferably a mammal, such as a domesticated animal or a livestock animal. More preferably, the patient is a human.

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficincy virus, protozoa, toxoplasmosis or parapoxvirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease, in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

The compounds of the present invention are also useful in the treatment of Crow-Fukase (POEMS) syndrome and diabetic conditions such as glaucoma, diabetic retinopathy and microangiopathy.

The Src, Tec, Jak, Map, Csk, NFKB and Syk families of kinases play pivotal roles in the regulation of immune function. The Src family currently includes Fyn, Lck, Fgr, Fes, Lyn, Src, Yrk, Fyk, Yes, Hck, and Blk. The Syk family is currently understood to include only Zap and Syk. The TEC family includes Tec, Btk, Rlk and Itk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The Csk family is currently understood to include Csk and Chk. The kinases RIP, IRAK-1, IRAK-2, NIK, p38 MAP kinases, Jnk, IKK-1 and IKK-2 are involved in the signal transduction pathways for key pro-inflammatory cytokines, such as TNF and IL-1. By virtue of their ability to inhibit one or more of these kinases, compounds of formula I may function as immunomodulatory agents useful for the maintenance of allografts, the treatment of autoimmune disorders and treatment of sepsis and septic shock. Through their ability to regulate the migration or activation of T cells, B-cells, mast cells, monocytes and neutrophils, these compounds could be used to treat such autoimmune diseases and sepsis. Prevention of transplant rejection, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the Itk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by an autocrine or paracrine ligand/growth factor receptor interactions. Members of the src-family kinases are typically involved in downstream signal transduction thereby potentiating the oncogenesis and themselves may become oncogenic by over-expression or mutation. By inhibiting the protein kinase activity of these proteins the disease process may be disrupted. Vascular restenosis may involve FGF and/or PDGF - promoted smooth muscle and endothelial cell proliferation. The ligand stimulation of FGFR, PDGFR, IGF1-R and c-Met in vivo is proangiogenic, and potentiates angiogenesis dependent disorders. Inhibition of FGFr, PDGFr, c-Met, or IGF1-R kinase activities individually or in combination may be an efficacious strategy for inhibiting these phenomena. Thus compounds of formula I which inhibit the kinase activity of normal or aberrant c-kit, c-met, c-fms, src-family members, EGFr, erbB2, erbB4, BCR-Abl, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Flt-4, Tie-2/Tek and Tie) are essential for the stimulation of endothelial cell growth, migration, organization, differentiation and the establishment of the requisite new functional vasculature. As a result of the vascular permeability factor activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and virally-encoded VEGF-E or HIV-Tat protein can also cause a vascular hyperpermeability response through the stimulation of a VEGFR kinase. KDRNEGFR-2 and/or Tie-2 are expressed also in a select population of hematopoietic stem cells. Certain members of this population are pluripotent in nature and can be stimulated with growth factors to differentiate into endothelial cells and participate in vasculogenetic angiogenic processes. For this reason these have been called Endothelial Progenitor Cells (EPCs) (*J. Clin. Investig*. 103: 1231–1236 (1999)). In some progenitors, Tie-2 may play a role in their recruitment, adhesion, regulation and differentiation (*Blood*, 4317–4326 (1997)). Certain agents according to formula I capable of blocking the kinase activity of endothelial cell specific kinases could therefore inhibit disease progression involving these situations.

Vascular destabilization of the antagonist ligand of Tie-2 (Ang2) is believed to induce an unstable "plastic" state in the endothelium. In the presence of high VEGF levels a robust angiogenic response may result; however, in the absence of VEGF or a VEGF-related stimulus, frank vessel regression and endothelial apoptosis can occur (Genes and Devel. 13: 1055–1066 (1999)). In an analogous manner a Tie-2 kinase inhibitor can be proangiogenic or antiangiogenic in the presence or absence of a VEGF-related stimulus, respectively. Hence, Tie-2 inhibitors can be employed with appropriate proangiogenic stimoli, such as VEGF, to promote therapeutic angiogenesis in situations such as wound healing, infarct and ischemia.

The compounds of formula I or a salt thereof or pharmaceutical compositions containing a therapeutically effective amount thereof may be used in the treatment of protein kinase-mediated conditions, such as benign and neoplastic proliferative diseases and disorders of the immune system, as described above. For example, such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, acute lung injury and adult respiratory distress syndrome (ARDS).

The compounds of the present invention may also be useful in the prophylaxis of the above diseases.

It is envisaged that the disorders listed above are mediated to a significant extent by protein tyrosine kinase activity involving the VEGF receptors (e.g. KDR, Flt-1 and/or Tie-2). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above for use as medicaments, particularly as inhibitors of protein kinase activity for example tyrosine kinase activity, serine kinase activity and threonine kinase activity. In yet another aspect the present invention provides the use of compounds of formula I as defined initially above in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

Phamaceutical Formulations

The compounds of this invention can be administered to a human patient by themselves or in pharmaceutical compositions where they are mixed with suitable carriers or excipient(s) at doses to treat or ameliorate vascular hyperpermeability, edema and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g.in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared from the following ingredients.

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl-pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors and PI3 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536–539) by a test compound relative to control.

KDR Tyrosine Kinase Production Using Baculovirus System

The coding sequence for the human KDR intra-cellular domain (aa789–1354) was generated through PCR using cDNAs isolated from HUVEC cells. A poly-His 6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6KDR(aa789–1354)$ were lysed by adding 50 ml of Triton X-100 lysis buffer (20 mM Tris, pH 8.0, 137 mM NaCl, 10% glycerol, 1% Triton X-100, 1 mM PMSF, 10 $\mu$g/ml aprotinin, 1 $\mu$g/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at –80° C.

Human Tie-2 Kinase Production and Purification

The coding sequence for the human Tie-2 intra-cellular domain (aa775–1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-I Tyrosine Kinase Production and Purification

The baculoviral expression vector pVL1393 (Phar Mingen, Los Angeles, Calif.) was used. A nucleotide sequence encoding poly-His 6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat #E-3641; 500 units/50 $\mu$l) and the EGF ligand was acquired from Oncogene Research Products/Calbiochem (Cat #PF011-100).

Expression of ZAP70

The baculoviral expression vector used was pVL1393. (Pharmingen, Los Angeles, Calif.) The nucleotide sequence encoding amino acids M(H)6 $LVPR_9S$ was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 $\mu$g/ml leupeptin, 10 $\mu$g/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g. from Upstate Biotechnology Inc. (Saranac Lake, N.Y.) and Santa Cruz Biotechnology Inc. (Santa Cruz, Calif.)) or purified from known natural or recombinant sources using conventional methods.

Enzyme Linked Immunosorbent Assay (ELISA) for PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly($Glu_4$ Tyr), 20,000–50,000 MW) was employed together with ATP (typically 5 $\mu$M) at concentrations approximately twice the apparent Km in the assay.

The following procedure was used to assay the inhibitory effect of compounds of this invention on KDR, Flt-1, Flt-4/VEGFR-3, Tie-1, Tie-2, EGFR, FGFR, PDGFR, IGF-1-R, c-Met, Lck, Blk, Csk, Src, Lyn, Fyn and ZAP70 tyrosine kinase activity:

Buffers and Solutions:
PGTPoly (Glu,Tyr) 4:1
   Store powder at –20° C. Dissolve powder in phosphate buffered saline (PBS) for 50 mg/ml solution. Store 1ml aliquots at −20° C. When making plates dilute to 250 μg/ml in Gibco PBS.

Reaction Buffer: 100 mM Hepes, 20 mM MgCl$_2$, 4 mM MnCl$_2$, 5 mM DTT, 0.02%BSA, 200 μM NaVO$_4$, pH 7.10

ATP: Store aliquots of 100 mM at −20° C. Dilute to 20μM in water

Washing Buffer: PBS with 0. 1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 μg/ml. Add 125 μl per well of Corning modified flat bottom high affinity ELISA plates (Corning #25805-96). Add 125 μl PBS to blank wells. Cover with sealing tape and incubate overnight 37° C. Wash 1× with 250 μl washing buffer and dry for about 2 hrs in 37° C. dry incubator. Store coated plates in sealed bag at 4° C. until used.

2. Tyrosine Kinase Reaction:

Prepare inhibitor solutions at a 4×concentration in 20% DMSO in water.

Prepare reaction buffer

Prepare enzyme solution so that desired units are in 50 μl, e.g. for KDR make to 1 ng/μl for a total of 50 ng per well in the reactions. Store on ice.

Make 4×ATP solution to 20 μM from 100 mM stock in water. Store on ice

Add 50 μl of the enzyme solution per well (typically 5–50 ng enzyme/well depending on the specific activity of the kinase)

Add 25 μl 4×inhibitor

Add 25 μl 4×ATP for inhibitor assay

Incubate for 10 minutes at room temperature

Stop reaction by adding 50 μl 0.05N HCl per well

Wash plate

Final Concentrations for Reaction: 5 μM ATP, 5% DMSO

3. Antibody Binding

Dilute 1 mg/ml aliquot of PY20-HRP (Pierce) antibody (a phosphotyrosine antibody) to 50 ng/ml in 0.1% BSA in PBS by a 2 step dilution (100×, then 200×)

Add 100 μl Ab per well. Incubate 1 hr at room temp. Incubate 1 hr at 4C.

Wash 4×plate

4. Color Reaction

Prepare TMB substrate and add 100 μl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot. For Lck, the Reaction Buffer utilized was 100 mM MOPSO, pH 6.5, 4 MM MnCl$_2$, 20 mM MgCl$_2$, 5 mM DTT, 0.2% BSA, 200 mM NaVO$_4$ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit either FGFR, PDGFR, KDR, Tie-2, Lck, Fyn, Blk, Lyn or Src at concentrations of 50 micromolar or below. Some compounds of this invention also significantly inhibit other tyrosine or serine/threonine kinases such as cdc2 (cdkl) at concentrations of 50 micromolar or below.

Cdc2 Source

The human recombinant enzyme and assay buffer may be obtained commercially (New England Biolabs, Beverly, Mass. USA) or purified from known natural or recombinant sources using conventional methods.

Cdc2 Assay

The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM MgCl$_2$ (commercial buffer) supplemented with fresh 300 μM ATP (31 μCi/ml) and 30 μg/ml histone type IIIss final concentrations. A reaction volume of 80 μL, containing units of enzyme, was run for 20 minutes at 25 degrees C., in the presence or absence of inhibitor. The reaction was terminated by the addition of 120 μL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant. Certain compounds of this invention significantly inhibit cdc2 at concentrations below 50 uM.

PKC Kinase Source

The catalytic subunit of PKC may be obtained commercially (Calbiochem).

PKC Kinase Assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10 mM MgCl$_2$, 2 mM DTT, lmM EGTA, 100 μM ATP, 8 μM peptide, 5% DMSO and $^{33}$P ATP (8 Ci/mM). Compound and enzyme were mixed in the reaction vessel and the reaction initiated by addition of the ATP and substrate mixture. Following termination of the reaction by the addition of 10 μL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction was carried out in a buffer consisting of 50 mM Tris pH 7.5, 1 mM EGTA, 2 mM DTT, 0.01%

Brij, 5% DMSO and 10 mM $MgCl_2$ (commercial buffer) supplemented with fresh 100 $\mu$M ATP (31 $\mu$Ci/ml) and 30 $\mu$M myelin basic protein under conditions recommended by the supplier. Reaction volumes and method of assaying incorporated radioactivity were as described for the PKC assay (vide supra).

In Vitro Models for T-cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 $\mu$l volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$ M 2-mercaptoethanol and 0.5% DMSO, The cultures are pulsed with 0.5 $\mu$Ci of $^3$H thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-vivo Models of T—Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti—CD3 antibody (Ab). In this model, BALB/c mice are given 10 $\mu$g of anti—CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-$\gamma$(IFN-$\gamma$) and tumor necrosis factor-$\alpha$(TNF-$\alpha$), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 $\mu$g KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6 \times 10^6$ per ml in tissue culture medium (RPMI 1640 supplemented with heat inactivated fetal bovine serum (Hyclone Laboratories) $5 \times 10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-$\gamma$ levels by ELISA.

Lead compounds can also be tested in animal models of human disease. These are exemplified by experimental auto-immune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model: J. Immunol 146(4):1163–8, 1991). Briefly, mice or rats are immunized with an emulsion of myelin basic protein (MBP), or neurogenic peptide derivatives thereof, and CFA. Acute disease can be induced with the addition of bacterial toxins such as bordetella pertussis. Relapsing/remitting disease is induced by adoptive transfer of T-cells from MBP/peptide immunized animals.

CIA may be induced in DBA/1 mice by immunization with type II collagen (J. Immunol:142(7):2237–2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as lck involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation: 57(12): 1701–17D6, 1994) or heart (Am.J.Anat.:1 13:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3–8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5-1.0 \times 10^5$ cells/well in each well of 6-well cluster plates (Costar; Cambridge, Mass.).

3. 3–4 days after seeding, plates were 90–100% confluent. Medium was removed from all the wells, cells were rinsed with 5–10 ml of PBS and incubated 18–24 h with 5 ml of EBM base media with no supplements added (i.e., serum starvation).

4. Serial dilutions of inhibitors were added in 1 ml of EBM media (25 µM, 5 µM, or 1 µM final concentration to cells and incubated for one hour at 37° C. Human recombinant $VEGF_{165}$ (R & D Systems) was then added to all the wells in 2 ml of EBM medium at a final concentration of 50 ng/ml and incubated at 37° C. for 10 minutes. Control cells untreated or treated with VEGF only were used to assess background phosphorylation and phosphorylation induction by VEGF.

All wells were then rinsed with 5–10 ml of cold PBS containing 1 mM Sodium Orthovanadate (Sigma) and cells were lysed and scraped in 200 µl of RIPA buffer (50 mM Tris-HCl) pH7, 150 mM NaCl, 1% NP-40, 0.25% sodium deoxycholate, 1 nM EDTA) containing protease inhibitors (PMSF 1 mM, aprotinin 1 µg/ml, pepstatin 1 µg/ml, leupeptin 1 µg/ml, Na vanadate 1 mM, Na fluoride 1 mM) and 1 µg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (−20° C.) Ethanol (2 volumes) for a minimum of 1 hour or a maximum of overnight. Pellets were reconstituted in Laemli sample buffer containing 5% -mercaptoethanol (BioRad; Hercules, Calif.) and boiled for 5 min. The proteins were resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated F(ab)$_2$ of goat anti-rabbit or goat-anti-mouse IgG the bands were visualized using the emission chemiluminescence (ECL) system (Amersham Life Sciences, Arlington Height, Ill.). Certain examples of the present invention significantly inhibit cellular VEGF-induced KDR tyrosine kinase phosphorylation at concentrations of less than 50 µM.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones were purchased from Sigma (St. Louis, Mo.) or Cal Biochem (La Jolla, Calif.) as lyophilized powders and prepared according to supplier instructions.

Vehicle components (DMSO, Cremaphor EL) were purchased from Sigma (St. Louis, Mo.).

Mice (Balb/c, 8–12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5–10. Test compounds were administered by i.p., i.v. or p.o. routes depending on solubility and vehicle at doses ranging from 1–100 mg/kg. Vehicle control group received vehicle only and two groups were left untreated.

Thirty minutes later, experimental, vehicle and 1 of the untreated groups were given an i.p. injection of 17-estradiol (500 g/kg). After 2–3 hours, the animals were sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri were blotted to remove fluid by pressing between two sheets of filter paper with a one liter glass bottle filled with water. Uteri were weighed following blotting (blotted weight). The difference between wet and blotted weights was taken as the fluid content of the uterus. Mean fluid content of treated groups was compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. 1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

EXAMPLES

Example 1

1(1-Benzyl-4-piperidinyl)-3-(4-phenoxyphenyl)-1H-pyrazolo[3,4-d]pyrimidin-4-amine (Compound 1)

3-Bromo-1H-pyrazolo[3,4-d]pyrimidin-4-ol (Intermediate A)

1H-pyrazolo[3,4-d]pyrimidin-4-ol (10 g, 73.5 mmol) was suspended in 700 ml of water. Bromine (10 ml, 194 mmol)

was added and the resulting reaction mixture was heated to 91° C. overnight. After cooling on ice-water, the solid was collected by filtration to give 1.508 g of 3-bromo-1H-pyrazolo[3,4-d]pyrimidin-4-ol as light yellow solid. $^1$H NMR (DMSO) 8.06 (s, 1H), 12.25(bs, 1H), 14.06 (bs, 1H).

3-Bromo-4-chloro-1H-pyrazolo[3,4-d]pyrimidine (Intermediate B)

3-bromo-1H-pyrazolo[3,4-d]pyrimidin-4-ol (Intermediate A) (15.08 g, 70.5 mmol) was suspended in 189 ml of phosphous oxychloride. Diethylaniline (19 ml, 119.4 mmol) was added and the resulting reaction mixture was heated to 106° C. for 2 hours. After cooling to room temperature, the solvent was removed and the resulting amber syrup was poured to 300 ml of ice-water. 20 minutes later, the aqueous layer was extracted with diethyl ether (500 ml×4). The combined organic layer was washed, dried and evaporated to give 6.87 g of 3-bromo-4-chloro-1H-pyrazolo[3,4-d]pyrimidine as light yellow solid. $^1$H NMR (DMSO) 8.857 (s, 1H), 14.84 (bs, 1H); LC/MS (MH$^+$=233).

1-(1-Benzyl-4-piperidinyl)-3-bromo-4-chloro-1H-pyrazolo[3,4-d]pyrimidine (Intermediate C)

3-bromo-4-chloro-1H-pyrazolo[3,4-d]pyrimidine (Intermediate B) (5.0 g, 21.42 mmol), 1-benzyl-4-piperidinol (8.2 g, 42.83 mmol) and triphenylphosphine (11.23 g, 42.83 mmol)were suspended in 250 ml of tetrahydrofuran. The reaction mixture was cooled in an ice-water bath and diethyl azodicarboxylate (6.8 ml, 42.83 mmol) was added dropwise. 10 minutes later, the reaction mixture was allowed to warm up to room temperature. After stirring for 2 hours, solvent was removed and the residue was taking into ethyl acetate. The organic layer was washed, dried and evaporated. The crude product was passed through Biotage flash column using dichloromethane/ethyl acetate (90:10) as the mobile phase to yield 10.56 g of 1-(1-benzyl-4-piperidinyl)-3-bromo-4-chloro-1H-pyrazolo[3,4-d]pyrimidine. The product was 61% pure with a HPLC retention time of 12.46 min. (HPLC condition: 5 to 95% CH$_3$CN in 0.1 N aqueous ammonium acetate over 20 min., the column size is 3.9×150 mm, 300 A).

1-(1-Benzyl-4-piperidinyl)-3-bromo-1H-pyrazolo[3,4-d]pyrimidin-4-amine (Intermediate D)

1-(1-benzyl-4-piperidinyl)-3-bromo-4-chloro-1H-pyrazolo[3,4-d]pyrimidine (Intermediate C) (9 g, 61% purity) was mixed with dioxane (100 ml) and ammonium hydroxide (100 ml) in a pressure vessel. The mixture was heated to 120° C. overnight. Solvent was removed and the residue was purified via flash column chromatography using ethyl acetate as the mobile phase to give 1-(1-benzyl-4-piperidinyl)-3-bromo-1H-pyrazolo[3,4-d]pyrimidin-4-amine. $^1$H NMR (CDCl$_3$) 1.94 (d, J=11.23 Hz, 2H), 2.21(m, 2H), 2.35 (m, 2H), 3.04 (d, J=11.48 Hz), 3.57 (s, 2H), 4.71 (m, 1H), 5.98 (s, 2H), 7.34(m, 5H), 8.33 (s,1H); LC/MS (MH$^+$=389).

1-(1-Benzyl-4-piperidinyl)-3-(4-phenoxyphenyl)-1H-pyrazolo[3,4-d]pyrimidin-4-amine 1-(1-benzyl-4-piperidinyl)-3-bromo-1H-pyrazolo[3,4-d]pyrimidin-4-amine (Intermediate D) (4.3 g, 11.10 mmol), 4-phenoxyphenylboronic acid (Intermediate V) (2.61 g, 12.21 mmol), palladium tetrakistriphenyphosphine(0.77 g, 0.67 mmol) and sodium carbonate(2.82 g, 26.65 mmol) were mixed with ethylene glycol dimethyl ether(100 ml) and water(50 ml). The reaction mixture was heated to reflux overnight. Organic solvent was removed and the aqueous layer was extracted with ethyl acetate. The combined organic layer was washed, dried and evaporated. The residue was purified via flash column chromatography using ethyl acetate/methanol (98/2) as mobile phase to give 2.65 g of 1-(1-benzyl-4-piperidinyl)-3-(4-phenoxyphenyl)-1H-pyrazolo[3,4-d]pyrimidin-4-amine. $^1$H NMR (CDCl$_3$) 1.99 (d, J=1.02 Hz, 2H), 2.25(m, 2H), 2.47 (m, 2H), 3.07 (d, J=1.12 Hz), 3.59 (s, 2H), 4.80 (m, 1H), 5.52 (s, 2H), 7.07 (d, J=0.67, 1H), 7.15 (m, 3H), 7.37 (m, 6H), 7.66 (d, J=8.51, 2H), 8.37 (s,1H); LC/MS (MH$^+$=477).

Example 2

3-(4-Phenoxyphenyl)-1-(4-piperidinyl)-1H-pyrazolo[3,4-d]pyrimidin-4-amine 1-(1-benzyl-4-piperidinyl)-3-(4-phenoxyphenyl)-1H-pyrazolo[3,4-d]pyrimidin-4-amine (Compound 1) (1.224 g, 2.57 mmol), 10% Palladium on carbon (1.22 g) and ammonium formate(0.81 g, 12.84 mmol) were mixed with 21 ml of methanol. After stirring at room temperature for 6 hours, the reaction mixture was filtered and washed with hot methanol. Solvent was removed and the residue was taking into dichloromethane and the organic layer was washed, dried, and evaporated to give 0.77 g of 3-(4-phenoxyphenyl)-1-(4-piperidinyl)-1H-pyrazolo[3,4-d]pyrimidin-4-amine. $^1$H NMR (CDCl$_3$) 2.05 (d, J=12.17 Hz, 2H), 2.26 (m, 2H), 2.87 (m, 2H), 3.29 (d, J=12.76 Hz), 4.89 (m, 1H), 5.54 (s, 2H), 7.09 (m, 2H), 7.15 (m, 3H), 7.39 (m, 2H), 7.67 (d, J=9.39 Hz, 2H), 8.37 (s, 1H); LC/MS (MH$^+$32 387).

Example 3

1-[1-(1-Methyl-4-piperidinyl)-4-piperidinyl]-3-(4-phenoxyphenyl)-1H-pyrazolo[3,4-d]pyrimidin-4-amine, Trimaleate Salt (Compound 3)

1-[1-(1-Methyl-4-piperidinyl)-4-piperidinyl]-3-(4-phenoxyphenyl)-1H-pyrazolo[3,4-d]pyrimidin-4-amine (Intermediate E)

3-(4-phenoxyphenyl)-1-(4-piperidyl)-1H-pyrazolo[3,4-d]pyrimidin-4-amine (Compound 2) (199 mg, 0.515 mmol), 1-methyl-4-piperidone(70 ul, 0.566 mmol), sodium triacetoxyborohydride (163 mg, 0.772 mmol) and glacial acetic acid(34 mg, 0.566 mmol) were mixed with 3 ml of 1,2-dichloroethane. After stirring at room temperature overnight, 2 ml of water was added followed by solid sodium bicarbonate until the pH reached about 8. The layers were separated and the aqueous layer was extracted with dichloromethane. The combined organic layer was washed, dried and evaporated. The residue was purified via flash column chromatography to give 92 mg of 1-[1-(1-methyl-4-piperidinyl)-4-piperidinyl](4-phenoxyphenyl)-1H-pyrazolo[3,4-d]pyrimidin-4-amine. $^1$H NMR (DMSO) 1.47 (m, 2H), 1.72 (d, J=1 1.75 Hz, 2H), 1.88 (m, 4H), 2.14 (s, 3H), 2.35 (m, 5H), 2.81(d, J=11.32 Hz, 2H), 3.01(d, J=11.26 Hz, 2H), 4.62 (m, 1H), 7.16 (m, 5H), 7.44 (m, 2H), 7.67 (d, J=8.69 Hz, 2H), 8.23 (s, 1H); LC/MS (MH$^+$32 484).

1-[1-(1-Methyl-4-piperidinyl)-4-piperidinyl]-3-(4-phenoxyphenyl)-1H-pyrazolo[3,4-d]pyrimidin-4-amine, Trimaleate Salt 1-[1-(1-methyl-4-piperidinyl)-4-piperidinyl]-3-(4-phenoxyphenyl)-1H-pyrazolo[3,4-d]pyrimidin-4-amine (92 mg, 0.190 mmol) was dissolved in 25 ml of hot ethyl acetate and maleic acid(66 mg, 0.571 mmol) in 5 ml of hot ethyl acetate was added. After 2 hours at room temperature, the solid was filtered and then dried to give 135 mg of 1-[1-(1-methyl-4-piperidinyl)-4-piperidinyl]-3-(4-phenoxyphenyl)-1H-pyrazolo[3,4-d]pyrimidin-4-amine, trimaleate salt. $^1$H NMR (DMSO) 1.87 (m, 2H), 2.22 (m, 4), 2.45 (m, 2H), 2.77

(s, 3H), 2.18 (m, 9H), 5.06 (m, 1H), 6.11 (s, 6H), 7.15(m, 5H), 7.45 (m, 2H), 7.67 (d, J=8.51 Hz, 2H), 8.27 (s, 1H); LC/MS (MH+32 484).

Example 4

1-[1-(1-Isopropyl-4-piperidinyl)-4-piperidinyl]-3-(4-phenoxyphenyl)-1H-pyrazolo[3,4-d]pyrimidin-4-amine, Trimaleate Salt (Compound 4)

1-[1-(1-Isopropyl-4-piperidyl)-4-piperidyl]-3-(4-phenoxyphenyl)-1H-pyrazolo[3,4-d]pyrimidin-4-amine (Intermediate F)

3-(4-phenoxyphenyl)-1-(4-piperidinyl)-1H-pyrazolo[3,4-d]pyrimidin-4-amine (Compound 2) (221 mg, 0.572 mmol), 1-isopropyl-4-piperidone(89 mg, 0.63 mmol), sodium triacetoxyborohydride (182 mg, 0.86 mmol) and glacial acetic acid(40 ul, 0.63 mmol) were mixed with 3 ml of 1,2-dichloroethane. After stirring at room temperature overnight, 2 ml of water was added followed by solid sodium bicarbonate until PH reached about 8. The layers were separated and the aqueous layer was extracted with dichloromethane. The combined organic layer was washed, dried and evaporated. The residue was purified by flash column chromatography to give 132 mg of 1-[1-(1-isopropyl-4-piperidinyl)-4-piperidinyl]-3-(4-phenoxyphenyl)-1H-pyrazolo[3,4-d]pyrimidin-4-amine. $^1$H NMR (DMSO) 0.99 (d, J=6.54 Hz, 6H), 1.42 (m, 2H), 1.72(d, J=11.41 Hz, 2H), 1.88 (d, J=9.61 Hz, 2H), 2.14 (s, 3H), 2.16 (m, 6H), 2.66 (m, 2H), 2.83(d, J=10.98 Hz, 2H), 2.98(d, J=8.25 Hz, 2H), 4.62 (m, 1H), 7.16 (m, 5H), 7.44 (m, 2H), 7.67 (d, J=8.69 Hz, 2H), 8.23 (s, 1H); LC/MS (MH+= 512).

1-[1-(1-Isopropyl-4-piperidinyl)-4-piperidinyl]-3-(4-phenoxyphenyl)-1H-pyrazolo[3,4-d]pyrimidin-4-amine, Trimaleate Salt 1-[1-(1-isopropyl-4-piperidinyl)-4-piperidinyl]-3-(4-phenoxyphenyl)-1H-pyrazolo[3,4-d]pyrimidin-4-amine (Intermediate F) (132 mg, 0.258 mmol) was dissolved in 30 ml of hot ethyl acetate and maleic acid(90 mg, 0.774 mmol) in 5 ml of hot ethyl acetate was added. After 2 hours at room temperature, the solid was filtered and then dried to give 205 mg of 1-[1-(1-isopropyl-4-piperidinyl)-4-piperidinyl]-3-(4-phenoxyphenyl)-1H-pyrazolo[3,4-d]pyrimidin-4-amine, trimaleate salt. $^1$H NMR (DMSO) 1.26 (d, J=6.34 Hz, 6H), 1.90 (m, 2H), 2.23(m,4H), 2.50 (m, 2H), 3.53 (bm, 9H), 5.08 (m, 1H), 7.16 (m, 5H), 7.44 (m, 2H), 7.67 (d, J=8.30 Hz, 2H), 8.28 (s, 1H); LC/MS (MH+32 512).

Example 5

1-[1-(1-tert-Butoxycarbonyl-4-piperidinyl)-4-piperidinyl]-3-(4-phenoxyphenyl)-1H-pyrazolo[3,4-d]pyrimidin-4-amine, Trimaleate Salt (Compound 5)

1-[1-(1-tert-Butoxycarbonyl-4-piperidinyl)-4-piperidinyl]-3-(4-phenoxyphenyl)-1H-pyrazolo[3,4-d]pyrimidin-4-amine (Intermediate G)

3-(4-phenoxyphenyl)-1-(4-piperidyl)-1H-pyrazolo[3,4-d]pyrimidin-4-amine (Compound 2) (350 mg, 0.906 mmol), 1-tert-butoxycarbonyl-4-piperidone(198mg, 0.996 mmol), sodium triacetoxyborohydride (288 mg, 1.358 mmol) and glacial acetic acid(60 ul, 0.996 mmol) were mixed with 5 ml of 1,2-dichloroethane. After stirring at room temperature overnight, 2 ml of water was added followed by solid sodium bicarbonate until the pH reached about 8. The layers were separated and the aqueous layer was extracted with dichloromethane. The combined organic layer was washed, dried and evaporated. The residue was purified via flash column chromatography to give 254 mg of 1-[1-(1-tert-butoxycarbonyl-4-piperidyl)-4-piperidyl]-3-(4-phenoxyphenyl)-1H-pyrazolo[3,4-d]pyrimidin-4-amine. $^1$H NMR (DMSO) 1.39(m, 13H), 1.75 (m, 2H), 1.91 (m, 2H), 2.17(m, 2H), 2.35 (m, 2H), 2.72 (m, 2H), 3.0 (m, 2H), 3.63 (m, 1H), 3.98 (m, 2H), 4.63 (m, 1H), 7.16 (m, 5H), 7.44 (m, 2H), 7.67 (d, J=8.60 Hz, 2H), 8.23 (s, 1H); LC/MS (MH+32 484).

1-[1-(1-tert-Butoxycarbonyl-4-piperidinyl)-4-piperidinyl]-3-(4-phenoxyphenyl)-1H-pyrazolo[3,4-d]pyrimidin-4-amine, Trimaleate Salt 1-[ 1-(1-tert-butoxycarbonyl-4-piperidinyl)-4-piperidinyl]-3-(4-phenoxyphenyl)-1H-pyrazolo[3,4-d]pyrimidin-4-amine (254 mg, 0.446 mmol) was stirred in 25 ml of 10% trifluoroacetic acid in dichloromethane overnight. The solvent was evaporated and the residue was dissolved in dichloromethane. Saturated sodium bicarbonate was added and the resulting mixture was stirred for 30 minutes. The layers were separated and the aqueous layer was extracted with dichloromathane. The combined organic layer was washed, dried and evaporated to give 108 mg of 1-[1-(4-piperidinyl)-4-piperidinyl]-3-(4-phenoxyphenyl)-1H-pyrazolo[3,4-d]pyrimidin-4-amine (Intermediate GG) which was used without further purification.

1-[1-(4-piperidyl)-4-piperidyl]-3-(4-phenoxyphenyl)-1H-pyrazolo[3,4-d]pyrimidin-4-amine (108 mg, 0.230 mmol) was dissolved in 25 ml of ethanol and maleic acid (80 mg, 0.690 mmol) in 5 ml of hot ethanol was added. After 2 hours at room temperature, the solid was filtered and dried to give 155 mg of 1-[1-(4-piperidyl)-4-piperidyl]-3-(4-phenoxyphenyl)-1H-pyrazolo[3,4-d]pyrimidin-4-amine, trimaleate salt. $^1$H NMR (DMSO) 1.80 (m, 2H), 2.42 (m, 4), 2.51 (m, 2H), 2.95 (m, 3H), 3.44 (bm, 7H), 5.06 (m, 1H), 6.10 (s, 6H), 7.15 (m, 5H), 7.45 (m, 2H), 7.67 (d, J=8.5 Hz, 2H), 8.27 (s, 1H); LC/MS (MH+32 484).

Example 6

1-(trans-4-(4-Methylpiperazino)cyclohexyl)-3-(4-phenoxyphenyl)-1H-pyrazolo[3,4-d]pyrimidin-4-amine, Dimaleate Salt (Compound 6)

1-(1,4-Dioxaspiro[4.5]dec-8-yl)-3-(4-phenoxyphenyl)-1H-pyrazolo[3,4-d]pyrimidin-4-amine (Compound 9) (Intermediate I)

3-(4-phenoxyphenyl)-1H-pyrazolo[3,4-d]pyrimidin-4-amine (Compound 15) (3.36 g, 11.1 mmol, 1,4-dioxaspiro[4.5]decan-8-ol (Intermediate M) (5.26 g, 33.3 mmol), Triphenylphosphine (5.81 g, 22.2 mmol) were suspended in 130 ml of tetrahydrofuran. The reaction mixture was cooled in an ice-water bath and diethyl azodicarboxylate (3.9 ml, 22.2 mmol) was added dropwise. 10 minutes later, the reaction mixture was allowed to warm up to room temperature. After stirring for 2 hours, solvent was removed and the residue was taking into ethyl acetate. The organic layer was washed, dried and evaporated. The crude product was purified via Biotage flash column chromatography using dichloromethane/ethyl acetate (from 50:50 to 10:90) as the mobile phase to yield 3.829 g of 1-(1,4-dioxaspiro[4.5]dec-8-yl)-3-(4-phenoxyphenyl)-1H-pyrazolo[3,4-d]pyrimidin-4-amine. $^1$H NMR (CDCl$_3$) 1.83 (m, 2H), 1.945 (m, 2H), 2.05 (m, 2H), 2.45 (m, 2H), 3.99 (s, 4H), 4.86 (m, 1H), 5.74 (bs, 2H), 7.09 (m, 2H), 7.15 (m, 3H), 7.39 (m, 2H), 7.66 (d, J=8.70 Hz, 2H), 8.37 (s, 1H); LC/MS (MH+32 444).

4-(4-Amino-3-(4-phenoxyphenyl)-1H-pyrazolo[3,4-d]pyrimidin-1-yl)-1-cyclohexanone (Compound 10) (Intermediate J)

1-(1,4-dioxaspiro[4.5]dec-8-yl)-3-(4-phenoxyphenyl)-1H-pyrazolo[3,4-d]pyrimidin-4-amine (Compound 9) (3.80 g, 8.57 mmol) was suspended in 190 ml of acetone and cooled to 0° C. 48 ml of 5.0N hydrochloric acid was added slowly through an additional funnel. The ice-water bath was removed and reaction mixture was stirred at room temperature overnight. Acetone was removed and aqueous layer was neutralized with 1.0N sodium hydroxide to PH about 10. The solid was filtered and dried to give 2.926 g of 4-(4-amino-3-(4-phenoxyphenyl)-1H-pyrazolo[3,4-d]pyrimidin-1-yl)-1-cyclohexanone. $^1$H NMR (CDCl$_3$) 2.39 (m, 2H), 2.62 (m, 6H), 5.3 0 (m, 1H), 6.08 (bs, 2H), 7.09 (m, 2H), 7.15 (m, 3H), 7.42 (m, 2H), 7.64 (d, J=8.70 Hz, 2H), 8.39 (s, 1H); LC/MS (MH$^+$=400).

1-(trans-4-(4-Methylpiperazino)cyclohexyl)-3-(4-phenoxyphenyl)-1H-p yrazolo[3,4-d]pyrimidin-4-amine (Intermediate K) and 1-(cis-4-(4-methylpiperazino) cyclohexyl)-3-(4-phenoxyphenyl)-1H-pyrazolo[3,4-d] pyrimidin-4-amine (Intermediate L)

4-(4-amino-3-(4-phenoxyphenyl)-1H-pyrazolo[3,4-d] pyrimidin-1-yl)-1-cyclohexanone (Compound 10) (2.916 g, 7.30 mmol), 4-methylpiperazine (2.4 ml, 21.90 mmol), sodium triacetoxyborohydride (2.01 mg, 9.49 mmol) and glacial acetic acid (1.31 g, 21.90 mmol) were mixed with 147 ml of 1,2-dichloroethane. After stirring at room temperature for 6 hours, 57 ml of water was added followed by 3.8 g of solid sodium bicarbonate. The layers were separated and the aqueous layer was extracted with dichloromethane. The combined organic layer was washed, dried and evaporated.

The residue was purified via flash column chromatography using dichloromethane/methanol/aqueous ammonia (90/10/0.2 to 80/20/0.5) as mobile phase to give (A), 0.47 g of trans-1-(4-(4-methylpiperazino)cyclohexyl)-3-(4-phenoxyphenyl)-1H-pyrazolo[3,4-d]pyrimidin-4-amine. $^1$H NMR (DMSO) 1.49 (m, 2H), 2.00 (m, 6H), 2.23 (s, 3H), 2.59 (m, 9H), 4.66 (m, 1H), 7.17 (m, 5H), 7.44 (m, 2H), 7.64 (d, J=8.69 Hz, 2H), 8.23 (s, 1H); LC/MS (MH$^+$=484). (B), 2.582 g of 1-(cis-4-(4-methylpiperazino)cyclohexyl)-3-(4-phenoxyphenyl)-1H-pyrazolo[3,4-d]pyrimidin-4-amine. $^1$H NMR (DMSO) 1.58 (m, 2H), 1.68 (m, 2H), 2.08 (m, 2H), 2.15 (s, 3H), 2.28 (m, 11H), 4.79 (m, 1H), 7.17 (m, 5H), 7.44 (m, 2H), 7.64(d, J=8.69 Hz, 2H), 8.23 (s, 1H); LC/MS (MH$^+$=484).

1-(trans-4-(4-Methylpiperazino)cyclohexyl)-3-(4-phenoxyphenyl)-1H-pyrazolo [3,4-d]pyrimidin-4-amine, Dimaleate Salt Trans-1-(4-(4-methylpiperazino)cyclohexyl)-3-(4-phenoxyphenyl)-1H-pyrazolo[3,4-d]pyrimidin-4-amine (0.47 g, 0.972 mmol) was dissolved in 140 ml of hot ethanol and maleic acid (0.40 g, 2.47 mmol) in 10 ml of hot ethanol was added. After 2 hours at room temperature, the solid was filtered and then dried to give 0.62 g of 1-(trans-4-(4-methylpiperazino)cyclohexyl)-3-(4-phenoxyphenyl)-1H-pyrazolo[3,4-d]pyrimidin-4-amine, dimaleate salt. $^1$H NMR (DMSO) 1.58(m, 2H), 2.04 (m, 6), 2.67 (m, 3H), 2.79(vbm, 9H), 4.70 (m, 1H), 7.41 (s, 4H), 7.17 (m, 5H), 7.44 (m, 2H), 7.66 (d, J=8.63 Hz, 2H), 8.24 (s, 1H); LC/MS (MH$^+$32 484).

Example 7

1-[4-(4-Methylpiperazino)cyclohexyl]-3-(4-phenoxyphenyl)-1H-pyrazolo[3,4-d]pyrimidin-4-ylamine Trimaleate (Compound 7)

4-[4-amino-3-(4-phenoxyphenyl)-1H-pyrazolo[3,4-d] pyrimidin-1-yl]-1-cyclohexanone (Compound 10) (Intermediate J) (4.45 g) in 300 mL dichloromethane was stirred under nitrogen while adding 3.72 mL N-methylpiperazine and 1.92 mL acetic acid. After 30 minutes sodium triacetoxyborohydride (3.40 g) was added and the mixture stirred overnight. The next day 2 mL N-methylpiperazine, 1.2 mL acetic acid and 1.85 g sodium triacetoxyborohydride were added and stirred overnight. Another 2 mL N-methylpiperazine, 1.2 mL acetic acid and 1.85 g sodium triacetoxyborohydride were added and stirred overnight. The mixture was evaporated in vacuo, the residue stirred with 250 mL water and 100 mL 6M-hydrochloric acid and left overnight. The mixture was washed with ethyl acetate twice. The aqueous layer was basified (excess aqueous ammonia), extracted into ethyl acetate and this extract dried and evaporated giving 3.5 g pale brown gum which was purified by flash chromatography eluting with 8:1:1 ethyl acetate: ethanol: triethylamine giving 1.2 g pure product as colourless gum. Treatment of an ethyl acetate solution of the gum with 0.9 g maleic acid in ethyl acetate gave the maleate salt as an amorphous solid which was collected and washed with ethyl acetate. Drying in air then at 80° C./20mbar gave 1.9 g 1-[4-(4-methylpiperazino) cyclohexyl]-3-(4-phenoxyphenyl)-1H-pyrazolo[3,4-d] pyrimidin-4-ylamine trimaleate as a 0.8 ethyl acetate solvate m.p. 169–170° C. Calculated for $C_{43.2}H_{51.4}N_7O_{14.6}$ C 57.5H 5.7 N 10.9 Found C57.7H 5.7 N 10.9.

Example 8

N1-(4-{4-Amino-1-[4-(4-methylpiperazino) cyclohexyl]-1H-pyrazolo[3,4-d]pyrimidin-3-yl }-2-fluorophenyl)-4-fluoro-1-benzenesulfonamide Dimaleate Salt (Compound 8)

1H-Pyrazolo[3,4-d]pyrimidin-4-ylamine (Intermediate KA)

A suspension of 3-amino-4-pyrazole carbonitrile (26.85 g, 0.248 mol) in formamide (140 mL) was heated at 180° C. under nitrogen for 4 h. A precipitate formed upon cooling which was collected by filtration and washed with water. The solid was dried on the lyophilizer to give 1H-pyrazolo [3,4-d]pyrimidin-4-ylamine as a tan powder (87%, 29.25 g, 0.217 mol): $^1$H NMR (DMSO-d$_6$, 400 MHz) 13.34 (br s, 1H), 8.13 (s, 1H), 8.07 (s, 1H), 7.56 (br s, 2H); TLC (dichloromethane/methanol=9:1) $R_f$ 0.16.

3-Iodo-1H-pyrazolo[3,4-d]pyrimidin-4-ylamine (Intermediate LA)

A mixture of 4-aminopyrazolo[3,4-d]pyrimidine (Intermediate KA) (11.75 g, 0.087 mol) and N-iodosuccinimide (25.45 g, 0.113 mol) in dimethylformamide (300 mL) was heated at 50° C. for 24 h. Additional N-iodosuccinimide (3.92 g, 0.017 mol) was added and heating at 50° C. was continued for another 24 h. The mixture was allowed to cool to ambient temperature and the volume was reduced by ⅓ under reduced pressure. Water (500 mL) was added to the resulting slurry to yield a dark brown precipitate which was collected by filtration, washed with water and ethanol and dried in vacuo to give 3-iodo-1H-pyrazolo[3,4-d]pyrimidin-4-ylamine as a light yellow powder (97%, 22 g, 0.084 mol): $^1$H NMR (DMSO-d$_6$, 400 MHz) 13.81 (s, 1H), 8.17 (s, 1H), 2.73 (s, 1H), 2.57 (s, 1H); TLC (dichloromethane/methanol=9:1) $R_f$ 0.4.

1,4-Dioxaspiro[4.5]decan-8-ol (Intermediate M)

A solution of 1,4-cyclohexanedione monoethylene ketal (125 g, 0.8 mol) in methanol (2 1) was cooled to 0° C. then sodium borohydride (30.3 g, 0.8 mol) was added portionwise over 30 min. The reaction mixture was stirred at 0° C. for 3 h and the solvent removed under reduced pressure. The yellow syrup was redissolved in dichloromethane/isopropanol (3:1, 1.5 l) and washed with 2N sodium hydroxide (1 L). The aqueous layer was further extracted with dichloromethane/isopropanol (3:1) and the combined organic layers were washed with water, dried over sodium sulfate and concentrated under reduced pressure. Collected 1,4-dioxaspiro[4.5]decan-8-ol as a colorless oil (65%, 82.4 g, 0.65 mol): $^1$H NMR (CDCl$_3$ 400 MHz) 3.95 (m, 4H), 3.79 (m, 1H), 1.84 (m, 4H), 1.60 (m, 4H). TLC (ethylacetate/heptane=1:1) R$_f$ 0.16.

1-(1,4-Dioxaspiro[4.5]dec-8-yl)-3-iodo-1H-pyrazolo[3,4-d]pyrimidin-4-ylamine (Intermediate N)

3-Iodo-1H-pyrazolo[3,4-d]pyrimidin-4-ylamine (Intermediate LA) (11 g, 0.042 mol) was suspended in tetrahydrofuran (500 mL) at room temperature under a nitrogen atmosphere. A solution of 1,4-dioxaspiro[4.5]decan-8-ol (Intermediate M) (19.98 g, 0.126 mol) in tetrahydrofuran (50 mL) and subsequently triphenylphosphine (22.1 g, 0.084 mol ) was added to the suspension. The suspension was cooled to 0° C. and then diethyl azodicarboxylate (14.67 g, 0.084 mol) was added slowly. After stirring the reaction mixture at 0° C. for 15 min, it was allowed to warm to room temperature for 1 hour. The reaction mixture was concentrated under reduced pressure. The residue was dissolved in ethyl acetate (300–400 mL) and allowed to stand overnight. A precipitate formed which was collected by filtration, washed with ethyl acetate, and dried on the lyophilizer to give 1-(1,4-dioxaspiro[4.5]dec-8-yl)-3-iodo-1H-pyrazolo[3,4-d]pyrimidin-4-ylamine as a pale yellow solid (54%, 9.12 g, 0.023 mol): $^1$H NMR (DMSO-d$_6$, 400 MHz) 8.19 (s, 1H), 4.70 (m, 1H), 3.90 (m, 4H), 2.13 (m, 2H), 1.74 (m, 6H). TLC (dichloromethane/methanol=9:1) R$_f$ 0.61.

Tert-Butyl N-[2-fluoro-4-(4,4,5,5-tetramethyl-1,3,2-dioxaborolan-2-yl)phenyl]carbamate (Intermediate P)

Sodium bis(trimethylsilyl)amide (1.0M soln. in tetrahydrofuran, 270 mL, 0.27 mol) solution was added dropwise to a solution of 4-bromo-2-fluoroaniline (24.78 g, 0.130 mol) in tetrahydrofuran (250 mL) over 15 min. under nitrogen. After an additional 15 min, the di-tert-butyl dicarbonate (34.12 g, 0.156 mol) was added portionwise (note: a slight exotherm was observed) and stirring was continued for 4 h. The reaction mixture was concentrated under reduced pressure and the residue was partitioned between ethyl acetate (300 mL) and saturated aqueous sodium bicarbonate (150 mL). The aqueous layer was further extracted with ethyl acetate (2×200 mL) and the combined organic layers were dried over sodium sulfate and concentrated under reduced pressure. Purification by column chromatography on silica gel using a 10% to 15% ethyl acetate/heptane gradient afforded a light yellow waxy solid (Intermediate O) (79%, 30.0 g), $^1$H NMR (CDCl$_3$, 400 MHz) δ 1.51 (9H, s), 7.22 (1H, m), and 7.24 (2H, m).

A solution of the protected bromo aniline (Intermediate O) (54.0 g, 0.186 mol), bis-pinacolatodiborane (56.8 g, 0.223 mol), potassium acetate (54.7 g, 0.558 mol) and [1,1'-bis(diphenylphosphino)ferrocene]dichloropalladium (II) (4.65 g, 5.58 mmol) in dimethylformamide (1 L) was heated at 80° C. under nitrogen for 16 h. The dimethylformamide was removed under reduced pressure and the resulting dark solid residue was dissolved in dichloromethane (500 mL). The inorganic residues were removed by filtration through a silica gel pad and the filtrate was purified by column chromatography on silica gel using a 10% to 15% ethyl acetate/heptane gradient to afford the product as a yellow viscous oil which crystallized on standing (92%, 56.5 g), $^1$H NMR (CDCl$_3$, 400 MHz) 6 1.33 (12H, s), 1.53 (9H, s), 6.82 (1H, brs), 7.46 (1H, d), 7.55(1H, brd), and 8.12(1H, brt).

tert-Butyl N-{4-[4-amino-1-(1,4-dioxaspiro[4.5]dec-8-yl-1H-pyrazolo[3,4-d]pyrimidin-3-yl]-2-fluorophenyl}carbamate (Intermediate Q)

A suspension of 1-(1,4-dioxaspiro[4.5]dec-8-yl)-3-iodo-1H-pyrazolo[3,4-d]pyrimidin-4-ylamine (Intermediate N) (6.5 g, 0.016 mol), tert-butyl N-[2-fluoro-4-(4,4,5,5-tetramethyl-1,3,2-dioxaborolan-2-yl)phenyl]carbamate (Intermediate P) (24.3 g, 0.024 mol), tetrakis(triphenylphosphine)palladium(0) (749 mg, 0.648 mmol) and sodium carbonate (4.29 g, 0.04 mol) in degassed water (50 mL) and dimethoxyethane (300 mL) was heated at 80° C. for 18 h. The reaction mixture was concentrated under reduced pressure, then diluted with ethyl acetate (500 mL) and brine (500 mL). A solid formed which was collected by filtration, washed with ethyl acetate and dried in vacuo to give tert-butyl N-{4-[4-amino-1-(1,4-dioxaspiro[4.5]dec-8-yl-1H-pyrazolo[3,4-d]pyrimidin-3-yl]-2-fluorophenyl}carbamate as a tan solid (81%, 6.38 g, 0.013 mol): $^1$H NMR (DMSO-d$_6$, 400 MHz) 9.19 (s, 1H), 8.23 (s, 1H), 7.83 (t, 1H), 7.43 (m, 2H), 4.78 (m, 1H), 3.91 (m, 4H), 2.24 (m, 2H), 1.79 (m, 6H), 1.49 (s, 9H). TLC (dichloromethane/methanol=95:5) R$_f$ 0.42.

4-[4-Amino-3-(4-amino-3-fluorophenyl)-1H-pyrazolo[3,4-d]pyrimidin-1-yl]-1-cyclohexanone (Intermediate R)

tert-Butyl N-{4-[4-amino-1-(1,4-dioxaspiro[4.5]dec-8-yl-1H-pyrazolo[3,4-d]pyrimidin-3-yl]-2-fluorophenyl}carbamate (Intermediate Q) (6.38 g, 0.013 mol) was suspended in acetone (400 mL) and cooled to room temperature. 5M hydrochloric acid (96 mL) was slowly added to this suspension. The reaction mixture was then heated at 60° C. for 3 h and concentrated under reduced pressure. The remaining acidic layer was adjusted to pH 8 with aqueous sodium bicarbonate solution. A precipitate formed which was collected by filtration, washed with water, and dried on the lyophilizer to give 4-[4-amino-3-(4-amino-3-fluorophenyl)-1H-pyrazolo[3,4-d]pyrimidin-1-yl]-1-cyclohexanone as a tan solid (91%, 4.1 g, 0.012 mol): $^1$H NMR (DMSO-d$_6$, 400 MHz) 8.24 (s, 1H), 7.20 (m, 2H), 6.89 (m, 1H), 5.48 (s, 1H), 5.21 (m, 1H), 2.69 (m, 2H), 2.37 (m, 4H), 2.20 (m, 2H); TLC (ethyl acetate/heptane)=4:1; MH$^+$341.

Cis- and trans-3-(4-Amino-3-fluorophenyl)-1-[4-(4-methylpiperazino)cyclohexyl]-1H-pyrazolo[3,4-d]pyrimidin-4-amine (Intermediates S and T)

N-methylpiperazine (3.6 g, 0.036 mol) and acetic acid (2.17 g, 0.036 mol) were added to a suspension of 4-[4-amino-3-(4-amino-3-fluorophenyl)-1H-pyrazolo[3,4-d]pyrimidin-1-yl]-1-cyclohexanone (Intermediate R) (4.1 g, 0.012 mol) in dichloroethane (200 mL). Sodium triacetoxyborohydride (3.32 g, 0.016 mol) was then added portionwise to the reaction suspension. The reaction mixture was stirred at room temperature for 18 h. Additional sodium triacetoxyborohydride (1.79 g, 0.084 mol and 1.28 g, 0.06 mol) was added in two batches over 5 days. The reaction mixture was filtered, washed with dichloroethane (100 mL) and the filtrate was concentrated under reduced pressure to give 3-(4-amino-3-fluorophenyl)-1-[4-(4-methylpiperazino)cyclohexyl]-1H-pyrazolo[3,4-d]pyrimidin-4-amine as a yellow solid (14.5 g, 0.034 mol). The yellow solid was purified and the cis/trans isomers were separated by flash column chromatography on silica gel using dichloromethane/methanol/ammonium hydroxide (93:5:2) as the eluent to give trans 3-(4-amino-3-fluorophenyl)-1-[4-(4-methylpiperazino)cyclohexyl]-1H-pyrazolo[3,4-d]pyrimidin-4-amine (lower running component) as a white solid (115 mg, 0.27 mmol). $^1$H NMR (DMSO-d$_6$, 400 MHz) 8.19 (s, 1H), 7.18 (m, 2H), 6.88 (m, 1H), 5.46 (s, 2H), 4.60 (m, 1H), 2.35 (br m, 4H), 2.14 (s, 3H), 1.95 (br m, 6H), 1.44 (m, 2H), 1.26 (m, 4H), 0.86 (m, 2H). TLC (dichloromethane/methanol/ammonium hydroxide=95:5) R$_f$ 0.31.

Also collected cis-3-(4-amino-3-fluorophenyl)-1-[4-(4-methylpiperazino)cyclohexyl]-1H-pyrazolo[3,4-d]pyrimidin-4-amine as a white solid (1.1 g, 2.59 mmol). $^1$H NMR (DMSO-d$_6$, 400 MHz) 8.19 (s, 1H), 7.20 (m, 2H), 6.90 (m, 1H), 5.47 (s, 2H), 4.75 (m, 1H), 3.40 (m, 4H), 2.23 (m, 6H), 2.17 (m, 2H), 1.98 (s, 3H), 1.61 (m, 4H); TLC (dichloromethane/methanol/ammonium hydroxide=95:5) R$_f$ 0.37.

N1-(4-{4-amino-1-[4-(4-methylpiperazino)cyclohexyl]-1H-pyrazolo[3,4-d]pyrimidin-3-yl}-2-fluorophenyl)-4-fluoro-1-benzenesulfonamide di maleate salt A mixture of 3-(4-amino-3-fluorophenyl)-1-[4-(4-methylpiperazino)cyclohexyl]-1H-pyrazolo[3,4-d]pyrimidin-4-amine (Intermediate T) (107 mg, 0.252 mmol) and 4-fluorobenzenesulfonyl chloride (49 mg, 0.252 mmol) in pyridine (2.5 mL) was heated at 40° C. for 20 h. Additional 4-fluorobenzenesulfonyl chloride (15 mg, 0.063 mmol and 10 mg, 0.051 mmol) was added over 24 h. The reaction mixture was concentrated under reduced pressure to give an orange oil (220 mg, 0.378 mmol). The crude oil was purified by preparative RP-HPLC (Gilson C1 8) using an ammonium acetate gradient/acetonitrile gradient to give N1-(4-{4-amino-1-[4-(4-methylpiperazino)cyclohexyl]-1H-pyrazolo[3,4-d]pyrimidin-3-yl}-2-fluorophenyl)-4-fluoro-1-benzenesulfonamide (Intermediate U) as a white solid (220 mg). Maleic acid (55 mg, 0.474 mmol) and the free base N1-(4-{4-amino-1-[4-(4-methylpiperazino)cyclohexyl]-1H-pyrazolo[3,4-d]pyrimidin-3-yl}-2-fluorophenyl)-4-fluoro-1-benzenesulfonamide (92 mg, 0.158 mmol) were dissolved in hot ethanol (3 mL). A precipitate formed upon cooling which was collected by filtration, and dried on the lyophilizer to give N1-(4-{4-amino-1-[4-(4-methylpiperazino)cyclohexyl]-1-pyrazolo[3,4-d]pyrimidin-3-yl}-2-fluorophenyl)-4-fluoro-1-benzenesulfonamide dimaleate salt as a white solid (100 mg, 0.172 mmol). $^1$H NMR (DMSO-d$_6$, 400 MHz) 10.42 (s, 1H), 8.23 (s, 1H), 7.86 (m, 2H), 7.41 (m, 5H), 6.16 (s, 4H), 4.67 (br m, 1H), 2.62 (br m, 6H), 2.01 (br m, 6H), 1.56 (br m, 2H); MH$^+$583.6.

Example 9

(Intermediate 1)1-(1,4-dioxaspiro[4.5]dec-8-yl)-3-(4-phenoxyphenyl)-1H-pyrazolo[3,4-d]pyrimidin-4-ylamine (Compound 9, Intermediate I)

4-Phenoxyphenylboronic Acid (Intermediate V)

To a solution of 4-phenoxybromobenzene (98.2 g, 0.39 mol) in dry THF (800 mL) under nitrogen at −78° C. was added n-BuLi (2.5M solution in hexanes) (172 mL, 0.43 mol) dropwise. A temperature rise to −65° C. was observed. On complete addition, the mixture was allowed to stir at −78° C. for 15 min. Triisopropylborate (109.2 mL, 0.473 mol) was added dropwise over 30 min. On complete addition, a suspension was observed. The mixture was allowed to warm to 0° C. over 1 hr, stirred at 0° C. for 4 hrs. The reaction was quenched by the dropwise addition of water (300 mL) such that the internal temperature<20° C. (ice-cooling required). The mixture was allowed to warm to room temperature overnight then evaporated to dryness. The residue was suspended in water (600 mL) and acidified by the cautious addition of conc. HCl. The resulting precipitate was collected by filtration and dried in vacuo at 45° C. The solid was ground to a fine powder and triturated with petroleum ether (40–60° C.). The pale solid was filtered and dried to give 4-phenoxyphenylboronic acid (68.8 g, 83%). 1H NMR (250 MHz, d$_6$-DMSO):7.99 (1H, m), 7.91 (1H, t), 7.83 (1H, d), 7.4 (2H, m), 7.14 (1H, m), 6.92–7.07 (5H, m). Microanalysis:Req. C(71.4%), H(5.45%), Found C(70.25%), H(4.7%).

1,4-Dioxaspiro[4.5]decan-8-ol (Intermediate M)

1,4-dioxaspiro[4.5]decan-8-one (150 g, 0.96 mol) was stirred with MeOH (1200 mL) under N$_2$ until dissolution occurred. Cooled to −5° C. in a drykold/acetone bath and treated portionwise with NaBH$_4$ (72.6 g, 1.82 mol) over 2 hrs. (T<10° C.). On complete addition, the mixture was cooled to −10° C. and then left to warm to room temperature. Stirred overnight at room temperature. The resulting mixture was evaporated and treated with ice-cold 5N NaOH (400 mL) and extracted with CH$_2$Cl$_2$ (2×500 mL) followed by extraction with 4:1 dichloromethane: isopropanol (2×250 mL). The combined extracts were washed with brine (2×200 mL), dried overnight (Na$_2$SO$_4$) and evaporated to give a colourless oil. This was further dried in vacuo to give 1,4-dioxaspiro[4.5]decan-8-ol (141.8 g, 93% yield.) $^1$H NMR: CDCl$_3$ (250 MHz) 3.91 (4H, m), 3.81 (1H, m), 1.21–1.88 (8H, m, aliphatic H's).

3-Bromo-4-chloro-1-(1,4-dioxaspiro[4.5]dec-8-yl)-1H-pyrazolo[3,4-d]pyrimidine (Intermediate W)

To a solution of 3-bromo-4-chloropyrazolo[3,4-d]pyrimidine (Intermediate B) (7.5 g, 32 mmol), 1,4-dioxaspiro[4.5]decan-8-ol (Intermediate M) (15.17 g, 96 mmol), triphenylphosphine (16.86 g, 64 mmol) in THF (275 mL) was added diethylazodicarboxylate (11.14 g, 64 mmol) in THF (50 mL) at 0° C. under nitrogen. The reaction mixture was stirred at 0° C. for 1 hour, warmed to room temperature and then stirred at room temperature for 3 hrs. The reaction mixtures was concentrated in vacuo and dissolved in hot heptane/EtOAc/DCM (5:1:5). Flash silica gel column chromatography using heptane, heptane/EtOAc (5/1) then heptane/EtOAc (4/1) gave a solid which was triturated with heptane and the solids removed by filtration to furnish 8.2 g of 3-bromo-4-chloro-1-(1,4-dioxaspiro[4.5]dec-8-yl)-1H-pyrazolo[3,4-d]pyrimidine as a white solid (69%) [R$_f$ in 1:1 heptane:EtOAc=0.5]1H NMR (400 MHz, d$_6$-DMSO): 8.89 (1H, s), 4.92 (1H, m), 3.90 (4H, m), 2.16 (2H, m), 1.96 (2H, m), 1.81 (6H, m) HPLC: Tr=17.11 mins, 96.6%.

3-Bromo-1-(1,4-dioxaspiro[4.5]dec-8-yl)-1H-pyrazolo[3,4-d]pyrimidin-4-ylamine (Intermediate X)

3-bromo-4-chloro-1-(1,4-dioxaspiro[4.5]dec-8-yl)-1H-pyrazolo[3,4-d]pyrimidine (Intermediate W) (8.2 g, 21 mmol), conc. ammonia (100 mL) and dioxan (100 mL) were heated in a Parr pressure vessel at 120° C. for 20 hrs. The solvents were evaporated and the residue partioned between EtOAc and water. The EtOAc layer was dried over NASO$_4$, filtered and evaporated to leave 3-bromo-1-(1,4-dioxaspiro[4.5]dec-8-yl)-1H-pyrazolo[3,4-d]pyrimidin-4-ylamine as a solid (4.7 g, 61%) which was used without further purification. 1H NMR (400 MHz, d$_6$-DMSO): 8.21 (1H, s), 4.71 (1H, m), 3.90 (4H, m), 2.11(2H, m), 1.72–1.88 (6H, m ) HPLC: Tr=11.84 mins, 92.1%.

1-(1,4-Dioxaspiro[4.5]dec-8-yl)-3-(4-phenoxyphenyl)-1H-pyrazolo[3,4-d]pyrimidin-4-ylamine 3-bromo-1-(1,4-dioxaspiro[4.5]dec-8-yl)-1H-pyrazolo[3,4-d]pyrimidin-4-ylamine (Intermediate X) (4.0 g, 11.3 mmol), 4-phenoxyphenylboronic acid (Intermediate V) (2.66 g, 12 mmol), sodium carbonate (2.87 g, 27 mmol), palladium tetrakis(triphenyphosphine) (0.78 g, 0.6 mmol) in dimethoxyethane (120 mL)/water (60 mL) mixture was heated at 85° C. under nitrogen for 4 hrs. Cool to room temperature and stand for 72 hrs. The solid which precipitated was filtered and washed with water and diethylether (100 mL of each). Dry in vacuo for 3 hrs to furnish 4.2 g of 1-(1,4-dioxaspiro[4.5]dec-8-yl)-3-(4-phenoxyphenyl)-1H-pyrazolo[3,4-d]pyrimidin-4-ylamine as a beige solid (87%). 1H NMR (400 MHz, d$_6$-DMSO) 8.24 (1H, s), 7.67 (2H, m), 7.45 (2H, m), 7.19 (5H, m), 4.78 (1H, m), 3.90 (4H, m), 2.25 (2H, m), 1.71–1.84 (6H, m) Mass Spec.: MH$^+$=444.2.

1-(1,4-Dioxaspiro[4.5]dec-8-yl)-3-(4-phenoxyphenyl)-1H-pyrazolo[3,4-d]pyrimidin-4-ylamine. Second Route 4-Amino-3-(4-phenoxyphenyl)-1H-pyrazolo[3,4-d] pyrimidine (Compound 15) (4.9 g) in 200 mL dry dimethylacetamide was treated under nitrogen with 60% sodium hydride (2.0 g) and stirred 30 minutes. 1,4-dioxaspiro[4.5] dec-8-yl 4-methyl-1-benzenesulfonate (Intermediate Y) (15 g) was added and the mixture heated at 105° C. for 42 hours. Evaporation in vacuo and treating with water gave solid which was collected and washed well with water then dried in air. The solid was boiled with diethyl ether (6×120 mL) and the filtered solution evaporated. Treatment with acetone gave 1-(1,4-dioxaspiro[4.5]dec-8-yl)-3-(4-phenoxyphenyl)-1H-pyrazolo[3,4-d]pyrimidin-4-ylamine as an off-white solid which was collected and washed with acetone then dried in air m.p. 200–202.5° C. Calculated for $C_{25}H_{25}N_5O_3$ C 67.7 H 5.6 N 15.8 Found C 67.6 H5.8 N15.4.

Example 10

4-[4-Amino-3-(4-phenoxyphenyl)-1H-pyrazolo[3,4-d]pyrimidin-1-yl]-1-cyclohexanone (Compound 10, Intermediate J)

To 1-(1,4-dioxaspiro[4.5]dec-8-yl)-3-(4-phenoxyphenyl)-pyrazolo[3,4d]pyrimidin4-ylamine (Compound 9) (4.2 g, 95 mmol) in acetone (200 mL) was added HCl (5N, 50 mL) dropwise. Stir at room temperature for 24 hrs. Evaporate the acetone and basify with NaOH (5N, 60 mL). Extract with EtOAc (3×200 mL). Dry, filter and evaporate to leave a solid which was triturated with EtOAc: Et$_2$O (1:20) and filtered to give 4-[4-amino-3-(4-phenoxyphenyl)-1H-pyrazolo[3,4-d] pyrimidin-1-yl]-1-cyclohexanone as a cream solid (3.4 g, 90%), m.pt. 203–205° C.1H NMR (400 MHz, d$_6$-DMSO) 8.28 (1H, s), 7.66 (2H, m), 7.44 (2H, m), 7.08–7.20 (5H, m), 6.1–7.3 (2H, bs), 5.26 (1H, m), 2.71 (2H, m), 2.41 (4H, m), 2.24 (2H, m) HPLC: Tr=15.43 mins, 95%.

Example 11

Tert-butyl 4-4-[4-amino-3-(4-phenoxyphenyl)-1H-pyrazolo[3,4-d]pyrimidin-1-yl]cyclohexyl-1-piperazinecarboxylate (Compounds 11 and 12)

To a solution of 4-[4-amino-3-(4-phenoxyphenyl)-1H-pyrazolo[3,4-d]pyrimidin-1-yl]-1-cyclohexanone (Compound 10) (2.0 g, 5 mmol) and tert-butoxycarbonylpiperazine (2.8 g, 15 mmol) in dichloroethane (200 mL) was added glacial acetic acid (0.9 g, 15 mmol) and sodium triacetoxyborohydride (1.59 g, 7.5 mmol). Stir at room temperature under a N$_2$ atmosphere for 20 hrs. Quench with NaOH solution (2.5N, 200 mL). Separate organic layer and extract aqueous layer with dichloromethane (2×100 mL). Wash combined organic layers with water, dry (Na$_2$SO$_4$) and filter. The solution was evaporated to leave a red oil which was subjected to flash silica gel column chromatography using ethyl acetate to 10% MeOH/ethyl acetate in 2.5% MeOH increments. The fractions corresponding to the faster running material (R$_f$ in 9:1 EtOAc:MeOH=0.27) were combined and evaporated to give tert-butyl 4-4-[4-amino-3-(4-phenoxyphenyl)-1H-pyrazolo[3,4-d]pyrimidin-1-yl]cyclohexyl-1-piperazinecarboxylate as a white solid (1.48 g, 53%), m.pt. 170–172° C., identified as the cis diastereoisomer (Compound 11) $^1$H NMR (400 MHz, d$_6$-DMSO) 8.23 (1H, s), 7.65 (2H, d, J=8.8 Hz), 7.43 (2H, m), 7.12–7.20 (5H, m), 4.82 (1H, m), 3.34 (4H, m), 2.40 (4H, m), 2.30 (3H, m), 2.04 (2H, m), 1.60–1.72 (4H, m), 1.39 (9H, s).HPLC: Tr=15.74 mins, 98.16% Mass Spec.:MH$^+$=570.1. The fractions corresponding to the slower running material (R$_f$ $_{in}$ 9:1 EtOAc:MeOH=0.18) were combined and evaporated to give tert-butyl 4-4-[4-amino-3-(4-phenoxyphenyl)-1H-pyrazolo [3,4-d]pyrimidin-1-yl]cyclohexyl-1-piperazinecarboxylate as a cream solid (0.5 g, 18%), m.pt. 178–179° C., identified as the trans diastereoisomer. (Compound 12) 1H NMR (400 MHz, d$_6$-DMSO) 8.23 (1H, s), 7.65 (2H, d, J=8.4 Hz), 7.42 (2H, m), 7.11–7.20 (5H, m), 4.63 (1H, m), 3.34 (4H, m), 2.47 (5H, m), 1.89–2.06 (6H, m), 1.34–1.55 (1H, m) HPLC:Tr=15.29 mins, 98.15% Mass Spec.:MH$^{+=570.1.}$

Example 12 cis-3-(4-Phenoxyphenyl)-1-(4-piperazinocyclohexyl)-1H-pyrazolo[3,4-d] pyrimidin-4-ylamine trimaleate (Compound 13)

To cis-tert-butyl 4-4-[4-amino-3-(4-phenoxyphenyl)-1H-pyrazolo[3,4-d]pyrimidin-1-yl]cyclohexyl-1-piperazinecarboxylate (compound 11) (1.4 g, 2.46 mmol) in dichloromethane (35 mL) was added TFA (6 mL) dropwise at 0° C. under nitrogen. The reaction mixture was stirred at room temperature for 48 hrs, quenched with NaOH (5 Naq, 50 mL) and extracted with dichloromethane (3×50 mL). Wash with water, dry (Na$_2$SO$_4$), filter and evaporate to leave a colourless oil (1.23 g) which was dissolved in EtOAc (40 mL). To this solution was added a solution of maleic acid (913 mg) in EtOAc (10 mL). Filter the resulting solid under a stream of nitrogen and dry for a further 2 hrs in vacuo. This furnished 1.8 g (90%) of Cis-3-(4-phenoxyphenyl)-1-(4-piperazinocyclohexyl)-1H-pyrazolo[3,4-d]pyrimidin-4-ylamine trimaleate as a white solid m.pt. 173–175° C. 1H NMR (400 MHz, d$_6$-DMSO) 8.26 (1H, s), 7.67 (2H, d, J=8.8 Hz), 7.42 (2H, m), 7.12–7.21 (5H, m), 6.19 (6H, s), 4.86 (1H, m), 3.18 (4H, m), 2.89 (4H, m), 2.67 (1H, m), 2.28 (2H, m), 2.05 (2H, m), 1.74–1.80 (4H, m) HPLC: Tr=12.52 mins, 100% Mass Spec.:MH$^+$=470.3 Microanalysis: Calculated for $C_{39}H_{43}N_7O_{13}$ C: 57.3% H: 5.3% N: 12.0% Found C: 57.0% H: 5.3% N: 11.97%.

Example 13 trans-3-(4-Phenoxyphenyl)-1-(4-piperazinocyclohexyl)-1H-pyrazolo[3,4-d] pyrimidin-4-ylamine Trimaleate (Compound 14)

To trans-tert-butyl 4-4-[4-amino-3-(4-phenoxyphenyl)-1H-pyrazolo[3,4-d]pyrimidin-1-yl]cyclohexyl-1-piperazinecarboxylate (compound 12) (0.5 g, 0.88 mmol) in dichloromethane (15 mL) was added TFA (4 mL) dropwise at 0° C. under nitrogen. Stir at room temperature for 48 hrs. Quench with NaOH solution (5N, 25 mL) and extraxt with dichloromethane (3×25 mL). Wash with water, dry (Na$_2$SO$_4$), filter and evaporate to leave a beige solid (0.39 g) which was dissolved in EtOAc (20 mL). To this solution was added a solution of maleic acid (290 mg) in EtOAc (5 mL). Filter the resulting solid under a stream of nitrogen and dry for a further 2 hrs in vacuo. This furnished 0.6 g (83%) of trans-3-(4-phenoxyphenyl)-1-(4-piperazinocyclohexyl)-1H-pyrazolo[3,4-d]pyrimidin-4-ylamine trimaleate as a white solid m.pt. 153–155° C. 1H NMR (400 MHz, d$_6$-DMSO) 8.25 (1H, s), 7.65 (2H, m), 7.43 (2H, m), 7.11–7.21 (5H, m), 6.17 (6H, s), 4.69 (1H, m), 3.20 (4H, m), 2.97 (4H, m), 2.84 (1H, m), 2.04–2.09 (6H, m), 1.59 (2H, m). HPLC:Tr=12.65 mins, 100% Mass Spec.: MH$^+$=470.1 Microanalysis:Calculated for $C_{39}H_{43}N_7O_{13}$ C: 57.3% H: 5.3% N: 12.0% Found C: 57.1% H: 5.4% N: 12.10%.

Example 14

4-Amino-3-(4-phenoxyphenyl)-1H-pyrazolo[3,4-d] pyrimidine (Compound 15)

1,4-Dioxaspiro[4.5]decan-8-ol (Intermediate M)

1,4-dioxaspiro[4.5]decan-8-one (150 g, 0.96 mol) was stirred with MeOH (1200 mL) under $N_2$ until dissolution occurred. The reaction mixture was cooled to −5° C. in a drykold/acetone bath and treated portionwise with $NaBH_4$ (72.6 g, 1.82 mol) over 2 hrs. (T<10° C.). On complete addition, the mixture was cooled to −10° C. and then left to warm to room temperature and stirred overnight at room temperature. The resulting mixture was evaporated and treated with ice-cold 5N NaOH (400 mL) and extracted with $CH_2Cl_2$ (2×500 mL) followed by extraction with 4:1 dichloromethane: isopropanol (2×250 mL). The combined extracts were washed with brine (2×200 mL), dried overnight ($Na_2SO_4$) and evaporated to give a colourless oil. This was further dried in vacuo (to remove residual isopropanol) to give 1,4-dioxaspiro[4.5]decan-8-ol 141.8 g, 93% yield. $^1$H NMR: $CDCl_3$ (250 MHz): 3.91 (4H, m), 3.81 (1H, m), 1.21–1.88 (8H, m, aliphatic H's).

1,4-Dioxaspiro[4.5]dec-8-yl 4-methyl-1-benzenesulfonate (Intermediate Y)

To a stirred solution of 1,4-dioxaspiro[4.5]decan-8-ol (Intermediate M) (99.8 g, 0.63 mol) in pyridine (450 mLs) at 0° C. under nitrogen was added tosylchloride (132.4 g, 0.69 mol) portionwise such that T<2° C. On complete addition, the mixture was allowed to warm slowly to room temperature and stirred at room temperature overnight. Treated with water (750 mL) and extracted with EtOAc (500 mL then 2×250 mL). Combined extracts were washed with 3N HCl (3×300 mL), brine (300 mL) and dried over $Na_2SO_4$. Filtered and evaporated to yield a pale yellow oil (200 g crude). This oil was treated with petroleum ether (40–60°) (200 mL) and scratched to induce solid formation. 1,4-dioxaspiro[4.5]dec-8-yl 4-methyl-1-benzenesulfonate was filtered, washed with petroleum ether (40–60°) (200 mL) and dried in vacuo. Yield=181.0 g, 92%.

1,1-Dicyano-2-hydroxy-2-(4-phenoxyphenyl)ethene (Intermediate Z)

4-Phenoxybenzoic acid (48 g) was added to 100 mL thionyl chloride and heated under gentle reflux for 1 hour. Thionyl chloride was removed by distillation, the residual oil dissolved in toluene and volatile material removed at 80° C./20 mbar. The resulting acid chloride was dissolved in 200 mL toluene and 35 mL tetrahydrofuran. 14.8 g Malononitrile was added and the solution stirred at −10° C. while adding 57.9 g diisopropylethylethylamine in 150 mL toluene below 0° C. After 1 hour at 0° C. the mixture was stirred at 20° C. overnight. Amine hydrochloride was removed by filtration and the filtrate evaporated in vacuo, the residue taken up in ethyl acetate and washed with 1.25 M sulphuric acid then brine and dried over sodium sulphate. Evaporation gave a semisolid residue which was treated with a little ethyl acetate giving 4.1 g pure product as white solid m.p. 160–162° C. The filtrate on evaporation gave 56.5 g (96%) of 1,1-dicyano-2-hydroxy-2-(4-phenoxyphenyl)ethene as a grey-brown solid sufficiently pure for further use. $^1$H NMR (DMSO-$d_6$, 400 MHz) 8.18 (broad s, 1H), 7.62 (d, 2H), 7.42 (m, 2H), 7.19 (m, 1H), 7.07 (d, 2H), 6.94 (d, 2H).

1,1-Dicyano-2-methoxy-2-(4-phenoxyphenyl)ethene (Intermediate AA)

1,1-Dicyano-2-hydroxy-2-(4-phenoxyphenyl)ethene (Intermediate Z) (56.5 g) in 780 mL acetonitrile and 85 mL methanol was stirred under nitrogen at 0° C. while adding 52.5 mL diisopropylethylamine then 150 mL 2M-trimethylsilyldiazomethane in THF. After stirring for 2 days at 20° C., 2 g silica for chromatography was added: no further evolution of nitrogen was noted. The brown-red solution was evaporated in vacuo, the residue dissolved in ethyl acetate and washed well with water then brine, dried and evaporated. The residue was extracted with diethyl ether (3×250 mL), decanting from insoluble oil. Evaporation of the ether extracts gave 22.5 g of 1,1-Dicyano-2-methoxy-2-(4-phenoxyphenyl)ethene as a pale orange solid almost pure by t.l.c. (3:2 ethyl acetate:cyclohexane). The insoluble oil was purified by flash chromatography giving 15.0 g red-orange oil. Combined yield (63%) $^1$H NMR (DMSO-$d_6$, 400 MHz) 7.71 (d, 2H), 7.48 (m, 2H), 7.29 (m, 1H), 7.16 (m, 4H), 3.93 (s, 3H).

3-Amino-4-cyano-5-(4-phenoxyphenyl)pyrazole (Intermediate AB)

1,1-Dicyano-2-methoxy-2-(4-phenoxyphenyl)ethene (Intermediate AA) (22.5 g) and 1,1-dicyano-2-methoxy-2-(4-phenoxyphenyl)ethene oil (15 g) were treated with a solution of 18 mL hydrazine hydrate in 25 mL ethanol and heated on the steambath for 1 hour, 15 mL ethanol added followed 10 mL water. The precipitated solid was collected and washed with 4:1 ethanol:water then dried in air giving 3-amino-4-cyano-5-(4-phenoxyphenyl)pyrazole as a pale orange solid 30.0 g (80%) m.p. 187–188.5° C. $^1$H NMR (DMSO-$d_6$, 400 MHz) 12.11 (broad s, 1H), 7.80 (d, 2H), 7.42 (m, 2H), 7.18 (m, 1H), 7.09 (m, 4H), 6.47 (broad s, 2H). Calculated for $C_{16}H_{12}N_4O$ C 69.6H 4.3 N 20.3 Found C 69.5H 4.4 N 20.2.

4-Amino-3-(4-phenoxyphenyl)-1H-pyrazolo[3,4-d]pyrimidine

3-Amino-4-cyano-5-(4-phenoxyphenyl)pyrazole (Intermediate AB) (29.5 g) was suspended in 300 mL formamide and heated under nitrogen at 180° C. for 4 hours, cooled to 30 C, 300 mL water added and the solid collected, washed well with water then methanol and dried in air giving 24.6 g pure product (80%) of 4-amino-3-(4-phenoxyphenyl)-1H-pyrazolo[3,4-d]pyrimidine m.p. 267–269° C. as pale brown-grey solid. Calculated for $C_{17}H_{13}N_5O$ C 67.3H 4.3 N 23.1 Found C 67.0H 4.4 N 23.1.

Example 15

4-Amino-1-cyclopentyl-3-(4-phenoxyphenyl)-1H-pyrazolo[3,4-d]pyrimidine (Compound 16)

4-Amino-3-(4-phenoxyphenyl)-1H-pyrazolo[3,4-d]pyrimidine (Compound 15) (0.91 g) in 50 mL dry dimethylacetamide was stirred under nitrogen at 25° C. while adding 60% sodium hydride (0.20 g). After stirring for 30 minutes bromocyclopentane (0.8 mL) was added and the mixture stirred overnight. After evaporation in vacuo the residue was treated with water and extracted into ethyl acetate. Flash chromatography (3:2 cyclohexane:ethyl acetate) eluted 0.36 g of 1-cyclopentyl-4-(cyclopentylamino)-3-(4-phenoxyphenyl)-1H-pyrazolo[3,4-d]pyrimidine as colourless oil. $^1$H n.m.r. (DMSO) 8.319 (s, 1H), 7.65–7.69(m,2H), 7.40–7.48(m,2H), 7.09–7.23(m,5H), 5.926/5.955(d,1H), 5.17–5.29(quin, 1H), 4.44–4.52(m,1H), 1.86–2.12(m,8H), 1.39–1.72(m,8H).

Futher elution with ethyl acetate gave 4-amino-1-cyclopentyl-3-(4-phenoxyphenyl-1H-pyrazolo[3,4-d]pyrimidine. Recrystallisation from methyl tert-butylether gave colourless needles m.p. 134.7–135.6° C. (0.2 g, 18%). Calculated for $C_{22}H_{21}N_5O$ C 71.2H 5.7 N 18.9 Found C 71.05H 5.7 N 18.8 $^1$H n.m.r. (DMSO) 8.237 (s, 1H), 7.64–7.68(m,2H), 7.40–7.47(m,2H), 7.10–7.22(m,5H), 6.85 (very broad s, 2H), 5.17–5.30(quin,1H), 1.67–2.09(m,8H).

Example 16

3-(4-Phenoxyphenyl)-1-(tetrahydropyran-4-yl)-1H-pyrazolo[3,4-d]pyrimidin-4-ylamine (Compound 17)

3-(4-phenoxyphenyl)-1H-pyrazolo[3,4-d]pyrimidin-4-ylamine (Compound 15) (0.97 g) in 33 mL dry dimethylacetamide was stirred under nitrogen while adding 60% sodium hydride (0.22 g). After 30 minutes tetrahydropyran-4-yl tosylate (1.0 g) was added and the mixture heated at 105° C. for 4 hours then 135° C. for 3.5 hours. Evaporation in vacuo and treating with water gave pale brown solid which was collected and washed well with water then dried in air. Flash chromatography in 19:1 ethyl acetate:triethylamine afforded 0.22 g (18%) of 3-(4-phenoxyphenyl)-1-(tetrahydropyran-4-yl)-1H-pyrazolo[3,4-d]pyrimidin-4-ylamine m.p. 187–187.5° C. Calculated for $C_{22}H_{21}N_5O_2$ C 68.2H 5.4 N 18.1 Found C 68.1H 5.5 N 18.0.

Example 17 cis-(4-{4-Amino-1-[4-(4-methylpiperazino)cyclohexyl]-1H-pyrazolo[3,4-d]pyrimidin-3-yl}phenyl)(phenyl)methanone Dimaletate (Compound 18) and trans-(4-{4-amino-1-[4-(4-methylpiperazino)cyclohexyl]-1H-pyrazolo[3,4-d]pyrimidin-3-yl}phenyl)(phenyl)methanone Dimaleate (Compound 19)

Phenyl-[4-(4,4,5,5-tetramethyl-1,3,2-dioxaborolan-2-yl)phenyl]methanone (Intermediate AL)

A mixture of 4-bromobenzophenone (2.97 g, 0.011 mol), diboron pinacol ester (3.47 g, 0.014 mol), [1.1'-bis(diphenylphosphino)ferrocene]dichloropalladium (II) complex with dichloromethane (1:1) (0.28 g, 0.00034 mol) and potassium acetate (3.34 g, 0.034 mol) in N,N-dimethylformamide (65 mL) was heated at 80° C. under an atmosphere of nitrogen for 16 hours. The mixture was allowed to cool to ambient temperature and the solvent removed under reduced pressure. Dichloromethane (50 mL) was added to the residue and the resulting solid was removed by filtration through a pad of celite. The filtrate was concentrated to leave a yellow oil which was purified by flash chromatography on silica using ethyl acetate/n-heptane (5:95) as mobile phase to yield phenyl[4-(4,4,5,5-tetramethyl-1,3,2-dioxaborolan-2-yl)phenyl]methanone (2.01 g, 0.0065 mol):
$^1$H NMR (DMSO-$d_6$, 400 MHz) 7.85 (d, 2H), 7.71 (m, 5H), 7.56 (d, 2H), 1.32 (s, 12H); TLC (ethyl acetate/heptane 1:9) $R_f$ 0.36.

4-(4-amino-3-iodo-1H-pyrazolo[3,4-d]pyrimidin-1-yl)-1-cyclohexanone (Intermediate AK).

1-(1,4-dioxaspiro[4.5]dec-8-yl)-3-iodo-1H-pyrazolo[3,4-d]pyrimidin-4-ylamine (intermediate N) (13.12 g, 32.7 mmol) was suspended in acetone (240 mL) and the mixture was cooled to 0° C. Added aqueous 5 N HCl (200 mL) dropwise, keeping the temperature less than 4° C. during the addition. After the addition was complete the mixture was allowed to come to ambient temperature and stirred for 18 hours. The remaining solid was removed by filtration, and the filtrate was neutralized with saturated aqueous sodium bicarbonate. The precipitate was collected by filtration and washed with water and dried in vacuo to give 4-(4-amino-3-iodo-1H-pyrazolo[3,4-d]pyrimidin-1-yl)-1-cyclohexanone (8.20 g, 32.8 mmol): $^1$H NMR (DMSO-$d_6$, 400 MHz) 8.23 (s, 1H), 5.18 (m, 1H), 2.64–2.73 (m, 2H), 2.26–2.37 (m, 4H), 2.17–2.30 (m, 2H).

cis- and trans-3-Iodo-1-[4-(4-methylpiperazino)cyclohexyl]-1H-pyrazolo[3,4-d]pyrimidin-4-amine (Intermediates AC and AD)

A mixture of 4-(4-amino-3-iodo-1H-pyrazolo[3,4-d]pyrimidin-1-yl)-1-cyclohexanone (Intermediate AK) (1.32 g, 0.0037 mol), N-methylpiperazine (1.11 g, 0.011 mol) and acetic acid (0.66 g, 0.011 mol) in 1,2-dichloroethane (50 mL) was stirred for 10 min at 40° C. and sodium triacetoxyborohydride (1.09 g, 0.0052 mol) was added at once. The mixture was stirred at ambient temperature under an atmosphere of nitrogen for 24 hours and sodium triacetoxyborohydride (0.25 g, 0.0012 mol) was added. The mixture was stirred for another 48 hours, the solvent removed under reduced pressure and the residue partitioned between saturated aqueous sodium bicarbonate solution (80 mL) and chloroform (50 mL). The organic layer was separated and the aqueous layer further extracted with chloroform (3×50 mL). The combined organic extracts were dried over magnesium sulfate and the solvent removed under reduced pressure to yield a yellow oil. The compound was further purified by flash chromatography on silica gel using dichloromethane/triethylamine/methanol (88:11:1) as a mobile phase to yield cis-3-iodo-1-[4-(4-methylpiperazino)cyclohexyl]-1H-pyrazolo[3,4-d]pyrimidin-4-amine as a white solid (0.93 g, 0.0021 mol): $^1$H NMR (DMSO-$d_6$, 400 MHz) 8.18 (s, 1H), 4.71 (m, 1H), 2.38–1.9 (m, 13H), 2.17 (s, 3H), 1.63–1.5 (m, 4H); TLC (dichloromethane/triethylamine=9:1) $R_f$ 0.24 and trans-3-iodo-1-[4-(4-methylpiperazino)cyclohexyl]-1H-pyrazolo[3,4-d]pyrimidin-4-amine as a white solid (0.38 g, 0.00086 mol): $^1$H NMR (DMSO-$d_6$, 400 MHz) 8.18 (s, 1H), 4.55 (m, 1H), 2.38–1.9 (m, 15H), 2.15 (s, 3H), 1.42 (m, 2H); TLC (dichloromethane/triethylamine=9:1) $R_f$ 0.11.

cis-(4-{4-Amino-1-[4-(4-methylpiperazino)cyclohexyl]-1H-pyrazolo[3,4-d]pyrimidin-3-yl}phenyl)(phenyl)methanone Dimaletate A mixture of phenyl[4-(4,4,5,5-tetramethyl-1,3,2-dioxaborolan-2-yl)phenyl]-methanone (Intermediate AL) (0.241 g, 0.00078 mol), cis-3-iodo-1-[4-(4-methylpiperazino)cyclohexyl]-1H-pyrazolo[3,4-d]pyrimidin-4-amine (Intermediate AC) (0.30 g, 0.00068 mol), tetrakis(triphenyl-phosphine)palladium (0.047 g, 0.000041 mol) and sodium carbonate (0.18 g, 0.0017 mol) was heated in a mixture of ethylene glycol dimethyl ether (10 mL) and water (5 mL) at 80° C. for 16 hours under an atmosphere of nitrogen. The mixture was allowed to cool to ambient temperature and solvents were removed under the reduced pressure. The residue was partitioned between saturated aqueous sodium bicarbonate solution (50 mL) and ethyl acetate, the organic layer separated and the aqueous layer further extracted with ethyl acetate twice. The combined organic extracts were dried over magnesium sulfate. The solvents were evaporated under the reduced pressure to leave a tan solid which was purified by flash column chromatography on silica using dichloromethane/triethylamine/methanol (95:4:1) as a mobile phase to give cis-{4-[4-amino-1-(4-(4-methylpiperazino)cyclohexy]-1H-pyrazolo[3,4-d]pyrimidin-3-yl-]-phenyl}(phenyl)methanone as a white solid (0.195 g, 0.0004 mol). It was dissolved in refluxing ethanol (17 mL) and a preheated solution of maleic acid (0.137 g, 0.0018 mol) was added. The mixture was refluxed for 10 min, cooled to ambient temperature and the precipitate collected by filtration, washed with ethyl acetate and dried to give cis-(4-{4-amino-1-[4-(4-methylpiperazino)cyclohexyl]-1H-pyrazolo[3,4-d]pyrimidin-3-yl}phenyl)(phenyl)methanone dimaletate as a white solid (0.221 g, 0.0003 mol): $^1$H NMR (DMSO-$d_6$, 400 MHz) 8.28 (s, 1H), 7.90 (d, 2H), 7.83 (m, 4H), 7.73 (t, 1H), 7.61 (m, 2H), 6.15 (s, 4H), 4.88 (m, 1H), 3.1 (br, 9H), 2.71 (s, 3H), 2.28 (m, 2H), 2.07 (m, 2H), 1.74 (m, 4H); RP-HPLC (Delta Pak C18, 5 μm, 300 A, 15 cm; 5%–85% acetonitrile—0.1M ammonium acetate over 20 min, 1 mL/min) $R_t$ 12.63 min. MS: MH$^+$496.

trans-(4-{4-Amino-1-[4-(4-methylpiperazino)cyclohexyl]-1H-pyrazolo[3,4-d]pyrimidin-3-yl}phenyl)(phenyl)methanone Dimaleate A similar procedure for the trans-isomer yielded trans-(4-{4-amino-1-[4-(4-methylpiperazino)cyclohexyl]-1H-pyrazolo[3,4-d]pyrimidin-3-yl}phenyl)(phenyl)methanone dimaleate as a white solid (0.155 g, 0.0002 mol): $^1$H NMR (DMSO-$d_6$, 400 MHz) 8.27 (s, 1H), 7.90 (d, 2H), 7.83 (m, 4H), 7.73 (t, 1H), 7.61 (m, 2H), 6.17 (s, 4H), 4.77 (m, 1H), 3.1 (br, 9H), 2.68 (s, 3H), 2.05 (br, 6H), 1.61 (br, 2H) RP-HPLC (Hypersil C18, 5m, 100 A, 25 cm; 5%–85% acetonitrile—0.1M ammonium acetate over 20 min, 1 mL/min) $R_t$ 12.59 min. MS: MH$^+$496.

Example 18 cis-3-(4-Anilinophenyl)-1-[4-(4-methylpiperazino)cyclohexyl]-1H-pyrazolo[3,4-d]pyrimidin-4-amine trimaleate (Compound 20)

N-phenyl-N-[4-(4,4,5,5-tetramethyl-1,3,2-dioxaborolan-2-yl)phenyl]amine (Intermediate AE)

A mixture of N,N-(4-bromophenyl)-phenylamine (0.60 g, 0.0024 mol), diboron pinacol ester (0.74 g, 0.0029 mol), [1,1'-bis(diphenylphosphino)ferrocene]dichloro-palladium (II) complex with dichloromethane (1:1) (0.059 g, 0.000073 mol) and potassium acetate (0.71 g, 0.0073 mol) in N,N-dimethylformamide (25 mL) was heated at 80° C. under an atmosphere of nitrogen for 16 hours. The mixture was allowed to cool to ambient temperature and the solvent removed under reduced pressure. Dichloromethane (50 mL) was added to the residue and the resulting solid was removed by filtration through a pad of celite. The filtrate was concentrated to leave a yellow oil which was purified by flash chromatography on silica using ethyl acetate/n-heptane (2:98) as mobile phase to give N-phenyl—N-[4-(4,4,5,5-tetramethyl-1,3,2-dioxaborolan-2-yl)phenyl]amine (0.33 g, 0.0011 mol): $^1$H NMR (DMSO-$d_6$, 400 MHz) 8.42 (s, 1H), 7.51 (d, 2H), 7.27 (m, 2H), 7.12 (d, 2H), 7.01 (d, 2H), 6.83 (t, 1H), 1.27 (s, 12H); TLC (ethyl acetate/heptane 1:9) $R_f$ 0.54.

cis-3-(4-Anilinophenyl)-1-[4-(4-methylpiperazino)cyclohexyl]-1H-pyrazolo[3,4-d]pyrimidin-4-amine Trimaleate A mixture of N-phenyl—N-[4-(4,4,5,5-tetramethyl-1,3,2-dioxaborolan-2-yl)phenyl]amine (Intermediate AE) (0.33 g, 0.0011 mol), cis-3-iodo-1-[4-(4-methylpiperazino)cyclohexyl]-1H-pyrazolo[3,4-d]pyrimidin-4-amine (Intermediate AC) (0.43 g, 0.00097 mol), tetrakis(triphenylphosphine)palladium (0.0067 g, 0.000058 mol) and sodium carbonate (0.26 g, 0.0024 mol) was heated in a mixture of ethylene glycol dimethyl ether (16 mL) and water (8 mL) at 80° C. for 16 hours under an atmosphere of nitrogen. The mixture was allowed to cool to ambient temperature and solvents were removed under reduced pressure. The residue was partitioned between saturated aqueous sodium bicarbonate solution (50 mL) and ethyl acetate (50 mL), the organic layer separated and the aqueous layer further extracted with ethyl acetate twice. The combined organic extracts were dried over magnesium sulfate and evaporated under reduced pressure to give a tan solid which was purified by flash column chromatography on silica using dichloromethane/triethylamine/methanol (92:7:1) as a mobile phase to give 3-(4-anilinophenyl)-1-[4-(4-methylpiperazino)-cyclohexyl]-1H-pyrazolo[3,4-d]pyrimidin-4-amine as a white solid (0.400 g, 0.00074 mol). It was dissolved at reflux in ethanol (17 mL) and a preheated solution of maleic acid (0.342 g, 0.003 mol) in ethanol (8 mL) was added. The mixture was refluxed for 10 min, cooled to ambient temperature and the precipitate collected by filtration, washed with ethyl acetate and dried to give cis-3-(4-anilinophenyl)-1-[4-(4-methylpiperazino)cyclohexyl]-1H-pyrazolo[3,4-d]pyrimidin-4-amine trimaleate (0.44 g, 0.00053 mol) $^1$H NMR (DMSO-$d_6$, 400 MHz) 8.45 (s, 1H), 8.23 (s, 1H) 7.52 (d, 2H), 7.28 (m, 2H), 7.20 (m, 4H), 6.89 (t, 1H), 6.19 (s, 6H), 4.83 (m, 1H), 3.1 (br, 9H), 2.72 (s, 3H), 2.28 (m, 2H), 2.07 (m, 2H), 1.74 (m, 4H); RP-HPLC (Delta Pak C18, 5$\mu$m, 300 A, 15 cm; 5%–85% acetonitrile—0.1M ammonium acetate over 20 min, 1 mL/min) $R_t$ 13.12 min. MH$^+$483.

Example 19 cis-1-[4-(4-Methylpiperazino)cyclohexyl]-3-(6-phenoxy-3-pyridyl)-1H-pyrazolo[3,4-d]pyrimidin-4-amine dimaleate (Compound 21) and trans-1-[4-(4-Methylpiperazino)cyclohexyl]-3-(6-phenoxy-3-pyridyl)-1H-pyrazolo[3,4-d]pyrimidin-4-amine Maleate (Compound 22)

5-Bromo-2-phenoxypyridine (Intermediate AF)

A solution of phenol (1.99 g, 0.021 mol) in N,N-dimethylformamide (60 mL) was cooled to 0° C. and a 60% suspension of sodium hydride in parafine (0.89 g, 0.022 mol) was added at once. The mixture was stirred at this temperature for 10 min and 2,4-dibromopyridine was added at once. The mixture was allowed to warm up to ambient temperature while stirring under nitrogen for 72 hours and heated at 70° C. for 24 hours. The solvent was removed under reduced pressure; the residue was dissolved in ethyl acetate (150 mL) and washed with saturated aqueous sodium bicarbonate solution (100 mL), brine (80 mL), dried with magnesium sulfate and evaporated. The residue was purified by preparative RP-LC/MS (Gilson-Micromass C18, 5m, 130 A, 21 cm, 0%–100% acetonitrile-0.1M ammonium acetate over 9 min, 25 mL/min) to give 2-bromo-5-phenoxypyridine as a yellow oil (1.40 g, 0.0056 mol): $^1$H NMR (DMSO-$d_6$, 400 MHz) 8.28 (s, 1H), 8.07 (d, 1H), 7.45 (t, 2H), 7.25 (t, 1H), 7.16 (d, 2H), 7.04 (d, 1H); MS: MH$^+$250.

2-Phenoxy-5-(4,4,5,5-tetramethyl-1,3,2-dioxaborolan-2-yl)pyridine (Intermediate AG)

A mixture of 5-bromo-2-phenoxypyridine (1.40 g, 0.0056 mol), diboron pinacol ester (Intermediate AF) (1.71 g, 0.0067 mol), [1.1'-bis(diphenylphosphino)-ferrocene]dichloropalladium (II) complex with dichloromethane (1:1) (0.137 g, 0.00017 mol) and potassium acetate (1.65 g, 0.0168 mol) in N,N-dimethylformamide (50 mL) was heated at 80° C. under an atmosphere of nitrogen for 16 hours. The mixture was allowed to cool to ambient temperature and the solvent removed under reduced pressure. Dichloromethane (40 mL) was added to the residue and the resulting solid was removed by filtration through a pad of celite. The filtrate was concentrated to leave a yellow oil which was purified by flash chromatography on silica using ethyl acetate/n-heptane (1:9) as mobile phase to give 2-phenoxy-5-(4,4,5,5-tetramethyl-1,3,2-dioxaborolan-2-yl)-pyridine as a white solid (purity 93% (HPLC), 1.20 g, 0.004 mol): $^1$H NMR (DMSO-$d_6$, 400 MHz) 8.36 (s, 1H), 8.03 (d, 1H), 7.45 (t, 2H), 7.25 (t, 1H), 7.16 (d, 2H), 7.01 (d, 1H), 1.30 (s, 12H); MS: MH$^+$298.

1-(1,4-Dioxaspiro[4.5]dec-8-yl)-3-(6-phenoxy-3-pyridyl)-1H-pyrazolo[3,4-d]pyrimidin-4-amine (Intermediate AH)

A mixture of 2-phenoxy-5-(4,4,5,5-tetramethyl-1,3,2-dioxaborolan-2-yl)pyridine (Intermediate AG) (1.1 g, 0.0037 mol), 1-(1,4-dioxaspiro[4.5]dec-8-yl)-3-iodo-1H-pyrazolo[3,4-d]pyrimidin-4-amine (Intermediate N) (1.29 g, 0.0032 mol), tetrakis(triphenylphosphine)palladium (0.22 g, 0.00019 mol) and sodium carbonate (0.85 g, 0.008 mol) was heated in a mixture of ethylene glycol dimethyl ether (40 mL) and water (20 mL) at 80° C. for 16 hours under an atmosphere of nitrogen. The mixture was allowed to cool to ambient temperature and ethylene glycol dimethyl ether was removed under reduced pressure. The precipitate was collected by filtration, washed with water once, acetonitrile twice and diethyl ether twice to give 1-(1,4-dioxaspiro[4.5]dec-8-yl)-3-(6-phenoxy-3-pyridyl)-1H-pyrazolo[3,4-d]pyrimidin-4-amine as an off-white solid (1.03 g, 0.0023 mol): $^1$H NMR (DMSO-d$_6$, 400 MHz) 8.36 (s, 1H), 8.24 (s, 1H), 8.03 (d, 1H), 7.45 (t, 2H), 7.22 (m, 3H), 7.16 (d, 1H), 4.81 (m, 1H), 3.93 (s, 4H), 2.24 (m, 2H), 1.88 (m, 6H); MS: MH$^+$445.

4-[4-Amino-3-(6-phenoxy-3-pyridyl)-1H-pyrazolo[3,4-d]pyrimidin-1-yl]-1-cyclohexanone (Intermediate AI)

1-(1,4-dioxaspiro[4.5]dec-8-yl)-3-(6-phenoxy-3-pyridyl)-1H-pyrazolo[3,4-d]pyrimidin-4-amine (Intermediate AH) (1.00 g, 0.0022 mol) was triturated in acetone (20 mL) and 5N hydrochloric acid solution was added dropwise. The mixture was stirred at ambient temperature for 20 hours and neutralized with saturated sodium bicarbonate solution. The precipitate was collected by filtration, washed with water twice and dried to give 4-[4-amino-3-(6-phenoxy-3-pyridyl)-1H-pyrazolo[3,4-d]pyrimidin-1-yl]-1-cyclo-hexanone as an off-white solid (purity 94% (HPLC), 0.90 g, 0.0022 mol) ):

$^1$H NMR (DMSO-d$_6$, 400 MHz) 8.36 (s, 1H), 8.24 (s, 1H), 8.07 (d, 1H), 7.45 (t, 2H), 7.22 (m, 3H), 7.16 (d, 1H), 5.27 (m, 1H), 2.74 (m, 2H), 2.35 (m, 6H); RP-HPLC (C18, 5 μm, 300 A, 15 cm; 5%–85% acetonitrile—0.1M ammonium acetate over 20 min, 1 mL/min) R$_t$ 14.29 min.

cis-1-[4-(4-Methylpiperazino)cyclohexyl]-3-(6-phenoxy-3-pyridyl)-1H-pyrazolo[3,4-d]pyrimidin-4-amine Dimaleate and trans-1-[4-(4-methylpiperazino)cyclohexyl]-3-(6-phenoxy-3-pyridyl)-1H-pyrazolo[3,4-d]pyrimidin-4-amine Maleate A mixture of 4-[4-amino-3-(6-phenoxy-3-pyridyl)-1H-pyrazolo[3,4-d]pyrimidin-1-yl]-1-cyclo-hexanone (Intermediate AI) (0.90 g, 0.0022 mol), N-methylpiperazine (0.676 g, 0.0067 mol) and acetic acid (0.405 g, 0.0067 mol) in 1,2-dichloroethane (40 mL) was stirred for 10 min and sodium triacetoxyborohydride (0.62 g, 0.0029 mol) was added at once. The mixture was stirred at ambient temperature under an atmosphere of nitrogen for 24 hours and sodium triacetoxyborohydride (0.30 g, 0.0014 mol) was added. The mixture was stirred for another 48 hours, the solvent removed under reduced pressure and the residue partitioned between saturated aqueous sodium bicarbonate solution (80 mL) and dichloromethane (50 mL). The organic layer was separated and the aqueous layer further extracted with dichloromethane twice (50 mL). The combined organic extracts were dried over magnesium sulfate and the solvent removed under reduced pressure to yield a yellow oil. The compound was further purified by flash chromatography on silica gel using dichloromethane/triethylamine/methanol (89:10:1) as a mobile phase to yield cis-1-[4-(4-methylpiperazino)cyclohexyl]-3-(6-phenoxy-3-pyridyl)-1H-pyrazolo[3,4-d]pyrimidin-4-amine (Intermediate AJ): TLC (dichloromethane/triethylamine=9:1) R$_f$ 0.29 and trans-1-[4-(4-methylpiperazino)cyclohexyl]-3-(6-phenoxy-3-pyridyl)-1H-pyrazolo[3,4-d]pyrimidin-4-amine: TLC (dichloromethane/triethylamine=9:1) R$_f$ 0.14.

A solution of cis-1-[4-(4-methylpiperazino)cyclohexyl]-3-(6-phenoxy-3-pyridyl)-1H-pyrazolo[3,4-d]pyrimidin-4-amine (Intermediate AJ) (0.53 g, 0.0011 mol) in a mixture of ethyl acetate (25 mL) and ethanol (4 mL) was heated at reflux and a preheated solution of maleic acid (0.51 g, 0.0044 mol) in ethyl acetate (15 mL) was added. The mixture was refluxed for another 10 min, cooled to ambient temperature and the precipitate collected by filtration, washed with ethyl acetate and dried to yield cis-1-[4-(4-methylpiperazino)cyclohexyl]-3-(6-phenoxy-3-pyridyl)-1H-pyrazolo [3,4-d]pyrimidin-4-amine dimaleate as a white solid (0.61 g, 0.00084 mol): $^1$H NMR (DMSO-d$_6$, 400 MHz) 8.38 (s, 1H), 8.25 (s, 1H), 8.06 (d, 1H), 7.46 (t, 2H), 7.22 (m, 4H), 6.15 (s, 4H), 4.85 (m, 1H), 3.1 (br, 9H), 2.70 (s, 3H), 2.25 (m, 2H), 2.04 (m, 2H), 1.74 (m, 4H); RP-HPLC (Delta Pak C18, 5 μm, 300A, 15 cm; 5%–85% acetonitrile-0.1M ammonium acetate over 20 min, 1 mL/min) R$_t$ 11.93 min. MS: MH$^+$485.

A similar procedure for the trans-isomer yielded trans-1-[4-(4-methylpiperazino)cyclohexyl]-3-(6-phenoxy-3-pyridyl)-1H-pyrazolo[3,4-d]pyrimidin-4-amine maleate as a white solid (0.049 g, 0.00008 mol): $^1$H NMR (DMSO-d$_6$, 400 MHz) 8.35 (s, 1H), 8.25 (s, 1H), 8.06 (d, 1H), 7.46 (t, 2H), 7.22 (m, 4H), 6.21 (s, 4H), 4.70 (m, 1H), 3.1 (br, 9H), 2.69 (s, 3H), 2.05 (br, 6H), 1.61 (br, 2H): RP-HPLC (Hypersil C18, 5 m, 100 A, 25 cm; 5%–85% acetonitrile—0.1M ammonium acetate over 20 min, 1 mL/min) Rt 12.40 min. MS: MH$^+$485.

Example 20 trans-Benzyl-N-{4-{4-amino-1-[4-(4-methylpiperazino)cyclohexyl]-1H-pyrazolo[3,4-d]pyrimidin-3-yl}-2-methoxyphenyl}carbamate Dimaleate (Compound 23)

Benzyl N-(4-bromo-2-methoxyphenyl)carbamate (Intermediate AM)

A solution of sodium bicarbonate (3.12 g, 0.0371 mol) in water (35 mL) was added to a solution of 4-bromo-2-methoxyaniline (3.00 g, 0.0148 mol) in dioxane (50 mL). The resulting mixture was stirred for 5 minutes and benzyl chloroformate (3.8 g, 0.022 mol) was added dropwise over 3 minutes. The reaction mixture was for two hours, then dioxane was removed under reduced pressure and the water phase was extracted twice with ethyl acetate (100 mL each). The combined organic extracts were dried over magnesium sulfate and after filtration concentrated under reduced pressure. The resulting residue was purified by flash chromatography on silica using ethyl acetate/n-heptane (5:95) as mobile phase to yield benzyl N-(4-bromo-2-methoxyphenyl)carbamate (3.75 g, 0.011 mol) as a white solid: $^1$H NMR (DMSO-d$_6$, 400 MHz) 8.72 (s, 1H), 7.61 (d, 1H), 7.38 (m, 5H), 7.20 (s, 1H), 7.10 (d, 1H), 5.14 (s, 2H), 3.81 (s, 3H). TLC (ethyl acetate/heptane 1:9) R$_f$ 0.21.

Benzyl N-[2-methoxy-4-(4,4,5,5-tetramethyl-1,3,2-dioxaborolan-2-yl)phenyl]-carbamate (Intemediate AN)

A mixture of benzyl N-(4-bromo-2-methoxyphenyl)carbamate (intermediate AM) (3.0 g, 0.0089 mol), diboron pinacol ester (2.72 g, 0.0107 mol), [1.1'-bis(diphenylphosphino)ferrocene]-dichloropalladium (II) complex with dichloromethane (1:1) (0.219 g, 0.00027 mol) and potassium acetate (2.65 g, 0.027 mol) in N,N-dimethylformamide (70 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of celite. The filtrate was concentrated to leave a yellow oil which was purified by flash chromatography on silica using ethyl acetate/n-heptane (1:9) as mobile phase to yield benzyl N-[2-methoxy-4-(4,4,5,5-tetramethyl-1,3,2-dioxaborolan-2-yl)phenyl]carbamate (1.6 g, 0.0042 mol) as a white solid: $^1$H NMR (DMSO-d$_6$, 400 MHz)8.66 (s, 1H), 7.80(d, 1H), 7.38 (m, 5H), 7.25 (d, 1H), 7.17 (s, 1H), 5.15 (s, 2H), 3.81 (s, 3H), 1.29 (s, 12H); TLC (ethyl acetate/heptane 1:9) R$_f$ 0.13.

Trans-benzyl N-{4-{4-amino-1-[4-(4-methylpiperazino)cyclohexyl]-1H-pyrazolo-[3,4-d]pyrimidin-3-yl}-2-methoxyphenyl}carbamate Dimaleate A mixture of benzyl N-[2-methoxy-4-(4,4,5,5-tetramethyl-1,3,2-dioxaborolan-2-yl)-phenyl]carbamate (Intermediate AD) (1.26 g, 0.0033 mol), cis-3-iodo-1-[4-(4-methylpiperazino)-cyclohexyl]-1H-pyrazolo[3,4-d]pyrimidin-4-amine (1.21 g, 0.0027 mol), tetrakis-(triphenylphosphine)palladium (0.19 g, 0.00016 mol) and sodium carbonate (0.726 g, 0.00685 mol) was heated in a mixture of ethylene glycol dimethyl ether (40 mL) and water (20 mL) at 80° C. for 16 hours under an atmosphere of nitrogen. The mixture was allowed to cool to ambient temperature and solvents were removed under the reduced pressure. The residue was partitioned between saturated aqueous sodium bicarbonate solution (100 mL) and ethyl acetate (100 mL), the organic layer separated and the aqueous layer further extracted twice with ethyl acetate (600 mL each). The combined organic extracts were dried over magnesium sulfate. The solvents were evaporated under the reduced pressure to leave a tan solid which was purified by flash column chromatography on silica using dichloromethane/triethylamine/methanol (94:5:1) as a mobile phase to give trans-benzyl N-({4-{4-amino-1-[4-(4-methylpiperazino)-cyclohexyl]-1H-pyrazolo[3,4-d]pyrimidin-3-yl}-2-methoxyphenyl}carbamate (intermediate AO) as a white solid (1.29 g, 0.0023 mol). Trans-benzyl N-({4-{4-amino-1-[4-(4-methylpiperazino)-cyclohexyl]-1H-pyrazolo[3,4-d]pyrimidin-3-yl}-2-methoxyphenyl}carbamate (intermediate AO) (0.222 g, 0.00039 mol) was dissolved in refluxing ethanol (17 mL) and a preheated solution of maleic acid (0.135 g, 0.00117 mol) in ethanol (8 mL) was added. The mixture was refluxed for 10 min, cooled to ambient temperature and the precipitate collected by filtration, washed with ethyl acetate and dried to give trans-benzyl N-{4-{4-amino-1-[4-(4-methylpiperazino)cyclohexyl]-1H-pyrazolo[3,4-d]pyrimidin-3-yl}-2-methoxyphenyl}-carbamate dimaleate as a white solid (0.250 g, 0.00031 mol): $^1$H NMR (DMSO-$d_6$, 400 MHz) 8.76 (s, 1H), 8.23 (s, 1H), 7.89 (d, 1H), 7.40 (m, 5H), 7.20 (m, 2H), 6.15 (s, 4H), 5.18 (s, 2H), 4.69 (m, 1H), 3.87 (s, 3H), 3.1 (br, 9H), 2.67 (s, 3H), 2.05 (m, 6H), 1.57 (m, 2H); RP-HPLC (Delta Pak C18, 5 μm, 300 A, 15 cm; 5%–85% acetonitrile—0.1M ammonium acetate over 20 min, 1 mL/min) $R_t$ 13.86 min. MS: MH$^+$570.

Example 21 trans-N-{4-{4-Amino-1-[4-(4-methylpiperazino)cyclohexyl]-1H-pyrazolo[3,4-d]pyrimidin-3-yl}-2-methoxyphenyl}benzamide Dimaleate
(Compound 24)

3-(4-amino-3-methoxyphenyl)-1-[4-(4-methylpiperazino)cyclohexyl]-1H-pyrazolo[3,4-d]pyrimidin-4-amine (Intermediate AP)

To a stirred solution of trans-benzyl N-(4-4-amino-1-[4-(4-methylpiperazino)-cyclohexyl]-1H-pyrazolo[3,4-d]pyrimidin-3-yl-2-methoxyphenyl)-carbamate (Intermediate AO) (0.95 g, 0.00167 mol) in ethanol (35 mL) 10% palladium on carbon (0.33 g) was added and the resulting mixture was hydrogenated under an atmospheric pressure of hydrogen for 18 hours. The catalyst was removed by filtration through a pad of celite and the filtrate was concentrated under reduced pressure to yield 3-(4-amino-3-methoxyphenyl)-1-[4-(4-methylpiperazino)cyclohexyl]-1H-pyrazolo[3,4-d]pyrimidin-4-amine as a white solid (0.71 g, 0.00164 mol) RP-HPLC (Delta Pak C18, 5 μm, 300 A, 15 cm; 5%–85% acetonitrile—0.1M ammonium acetate over 20 min, 1 mL/min) $R_t$ 8.81 mm. MS: MH$^+$437.

trans-N-(4-4-Amino-1-[4-(4-methylpiperazino)cyclohexyl]-1H-pyrazolo[3,4-d]pyrimidin-3-yl-2-methoxyphenyl)benzamide Dimaleate To a stirred solution of 3-(4-amino-3-methoxyphenyl)-1-[4-(4-methylpiperazino)-cyclohexyl]-1H-pyrazolo[3,4-d]pyrimidin-4-amine (Intermediate AP) (0.31 g, 0.00071 mol) and benzoyl chloride (0.105 g, 0.00075 mol) in anhydrous dichloromethane (10 mL) N-ethyl-N,N-diisopropylamine (0.11 g, 0.00085 moL) was added dropwise over a 5 min. period. The stirring under nitrogen was continued for an additional 4 hours, the solvent was removed under reduced pressure and the residue was partitioned between ethyl acetate (30 mL) and water (25 mL). The organic phase was dried with magnesium sulfate and concentrated under the reduced pressure to yield a yellow oil which was purified by flash column chromatography on silica using dichloromethane/triethylamine/methanol (94:5:1) as a mobile phase to give trans-N-{4-{4-amino-1-[4-(4-methylpiperazino)cyclohexyl]-1H-pyrazolo[3,4-d]pyrimidin-3-yl}-2-methoxyphenyl}benzamide as a white solid (0.250 g, 0.00045 mol). It was dissolved in refluxing ethanol (17 mL) and a preheated solution of maleic acid (0.155 g, 0.00133 mol) in ethanol (8 mL) was added. The mixture was refluxed for 10 min, cooled to ambient temperature and the precipitate collected by filtration, washed with ethyl acetate and dried to give trans—N-{4-{4-amino-1-[4-(4-methylpiperazino)cyclohexyl]-1H-pyrazolo[3,4-d]pyrimidin-3-yl }-2-methoxyphenyl}benzamide dimaleate as a white solid (0.196 g, 0.000254 mol):
$^1$H NMR (DMSO-$d_6$, 400 MHz) 9.49 (s, 1H), 8.25 (s, 1H), 8.08 (d, 1H), 7.98 (d, 2H), 7.62 (m, 3H), 7.29 (m, 2H), 6.16 (s, 4H), 4.71 (m, 1H), 3.94 (s, 3H), 3.1 (br, 9H), 2.67 (s, 3H), 2.05 (m, 6H), 1.58 (m, 2H); RP-HPLC (Delta Pak C18, 5 μm, 300 A, 15 cm; 5%–85% acetonitrile—0.1M ammonium acetate over 20 min, 1 mL/min) $R_t$ 12.20 min. MS: MH$^+$571.

Example 22 n-{4-{4-Amino- -[4-(4-methylpiperazino)cyclohexyl]-1H-pyrazolo[3,4-d]pyrimidin-3-yl}-2-methoxyphenyl}-N'-phenylsulfamide Dimaleate
(Compound 25)

3-(4-amino-3-methoxyphenyl)-1-[4-(4-methylpiperazino)cyclohexyl]-1H-pyrazolo[3,4-d]pyrimidin-4-amine (Intermediate AP) (0.37 g, 0.00085 mol) and triethylamine (0.086 g, 0.00085 mol) were suspended in anhydrous acetonitrile (15 mL) at 0° C. and a solution of N-phenylsulfamoyl chloride (0.88 g, 0.0046 mol) in anhydrous acetonitrile (15 mL)was added dropwise over a 5 min. period. The mixture was allowed to warm up to ambient temperature under an atmosphere of nitrogen and stirred for 2.5 hours. The solvent was removed under the reduced pressure and the residue purified by preparative RP-HPLC (Rainin, Hypersil C18, 8 m, 100 A, 25 cm; 5%–85% acetonitrile—0.1% ammonium acetate over 20 min, 21 ml/min) to N-{4-{4-amino-1-[4-(4-methylpiperazino)-cyclohexyl]-1H-pyrazolo[3,4-d]pyrimidin-3-yl}-2-methoxyphenyl}-N'-phenylsulfamide (0.1 g, 0.00017 mol). It was dissolved in refluxing ethyl acetate (17 mL) and a preheated solution of maleic acid (0.039 g, 0.00034 mol) in ethyl acetate (8 mL) was added. The mixture was refluxed for 10 min, cooled to ambient temperature and the precipitate collected by filtration, washed with ethyl acetate and dried to N-{4-{4-amino-1-[4-(4-methylpiperazino)cyclohexyl]-1H-pyrazolo[3,4-d]pyrimidin-3-yl}-2-methoxyphenyl}-N'-phenylsulfamide dimaleate as a white solid (0.089 g, 0.00011 mol)

¹H NMR (DMSO-d₆, 400 MHz) 10.12 (s, 1H), 9.31 (s, 1H), 8.23 (s, 1H), 7.50 (d, 1H), 7.19 (m, 6H), 6.99 (m, 1H), 6.15 (s, 4H), 4.67 (m, 1H), 3.83 (s, 3H), 3.1 (br, 9H), 2.67 (s, 3H), 2.05 (m, 6H), 1.57 (m, 2H); RP-HPLC (Delta Pak C18, 5 µm, 300 A, 15 cm; 5%–85% acetonitrile—0.1M ammonium acetate over 20 min, 1 mL/min) R$_t$ 11.83 min. MS: MH⁺592.

Example 23 cis-{4-{4-Amino-1-[4-(4-methylpiperazino)cyclohexyl]-1H-pyrazolo[3,4-d]pyrimidin-3-yl}-phenyl}(phenyl)methanone O-methyloxime Dimaleate (Compound 27) trans{4-{4-Amino-1-[4-(4-methylpiperazino)cyclohexyl]-1H-pyrazolo[3,4-d]pyrimidin-3-yl}-phenyl}(phenyl)methanone O-methyloxime Dimaleate (Compound 26)

(4-Bromophenyl)(phenyl)methanone O-methyloxime (Intermediate AQ)

A mixture of 4-bromobenzophenone (3.02 g, 0.0116 mol) and methoxyamine hydrochloride (4.83 g, 0.0578 mol) was heated in a mixture of ethanol (90 mL) and pyridine (18 mL) at reflux for 2 hours under an atmosphere of nitrogen. The solvents were removed under reduced pressure and the residue was partitioned between water (150 mL) and dichloromethane (100 mL). The water phase was further extracted twice with dichloromethane (80 mL each) and the combined organic extracts were dried over magnesium sulfate. The solvent was removed under reduced pressure and the residue was purified by flash chromatography on silica gel using ethyl acetate/n-heptane (2:98) as mobile phase to yield (4-bromophenyl)(phenyl)methanone O-methyloxime as a colorless oil (3.13 g, 0.0108 mol): ¹H NMR (DMSO-d₆, 400 MHz) 7.67 (d, 1H), 7.59 (d, 1H), 7.48 (m, 4H), 7.32 (m, 1H), 7.26 (m, 2H), 3.93 (s, 3H) TLC (ethyl acetate/heptane 1:9) R$_f$ 0.44.

Phenyl-[4-(4,4,5,5-tetramethyl-1,3,2-dioxaborolan-2-yl)phenyl]methanone O-methyloxime (Intermediate AR)

A mixture of (4-bromophenyl)(phenyl)methanone O-methyloxime (Intermediate AQ) (2.41 g, 0.0083 mol), diboron pinacol ester (2.53 g, 0.010 mol), [1.1'-bis(diphenylphosphino)ferrocene]-dichloropalladium (II) complex with dichloromethane (1:1) (0.203 g, 0.00025 mol) and potassium acetate (2.44 g, 0.025 mol) in N,N-dimethylformamide (65 mL) was heated at 80° C. under an atmosphere of nitrogen for 16 hours. The mixture was allowed to cool to ambient temperature and the solvent removed under reduced pressure. Dichloromethane (50 mL) was added to the residue and the resulting solid was removed by filtration through a pad of celite. The filtrate was concentrated to leave a yellow oil which was purified by flash chromatography on silica using ethyl acetate/n-heptane (2:98) as mobile phase to yield phenyl-[4-(4,4,5,5-tetramethyl-1,3,2-dioxaborolan-2-yl)phenyl]methanone O-methyloxime (1.9 g, 0.0056 mol): ¹H NMR (DMSO-d₆, 400 MHz) 7.76 (d, 1H), 7.67 (d, 1H), 7.41 (m, 5H), 7.26 (d, 2H), 3.88 (s, 3H)1.30 (s, 12H); TLC (ethyl acetate/heptane 1:9) R$_f$ 0.27.

cis-{4-{4-Amino-1-[4-(4-methylpiperazino)cyclohexyl]-1H-pyrazolo[3,4-d]pyrimidin-3-yl}-phenyl}(phenyl)methanone O-methyloxime Dimaleate A mixture of phenyl-[4-(4,4,5,5-tetramethyl-1,3,2-dioxaborolan-2-yl)phenyl]-methanone O-methyloxime (intermediate AQ) (0.701 g, 0.0021 mol), cis-3-iodo-1-[4-(4-methylpiperazino)-cyclohexyl]-1H-pyrazolo[3,4-d]pyrimidin-4-amine (Intermediate AC) (0.80 g, 0.0018 mol), tetrakis-(triphenylphosphine)palladium (0.125 g, 0.00011 mol) and sodium carbonate (0.48 g, 0.0045 mol) was heated in a mixture of ethylene glycol dimethyl ether (40 mL) and water (20 mL) at 80° C. for 16 hours under an atmosphere of nitrogen. The mixture was allowed to cool to ambient temperature and solvents were removed under the reduced pressure. The residue was partitioned between saturated aqueous sodium bicarbonate solution (100 mL) and ethyl acetate (100 mL), the organic layer separated and the aqueous layer further extracted with ethyl acetate twice (70 mL each). The combined organic extracts were dried over magnesium sulfate. The solvents were evaporated under reduced pressure to leave a tan solid which was purified by flash column chromatography on silica using dichloromethane/triethylamine/methanol (96:3:1) as a mobile phase to give cis-{4-{4-amino-1-[4-(4-methylpiperazino)cyclohexyl]-1H-pyrazolo[3,4-d]pyrimidin-3-yl}-phenyl}(phenyl)methanone O-methyloxime as a white solid (0.700 g, 0.00133 mol). Cis-{4-{4-amino-1-[4-(4-methylpiperazino)cyclohexyl]-1H-pyrazolo[3,4-d]pyrimidin-3-yl}-phenyl}(phenyl) methanone O-methyloxime (0.201 g, 0.00039 mol) was dissolved in refluxing ethanol (17 mL) and a preheated solution of maleic acid (0.178 g, 0.0015 mol) in ethanol (8 mL) was added. The mixture was refluxed for 10 min, cooled to ambient temperature and the precipitate collected by filtration, washed with ethyl acetate and dried to give cis-{4-{4-amino-1-[4-(4-methylpiperazino)cyclohexyl]-1H-pyrazolo[3,4-d]pyrimidin-3-yl}-phenyl}(phenyl) methanone O-methyloxime dimaleate as a white solid (0.212 g, 0.00028 mol): ¹H NMR (DMSO-d₆, 400 MHz) 8.26 (s, 1H), 7.74 (d, 1H), 7.66 (d, 1H), 7.51 (m, 6H), 7.33 (d, 1H), 6.14 (s, 4H), 4.85 (m, 1H), 3.91 (s, 3H) 3.1 (br, 9H), 2.71 (s, 3H), 2.33 (m, 2H), 2.07 (m, 2H), 1.74 (m, 4H); RP-HPLC (Delta Pak C18, 5 µm, 300 A, 15 cm; 5%–85% acetonitrile—0.1M ammonium acetate over 20 min, 1 mL/min) R$_t$ 14.25 min. MS: MH⁺525.

trans-{4-{4-Amino-1-[4-(4-methylpiperazino)cyclohexyl]-1H-pyrazolo[3,4-d]pyrimidin-3-yl}-phenyl}(phenyl) methanone O-methyloxime Dimaleate A similar procedure (c) for the trans-isomer starting with trans-3-iodo-1-[4-(4-methylpiperazino)cyclohexyl]-1H-pyrazolo[3,4-d]pyrimidin-4-amine (intermediate AD) (0.317 g, 0.00072 mol) yielded trans-{4-{4-amino-1-[4-(4-methylpiperazino)cyclohexyl]-1H-pyrazolo[3,4-d]pyrimidin-3-yl}-phenyl}(phenyl)methanone O-methyloxime dimaleate as a white solid (0.255 g, 0.000337 mol): ¹H NMR (DMSO-d₆, 400 MHz) 8.25 (s, 1H), 7.75 (d, 1H), 7.66 (d, 1H), 7.51 (m, 6H), 7.33 (d, 1H), 6.17 (s, 4H), 4.71 (m, 1H), 3.91 (s, 3H), 3.1 (br, 9H), 2.67 (s, 3H), 2.05 (br, 6H), 1.59 (br, 2H) RP-HPLC (Hypersil C18, 5m, 100 A, 25 cm; 5%–85% acetonitrile—0.1M ammonium acetate over 20 min, 1 mL/min) R$_t$ 14.10 min. MS: MH⁺525.

Example 24 trans-{4-{4-Amino-1-[4-(4-methylpiperazino)cyclohexyl]-1H-pyrazolo[3,4-d]pyrimidin-3-yl}phenyl}(phenyl)methanone Oxime Dimaleate (Compound 28)

(4-Bromophenyl)(phenyl)methanone Oxime (intermediate AS)

A mixture of 4-bromobenzophenone (10.0 g, 0.0383 mol) and hydroxylamine hydrochloride (13.3 g, 0.192 mol) was heated in a mixture of ethanol (250 mL) and pyridine (50 mL) at reflux for 2 hours under an atmosphere of nitrogen. The solvents were removed under the reduced pressure and the residue was partitioned between water (300 mL) and dichloromethane (300 mL). The water phase was further extracted with dichloromethane twice (180 mL each) and the combined organic extracts were dried over magnesium sulfate. The solvent was removed under the reduced pressure and the residue was purified by flash chromatography on silica gel using ethyl acetate/n-heptane (1:9) as mobile phase to yield (4-bromophenyl)(phenyl)methanone oxime as a white solid (9.93 g, 0.036 mol): $^1$H NMR (DMSO-$d_6$, 400 MHz) 7.66 (d, 1H), 7.57(d, 1H), 7.33 (m, 7H) TLC (ethyl acetate/heptane 1:5) $R_f$ 0.38.

Phenyl[4-(4,4,5,5-tetramethyl-1,3,2-dioxaborolan-2-yl) phenyl]methanone Oxime (Intermediate AT)

A mixture of (4-bromophenyl)(phenyl)methanone oxime (1.02 g, 0.0037 mol), diboron pinacol ester (1.13 g, 0.0044 mol), [1.1'-bis(diphenylphosphino)ferrocene]-dichloropalladium (II) complex with dichloromethane (1:1) (0.09 g, 0.00011 mol) and potassium acetate (1.09 g, 0.011 mol) in N,N-dimethylformamide (30 mL) was heated at 80° C. under an atmosphere of nitrogen for 16 hours. The mixture was allowed to cool to ambient temperature and the solvent removed under reduced pressure. Dichloromethane (50 mL) was added to the residue and the resulting solid was removed by filtration through a pad of celite. The filtrate was concentrated to leave a yellow oil which was purified by flash chromatography on silica using ethyl acetate/n-heptane (1:7) as mobile phase to yield phenyl[4-(4,4,5,5-tetramethyl-1,3,2-dioxaborolan-2-yl)phenyl]methanone oxime (0.82 g, 0.00254 mol): $^1$H NMR (DMSO-$d_6$, 400 MHz) 11.40 (s, 1H), 7.76 (d, 1H), 7.66 (d, 1H), 7.41 (m, 5H), 7.26 (d, 2H), 1.32 (s, 12H); TLC (ethyl acetate/heptane 1:5) $R_f$ 0.22.

trans-{4-{4-Amino-1-[4-(4-methylpiperazino)cyclohexyl]-1H-pyrazolo[3,4-d]pyrimidin-3-yl}phenyl}(phenyl) methanone Oxime Dimaleate A mixture of phenyl[4-(4,4,5,5-tetramethyl-1,3,2-dioxaborolan-2-yl)phenyl]-methanone oxime (0.357 g, 0.0011 mol), transs-3-iodo-1-[4-(4-methylpiperazino)-cyclohexyl]-1H-pyrazolo[3,4-d]pyrimidin-4-amine (Intermediate AD) (0.80 g, 0.00096 mol), tetrakis-(triphenylphosphine)palladium (0.067 g, 0.00006 mol) and sodium carbonate (0.26 g, 0.0024 mol) was heated in a mixture of ethylene glycol dimethyl ether (22 mL) and water (11 mL) at 80° C. for 16 hours under an atmosphere of nitrogen. The mixture was allowed to cool to ambient temperature and solvents were removed under the reduced pressure. The residue was partitioned between saturated aqueous sodium bicarbonate solution (50 mL) and ethyl acetate (50 mL), the organic layer separated and the aqueous layer further extracted with ethyl acetate twice (40 mL each). The combined organic extracts were dried over magnesium sulfate. The solvents were evaporated under the reduced pressure to leave a tan solid which was purified by flash column chromatography on silica using dichloromethane/ triethylamine/methanol (93:6:1) as a mobile phase to give) trans-{4-{4-amino-1-[4-(4-methylpiperazino)cyclohexyl]-1H-pyrazolo[3,4-d]pyrimidin-3-yl}phenyl}(phenyl) methanone oxime as a white solid (0.211 g, 0.00041 mol). It was suspended in refluxing chloroform (17 mL) and methanol (4 mL) was added at which point the mixture became transparent. A preheated solution of maleic acid (0.096 g, 0.00082 mol) in methanol (8 mL) was added and the mixture was refluxed for 10 min, cooled to ambient temperature and the solvents were removed under reduced pressure. The residue was suspended in ethyl acetate and the precipitate was collected by filtration, washed with ethyl acetate and dried to give trans-{4-{4-amino-1-[4-(4-methyl-piperazino)cyclohexyl]-1H-pyrazolo[3,4-d]pyrimidin-3-yl}phenyl}(phenyl)methanone oxime dimaleate as a white solid (0.295 g, 0.0004 mol):

$^1$H NMR (DMSO-$d_6$, 400 MHz) 8.26 (s, 1H), 7.75 (d, 1H), 7.65 (d, 1H), 7.51 (m, 6H), 7.33 (d, 1H), 6.14 (s, 4H), 4.72 (m, 1H), 3.1 (br, 9H), 2.68 (s, 3H), 2.05 (m, 6H), 1.60 (m, 2H); RP-HPLC (Delta Pak C18, 51 μm, 300 A, 15 cm; 5%–85% acetonitrile—0.1M ammonium acetate over 20 min, 1 mL/min) $R_t$ 11.82 min. MS: MH$^+$511.

Example 25 trans-1-{4-[4-Amino-3-(4-(1-phenylammonio) phenyl)-1H-pyrazolo[3,4-d]pyrimidin-1-yl]-cyclohexyl}-4-methylhexahydropyrazinediium tri [(Z)-3-carboxy-2-propenoate] (Compound 29)

A similar procedure as for compound 20 starting from the trans-3-iodo-1-[4-(4-methylpiperazino)-cyclohexyl]-1H-pyrazolo[3,4-d]pyrimidin-4-amine (Intermediate AD) (0.33 g, 0.00075 mol) gave trans-1-{4-[4-amino-3-(4-(1-phenylammonio)phenyl)-1H-pyrazolo[3,4-d]pyrimidin-1-yl]-cyclohexyl}-4-methylhexahydropyrazinediium tri[(Z)-3-carboxy-2-propenoate] (0.245 g, 0.00034 mol): $^1$H NMR (DMSO-$d_6$, 400 MHz) 8.43 (s, 1H), 8.22 (s, 1H) 7.51 (d, 2H), 7.28 (m, 2H), 7.20 (m, 4H), 6.89 (t, 1H), 6.17 (s, 6H), 4.67 (m, 1H), 3.1 (br, 9H), 2.73 (s, 3H), 2.08 (m, 6H), 1.56 (m, 2H); RP-HPLC (Delta Pak C18, 5 μm, 300 A, 15 cm; 5%–85% acetonitrile—0.1M ammonium acetate over 20 min, 1 mL/min) $R_t$ 12.63 min. MH$^+$483.

Example 26 cis-1-[4-(4-Methylpiperazino)cyclohexyl]-3-(2-phenoxy-5-pyrimidinyl)-1H-pyrazolo[3,4-d] pyrimidin-4-amine (Compound 30)

5-Bromo-2-phenoxypyrimidine (intermediate AU)

A mixture of 5-bromo-2-chloropyrimidine (5.00 g, 0.0259 mol), phenol (3.16 g, 0.0336 mol), dibenzo-18-crown-6 (0.47 g, 0.0013 mol) and ground potassium hydroxide (3.51 g, 0.0626 mol) in toluene (75 ml) was heated at reflux for 5 hours with azeotropic removal of water. The mixture was allowed to cool to ambient temperature and the solvent was removed under reduced pressure. The residue was partitioned between water and chloroform. The layers were separated and the aqueous phase was extracted with chloroform three times. The combined organic layers were dried over magnesium sulfate, filtered and evaporated. The residue was purified by flash column chromatography on silica using n-heptane/ethyl acetate (98:2) as an eluent to give 5-bromo-2-phenoxy-pyrimidine as a white solid (3.55 g, 0.0141 mol): $^1$H NMR (DMSO-$d_6$, 400 MHz) 8.80 (s, 2H), 7.45 (t, 2H), 7.27 (t, 1H), 7.22 (d 2H); TLC (n-heptane/ethyl acetate=95:5) $R_f$ 0.20.

2-Phenoxy-5-(4,4,5,5-tetramethyl-1,3,2-dioxaborolan-2-yl) pyrimidine (Intermediate AV)

A mixture of 5-bromo-2-phenoxy-pyrimidine (intermediate AU) (3.00 g, 0.0119 mol), diboron pinacol ester (3.64 g, 0.0143 mol), [1,1'-bis(diphenylphosphino) ferrocene]dichloropalladium(II) complex with dichloromethane (1:1) (0.29 g, 0.00036 mol) and potassium acetate (3.52 g, 0.0358 mol) in N,N-dimethylformamide (70 ml) was heated at 80° C. under a nitrogen atmosphere overnight. The mixture was allowed to cool to ambient temperature and then most of the solvent was removed under reduced pressure. Dichloromethane (70 ml) was added to the residue and the resulting solids were removed by filtration through a pad of celite. The filtrate was concentrated to leave dark oil. The residue was dissolved in dichloromethane (5 mL) and added to heptane (75 mL). The mixture was filtered, and the precipitate was slurried in heptane (75 mL)

for 17 hours. After filtration and drying and dried in vacuo 2-phenoxy-5-(4,4,5,5-tetramethyl-1,3,2-dioxaborolan-2-yl)-pyrimidine was obtained as a grey solid (2.95 g, 0.00989 mol): $^1$H NMR (DMSO-$d_6$, 400 MHz) 8.75 (s, 2H), 7.45 (t, 2H), 7.27 (t, 1H), 7.20 (d, 2H), 1.31 (s, 12H)

cis-1-[4-(4-Methylpiperazino)cyclohexyl]-3-(2-phenoxy-5-pyrimidinyl)-1H-pyrazolo[3,4-d]pyrimidin-4-amine. (Intermediate AW)

A mixture of cis-3-iodo-1-[4-(4-methylpiperazino) cyclohexyl]-1H-pyrazolo[3,4-d]pyrimidin-4-amine (Intermediate AC) (0.297 g, 0.000674 mol), 2-phenoxy-5-(4,4,5,5-tetramethyl-1,3,2-dioxaborolan-2-yl)pyrimidine (int AV) (0.221 g, 0.000741 mol), sodium carbonate (0.179 g, 0.001684 mol) in 1,2-dimethoxyethane (10 mL) and water (20 mL) was stirred rapidly and tetrakis(triphenylphosphine) palladium(0) (0.047 g, 0.000040 mol) added. The reaction mixture was stirred 18 hours at 80° C. The solvents were removed in vacuo and the residue was partitioned between ethyl acetate (50 mL) and saturated aqueous sodium bicarbonate (50 mL). The phases were separated and the aqueous phase was extracted with ethyl acetate (3×25 mL). The combined organic phases were dried over magnesium sulfate, and the solvent was removed in vacuo. The product was purified by flash column chromatography on silica using dichloromethane/methanol/ammonium hydroxide (95:5:0.5). The solvent was removed in vacuo to give cis-1-[4-(4-methylpiperazino)cyclohexyl]-3-(2-phenoxy-5-pyrimidinyl)-1H-pyrazolo[3,4-d]pyrimidin-4-amine as a white solid (0.185 g, 0.000381 mol): $^1$H NMR (DMSO-$d_6$, 400 MHz) 8.79 (s, 2H), 8.24 (s, 1H), 7.48 (t, 2H), 7.28 (t, 1H), 7.27 (d, 2H), 4.81 (m, 1H), 1.55–2.56 (m, 20H); TLC (dichloromethane/methanol/ammonium hydroxide= 90:10:0.5) $R_f$ 0.23.

cis-1-[4-(4-Methylpiperazino)cyclohexyl]-3-(2-phenoxy-5-pyrimidinyl)-1H-pyrazolo[3,4-d]pyrimidin-4-amine bis Maleate A solution of cis-1-[4-(4-methylpiperazino)cyclohexyl]-3-(2-phenoxy-5-pyrimidinyl)-1H-pyrazolo[3,4-d] pyrimidin-4-amine (int AW) (0.193 g, 0.00040 mol) in absolute ethanol (15 mL) was heated to reflux. A solution of maleic acid (0.184 g, 0.00159 mol) in absolute ethanol (10 mL) heated to 78° C. was added and the mixture was heated at reflux for 10 minutes. The mixture was allowed to cool to room temperature, and the white precipitate which formed was collected by filtration and washed with absolute ethanol (2×10 mL). The residual solvent was removed in vacuo to give 1-[4-(4-methylpiperazino)cyclohexyl]-3-(2-phenoxy-5-pyrimidinyl)-1H-pyrazolo[3,4-d]pyrimidin-4-amine bis maleate as a white solid (0.254 g, 0.00035 mol):

$^1$H NMR (DMSO-$d_6$, 400 MHz) 8.81 (s, 2H), 8.26 (s, 1H), 7.49 (t, 2H), 7.28 (t, 1H), 7,26 (d, 2H), 6.14 (s, 4H), 4.87 (m, 1H), 1.60–2.85 (m, 20H); RP-HPLC (Delta Pak C18, 5 μm, 300 A, 15 cm; 5%–85% acetonitrile—0.1M ammonium acetate over 20 min, 1 mL/min) $R_t$ 11.12 min.MS: MH$^+$486.

Example 27 trans-1-[4-(4-Methylpiperazino)cyclohexyl]-3-(2-phenoxy-5-pyrimidinyl)-1H-pyrazolo[3,4-d] pyrimidin-4-amine bis Maleate (Compound 31)

trans-1-[4-(4-Methylpiperazino)cyclohexyl]-3-(2-phenoxy-5-pyrimidinyl)-1H-pyrazolo[3,4-d]pyrimidin-4-amine. (Intermediate AX)

A mixture of trans 3-iodo-1-[4-(4-methylpiperazino) cyclohexyl]-1H-pyrazolo[3,4-d]pyrimidin-4-amine (Intermediate AD) (0.300 g, 0.00068 mol), 2-phenoxy-5-(4, 4,5,5-tetramethyl-1,3,2-dioxaborolan-2-yl)pyrimidine (int AV) (0.304 g, 0.00102 mol), sodium carbonate (0.180 g, 0.00170 mol) in 1,2-dimethoxyethane (10 mL) and water (20 mL) was stirred rapidly and tetrakis(triphenylphosphine) palladium(0) (0.047 g, 0.000040 mol) added. The reaction mixture was stirred 18 hours at 80° C. The solvents were removed in vacuo and the residue was partitioned between ethyl acetate (50 mL) and saturated aqueous sodium bicarbonate (50 mL). The phases were separated and the aqueous phase was extracted with ethyl acetate (3×25 mL). The combined organic phases were dried over magnesium sulfate, and the solvent was removed in vacuo. The product was purified by flash column chromatography on silica using dichloromethane/methanol/ammonium hydroxide (95:5:0.5). The solvent was removed in vacuo to give trans-1-[4-(4-methylpiperazino)cyclohexyl]-3-(2-phenoxy-5-pyrimidinyl)-1H-pyrazolo[3,4-d]pyrimidin-4-amine as a white solid (0.155 g, 0.00032 mol): $^1$H NMR (DMSO-$d_6$, 400 MHz) 8.78 (s, 2H), 8.25 (s, 1H), 7.48 (t, 2H), 7.28 (t, 1H), 7.27 (d, 2H), 4.65 (m, 1H), 1.44–2.36 (m, 20H); TLC (dichloromethane/methanol/ammonium hydroxide= 90:10:0.5) $R_f$ 0.33.

trans-1-[4-(4-Methylpiperazino)cyclohexyl]-3-(2-phenoxy-5-pyrimidinyl)-1H-pyrazolo[3,4-d]pyrimidin-4-amine bis Maleate (Compound 31)

A solution of trans-1-[4-(4-methylpiperazino) cyclohexyl]-3-(2-phenoxy-5-pyrimidinyl)-1H-pyrazolo[3, 4-d]pyrimidin-4-amine (Int AX) (0.155 g, 0.00032 mol) in absolute ethanol (15 mL) was heated to reflux. A solution of maleic acid (0.148 g, 0.000128 mol) in absolute ethanol (10 mL) heated to 78° C. was added and the mixture was heated at reflux for 10 minutes. The mixture was allowed to cool to room temperature, and the white precipitate which formed was collected by filtration and washed with absolute ethanol (2×10 mL). The residual solvent was removed in vacuo to give trans-1-[4-(4-methylpiperazino)cyclohexyl]-3-(2-phenoxy-5-pyrimidinyl)-1H-pyrazolo[3,4-d]pyrimidin-4-amine bis maleate as a white solid (0.082 g, 0.00011 mol):

$^1$H NMR (DMSO-d6, 400 MHz) 8.78 (s, 2H), 8.26 (s, 1H), 7.48 (t, 2H), 7.28 (t, 1H), 7.26 (d, 2H), 4.70 (m, 1H), 1.50–3.00 (m, 20H); RP-HPLC (Delta Pak C18, 5 μm, 300 A, 15 cm; 5%–85% acetonitrile—0.1M ammonium acetate over 20 min, 1 mL/min) $R_t$ 10.83 min.MS: MH$^+$486.

Example 28 cis-1-[4-(4-Methylpiperazino)cyclohexyl]-3-[4-(2-pyrimidinyloxy)phenyl]-1H-pyrazolo[3,4-d] pyrimidin-4-amine (Compound 32)

2-Phenoxypyrimidine. (Intermediate AY)

A mixture of 5-chloropyrimidine (5.00 g, 0.0437 mol), phenol (5.38 g, 57.2 mmol), dibenzo-18-crown-6 (0.84 g, 0.0023 mol) and ground potassium hydroxide (5.92 g, 0.1055 mol) in toluene (75 ml) was heated at reflux for 3 hours with azeotropic removal of water. The mixture was allowed to cool to ambient temperature and the solvent was removed under reduced pressure. The residue was partitioned between water and chloroform. The layers were separated and the aqueous phase was extracted with chloroform three times. The combined organic layers were dried over magnesium sulfate, filtered and evaporated to give 2-phenoxypyrimidine as a white powder (95% pure, 4.56 g, 0.0265 mol): $^1$H NMR (CDCl$_3$, 400 MHz) 8.57 (d, 2H), 7.43 (t, 2H), 7.26 (t, 1H), 7.20 (d 2H); TLC (n-heptane/ethyl acetate=1:1) $R_f$ 0.42.

2-(4-Iodophenoxy)pyrimidine (Intermediate AZ)

A mixture of 2-phenoxypyrimidine (int AY) (4.03 g, 0.0234 mol) and N-iodosuccinimide (10.52 g, 0.0468 mol) in trifluoroacetic acid (40 mL) and trifluoroacetic anhydride (8 mL) was heated at reflux for 4 hours. The mixture was allowed to cool to ambient temperature and water (75 mL) was added. The mixture was extracted with three times with 50 mL. The combined organic layers were washed twice with saturated aqueous sodium bicarbonate (50 mL), twice with 10% aqueous sodium thiosulfate (50 mL) and brine (50 mL). The organic layer was dried over magnesium sulfate, filtered and the solvent was removed in vacuo. The crude solid was purified by flash column chromatography on silica gel using n-heptane/ethyl acetate (3:1) as an eluent to give 2-(4-iodophenoxy)pyrimidine as a light yellow solid (3.49 g, 0.0117 mol): $^1$H NMR (CDCl$_3$, 400 MHz) 8.57 (d, 2H), 7.73 (d, 2H), 7.07 (t, 1H), 6.98 (d 2H); TLC (n-heptane/ethyl acetate=1:1) R$_f$ 0.45.

2-[4-(4,4,5,5-Tetramethyl-1,3,2-dioxaborolan-2-yl) phenoxy]pyrimidine (Intermediate BA)

A mixture of 2-(4-iodophenoxy)pyrimidine (int AZ) (3.50 g, 0.0118 mol), diboron pinacol ester (3.58 g, 0.0141 mol), [1,1'-bis(diphenylphosphino)ferrocene]dichloropalladium (II) complex with dichloromethane (1:1) (0.29 g, 0.00035 mol) and potassium acetate (3.46 g, 0.00346 mol) in N,N-dimethylformamide (70 ml) was heated at 80° C. under a nitrogen atmosphere overnight. The mixture was allowed to cool to ambient temperature and then most of the solvent was removed under reduced pressure. Dichloromethane (70 ml) was added to the residue and the resulting solids were removed by filtration through a pad of celite. The filtrate was concentrated to leave a dark oil which was purified by flash column chromatography on silica using n-heptane/ethyl acetate (2:1) as an eluent to give 2-[4-(4,4,5,5-tetramethyl-1,3,2-dioxaborolan-2-yl)phenoxy]pyrimidine as a white solid (2.95 g, 0.00989 mol): $^1$H NMR (DMSO-d$_6$, 400 MHz) 8.65(d, 2H), 7.74 (d, 2H), 7.29 (t, 1H), 7.20 (d, 2H), 1.31 (s, 12H).

1-(1,4-Dioxaspiro[4,5]dec-8-yl)-3-[4-(2-pyrimidinyloxy) phenyl]-1H-pyrazolo[3,4-d]pyrimidin-4-amine (Intermediate BB)

A mixture of 1-(1,4-dioxaspiro[4,5]dec-8-yl)-3-iodo-1H-pyrazolo[3,4-d]pyrimidin-4-amine (Intermediate N) (1.50 g, 0.00374 mol), 2-[4-(4,4,5,5-tetramethyl-1,3,2-dioxaborolan-2-yl)phenoxy]-pyrimidine (intermediate BA) (1.23 g, 0.00412 mol), tetrakis(triphenylphosphine) palladium(0) (0.26 g, 0.00022 mol) and sodium carbonate (0.993 g, 0.00937 mol) in 40 mL 1,2-dimethoxyethane and 20 mL water was heated at 80° C. for eighteen hours, after which time additional 1-(1,4-dioxaspiro[4.5]dec-8-yl)-3-iodo-1H-pyrazolo[3,4-d]pyrimidin-4-amine (0.15 g, 0.00037 mol) was added. The mixture was stirred for an additional hour and then allowed to cool to ambient temperature. The precipitate was filtered and washed with 1,2-dimethoxyethane and dried in vacuo, to give 1-(1,4-dioxaspiro[4.5]dec-8-yl)-3-[4-(2-pyrimidinyloxy)phenyl]-1H-pyrazolo[3,4-d]pyrimidin-4-amine as a white solid (1.26 g, 0.00283 mol): $^1$H NMR (DMSO-d$_6$, 400 MHz) 8.68 (d, 2H), 8.254 (s, 1H), 7.73 (d, 2H), 7.37 (d, 2H), 7.31 (t, 1H), 6.30–7.20 (bs, 2H), 4.78–4.84 (m, 1H), 3.91 (s, 4H), 2.22–2.30 (m, 2H), 1.73–1.92 (m, 6H).

4-{4-Amino-3-[4-(2-pyrimidinyloxy)phenyl]-1H-pyrazolo[3,4-d]pyrimidin-1-yl}-cyclohexanone (Intermediate BC)

A slurry of 1-(1,4-dioxaspiro[4.5]dec-8-yl)-3-[4-(2-pyrimidinyloxy)phenyl]-1H-pyrazolo[3,4-d]pyrimidin-4-amine (int BB) (1.22 g, 0.00274 mol) in acetone was cooled to 0° C. and 5 N aqueous hydrochloric acid (15 mL) was added dropwise keeping the temperature less than 5° C. After the addition was complete, the mixture was stirred at ambient temperature for three hours. The solution was filtered through celite and neutralized with a saturated aqueous solution of sodium bicarbonate. The precipitate which formed was filtered, washing with water and dried in vacuo overnight to give 4{-4-amino-3-[4-(2-pyrimidinyloxy)phenyl]-1H-pyrazolo[3,4-d]pyrimidin-1-yl}-cyclohexanone as a white solid (0.937 g, 0.00243 mol): $^1$H NMR (DMSO-d$_6$, 400 MHz) 8.68 (d, 2H), 8.29 (s, 1H), 7.56 (d, 2H), 7.37 (d, 2H), 7.31 (t, 1H), 6.30–7.20 (bs, 2H), 5.25–5.30 (m, 1H), 2.67–2.75 (m, 2H), 2.24–2.43 (m, 6H).

cis-1-[4-(4-Methylpiperazino)cyclohexyl]-3-[4-(2-pyrimidinyloxy)phenyl]-1H-pyrazolo[3,4-d]pyrimidin-4-amine (intermediate BD)

A mixture of 4-4-amino-3-[4-(2-pyrimidinyloxy)phenyl]-1H-pyrazolo[3,4-d]-pyrimidin-1-yl-1-cyclohexanone (intermediate BC) (0.925 g, 0.0024 mol), N-methylpiperazine (0.721 g, 0.0072 mol) and acetic acid (0.432 g, 0.0072 mol) in dichloromethane (40 mL) was stirred rapidly and sodium triacetoxyborohydride (0.661 g, 0.00312 mol) was added in 2 portions at 30 minute intervals. The reaction mixturewas stirred 18 hours at room temperature. Additional sodium triacetoxyborohydride (0.300 g, 0.00142 mol) was added and the mixture was stirred for an additional four hours. The solvent was removed in vacuo and the residue was partitioned between dichloromethane (25 mL) and saturated aqueous sodium bicarbonate. The phases were separated and the aqueous phase was extracted with dichloromethane three times (25 mL). The combined organic phases were dried over magnesium sulfate, and the solvent was removed in vacuo. The cis- and trans-isomers were separated by flash column chromatography on silica using dichloromethane/triethylamine/methanol (87:10:3). The solvent was removed in vacuo from the trans 1-[4-(4-methylpiperazino)cyclohexyl]-3-[4-(2-pyrimidinyloxy) phenyl]-1H-pyrazolo[3,4-d]pyrimidin-4-amine fraction (TLC (dichloromethane/triethylamine/methanol=90:8:2) R$_f$ 0.45) and the residue was dissolved in dichloromethane and extracted twice with 1.0 M aqueous sodium carbonate. The organic phase was dried over magnesium sulfate, filtered and the solvent was removed in vacuo to give trans-1-[4-(4-methylpiperazino)cyclohexyl]-3-[4-(2-pyrimidinyloxy) phenyl]-1H-pyrazolo[3,4-d]pyrimidin-4-amine as a white solid (0.272 g, 0.00056 mol): $^1$H NMR (DMSO-d$_6$, 400 MHz) 8.68 (d, 2H), 8.25 (s, 1H), 7.73 (d, 2H), 7.39 (d, 2H), 7.31 (t, 1H), 6.30–6.20 (bs, 2H), 4.79–4.84 (m, 1H), 2.06–2.75 (m, 12H), 2.24–2.43 (m, 4H);

cis-1-[4-(4-Methylpiperazino)cyclohexyl]-3-[4-(2-pyrimidinyloxy)phenyl]-1H-pyrazolo[3,4-d]pyrimidin-4-amine tris Maleate A solution of cis-1-[4-(4-methylpiperazino)cyclohexyl]-3-[4-(2-pyrimidinyloxy)-phenyl]-1H-pyrazolo[3,4-d] pyrimidin-4-amine (intermediate BD) (0.193 g, 0.0004 mol) in absolute ethanol (15 mL) was heated to reflux. A solution of maleic acid (0.184 g, 0.00159 mol) in absolute ethanol (10 mL) was heated to 78° C. was added and the mixture was heated at reflux for 10 minutes. The mixture was allowed to cool to room temperature, and the white precipitate which formed was collected by filtration and washed with absolute ethanol (2×10 mL). The residual solvent was removed in vacuo to give cis-1-[4-(4-methylpiperazino)cyclohexyl]-3-[4-(2-pyrimidinyloxy)phenyl]-1H-pyrazolo[3,4-d] pyrimidin-4-amine tris maleate as a white solid (0.222 g, 0.00027 mol): $^1$H NMR (DMSO-d$_6$, 400 MHz) 8.68 (d, 2H), 8.26 (s, 1H), 7.72 (d, 2H), 7.39 (d, 2H), 7.32 (t, 1H), 6.17 (s, 6H), 4.85–4.87 (m, 1H), 3.85–2.85 (br, 9H), 2.71 (s, 3H), 2.23–2.43 (bs, 2H), 2.03–2.18 (bs, 2H), 1.71–2.89 (bs, 4H)RP-HPLC (Delta Pak C18, 5 μm, 300 A, 15 cm; 5%–85% acetonitrile—0.1M ammonium acetate over 20 min, 1 mL/min) R$_t$ 9.56 min. MS: MH$^+$486.

trans-1-[4-(4-Methylpiperazino)cyclohexyl]-3-[4-(2-pyrimidinyloxy)phenyl]-1H-pyrazolo[3,4-d]pyrimidin-4-amine (intermediate BE)

A similar procedure was used starting with trans-1-[4-(4-methylpiperazino)cyclohexyl]-3-[4-(2-pyrimidinyloxy) phenyl]-1H-pyrazolo[3,4-d]pyrimidin-4-amine (0.06 g, 0.000124 mol) to yield trans-1-[4-(4-methylpiperazino) cyclohexyl]-3-[4-(2-pyrimidinyloxy)-phenyl]-1H-pyrazolo [3,4-d]pyrimidin-4-amine dimaleate (Compound 33) as a white solid (0.06 g, 0.000084 mol).

$^1$H NMR (DMSO-$d_6$, 400 MHz) 8.68 (d, 2H), 8.25 (s, 1H), 7.71 (d, 2H), 7.37 (d, 2H), 7.31 (t, 1H), 6.18 (s, 4H), 4.71 (m, 1H), 3.1 (br, 9H), 2.67 (s, 3H) 2.06 (m, 6H) 1.58 (m, 2H); RP-HPLC (Delta Pak C18, 5 μm, 300 A, 15 cm; 5%–85% acetonitrile—0.1M ammonium acetate over 20 min, 1 mL/min) $R_t$ 9.45 min. MS: MH$^+$486.

Example 29

A series of 5 ml septum capped vials were charged with 3-(4-phenoxyphenyl)-1-(4-piperidylmethyl)-1H-pyrazolo [3,4-d]pyrimidin-4-ylamine (300 mg, 0.776 mmol), sodium triecetoxyborohydride (247 mg, 1.16 mmol) and the appropriate aldehyde or ketone (0.85 mmol). Dichloroethane (5 mL) and glacial acetic acid (50 uL, 0.87 mmol) was added sequentially. The vials were capped and shaken overnight on an orbital shaker. HPLC of the reaction mixture showed for some reactions there were still some starting amine left. For those reactions, more aldehydes or ketones (0.85 mmol), sodium triacetoxy borohydride (247 mg, 1.16 mmol) and glacial acetic acid (50 uL) were added and the resulting mixtures were shaken overnight again. Water (2 mL) was added, followed by excess solid sodium bicarbonate until no more gas evolved. The aqueous layer was removed by passing the mixtures through a 3M Empore extraction disk cartridge (Octadecyl C18 SD). The crude products were purified using Supelco's supelclean silica cartridges (10 g size ) with dichloromethane/methanol (95:5) as eluents to give the appropriate products.
Analytical LC/MS Conditions:
Column: Pecosphere, C18, 3 um, 33×4.6 mm. Eluent: 0% B/A to 100% B/A in 4.5 min.(B: acetonitrile, A: 50 mM ammonia acetate buffer, PH 4.5), 3.5 mL/min. The LCMS data is detailed below:

Example 30 cis-3-{4-[Amino(phenyl)methyl]phenyl}-1-[4-(4-methylpiperazino)-cyclohexyl]-1H-pyrazolo[3,4-d] pyrimidin-4-amine a) (4-Bromophenyl)(phenyl)methanamine Ammonium formate (20.1 g, 0.318 mol) was placed in a 3-neck flask equipped with temperature controller, mechanical stirrer and a condenser and heated at 150° C. 4-bromobenzophenone (7.2 g, 0.0276 mol) was added at once, the temperature was raised to 165° C. and the mixture was stirred at reflux for twnety-four hours. The reaction mixture was cooled to ambient temperature, triturated in ethyl acetate (350 mL), treated with charcoal and filtered through a Celite pad. The filtrate was concentrated, suspended in concentrated hydrochloric acid (120 mL) and heated at reflux for 8 hours. The reaction mixture was cooled to ambient temperature and the precipitate was collected by filtration. It was triturated in water (120 mL), basified with saturated solution of sodium bicarbonate in water and extracted with ethyl acetate (2×250 mL). The combined organic extracts were dried with magnesium sulfate and concentrated under reduced pressure to yield (4-bromophenyl)(phenyl) methanamine (5.25 g, 0.02 mol) as a white solid.

$^1$H NMR (DMSO-$d_6$, 400 MHz) δ 7.46 (d, 2H), 7.36 (m, 4H), 7.27 (t, 2H), 7.18 (t, 1H), 5.07 (s, 1H). RP-HPLC (Delta Pak C18, 5 μm, 300 A, 15 cm; 5%–85% acetonitrile—0.1M ammonium acetate over 20 min, 1 mL/min) $R_t$ 15.54 min.

b) tert-Butyl N-[(4-bromophenyl)(phenyl)methyl]carbamate

Di-tert-butyl-dicarbonate (5.63 g, 0.0258 mol) was dissolved in anhydrous dichloromethane (150 mL), cooled to 0° C. and the solution of (4-bromophenyl)(phenyl) methanamine (5.2 g, 0.0198 mol) in anhydrous dichloromethane (30 mL) was added dropwise. The mixture was warmed up to ambient temperature and stirred under an atmosphere of nitrogen for sixteen hours. The organic phase was washed with saturated solution of sodium bicarbonate in water (120 mL), dried with magnesium sulfate and concentrated under reduced pressure to yield a yellow oil which was purified by flash chromatography on silica using ethyl acetate/n-heptane (7:93) as mobile phase to yield tert-butyl N-[(4-bromophenyl)(phenyl)methyl]carbamate (5.9 g, 0.0163 mol) as a colorless oil.

$^1$H NMR (DMSO-$d_6$, 400 MHz) δ 8.01 (d, 1H), 7.51 (d, 2H), 7.36 (m, 7H), 5.81 (d, 1H), 1.39 (s, 9H). TLC (ethyl acetate/heptane 1:9) $R_f$ 0.24.

c) tert-Butyl N-{phenyl-[4-(4,4,5,5-tetramethyl-1,3,2-dioxaborolan-2-yl)phenyl]methyl}carbamate A mixture of tert-butyl N-[(4-bromophenyl)(phenyl) methyl]carbamate (4.5 g, 0.0123 mol), diboron pinacol ester (3.79 g, 0.0149 mol), [1.1'-bis(diphenylphosphino) ferrocene]-dichloropalladium (II) complex with dichloromethane (1:1) (0.305 g, 0.000373 mol) and potassium acetate (3.66 g, 0.0373 mol) in N,N-dimethylformamide (80 mL) was heated at 80° C. under an atmosphere of nitrogen for sixteen hours. The mixture was allowed to cool to ambient temperature and the solvent removed under reduced pressure. Dichloromethane (80 mL) was added to the residue and the resulting solid was removed by filtration through a pad of celite. The filtrate was concentrated to leave a yellow oil which was purified by flash chromatography on silica using ethyl acetate/n-heptane (1:9) as mobile phase. The resulting fractions were concentrated, the residue was triturated in n-heptane and the precipitate collected by filtration to yield tert-butyl N-{phenyl-[4-(4,4,5,5-tetramethyl-1,3,2-dioxaborolan-2-yl)phenyl] methyl}carbamate (3.0 g, 0.00733 mol) as a white solid.

$^1$H NMR (DMSO-$d_6$, 400 MHz) δ 8.01 (d, 1H), 7.61 (d, 2H), 7.33 (d, 2H), 7.28 (m, 5H), 5.81 (d, 1H), 1.39 (s, 9H), 1.27 (s, 12H). TLC (ethyl acetate/heptane 1:5) $R_f$ 0.34.

d) cis-tert-Butyl N-[(4-{4-amino-1-[4-(4-methylpiperazino) cyclohexyl]-1H-pyrazolo[3,4-d]pyrimidin-3-yl}phenyl) (phenyl)methyl]carbamate A mixture of tert-butyl N-{phenyl[4-(4,4,5,5-tetramethyl-1,3,2-dioxaborolan-2-yl)phenyl]methyl}carbamate (3.0 g,0.00733 mol), cis-3-iodo-1-[4-(4-methylpiperazino)-cyclohexyl]-1H-pyrazolo[3,4-d]pyrimidin-4-amine (2.4 g, 0.0054 mol), tetrakis-(triphenylphosphine)palladium (0.381 g, 0.00033 mol) and sodium carbonate monohydrate (1.69 g, 0.0136 mol) was heated in a mixture of ethylene glycol dimethyl ether (80 mL) and water (40 mL) at 80° C. for sixteen hours under an atmosphere of nitrogen. The mixture was allowed to cool to ambient temperature and solvents were removed under the reduced pressure. The residue was partitioned between saturated aqueous sodium bicarbonate solution (200 mL) and ethyl acetate (200 mL), the organic layer separated and the aqueous layer further extracted with ethyl acetate twice (100 mL each). The combined organic extracts were dried over magnesium sulfate. The solvents were evaporated under reduced pressure to leave a tan solid which was purified by flash column chromatography on silica using dichloromethane/triethylamine/methanol (96:3:1) as a mobile phase to give cis-tert-butyl N-[(4-{4-amino-1-[4-(4-methylpiperazino)cyclohexyl]-1H-pyrazolo[3,4-d]pyrimidin-3-yl}phenyl)(phenyl)-methyl]carbamate (2.24 g, 0.00375 mol) as a white solid.

$^1$H NMR (DMSO-d$_6$, 400 MHz) δ 8.23 (s, 1H), 8.01 (d, 1H), 7.60 (d, 2H), 7.49 (d, 2H), 7.35 (m, 4H), 7.23 (t, 1H), 5.91 (d, 4H), 4.78 (m, 1H), 2.5–2.1 (br, 9H), 2.17 (s, 3H), 1.68 (m, 2H), 1.58 (m, 2H), 1.42 (m, 4H), 1.40 (s, 9H); RP-HPLC (Delta Pak C18, 5 µm, 300 A, 15 cm; 5%–85% acetonitrile—0.1M ammonium acetate over 20 min, 1 mL/min) R$_t$ 14.45 min.

e) cis-3-{4-[Amino(phenyl)methyl]phenyl}-1-[4-(4-methylpiperazino)cyclohexyl]-1H-pyrazolo[3,4-d] pyrimidin-4-amine Cis-tert-butyl N-[(4-{4-amino-1-[4-(4-methylpiperazino) cyclohexyl]-1H-pyrazolo[3,4-d]pyrimidin-3-yl}phenyl) (phenyl)methyl]carbamate (2.05 g, 0.00344 mol) was triturated in anhydrous dichloromethane (50 mL) and the reaction mixture was cooled to 0° C. Trifluoroacetic acid (10 mL) was added dropwise and the resulting solution was warmed up to ambient temperature and stirred under an atmosphere of nitrogen for one and a half hour. The solvents were removed under reduced pressure, the residue suspended in water (50 mL) and basified with saturated aqueous sodium bicarbonate solution. It was extracted with dichloromethane (3×150 mL), the combined organic extracts were dried with magnesium sulfate and the solvent was removed under reduced pressure to yield cis-3-{4-[amino(phenyl) methyl]phenyl}-1-[4-(4-methylpiperazino) cyclohexyl]-1H-pyrazolo[3,4-d]pyrimidin-4-amine (1.60 g, 0.00322 mol) as an off-white solid.

$^1$H NMR (DMSO-d$_6$, 400 MHz) δ 8.23 (s, 1H), 7.57 (m, 4H), 7.45 (d, 2H), 7.31 (dd, 2H), 7.20 (t, 1H), 5.17 (s, 1H), 4.78 (m, 1H), 2.5–2.1 (br, 13H), 2.17 (s, 3H), 1.68 (m, 2H), 1.56 (m, 2H); RP-HPLC (Delta Pak C18, 5 µm, 300 A, 15 cm; 5%–85% acetonitrile—0.1M ammonium acetate over 20 min, 1 mL/min) R$_t$ 9.36 min.

f) cis-N1-[(4-{4-Amino-1-[4-(4-methylpiperazino) cyclohexyl]-1H-pyrazolo[3,4-d]pyrimidin-3-yl}phenyl) (phenyl)methyl]acetamide Diacetate Cis-3-{4-[amino(phenyl)methyl]phenyl}-1-[4-(4-methylpiperazino)cyclohexyl]-1H-pyrazolo[3,4-d] pyrimidin-4-amine (0.05 g, 0.0001 mol) was dissolved in anhydrous pyridine (1 mL), acetic anhydride (0.010 g, 0.0001 mol) was added and the resulting solution was stirred at ambient temperature for twenty hours. The solvent was removed under reduced pressure and the resulting residue purified by preparative HPLC (Hypersil C18, 8 µm, 25 cm; 10–60% acetonitrile—0.1M ammonium acetate over 25 min, 21 mL/min) to yield cis-N1-[(4-{4-amino-1-[4-(4-methylpiperazino)cyclohexyl]-1H-pyrazolo[3,4-d] pyrimidin-3-yl}phenyl)(phenyl)methyl]acetamide diacetate (0.015 g, 0.000021 mol) as a white solid.

$^1$H NMR (DMSO-d$_6$, 400 MHz) δ 8.84 (d, 1H), 8.23 (s, 1H), 7.62 (d, 2H), 7.46 (d, 2H), 7.35 (m, 4H), 7.28 (m, 1H), 6.21 (d, 1H), 4.78 (m, 1H), 2.5–2.1 (br, 13H), 2.17 (s, 3H), 1.95 (s, 3H), 1.90 (s, 6H), 1.68 (m, 2H), 1.56 (m, 2H); RP-HPLC (Delta Pak C18, 5 µm, 300 A, 15 cm; 5%–85% acetonitrile—0.1M ammonium acetate over 20 min, 1 mL/min) R$_t$ 11.15 min. MS: MH$^+$539.

Example 31 cis-N1-[(4-{4-Amino-1-[4-(4-methylpiperazino) cyclohexyl]-1H-pyrazolo [3,4-d]pyrimidin-3-yl}phenyl)(phenyl)methyl]benzamide Diacetate Cis-3-{4-[amino(phenyl)methyl]phenyl}-1-[4-(4-methylpiperazino) cyclohexyl]-1H-pyrazolo[3,4-d] pyrimidin-4-amine (0.05 g, 0.0001 mol) was dissolved in anhydrous pyridine (1 mL), benzoyl chloride (0.014 g, 0.0001 mol) was added and the resulting solution was stirred at ambient temperature for twenty hours. The solvent was removed under reduced pressure and the resulting residue purified by preparative HPLC (Hypersil C18, 8 µm, 25 cm; 10–60% acetonitrile—0.1M ammonium acetate over 25 min, 21 mL/min) to yield cis-N1-[(4-{4-amino-1-[4-(4-methylpiperazino)cyclohexyl]-1H-pyrazolo[3,4-d] pyrimidin-3-yl}phenyl)(phenyl)methyl]benzamide diacetate (0.017 g, 0.000024 mol) as a white solid.

$^1$H NMR (DMSO-d$_6$, 400 MHz) δ 9.32 (d, 1H), 8.23 (s, 1H), 7.96 (d, 2H), 7.62 (d, 2H), 7.58–7.29 (b, 10H), 6.51 (d, 1H), 4.78 (m, 1H), 2.5–2.1 (br, 13H), 2.17 (s, 3H), 1.90 (s, 6H), 1.68 (m, 2H), 1.56 (m, 2H); RP-HPLC (Delta Pak C 18, 5 µm, 300 A, 15 cm; 5%–85% acetonitrile—0.1M ammonium acetate over 20 min, 1 mL/min) R$_t$ 13.53 min. MS: MH$^+$601.

Example 32 cis-N-[(4-{4-Amino-1-[4-(4-methylpiperazino) cyclohexyl]-1H-pyrazolo[3,4-d]pyrimidin-3yl}phenyl)(phenyl)methyl]methanesulfonamide Cis-3-{4-[amino(phenyl)methyl]phenyl}-1-[4-(4-methylpiperazino) cyclohexyl]-1H-pyrazolo[3,4-d] pyrimidin-4-amine (0.05 g, 0.0001 mol) was dissolved in anhydrous pyridine (1 mL), methanesulfonyl chloride (0.011 g, 0.0001 mol) was added and the resulting solution was stirred at ambient temperature for twenty hours. The solvent was removed under reduced pressure and the resulting residue purified by preparative HPLC (Hypersil C18, 8 µm, 25 cm; 10–60% acetonitrile—0.1M ammonium acetate over 25 min, 21 mL/min) to yield cis-N-[(4-{4-amino-1-[4-(4-methylpiperazino)cyclohexyl]-1H-pyrazolo[3,4-d] pyrimidin-3-yl}phenyl)(phenyl)methyl] methanesulfonamide diacetate (0.021 g, 0.00003 mol) as a white solid.

$^1$H NMR (DMSO-d$_6$, 400 MHz) δ 8.39 (d, 1H), 8.23 (s, 1H), 7.65 (d, 2H), 7.57 (d, 2H), 7.47 (d, 2H), 7.37 (t, 2H), 7.27 (t, 1H), 5.72 (d, 1H), 4.78 (m, 1H), 2.70 (s, 3H), 2.5–2.1 (br, 13H), 2.17 (s, 3H), 1.90 (s, 6H), 1.68 (m, 2H), 1.56 (m, 2H); RP-HPLC (Delta Pak C18, 5 µm, 300 A, 15 cm; 5%–85% acetonitrile—0.1M ammonium acetate over 20 min, 1 mL/min) R$_t$ 11.81 min. MS: MH$^+$575.

Example 33 cis-N1-[(4-{4-Amino-1-[4-(4-methylpiperazino) cyclohexyl]-1H-pyrazolo[3,4-d]pyrimidin-3-yl}phenyl)(phenyl)methyl]-1-benzenesulfonamide Acetate Cis-3-{4-[amino(phenyl)methyl]phenyl}-1-[4-(4-methylpiperazino)cyclohexyl]-1H-pyrazolo[3,4-d] pyrimidin-4-amine (0.05 g, 0.0001 mol) was dissolved in anhydrous pyridine (1 mL), benzenesulfonyl chloride (0.018 g, 0.0001 mol) was added and the resulting solution was stirred at ambient temperature for twenty hours. The solvent was removed under reduced pressure and the resulting residue purified by preparative HPLC (Hypersil C18, 8 µm, 25 cm; 10–60% acetonitrile—0.1M ammonium acetate over 25 min, 21 mL/min) to yield cis-N1-[(4-{4-amino-1-[4-(4-methylpiperazino)cyclohexyl]-1H-pyrazolo[3,4-d] pyrimidin-3-yl}phenyl)(phenyl)methyl]-1-benzenesulfonamide acetate (0.045 g, 0.000065 mol) as a white solid.

¹H NMR (DMSO-d₆, 400 MHz) δ 8.89 (d, 1H), 8.23 (s, 1H), 7.65 (d, 2H), 7.57 –7.27 (br, 12H), 5.66 (d, 1H), 4.78 (m, 1H), 2.70 (s, 3H), 2.5–2.1 (br, 13H), 2.17 (s, 3H), 1.90 (s, 3H), 1.68 (m, 2H), 1.56 (m, 2H); RP-HPLC (Delta Pak C18, 5 μm, 300 A, 15 cm; 5%–85% acetonitrile—0.1M ammonium acetate over 20 min, 1 mL/min) R$_t$ 13.78 min. MS: MH⁺637.

Example 34 cis-N1-[(4-{4-Amino-1-[4-(4-methylpiperazino) cyclohexyl]-1H-pyrazolo[3,4-d]pyrimidin-3-yl}phenyl)(phenyl)methyl]-3-hydroxybutanamide Acetate Cis-3-{4-[amino(phenyl)methyl]phenyl}-1-[4-(4-methylpiperazino) cyclohexyl]-1H-pyrazolo[3,4-d] pyrimidin-4-amine (0.05 g, 0.0001 mol) and β-butyrolactone (0.009 g, 0.0001 mol) were heated in dioxane at reflux for three hours. The solvent was removed under reduced pressure and the resulting residue purified by preparative HPLC (Hypersil C18, 8 μm, 25 cm; 10–60% acetonitrile—0.1M ammonium acetate over 25 min, 21 mL/min) to yield cis-N1-[(4-{4-amino-1-[4-(4-methylpiperazino)cyclohexyl]-1H-pyrazolo[3,4-d] pyrimidin-3-yl}phenyl)(phenyl)methyl]-3-hydroxybutanamide acetate (0.027 g, 0.000042 mol) as a white solid.

¹H NMR (DMSO-d₆, 400 MHz) δ 8.78 (d, 1H), 8.23 (s, 1H), 7.62 (d, 2H), 7.45 (d, 2H), 7.35 (m, 4H), 7.27 (t, 1H), 6.21 (d, 1H), 4.78 (m, 1H), 4.67 (d, 1H), 4.02 (m, 1H), 2.5–2.1 (br, 15H), 2.17 (s, 3H), 1.90 (s, 3H), 1.68 (m, 2H), 1.56 (m, 2H), 1.07 (d, 3H); RP-HPLC (Delta Pak C18, 5 μm, 300 A, 15 cm; 5%–85% acetonitrile—0.1M ammonium acetate over 20 min, 1 mL/min) R$_t$ 10.97 and 11.13 min. MS: MH⁺583.

Example 35 cis-4-(4-{4-Amino-1-[4-(4-methylpiperazino) cyclohexyl]-1H-pyrazolo[3,4-d]pyrimidin-3-yl}phenoxy)benzamide a) 4-(4-Bromophenoxy)benzonitrile A mixture of 4-bromophenol (4.56 g, 0.0264 mol), 4-fluorobenzonitrile (0.0264 mol), 18-crown-6 (0.7 g, 0.00264 mol) and 40% potassium fluoride on alumina (10.8 g) in anhydrous acetonitrile (100 mL) was heated at reflux under an atmosphere of nitrogen for twelve hours. It was cooled to ambient temperature, filtered through a Celite pad and concentrated under reduced pressure. The residue was partitioned between diethyl ether (120 mL) and water (100 mL), the organic phase was further washed with saturated solution of potassium chloride in water, dried with magnesium sulfate and concentrated. The residue was purified by flash chromatography on silica using ethyl acetate/n-heptane (3:97) as mobile phase to yield 4-(4-bromophenoxy) benzonitrile (3.7 g, 0.0135 mol) as a white solid.

¹H NMR (DMSO-d₆, 400 MHz) δ 7.85 (d, 2H), 7.64 (d, 2H), 7.13 (dd, 4H), TLC (ethyl acetate/heptane 3:97) R$_f$ 0.21.

b) 4-[4-(4,4,5,5-Tetramethyl-1,3,2-dioxaborolan-2-yl) phenoxy]benzonitrile

A mixture of 4-(4-bromophenoxy)benzonitrile (4.55 g, 0.0166 mol), diboron pinacol ester (5.06 g, 0.020 mol), [1,1'-bis(diphenylphosphino)ferrocene]-dichloropalladium (II) complex with dichloromethane (1:1) (0.407 g, 0.000498 mol) and potassium acetate (4.88 g, 0.0498 mol) in N,N-dimethylformamide (90 mL) was heated at 80° C. under an atmosphere of nitrogen for sixteen hours. The mixture was allowed to cool to ambient temperature and the solvent was removed under reduced pressure. Dichloromethane (120 mL) was added to the residue and the resulting solid was removed by filtration through a pad of celite. The filtrate was concentrated to leave a yellow oil which was purified by flash chromatography on silica using ethyl acetate/n-heptane (5:95) as mobile phase. The combined fractions were concentrated under reduced pressure, the residue was triturated in n-heptane and the precipitate collected by filtration to yield 4-[4-(4,4,5,5-tetramethyl-1,3,2-dioxaborolan-2-yl) phenoxy]benzonitrile (2.75 g, 0.0086 mol) as a white solid.

¹H NMR (DMSO-d₆, 400 MHz) δ 7.85 (d, 2H), 7.64 (d, 2H), 7.13 (dd, 4H), 1.28 (s, 12H) TLC (ethyl acetate/heptane 1:5) R$_f$ 0.63.

c) cis-4-(4-{4-Amino-1-[4-(4-methylpiperazino) cyclohexyl]-1H-pyrazolo[3,4-d]pyrimidin-3-yl}phenoxy) benzonitrile A mixture of 4-[4-(4,4,5,5-tetramethyl-1,3,2-dioxaborolan-2-yl)phenoxy]benzonitrile (2.63 g, 0.00819 mol), cis-3-iodo-1-[4-(4-methylpiperazino)-cyclohexyl]-1H-pyrazolo[3,4-d]pyrimidin-4-amine (3.01 g, 0.00683 mol), tetrakis-(triphenylphosphine)palladium (0.473 g, 0.00041 mol) and sodium carbonate monohydrate (2.12 g, 0.0171 mol) was heated in a mixture of ethylene glycol dimethyl ether (80 mL) and water (40 mL) at 80° C. for sixteen hours under an atmosphere of nitrogen. The mixture was allowed to cool to ambient temperature and solvents were removed under the reduced pressure. The residue was partitioned between saturated aqueous sodium bicarbonate solution (200 mL) and ethyl acetate (200 mL), the organic layer separated and the aqueous layer further extracted with ethyl acetate twice (100 mL each). The combined organic extracts were dried over magnesium sulfate. The solvents were evaporated under reduced pressure to leave a tan solid which was purified by flash column chromatography on silica using dichloromethane/triethylamine/methanol (96:3:1) as a mobile phase to give cis-4-(4-{4-amino-1-[4-(4-methylpiperazino)cyclohexyl]-1H-pyrazolo[3,4-d] pyrimidin-3-yl}phenoxy)benzonitrile (2.45 g, 0.00483 mol) as a white solid.

¹H NMR (DMSO-d₆, 400 MHz) δ 8.23 (s, 1H), 7.87 (d, 2H), 7.71 (d, 2H), 7.30 (d, 2H), 7.25 (d, 2H), 4.78 (m, 1H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile—0.1M ammonium acetate over 20 min, 1 mL/min) R$_t$ 13.04 min.

d) cis-4-(4-{4-Amino-1-[4-(4-methylpiperazino) cyclohexyl]-1H-pyrazolo[3,4-d]pyrimidin-3-yl}phenoxy) benzamide Cis-4-(4-{4-amino-1-[4-(4-methylpiperazino) cyclohexyl]-1H-pyrazolo[3,4-d]pyrimidin-3-yl}phenoxy) benzonitrile (0.200 g, 0.000394 mol) was dissolved in dioxane (3 mL), the solution of sodium hydroxide (0.15 g, 0.00197 mol) in water (2 mL) was added followed by the addition of 30% hydrogen peroxide solution in water (5 drops). The reaction mixture was heated at reflux under an atmosphere of nitrogen for 1.5 hours, cooled to ambient temperature and neutralized with 5% solution of citric acid in water. The solvents were removed under reduced pressure and the residue purified by preparative HPLC (Hypersil C18, 8 μm, 25 cm; 10–60% acetonitrile—0.1M ammonium acetate over 25 min, 21 mL/min) to yield cis-4-(4-{4-amino-1-[4-(4-methylpiperazino)cyclohexyl]-1H-pyrazolo[3,4-d] pyrimidin-3-yl}phenoxy)benzamide (0.120 g, 0.000223 mol) as an off-white solid.

¹H NMR (DMSO-d₆, 400 MHz) δ 8.23 (s, 1H), 7.93 (m, 3H), 7.68 (d, 2H), 7.30 (s, 1H), 7.24 (d, 2H), 7.15 (d, 2H), 4.78 (m, 1H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile—0.1M ammonium acetate over 20 min, 1 mL/min) R$_t$ 10.87 min. MS: MH$^+$527.

Example 36 cis-4-(4-{4-Amino-1-[4-(4-methylpiperazino) cyclohexyl]-1H-pyrazolo[3,4-d]pyrimidin-3-yl}phenoxy)benzoic Acid Cis-4-(4-{4-amino-1-[4-(4-methylpiperazino) cyclohexyl]-1H-pyrazolo[3,4-d]pyrimidin-3-yl}phenoxy) benzonitrile (0.200 g, 0.000394 mol) was dissolved in a mxture of acetic acid (15 mL) and 6N solution of hydrochloric acid in water (15 mL) and the solution was heated at reflux for 12 hours. It was cooled to ambient temperature and concentrated under reduced pressure and the residue recrystallized from N,N-dimethylformamide to yield cis-4-(4-{4-amino-1-[4-(4-methylpiperazino)cyclohexyl]-1H-pyrazolo[3,4-d]pyrimidin-3-yl}phenoxy)benzoic acid (0.100 g, 0.00019 mol) as an off-white solid.

$^1$H NMR (DMSO-d$_6$, 400 MHz) δ 8.23 (s, 1H), 7.97 (d, 2H), 7.70 (d, 2H), 7.24 (d, 2H), 7.15 (d, 2H), 4.78 (m, 1H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile—0.1M ammonium acetate over 20 min, 1 mL/min) R$_t$ 10.95 min. MS: MH$^+$528.

Example 37 cis-N1-[4-(4-{4-Amino-1-[4-(4-methylpiperazino) cyclohexyl]-1H-pyrazolo[3,4-d]pyrimidin-3-yl}phenoxy)benzyl]acetamide Acetate a) cis-3-{4-[4-(Aminomethyl)phenoxy]phenyl}-1-[4-(4-methylpiperazino)cyclohexyl]-1H-pyrazolo[3,4-d] pyrimidin-4-amine Cis-4-(4-{4-amino-1-[4-(4-methylpiperazino) cyclohexyl]-1H-pyrazolo[3,4-d]pyrimidin-3-yl}phenoxy) benzonitrile (0.600 g, 0.00118 mol) was dissolved in a mixture of methanol (50 mL) and concentrated solution of ammonium hydroxide in water (3 mL), 50% slurry of Raney nickel in water (2 mL) was added and the resulting mixture was hydrogenated at atmospheric pressure for 18 hours. The reaction mixture was filtered through a Celite pad, concentrated under reduced pressure and the residue digested with dichloromethane (50 mL). The organic phase was dried with magnesium sulfate, concentrated under reduced pressure and the residue suspended in diethyl ether (25 mL). The precipitate was collected by filtration and dried to yield cis-3-{4-[4-(aminomethyl)phenoxy]phenyl}-1-[4-(4-methylpiperazino)cyclohexyl]-1H-pyrazolo[3,4-d] pyrimidin-4-amine (0.45 g, 0.0088 mol).

$^1$H NMR (DMSO-d$_6$, 400 MHz) δ 8.23 (s, 1H), 7.63 (d, 2H), 7.39 (d, 2H), 7.12 (d, 2H), 7.08 (d, 2H), 4.78 (m, 1H), 3.73 (s, 2H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile—0.1M ammonium acetate over 20 min, 1 mL/min) R$_t$ 9.72 min.

b) cis-N1-[4-(4-{4-Amino-1-[4-(4-methylpiperazino) cyclohexyl]-1H-pyrazolo[3,4-d]pyrimidin-3-yl}phenoxy) benzyl]acetamide Acetate Cis-3-{4-[4-(aminomethyl)phenoxy]phenyl}-1-[4-(4-methylpiperazino) cyclohexyl]-1H-pyrazolo[3,4-d] pyrimidin-4-amine (0.051 g, 0.0001 mol) was dissolved in anhydrous pyridine (1 mL), acetic anhydride (0.010 g, 0.0001 mol) was added and the resulting solution was stirred at ambient temperature for twenty hours. The solvent was removed under reduced pressure and the resulting residue purified by preparative HPLC (Hypersil C18, 8 μm, 25 cm; 10–60% acetonitrile—0.1M ammonium acetate over 25 min, 21 mL/min) to yield cis-N1-[4-(4-{4-amino-1-[4-(4-methylpiperazino)cyclohexyl]-1H-pyrazolo[3,4-d] pyrimidin-3-yl}phenoxy)benzyl]acetamide acetate (0.046 g, 0.0000749 mol) as a white solid.

$^1$H NMR (DMSO-d$_6$, 400 MHz) δ 8.38 (t, 1H), 8.23 (s, 1H), 7.63 (d, 2H), 7.31 (d, 2H), 7.12 (d, 2H), 7.08 (d, 2H), 4.78 (m, 1H), 4.25 (d, 2H), 2.5–2.1 (br, 13H), 2.17 (s, 3H), 1.91 (s, 3H), 1.87 (s, 3H), 1.68 (m, 2H), 1.58 (m, 2H), RP-HPLC (Delta Pak C18, 5 μm, 300 A, 15 cm; 5%–85% acetonitrile—0.1M ammonium acetate over 20 min, 1 mL/min) R$_t$ 11.33 min. MS: MH$^+$555.

Example 38 cis-N-[4-(4-{4-Amino-1-[4-(4-methylpiperazino) cyclohexyl]-1H-pyrazolo [3,4-d]pyrimidin-3-yl}phenoxy)benzyl]methanesulfonamide Acetate Cis-3-{4-[4-(aminomethyl)phenoxy]phenyl}-1-[4-(4-methylpiperazino)cyclohexyl]-1H-pyrazolo[3,4-d] pyrimidin-4-amine (0.051 g, 0.0001 mol) was dissolved in anhydrous pyridine (1 mL), methanesulfonyl chloride (0.011 g, 0.0001 mol) was added and the resulting solution was stirred at ambient temperature for 20 hours. The solvent was removed under reduced pressure and the resulting residue purified by preparative HPLC (Hypersil C18, 8 μm, 25 cm; 10–60% acetonitrile—0.1M ammonium acetate over 25 min, 21 mL/min) to yield cis N-[4-(4-{4-amino-1-[4-(4-methylpiperazino)cyclohexyl]-1H-pyrazolo[3,4-d] pyrimidin-3-yl}phenoxy)benzyl]methanesulfonamide acetate (0.011 g, 0.000017 mol) as a white solid.

$^1$H NMR (DMSO-d$_6$, 400 MHz) δ 8.23 (s, 1H), 7.64 (d, 2H), 7.57 (t, 1H), 7.40 (d, 2H), 7.13 (m, 4H), 4.78 (m, 1H), 4.17 (d, 2H), 2.89 (s, 3H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile—0.1M ammonium acetate over 20 min, 1 mL/min) R$_t$ 11.97 min. MS: MH$^+$591.

The protocols to prepare cis-3-{4-[3-(aminomethyl) phenoxy]phenyl}-1-[4-(4-methylpiperazino)cyclohexyl]-1H-pyrazolo[3,4-d]pyrimidin-4-amine and its derivatives are identical to the ones for cis-3-{4-[4-(aminomethyl) phenoxy]phenyl}-1-[4-(4-methylpiperazino)cyclohexyl]-1H-pyrazolo[3,4-d]pyrimidin-4-amine and its derivatives, using the appropriate starting materials.

Example 39 cis-3-(4-{4-Amino-1-[4-(4-methylpiperazino) cyclohexyl]-1H-pyrazolo[3,4-d]pyrimidin-3-yl}phenoxy)benzamide Diacetate a) 3-(4-Bromophenoxy)benzonitrile $^1$H NMR (DMSO-d$_6$, 400 MHz) δ 7.59 (m, 5H), 7.38 (m, 1H), 7.06 (d, 2H), TLC (ethyl acetate/heptane 3:97) R$_f$ 0.19.

b) 3-[4-(4,4,5,5-Tetramethyl-1,3,2-dioxaborolan-2-yl) phenoxy]benzonitrile $^1$H NMR (DMSO-d$_6$, 400 MHz) δ 7.65 (m, 5H), 7.41 (m, 1H), 7.06 (d, 2H), 1.27 (s, 12H) TLC (ethyl acetate/heptane 1:5) R$_f$ 0.56.

c) cis-3-(4-{4-Amino-1-[4-(4-methylpiperazino) cyclohexyl]-1H-pyrazolo[3,4-d]pyrimidin-3-yl}phenoxy) benzonitrile $^1$H NMR (DMSO-d$_6$, 400 MHz) δ 8.23 (s, 1H), 7.68 (d, 2H), 7.61 (m, 3H), 7.47 (m, 1H), 7.25 (d, 2H), 4.78 (m, 1H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile-0.1 M ammonium acetate over 20 min, 1 mL/min) $R_t$ 12.96 min.

d) cis-3-(4-{4-Amino-1-[4-(4-methylpiperazino) cyclohexyl]-1H-pyrazolo[3,4-d]pyrimidin-3-yl}phenoxy) benzamide Diacetate $^1$H NMR (DMSO-$d_6$, 400 MHz) δ 8.23 (s, 1H), 8.02 (s, 1H), 7.68 (m, 3H), 7.60 (s, 1H), 7.50 (t, 1H), 7.44 (s, 1H), 7.27 (m, 1H), 7.15 (d, 2H), 4.78 (m, 1H), 2.5–2.1 (br, 13H), 2.17 (s, 3H), 1.91 (s, 6H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 10.99 min. MS: MH$^+$ 527.

Example 40 cis-3-(4-{4-Amino-1-[4-(4-methylpiperazino) cyclohexyl]-1H-pyrazolo[3,4-d]pyrimidin-3-yl}phenoxy)benzoic Acid $^1$H NMR (DMSO-d6, 400 MHz) δ 8.23 (s, 1H), 7.75 (d, 1H), 7.68 (d, 2H), 7.56 (m, 2H), 7.39 (m, 1H), 7.20 (d, 2H), 4.78 (m, 1H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 11.01 min. MS: MH$^+$ 528.

Example 41 cis-N1-[3-(4-{4-Amino-1-[4-(4-methylpiperazino) cyclohexyl]-1H-pyrazolo[3,4-d]pyrimidin-3-yl}phenoxy)benzyl]acetamide Acetate a) cis-3-{4-[3-(Aminomethyl)phenoxy]phenyl}-1-[4-(4-methylpiperazino)cyclohexyl]-1H-pyrazolo[3,4-d] pyrimidin-4-amine $^1$H NMR (DMSO-$d_6$, 400 MHz) δ 8.23 (s, 1H), 7.63 (d, 2H), 7.38 (m, 1H), 7.15 (m, 4H), 6.96 (d, 1H), 4.78 (m, 1H), 3.73 (s, 2H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 9.32 min.

b) cis-N1-[3-(4-{4-Amino-1-[4-(4-methylpiperazino) cyclohexyl]-1H-pyrazolo[3,4-d]pyrimidin-3-yl}phenoxy) benzyl]acetamide Acetate $^1$H NMR (DMSO-$d_6$, 400 MHz) δ 8.38 (t, 1H), 8.23 (s, 1H), 7.65 (d, 2H), 7.36 (t, 1H), 7.15 (d, 2H), 7.07 (d, 1H), 7.00 (m, 2H), 4.78 (m, 1H), 4.25 (d, 2H), 2.5–2.1 (br, 13H), 2.17 (s, 3H), 1.91 (s, 3H), 1.87 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 11.44 min. MS: MH$^+$ 555.

Example 42 cis-N1-[3-(4-{4-Amino-1-[4-(4-methylpiperazino) cyclohexyl]-1H-pyrazolo[3,4-d]pyrimidin-3-yl}phenoxy)benzyl]benzamide $^1$H NMR (DMSO-$d_6$, 400 MHz) δ 9.07 (t, 1H), 8.23 (s, 1H), 7.86 (d, 2H), 7.63 (d, 2H), 7.48 (m, 4H), 7.10 (m, 5H), 4.78 (m, 1H), 4.49 (d, 2H), 2.5–2.1 (br, 13H), 2.17 (s, 3H), 1.91 (s, 6H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 13.58 min. MS: MH$^+$ 617.

Example 43 cis-N-[3-(4-{4-Amino-1-[4-(4-methylpiperazino) cyclohexyl]-1H-pyrazolo[3,4-d]pyrimidin-3-yl}phenoxy)benzyl]methanesulfonamide Acetate $^1$H NMR (DMSO-$d_6$, 400 MHz) δ 8.23 (s, 1H), 7.64 (d, 2H), 7.58 (t, 1H), 7.42 (t, 1H), 7.16 (m, 3H), 7.12 (s, 1H), 7.03 (d, 1H), 4.78 (m, 1H), 4.17 (d, 2H), 2.89 (s, 3H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 12.12 min. MS: MH$^+$ 591.

Example 44 cis-Benzyl N-{4-{4-amino-1-[4-(4-methylpiperazino)cyclohexyl]-1H-pyrazolo-[3,4-d] pyrimidin-3-yl}-2-methoxyphenyl}carbamate Dimaleate A mixture of benzyl N-[2-methoxy-4-(4,4,5,5-tetramethyl-1,3,2-dioxaborolan-2-yl)-phenyl]carbamate (2.00 g, 0.0052 mol), cis-3-iodo-1-[4-(4-methylpiperazino)-cyclohexyl]-1H-pyrazolo[3,4-d]pyrimidin-4-amine (1.92 g, 0.0044 mol), tetrakis-(triphenylphosphine)palladium (0.300 g, 0.00026 mol) and sodium carbonate (1.35 g, 0.0109 mol) was heated in a mixture of ethylene glycol dimethyl ether (70 mL) and water (35 mL) at 80° C. for sixteen hours under an atmosphere of nitrogen. The mixture was allowed to cool to ambient temperature and solvents were removed under reduced pressure. The residue was partitioned between saturated aqueous sodium bicarbonate solution (150 mL) and ethyl acetate (180 mL), the organic layer separated and the aqueous layer further extracted twice with ethyl acetate (250 mL each). The combined organic extracts were dried over magnesium sulfate. The solvents were evaporated under reduced pressure to leave a tan solid which was purified by flash column chromatography on silica using dichloromethane/triethylamine/methanol (96:3:1) as a mobile phase to give cis-benzyl N-{4-{4-amino-1-[4-(4-methylpiperazino)-cyclohexyl]-1H-pyrazolo[3,4-d] pyrimidin-3-yl}-2-methoxyphenyl}carbamate as a white solid (1.88 g, 0.0023 mol). Cis-benzyl N-{4-{4-amino-1-[4-(4-methylpiperazino)-cyclohexyl]-1H-pyrazolo[3,4-d] pyrimidin-3-yl}-2-methoxyphenyl}carbamate (0.206 g, 0.00036 mol) was dissolved in refluxing ethanol (17 mL) and a preheated solution of maleic acid (0.126 g, 0.00108 mol) in ethanol (8 mL) was added. The mixture was refluxed for 10 min, cooled to ambient temperature and the precipitate collected by filtration, washed with ethyl acetate and dried to give cis-benzyl N-{4-{4-amino-1-[4-(4-methylpiperazino)cyclohexyl]-1H-pyrazolo[3,4-d] pyrimidin-3-yl}-2-methoxyphenyl}-carbamate dimaleate as a white solid (0.224 g, 0.00028 mol):

$^1$H NMR (DMSO-$d_6$, 400 MHz) δ 8.76 (s, 1H), 8.23 (s, 1H), 7.89 (d, 1H), 7.40 (m, 5H), 7.20 (m, 2H), 6.15 (s, 4H), 5.18 (s, 2H), 4.85 (m, 1H), 3.87 (s, 3H), 3.1 (br, 11H), 2.67 (s, 3H), 2.05 (m, 2H), 1.57 (m, 4H); RP-HPLC (Delta Pak C18, 5 μm, 300 A, 15 cm; 5%–85% acetonitrile-0.1M ammonium acetate over 20 min, 1 mL/min) $R_t$ 13.83 min. MS: MH$^+$ 571.

Example 45 cis-N-(4-{4-Amino-1-[4-(4-methylpiperazino) cyclohexyl]-1H-pyrazolo[3,4-d]pyrimidin-3-yl}-2-methoxyphenyl)—N'-benzylurea Acetate Cis-3-(4-amino-3-methoxyphenyl)-1-[4-(4-methylpiperazino)cyclohexyl]-1H-pyrazolo[3,4-d] pyrimidin-4-amine (0.082 g, 0.000188 mol) was dissolved in anhydrous pyridine (1 mL), benzyl isocyanate (0.025 g, 0.000188 mol) was added and the resulting solution was stirred at ambient temperature for 20 hours. The solvent was removed under reduced pressure and the resulting residue purified by preparative HPLC (Hypersil C 18, 8 μm, 25 cm; 10–60% acetonitrile-0.1M ammonium acetate over 25 min, 21 mL/min) to yield cis-N-(4-{4-amino-1-[4-(4-methylpiperazino)cyclohexyl]-1H-pyrazolo[3,4-d]pyrimidin-3-yl}-2-methoxyphenyl)-N'-benzylurea acetate (0.009 g, 0.0000142 mol) as a white solid.

$^1$H NMR (DMSO-d$_6$, 400 MHz) δ 8.29 (d, 1H), 8.18 (m, 2H), 7.33 (m, 5H), 7.26 (t, 1H), 7.19 (s, 1H), 7.13 (d, 1H), 4.78 (m, 1H), 4.33 (d, 2H), 3.91 (s, 3H), 2.5–2.1 (br, 13H), 2.17 (s, 3H), 1.90 (s, 3H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 12.35 min. MS: MH$^+$ 570.

General Procedure for Reductive Alkylation of cis- or trans-3-(4-amino-3-methoxyphenyl)-1-[4-(4-methylpiperazino)cyclohexyl]-1H-pyrazolo[3,4-d]pyrimidin-4-amine Protocol A:

A mixture of the cis- or trans-3-(4-amino-3-methoxyphenyl)-1-[4-(4-methylpiperazino)cyclohexyl]-1H-pyrazolo[3,4-d]pyrimidin-4-amine (or just the cis or trans) (1 eq.), aldehyde (1 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10–60% acetonitrile-0.1M ammonium acetate over 25 min, 21 mL/min) to yield the desired products.

Protocol B:

After synthesis and purification (protocol A) the residue was digested with dichloromethane (1 mL), loaded onto Trikonex column (7 cm) and eluted with dichloromethane (5 mL). The desired band (UV-detection) was cut and the compound was extracted with the mixture of dichloromethane:methanol:triethylamine=90:5:5 (10 mL), filtered and the filtrate was concentrated under reduced pressure. The residue was suspended in diethyl ether (4 mL) and the precipitate was collected by filtration and dried.

Example 46 cis-3-[4-(Benzylamino)-3-methoxyphenyl]-1-[4-(4-methylpiperazino)cyclohexyl]-1H-pyrazolo[3,4-d]pyrimidin-4-amine Acetate Protocol A $^1$H NMR (DMSO-d$_6$, 400 MHz) δ 8.18 (s, 1H), 7.34 (m, 4H), 7.22 (t, 1H), 7.06 (s, 1H), 6.99 (d, 1H), 6.55 (d, 1H), 5.90 (t, 1H), 4.78 (m, 1H), 4.40 (d, 2H), 3.88 (s, 3H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 13.81 min. MS: MH$^+$ 527.

Example 47 cis-3-(3-Methoxy-4-[4-(trifluoromethyl)benzyl]aminophenyl)-1-[4-(4-methylpiperazino)cyclohexyl]-1H-pyrazolo[3,4-d]pyrimidin-4-amine Diacetate Protocol A $^1$H NMR (DMSO-d$_6$, 400 MHz) δ 8.18 (s, 1H), 7.69 (d, 2H), 7.59 (d, 2H), 7.06 (s, 1H), 6.99 (d, 1H), 6.49 (d, 1H), 6.14 (t, 1H), 4.78 (m, 1H), 4.50 (d, 2H), 3.88 (s, 3H), 2.5–2.1 (br, 13H), 2.17 (s, 3H), 1.91 (s, 6H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 15.50 min. MS: MH$^+$ 595.

Example 48 cis-3-{4-[(1H-4-Imidazolylmethyl)amino]-3-methoxyphenyl}-1-[4-(4-methylpiperazino)cyclohexyl]-1H-pyrazolo[3,4-d]pyrimidin-4-amine Acetate Protocol A $^1$H NMR (DMSO-d$_6$, 400 MHz) δ 11.85 (br, 1H), 8.19 (s, 1H), 7.59 (s, 1H), 7.06 (br, 3H), 6.77 (d, 1H), 5.30 (br, 1H), 4.78 (m, 1H), 4.24 (d, 2H), 3.88 (s, 3H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 8.70 min. MS: MH$^+$ 517.

Example 49 trans-3-[4-(Benzylamino)-3-methoxyphenyl]-1-[4-(4-methylpiperazino)cyclohexyl]-1H-pyrazolo[3,4-d]pyrimidin-4-amine Dimaleate Trans-3-[4-(benzylamino)-3-methoxyphenyl]-1-[4-(4-methylpiperazino)cyclohexyl]-1H-pyrazolo[3,4-d]pyrimidin-4-amine was prepared according to protocol A. Trans-3-[4-(benzylamino)-3-methoxyphenyl]-1-[4-(4-methylpiperazino)cyclohexyl]-1H-pyrazolo[3,4-d]pyrimidin-4-amine (0.190 g, 0.00036 mol) was dissolved in ethanol (20 mL) and the solution was heated at reflux. The solution of maleic acid (0.126 g, 0.00108 mol) was added at once and the reflux was continued for an additional 10 min. The reaction mixture was cooled to ambient temperature, the precipitate was collected by filtration and dried.

$^1$H NMR (DMSO-d$_6$, 400 MHz) δ 8.18 (s, 1H), 7.34 (m, 4H), 7.22 (t, 1H), 7.06 (s, 1H), 6.99 (d, 1H), 6.55 (d, 1H), 6.16 (d, 4H), 4.68 (m, 1H), 4.40 (d, 2H), 3.88 (s, 3H), 3.1 (br, 9H), 2.67 (s, 3H), 2.05 (m, 6H), 1.57 (m, 2H); RP-HPLC (Delta Pak C 18, 5 μm, 300 A, 15 cm; 5%–85% acetonitrile-0.1 M ammonium acetate over 20 min, 1 mL/min) R$_t$ 13.89 min. MS: MH$^+$ 527.

Example 50 trans-3-{4-[(2,6-Dimethoxybenzyl)amino]-3-methoxyphenyl}-1-[4-(4-methylpiperazino)cyclohexyl]-1H-pyrazolo[3,4-d]pyrimidin-4-amine Diacetate Protocol A $^1$H NMR (DMSO-d$_6$, 400 MHz) δ 8.18 (s, 1H), 7.25 (t, 1H), 7.09 (d, 1H), 7.02 (s, 1H), 6.92 (d, 1H), 6.69 (d, 2H), 4.68 (m, 1H), 4.60 (t, 1H), 4.31 (d, 2H), 3.83 (m, 9H), 3.1 (br, 9H), 2.67 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) R$_t$ 14.87 min. MS: MH$^+$ 587.

Example 51 trans-3-{4-[(2-Chloro-6-fluorobenzyl)amino]-3-methoxyphenyl}-1-[4-(4-methylpiperazino)cyclohexyl]-1H-pyrazolo[3,4-d]pyrimidin-4-amine Diacetate Protocol A $^1$H NMR (DMSO-d$_6$, 400 MHz) δ 8.18 (s, 1H), 7.39 (m, 2H), 7.26 (t, 1H), 7.10 (d, 1H), 7.02 (s, 1H), 6.86 (d, 1H), 5.21 (t, 1H), 4.68 (m, 1H), 4.31 (d, 2H), 3.83 (s, 3H), 3.1 (br, 9H), 2.67 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 15.23 min. MS:MH$^+$ 579.

Intermediate for Reductive Alkylation:

cis- and trans-3-(4-Aminophenyl)-1-[4-(4-methylpiperazino)cyclohexyl]-1H-pyrazolo[3,4-d]pyrimidin-4-amine a) tert-Butyl N-(4-Bromophenyl)carbamate Di-tert-butyl-dicarbonate (16.5 g, 0.0756 mol) was dissolved in anhydrous dichloromethane (150 mL), cooled to 0° C. and the solution of 4-bromoaniline (9.75 g, 0.0567 mol) in anhydrous dichloromethane (50 mL) was added dropwise. The mixture was warmed up to ambient temperature and stirred under an atmosphere of nitrogen for sixteen hours. The organic phase was washed with saturated solution of sodium bicarbonate in water (120 mL), dried with magnesium sulfate and concentrated under reduced pressure to yield a yellow oil which was purified by flash chromatography on silica using ethyl acetate/n-heptane (3:97) as mobile phase to yield tert-butyl N-[(4-bromophenyl)carbamate (7.1 g, 0.0257 mol) as a colorless oil.

$^1$H NMR (DMSO-d$_6$, 400 MHz) δ 9.49 (s, 1H), 7.42 (s, 4H) 1.47 (s, 9H). TLC (ethyl acetate/heptane 1:5) $R_f$ 0.74.

b) tert-Butyl N-[4-(4,4,5,5-Tetramethyl-1,3,2-dioxaborolan-2-yl)phenyl]carbamate A mixture of tert-butyl N-[(4-bromophenyl)carbamate (5.95 g, 0.0219 mol), diboron pinacol ester (6.67 g, 0.0263 mol), [1.1'-bis(diphenylphosphino)ferrocene]-dichloropalladium (II) complex with dichloromethane (1:1) (0.536 g, 0.00066 mol) and potassium acetate (6.47 g, 0.066 mol) in N,N-dimethylformamide (120 mL) was heated at 80° C. under an atmosphere of nitrogen for 16 hours. The mixture was allowed to cool to ambient temperature and the solvent removed under reduced pressure. Dichloromethane (100 mL) was added to the residue and the resulting solid was removed by filtration through a pad of Celite. The filtrate was concentrated to leave a yellow oil which was purified by flash chromatography on silica using ethyl acetate/n-heptane (7:93) as mobile phase. The resulting fractions were concentrated, the residue was triturated in n-heptane and the precipitate collected by filtration to yield tert-butyl N-[4-(4,4,5,5-tetramethyl-1,3,2-dioxaborolan-2-yl)phenyl]carbamate (6.0 g, 0.0188 mol) as a white solid.

$^1$H NMR (DMSO-d$_6$, 400 MHz) δ 9.50 (s, 1H), 7.55 (d, 2H), 7.46 (d, 2H), 1.47 (s, 9H), 1.27 (s, 12H). TLC (ethyl acetate/heptane 1:5) $R_f$ 0.56.

c) cis-tert-Butyl N-(4-{4-Amino-1-[4-(4-methylpiperazino)cyclohexyl]-1H-pyrazolo[3,4-d]pyrimidin-3-yl}phenyl)carbamate A mixture of tert-butyl N-[4-(4,4,5,5-tetramethyl-1,3,2-dioxaborolan-2-yl)phenyl]carbamate (3.71 g, 0.0116 mol), cis-3-iodo-1-[4-(4-methylpiperazino)-cyclohexyl]-1H-pyrazolo[3,4-d]pyrimidin-4-amine (4.46 g, 0.0101 mol), tetrakis-(triphenylphosphine)palladium (0.700 g, 0.00061 mol) and sodium carbonate monohydrate (3.13 g, 0.0253 mol) was heated in a mixture of ethylene glycol dimethyl ether (140 mL) and water (70 mL) at 80° C. for sixteen hours under an atmosphere of nitrogen. The mixture was allowed to cool to ambient temperature and solvents were removed under the reduced pressure. The residue was partitioned between saturated aqueous sodium bicarbonate solution (300 mL) and ethyl acetate (300 mL), the organic layer separated and the aqueous layer further extracted with ethyl acetate twice (150 mL each). The combined organic extracts were dried over magnesium sulfate. The solvents were evaporated under reduced pressure to leave a tan solid which was purified by flash column chromatography on silica using dichloromethane/triethylamine/methanol (95:4:1) as a mobile phase to give cis-tert-butyl N-(4-{4-amino-1-[4-(4-methylpiperazino)cyclohexyl]-1H-pyrazolo[3,4-d]pyrimidin-3-yl}phenyl)carbamate (4.1 g, 0.0081 mol) as a white solid.

$^1$H NMR (DMSO-d$_6$, 400 MHz) δ 9.57 (s, 1H), 8.21 (s, 1H), 7.63 (d, 2H), 7.52 (d, 2H), 4.78 (m, 1H), 2.5–2.1 (br, 9H), 2.17 (s, 3H), 1.68 (m, 2H), 1.58 (m, 2H), 1.50 (s, 9H), 1.42 (m, 4H); RP-HPLC (Delta Pak C18, 5 μm, 300 A, 15 cm; 5%–85% acetonitrile-0.1M ammonium acetate over 20 min, 1 mL/min) $R_t$ 12.41 min.

cis-3-(4-Aminophenyl)-1-[4-(4-methylpiperazino)cyclohexyl]-1H-pyrazolo[3,4-d]pyrimidin-4-amine Cis-tert-butyl N-(4-{4-amino-1-[4-(4-methylpiperazino)cyclohexyl]-1H-pyrazolo[3,4-d]pyrimidin-3-yl}phenyl)carbamate (4.0 g, 0.0079 mol) was triturated in anhydrous dichloromethane (75 mL) and the reaction mixture was cooled to 0° C. Trifluoroacetic acid (10 mL) was added dropwise and the resulting solution was warmed up to ambient temperature and stirred under an atmosphere of nitrogen for 1.5 hours. The solvents were removed under reduced pressure, the residue suspended in water (70 mL) and basified with saturated aqueous sodium bicarbonate solution. It was extracted with dichloromethane (3×150 mL), the combined organic extracts were dried with magnesium sulfate and the solvent was removed under reduced pressure to yield cis-3-(4-aminophenyl)-1-[4-(4-methylpiperazino)cyclohexyl]-1H-pyrazolo[3,4-d]pyrimidin-4-amine (3.0 g, 0.00739 mol) as an off-white solid.

$^1$H NMR (DMSO-d$_6$, 400 MHz) 8.18 (s, 1H), 7.30 (d, 2H), 6.71 (d, 2H), 5.41 (s, 2H), 4.78 (m, 1H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 8.64 min. Trans-3-(4-aminophenyl)-1-[4-(4-methylpiperazino)cyclohexyl]-1H-pyrazolo[3,4-d]pyrimidin-4-amine was prepared via a route similar to cis-3-(4-aminophenyl)-1-[4-(4-methylpiperazino)cyclohexyl]-1H-pyrazolo[3,4-d]pyrimidin-4-amine. Trans-3-(4-aminophenyl)-1-[4-(4-methylpiperazino)cyclohexyl]-1H-pyrazolo[3,4-d]pyrimidin-4-amine $^1$H NMR (DMSO-d$_6$, 400 MHz) δ 8.18 (s, 1H), 7.30 (d, 2H), 6.69 (d, 2H), 5.40 (s, 2H), 4.60 (m, 1H), 4.40 (d, 2H), 3.1 (br, 9H), 2.67 (s, 3H), 2.05 (m, 6H), 1.50 (m, 2H); RP-HPLC (Delta Pak C18, 5 μm, 300 A, 15 cm; 5%–85% acetonitrile-0.1M ammonium acetate over 20 min, 1 mL/min) $R_t$ 8.32 min.

General Procedure for Reductive Alkylation of cis- or trans-3-(4-Amino-phenyl)-1-[4-(4-methylpiperazino)cyclohexyl]-1H-pyrazolo[3,4-d]pyrimidin-4-amine Protocol C:

A mixture of the cis- or trans-3-(4-amino-phenyl)-1-[4-(4-methylpiperazino)cyclohexyl]-1H-pyrazolo[3,4-d]pyrimidin-4-amine (either intermediate . . . or . . . ) (1 eq.), aldehyde (1 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10–60% acetonitrile-0.1M ammonium acetate over 25 min, 21 mL/min) to yield the desired products.

Protocol D:

After synthesis and purification (protocol C) the residue was digested with dichloromethane (1 mL), loaded onto Trikonex column (7 cm) and eluted with dichloromethane (5 mL). The desired band (UV-detection) was cut and the compound was extracted with the mixture of dichloromethane:methanol:triethylamine=90:5:5 (10 mL), filtered and the filtrate was concentrated under reduced pressure. The residue was suspended in diethyl ether (4 mL) and the precipitate was collected by filtration and dried.

Example 52 cis-3-[4-(Benzylamino)phenyl]-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.34 (m, 6H), 7.26 (t, 1H), 6.74 (d, 1H), 6.62 (t, 1H), 4.78 (m, 1H), 4.35 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 13.10 min. MS: MH$^+$ 497.

Example 53 cis-3-{4-[(2-Methylbenzyl)amino]phenyl}-1-[4-(4-methylpiperazino)cyclo-hexyl]-1H-pyrazolo[3,4-d]pyrimidin-4-amine Diacetate Protocol C $^1$H NMR (DMSO-d$_6$, 400 MHz) δ 8.18 (s, 1H), 7.37 (m, 3H), 7.18 (m, 3H), 6.75 (d, 2H), 6.43 (t, 1H), 4.76 (m, 1H), 4.28 (d, 2H), 2.5–2.1 (br, 13H), 2.35 (s, 3H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 14.25 min. MS: MH$^+$ 511.

Example 54 cis-1-[4-(4-Methylpiperazino)cyclohexyl]-3-(4-[2-(trifluoromethyl)benzyl]aminophenyl)-1H-pyrazolo[3,4-d]pyrimidin-4-amine Diacetate Protocol C $^1$H NMR (DMSO-d$_6$, 400 MHz) δ 8.18 (s, 1H), 7.76 (d, 1H), 7.64 (d, 2H), 7.48 (t, 1H), 7.36 (d, 2H), 6.75 (t, 1H), 6.69 (d, 2H), 4.76 (m, 1H), 4.52 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 14.95 min. MS: MH$^+$ 565.

Example 55 cis-3-{4-[(2-Chlorobenzyl)amino]phenyl}-1-[4-(4-methylpiperazino)cyclohexyl]-1H-pyrazolo[3,4-d]pyrimidin-4-amine Protocol D $^1$H NMR (DMSO-d$_6$, 400 MHz) δ 8.18 (s, 1H), 7.38 (m, 6H), 6.74 (d, 2H), 6.55 (t, 1H), 4.76 (m, 1H), 4.39 (d, 2H), 2.5–2.1 (br, 13H), 2.17 (s, 3H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 14.43 min. MS: MH$^+$ 531.

Example 56 cis-3-{4-[(2-Bromobenzyl)amino]phenyl}-1-[4-(4-methylpiperazino)cyclohexyl]-1H-pyrazolo[3,4-d]pyrimidin-4-amine Protocol D $^1$H NMR (DMSO-d$_6$, 400 MHz) δ 8.18 (s, 1H), 7.68 (d, 1H), 7.38 (m, 4H), 7.20 (t, 1H), 6.70 (m, 3H), 4.76 (m, 1H), 4.39 (d, 2H), 2.5–2.1 (br, 13H), 2.17 (s, 3H), 1.65 (m, 2H), 1.58 (m, 2H); RP-HPLC (Delta Pak C 18, 5 μm, 300 A, 15 cm; 5%–85% acetonitrile-0.1M ammonium acetate over 20 min, 1 mL/min) R$_t$ 14.76 min. MS: MH$^+$ 576.

Example 57 cis-3-{4-[(2-Ethoxybenzyl)amino]phenyl}-1-[4-(4-methylpiperazino)cyclohexyl]-1H-pyrazolo[3,4-d]pyrimidin-4-amine Protocol D $^1$H NMR (DMSO-d$_6$, 400 MHz) δ 8.18 (s, 1H), 7.34 (d, 2H), 7.29 (s, 1H), 7.20 (t, 1H), 6.99 (d, 1H), 6.88 (t, 1H), 6.72 (d, 2H), 6.42 (t, 1H), 4.76 (m, 1H), 4.30 (d, 2H), 4.12 (q, 2H), 2.5–2.1 (br, 13H), 2.17 (s, 3H), 1.65 (m, 2H), 1.58 (m, 2H), 1.38 (t, 3H); RP-HPLC (Delta Pak C 18, 5 μm, 300 A, 15 cm; 5%–85% acetonitrile-0.1M ammonium acetate over 20 min, 1 mL/min) R$_t$ 14.71 min. MS: MH$^+$ 541.

Example 58 cis-3-(4-[2-(Difluoromethoxy)benzyl]aminophenyl)-1-[4-(4-methylpiperazino)cyclohexyl]-1H-pyrazolo[3,4-d]pyrimidin-4-amine Protocol D $^1$H NMR (DMSO-d$_6$, 400 MHz) δ 8.18 (s, 1H), 7.33 (m, 7H), 6.83 (d, 2H), 6.62 (t, 1H) 4.76 (m, 1H), 4.38 (d, 2H), 2.5–2.1 (br, 13H), 2.17 (s, 3H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 14.25 min. MS: MH$^+$ 563.

Example 59 cis-1-[4-(4-Methylpiperazino)cyclohexyl]-3-(4-[2-(trifluoromethoxy)benzyl]aminophenyl)-1H-pyrazolo[3,4-d]pyrimidin-4-amine Diacetate Protocol C $^1$H NMR (DMSO-d$_6$, 400 MHz) δ 8.18 (s, 1H), 7.62 (d, 1H), 7.38 (m, 4H), 6.73 (d, 2H), 6.64 (t, 1H), 4.76 (m, 1H), 4.40 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 15.33 min. MS: MH$^+$ 581.

Example 60 cis-2-[2-(4-{4-Amino-1-[4-(4-methylpiperazino)cyclohexyl]-1H-pyrazolo[3,4-d]pyrimidin-3-yl}anilino)methyl]phenoxy-1-ethanol Diacetate Protocol C $^1$H NMR (DMSO-d$_6$, 400 MHz) δ 8.18 (s, 1H), 7.32 (m, 3H), 7.21 (t, 1H), 7.00 (d, 1H), 6.90 (t, 1H), 6.74 (d, 2H), 6.42 (t, 1H), 4.76 (m, 1H), 4.33 (d, 2H), 4.07 (t, 2H), 3.78 (t, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 12.08 min. MS: MH$^+$ 557.

Example 61 cis-2-[(4-{4-Amino-1-[4-(4-methylpiperazino)cyclohexyl]-1H-pyrazolo[3,4-d]pyrimidin-3-yl}anilino)methyl]benzonitrile Diacetate Protocol C $^1$H NMR (DMSO-d$_6$, 400 MHz) δ 8.18 (s, 1H), 7.86 (d, 1H), 7.69 (t, 1H), 7.59 (d, 1H), 7.47 (t, 1H), 7.37 (d, 2H), 6.73 (m, 3H), 4.76 (m, 1H), 4.53 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 12.72 min. MS: MH$^+$ 522.

Example 62 cis-3-{4-[(2,6-Difluorobenzyl)amino]phenyl}-1-[4-(4-methylpiperazino)cyclohexyl]-1H-pyrazolo[3,4-d]pyrimidin-4-amine Protocol C $^1$H NMR (DMSO-d$_6$, 400 MHz) δ 8.18 (s, 1H), 7.40 (m, 3H), 7.17 (dd, 2H), 6.82 (d, 2H), 6.38 (t, 1H), 4.78 (m, 1H), 4.33 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 13.59 min. MS: MH$^+$ 533.

Example 63 cis-3–4-[(2-Chloro-6-fluorobenzyl)amino]phenyl-1-[4-(4-methylpiperazino)cyclohexyl]-1H-pyrazolo[3,4-d]pyrimidin-4-amine Acetate Protocol C $^1$H NMR (DMSO-d$_6$, 400 MHz) δ 8.18 (s, 1H), 7.41 (m, 4H), 7.30 (t, 1H), 6.84 (d, 2H), 6.29 (t, 1H), 4.76 (m, 1H), 4.38 (d, 2H), 2.5–2.1 (br, 13H), 2.17 (s, 3H), 1.91 (s, 3H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 14.36 min. MS: MH$^+$ 549.

Example 64 cis-3-(4-[2-Fluoro-6-(trifluoromethyl)benzyl]aminophenyl)-1-[4-(4-methylpiperazino)cyclohexyl]-1H-pyrazolo[3,4-d]pyrimidin-4-amine Protocol D $^1$H NMR (DMSO-d$_6$, 400 MHz) δ 8.18 (s, 1H), 7.67 (m, 3H), 7.39 (m, 2H), 6.84 (d, 2H), 6.18 (t, 1H), 4.76 (m, 1H), 4.38 (d, 2H), 2.5–2.1 (br, 13H), 2.17 (s, 3H), 1.65 (m, 2H), 1.58 (m, 2H); RP-HPLC (Delta Pak C 18, 5μm, 300 A, 15 cm; 5%–85% acetonitrile-0.1M ammonium acetate over 20 min, 1 mL/min) $R_t$ 15.02 min. MS: MH$^+$ 583.

Example 65

Cis-3-{4-[(2-Fluoro-6-methoxybenzyl)amino]phenyl}-1-[4-(4-methylpiperazino)cyclohexyl]-1H-pyrazolo [3,4-d]pyrimidin-4-amine Diacetate a) 2-Fluoro-6-methoxybenzaldehyde The solution of 3-fluoroanisole (3.36 g, 0.0266 mol) in anhydrous tetrahydrofuran was cooled to −78° C. and 1.4M solution of n-butyllithium in hexanes (19 mL, 0.0266 mol) was added dropwise keeping the reaction mixture temperature below −75° C. Upon the completion of the addition, N,N,N',N',N"-pentamethyldiethylenetriamine was added dropwise and the stirring at −78° C. was continued under an atmosphere of nitrogen for an additional two hours. N,N-dimethylformamide (3.89 g, 0.0532 mol) was added dropwise and the reaction mixture was slowly warmed up while stirring for half an hour. It was quenched by dropwise addition of 1N hydrochloric acid and the layers were separated. The aqueous phase was further extracted with ethyl acetate (2×150 mL) and the combined organic extracts were dried with magnesium sulfate. The organic phase was concentrated under reduced pressure and the residue was triturated in n-heptane. The precipitate was collected by filtration and dried to yield 2-fluoro-6-methoxybenzaldehyde (2.95 g, 0.0191 mol) as an off-white solid.

$^1$H NMR (DMSO-d$_6$, 400 MHz) δ 10.31 (s, 1H), 7.66 (dd, 1H), 7.06 (d, 1H), 6.89 (dd, 1H), 3.92 (s, 3H). TLC (ethyl acetate/heptane 5:95) $R_f$ 0.24.

b) cis-3-{4-[(2-Fluoro-6-methoxybenzyl)amino]phenyl}-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.35 (m, 3H), 6.90 (m, 4H), 6.08 (t, 1H), 4.76 (m, 1H), 4.25 (d, 2H), 3.87 (s, 3H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 14.84 min. MS: MH$^+$ 550.

Example 66 cis-3–4-[(2,6-Dichlorobenzyl)amino]phenyl-1-[4-(4-methylpiperazino)cyclohexyl]-1H-pyrazolo[3,4-d]pyrimidin-4-amine Protocol D $^1$H NMR (DMSO-d$_6$, 400 MHz) δ 8.18 (s, 1H), 7.54 (d, 2H), 7.39 (m, 3H), 6.84 (d, 2H), 6.18 (t, 1H), 4.76 (m, 1H), 4.44 (d, 2H), 2.5–2.1 (br, 13H), 2.17 (s, 3H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 15.20 min. MS: MH$^+$ 566.

Example 67 cis-3-{4-[(2,6-Dimethoxybenzyl)amino]phenyl}-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.34 (d, 2H), 7.26 (t, 1H), 6.82 (d, 2H), 6.69 (d, 2H), 5.75 (t, 1H), 4.78 (m, 1H), 4.22 (d, 2H), 3.82 (s, 6H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 14.01 min. MS: MH$^+$ 557.

Example 68 cis-3-{4-[(2-Fluoro-4-methylbenzyl)amino]phenyl}-1-[4-(4-methylpiperazino)cyclohexyl]-1H-pyrazolo[3,4-d]pyrimidin-4-amine Diacetate a) 2-Fluoro-4-methylbenzaldehyde The solution of 3-fluorotoluene (2.91 g, 0.0266 mol) in anhydrous tetrahydrofuran was cooled to −78° C. and a 1.4M solution of n-butyllithium in hexanes (19 mL, 0.0266 mol) was added dropwise keeping the reaction mixture temperature below −75° C. Upon the completion of the addition, N,N,N',N',N"-pentamethyldiethylenetriamine was added dropwise and the stirring at −78° C. was continued under an atmosphere of nitrogen for an additional 2 hours. N,N-dimethylformamide (3.89 g, 0.0532 mol) was added dropwise and the reaction mixture was slowly warmed up while stirring for 0.5 hours. It was quenched by dropwise addition of 1N hydrochloric acid and the layers were separated. The aqueous phase was further extracted with ethyl acetate (2×150 mL) and the combined organic extracts were dried with magnesium sulfate. The organic phase was concentrated under reduced pressure and the residue was purified by flash chromatography on silica using ethyl acetate/n-heptane (5:95) as mobile phase to yield 2-fluoro-4-methylbenzaldehyde (0.83 g, 0.006 mol) as a white solid.

$^1$H NMR (DMSO-$d_6$, 400 MHz) δ 10.17 (s, 1H), 7.74 (d, 1H), 7.23 (m, 2H), 2.41 (s, 3H). TLC (ethyl acetate/heptane 5:95) $R_f$ 0.18.

b) cis-3-{4-[(2-Fluoro-4-methylbenzyl)amino]phenyl}-1-[4-(4-methylpiperazino)cyclohexyl]-1H-pyrazolo[3,4-d]pyrimidin-4-amine Diacetate Protocol C $^1$H NMR (DMSO-$d_6$, 400 MHz) δ 8.18 (s, 1H), 7.33 (m, 3H), 7.00 (m, 2H), 6.74 (d, 2H), 6.52 (t, 1H), 4.76 (m, 1H), 4.32 (d, 2H), 2.5–2.1 (br, 13H), 2.34 (s, 3H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 14.58 min. MS: MH$^+$ 529.

Example 69 cis-3-{4-[(1H-2-Indolylmethyl)amino]phenyl}-1-[4-(4-methylpiperazino)cyclohexyl]-1H-pyrazolo[3,4-d]pyrimidin-4-amine Diacetate Protocol C $^1$H NMR (DMSO-$d_6$, 400 MHz) δ 11.04 (s, 1H), 8.18 (s, 1H), 7.44 (d, 1H), 7.35 (m, 3H), 7.01 (t, 1H), 6.95 (t, 1H), 6.83 (d, 2H), 6.48 (t, 1H), 6.36 (s, 1H), 4.76 (m, 1H), 4.46 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 13.75 min. MS: MH$^+$ 536.

Example 70 cis-3-(4-[(1-Methyl-1H-2-indolyl)methyl]aminophenyl)-1-[4-(4-methylpiperazino)-cyclohexyl]-1H-pyrazolo[3,4-d]pyrimidin-4-amine Diacetate Protocol C $^1$H NMR (DMSO-$d_6$, 400 MHz) δ 8.18 (s, 1H), 7.49 (d, 1H), 7.41 (d, 1H), 7.33 (d, 2H), 7.11 (t, 1H), 7.00 (t, 1H), 6.87 (d, 2H), 6.50 (t, 1H), 6.43 (s, 1H), 4.76 (m, 1H), 4.56 (d, 2H), 3.77 (s, 3H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 14.84 min. MS: MH$^+$ 550.

Example 71 trans-3-[4-(Benzylamino)phenyl]-1-[4-(4-methylpiperazino)cyclohexyl]-1H-pyrazolo[3,4-d]pyrimidin-4-amine tris-Maleate Trans-3-[4-(benzylamino)-3-methoxyphenyl]-1-[4-(4-methylpiperazino)cyclohexyl]-1H-pyrazolo[3,4-d]pyrimidin-4-amine was prepared according to protocol C. Trans-3-[4-(benzylamino)-3-methoxyphenyl]-1-[4-(4-methylpiperazino)cyclohexyl]-1H-pyrazolo[3,4-d]pyrimidin-4-amine (0.215 g, 0.00043 mol) was dissolved in ethanol (20 mL) and the solution was heated at reflux. The solution of maleic acid (0.151 g, 0.00129 mol) was added at once and the reflux was continued for an additional 10 min. The reaction mixture was cooled to ambient temperature, the precipitate was collected by filtration and dried.

$^1$H NMR (DMSO-$d_6$, 400 MHz) δ 8.18 (s, 1H), 7.34 (m, 7H), 6.74 (d, 2H), 6.16 (s, 6H), 4.65 (m, 1H), 4.33 (s, 2H), 3.1 (br, 9H), 2.67 (s, 3H), 2.05 (m, 6H), 1.57 (m, 2H); RP-HPLC (Delta Pak C18, 5 μm, 300 A, 15 cm; 5%–85% acetonitrile-0.1M ammonium acetate over 20 min, 1 mL/min) $R_t$ 13.09 min. MS: MH$^+$ 497.

Example 72 trans-3-{4-[(2-Methylbenzyl)amino]phenyl}-1-[4-(4-methylpiperazino)cyclohexyl]-1H-pyrazolo[3,4-d]pyrimidin-4-amine Diacetate Protocol C $^1$H NMR (DMSO-$d_6$, 400 MHz) δ 8.18 (s, 1H), 7.35 (d, 2H), 7.30 (t, 1H), 7.17 (m, 3H), 6.74 (d, 2H), 6.42 (t, 1H), 4.60 (m, 1H), 4.28 (d, 2H), 3.1 (br, 9H), 2.67 (s, 3H), 2.14 (s, 3H), 2.05 (m, 6H), 1.91 (s, 6H), 1.44 (m, 2H); RP-HPLC (Delta Pak C18, 5 μm, 300 A, 15 cm; 5%–85% acetonitrile-0.1M ammonium acetate over 20 min, 1 mL/min) $R_t$ 14.24 min. MS: MH$^+$ 511.

Example 73 trans-3-{4-[(2,6-Dimethoxybenzyl)amino]phenyl}-1-[4-(4-methylpiperazino)cyclohexyl]-1H-pyrazolo[3,4-d]pyrimidin-4-amine Diacetate Protocol C $^1$H NMR (DMSO-$d_6$, 400 MHz) δ 8.18 (s, 1H), 7.35 (d, 2H), 7.24 (t, 1H), 6.81 (d, 2H), 6.69 (d, 2H), 5.75 (t, 1H), 4.60 (m, 1H), 4.20 (d, 2H), 3.82 (s, 6H), 3.1 (br, 9H), 2.67 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 14.15 min. MS: MH$^+$ 557.

Example 74 trans-3-{4-[(2-Chlorobenzyl)amino]phenyl}-1-[4-(4-methylpiperazino)cyclohexyl]-1H-pyrazolo[3,4-d]pyrimidin-4-amine Diacetate Protocol C $^1$H NMR (DMSO-$d_6$, 400 MHz) δ 8.18 (s, 1H), 7.40 (m, 6H), 6.65 (m, 3H), 4.60 (m, 1H), 4.40 (d, 2H), 3.1 (br, 9H), 2.67 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 14.53 min. MS: MH$^+$ 531.

Example 75 trans-3-{4-[(2-Bromobenzyl)amino]phenyl}-1-[4-(4-methylpiperazino)cyclohexyl]-1H-pyrazolo[3,4-d]pyrimidin-4-amine Acetate Protocol D $^1$H NMR (DMSO-$d_6$, 400 MHz) δ 8.18 (s, 1H), 7.64 (d, 1H), 7.39 (m, 4H), 7.22 (t, 1H), 6.65 (m, 3H), 4.60 (m, 1H), 4.36 (d, 2H), 3.1 (br, 9H), 2.67 (s, 3H), 2.05 (m, 6H), 1.91 (s, 3H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 14.79 min. MS: MH$^+$ 576.

General Procedure for Reductive Alkylation of 3-(4-Amino-phenyl)-1-[1-(1-methylpiperid-4-yl)piperid-4-yl]-1H-pyrazolo[3,4-d]pyrimidin-4-amine:

Protocol E:

A mixture of 3-(4-amino-phenyl)-1-[1-(1-methylpiperid-4-yl)piperid-4-yl]-1H-pyrazolo[3,4-d]pyrimidin-4-amine (1 eq.), aldehyde (1 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10–60% acetonitrile-0.1M ammonium acetate over 25 min, 21 mL/min) to yield the desired products.

Protocol F:

After synthesis and purification (protocol E) the residue was digested with dichloromethane (1 mL), loaded onto Trikonex column (7 cm) and eluted with dichloromethane (5 mL). The desired band (UV-detection) was cut and the compound was extracted with the mixture of dichloromethane:methanol:triethylamine=90:5:5 (10 mL), filtered and the filtrate was concentrated under reduced pressure. The residue was suspended in diethyl ether (4 mL) and the precipitate was collected by filtration and dried.

Example 76

3-[4-(Benzylamino)phenyl]-1-[1-(1-methylpiperid-4-yl)piperid-4-yl]-1H-pyrazolo[3,4-d]pyrimidin-4-amine Acetate Protocol E $^1$H NMR (DMSO-$d_6$, 400 MHz) δ 8.18 (s, 1H), 7.33 (m, 4H), 7.22 (t, 1H), 7.07 (s, 1H), 6.98 (d, 1H), 6.54 (d, 1H), 5.89 (t, 1H), 4.60 (m, 1H), 4.39 (d, 2H), 3.89 (s, 3H), 2.98 (d, 2H), 2.79 (d, 2H), 2.25 (br, 5H), 2.15 (s, 3H), 1.91 (m, 7H), 1.69 (d, 2H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 12.88 min. MS: MH$^+$ 527.

Example 77

3-{4-[(2,6-Dimethoxybenzyl)amino]phenyl}-1-[1-(1-methylpiperid-4-yl)piperid-4-yl]-1H-pyrazolo[3,4-d]pyrimidin-4-amine Acetate Protocol E $^1$H NMR (DMSO-$d_6$, 400 MHz) δ 8.18 (s, 1H), 7.24 (t, 1H), 7.12 (d, 1H), 7.04 (s, 1H), 6.93 (d, 1H), 6.68 (d, 2H), 4.81 (t, 1H), 4.60 (m, 1H), 4.31 (d, 2H), 3.82 (s, 9H), 2.98 (d, 2H), 2.79 (d, 2H), 2.25 (br, 5H), 2.15 (s, 3H), 1.91 (m, 7H), 1.69 (d, 2H), 1.46 (m, 2H); RP-HPLC (Delta Pak C 18, 5 μm, 300 A, 15 cm; 5%–85% acetonitrile-0.1 M ammonium acetate over 20 min, 1 mL/min) $R_t$ 13.71 min. MS: MH$^+$ 587.

Example 78

3-{4-[(2-Chloro-6-fluorobenzyl)amino]phenyl}-1-[1-(1-methylpiperid-4-yl)piperid-4-yl]-1H-pyrazolo[3,4-d]pyrimidin-4-amine Protocol F $^1$H NMR (DMSO-$d_6$, 400 MHz) δ 8.18 (s, 1H), 7.37 (m, 2H), 7.25 (t, 1H), 7.11 (d, 1H), 7.07 (s, 1H), 6.86 (d, 1H), 5.21 (t, 1H), 4.60 (m, 1H), 4.49 (d, 2H), 3.83 (s, 3H), 2.98 (d, 2H), 2.79 (d, 2H), 2.25 (br, 5H), 2.15 (s, 3H), 1.89 (m, 4H), 1.69 (d, 2H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 13.94 min. MS: MH$^+$ 579.

Example 79 cis-3–4-[Benzyl(methyl)amino]phenyl-1-[4-(4-methylpiperazino)cyclohexyl]-1H-pyrazolo[3,4-d]pyrimidin-4-amine Diacetate a) N-benzyl-N-methyl-N-phenylamine 60% dispersion of sodium hydride in mineral oil (2.37 g, 0.0592 mol) was added to a solution of N-phenyl-N-benzylamine (10.33 g, 0.0564 mol) in anhydrous N,N-dimethylformamide (200 mL) at 0° C. The reaction mixture was warmed up to ambient temperature and stirred for 45 min. Iodomethane (7.99 g, 0.0564 mol) was added dropwise and the stirring at ambient temperature was continued under an atmosphere of nitrogen for 20 hours. The solvent was removed under reduced pressure and the residue partitioned between ethyl acetate (250 mL) and water (200 mL). The organic phase was dried with magnesium sulfate and concentrated under reduced pressure. The residue was purified by flash chromatography on silica using ethyl acetate/n-heptane (2:98) as mobile phase to yield N-benzyl-N-methyl-N-phenylamine (4.4 g, 0.0223 mol) as a yellow oil.

$^1$H NMR (DMSO-$d_6$, 400 MHz) δ 7.30 (m, 2H), 7.20 (m, 5H), 6.70 (d, 2H), 6.60 (t, 1H), 4.55 (s, 2H), 2.99 (s, 3H); TLC (ethyl acetate/heptane 5:95) $R_f$ 0.53.

b) N-benzyl-N-(4-bromophenyl)-N-methylamine

N-benzyl-N-phenyl-N-methylamine (4.41 g, 0.0224 mol) was dissolved in anhydrous dichloromethane (150 mL) and 2,4,4,6-tetrabromocyclohexadiene-1-one(9.16 g, 0.0224 mol) was added in 10 equal portions over a 30 min. period. Stirring was continued at ambient temperature for 20 hours. The organic phase was successively washed with 0.5N solution of sodium hydroxide in water (100 mL), 1N solution of sodium hydroxide in water (100 mL), water (120 mL) and brine (120 mL). The organic phase was dried with magnesium sulfate and concentrated under reduced pressure. The residue was purified by flash chromatography on silica using ethyl acetate/n-heptane (1:99) as mobile phase to yield N-benzyl-N-(4-bromophenyl)-N-methylamine (3.52 g, 0.0127 mol) as a colorless oil.

$^1$H NMR (DMSO-$d_6$, 400 MHz) δ 7.27 (m, 7H), 6.65 (d, 2H), 4.55 (s, 2H), 2.99 (s, 3H); TLC (ethyl acetate/heptane 5:95) $R_f$ 0.67.

c) N-Benzyl-N-methyl-N-[4-(4,4,5,5-tetramethyl-1,3,2-dioxaborolan-2-yl)phenyl]amine A mixture of N-benzyl-N-(4-bromophenyl)-N-methylamine (3.52 g, 0.0128 mol), diboron pinacol ester (3.89 g, 0.0153 mol), [1.1'-bis(diphenylphosphino)ferrocene]-dichloropalladium (II) complex with dichloromethane (1:1) (0.312 g, 0.00038 mol) and potassium acetate (3.72 g, 0.038 mol) in N,N-dimethylformamide (75 mL) was heated at 80° C. under an atmosphere of nitrogen for 16 hours. The mixture was allowed to cool to ambient temperature and the solvent removed under reduced pressure. Dichloromethane (120 mL) was added to the residue and the resulting solid was removed by filtration through a pad of Celite. The filtrate was concentrated to leave a yellow oil which was purified by flash chromatography on silica using ethyl acetate/n-heptane (2:98) as mobile phase. The resulting fractions were concentrated, the residue was triturated in n-heptane and the precipitate collected by filtration to yield N-benzyl-N-methyl-N-[4-(4,4,5,5-tetramethyl-1,3,2-dioxaborolan-2-yl)phenyl]amine (0.75 g, 0.00232 mol) as a white solid.

$^1$H NMR (DMSO-$d_6$, 400 MHz) δ 7.45 (d, 2H), 7.30 (m, 5H), 6.68 (d, 2H), 4.62 (s, 2H), 3.03 (s, 3H), 1.27 (s, 12H); TLC (ethyl acetate/heptane 5.95) $R_f$ 0.62.

d) cis-3-{4-[Benzyl(methyl)amino]phenyl}-1-[4-(4-methylpiperazino)cyclohexyl]-1H-pyrazolo[3,4-d]pyrimidin-4-amine Diacetate A mixture of N-benzyl-N-methyl-N-[4-(4,4,5,5-tetramethyl-1,3,2-dioxaborolan-2-yl)phenyl]amine (0.076 g, 0.000235 mol), cis-3-iodo-1-[4-(4-methylpiperazino)-cyclohexyl]-1H-pyrazolo[3,4-d]pyrimidin-4-amine (0.080 g, 0.000181 mol), tetrakis-(triphenylphosphine)palladium (0.012 g, 0.000011 mol) and sodium carbonate monohydrate (0.056 g, 0.00045 mol) was heated in a mixture of ethylene glycol dimethyl ether (5 mL) and water (3 mL) at 80° C. for sixteen hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield cis-3-{4-[benzyl(methyl)amino] phenyl}-1-[4-(4-methylpiperazino)cyclohexyl]-1H-pyrazolo[3,4-d]pyrimidin-4-amine diacetate (0.069 g, 0.00011 mol) as a white solid.

$^1$H NMR (DMSO-$d_6$, 400 MHz) 8.19 (s, 1H), (d, 2H), 7.34 (m, 2H), 7.26 (m, 3H), 6.89 (d, 2H), 4.78 (m, 1H), 4.66 (s, 2H), 3.09 (s, 3H), 2.5–2.1 (br, 13H), 2.17 (s, 3H), 1.91 (s, 6H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 14.60 min. MS: MH$^+$ 511.

Example 80 cis-3-{4-[Benzyl(ethyl)amino]phenyl}-1-[4-(4-methylpiperazino)cyclohexyl]-1H-pyrazolo[3,4-d]pyrimidin-4-amine Diacetate a) N-Benzyl-N-(4-bromophenyl)-N-ethylamine N-benzyl-N-phenyl-N-ethylamine (2.25 g, 0.0107 mol) was dissolved in anhydrous dichloromethane (80 mL) and 2,4,4,6-tetrabromocyclohexadiene-1-one (4.36 g, 0.0107 mol) was added in 6 equal portions over a 20 min. period. Stirring was continued at ambient temperature for 20 hours; the organic phase was successively washed with 0.5N solution of sodium hydroxide in water (50 mL), 1N solution of sodium hydroxide in water (50 mL), water (70 mL) and brine (75 mL). The organic phase was dried with magnesium sulfate and concentrated under reduced pressure. The residue was purified by flash chromatography on silica using ethyl acetate/n-heptane (1:99) as mobile phase to yield N-benzyl-N-(4-bromophenyl)-N-ethylamine (2.38 g, 0.0082 mol) as a colorless oil.

$^1$H NMR (DMSO-$d_6$, 400 MHz) δ 7.27 (m, 7H), 6.59 (d, 2H), 4.51 (s, 2H), 3.46 (q, 2H), 1.11 (t, 3H); TLC (ethyl acetate/heptane 1:99) $R_f$ 0.23.

b) N-Benzyl-N-ethyl-N-[4-(4,4,5,5-tetramethyl-1,3,2-dioxaborolan-2-yl)phenyl]amine A mixture of N-benzyl-N-(4-bromophenyl)-N-ethylamine (2.22 g, 0.00765 mol), diboron pinacol ester (2.33 g, 0.00919 mol), [1.1'-bis(diphenylphosphino)ferrocene]-dichloropalladium (II) complex with dichloromethane (1:1) (0.188 g, 0.00023 mol) and potassium acetate (2.25 g, 0.023 mol) in N,N-dimethylformamide (50 mL) was heated at 80° C. under an atmosphere of nitrogen for 16 hours. The mixture was allowed to cool to ambient temperature and the solvent removed under reduced pressure. Dichloromethane (100 mL) was added to the residue and the resulting solid was removed by filtration through a pad of Celite. The filtrate was concentrated to leave a yellow oil which was purified by flash chromatography on silica using ethyl acetate/n-heptane (3:97) as mobile phase. The resulting fractions were concentrated, the residue was triturated in n-heptane and the precipitate collected by filtration to yield N-benzyl-N-ethyl-N-[4-(4,4,5,5-tetramethyl-1,3,2-dioxaborolan-2-yl)phenyl]amine (0.24 g, 0.000712 mol).

$^1$H NMR (DMSO-$d_6$, 400 MHz) δ 7.42 (d, 2H), 7.30 (m, 2H), 7.20 (m, 3H), 6.63 (d, 2H), 4.57 (s, 2H), 3.48 (q, 2H), 1.27 (s, 12H), 1.09 (t, 3H); TLC (ethyl acetate/heptane 1:99) $R_f$ 0.14.

c) cis-3-{4-[Benzyl(ethyl)amino]phenyl}-1-[4-(4-methylpiperazino)cyclohexyl]-1H-pyrazolo[3,4-d]pyrimidin-4-amine Diacetate A mixture of N-benzyl-N-ethyl-N-[4-(4,4,5,5-tetramethyl-1,3,2-dioxaborolan-2-yl)phenyl]amine (0.065 g, 0.000193 mol), cis-3-iodo-1-[4-(4-methylpiperazino)-cyclohexyl]-1H-pyrazolo[3,4-d]pyrimidin-4-amine (0.071 g, 0.000161 mol), tetrakis-(triphenylphosphine)palladium (0.011 g, 0.00001 mol) and sodium carbonate monohydrate (0.056 g, 0.00045 mol) was heated in a mixture of ethylene glycol dimethyl ether (5 mL) and water (3 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield cis-3-{4-[benzyl(ethyl)amino]phenyl}-1-[4-(4-methylpiperazino)cyclohexyl]-1H-pyrazolo[3,4-d]pyrimidin-4-amine diacetate (0.049 g, 0.000076 mol) as a white solid.

$^1$H NMR (DMSO-$d_6$, 400 MHz) δ 8.19 (s, 1H), 7.42 (d, 2H), 7.34 (m, 2H), 7.26 (m, 3H), 6.83 (d, 2H), 4.78 (m, 1H), 4.61 (s, 2H), 3.55 (q, 2H), 2.5–2.1 (br, 13H), 2.17 (s, 3H), 1.91 (s, 6H), 1.68 (m, 2H), 1.58 (m, 2H), 1.19 (t, 3H); RP-HPLC (Delta Pak C18, 5 μm, 300 A, 15 cm; 5%–85% acetonitrile-0.1M ammonium acetate over 20 min, 1 mL/min) $R_t$ 15.47 min. MS: MH$^+$ 525.

Example 81 cis- N-(4-{4-Amino-1-[4-(4-methylpiperazino)cyclohexyl]-1-pyrazolo[3,4-d]pyrimidin-3-yl}phenyl)-2-phenylacetamide Diacetate Cis-3-(4-aminophenyl)-1-[4-(4-methylpiperazino)cyclohexyl]-1H-pyrazolo[3,4-d]pyrimidin-4-amine (0.255 g, 0.00063 mol) and phenylacetyl chloride (0.102 g, 0.00066 mol) were dissolved in anhydrous dichloromethane (20 mL) and the resulting mixture was stirred at ambient temperature under an atmosphere of nitrogen for 5 min. N,N-diisopropylethylamine (0.097 g, 0.00076 mol) was added dropwise and the stirring was continued for 16 hours. The organic phase was washed with saturated solution of sodium bicarbonate in water (25 mL), concentrated under reduced pressure and the residue was purified by preparative HPLC (Hypersil C18, 8 m, 25 cm; 10–60% acetonitrile-0.1M ammonium acetate over 25 min, 21 mL/min) to yield cis-N-(4-{4-amino-1-[4-(4-methylpiperazino)cyclohexyl]-1H-pyrazolo[3,4-d]pyrimidin-3-yl}phenyl)-2-phenylacetamide diacetate (0.250 g, 0.000388 mol) as a white solid.

$^1$H NMR (DMSO-$d_6$, 400 MHz) δ 10.37 (s, 1H), 8.20 (s, 1H), 7.77 (d, 2H), 7.57 (d, 2H), 7.33 (m, 4H), 7.23 (t, 1H), 4.78 (m, 1H), 3.68 (s, 2H), 2.5–2.1 (br, 13H), 2.17 (s, 3H), 1.91 (s, 6H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 11.86 min. MS: MH$^+$ 525.

Example 82 cis-1-[4-(4-Methylpiperazino)cyclohexyl]-3-[4-(phenethylamino)phenyl]-1H-pyrazolo[3,4-d]pyrimidin-4-amine Diacetate Cis-N1-(4-{4-amino-1-[4-(4-methylpiperazino)cyclohexyl]-1H-pyrazolo[3,4-d]pyrimidin-3-yl}phenyl)-2-phenylacetamide diacetate (0.200 g, 0.00031 mol) was suspended in anhydrous tetrahydrofuran (15 mL), the suspension was cooled to 0° C. and lithium aluminum hydride (0.177 g, 0.00416 mol) was added at once. The resulting mixture was warmed up to ambient temperature and stirred under an atmosphere of nitrogen for 18 hours. It was quenched by dropwise addition of water, the solvents were removed under reduced pressure and the residue purified by preparative HPLC (Hypersil C18, 8 µm, 25 cm; 10–60% acetonitrile-0.1M ammonium acetate over 25 min, 21 mL/min) to yield cis-1-[4-(4-methylpiperazino) cyclohexyl]-3-[4-(phenethylamino)phenyl]-1H-pyrazolo[3, 4-d]pyrimidin-4-amine diacetate (0.039 g, 0.0000619 mol) as a white solid.

$^1$H NMR (DMSO-$d_6$, 400 MHz) δ 8.20 (s, 1H), 7.37 (d, 2H), 7.31 (m, 4H), 7.22 (m, 1H), 6.75 (d, 2H), 6.07 (t, 1H), 4.78 (m, 1H), 3.32 (m, 2H), 2.86 (t, 2H), 2.5–2.1 (br, 13H), 2.17 (s, 3H), 1.91 (s, 6H), 1.68 (m, 2H), 1.58 (m, 2H), RP-HPLC (Delta Pak C18, 5 µm, 300 A, 15 cm; 5%–85% acetonitrile-0.1M ammonium acetate over 20 min, 1 mL/min) $R_t$ 14.03 min. MS:MH$^+$ 511.

Example 83 cis-N-(4-{4-Amino-1-[4-(4-methylpiperazino) cyclohexyl]-1H-pyrazolo[3,4-d]pyrimidin-3-yl}phenyl)-3-phenylpropanamide Diacetate Cis-3-(4-aminophenyl)-1-[4-(4-methylpiperazino) cyclohexyl]-1H-pyrazolo [3,4-d]pyrimidin-4-amine (0.250 g, 0.000616 mol) and 3-phenylpropanoyl chloride (0.109 g, 0.000646 mol) were dissolved in anhydrous dichloromethane (20 mL) and the resulting mixture was stirred at ambient temperature under an atmosphere of nitrogen for 5 min. N,N-diisopropylethylamine (0.095 g, 0.00074 mol) was added dropwise and the stirring was continued for 16 hours. The organic phase was washed with saturated solution of sodium bicarbonate in water (25 mL), concentrated under reduced pressure and the residue was purified by preparative HPLC (Hypersil C18, 8 m, 25 cm; 10–60% acetonitrile-0.1M ammonium acetate over 25 min, 21 mL/min) to yield cis-N-(4-{4-amino-1-[4-(4-methylpiperazino)cyclohexyl]-1H-pyrazolo[3,4-d] pyrimidin-3-ylphenyl)-3-phenyl}propanamide diacetate (0.225 g, 0.00034 mol) as a white solid.

$^1$H NMR (DMSO-$d_6$, 400 MHz) δ 10.12 (s, 1H), 8.20 (s, 1H), 7.77 (d, 2H), 7.57 (d, 2H), 7.29 (m, 4H), 7.19 (t, 1H), 4.78 (m, 1H), 2.94 (m, 2H), 2.67 (m 2H), 2.5–2.1 (br, 13H), 2.17 (s, 3H), 1.91 (s, 6H), 1.68 (m, 2H), 1.58 (m, 2H); RP-HPLC (Delta Pak C18, 5 µm, 300 A, 15 cm; 5%–85% acetonitrile-0.1M ammonium acetate over 20 min, 1 mL/min) $R_t$ 12.57 min. MS: MH$^+$ 539.

Example 84 cis-1-[4-(4-Methylpiperazino)cyclohexyl]-3-{4-[(3-phenylpropyl)amino]phenyl}-1H-pyrazolo[3,4-d] pyrimidin-4-amine Diacetate Cis-N1-(4-{4-amino-1-[4-(4-methylpiperazino) cyclohexyl]-1H-pyrazolo[3,4-d]pyrimidin-3-yl}phenyl)-3-phenylpropanamide diacetate (0.090 g, 0.000167 mol) was suspended in anhydrous tetrahydrofuran (5 mL), the suspension was cooled to 0° C. and lithium aluminum hydride (0.01 g, 0.00025 mol) was added at once. The resulting mixture was warmed up to ambient temperature and stirred under an atmosphere of nitrogen for 18 hours. It was quenched by dropwise addition of water, the solvents were removed under reduced pressure and the residue purified by preparative HPLC (Hypersil C18, 8 µm, 25 cm; 10–60% acetonitrile-0.1M ammonium acetate over 25 min, 21 mL/min) to yield cis-1-[4-(4-methylpiperazino)cyclohexyl]-3-{4-[(3-phenylpropyl)amino]phenyl}-1H-pyrazolo[3,4-d] pyrimidin-4-amine diacetate (0.037 g, 0.000057 mol) as a white solid.

$^1$H NMR (DMSO-$d_6$, 400 MHz) δ 8.20 (s, 1H), 7.29 (m, 7H), 6.70 (d, 2H), 6.02 (t, 1H), 4.78 (m, 1H), 3.08 (m, 2H), 2.71 (m, 2H), 2.5–2.1 (br, 13H), 2.17 (s, 3H), 1.91 (m, 8H), 1.68 (m, 2H), 1.58 (m, 2H), RP-HPLC (Delta Pak C18, 5 µm, 300 A, 15 cm; 5%–85% acetonitrile-0.1M ammonium acetate over 20 min, 1 mL/min) $R_t$ 14.84 min. MS: MH$^+$ 525.

Intermediate A: 3-(Benzyloxy)phenylboronic Acid

To a −78° C. mixture of 3-benzyloxobromobenzene (0.590 g, 2.24 mmol, 1 equiv) in THF (10 mL) was added n-butyllithium (1.6 M in hexanes, 2.9 mL, 4.7 mmol, 2.1 equiv). The reaction mixture was stirred for 45 min and then triisopropylborate (0.77 mL, 3.4 mmol, 1.5 equiv) was added. The reaction mixture was stirred at −78° C. for 30 min and was allowed to warm to ambient temperature over 2 h. Hydrochloric acid (2.5M, 10 mL) was added and the mixture was stirred vigorously for 16 h. The organic portion was separated and the aqueous layer was extracted with two portions of $Et_2O$ (50 mL each). The combined organic extracts were dried over $MgSO_4$, filtered, and concentrated to afford a brown oil. The residue was triturated from heptane (100 mL) and the precipitate was collected by filtration to afford 3-(benzyloxy)phenylboronic acid as a lavendar solid (0.111 g, 0.486 mmol): $^1$H NMR ($d_6$ DMSO, 400 MHz): δ H 8.00 (2H, bs), 7.02–7.46 (9H, m), and 5.09 (2H, s).

Intermediate B: 4-(4-Amino-1-cyclopentyl-1H-pyrazolo[3, 4-d]pyrimidin-3-yl)phenol A mixture of 3-[4-(benzyloxy)phenyl]-1-cyclopentyl-1H-pyrazolo[3,4-d]pyrimidin-4-amine (2.47 g, 6.41 mmol, 1 equiv), Pd black (0.341 g, 3.20 mmol, 0.5 equiv), and ammonium formate (2.02 g, 32 mmol, 5 equiv) in ethanol (50 mL) was heated at 80° C. for 4 h. The reaction mixture was allowed to cool to ambient temperature and the resulting solids were removed by filtration through a pad of Celite with the aid of EtOH (300 mL). The filtrate was concentrated to give a pale yellow solid which was purified by washing with $CH_2Cl_2$ (200 mL) to afford 4-(4-amino-1-cyclopentyl-1H-pyrazolo[3,4-d]pyrimidin-3-yl)phenol as a white solid (1.89 g, 6.4 mmol): $^1$H NMR ($d_6$ DMSO, 400 MHz): δ H 8.22 (1H, s), 7.45 (2H, d, J=8.5 Hz), 6.92 (2H, d, J=8.5 Hz), 5.17–5.24 (1H, m), 2.01–2.10 (4H, m), 1.87–1.90 (2H, m), 1.67–1.70 (2H, m). RP-HPLC (Delta Pak C18, 5 µm, 300 A, 15 cm; 5%–85% acetonitrile-0.1M ammonium acetate over 20 min, 1 mL/min) $R_t$ 13.13 min. MS: MH$^+$ 296.

Intermediate C: tert-Butyl N-(3-Bromophenyl)carbamate

To a 0° C. mixture of di-t-butyldicarbonate (9 mL, 39 mmol, 1.3 equiv) in $CH_2Cl_2$ (75 mL) was added a solution of 3-bromoaniline (3.3 mL, 30 mmol, 1 equiv) in $CH_2Cl_2$ (75 mL). The reaction mixture was allowed to warm slowly to ambient temperature and was stirred for 16 h. The crude reaction mixture was partitioned between saturated aqueous sodium bicarbonate (50 mL) and EtOAc (50 mL). The organic layer was separated, and the aqueous layer was extracted with EtOAc (100 mL). The combined organic extracts were dried over $MgSO_4$, filtered, and concentrated to afford a red oil. Purification by column chromatography on silica gel (elution with 1 L of 3% EtOAc/heptane and 1 L 5% EtOAc/heptane) afforded tert-butyl N-(3-bromophenyl)carbamate as a sticky yellow solid (9.0 g, 33 mmol): $^1$H NMR ($d_6$ DMSO, 400 MHz): δ H 9.54 (1H, s), 7.75 (1H, s), 7.37–7.39 (1H, m), 7.12–7.22 (2H, m), and 1.47 (9H, s).

Intermediate D: tert-Butyl N-[3-(4,4,5,5-Tetramethyl-1,3,2-dioxaborolan-2-yl)phenyl]carbamate A mixture of tert-butyl N-(3-bromophenyl)carbamate (8.19 g, 30.1 mmol, 1 equiv), $PdCl_2(dppf)_2$ (0.675 g, 0.90 mmol, 0.03 equiv), diboronpinacol ester (9.17 g, 36.1 mmol, 1.2 equiv), and potassium acetate (8.86 g, 90.3 mmol, 3.0 equiv) in DMF (150 mL) was heated at 80° C. for 12 h. The reaction mixture was allowed to cool to ambient temperature and the solvent was removed under reduced pressure. The residue was dissolved in $CH_2Cl_2$ (100 mL) and the resulting solids were removed by filtration through a pad of Celite with the aid of $CH_2Cl_2$ (100 mL) and $Et_2O$ (100 mL). The solvents were removed under reduced pressure and the residue was purified via silica gel column chromatography (elution with 1 L of 5% EtOAc/heptane) to afford tert-butyl N-[3-(4,4,5,5-tetramethyl-1,3,2-dioxaborolan-2-yl)phenyl] carbamate as a white solid (6.77 g, 21.2 mmol): $^1H$ NMR ($d_6$ DMSO, 400 MHz): δ H 9.30 (1H, s), 7.85 (1H, s), 7.45–7.50 (1H, m), 7.25–7.30 (2H, m), 1.47 (9H, s), and 1.29 (12H, s).

Intermediate E: cis-tert-Butyl N-(3-{4-amino-1-[4-(4-methylpiperazino)cyclohexyl]-1H-pyrazolo[3,4-d]pyrimidin-3-yl}phenyl)carbamate A mixture of cis-3-iodo-1-[4-(4-methylpiperazino)cyclohexyl]-1H-pyrazolo[3,4-d]pyrimidin-4-amine (1.89 g, 4.28 mmol, 1 equiv), tert-butyl N-[3-(4,4,5,5-tetramethyl-1,3,2-dioxaborolan-2-yl)phenyl]carbamate (1.64 g, 5.14 mmol, 1.2 equiv), tetrakis(triphenylphosphine)palladium (0.271 g, 0.257 mmol, 0.06 equiv), and sodium carbonate monohydrate (1.28 g, 10.3 mmol, 2.4 equiv) in water (13 mL) and DME (18 mL) was heated at 85° C. for 14 h. The mixture was allowed to cool to ambient temperature. Saturated aqueous sodium bicarbonate solution (15 mL) was added and the aqueous portion was extracted with EtOAc (30 mL). The organic extract was dried over $MgSO_4$, filtered, and concentrated to afford a pale yellow solid. Purification by column chromatography on silica gel (elution with 2 L of 95:4:1 $CH_2Cl_2$:$Et_3N$:MeOH) afforded cis-tert-butyl N-(3-{4-amino-1-[4-(4-methylpiperazino)cyclohexyl]-1H-pyrazolo[3,4-d]pyrimidin-3-yl}phenyl) carbamate as a white solid (1.76 g, 3.47 mmol): $^1H$ NMR ($d_6$ DMSO, 400 MHz): δ H 9.55 (1H, s), 8.23 (1H, s), 7.81 (1H, s), 7.40–7.52 (2H, m), 7.24 (1H, d, J=7.5 Hz), 4.79–4.81 (1H, m), 2.05–2.44 (11H, m), 2.14 (3H, s), 1.54–1.70 (6H, m), 1.49 (9H, s); RP-HPLC (Delta Pak C18, 5 µm, 300 Å, 15cm; 5%–85% acetonitrile-0.1M ammonium acetate over 20 min, 1 mL/min) $R_t$ 12.61 min.

Intermediate F: cis-3-(3-Aminophenyl)-1-[4-(4-methylpiperazino)cyclohexyl]-1H-pyrazolo[3,4-d]pyrimidin-4-amine A mixture of cis-tert-butyl N-(3-{4-amino-1-[4-(4-methylpiperazino)cyclohexyl]-1H-pyrazolo[3,4-d]pyrimidin-3-yl}phenyl)carbamate (1.7 g, 3.3 mmol, 1 equiv) and dichloromethane (40 mL) was cooled at 0° C. and then trifluoroacetic acid (10.5 mL, 137 mmol, 41 equiv) was added. The reaction mixture was allowed to warm to ambient temperature over 3 h, the solvent was removed under reduced pressure, and the residue was partitioned between $CH_2Cl_2$ (50 mL) and water (50 mL). The organic layer was separated and treated with saturated aqueous sodium bicarbonate solution (50 mL). The organic extract was dried over $MgSO_4$, filtered, and concentrated to afford cis-3-(3-aminophenyl)-1-[4-(4-methylpiperazino)cyclohexyl]-1H-pyrazolo[3,4-d]pyrimidin-4-amine as a white solid (1.34 g, 3.30 mmol): $^1H$ NMR ($d_6$ DMSO, 400 MHz): δ H 8.21 (1H, s), 7.17–7.21 (1H, m), 6.85 (1H, s), 6.72–6.74 (1H, m), 6.65–6.68 (1H, m), 5.36 (2H, bs), 4.75–4.80 (1H, m), 2.22–2.51 (11H, m), 2.20 (3H, s), 2.06–2.08 (2H, m), 1.58–1.68 (4H, m); RP-HPLC (Delta Pak C18, 5 µm, 300 Å, 15 cm; 5%–85% acetonitrile-0.1M ammonium acetate over 20 min, 1 mL/min) $R_t$ 9.06 min. MS: $MH^+$ 407.

Intermediate G: 2-[4-(4,4,5,5-Tetramethyl-1,3,2-dioxaborolan-2-yl)phenoxy]benzonitrile A mixture of [2-(4-bromophenoxy)phenyl](methylidyne) ammonium (4.00 g, 14.6 mmol, 1 equiv), $PdCl_2(dppf)_2$ (0.320 g, 0.44 mmol, 0.03 equiv), diboronpinacol ester (4.45 g, 17.5 mmol, 1.2 equiv), and potassium acetate (4.30 g, 43.8 mmol, 3.0 equiv) in DMF (70 mL) was heated at 80° C. for 16 h. The mixture was allowed to cool to ambient temperature and the solvent was removed under reduced pressure to afford a black sludge. The resulting solids were removed by filtration through a pad of Celite with the aid of $CH_2Cl_2$ (200 mL) and EtOAc (200 mL). The filtrate was concentrated to yield a dark brown oil which was purified by column chromatography on silica gel (elution with 500 mL of 5% MeOH/$CH_2Cl_2$) to afford 2-[4-(4,4,5,5-tetramethyl-1,3,2-dioxaborolan-2-yl)phenoxy]benzonitrile as a pale yellow oil (2.04 g, 6.35 mmol): $^1H$ NMR ($d_6$ DMSO, 400 MHz): H 7.92–7.94 (1H, m), 7.69–7.92 (3H, m), 7.33–7.37 (1H, m), 7.08–7.12 (3H, m), and 1.30 (12H, s).

Example 85

1-Cyclopentyl-3-[4-(3-methoxyphenoxy)phenyl]-1H-pyrazolo[3,4-d]pyrimidin-4-amine A mixture of 4-(4-amino-1-cyclopentyl-1H-pyrazolo[3,4-d]pyrimidin-3-yl)phenol (0.195 g, 0.660 mmol, 1 equiv), 3-methoxyboronic acid (0.240 g, 1.58 mmol, 2.4 equiv), copper (II) acetate (0.180 g, 0.990 mmol, 1.5 equiv), and 4 Å molecular sieves in pyridine (0.27 mL) was heated at reflux for 5 h. The mixture was allowed to cool to ambient temperature and the resulting solid was removed by filtration through a pad of Celite with the aid of $CH_2Cl_2$ (20 mL) and MeOH (20 mL). The filtrate was concentrated to afford an oily green solid which was purified by column chromatography on silica gel (elution with 1 L of $CH_2Cl_2$, 600 mL of 20% MeOH/$CH_2Cl_2$, and 600 mL of 40 % MeOH/$CH_2Cl_2$) to afford 1-cyclopentyl-3-[4-(3-methoxyphenoxy)phenyl]-1H-pyrazolo[3,4-d]pyrimidin-4-amine as a yellow-brown solid (0.072 g, 0.179 mmol): $^1H$ NMR ($d_6$ DMSO, 400 MHz): δ H 8.23 (1H, s), 7.67 (2H, d, J=8.6 Hz), 7.34 (1H, t, J=8.2 Hz), 7.16 (2H, d, J=8.6 Hz), 6.78 (1H, d, J=8.3 Hz), 6.65–6.70 (2H, m), 5.21–5.25 (1H, m), 3.76 (3H, s), 2.02–2.11 (4H, m), 1.87–1.91 (2H, m), 1.67–1.71 (2H, m); RP-HPLC (Hypercil C18, 5 µm, 100 Å, 15 cm; 5%–100% acetonitrile-0.1M ammonium acetate over 15 min, 1 mL/min). $R_t$ 13.35 min. MS: $MH^+$ 402.

Example 86

3-[4-(Benzyloxy)phenyl]-1-cyclopentyl-1H-pyrazolo[3,4-d]pyrimidin-4-amine

To a mixture of 1-cyclopentyl-3-iodo-1H-pyrazolo[3,4-d]pyrimidin-4-amine (5.41 g, 17.1 mmol, 1 equiv) and 4-(benzyloxy)phenylboronic acid (4.87 g, 21.4 mmol, 1.2 equiv) in DME (100 mL) was added tetrakis(triphenylphosphine)palladium (1.19 g, 1.03 mmol, 0.06 equiv) and a solution of sodium carbonate monohydrate (5.09 g, 41 mmol, 2.4 equiv) in water (54 mL). The mixture was heated at 85° C. for 2 h. Additional tetrakis(triphenylphosphine)palladium (1.19 g, 1.03 mmol, 0.06 equiv) was added and the reaction mixture was heated at 85° C. for 3 h. The mixture was allowed to cool to ambient temperature and a white crystalline solid (3.868 g) was collected by filtration. In order to recover more product, the filtrate was concentrated in vacuo and the residue was partitioned between water (50 mL) and EtOAc (50 mL). The aqueous layer was extracted with three portions of EtOAc (150 mL each) and the combined organic extracts were washed with three portions of water (100 mL each) and brine (100 mL), dried over MgSO$_4$, filtered, and concentrated to afford a yellow solid (0.916 g). The two solids were combined and recrystallized from hot EtOAc to afford 3-[4-(benzyloxy)phenyl]-1-cyclopentyl-1H-pyrazolo[3,4-d]pyrimidin-4-amine as a white solid (3.41 g, 8.8 mmol): $^1$H NMR (d$_6$ DMSO, 400 MHz): δ H 8.22 (1H, s), 7.19–7.62 (7H, m), 7.18 (2H, d, J=6.9 Hz), 5.18–5.23 (1H, m), 5.22 (2H, s), 2.00–2.10 (4H, m), 1.87–1.89 (2H, m), 1.66–1.70 (2H, m). RP-HPLC (Hypercil C18, 5 μm, 100 Å, 15 cm; 5%–100% acetonitrile-0.1M ammonium acetate over 15 min, 1 mL/min). R$_t$ 13.05 min.

Example 87

1-Cyclopentyl-3-[4-(4-fluorophenoxy)phenyl]-1H-pyrazolo[3,4-d]pyrimidin-4-amine

A mixture of 4-(4-amino-1-cyclopentyl-1H-pyrazolo[3,4-d]pyrimidin-3-yl)phenol (0.151 g, 0.511 mmol, 1 equiv), 4-(fluorophenyl)boronic acid (0.357 g, 2.55 mol, 5.0 equiv), copper (II) acetate (0.139 g, 0.766 mmol, 1.5 equiv), and 4 Å molecular sieves in pyridine (0.21 mL) and dichloroethane (5 mL) was heated at reflux for 48 h. The mixture was allowed to cool to ambient temperature and the resulting solids were removed by filtration through a pad of Celite with the aid of MeOH (20 mL). The filtrate was concentrated to afford a brown oil which was purified by column chromatography over silica gel (elution with 300 mL of CH$_2$Cl$_2$, 400 mL of 10% MeOH/CH$_2$Cl$_2$, and 400 mL of 20% MeOH/CH$_2$Cl$_2$) to afford a red oil which was further purified by preparative RP-HPLC (Rainin C18, 8 μm, 300 Å, 25 cm; 50%–100% acetonitrile-0.1M ammonium acetate over 20 min, 21 mL/min). The solvent was removed in vacuo to afford 1-cyclopentyl-3-[4-(4-fluorophenoxy)phenyl]-1H-pyrazolo[3,4-d]pyrimidin-4-amine as a white solid (0.010 g, 0.025 mmol): $^1$H NMR (d$_6$ CDCl$_3$, 400 MHz): δ H 8.37 (1H, s), 7.65 (2H, d, J=8.6 Hz), 7.03–7.26 (6H, m), 5.59 (2H, bs), 5.27–5.35 (1H, m), 2.09–2.21 (4H, m), 1.95–2.02 (2H, m), 1.68–1.79 (2H, m); RP-HPLC (Hypercil C18, 5 μm, 100 Å, 15 cm; 5%–100% acetonitrile-0.1M ammonium acetate over 15 min, 1 mL/min) R$_t$ 14.63 min. MS: MH$^+$ 390.

Example 88

1-Cyclopentyl-3-4-[3-(trifluoromethyl)phenoxy] phenyl-1H-pyrazolo[3,4-d]pyrimidin-4-amine A mixture of 4-(4-amino-1-cyclopentyl-1H-pyrazolo[3,4-d]pyrimidin-3-yl)phenol (0.170 g, 0.576 mmol, 1 equiv), 3-(trifluoromethylphenyl)boronic acid (0.328 g, 1.73 mmol, 3.0 equiv), copper (II) acetate (0.108 g, 0.594 mmol, 1.0 equiv), and 4 Å molecular sieves in pyridine (0.23 mL) and dichloroethane (5.8 mL) was heated at reflux for 6 h. Copper (II) acetate (0.050 g, 0.5 equiv) was added and the reaction mixture was heated at reflux for 16 h. Additional molecular sieves and 3-(trifluoromethylphenyl)boronic acid (0.250 g, 2.3 equiv) were added and the reaction mixture was heated at reflux for 54 h. The reaction mixture was allowed to cool to ambient temperature and the resulting solid was removed by filtration through a pad of Celite with the aid of MeOH (20 mL). The filtrate was concentrated to afford a brown solid which was purified by silica gel column chromatography (elution with 400 mL of eptane, 400 mL of 10% EtOAc/heptane, 400 mL of 20% EtOAc/heptane, and 400 mL of 50% EtOAc/heptane) to afford a yellow solid. Further purification by preparative RP-LC/MS (Gilson-Micromass C18, 5 μm, 130 Å, 21 cm, 0%–100% acetonitrile-0.1M ammonium acetate over 9 min, 25 mL/min), removal of the acetonitrile in vacuo, and lyopholyzation of the aqueous mixture gave 1-cyclopentyl-3-4-[3-(trifluoromethyl)phenoxy]phenyl-1H-pyrazolo[3,4-d]pyrimidin-4-amine as a light brown solid (0.017 g, 0.039 mmol): $^1$H NMR (d$_6$ DMSO, 400 MHz): δ H 8.29 (1H, s), 7.68–7.74 (3H, m), 7.65 (1H, d, J=8.1 Hz), 7.52–7.54 (2H,m), 7.24 (2H, d, J=8.7 Hz), 7.7 (2H, bs), 5.20–5.28 (1H, m), 2.03–2.11 (4H, m), 1.90–1.91 (2H, m), 1.68–1.70 (2H, m); RP-HPLC (Hypercil C18, 5 μm, 100 Å, 15 cm; 5%–100% acetonitrile-0.1M ammonium acetate over 15 min, 1 mL/min) R$_t$ 15.72 min. MS: MH$^+$ 440.

Example 89

1-Cyclopentyl-3-[4-(3-nitrophenoxy)phenyl]-1H-pyrazolo[3,4-d]pyrimidin-4-amine

A mixture of 4-(4-amino-1-cyclopentyl-1H-pyrazolo[3,4-d]pyrimidin-3-yl)phenol (0.202 g, 0.684 mmol, 1 equiv), 3-nitrophenylboronic acid (0.571 g, 3.42 mmol, 5.0 equiv), copper (II) acetate (0.186 g, 1.02 mmol, 1.5 equiv), and 4 Å molecular sieves in pyridine (0.28 mL) and dichloroethane (6.8 mL) was heated at reflux for 24 h. The reaction mixture was allowed to cool to ambient temperature. Dichloromethane (25 mL) was added to the residue and the resulting solid was removed by filtration through a pad of Celite with the aid of MeOH (20 mL). The filtrate was concentrated to afford a brown liquid which was purified by column chromatography over silica gel (elution with 400 mL of heptane, 400 mL of 10% EtOAc/heptane, 400 mL of 20% EtOAc/heptane, and 800 mL of MeOH) to afford a red oil which was further purified by preparative RP-LC/MS (Gilson-Micromass C18, 5 μm, 130 Å, 21 cm, 0%–100% acetonitrile-0.1M ammonium acetate over 9 min, 25 mL/min). The acetonitrile was removed in vacuo and the aqueous mixture was lyopholyzed to give 1-cyclopentyl-3-[4-(3-nitrophenoxy)phenyl]-1H-pyrazolo[3,4-d]pyrimidin-4-amine as a pale yellow solid (0.034 g, 0.081 mmol): $^1$H NMR (d$_6$ DMSO, 400 MHz): δ H 8.22 (1H, s), 7.28–7.74 (6H, m), 7.18 (2H, d, J=8.6 Hz), 7.7 (2H, bs), 5.13–5.26 (1H, m), 2.02–2.10 (4H, m), 1.89–1.91 (2H, m), 1.68–1.70 (2H, m); RP-HPLC (Hypercil C18, 5 μm, 100 Å, 15 cm; 5%–100% acetonitrile-0.1M ammonium acetate over 15 min, 1 mL/min) R$_t$ 19.98 min. MS: MH$^+$ 417.

Example 90

1-Cyclopentyl-3-4-[4-(trifluoromethoxy)phenoxy] phenyl-1H-pyrazolo[3,4-d]pyrimidin-4-amine A mixture of 4-(4-amino-1-cyclopentyl-1H-pyrazolo[3,4-d]pyrimidin-3-yl)phenol (0.100 g, 0.339 mmol, 1 equiv), 4-trifluoromethoxyphenylboronic acid (0.349 g, 1.69 mmol, 5.0 equiv), copper (II) acetate (0.092 g, 0.51 mmol, 1.5 equiv), and 4 Å molecular sieves in pyridine (0.12 mL) and dichloroethane (3.4 mL) was heated at reflux for 72 h. The reaction mixture was allowed to cool to ambient temperature. Dichloromethane (25 mL) was added and the resulting solid was removed by filtration through a pad of Celite. The solvent was removed under reduced pressure to afford a brown oil which was purified by preparative RP-HPLC (Rainin C 18, 8 μm, 300 Å, 25 cm; 10%–60% acetonitrile-0.1M ammonium acetate over 20 min, 21 mL/min). The acetonitrile was removed in vacuo and the aqueous mixture was lyopholyzed to afford 1-cyclopentyl-3-4-[4-

(trifluoromethoxy)phenoxy]phenyl-1H-pyrazolo[3,4-d]pyrimidin-4-amine as a white solid (0.020 g, 0.044 mmol): $^1$H NMR (d$_6$ CDCl$_3$, 400 MHz): δ H 8.53 (1H, s), 7.69 (2H, d, J=8.6 Hz), 7.07–7.26 (6H, m), 5.55 (2H, bs), 5.28–5.36 (1H, m), 2.16–2.21 (4H, m), 1.94–2.04 (2H, m), 1.72–1.79 (2H, m); RP-HPLC (Hypercil C18, 5 µm, 100 Å, 15 cm; 5%–100% acetonitrile-0.1M ammonium acetate over 15 min, 1 mL/min) R$_t$ 16.33 min. MS: MH$^+$ 456.

Example 91

1-Cyclopentyl-3–4-[4-(trifluoromethyl)phenoxy]phenyl-1H-pyrazolo[3,4-d]pyrimidin-4-amine Using the procedure detailed for the synthesis of 1-cyclopentyl-3-4-[4-(trifluoromethoxy)phenoxy]phenyl-1H-pyrazolo[3,4-d]pyrimidin-4-amine, 1-cyclopentyl-3-4-[4-(trifluoromethyl)phenoxy]phenyl-1H-pyrazolo[3,4-d]pyrimidin-4-amine was prepared as a white solid (0.008 g, 0.018 mmol): $^1$H NMR (d$_6$ CDCl$_3$, 400 MHz): δ H 8.34 (1H, s), 7.60–7.73 (4H, m), 7.05–7.32 (4H, m), 5.89 (2H, bs), 5.27–5.34 (1H, m), 2.17–2.21 (4H, m), 2.00–2.03 (2H, m), 1.72–1.79 (2H, m); RP-HPLC (Hypercil C18, 5 µm, 100 Å, 15 cm; 5%–100% acetonitrile-0.1M ammonium acetate over 15 min, 1 mL/min) R$_t$ 15.77 min. MS: MH$^+$ 440.

Example 92

3-[3-(Benzyloxy)phenyl]-1-cyclopentyl-1H-pyrazolo[3,4-d]pyrimidin-4-amine

To a mixture of 1-cyclopentyl-3-iodo-1H-pyrazolo[3,4-d]pyrimidin-4-amine (0.200 g, 0.631 mmol, 1 equiv) and 3-(benzyloxy)phenylboronic acid (0.110 g, 0.487 mmol, 1.0 equiv) in DME (6 mL) was added tetrakis(triphenylphosphine)palladium (0.044 g, 0.038 mmol, 0.07 equiv) and a solution of sodium carbonate monohydrate (0.187 g, 1.51 mmol, 2.4 equiv) in water (2 mL). The mixture was heated at 85° C. for 16 h, then allowed to cool to ambient temperature. The solvent was removed under reduced pressure and the residue was partitioned between EtOAc (50 mL) and water (50 mL). The organic layer was dried over MgSO$_4$, filtered, and concentrated to afford an oily red-orange solid. Recrystallization from hot EtOAc afforded a red-orange solid which was purified by preparative RP-HPLC (Rainin C18, 8µm, 300 Å, 25 cm; 10%–60% acetonitrile-0.1M ammonium acetate over 20 min, 21 mL/min). The acetonitrile was removed in vacuo and the aqueous mixture was lyopholyzed to afford 3-[3-(benzyloxy)phenyl]-1-cyclopentyl-1H-pyrazolo[3,4-d]pyrimidin-4-amine as a white solid (0.023 g, 0.060 mmol): $^1$H NMR (d$_6$ CDCl$_3$, 400 MHz): δ H 8.34 (1H, s), 7.27–7.46 (8H, m), 7.07–7.10 (1H, m), 5.63 (2H, bs), 5.31 (1H, quint, J=7.6 Hz), 5.16 (2H, s), 2.15–2.20 (4H, m), 1.96–2.01 (2H, m), 1.72–1.75 (2H, m); RP-HPLC (Hypercil C18, 5 µm, 100 Å, 15 cm; 5%–100% acetonitrile-0.1M ammonium acetate over 15 min, 1 mL/min) R$_t$ 14.00 min. MS: MH$^+$ 386.

Examples 93–99

A General Procedure for the Synthesis of [Substituted (Methylamino)]phenyl-pyrazolopyrimidines is as Follows:

To a 0.10 M solution of cis-3-(4-aminophenyl)-1-[4-(4-methylpiperazino)-cyclohexyl]-1H-pyrazolo[3,4-d]pyrimidin-4-amine in dichloroethane was added 1.5 equivalents of the substituted benzaldehyde, 3.8 equivalents of glacial acetic acid, and 3.5 equivalents of sodium triacetoxyborohydride. This mixture was stirred at ambient temperature for 16 h. An additional 3.3 equivalents of sodium triacetoxyborohydride was added (if necessary). The reaction mixture was stirred for 1.5 h and then diluted with dichloroethane (5 mL) and saturated aqueous NaHCO$_3$ solution (5 mL). The organic portion was separated and the aqueous portion was extracted with CH$_2$Cl$_2$ (10 mL). The combined organic extracts were dried over MgSO$_4$, filtered, and concentrated. The residue was purified by preparative RP-HPLC (Rainin C18, 8 µm, 300 Å, 25 cm; 10%–60% acetonitrile-0.1M ammonium acetate over 20 min, 21 mL/min). The acetonitrile was removed in vacuo and the aqueous mixture was lyopholyzed to afford the desired product.

Compounds Synthesized by the Above Procedure Include:

| Name | HPLC rt (min) | M+ |
|---|---|---|
| Example 93 Cis-3-{4-[(3-fluorobenzyl)amino]phenyl}-1-[4-(4-methylpiperazino)cyclohexyl]-1H-pyrazolo[3,4-d]pyrimidin-4-amine triacetate salt | 13.25 | 515.3 |
| Example 94 Cis-3-{4-[(2-fluorobenzyl)amino]phenyl}-1-[4-(4-methylpiperazino)cyclohexyl]-1H-pyrazolo[3,4-d]pyrimidin-4-amine triacetate salt | 13.24 | 515.3 |
| Example 95 Cis-3-{4-[(4-methoxybenzyl)amino]phenyl}-1-[4-(4-methylpiperazino)cyclohexyl]-1H-pyrazolo[3,4-d]pyrimidin-4-amine diacetate salt | 13.08 | 527.3 |
| Example 96 Cis-3-{4-[(3-methoxybenzyl)amino]phenyl}-1-[4-(4-methylpiperazino)cyclohexyl]-1H-pyrazolo[3,4-d]pyrimidin-4-amine triacetate salt | 13.12 | 527.3 |
| Example 97 Cis-3-{4-[(4-fluorobenzyl)amino]phenyl}-1-[4-(4-methylpiperazino)cyclohexyl]-1H-pyrazolo[3,4-d]pyrimidin-4-amine triacetate salt | 13.35 | 515.3 |
| Example 98 Cis-1-[4-(4-methylpiperazino)cyclohexyl]-3-4-[(3-pyridylmethyl)amino]phenyl-1H-pyrazolo[3,4-d]pyrimidin-4-amine | 10.19 | 498.5 |
| Example 99 Cis-3-{4-[(2-methoxybenzyl)amino]phenyl}-1-[4-(4-methylpiperazino)cyclohexyl]-1H-pyrazolo[3,4-d]pyrimidin-4-amine | 13.57 | 527.4 |

RP-HPLC (Delta Pak C18, 5mm, 300 Å, 15 cm; 5%–85% acetonitrile-0.1M ammonium acetate over 20 min, 1 mL/min)

Example 100 cis-3-[3-(Benzylamino)phenyl]-1-[4-(4-methylpiperazino)cyclohexyl]-1H-pyrazolo[3,4-d]pyrimidin-4-amine triacetate Salt To a solution of cis-3-(3-aminophenyl)-1-[4-(4-methylpiperazino)-cyclohexyl]-1H-pyrazolo[3,4-d]pyrimidin-4-amine (0.104 g, 0.256 mmol, 1 equiv) in dichloroethane (2 mL) was added benzaldehyde (0.03 mL, 0.282 mmol, 1.1 equiv), glacial acetic acid (0.06 mL, 1.0 mmol, 3.9 equiv), and sodium triacetoxyborohydride (0.212 g, 1.0 mmol, 3.9 equiv). This mixture was stirred at ambient temperature for 16 h. Saturated aqueous NaHCO$_3$ solution (5 mL) was added, the organic portion was separated, and the aqueous portion extracted with two portions of CH$_2$Cl$_2$ (15 mL each). The combined organic extracts were dried over MgSO$_4$, filtered, and concentrated to afford a yellow oil which was purified (twice) by preparative RP-HPLC (Rainin C18, 8 µm, 300 Å, 25 cm; 10%–60% acetonitrile-0.1M ammonium acetate over 20 min, 21 mL/min). The acetonitrile was removed in vacuo and the aqueous mixture was lyopholyzed to afford cis-3-[3-(benzylamino)phenyl]-1-[4-(4-methylpiperazino)cyclohexyl]-1H-pyrazolo[3,4-d]pyrimidin-4-amine triacetate salt as a white solid (0.023 g, 0.046 mmol): $^1$H NMR (d$_6$ DMSO, 400 MHz): δ H 8.21

(1H, s), 7.40 (4H, m), 7.20–7.25 (2H, m), 6.88 (1H, s), 6.78 (1H, d, J=7.7 Hz), 6.67–6.69 (1H, m), 6.56–6.58 (1H, m), 4.75–4.79 (1H, m), 4.32 (2H, d, J=5.8 Hz), 2.21–2.49 (11H, m), 2.14 (3H, s), 2.05–2.14 (2H, m), 1.89 (9H, s), 1.54–1.68 (4H, m); RP-HPLC (Hypercil C18, 5 μm, 100 Å, 15 cm; 5%–100% acetonitrile-0.1M ammonium acetate over 15 min, 1 mL/min) $R_t$ 13.04 min. MS: MH$^+$ 497.

Example 101 cis-2-(4-{4-Amino-1-[4-(4-methylpiperazino)cyclohexyl]-1H-pyrazolo[3,4-d]pyrimidin-3-yl}phenoxy)benzonitrile A mixture of cis-3-iodo-1-[4-(4-methylpiperazino)cyclohexyl]-1H-pyrazolo[3,4-d]pyrimidin-4-amine (2.29 g, 5.19 mmol, 1 equiv), 2-[4-(4,4,5,5-tetramethyl-1,3,2-dioxaborolan-2-yl)phenoxy]benzonitrile (2.0 g, 6.2 mmol, 1.2 equiv), tetrakis(triphenylphosphine)palladium (0.329 g, 0.311 mmol, 0.06 equiv), DME (21 mL), and sodium carbonate monohydrate (1.54 g, 12.5 mmol, 2.4 equiv) in water (16 mL) was heated at 85° C. for 60 h. Additional tetrakis(triphenylphosphine)palladium (0.100 g, 0.02 equiv) was added and the reaction mixture was heated at 85° C. for 6.5 h. The reaction mixture was allowed to cool to ambient temperature and was partitioned between saturated aqueous sodium bicarbonate solution (25 mL) and EtOAc (25 mL). The organic extract was dried over MgSO$_4$, filtered, and concentrated. The residue was triturated from Et$_2$O and purified by column chromatography on silica gel (elution with 1 L of 5% MeOH/CH$_2$Cl$_2$, 1 L of 10% MeOH/CH$_2$Cl$_2$, 1 L of 20% MeOH/CH$_2$Cl$_2$, and 1 L of 25% MeOH/CH$_2$Cl$_2$) to give cis-2-(4-{4-amino-1-[4-(4-methylpiperazino)cyclohexyl]-1H-pyrazolo[3,4-d]pyrimidin-3-yl}phenoxy)benzonitrile as a pale yellow solid (1.79 g, 3.52 mmol): $^1$H NMR (d$_6$ DMSO, 400 MHz): δ H 8.24 (1H, s), 7.94 (1H, d, J=7.7 Hz), 7.68–7.73 (3H, m), 7.31–7.34 (3H, m), 7.18 (1H, d, J=8.5 Hz), 4.78–4.83 (1H, m), 2.21–2.51 (11H, m), 2.19 (3H, s), 2.05–2.08 (2H, m), 1.56–1.71 (4H, m); RP-HPLC (Delta Pak C18, 5 μm, 300 Å, 15 cm; 5%–85% acetonitrile-0.1M ammonium acetate over 20 min, 1 mL/min) $R_t$ 13.16 min. MS: MH$^+$ 509.

Example 102 cis-2-(3-{4-Amino-1-[4-(4-methylpiperazino)cyclohexyl]-1H-pyrazolo[3,4-d]pyrimidin-3-yl}phenoxy)benzamide Triacetate Salt A mixture of cis-2-(4-{4-amino-1-[4-(4-methylpiperazino)cyclohexyl]-1H-pyrazolo[3,4-d]pyrimidin-3-yl}phenoxy)benzonitrile (0.111 g, 0.218 mmol, 1 equiv), 25% aqueous sodium hydroxide (1 mL), and 30% H$_2$O$_2$ (1 mL) in dioxane (1 mL) was heated at 100° C. for 16 h. An additional portion of 30% H$_2$O$_2$ (1 mL) was added and the reaction mixture was heated at 100° C. for 2 h. The reaction mixture was allowed to cool to ambient temperature and diluted with CH$_2$Cl$_2$ (15 mL). The organic portion was separated and the solvents were removed under reduced pressure to afford a pale yellow solid which was purified by preparative RP-HPLC (Rainin C18, 8 μm, 300 Å, 25 cm; 10%–60% acetonitrile-0.1M ammonium acetate over 20 min, 21 mL/min). The acetonitrile was removed in vacuo and the aqueous mixture was lyopholyzed to afford cis-2-(3-{4-amino-1-[4-(4-methylpiperazino)cyclohexyl]-1H-pyrazolo[3,4-d]pyrimidin-3-yl}phenoxy)benzamide triacetate salt as an off-white solid (0.020 g, 0.038 mmol): $^1$H NMR (d$_6$ DMSO, 400 MHz): δ H 8.23 (1H, s), 7.75 (1H, d, J=7.7 Hz), 7.64 (3H, d, J=6.7 Hz), 7.56 (1H, s), 7.48 (1H, t, J=7.5 Hz), 7.27 (1H, t, J=7.4 Hz), 7.19 (2H, d, J=8.6 Hz), 7.06 (1H, d, J=7.7 Hz), 4.76–4.82 (1H, m), 2.20–2.50 (1 1H, m), 2.14 (3H, s), 2.04–2.08 (2H, m), 1.89 (9H, s), 1.58–1.70 (4H, m); RP-HPLC (Delta Pak C18, 5 μm, 300 Å, 15 cm; 5%–85% acetonitrile-0.1M ammonium acetate over 20 min, 1 mL/min) $R_t$ 10.79 min. MS: MH$^+$ 527.

Example 103 cis-3-4-[2-(Aminomethyl)phenoxy]phenyl-1-[4-(4-methylpiperazino)cyclohexyl]-1H-pyrazolo[3,4-d]pyrimidin-4-amine A mixture of cis-2-(4-{4-amino-1-[4-(4-methylpiperazino)cyclohexyl]-1H-pyrazolo[3,4-d]pyrimidin-3-yl}phenoxy)benzonitrile (0.097 g, 0.19 mmol, 1 equiv) and lithium aluminum hydride (0.036 g, 0.95 mmol, 5 equiv) in THF (2 mL) was heated at 66° C. for 2 h. The reaction mixture was allowed to cool to ambient temperature and was partitioned between ice water (30 mL) and CH$_2$Cl$_2$ (50 mL). The organic extract was dried over MgSO$_4$, filtered, and concentrated to afford a yellow solid which was purified by preparative RP-HPLC (Rainin C18, 8 μm, 300 Å, 25 cm; 10%–60% acetonitrile-0.1M ammonium acetate over 20 min, 21 mL/min). The acetonitrile was removed in vacuo and the aqueous mixture was lyopholyzed to afford cis-3-4-[2-(aminomethyl)phenoxy]phenyl-1-[4-(4-methylpiperazino)cyclohexyl]-1H-pyrazolo[3,4-d]pyrimidin-4-amine as a white solid (0.078 g, 0.152 mmol): $^1$H NMR (d$_6$ DMSO, 400 MHz): δ H 8.22 (1H, s), 7.57–7.64 (3H, m), 7.21–7.29 (2H, m), 7.04 (2H, d, J=8.7 Hz), 7.01 (1H, d, J=7.9 Hz), 4.76–4.81 (1H, m), 3.74 (2H, s), 2.20–2.51 (11H, m), 2.14 (3H, s), 2.05–2.08 (2H, m), 1.57–1.70 (4H, m); RP-HPLC (Delta Pak C18, 5 μm, 300 Å, 15 cm; 5%–85% acetonitrile-0.1M ammonium acetate over 20 min, 1 mL/min) $R_t$ 9.85 min. MS: MH$^+$ 513.

Example 104 cis-1-[4-(4-Methylpiperazino)cyclohexyl]-3-4-[2-(2H-1,2,3,4-tetraazol-5-yl)phenoxy]phenyl-1H-pyrazolo[3,4-d]pyrimidin-4-amine Diacetate Salt A mixture of cis-2-(4-{4-amino-1-[4-(4-methylpiperazino)cyclohexyl]-1H-pyrazolo[3,4-d]pyrimidin-3-yl}phenoxy)benzonitrile (0.070 g, 0.14 mmol, 1 equiv) and azidotributyl tin (0.8 mL, 2.4 mmol, 17 equiv) was heated at 85° C. for 80 h. The reaction mixture was allowed to cool to room temperature and was diluted with EtOAc (15 mL). The resulting precipitate was collected by filtration to give a beige solid which was purified by preparative RP-HPLC (Rainin C18, 8 μm, 300 Å, 25 cm; 10%–60% acetonitrile-0.1M ammonium acetate over 20 min, 21 mL/min). The acetonitrile was removed in vacuo and the aqueous portion was treated with saturated aqueous sodium bicarbonate (10 mL) in order to remove residual acetic acid. The aqueous mixture was extracted with CH$_2$Cl$_2$ (25 mL), and the organic extract was dried over MgSO$_4$, filtered, and concentrated to give cis-1-[4-(4-methylpiperazino)cyclohexyl]-3-4-[2-(2H-1,2,3,4-tetraazol-5-yl)phenoxy]phenyl-1H-pyrazolo[3,4-d]pyrimidin-4-amine diacetate salt as a white solid (0.009 g, 0.016 mmol): $^1$H NMR (d$_6$ DMSO, 400 MHz): δ H 8.20 (1H, s), 7.94 (1H, d, J=7.7 Hz), 7.54 (2H, d, J=8.7 Hz), 7.32–7.37 (1H, m), 7.24–7.28 (1H, m), 7.11 (1H, d, J=9.1 Hz), 6.99 (2H, d, J=8.7 Hz), 4.73–4.80 (1H, m), 2.23–2.34 (11H, m), 2.14 (3H, s), 2.05–2.07 (2H, m), 1.68 (6H, s), 1.56–1.65 (4H, m); RP-HPLC (Delta Pak C18, 5 μm, 300 Å, 15 cm; 5%–85% acetonitrile-0.1M ammonium acetate over 20 min, 1 mL/min) $R_t$ 10.86 min. MS: MH$^+$ 552.

Example 105 cis-1-[4-(4-Methylpiperazino)cyclohexyl]-3-[4-(2-nitrophenoxy)phenyl]-1H-pyrazolo[3,4-d]pyrimidin-4-amine Diacetate Salt A mixture of 4-{4-amino-1-[4-(4-methylpiperazino)cyclohexyl]-1H-pyrazolo[3,4-d]pyrimidin-3-yl}phenol (0.200 g, 0.491 mmol, 1 equiv) and 60% sodium hydride (0.020 g, 0.49 mmol, 1 equiv) in dioxane (4.9 mL) was stirred at ambient temperature for 20 minutes. 2-Fluoronitrobenzene (0.06 mL, 0.6 mmol, 1.1 equiv) was added and the reaction mixture was heated at 100° C. for 3 h. Additional sodium hydride (0.010 g, 0.24 mmol, 0.5 equiv) and 2-fluoronitrobenzene (0.02 mL, 0.2 mmol, 0.4 equiv) were added and the reaction mixture was heated at 100° C. for 3 h. The reaction mixture was allowed to cool to room temperature and the resulting solid was removed by filtration with the aid of $CH_2Cl_2$ (10 mL) and EtOAc (10 mL). The filtrate was concentrated to afford a yellow semi-solid which was purified by preparative RP-HPLC (Rainin C18, 8 μm, 300 Å, 25 cm; 10%–60% acetonitrile-0.1M ammonium acetate over 20 min, 21 mL/min). The acetonitrile was removed in vacuo and the aqueous mixture was lyopholyzed to afford cis-1-[4-(4-methylpiperazino)cyclohexyl]-3-[4-(2-nitrophenoxy)phenyl]-1H-pyrazolo[3,4-d]pyrimidin-4-amine diacetate salt as a white solid (0.023 g, 0.043 mmol): $^1$H NMR (d$_6$ DMSO, 400 MHz): δ H 8.23 (1H, s), 8.10 (1H, d, J=8.2 Hz), 7.68–7.73 (3H, m), 7.33–7.40 (1H, m), 7.31 (1H, d, J=7.3 Hz), 7.24 (2H, d, J=8.7 Hz), 4.76–4.82 (1H, m), 2.26–2.51 (1H, m), 2.24 (3H, s), 2.17–2.21 (2H, m), 2.05 (6H, s), 1.56–1.71 (4H, m); RP-HPLC (Delta Pak C18, 5 μm, 300 Å, 15 cm; 5%–85% acetonitrile-0.1M ammonium acetate over 20 min, 1 mL/min) R$_t$ 13.09 min.

Example 106 cis-3-[4-(2-Aminophenoxy)phenyl]-1-[4-(4-methylpiperazino)cyclohexyl]-1H-pyrazolo[3,4-d]pyrimidin-4-amine A mixture of cis-1-[4-(4-methylpiperazino)cyclohexyl]-3-[4-(2nitrophenoxy)phenyl]-1H-pyrazolo[3,4-d]pyrimidin-4-amine (0.059 g, 0.091 mmol, 1 equiv), glacial acetic acid (0.03 mL, 0.5 mmol, 5 equiv), and 10% Pd-C (0.024 g, 0.4 wt/wt equiv) in ethanol (1 mL) was stirred at room temperature under a positive pressure of $H_2$ for 16 h. Solids were removed by filtration with the aid of $CH_2Cl_2$ (10 mL) and the filtrate was concentrated to afford a yellow oil. The residue was purified by preparative RP-HPLC (Rainin C18, 8 μm, 300 Å, 25 cm; 10%–60% acetonitrile-0.1M ammonium acetate over 20 min, 21 mL/min). The acetonitrile was removed in vacuo and the aqueous mixture was lyopholyzed to afford cis-3-[4-(2-aminophenoxy)phenyl]-1-[4-(4-methylpiperazino)cyclohexyl]-1H-pyrazolo[3,4-d]pyrimidin-4-amine as an off-white solid (0.018 g, 0.036 mmol): $^1$H NMR (d$_6$ DMSO, 400 MHz): δ H 8.22 (1H, s), 7.59 (2H, d, J=8.6 Hz), 7.05 (2H, d, J=8.7 Hz), 6.85–6.98 (3H, m), 6.58–6.61 (1H, m), 4.93 (2H, bs), 4.78–4.80 (1H, m), 2.20–2.50 (11H, m), 2.14 (3H, s), 2.05–2.09 (2H, m), 1.55–1.70 (4H, m); RP-HPLC (Delta Pak C18, 5 μm, 300 Å, 15 cm; 5%–85% acetonitrile-0.1M ammonium acetate over 20 min, 1 mL/min) R$_t$ 12.00 min. MS: MH$^+$ 499.

Example 107

[2-(4-Amino-1-cyclopentyl-1H-pyrazolo[3,4-d]pyrimidin-3-yl)-5-phenoxyphenyl]methanol a) (2-Bromo-5-phenoxyphenyl)methanol To a solution of 3-phenoxyphenyl methanol (4.0 g, 0.020 mol) in anhydrous acetonitrile was added 1-bromo-2,5-pyrrolidinedione (3.73 g, 0.021 mol) at room temperature. The mixture was stirred at room temperature for one and a half hour under an atmosphere of nitrogen. The solvents were removed under the reduced pressure. Tetrachloromethane (100 mL) was added to the residue, and the mixture was filtered. The filtrate was concentrated into the residue, and the residue was purified by flash chromatography on silica gel using ethyl acetate/n-heptane (1:5) as mobile phase to yield (2-bromo-5-phenoxyphenyl)methanol (4.7 g, 0.017 mol): RP-HPLC (Hypersil C18, 5 μm, 250×4.6 mm; 25%–100% over 10 min with 0.1 M ammonium acetate, 1 mL/min) R$_t$ 11.7 min. TLC (ethyl acetate/heptane 1:5) R$_f$ 0.18.

b) 5-Phenoxy-1,3-dihydro-2,1-benzoxaborol-1-ol

A solution of n-butyl lithium in n-hexanes (2.24 M, 8.6 mL, 0.019 mol) was slowly added to a solution of (2-bromo-5-phenoxyphenyl)methanol (2.21 g, 0.0079 mol) in anhydrous tetrahydrofuran (50 mL) at –78° C. under an atmosphere of nitrogen. The reaction was stirred for thirty minutes at –78° C., then stirred for twenty minutes at –25° C. The reaction was cooled to –50° C. and triisopropylborate (4.075 g, 0.0216 mol) was slowly added. The reaction was warmed to room temperature and was stirred for one hour. An 1 N aqueous solution of hydrochloric acid (20 mL) was added to achieve pH 5, then the reaction was stirred at room temperature for one hour. The reaction mixture was extracted with ethyl ether (3×40 mL). The combined organic extracts were washed with water (60 mL) and brine (60 mL) and dried over sodium sulfate. The solvents were evaporated under the reduced pressure to give a residue, and the residue was purified by flash column chromatography on silica using ethyl acetate/n-heptane (1:5) followed by ethyl acetate/n-heptane (1:4) as mobile phase to yield 5-phenoxy-1,3-dihydro-2,1-benzoxaborol-1-ol (1.3 g, 0.0058 mol).

RP-HPLC (Hypersil C18, 5 μm, 250×4.6 mm; 25%–100% over 10 min with 0.1 M ammonium acetate, 1 mL/min) R$_t$ 10.8 min. TLC (ethyl acetate/heptane 1:2) R$_f$ 0.24 c) [2-(4-Amino-1-cyclopentyl-1H-pyrazolo[3,4-d]pyrimidin-3-yl)-5-phenoxyphenyl]methanol A mixture of 1-cyclopentyl-3-iodo-1H-pyrazolo[3,4-d]pyrimidin-4-amine (0.36 g, 0.0011 mol), 5-phenoxy-1,3-dihydro-2,1-benzoxaborol-1-ol (0.30 g, 0.0013 mol), tetrakis (triphenylphophine)palladium (0.077 g, 0.000067 mol) and sodium carbonate monohydrate (0.34 g, 0.0028 mol) in ethylene glycol dimethyl ether (7 mL) and water (5 mL) was heated at 80° C. under an atmosphere of nitrogen for seventeen hours. The mixture was allowed to cool to ambient temperature, and the solvent was removed under reduced pressure. The residue was partitioned between ethyl acetate (20 mL) and aqueous saturated solution of sodium carbonate (20 mL). The aqueous layer was further extracted with ethyl acetate (3×20 mL). The organic solvent was removed under reduced pressure. Ethyl acetate (15 mL) was added to the residue and white precipitate was formed. The solid was filtered and washed with acetone (2×15 mL) and dichloromethane (1×15 mL) to yield [2-(4-amino-1-cyclopentyl-1H-pyrazolo[3,4-d]pyrimidin-3-yl)-5-phenoxyphenyl]methanol (0.267 g, 0.00067 mol):

$^1$H NMR (DMSO-d$_6$, 400 MHz) δ 8.23 (s, 1H), 7.46 (m, 2H), 7.38 (m, 1H), 7.28 (m, 1H), 7.13 (m, 3H), 7.00 (m, 1H); 5.28 (m, 1H), 5.17 (m, 1H), 4.48 (d, 2H), 2.08 (br, 2H), 1.98 (br, 2H), 1.86 (br, 2H), 1.68 (br, 2H). RP-HPLC (Hypersil C18, 5 μm, 250×4.6 mm; 25%–100% over 10 min with 0.1 M ammonium acetate, 1 mL/min) R$_t$ 10.5 min. MS: MH$^+$ 402.

Example 108 cis-1-(Aminomethyl)-4-[4-amino-3-(4-phenoxyphenyl)-1H-pyrazolo[3,4-d]pyrimidin-1-yl]-1-cyclohexanol Maleate a) cis-1-(1-Oxaspiro[2.5]oct-6-yl)-3-(4-phenoxyphenyl)-1H-pyrazolo[3,4-d]pyrimidin-4-amine A mixture of trimethyl sulfoxonium iodide (0.33 g, 0.0015 mol) and sodium hydride (60% in oil, 0.055 g, 0.00138 mol) in methyl sulfoxide (4 mL) was stirred at room temperature under an atmosphere of nitrogen for thirty minutes. The reaction mixture was cooled to 10° C. and 4-[4-amino-3-(4-phenoxyphenyl)-1H-pyrazolo[3,4-d]pyrimidin-1-yl]-1-cyclohexanone (0.5 g, 0.00125 mol) in methyl sulfoxide (2 mL) was added. The reaction mixture was stirred at room temperature under an atmosphere of nitrogen for two hours. The mixture was partitioned between saturated aqueous ammonium chloride solution (20 mL) and dichloromethane, and the aqueous layer was extracted with dichloromethane (3×20 mL). The combined organic extracts were washed with water and brine and dried over sodium sulfate. The solvent was removed under reduced pressure to cis-1-(1-oxaspiro[2.5]oct-6-yl)-3-(4-phenoxyphenyl)-1H-pyrazolo[3,4-d]pyrimidin-4-amine (0.527 g, 0.00125 mmol).

$^1$H NMR (DMSO-d$_6$, 400 MHz) δ 8.25 (s, 1H), 7.68 (d, 2H), 7.42 (m, 2H), 7.19(m, 5H), 4.90 (br, 1H), 2.70 (s, 2H), 2.17 (br, 4H), 1.97 (br, 2H), 1.32 (br, 2H). RP-HPLC (Hypersil C18, 5 μm, 250×4.6 mm; 25%–100% over 23 min with 0.1 M ammonium acetate, 1 mL/min) R$_t$ 11.7 min. MS: MH$^+$ 413.

b) cis-1-(Aminomethyl)-4-[4-amino-3-(4-phenoxyphenyl)-1H-pyrazolo[3,4-d]pyrimidin-1-yl]-1-cyclohexanol Maleate Cis-1-(1-oxaspiro[2.5]oct-6-yl)-3-(4-phenoxyphenyl)-1H-pyrazolo[3,4-d]pyrimidin-4-amine (0.62 g, 0.0015 mol) in ammonia (2 M in methanol, 15 mL) and a solution of 20% N,N-dimethylformamide in isopropanol (15 mL) was heated at 65° C. in a pressure vessel for eighteen hours. The mixture was allowed to cool to ambient temperature and the solvent was removed under reduced pressure. The residue was purified by flash chromatography on silica gel using ammonium hydroxide/methanol/dichloromethane (2:5:93) followed by ammonium hydroxide/methanol/dichloromethane (2:8:90)as mobile phase to yield cis-1-(aminomethyl)-4-[4-amino-3-(4-phenoxyphenyl)-1H-pyrazolo[3,4-d]pyrimidin-1-yl]-1-cyclohexanol (0.11 g, 0.00026 mol). The compound was dissolved in ethyl acetate (10 mL) at 40° C. and a preheated solution of maleic acid (0.060 g, 0.000512 mol) in ethyl acetate (2 mL) was added. The mixture was heated at 40° C. for ten minutes, cooled to ambient temperature and the precipitate collected by filtration, washed with ethyl acetate and dried to give cis-1-(aminomethyl)-4-[4-amino-3-(4-phenoxyphenyl)-1H-pyrazolo[3,4-d]pyrimidin-1-yl]-1-cyclohexanol maleate (0.140 g, 0.00026 mol).

$^1$H NMR (DMSO-d$_6$, 400 MHz) δ 8.24 (s, 1H), 7.73 (br, 3H), 7.64 (d, 2H), 7.42 (m, 2H), 7.13 (m, 5H), 6.01 (s, 2H), 4.94 (s, 1H), 4.70 (br, 1H), 2.79 (s, 2H), 2.36 (br, 2H), 1.76 (br, 4H), 1.58 (br, 2H). RP-HPLC (Delta Pak C18, 5 μm, 300 A, 15 cm; 5%–85% acetonitrile-0.1M ammonium acetate over 10 min, 1 mL/min) Rt 8.9 min. MS: MH$^+$ 431.

Example 109 cis-1-(2-Aminoethyl)-4-[4-amino-3-(4-phenoxyphenyl)-1H-pyrazolo[3,4-d]pyrimidin-1-yl]-1-cyclohexanol Maleate a) cis-{4-[4-Amino-3-(4-phenoxyphenyl)-1H-pyrazolo[3,4-d]pyrimidin-1-yl]-1-hydroxycyclohexyl}methyl Cyanide To a mixture of cis-1-(1-oxaspiro[2.5]oct-6-yl)-3-(4-phenoxyphenyl)-1H-pyrazolo[3,4-d]pyrimidin-4-amine (4.4 g, 0.011 mol) and lithium perchlorate (1.7 g, 0.016 mol) was added potassium cyanide (1.04 g, 0.016 mol) in acetonitrile (600 ml). The reaction mixture was refluxed for six hours. The solvent was removed under reduced pressure. The mixture was diluted with water (200 mL) and extracted with diethyl ether (2×300 mL). The combined organic phases were washed with water and brine and dried over magnesium sulfate. The solvent was removed under reduced pressure to give cis-{4-[4-amino-3-(4-phenoxyphenyl)-1H-pyrazolo[3,4-d]pyrimidin-1-yl]-1-hydroxycyclohexyl} methyl cyanide (4.30 g, 0.0098 mol).

RP-HPLC (Delta Pak C18, 5 μm, 300 A, 15 cm; 5%–85% acetonitrile-0.1M ammonium acetate over 10 min, 1 mL/min) Rt 10.4 min. MS: MH$^+$ 441.

b) cis-1-(2-Aminoethyl)-4-[4-amino-3-(4-phenoxyphenyl)-1H-pyrazolo[3,4-d]pyrimidin-1-yl]-1-cyclohexanol Maleate To cis-{4-[4-amino-3-(4-phenoxyphenyl)-1H-pyrazolo[3,4-d]pyrimidin-1-yl]-1-hydroxycyclohexyl} methyl cyanide (3.4 g, 0.0077 mol).in methanol (100 ml) and ammonium hydroxide (5 mL) was added Raney® nickel (50% slurry in water, 3 mL). The mixture was stirred eighteen hours under hydrogen (1 atm). The reaction mixture was filtered through celite and the solvent was removed in vacuo to give crude cis-1-(2-aminoethyl)-4-[4-amino-3-(4-phenoxyphenyl)-1H-pyrazolo[3,4-d]pyrimidin-1-yl]-1-cyclohexanol (1.82 g, 0.0041 mol). 0.8 g of crude cis-1-(2-aminoethyl)-4-[4-amino-3-(4-phenoxyphenyl)-1H-pyrazolo[3,4-d]pyrimidin-1-yl]-1-cyclohexanol was purified by flash chromatography on silica gel using ammonium hydroxide/methanol/dichloromethane (2:3:95) followed by ammonium hydroxide/methanol/dichloromethane (2:12:86) as mobile phase to yield cis-1-(2-aminoethyl)-4-[4-amino-3-(4-phenoxyphenyl)-1H-pyrazolo[3,4-d]pyrimidin-1-yl]-1-cyclohexanol (0.423 g, 0.00095 mol). This compound was dissolved in ethyl acetate (40 mL) at 40° C. and a preheated solution of maleic acid (0.13 g, 0.0014 mol) in ethyl acetate (5 mL) was added. The mixture was heated at 40° C. for 10 minutes, cooled to ambient temperature and the precipitate collected by filtration, washed with ethyl acetate and dried to give cis-1-(2-aminoethyl)-4-[4-amino-3-(4-phenoxyphenyl)-1H-pyrazolo[3,4-d]pyrimidin-1-yl]-1-cyclohexanol maleate (0.186 g, 0.00033 mol).

$^1$H NMR (DMSO-d$_6$, 400 MHz) δ 8.23 (s, 1H), 7.67 (m, 2H), 7.60 (br, 3H), 7.42 (m, 2H), 7.16 (m, 5H), 6.01 (s, 2H), 4.73 (br, 1H), 4.53 (s, 1H), 2.92 (br, 2H), 2.38 (br, 2H), 1.72 (br, 6H), 1.54 (br, 2H). RP-HPLC (Delta Pak C18, 5 μm, 300 A, 15 cm; 5%–85% acetonitrile-0.1M ammonium acetate over 10 min, 1 mL/min) R$_t$ 9.1 min. MS: MH$^+$ 445.

c) cis-2-{4-[4-Amino-3-(4-phenoxyphenyl)-1H-pyrazolo[3,4-d]pyrimidin-1-yl]-1-hydroxycyclohexyl}acetamide To a mixture of cis-{4-[4-amino-3-(4-phenoxyphenyl)-1H-pyrazolo[3,4-d]pyrimidin-1-yl]-1-hydroxycyclohexyl} methyl cyanide (0.972 g, 0.0022 mol) and potassium carbonate (1.28 g, 0.00093) in methyl sulfoxide (20 mL) was slowly added a 30% sol;ution of hydrogen peroxide in water (3 mL) at 20° C. The reaction mixture was stirred at room temperature for eighteen hours. The reaction flask was placed in an ice bath, and ice water (20 mL) was slowly poured into the reaction. The mixture was extracted with ethyl acetate (2×30 mL). The combined organic layers were washed with water and brine and dried over magnesium sulfate. The solvent was removed in vacuo. The residue was triturated with dichloromethane (8 mL), and the solid was filtered to give cis-2-{4-[4-amino-3-(4-phenoxyphenyl)-1H-pyrazolo[3,4-d]pyrimidin-1-yl]-1-hydroxycyclohexyl}acetamide (0.542 g, 0.0012 mol).

¹H NMR (DMSO-d₆, 400 MHz) δ 8.24 (s, 1H), 7.67 (m, 2H), 7.42 (m, 3H), 7.16 (m, 5H), 7.06 (s, 1H), 4.95 (br, 1H), 4.65 (m, 1H), 2.39 (m, 2H), 2.24 (s, 2H), 1.70 (br, 6H). RP-HPLC (Delta Pak C18, 5 μm, 300 A, 15 cm; 5%–85% acetonitrile-0.1M ammonium acetate over 10 min, 1 mL/min) R$_t$ 9.6 min. MS: MH⁺ 459.

Example 110

1-(3-Azetanyl)-3-(4-phenoxyphenyl)-1H-pyrazolo[3, 4-d]pyrimidin-4-amine a) tert-Butyl 3-hydroxy-1-azetanecarboxylate To a mixture of 1-benzhydryl-3-azetanol (7.5 g, 0.031 mol) and di-tert-butyl dicarbonate (10.3 g, 0.047 mol), was added 20% palladium hydroxide on carbon (1.0 g) in ethyl acetate (200 mL). The mixture was shaken under hydrogen at room temperature for 20 hours in a Parr-hydrogenation apparatus. The mixture was filtered through celite, and the filtrate was concentrated under reduced pressure. The residue was purified by flash chromatography on silica gel using dichloromethane followed by methanol/dichloromethane (5:95) as mobile phase to yield tert-butyl 3-hydroxy-1-azetanecarboxylate (5.015 g, 0.029 mol).

¹H NMR (Chloroform-d, 400 MHz) δ 4.59 (m, 1H), 4.14 (m, 2H), 3.80 (m, 2H), 2.55 (br, 1H), 1.50 (s, 9H); TLC (methanol/dichloromethane=2:98) R$_f$ 0.13.

b) tert-Butyl 3-[(methylsulfonyl)oxy]-1-azetanecarboxylate

To a solution of tert-butyl 3-hydroxy-1-azetanecarboxylate (4.0 g, 0.023 mol) in anhydrous pyridine (50 mL), methanesulfonyl chloride (5.3 g, 0.046 mol) was added at −20° C. under an atmosphere of nitrogen. The yellow heterogeneous mixture was stirred between −20° C. to −30° C. for one hour, then between 0° C. to −5° C. for two hours. The mixture was poured into ice water (50 mL). The water phase was extracted with ethyl acetate (2×50 mL). The combined organic extracts were washed with water (1×50 mL), 5% aqueous citric acid (4×50 mL), water (1×50 mL), saturated sodium bicarbonate (1×50 mL), and brine (1×50 mL) and dried over sodium sulfate. The solvent was removed under reduced pressure to yield tert-butyl 3-[(methylsulfonyl)oxy]-1-azetanecarboxylate as brownish oil (4.85 g, 0.019 mol).

¹H NMR (Chloroform-d, 400 MHz) δ 5.19 (m, 1H), 4.25 (m, 2H), 4.07 (m, 2H), 3.04 (s, 3H), 1.42 (s, 9H); TLC (methanol/dichloromethane=2:98) R$_f$ 0.28.

c) tert-Butyl 3-[4-amino-3-(4-phenoxyphenyl)-1H-pyrazolo[3,4-d]pyrimidin-1-yl]-1-azetanecarboxylate To a mixture of 3-(4-phenoxyphenyl)-1H-pyrazolo[3,4-d]pyrimidin-4-amine (1.0 g, 0.0033 mol) and cesium carbonate (2.14 g, 0.0066 mol) in anhydrous N,N-dimethylformamide (30 mL) tert-butyl 3-[(methylsulfonyl)oxy]-1-azetanecarboxylate (1.66 g, 0.0066 mol) in anhydrous N,N-dimethylformamide (20 mL) was added at room temperature under an atmosphere of nitrogen. The mixture was stirred at 75° C. for twenty-two hours. The mixture was poured into ice water (50 mL). The water phase was extracted with ethyl acetate (3×50 mL). The combined organic extracts were washed with water (1×70 mL) and brine (1×70 mL) and dried over sodium sulfate. The solvent was removed under reduced pressure. The residue was purified by flash chromatography on silica gel using dichloromethane followed by methanol/dichloromethane (5:95) as mobile phase to yield tert-butyl 3-[4-amino-3-(4-phenoxyphenyl)-1H-pyrazolo[3,4-d]pyrimidin-1-yl]-1-azetanecarboxylate (0.81 g, 0.0018 mol).

¹H NMR (DMSO-d₆, 400 MHz) δ 8.25 (s, 1H), 7.69 (d, 2H), 7.44 (m, 2H), 7.19 (m, 5H), 5.70 (br, 1H), 4.35 (br, 4H), 1.39 (s, 9H). RP-HPLC (Hypersil C18, 5 μm, 250×4.6 mm; 25%–100% over 10 min with 0.1 M ammonium acetate, 1 mL/min) R$_t$ 12 min. MS: MH⁺ 459.

1-(3-Azetanyl)-3-(4-phenoxyphenyl)-1H-pyrazolo[3,4-d]pyrimidin-4-amine

To a solution of tert-butyl 3-[4-amino-3-(4-phenoxyphenyl)-1H-pyrazolo[3,4-d]pyrimidin-1-yl]-1-azetanecarboxylate (0.81 g, 0.0018 mol) in dichloromethane (5 mL) was slowly added a 20% solution of trifluoroacetic acid in dichloromethane (10 mL) at 0° C. under an atmosphere of nitrogen. The mixture was warmed to room temperature and stirred for eighteen hours. The solvent was removed under reduced pressure. An aqueous solution of 5 N sodium hydroxide was added to the residue to pH 11 at 0° C. The water phase was extracted with ethyl acetate (2×30 mL). The combined organic extracts were washed with water (1×60 mL) and brine (1×60 mL) and dried over sodium sulfate. The solvent was removed under reduced pressure to yield 1-(3-azetanyl)-3-(4-phenoxyphenyl)-1H-pyrazolo[3,4-d]pyrimidin-4-amine (0.44 g, 0.0012 mol).

¹H NMR (DMSO-d₆, 400 MHz) δ 8.28 (s, 1H), 7.70 (d, 2H), 7.45 (m, 2H), 7.18 (m, 5H), 5.70 (m, 1H), 4.20 (m, 2H), 4.05 (m, 2H); RP-HPLC (Delta Pak C18, 5 μm, 300 A, 15 cm; 5%–85% acetonitrile-0.1M ammonium acetate over 10 min, 1 mL/min) Rt 8.8 min. MS: MH⁺ 359.

General Procedure:
Alkylation of 1-(3-Azetanyl)-3-(4-phenoxyphenyl)-1H-pyrazolo[3,4-d]pyrimidin-4-amine To a mixture of 1-(3-azetanyl)-3-(4-phenoxyphenyl)-1H-pyrazolo[3,4-d]pyrimidin-4-amine (0.05 g, 0.00014 mol, 1 eq.) and potassium carbonate (0.058 g, 0.00042 mol, 3 eq.) in anhydrous acetonitrile was added the corresponding alkyl bromide (0.00014 mol, 1 eq.) at room temperature. The mixture was stirred for eighteen hours. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield the corresponding alkyl azetidines.

Example 111 a) Alkyl Bromide: 2-Bromo-1-ethanol 2-{3-[4-Amino-3-(4-phenoxyphenyl)-1H-pyrazolo[3,4-d]pyrimidin-1-yl]-1-azetanyl}-1-ethanol ¹H NMR (DMSO-d₆, 400 MHz) δ 8.24 (s, 1H), 7.69 (d, 2H), 7.44 (m, 2H), 7.14 (m, 5H), 5.41 (m, 1H), 4.69 (br, 1H), 3.83 (m, 2H), 3.63 (m, 2H), 3.42 (m, 2H), 2.62 (m, 2H). RP-HPLC (Delta Pak C18, 5 μm, 300 A, 15 cm; 5%–85% acetonitrile-0.1M ammonium acetate over 10 min, 1 mL/min) Rt 9.0 min. MS: MH⁺ 403.

Example 112 b) Alkyl Bromide: 2-Bromoethyl Methyl Ether 1-[1-(2-Methoxyethyl)-3-azetanyl]-3-(4-phenoxyphenyl)-1H-pyrazolo[3,4-d]pyrimidin-4-amine Acetate ¹H NMR (DMSO-d₆, 400 MHz) δ 9.09 (br, 1H), 8.27 (s, 1H), 7.67 (d, 2H), 7.42 (m, 2H), 7.15 (m, 5H), 5.69 (m, 1H), 4.13 (m, 2H), 3.94 (m, 2H), 3.51 (m, 2H), 3.36 (s, 3H), 2.95 (m, 2H), 2.08 (s, 3H). RP-HPLC (Delta Pak C18, 5 μm, 300 A, 15 cm; 5%–85% acetonitrile-0.1M ammonium acetate over 10 min, 1 mL/min) R$_t$ 9.6 min. MS: MH⁺ 417.

Example 113 c) Alkyl Bromide: 1-Bromo-2-(2-methoxyethoxy) ethane 1-{1-[2-(2-Methoxyethoxy)ethyl]-3-azetanyl}-3-(4-phenoxyphenyl)-1H-pyrazolo[3,4-d]pyrimidin-4-amine $^1$H NMR (DMSO-d$_6$, 400 MHz) δ 8.24 (s, 1H), 7.69 (d, 2H), 7.44 (m, 2H), 7.14 (m, 5H), 5.41 (m, 1H), 3.79 (m, 2H), 3.62 (m, 2H), 3.44 (br, 6H), 3.23 (s, 3H), 2.69 (br, 2H). RP-HPLC (Delta Pak C18, 5 μm, 300 A, 15 cm; 5%–85% acetonitrile-0.1M ammonium acetate over 10 min, 1 mL/min) Rt 9.6 min. MS: MH$^+$ 461.

Example 114

1-[1-(1-Methyl-4-piperidyl)-3-azetanyl]-3-(4-phenoxyphenyl)-1H-pyrazolo[3,4-d]pyrimidin-4-amine A mixture of 1-(3-azetanyl)-3-(4-phenoxyphenyl)-1H-pyrazolo[3,4-d]pyrimidin-4-amine (0.06 g, 0.00017 mol), 1-methyl-4-piperidinone (0.057 g, 0.0005 mol), and acetic acid (0.03 g, 0.0005 mol) in dichloroethane (2.5 mL) was stirred at room temperature under an atmosphere of nitrogen for one and a half hours. Sodium triacetoxyborohydride (0.072 g, 0.00034 mol) was added to the mixture and stirred at ambient temperature under an atmosphere of nitrogen for two hours. The solvent was removed under reduced pressure, and the residue was purified by flash chromatography on silica gel using ammonium hydroxide/methanol/dichloromethane (2:15:83) as mobile phase to yield 1-[1-(1-methyl-4-piperidyl)-3-azetanyl]-3-(4-phenoxyphenyl)-1H-pyrazolo[3,4-d]pyrimidin-4-amine (0.029 g, 0.000064 mol).

$^1$H NMR (Chloroform-d, 400 MHz) δ 8.38 (s, 1H), 7.68 (d, 2H), 7.42 (m, 2H), 7.18 (m, 3H), 7.08 (d, 2H), 5.64 (m, 1H), 5.57 (br, 2H), 3.93 (m, 2H), 3.73 (m, 2H), 2.83 (br, 2H), 2.40 (br, 3H), 2.00 (br, 1H), 1.78 (br, 4H), 1.46 (br, 2H). RP-HPLC (Delta Pak C18, 5 μm, 300 A, 15 cm; 5%–85% acetonitrile-0.1M ammonium acetate over 10 min, 1 mL/min) Rt 8.9 min. MS: MH$^+$ 456.

Example 115

1-{1-[(1-Methyl-1H-2-imidazolyl)methyl]-3-azetanyl}-3-(4-phenoxyphenyl)-1H-pyrazolo[3,4-d]pyrimidin-4-amine A mixture of 1-(3-azetanyl)-3-(4-phenoxyphenyl)-1H-pyrazolo[3,4-d]pyrimidin-4-amine (0.06 g, 0.00017 mol), 1-methyl-1H-2-imidazolecarboxylic acid (0.056 g, 0.0005 mol), and acetic acid (0.03 g, 0.0005 mol) in dichloroethane (2.5 mL) was stirred at room temperature under an atmosphere of nitrogen for one and a half hours. Sodium triacetoxyborohydride (0.072 g, 0.00034 mol) was added into the mixture and stirred at ambient temperature under an atmosphere of nitrogen for two hours. The solvent was removed under reduced pressure, and the residue was purified by RP-HPLC (Hypersilprep HS C18, 8 μm, 250×21.1 mm; 5%–100% over 25 min with 0.1 M ammonium acetate, 21 mL/min) to yield 1-{1-[(1-methyl-1H-2-imidazolyl)methyl]-3-azetanyl}-3-(4-phenoxyphenyl)-1H-pyrazolo[3,4-d]pyrimidin-4-amine (0.020 g, 0.000044 mol).

$^1$H NMR (Chloroform-d, 400 MHz) δ 8.35 (s, 1H), 7.67 (d, 2H), 7.42 (m, 2H), 7.20 (d, 3H), 7.18 (d, 2H), 6.93 (s, 1H), 6.85 (s, 1H), 5.59 (m, 3H), 3.93 (m, 6H), 3.85 (s, 3H). RP-HPLC (Delta Pak C18, 5 μm, 300 A, 15 cm; 5%–85% acetonitrile-0.1M ammonium acetate over 10 min, 1 mL/min) Rt 9.5 min. MS: MH$^+$ 453.

Example 116

1-{3-[4-Amino-3-(4-phenoxyphenyl)-1H-pyrazolo[3,4-d]pyrimidin-1-yl]-1-azetanyl}-1-ethanone To a mixture of 1-(3-azetanyl)-3-(4-phenoxyphenyl)-1H-pyrazolo[3,4-d]pyrimidin-4-amine (0.020 g, 0.000056 mol) and potassium carbonate (0.016 g, 0.00012 mol) in anhydrous N,N,-dimethylformamide (1 mL) was added acetic anhydride (0.009 g, 0.000084 mol) at room temperature. The reaction mixture was stirred for 1hours. The solvent was removed under reduced pressure. The residue was purified by RP-HPLC (Hypersilprep HS C18, 5 μm, 100×20 mm; 20%–85% over 7.5 min with 0.05 M ammonium acetate, 251 mL/min) to yield 1-{3-[4-amino-3-(4-phenoxyphenyl)-1H-pyrazolo[3,4-d]pyrimidin-1-yl]-1-azetany}-1-ethanone (0.014 g, 0.000035 mol).

$^1$H NMR (DMSO-d$_6$, 400 MHz) δ 8.27 (s, 1H), 7.71 (d, 2H), 7.44 (m, 2H), 7.17 (m, 5H), 5.72 (m, 1H), 4.66 (m, 1H), 4.58 (m, 1H), 4.35 (m, 1H), 4.29 (m, 1H), 1.84 (s, 3H). RP-HPLC (Delta Pak C18, 5 μm, 300 A, 15 cm; 5%–85% acetonitrile-0.1M ammonium acetate over 10 min, 1 mL/min) Rt 9.9 min. MS: MH$^+$ 401.

Example 117 cis 3-[4-Amino-3-(4-phenoxyphenyl)-1H-pyrazolo[3,4-d]pyrimidin-1-yl]-1-cyclobutanol a) 3-Propylidenecyclobutyl Methanesulfonate A solution of 3-propylidene-1-cyclobutanol (0.344 g, 0.00307 mol) in pyridine (5 mL) was cooled to 0° C. Methanesulfonyl chloride (0.422 g, 0.00369 mol) was added dropwise, keeping the temperature below 2° C. The mixture was stirred for two hours, and then poured into ice water (15 mL) and extracted with ethyl ether (2×10 mL). The combined organic layers were washed with water (3×10 mL). The organic layer was dried over magnesium sulfate and the solvent was removed in vacuo to give 3-propylidenecyclobutyl methanesulfonate (0.492 g, 0.00221 mol) as a yellow oil.

$^1$H NMR (DMSO-d$_6$, 400 MHz) δ 5.25–5.29 (m, 1H), 4.98–5.04 (m, 1H), 3.17 (s, 3H), 2.98–3.16 (m, 2H), 2.78–2.96 (m, 2H), 1.86–1.91 (m, 2H), 0.91 (t, 3H).

b) 3-(4-Phenoxyphenyl)-1-(3-propylidenecyclobutyl)-1H-pyrazolo[3,4-d]pyrimidin-4-amine.

A solution of 3-(4-phenoxyphenyl)-1H-pyrazolo[3,4-d]pyrimidin-4-amine (0.743 g, 0.00245 mol) in N,N-dimethylformamide (20 mL) was reacted with 3-propylidenecyclobutyl methanesulfonate (0.699 g, 0.00367 mol) and cesium carbonate (0.866 g, 0.00367 mol) at 70° C. for three days. The reaction mixture was poured into water (30 mL) and extracted with ethyl acetate (3×15 mL). The combined organic layers were washed with water (2×20 mL) and brine (20 mL). The organic layer was dried over magnesium sulfate and the solvent was removed in vacuo. The residue was purified by flash column chromatography on silica using dichloromethane/methanol (98:2). The solvent was removed in vacuo to give 3-(4- phenoxyphenyl)-1-(3-propylidenecyclobutyl)-1H-pyrazolo[3,4-d]pyrimidin-4-amine (0.655 g, 0.00165 mol) as a tan solid.

$^1$H NMR (DMSO-d$_6$, 400 MHz) δ 8.25 (s, 1H), 7.69 (d, 2H), 7.44 (t, 2H), 7.10–7.19 (m, 5H), 5.35–5.40 (m, 1H), 5.38–5.33 (m, 1H), 3.09–3.38 (m, 4H) 1.90–1.97 (m, 2H), 0.96 (t, 3H); MS: MH$^+$ 398; TLC (dichloromethane/methanol 95:5) R$_f$ 0.52.

c) 3-[4-Amino-3-(4-phenoxyphenyl)-1H-pyrazolo[3,4-d]pyrimidin-1-yl]-1-cyclobutanone A solution of 3-(4-phenoxyphenyl)-1-(3-propylidenecyclobutyl)-1H-pyrazolo[3,4-d]pyrimidin-4-amine (0.156 g, 0.00039 mol) in dichloromethane (25 mL) was cooled to −78° C. and ozone was bubbled in until the solution turned blue. The reaction mixture was stirred five minutes and nitrogen gas was bubbled in until the blue color disappeared. Dimethyl sulfide (0.12 mL, 0.097 g, 0.00157 mol) was added and the mixture was allowed to come to room temperature. The solvent was removed in vacuo to give 3-[4-amino-3-(4-phenoxyphenyl)-1H-pyrazolo[3,4-d]pyrimidin-1-yl]-1-cyclobutanone (0.144 g, 0.00038 mol) as a tan solid.

$^1$H NMR (DMSO-d$_6$, 400 MHz) δ 8.29 (s, 1H), 7.69 (d, 2H), 7.44 (t, 2H), 7.11–7.22 (m, 5H), 5.61–5.66 (m, 1H), 3.65–3.74 (m, 4H); MS: MH$^+$ 372; TLC (dichloromethane/methanol=90:10) R$_f$ 0.62.

cis 3-[4-Amino-3-(4-phenoxyphenyl)-1H-pyrazolo[3,4-d]pyrimidin-1-yl]-1-cyclobutanol A solution of 3-[4-amino-3-(4-phenoxyphenyl)-1H-pyrazolo[3,4-d]pyrimidin-1-yl]-1-cyclobutanone (0.208 g, 0.00056 mol) in tetrahydrofuran (10 mL) and absolute ethanol (5 mL) was reacted with sodium borohydride (0.021 g, 0.00056 mol) at room temperature for four hours. Added water (5 mL) and extracted with ethyl acetate (3×15 mL). The combined organics were dried over magnesium sulfate, and the solvent was removed in vacuo. The residue was purified by flash column chromatography on silica using dichloromethane/methanol (98:2). The solvent was removed in vacuo to give cis 3-[4-amino-3-(4-phenoxyphenyl)-1H-pyrazolo[3,4-d]pyrimidin-1-yl]-1-cyclobutanol (0.090 g, 0.00024 mol) as a white solid.

$^1$H NMR (DMSO-d$_6$, 400 MHz) δ 8.23 (s, 1H), 7.68 (d, 2H), 7.44 (t, 2H), 7.11–7.22 (m, 5H), 5.31 (d, 1H), 4.82–4.89 (m, 1H), 4.04–4.10 (m, 1H), 2.70–2.73 (m, 2H), 2.50–2.60 (m, 2H); RP-HPLC (Delta Pak C18, 5 μm, 300 A, 15 cm; 5%–85% acetonitrile-0.1M ammonium acetate over 20 min, 1 mL/min) R$_t$ 14.50 min.; MS: MH$^+$ 374.

Example 118 trans 3-[4-Amino-3-(4-phenoxyphenyl)-1H-pyrazolo[3,4-d]pyrimidin-1-yl]-1-cyclobutanol a) trans 3-[4-Amino-3-(4-phenoxyphenyl)-1H-pyrazolo[3,4-d]pyrimidin-1-yl]cyclobutyl 4-nitrobenzoate.

A solution of cis 3-[4-amino-3-(4-phenoxyphenyl)-1H-pyrazolo[3,4-d]pyrimidin-1-yl]-1-cyclobutanol (0.113 g, 0.000302 mol), 4-nitrobenzoic acid (0.101 g, 0.000605 mol) and triphenylphosphine (0.159 g, 0.000605 mol) in tetrahydrofuran (5 mL) was cooled to 0° C. Diethyl azodicarboxylate (0.096 mL, 0.159 g, 6.000605 mol) was added dropwise, keeping the temperature below 10° C. The mixture was allowed to come to room temperature over eighteen hours. The solvent was removed in vacuo and the residue was purified by flash column chromatography on silica using heptane/ethyl acetate (3:1). The solvent was removed in vacuo to give trans 3-[4-amino-3-(4-phenoxyphenyl)-1H-pyrazolo[3,4-d]pyrimidin-1-yl]cyclobutyl 4-nitrobenzoate (0.081 g, 0.000164 mmol) as a tan solid.

$^1$H NMR (DMSO-d$_6$, 400 MHz) δ 8.39 (d, 2H), 8.29 (d, 2H), 8.26 (s, 1H), 7.72 (d, 2H), 7.44 (t, 2H) 7.12–7.22 (m, 5H), 5.60–5.69 (m, 1H), 3.03–3.12 (m, 2H), 2.85–2.94 (m, 2H).

trans 3-[4-Amino-3-(4-phenoxyphenyl)-1H-pyrazolo[3,4-d]pyrimidin-1-yl]-1-cyclobutanol)

A solution of trans 3-[4-amino-3-(4-phenoxyphenyl)-1H-pyrazolo[3,4-d]pyrimidin-1-yl]cyclobutyl 4-nitrobenzoate (0.081 g, 0.000164 mol) in methanol (5 mL) was reacted with potassium hydroxide (0.091 g, 0.00164 mol) at reflux for one hour. The solvent was removed in vacuo and the residue was partitioned between water (10 mL) and ethyl acetate (5 mL). The layers were separated and the water layer was extracted aqueous with ethyl acetate (2×5 mL). The combined organics were washed with 1 N aqueous sodium hydroxide (5 mL) and brine (5 mL). The organic layer was dried over magnesium sulfate, and the solvent was removed in vacuo. The residue was suspended in water and lyopholyzed to give trans 3-[4-amino-3-(4-phenoxyphenyl)-1H-pyrazolo[3,4-d]pyrimidin-1-yl]-1-cyclobutanol (0.055 g, 0.000147 mol) as a white solid.

$^1$H NMR (DMSO-d$_6$, 400 MHz) δ 8.23 (s, 1H), 7.68 (d, 2H), 7.44 (t, 2H), 7.11–7.22 (m, 5H), 5.43–5.52 (m, 1H), 4.53–4.65 (m, 1H), 2.75–2.80 (m, 2H), 2.39–2.44 (m, 2H). RP-HPLC (Delta Pak C18, 5 μm, 300 A, 15 cm; 5%–85% acetonitrile-0.1M ammonium acetate over 20 min, 1 mL/min) R$_t$ 14.77 min. MS: MH$^+$ 374.

Example 119

1-{3-[4-Amino-3-(4-phenoxyphenyl)-1H-pyrazolo[3,4-d]pyrimidin-1-yl]cyclobutyl}-4-methylhexahydropyrazinediium Dimaleate A mixture of 3-[4-amino-3-(4-phenoxyphenyl)-1H-pyrazolo[3,4-d]pyrimidin-1-yl]-1-cyclobutanone (0.300 g, 0.00081 mol), N-methylpiperazine (0.243 g, 0.00242 mol) and acetic acid (0.146 g, 0.00242 mol) in 1,2-dichloroethane (20 ml) was stirred for twenty min at 40° C. and sodium triacetoxyborohydride (0.223 g, 0.00105 mol) was added in three portions over one hour. The mixture was stirred for eighteen hours at 40° C. The solvent was removed under reduced pressure and the residue partitioned between aqueous saturated sodium bicarbonate solution (30 ml) and chloroform (15 ml). The organic layer was separated and the aqueous layer was further extracted with chloroform three times (15 ml each). The combined organic extracts were dried over magnesium sulfate and the solvent removed under reduced pressure to yield yellow oil that was purified by flash chromatography on silica gel using dichloromethane/methanol (97:3) as a mobile phase. The solvent was removed in vacuo and the residue (0.120 g, 0.000263 mol) was dissolved in absolute ethanol (10 mL). A solution of maleic acid (0.122 g, 0.001053 mol) in absolute ethanol (5 mL) was added and the mixture was stirred at reflux for fifteen minutes. The solution was cooled to room temperature and the precipitate was filtered, washing with absolute ethanol (3×5 mL). The solvent was removed in vacuo to give 1-{3-[4-amino-3-(4-phenoxyphenyl)-1H-pyrazolo[3,4-d]pyrimidin-1-yl]cyclobutyl}-4- methylhexahydropyrazinediium dimaleate (0.181 g, 0.000397 mmol) as a white solid.

$^1$H NMR (DMSO-d$_6$, 400 MHz) δ 8.25 (s, 1H), 7.67 (d, 2H), 7.44 (t, 2H), 7.10–7.20 (m, 5H), 6.14 (s, 4H), 5.05–5.16 (m, 1H), 2.77 (s, 1H), 2.48–3.00 (m, 5H). RP-HPLC (Delta Pak C18, 5 μm, 300 A, 15 cm; 5%–85% acetonitrile-0.1M ammonium acetate over 20 min, 1 mL/min) R$_t$ 13.35 min. MS: MH$^+$ 456.

Example 120 trans 1-{3-[(Benzyloxy)methyl]cyclobutyl}-3-(4-phenoxyphenyl)-1H-pyrazolo[3,4-d]pyrimidin-4-amine a) cis 3-[(Benzyloxy)methyl]cyclobutyl Methanesulfonate.

A solution of cis 3-((benzyloxy)methyl)-1-cyclobutanol (2.50 g, 0.0130 mol) in pyridine (50 mL) was cooled to 0° C. Methanesulfonyl chloride (1.21 mL, 1.79 g, 0.0126 mol) was added dropwise, keeping the temperature below 2° C. The mixture was stirred for four hours, and then poured into ice water (100 mL) and extracted with ethyl ether (2×50 mL). The combined organic layers were washed with water (3×50 mL) and brine (50 mL). The organic layer was dried over magnesium sulfate and the solvent was removed in vacuo to give cis 3-[(benzyloxy)methyl]cyclobutyl methanesulfonate (2.73 g, 0.0101 mol) as a yellow oil.

$^1$H NMR (CDCl$_3$, 400 MHz) δ 7.29–7.38 (m, 5H), 4.88–4.94 (m, 1H), 4.52 (s, 2H), 3.45 (d, 2H), 2.99 (s, 3H), 2.50–2.56 (m, 2H), 2.12–2.19 (m, 3H).

b) trans 1-{3-[(Benzyloxy)methyl]cyclobutyl}-3-(4-phenoxyphenyl)-1H-pyrazolo[3,4-d]pyrimidin-4-amine A solution of 3-(4-phenoxyphenyl)-1H-pyrazolo[3,4-d]pyrimidin-4-amine (0.452 g, 0.00149 mol) in N,N-dimethylformamide (10 mL) was reacted with cis 3-[(benzyloxy)methyl]cyclobutyl methanesulfonate (0.483 g, 0.00179 mol) and cesium carbonate (0.582 g, 0.00179 mol) at 70° C. for two days. The reaction mixture was poured into water (30 mL) and extracted with ethyl acetate (3×15 mL). The combined organic layers were washed with water (2×20 mL) and brine (20 mL). The organic layer was dried over magnesium sulfate and the solvent was removed in vacuo. The residue was purified by flash column chromatography on silica using dichloromethane/methanol (98:2). The solvent was removed in vacuo to give trans 1-{3-[(benzyloxy)methyl]cyclobutyl}-3-(4-phenoxyphenyl)-1H-pyrazolo[3,4-d]pyrimidin-4-amine (0.325 g, 0.000681 mol) as a tan solid.

$^1$H NMR (DMSO-d$_6$, 400 MHz) δ 8.23 (s, 1H), 7.69 (d, 2H), 7.44 (t, 2H), 7.37–7.39 (m, 4H), 7.29–7.31 (m, 1H), 7.11–7.21 (m, 5H), 5.42–5.47 (m, 1H), 4.57 (s, 1H), 3.63 (d, 2H), 2.76–2.81 (m, 2H), 2.60–2.70 (m, 1H), 2.28–2.34 (m, 2H). RP-HPLC (Delta Pak C18, 5 μm, 300 A, 15 cm; 5%–85% acetonitrile-0.1M ammonium acetate over 20 min, 1 mL/min) R$_t$ 21.92 min. MS: MH$^+$ 478.

trans 3-[4-Amino-3-(4-phenoxyphenyl)-1H-pyrazolo[3,4-d]pyrimidin-1-yl]cyclobutylmethanol A solution of trans 1-{3-[(benzyloxy)methyl]cyclobutyl}-3-(4-phenoxyphenyl)-1H-pyrazolo[3,4-d]pyrimidin-4-amine (0.244 g, 0.00051 mol) in dichloromethane (10 mL) was cooled to −78° C. and a solution of 1.0 M boron trichloride in dichloromethane (1.53 mL, 0.00153 mol) was added dropwise, keeping the temperature less than −70° C. The reaction mixture was stirred seven hours at −78° C., after which time a 8 M solution of ammonia in methanol (1.5 mL) was added . The solvent was removed in vacuo. The residue was purified by flash column chromatography on silica using dichloromethane/methanol (93:7). The solvent was removed in vacuo to give to give trans 3-[4-amino-3-(4-phenoxyphenyl)-1H-pyrazolo[3,4-d]pyrimidin-1-yl]cyclobutylmethanol (0.192 g, 0.00049 mol) as a white solid.

$^1$H NMR (DMSO-d$_6$, 400 MHz) δ 8.23 (s, 1H), 7.69 (d, 2H), 7.44 (t, 2H), 7.11–7.22 (m, 5H), 5.36–5.46 (m, 1H), 4.70–4.80 (br, 1H), 3.58 (d, 2H) 2.70–2.75 (m, 2H), 2.43–2.50 (m, 1H), 2.26–2.32 (m, 2H); RP-HPLC (Delta Pak C18, 5 μm, 300 A, 15 cm; 5%–85% acetonitrile-0.1M ammonium acetate over 20 min, 1 mL/min) R$_t$ 15.31 min. MS: MH$^+$ 388.

Examples 121–137

General Procedure for the Synthesis of Aryl Alkyl cis-3-(4-Amino-3-fluorophenyl)-1-[4-(4-methylpiperazino)cyclohexyl]-1H-pyrazolo[3,4-d]pyrimidin-4-amine Analogs cis-3-(4-Amino-3-fluorophenyl)-1-[4-(4-methylpiperazino)cyclohexyl]-1H-pyrazolo[3,4-d]pyrimidin-4-amine (50 mg, 0.118 mmol) was suspended in 1,2-dichloroethane (4 mL). The appropriate aldehyde (0.177 mmol), acetic acid (35 mg, 0.59 mmol) and sodium triacetoxyborohydride (50 mg, 0.236 mmol) were added to the suspension. The reaction mixtures were then heated at 100° C. for 1.5 hours. All reactions were incomplete based on TLC and/or HPLC analysis. Additional sodium triacetoxyborohydride (100 mg, 0.472 mmol) was added to each reaction in two batches over a total of 3–5 days and shaking was continued at room temperature. Each reaction was diluted with dichloromethane (4 mL) then quenched with saturated sodium bicarbonate (4 mL). Where emulsions formed, brine (1 mL) was added. The organic layer was separated then concentrated under reduced pressure. The crude samples were purified on RP-HPLC using either mass actuation (Micromass/Gilson, Hypersil BDS C18, 5 μm, 100×21.2 mm column; 0–100% acetonitrile and 0.05M ammonium acetate buffered to pH 4.5 over 12.5 min at 25 mL/min) or uv actuation (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm column). The desired final compounds were obtained in 80%–100% purity obtained by analytical RP-HPLC (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column).

General Procedure for Generation of Maleate Salts

Example 137

Maleate Salt of cis-3-{4-[(4-Bromobenzyl)amino]-3-fluorophenyl}-1-[4-(4-methylpiperazino)cyclohexyl]-1H-pyrazolo[3,4-d]pyrimidin-4-amine tris Maleate Salt The free base of cis-3-{4-[(4-bromobenzyl)amino]-3-fluorophenyl}-1-[4-(4-methylpiperazino)cyclohexyl]-1H-pyrazolo[3,4-d]pyrimidin-4-amine (36 mg, 0.061 mmol) was dissolved in ethanol (2 mL) then added maleic acid (14 mg, 0.121 mmol). The mixture was heated to give a mostly clear solution. A precipitate formed as the solution cooled. The solid was collected by filtration, washed with a minimal volume of ethanol then dried under reduced pressure. Collected 16 mg of cis-3-{4-[(4-bromobenzyl)amino]-3-fluorophenyl}-1-[4-(4-methylpiperazino)cyclohexyl]-1H-pyrazolo[3,4-d]pyrimidin-4-amine tris maleate salt.

| Ex | Structure | m/z (MH+) | HPLC Rt (min) |
|---|---|---|---|
| 121 | 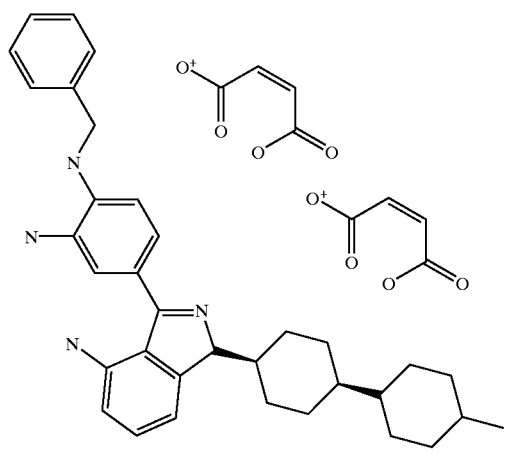 | 515.2 | 13.74 |
| 122 | 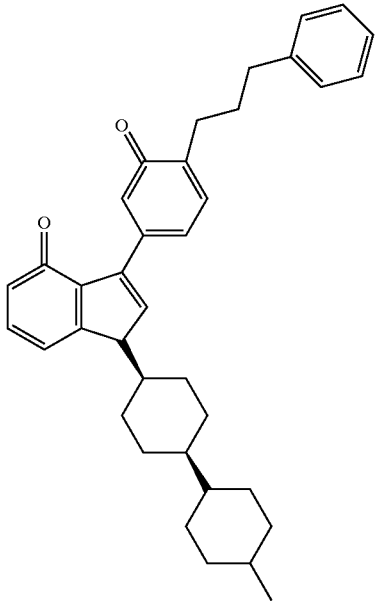 | 529.3 | 14.04 |

-continued
| Ex | Structure | m/z (MH+) | HPLC Rt (min) |
|---|---|---|---|
| 123 | 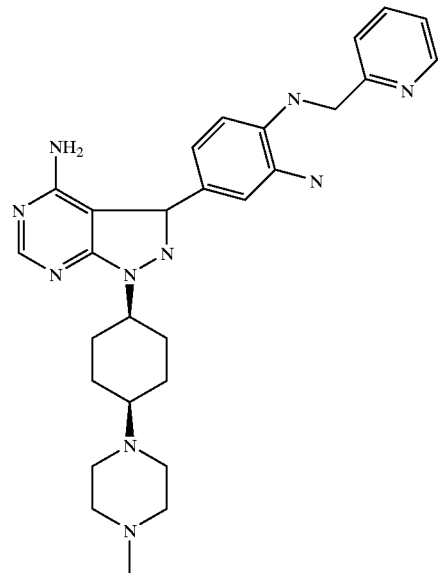 | 516.3 | 10.82 |
| 124 | 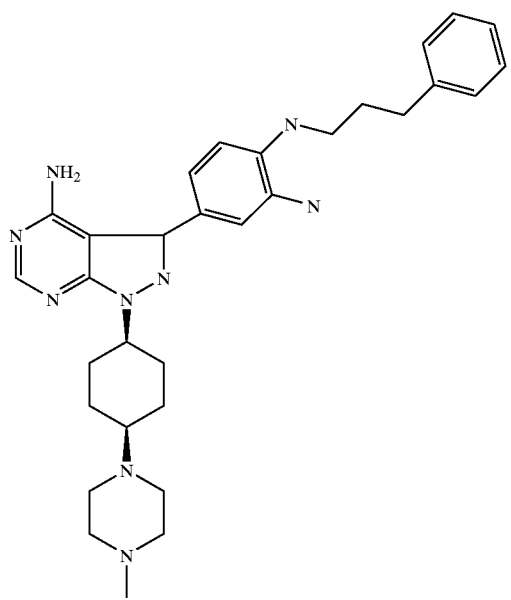 | 543.3 | 14.91 |

-continued

| Ex | Structure | m/z (MH+) | HPLC Rt (min) |
|---|---|---|---|
| 125 | 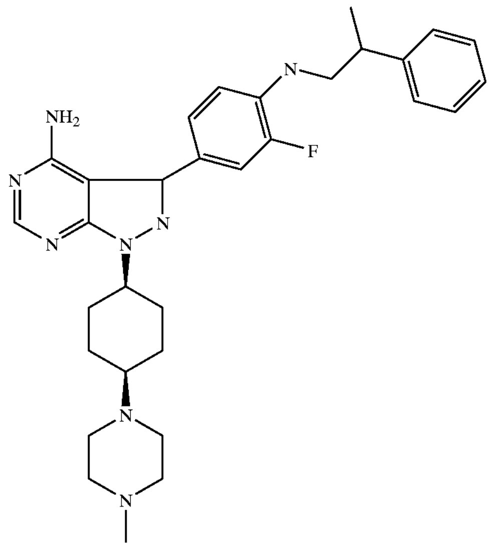 | 557.4 | 15.53 |
| 126 | 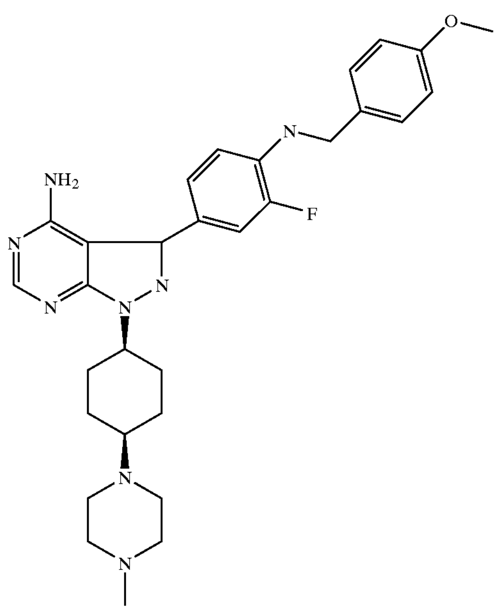 | 545.3 | 13.27 |

-continued
| Ex | Structure | m/z (MH+) | HPLC Rt (min) |
|---|---|---|---|
| 127 | 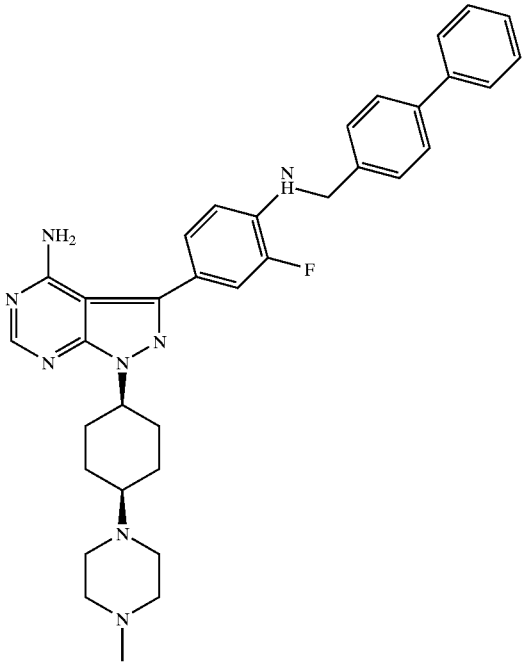 | 591.4 | 15.89 |
| 128 | 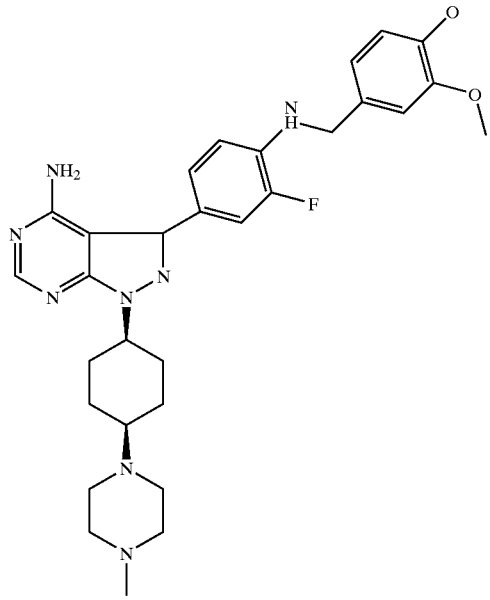 | 561.0 | 11.58 |

-continued
| Ex | Structure | m/z (MH+) | HPLC Rt (min) |
|---|---|---|---|
| 129 | 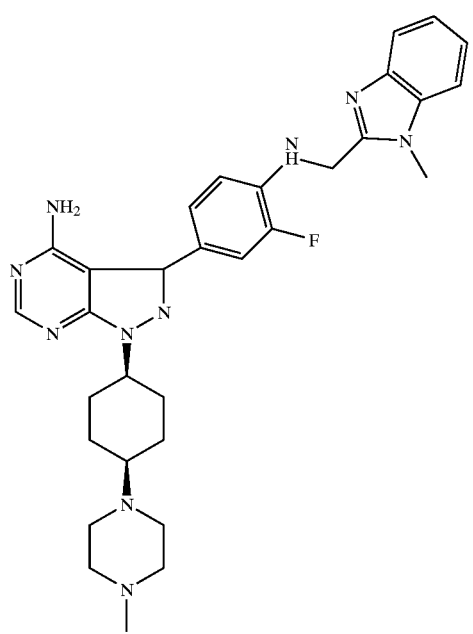 | 569.3 | 11.27 |
| 130 | 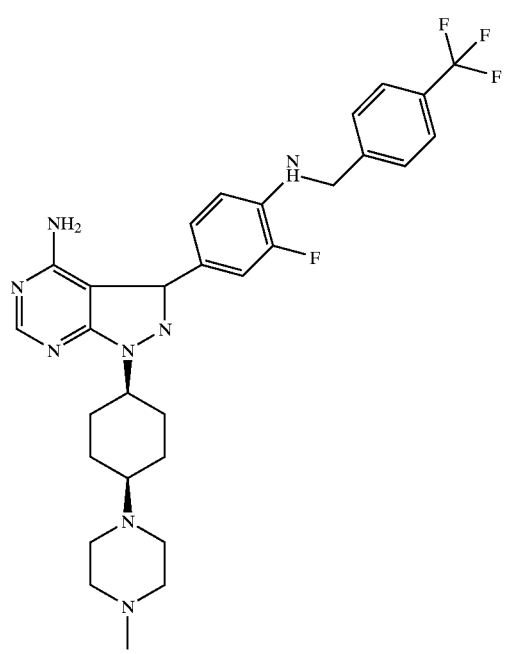 | 583.3 | 14.83 |

-continued
| Ex | Structure | m/z (MH+) | HPLC Rt (min) |
|---|---|---|---|
| 131 | 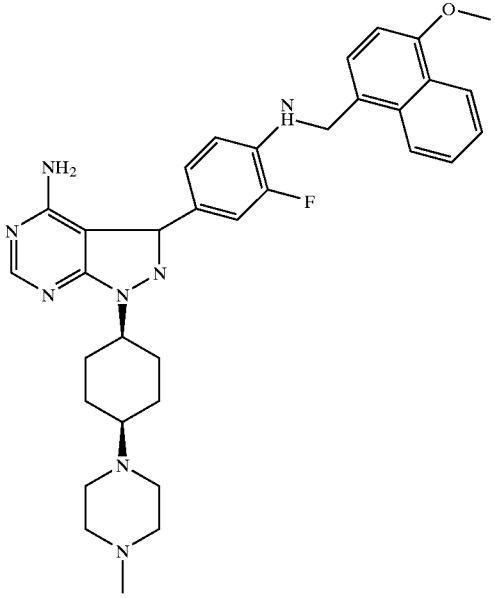 | 595.4 | 15.48 |
| 132 | 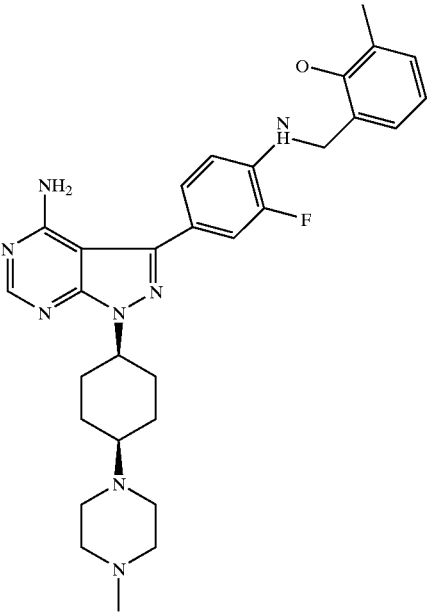 | 545.3 | 12.91 |

-continued
| Ex | Structure | m/z (MH+) | HPLC Rt (min) |
|---|---|---|---|
| 133 | 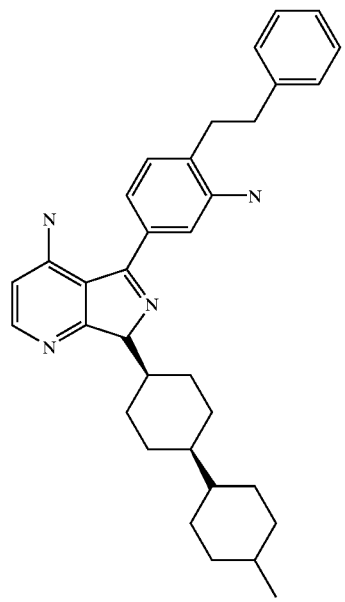 | 516.3 | 10.10 |
| 134 | 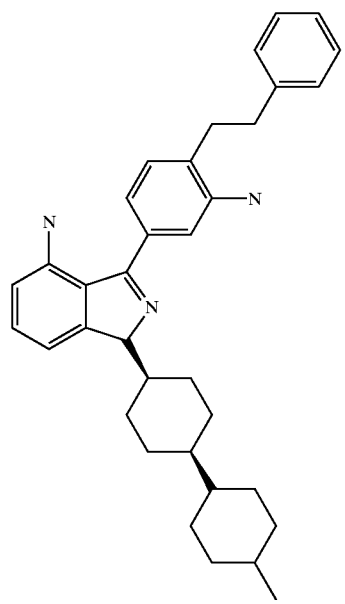 | 516.2 | 10.41 |

-continued
| Ex | Structure | m/z (MH+) | HPLC Rt (min) |
|---|---|---|---|
| 135 | 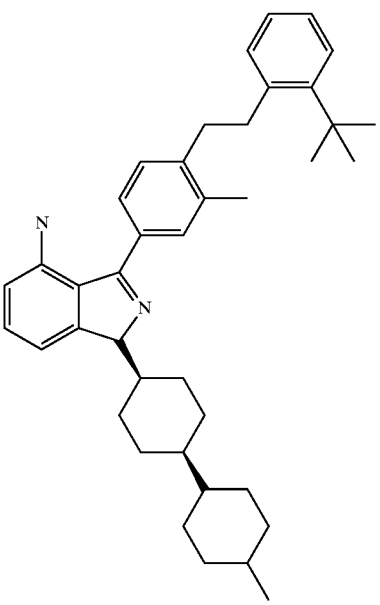 | 583.3 | 14.78 |
| 136 | 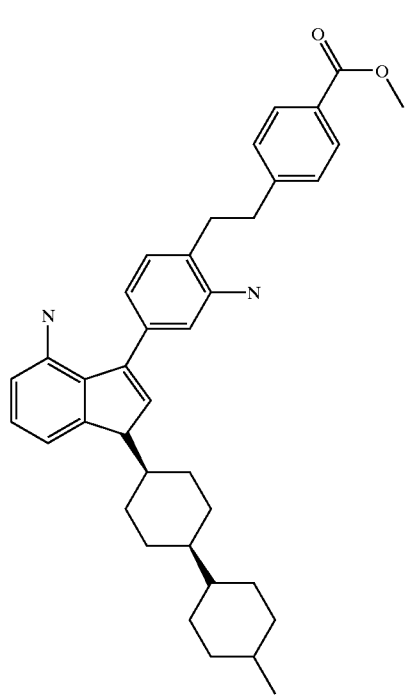 | 573.3 | 13.10 |

-continued

| Ex | Structure | m/z (MH+) | HPLC Rt (min) |
|---|---|---|---|
| 137 | 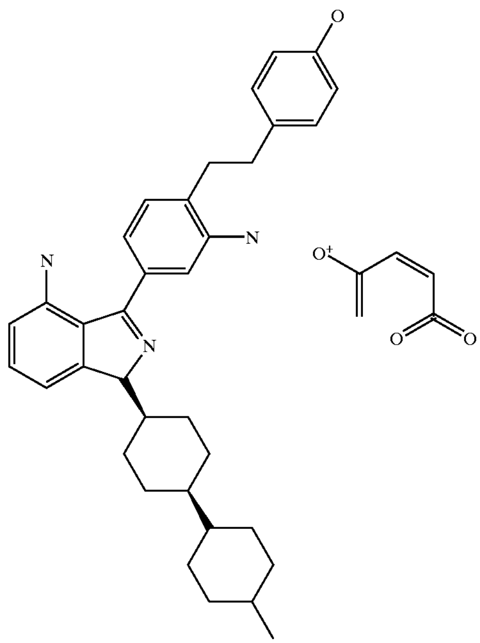 | 594.8 | 14.61 |

Examples 138–153

General procedure for the synthesis of sulfonamide variants of cis and trans-3-(4-Amino-3-fluorophenyl)-1-[4-(4-methylpiperazino)cyclohexyl]-1H-pyrazolo[3,4-d]pyrimidin-4-amine cis-3-(4-Amino-3-fluorophenyl)-1-[4-(4-methylpiperazino)cyclohexyl]-1H-pyrazolo[3,4-d]pyrimidin-4-amine (100 mg, 0.236 mmol) was dissolved in pyridine (3 mL). The appropriate sulfonyl chloride (0.472 mmol) was then added either as a solution in pyridine (0.25 mL) or as a solid. The reaction mixture was heated at 40° C. under a nitrogen atmosphere for approximately 1–7 days. Additional sulfonyl chloride (0.5 eq) was added where necessary. Each reaction was concentrated to half its original volume then diluted with N,N-dimethylformamide (1.5 mL).

These samples were purified on RP-HPLC using either mass actuation (Micromass/Gilson, Hypersil BDS C18, 5 μm, 100×21.2 mm column; 0–100% acetonitrile and 0.05M ammonium acetate buffered to pH 4.5 over 12.5 min at 25 mL/min) or uv actuation (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm column). The desired final compounds were obtained in 90%–100% purity obtained by analytical RP-HPLC: (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column). Maleate salts were prepared in certain cases.

| Ex | Structure | m/z (MH+) | HPLC Rt (min) |
|---|---|---|---|
| 140 | 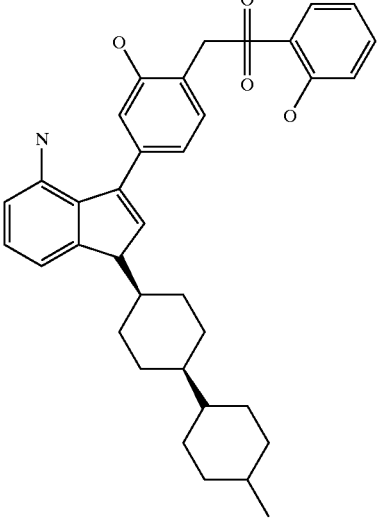 | 645.1 | 12.22 |
| 141 | 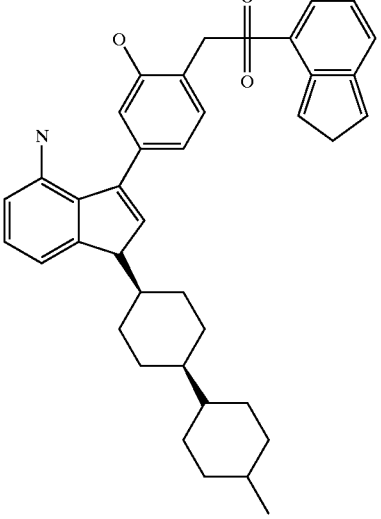 | 623.3 | 11.30 |

| Ex | Structure | m/z (MH+) | HPLC Rt (min) |
|---|---|---|---|
| 142 | 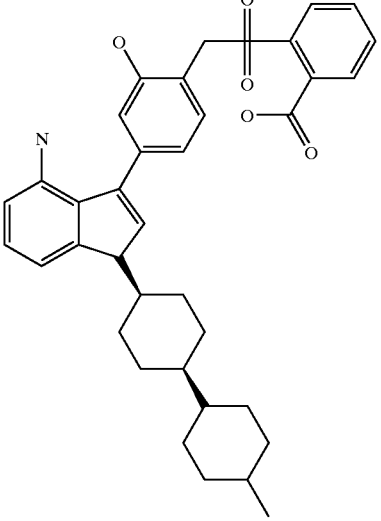 | 610.2 | 11.85 |
| 143 | 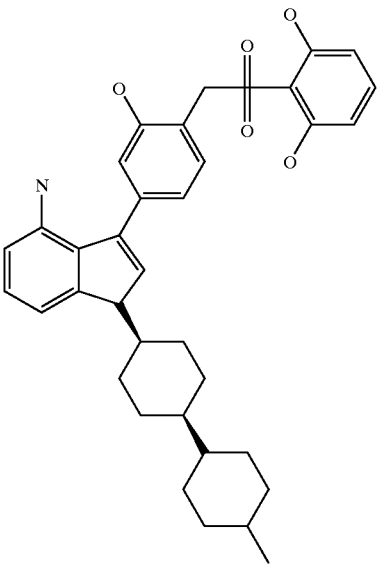 | 633.2 | 12.50 |

-continued
| Ex | Structure | m/z (MH+) | HPLC Rt (min) |
|---|---|---|---|
| 144 | 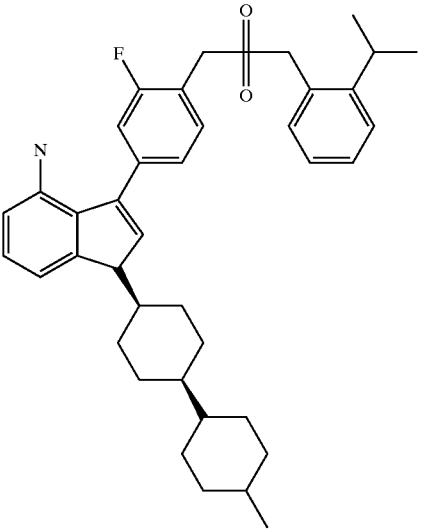 | 624.3 | 11.86 |
| 145 | 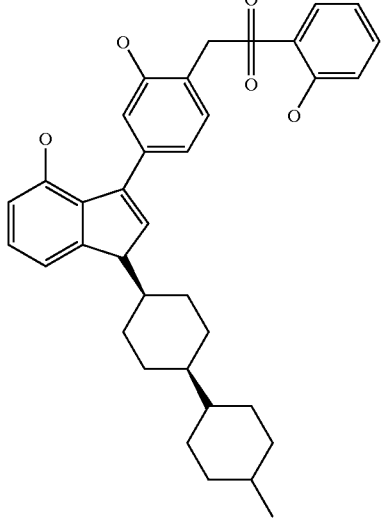 | 583.3 | 11.29 |

-continued
| Ex | Structure | m/z (MH+) | HPLC Rt (min) |
|---|---|---|---|
| 147 | 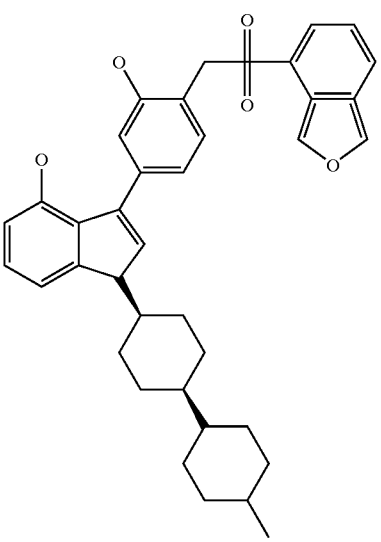 | 623.2 | 11.14 |
| 148 | 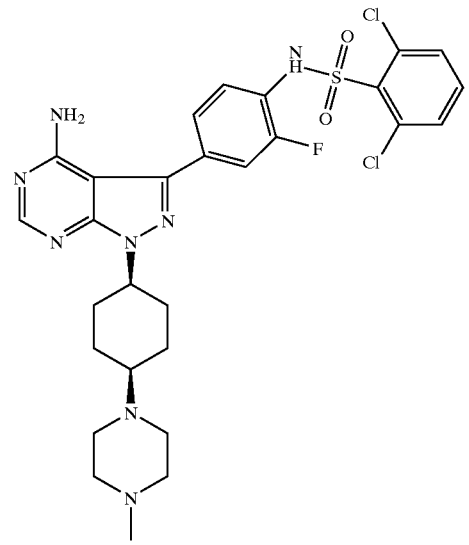 | 633.2 | 12.38 |

-continued
| Ex | Structure | m/z (MH+) | HPLC Rt (min) |
|---|---|---|---|
| 149 | 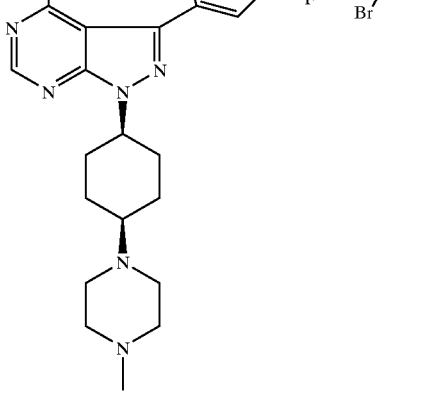 | 643.2 | 12.04 |
| 150 | 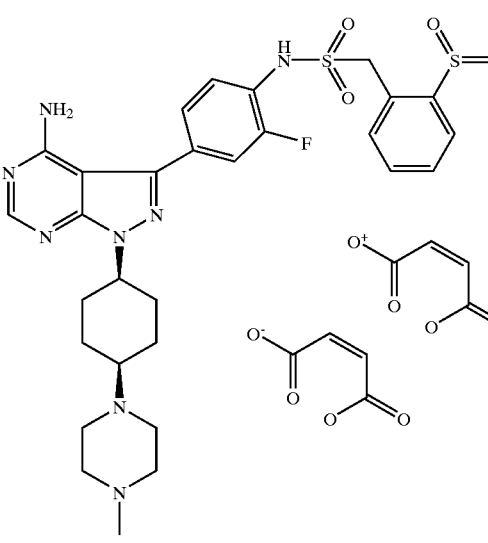 | 624.3 | 11.67 |
| 151 | 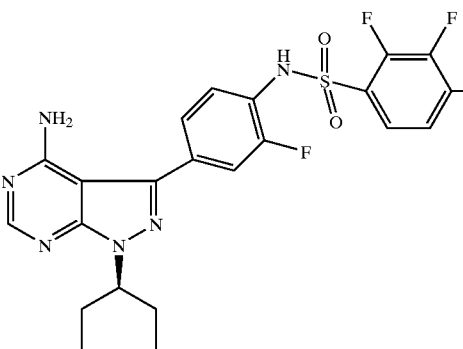 | 619.2 | 12.22 |

-continued

| Ex | Structure | m/z (MH⁺) | HPLC Rt (min) |
|---|---|---|---|
| 152 | 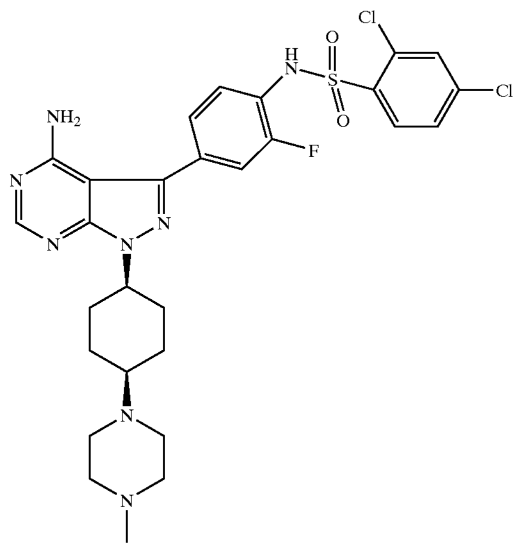 | 633.2 | 13.09 |
| 153 | 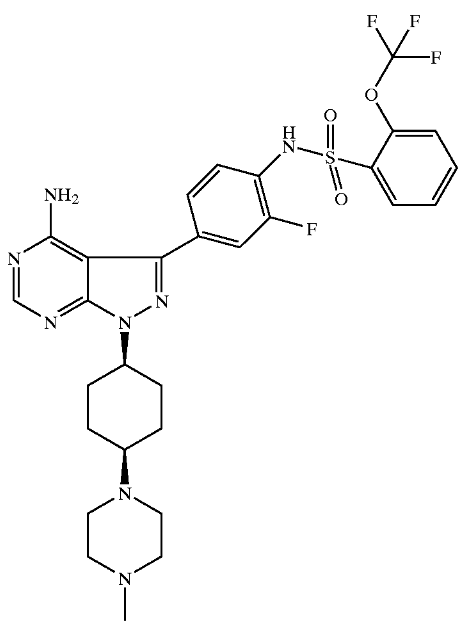 | 649.3 | 12.81 |

Example 154 cis-N-(4-{4-Amino-1-[4-(4-methylpiperazino)cyclohexyl]-1H-pyrazolo[3,4-d]pyrimidin-3-yl}-2-fluorophenyl)-N'-(2,4-difluorophenyl)urea cis-3-(4-Amino-3-fluorophenyl)-1-[4-(4-methylpiperazino)cyclohexyl]-1H-pyrazolo[3,4-d]pyrimidin-4-amine (100 mg, 0.236 mmol) was dissolved in acetic acid (6 mL) then 2,4-difluorophenyl isocyanate (44 mg, 0.283 mmol) was slowly added at room temperature. After 2 days, the reaction mixture was concentrated under reduced pressure to yield the crude product as a light yellow oil (185 mg). The crude material was purified on RP-HPLC (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm colunm). The desired product was collected as a white solid (52 mg, 0.090 mmol). HPLC-RT: 13.19 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH⁺)=580.3.

Example 155 trans-N-(4-{4-Amino-1-[4-(4-methylpiperazino)cyclohexyl]-1H-pyrazolo[3,4-d]pyrimidin-3-yl}-2-fluorophenyl)-N'-(3-methoxyphenyl)urea Monoacetate Salt trans-3-(4-Amino-3-fluorophenyl)-1-[4-(4-methylpiperazino)cyclohexyl]-1H-pyrazolo[3,4-d]

pyrimidin-4-amine (77 mg, 0.182 mmol) was suspended in pyridine (1 mL). A solution of 3-methoxyphenylisocyanate (30 mg, 0.200 mmol) in pyridine (1 mL) was added to the reaction mixture and stirring was continued for 19 hours. The reaction mixture was concentrated under reduced pressure to yield the crude product as a pale yellow oil (149 mg). The crude material was purified on RP-HPLC (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm column) to afford trans-N-(4-{4-amino-1-[4-(4-methylpiperazino)cyclohexyl]-1H-pyrazolo[3,4-d]pyrimidin-3-yl}-2-fluorophenyl)-N'-(3-methoxyphenyl)urea as a white solid (76 mg, 0.133 mmol). HPLC-RT: 12.33 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=574.2.

Example 156 trans-N-(4-{4-Amino-1-[4-(4-methylpiperazino)cyclohexyl]-1H-pyrazolo[3,4-d]pyrimidin-3-yl}-2-fluorophenyl)-N'-(3-methylphenyl)urea Monoacetate Salt, was Prepared in the Same Manner as Detailed Above HPLC-RT: 13.02 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=558.3.

Example 157 cis-N-(4-{4-Amino-1-[4-(4-methylpiperazino)cyclohexyl]-1H-pyrazolo[3,4-d]pyrimidin-3-yl}-2-fluorophenyl)-N'-(3-methylphenyl)urea was prepared using the same method as described for the trans isomer.

HPLC-RT: 13.03 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=558.5.

Example 158 cis-N-(4-{4-Amino-1-[4-(4-methylpiperazino)cyclohexyl]-1H-pyrazolo[3,4-d]pyrimidin-3-yl}-2-fluorophenyl)-N-ethyl-N'-(3-methylphenyl)urea a. cis-3-[4-(Ethylamino)-3-fluorophenyl]-1-[4-(4-methylpiperazino)cyclohexyl]-1H-pyrazolo[3,4-d]pyrimidin-4-amine cis-3-(4-Amino-3-fluorophenyl)-1-[4-(4-methylpiperazino)cyclohexyl]-1H-pyrazolo[3,4-d]pyrimidin-4-amine (75 mg, 0.177 mmol) was suspended in 1,2-dichloroethane (6 mL). A solution of acetaldehyde (12 mg, 0.266 mmol) in 1,2-dichloroethane (0.300 mL) and acetic acid (42 mg, 0.708 mmol) was added and the mixture was stirred for 1 hour. Sodium triacetoxyborohydride (75 mg, 0.354 mmol) was added. After 16 hours, more sodium triacetoxyborohydride (37 mg, 0.175 mmol) was added and the reaction continued for another 3 hours. The reaction mixture was then concentrated under reduced pressure. The residue was dissolved in dichloromethane (75 mL) then washed with saturated aqueous sodium bicarbonate (100 mL) and brine (100 mL). The organic layer was dried over anhydrous sodium sulfate and concentrated under reduced pressure. The crude product (80 mg) was collected as a colorless oil.
m/z (MH$^+$)=453.3.

b. cis-N-(4-{4-Amino-1-[4-(4-methylpiperazino)cyclohexyl]-1H-pyrazolo[3,4-d]pyrimidin-3-yl}-2-fluorophenyl)-N-ethyl-N'-(3-methylphenyl)urea cis-3-[4-(Ethylamino)-3-fluorophenyl]-1-[4-(4-methylpiperazino)cyclohexyl]-1H-pyrazolo[3,4-d]pyrimidin-4-amine (80 mg, 0.177 mmol) was dissolved in pyridine (3 mL) then cooled to 0° C. m-Tolylisocyanate (26 mg, 0.194 mmol) was added to the reaction and stirring was continued at 0° C. for 2.5 hours. The reaction mixture was warmed to room temperature and stirred overnight. Additonal m-tolylisocyanate (13 mg, 0.101 mmol) was added to the reaction mixture and stirring was continued for 1 week. The reaction mixture was concentrated under reduced pressure to give the crude product as a light yellow oil (110 mg). Purification was achieved by RP-HPLC (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm column). cis-N-(4-{4-Amino-1-[4-(4-methylpiperazino)cyclohexyl]-1H-pyrazolo[3,4-d]pyrimidin-3-yl}-2-fluorophenyl)-N-ethyl-N'-(3-methylphenyl)urea was collected as a white solid (10 mg). HPLC-RT: 13.18 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=586.5.

Example 159 cis-N-(4-{4-Amino-1-[4-(4-methylpiperazino)cyclohexyl]-1H-pyrazolo[3,4-d]pyrimidin-3-yl}-2-fluorophenyl)-N-benzyl-N'-(2,4-difluorophenyl)urea cis-3-[4-(Benzylamino)-3-fluorophenyl]-1-[4-(4-methylpiperazino)cyclohexyl]-1H-pyrazolo[3,4-d]pyrimidin-4-amine (28 mg, 0.054 mmol) was dissolved in acetic acid (3 mL) then added 2,4-difluorophenylisocyanate (28 mg, 0.183 mmol) over 4 days. The reaction mixture was concentrated under reduced pressure to yield a light yellow oil (65 mg). Purification was achieved by RP-HPLC (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm column) to afford cis-N-(4-{4-amino-1-[4-(4-methylpiperazino)cyclohexyl]-1H-pyrazolo[3,4-d]pyrimidin-3-yl}-2-fluorophenyl)-N-benzyl-N'-(2,4-difluorophenyl)urea as a white solid (13 mg, 0.019 mmol). HPLC-RT: 14.66 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=670.1.

Example 160 cis-N-(4-{4-Amino-1-[4-(4-methylpiperazino)cyclohexyl]-1H-pyrazolo[3,4-d]pyrimidin-3-yl}phenyl)-N'-(3-methylphenyl)urea cis-3-(4-Aminophenyl)-1-[4-(4-methylpiperazino)cyclohexyl]-1H-pyrazolo[3,4-d]pyrimidin-4-amine (50 mg, 0.123 mmol) was dissolved in pyridine (3.5 mL) then cooled to 0° C. m-Tolylisocyanate (18 mg, 0.135 mmol) was added and the reaction was allowed to warm to room temperature over 16 hours. The reaction mixture was concentrated under reduced pressure to yield a pale yellow oil (200 mg). Purification was achieved by RP-HPLC (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm column). The desired product was collected as a white solid (52 mg). HPLC-RT: 12.58 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=540.1.

Examples 161–164

Amide Analogs of N-{-4-[4-Amino-1-(4-piperidyl)-1H-pyrazolo[3,4-d]pyrimidin-3-yl]-2-fluorophenyl}-N'-(3-methylphenyl)urea a. tert-Butyl 4-[4-Amino-3-(4-amino-3-fluorophenyl)-1H-pyrazolo[3,4-d]pyrimidin-1-yl]-1-piperidinecarboxylate.

3-(4-amino-3-fluorophenyl)-1-(4-piperidyl)-1H-pyrazolo[3,4-d]pyrimidin-4-amine (2.12 g, 6.48 mmol) was dissolved in 1:1 dioxane/water (20 mL). Sodium carbonate (1.03 g, 9.72 mmol), and di-tert-butyldicarbonate (1.55 g, 7.12 mmol) were added to the reaction mixture. After 3 hours, the reaction was concentrated under reduced pressure. The remaining residue was partitioned between dichloromethane (100 mL) and water (100 mL) then extracted with dichloromethane (200 mL). The organic layers were combined and washed with a brine (100 mL). The organic layer was then dried over sodium sulfate and concentrated under reduced pressure to yield a yellowish-brown foam (2.85 g, 6.67 mmol). HPLC-RT: 14.41 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=428.1.

a. tert-Butyl 4-(4-Amino-3-{3-fluoro-4-[(3-toluidinocarbonyl)amino]phenyl}-1H-pyrazolo[3,4-d]pyrimidin-1-yl)-1-piperidinecarboxylate.

tert-Butyl 4-[4-amino-3-(4-amino-3-fluorophenyl)-1H-pyrazolo[3,4-d]pyrimidin-1-yl]-1-piperidinecarboxylate (600 mg, 1.41 mmol) was dissolved in pyridine (25 mL) and cooled to 0° C. m-Tolylisocyanate (206 mg, 1.54 mmol) was added and the reaction was stirred at 0° C. for 2.5 hours. The reaction mixture was concentrated under reduced pressure to yield the crude product as a brownish-yellow foam (841 mg). Purification by column chromatography on silica gel using a 25% to 50% ethyl acetate/heptane gradient followed by 5% methanol/dichloromethane as the eluent afforded tert-butyl 4-(4-amino-3-{3-fluoro-4-[(3-toluidinocarbonyl)amino]phenyl}-1H-pyrazolo[3,4-d]pyrimidin-1-yl)-1-piperidinecarboxylate as a light yellow solid (243 mg, 0.434 mmol). HPLC-RT: 17.82 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=561.4.

a. N-{4-[4-Amino-1-(4-piperidyl)-1H-pyrazolo[3,4-d]pyrimidin-3-yl]-2-fluorophenyl}-N'-(3-methylphenyl)urea Dihydrochloride Salt.

tert-Butyl 4-(4-amino-3-{3-fluoro-4-[(3-toluidinocarbonyl)amino]phenyl}-1H-pyrazolo[3,4-d]pyrimidin-1-yl)-1-piperidinecarboxylate (117 mg, 0.209 mmol) was suspended in acetone (7 mL) and cooled to 0° C. Aqueous hydrochloric acid (6N, 1.6 mL) was slowly added to the reaction mixture. The reaction mixture was warmed to room temperature then heated at 50° C. for 4 hours. Concentration of the reaction mixture under reduced pressure followed by trituration with dichloromethane (25 mL) afforded N-{4-[4-amino-1-(4-piperidyl)-1H-pyrazolo[3,4-d]pyrimidin-3-yl]-2-fluorophenyl}-N'-(3-methylphenyl)urea dihydrochloride salt as an off-white solid (111 mg, 0.241 mmol). HPLC-RT: 11.98 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=461.3.

a. General Synthesis of Amide Analogs of N-{4-[4-Amino-1-(4-piperidyl)-1H-pyrazolo[3,4-d]pyrimidin-3-yl]-2-fluorophenyl}-N'-(3-methylphenyl)urea.

i). General Procedure (A): for Unprotected Amino Acids.

Example 161

N-[4-(4-Amino-1-{1-[2-(dimethylamino)acetyl]-4-piperidyl}-1H-pyrazolo[3,4-d]pyrimidin-3-yl)-2-fluorophenyl]-N'-(3-methylphenyl)urea N-{4-[4-amino-1-(4-piperidyl)-1H-pyrazolo[3,4-d]pyrimidin-3-yl]-2-fluorophenyl}-N-(3-methylphenyl)urea dihydrochloride salt (50 mg, 0.109 mmol) was dissolved in dichloromethane (6 mL) and N-ethyl-N-isopropylamine (0.095 mL). N,N-dimethyl glycine (14 mg, 0.136 mmol), 1-hydroxy-7-azabenzotriazole (15 mg, 0.109 mmol) and 1-(3-dimethylaminopropyl)-3-ethylcarbodiimide hydrochloride (26 mg, 0.136 mmol) were added to the reaction mixture. After 16 hours, the reaction mixture was diluted with dichloromethane (100 mL) then washed with water (50 mL) and brine (50 mL). The organic layer was dried over anhydrous sodium sulfate and concentrated under reduced pressure. The remaining residue was triturated with diethyl ether (25 mL) to afford a pale yellow solid (52 mg, 0.097 mmol). Purification by RP-HPLC (Waters PrepLC 4000, flow rate: 10 mL/min. λ=254 nm Gradient: 10% to 30% acetonitrile/0.1M aqueous ammonium acetate gradient over 40 minutes; Deltapak C 18, 300A, 15 μm, 40×100 mm column) afforded N-[4-(4-amino-1-{1-[2-(dimethylamino)acetyl]-4-piperidyl}-1H-pyrazolo[3,4-d]pyrimidin-3-yl)-2-fluorophenyl]-N'-(3-methylphenyl)urea as a white solid (27 mg, 0.050 mmol). HPLC-RT: 12.48 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=546.0.

Example 162

N-[4-(4-Amino-1-{1-[3-(diethylamino)propanoyl]-4-piperidyl}-1H-pyrazolo[3,4-d]pyrimidin-3-yl)-2-fluorophenyl]-N'-(3-methylphenyl)urea Monoacetate Salt was prepared as described in general procedure A.

HPLC-RT: 13.16 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=588.2.

d. ii). General procedure (B): for tert-butoxycarbonyl protected amino acids.

Example 163

N-[4-(4-Amino-1-{1-[2-(methylamino)acetyl]-4-piperidyl}-1H-pyrazolo[3,4-d]pyrimidin-3-yl)-2-fluorophenyl]-N'-(3-methylphenyl)urea N-{4-[4-amino-1-(4-piperidyl)-1H-pyrazolo[3,4-d]pyrimidin-3-yl]-2-fluorophenyl}-N'-(3-methylphenyl)urea dihydrochloride salt (63 mg, 0.118 mmol) was dissolved in dichloromethane (7 mL) and N-ethyl-N-isopropylamine (0.113 mL), 2-[(tert-butoxycarbonyl)(methyl)amino]acetic acid (28mg, 0.147 mmol), 1-hydroxy-7-azabenzotriazole (16 mg, 0.118 mmol) and 1-(3-dimethylaminopropyl)-3-ethylcarbodiimide hydrochloride (28 mg, 0.147 mmol) were added to the reaction mixture. After 16 hours, the reaction mixture was diluted with dichloromethane (75 mL) then washed with water (75 mL). The organic layer was dried over anhydrous sodium sulfate and concentrated under reduced pressure. The crude product was isolated as a pale yellow solid (75 mg, 0.119 mmol). The crude tert-butyl N-{2-[4-(4-amino-3-{3-fluoro-4-[(3-toluidinocarbonyl) amino]phenyl}-1H-pyrazolo[3,4-d]pyrimidin-1-yl) piperidino]-2-oxoethyl}-N-methylcarbamate (75 mg, 0.119 mmol) was dissolved in acetone (5 mL) then aqueous hydrochloric acid (6N, 1 mL) was slowly added. The reaction mixture was heated at 45° C. for 2.5 hours then concentrated under reduced pressure. The remaining residue was triturated with dichloromethane (25 mL) to yield a light yellow solid. Purification by RP-HPLC (Waters PrepLC 4000, flow rate: 10 mL/min. λ=254 nm Gradient: 10% to 30% acetonitrile/0.1M aqueous ammonium acetate gradient over 40 minutes; Deltapak C18, 300A, 15 μm, 40×100 mm column) afforded N-[4-(4-amino-1-{1-[2-(methylamino) acetyl]-4-piperidyl}-1H-pyrazolo[3,4-d]pyrimidin-3-yl)-2-fluorophenyl]-N'-(3-methylphenyl)urea as a white solid (40 mg, 0.075 mmol). HPLC-RT: 12.22 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=532.1.

Example 164

N-{4-[4-Amino-1-(1-{3-[(2-hydroxyethyl)amino] propanoyl}-4-piperidyl)-1H-pyrazolo[3,4-d] pyrimidin-3-yl]-2-fluorophenyl}-N'-(3-methylphenyl)urea Monoacetate Salt a). 3-[(tert-Butoxycarbonyl)(2-hydroxyethyl)amino] propanoic Acid.

Commercially available 3-[(2-hydroxyethyl)amino] propanoic acid (76 mg, 0.571 mmol) was dissolved in dioxane/water (1.5 mL/1.5 mL) then added sodium carbonate (91 mg, 0.886 mmol) and di-tert-butyldicarbonate (137 mg, 0.628 mmol). The reaction mixture was stirred at room temperature for 2 days, filtered and concentrated under reduced pressure to yield 3-[(tert-butoxycarbonyl)(2-hydroxyethyl)amino]propanoic acid as a colorless oil (135 mg, 0.579 mmol). $^1$H NMR(d$_6$-DMSO): δ 1.40 (s, 9H); 2.36 (br s, 2H); 3.27 (br s, 3H); 3.46 (br s, 2H); 3.64 (br s, 2H); 5.71 (br s, 1H).

b). N-{4-[4-Amino-1-(1-{3-[(2-hydroxyethyl)amino] propanoyl}-4-piperidyl)-1H-pyrazolo[3,4-d]pyrimidin-3-yl]-2-fluorophenyl}-N'-(3-methylphenyl)urea Monoacetate Salt was Carried out via the Method Described in d. ii). General Procedure B.

HPLC-RT: 12.19 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=576.3.

Example 165 cis-3-{4-[(1-Methyl-1H-benzo[d]imidazol-2-yl) amino]phenyl}-1-[4-(4-methylpiperazino) cyclohexyl]-1H-pyrazolo[3,4-d]pyrimidin-4-amine a) N2-(4-Bromophenyl)-1-methyl-1H-benzo[d]imidazol-2-amine A mixture of 2-chloro-1-methyl-benzimidazole (0.639 g, 3.84 mmol) and 4-bromoaniline (0.710 g, 4.12 mmol) was heated at 170° C. for 21 h. The resulting brown solid was cooled to room temperature, washed with three 5-mL portions of heptane, and then triturated with toluene to afford N2-(4-bromophenyl)-1-methyl-1H-benzo[d]imidazol-2-amine (1.120 g, 90%) as a brown powder. RP-HPLC (25 to 100% CH$_3$CN in 0.1 N aqueous ammonium acetate over 10 min at 1 mL/min using a Hypersil HS C18, 250×4.6 mm column) tr=10.85 min, 96%; m/z 302 (MH$^+$).

b) N2-[4-(4,4,5,5-Tetramethyl-1,3,2-dioxaborolan-2-yl) phenyl]-1-methyl-1H-benzo[d]imidazol-2-amine To a solution of N2-(4-bromophenyl)-1-methyl-1H-benzo [d]imidazol-2-amine (1.12 g, 3.71 mmol) in dimethylformamide (15 mL) under nitrogen was added bis(pinacolato) diboron (1.129 g, 4.448 mmol), potassium acetate (1.204 g, 12.27 mmol), and [1,1'-bis(diphenylphosphino)ferrocene] dichloropalladium (II) complexed with dichloromethane (1:1) (0.334 g, 0.409 mmol). The violet solution was stirred at 80° C. for 18 h and then cooled to room temperature. The resulting dark brown mixture was concentrated in vacuo to give a dark brown solid. This material was triturated with dichloromethane, filtered, and the filtrate was concentrated to give a dark brown oil. Purification via flash chromatography on silica gel (eluting with 30% ethyl acetate/heptane) afforded N2-[4-(4,4,5,5-tetramethyl-1,3,2-dioxaborolan-2-yl)phenyl]-1-methyl-1H-benzo[d]imidazol-2-amine (0.515 g, 40%) as a white powder: $^1$H NMR (DMSO-d$_6$, 400 MHz) δ 9.10 (s, 1H), 7.88 (d, 2H), 7.63 (d, 2H), 7.40 (m, 1H), 7.30 (m, 1H), 7.08 (m, 2H), 3.72 (s, 3H), 1.29 (s, 12H); RP-HPLC (25 to 100% CH$_3$CN in 0.1 N aqueous ammonium acetate over 10 min at 1 mL/min using a Hypersil HS C18, 250×4.6 mm column) tr=11.70 min, 90%; m/z 350 (MH$^+$).

c) cis-3-{4-[(1-Methyl-1H-benzo[d]imidazol-2-yl)amino] phenyl}-1-[4-(4-methylpiperazino)cyclohexyl]-1H-pyrazolo[3,4-d]pyrimidin-4-amine To a solution of cis-3-iodo-1-[4-(4-methylpiperazino) cyclohexyl]-1H-pyrazolo[3,4-d]pyrimidin-4-amine (0.100 g, 0.227 mmol) in ethylene glycol dimethyl ether (3 mL) and water (1.5 mL) under nitrogen was added N2-[4-(4,4,5,5-tetramethyl-1,3,2-dioxaborolan-2-yl)phenyl]-1-methyl-1H-benzo[d]imidazol-2-amine (0.099 g, 0.28 mmol), tetrakis (triphenylphosphine) palladium (0) (0.013 mg, 0.011 mmol), and sodium carbonate (0.060 mg, 0.568 mmol). The solution was stirred at 83° C. for 15 h. The resulting yellow mixture was concentrated in vacuo to give a yellow oil. Purification by preparative HPLC (25 to 100% CH$_3$CN in 0.1 N aqueous ammonium acetate over 20 min at 21 mL/min using a 8μ Hypersil HS C18, 250×21 mm column, tr=7.3–11.2 min.) afforded cis-3-{4-[(1-methyl-1H-benzo[d]imidazol-2-yl) amino]phenyl}-1-[4-(4-methylpiperazino)cyclohexyl]-1H-pyrazolo[3,4-d]pyrimidin-4-amine as an off-white solid (0.061 g, 50%): $^1$H NMR (DMSO-d$_6$, 400 MHz) δ 9.17 (s, 1H), 8.23 (s, 1H), 8.08 (d, 2H), 7.62 (d, 2H), 7.42 (m, 1H), 7.33 (m, 1H), 7.08 (m, 1H), 4.80 (m, 1H), 3.76 (s, 3H), 2.50–2.07 (m, 12H), 1.80–1.60 (m, 8H); RP-HPLC (25 to 100% CH$_3$CN in 0.1 N aqueous ammonium acetate over 10 min at 1 mL/min using a Hypersil HS C18, 250×4.6 mm column) tr=5.92 min., 99%; m/z 537 (MH$^+$).

Examples 166–170

Amides Derived From cis-3-(4-Amino-3-methoxyphenyl)-1-[4-(4-methylpiperazino) cyclohexyl]-7H-pyrazolo[3,4-d]pyrimidin-4-amine Representative Procedure:

To the appropriate carboxylic acid (0.46 mmol) in dichloromethane (1.5 ml) was added oxalyl chloride (400 μl, 0.2 mmol) and DMF (1 drop). The vials were septum capped and a small bore needle inserted in each cap to relieve pressure. The vials were shaken overnight on a J-Kem shaker. 50% of the solution was separated and the excess oxalyl chloride and dichloromethane was then removed on a 12-port Supelco manifold under vacuum with nitrogen bleed. The crude acid chloride (0.23 mmol) was added to cis-3-(4-amino-3-methoxyphenyl)-1-[4-(4-methylpiperazino)cyclohexyl]-1H-pyrazolo[3,4-d]pyrimidin-4-amine (40 mg, 0.09 mmol) in dry pyridine (800 μl) and stirred at room temperature. The resulting solutions were submitted directly to purification by preparative HPLC (Hypersil BSD C18, 5 um, 100×21 mm, 0%–100% acetonitrile/0.05M ammonium acetate over 10 min, 25.0 mL/min). The resulting products were further purified by partioning between dichloromethane (4 ml) and 1.0 N sodium hydroxide (2 ml) and passing through an Empore™ high performance extraction disk cartridge (C18-SD octadecyl) to give the corresponding products. The compounds are detailed overleaf with corresponding LCMS (Micromass-Column: Pecosphere, C18, 3 um, 33×4.6 mm. Eluents: 0% B/A to 100% B/A in 4.5 min. (B: acetonitrile, A: 50 mM ammonia acetate buffer, PH 4.5), 3.5 mL/min.) data.

| Compound Name | R | Ex | Qty. (mg) | MH+ | R$_t$ (mins) |
|---|---|---|---|---|---|
| N2-(4-{4-amino-1-[4-(4-methylpiperazino)cyclohexyl]-1H-pyrazolo[3,4-d]pyrimidin-3-y}-2-methoxyphenyl)-1H-2-indolecarboxamide | | 166 | 34 | 580.5 | 1.98 |
| N2-(4-{4-amino-1-[4-(4-methylpiperazino)cyclohexyl]-1H-pyrazolo[3,4-d]pyrimidin-3-y}1-2-methoxyphenyl)-3-methyl-1H-2-indenecarboxamide | | 167 | 14 | 593.3 | 3.2 |
| N1-(4-{4-amino-1-[4-(4-methylpiperazino)cyclohexyl]-1H-pyrazolo[3,4-d]pyrimidin-3-yl}-2-methoxyphenyl)-(E)-3-phenyl-2-propenamide | | 168 | 17 | 567.3 | 2.85 |
| N2-(4-{4-amino-1-[4-(4-methylpiperazino)cyclohexyl]-1H-pyrazolo[3,4-d]pyrimidin-3-yl}2-methoxyphenyl)-1-methyl-1H-2-indolecarboxamide | | 169 | 20 | 594.3 | 3.18 |
| N3-(4-{4-amino-1-[4-(4-methylpiperazino)cyclohexyl]-1H-pyrazolo[3,4-d]pyrimidin-3-yl}-2-methoxyphenyl)-1H-3-indolecarboxamide | | 170 | 6 | 580.4 | 2.74 |

Example 171 cis-N1-(4-{4-Amino-1-[4-(4-methylpiperazino) cyclohexyl]-1H-pyrazolo[3,4-d]pyrimidin-3-yl}-2-methoxyphenyl)-3-phenylpropanamide To a solution of cis-3-(4-amino-3-methoxyphenyl)-1-[4-(4-methylpiperazino)cyclohexyl]-1H-pyrazolo[3,4-d] pyrimidin-4-amine (75 mg, 0.17 mmol) and triethylamine (34 mg, 0.34 mmol) in dichloromethane (2.5 ml) was added hydrocinnamoyl chloride (34 mg, 0.20 mmol) in dichloromethane (0.5 ml) dropwise. The solution was stirred at room temperature for 48 hr and a further equivalent of hydrocinnamoyl chloride was then added. The reaction mixture was stirred for a further 24 hr. The resulting mixture was partitioned between dichloromethane (4 ml) and 2N NaOH (1.5 ml) and passed through an Empore extraction cartridge. Evaporation of the solvent gave an oily solid which was purified by silica gel chromatography using 10–20% MeOH/dichloromethane to give cis-N1-(4-{4-amino-1-[4-(4-methylpiperazino)cyclohexyl]-1H-pyrazolo[3,4-d]pyrimidin-3-yl}-2-methoxyphenyl)-3-phenylpropanamide (12 mg, 13%). $^1$H NMR (CDCl$_3$): δ H 8.55 (1H, d), 8.36 (1H, s), 7.75 (1H, s), 7.25 (7H, m), 5.51 (2H, bs), 4.91 (1H, m), 3.92 (3H, s), 3.09 (2H, m), 2.76 (2H, m), 2.34–2.59 (9H, m), 2.29 (3H, s), 2.16 (2H, m), 1.85 (4H, m), 1.66 (2H, m). LCMS (Micromass-Column: Pecosphere, C18, 3 um, 33×4.6 mm. Eluents: 0% B/A to 100% B/A in 4.5 min.(B: acetonitrile, A: 50 mM ammonia acetate buffer, PH 4.5), 3.5 mL/min.) R$_t$=1.92 mins, MH$^+$=569.6.

Example 172 trans-N1-(4-{4-Amino-1-[4-(4-methylpiperazino) cyclohexyl]-1H-pyrazolo[3,4-d]pyrimidin-3-yl}-2-methoxyphenyl)-4-(dimethylamino)benzamide Trimaleate Salt To a solution of trans-3-(4-amino-3-methoxyphenyl)-1-[4-(4-methylpiperazino)cyclohexyl]-1H-pyrazolo[3,4-d]pyrimidin-4-amine (500 mg, 1.15 mmol) in pyridine (5 ml) was added 4-(dimethylamino)benzoylchloride (420 mg, 2.28 mol) dropwise. The solution was stirred overnight, the solvent evaporated and the residue partitioned between dichloromethane and 2N NaOH solution. The aqueous layer was extracted with dichloromethane (×3). The organics were dried, filtered and evaporated to leave a solid which was triturated with EtOAc/Et$_2$O (1:4) to leave a solid which was dissolved in EtOAc and treated with maleic acid (3 eqs.) to give trans-N1-(4-{4-amino-1-[4-(4-methylpiperazino) cyclohexyl]-1H-pyrazolo[3,4-d]pyrimidin-3-yl}-2-methoxyphenyl)-4-(dimethylamino)benzamide (320 mg, 30%). $^1$H NMR (d$_6$-DMSO)): δ H 9.05 (1H, s), 8.25 (1H, s), 8.18 (1H, d, J=8 Hz), 7.84 (2H, d, J=9.2 Hz), 7.29 (1H, s), 7.25 (1H, d, J=8 Hz), 6.78 (2H, d, J=8.8 Hz), 6.17 (6H, s), 4.71 (1H, m), 3.95 (3H, s), 3.01 (6H, s), 2.83–3.18 (9H, m), 2.68 (3H, s), 2.08 (6H, m), 1.56 (2H, m). HPLC (5.23 mins, 100%)

Example 173

N-4-[4-Amino-1-(3-cyano-2-pyridyl)-1H-pyrazolo [3,4-d]pyrimidin-3-yl]-2-fluorophenyl-N'-(3-methylphenyl)urea a). 2-(4-Amino-3-iodo-1H-pyrazolo[3,4-d]pyrimidin-1-yl)-3-pyridyl Cyanide Sodium hydride (60% dispersion in mineral oil, 3.825 mmol, 153 mg) was added to a suspension of 4-amino-3-iodo-1H-pyrazolo[3,4-d]pyrimidine (1.0 g, 3.825 mmol) in DMF (5 mL). After 10 min, 2-chloro-3-cyanopyridine (531 mg) was added and the reaction was heated at 60° C. for 16 h. The resulting dark mixture was poured into ice-water (50 mL) and the solid collected by filtration to afford 2-(4-amino-3-iodo-1H-pyrazolo[3,4-d]pyrimidin-1-yl)-3-pyridyl cyanide as a brown solid (1.1 g, 79%); $^1$H NMR (DMSO-d$_6$, 400 MHz) δ 7.82 (1H, m), 8.29 (1H, s), 8.64 (1H, m) and 8.93 (1H, m); RP-HPLC (Pecosphere, C18, 3 μm, 33×4.6 mm column, 0% to 100% acetonitrile in 50 mM ammonium acetate, buffered to pH 4.5, at 3.5 mL/min) R$_t$ 2.16 min.

b) 2-[4-Amino-3-(4-amino-3-fluorophenyl)-1H-pyrazolo[3,4-d]pyrimidin-1-yl]-3-pyridyl Cyanide 2-(4-amino-3-iodo-1H-pyrazolo[3,4-d]pyrimidin-1-yl)-3-pyridyl cyanide (1.35 g), tert-butyl N-[2-fluoro-4-(4,4,5,5-tetramethyl-1,3,2-dioxaborolan-2-yl)phenyl]carbamate (1.5 g), tetrakis-triphenylphosphine palladium (253 mg)and sodium carbonate (1.153 g) was suspended in degassed water (10 mL) and DME (20 mL) and heated at 85° C. for 16 h. The solvent was removed in vacuo and the residue was partitioned between ethyl acetate (200 mL) and water (200 mL). The resulting solid precipitate was removed and the organic layer was separated, dried over anhydrous sodium sulfate and concentrated under reduced pressure. The residue was crystallised from a minimal amount of ethyl acetate to afford tert-butyl N-4-[4-amino-1-(3-cyano-2-pyridyl)-1H-pyrazolo[3,4-d]pyrimidin-3-yl]-2-fluorophenylcarbamate as an off white solid (400 mg). TFA (4 mL) was slowly added to a suspension of tert-butyl N-4-[4-amino-1-(3-cyano-2-pyridyl)-1H-pyrazolo[3,4-d]pyrimidin-3-yl]-2-fluorophenylcarbamate (400 mg) in dichloromethane (4 mL). After 1 h the resulting red solution was concentrated under reduced pressure and the oily residue was neutralised with saturated aqueous sodium carbonate to afford 2-[4-amino-3-(4-amino-3-fluorophenyl)-1H-pyrazolo[3,4-d]pyrimidin-1-yl]-3-pyridyl cyanide as a yellow precipitate (300 mg); $^1$H NMR (DMSO-d$_6$, 400 MHz) δ 5.61 (2H, br s), 6.92 (1H, t), 7.36 (2H, m), 7.76 (1H, m), 8.32 (1H, s), 8.62 (1H, m) and 8.93 (1H, m); RP-HPLC (Pecosphere, C18, 3 μm, 33×4.6 mm column, 0% to 100% acetonitrile in 50 mM ammonium acetate, buffered to pH 4.5, at 3.5 mL/min) R$_t$ 2.25 min.

c). N-4-[4-Amino-1-(3-cyano-2-pyridyl)-1H-pyrazolo[3,4-d]pyrimidin-3-yl]-2-fluorophenyl-N'-(3-methylphenyl)urea m-Tolyl isocyanate (0.1 mmol) was added to a solution of (2-[4-amino-3-(4-amino-3-fluorophenyl)-1H-pyrazolo[3,4-d]pyrimidin-1-yl]-3-pyridyl cyanide (35 mg, 0.1 mmol) in pyridine and the reaction was stirred at room temperature for 2 days. The reaction was concentrated in vacuo. Purification was effected using mass actuated preparative RP-HPLC (Micromass/Gilson, Hypersil BDS C18, 5 μm, 100×21.2 mm column; 0–100% acetonitrile and 0.05M ammonium acetate buffered to pH 4.5 over 12.5 min at 25 mL/min) to afford N-4-[4-amino-1-(3-cyano-2-pyridyl)-1H-pyrazolo[3,4-d]pyrimidin-3-yl]-2-fluorophenyl-N'-(3-methylphenyl) urea (4 mg); $^1$H NMR (DMSO-d$_6$, 400 MHz) δ 2.30 (3H, s), 6.84 (1H, d), 7.19 (1H, t), 7.25 (1H, m), 7.33 (1H, br s), 7.58 (2H, m), 7.80 (1H, m), 8.35 (1H, s), 8.43 (1H, t), 8.65 (1H, m), 8.80 (1H, br s), 8.95 (1H, m) and 9.10 (1H, br s) and RP-HPLC (Pecosphere, C18, 3 μm, 33×4.6 mm column; 0% to 100% acetonitrile in 50 mM ammonium acetate, buffered to pH 4.5, at 3.5 mL/min) R$_t$ 3.09 min.

Example 174–185

General Route to N1-4-(4-Amino-1-{4-[1-(1-methylpiperid-4-yl)piperidyl]}-1H-pyrazolo[3,4-d] pyrimidin-3-yl)-2-fluorophenyl-1-arylsulfonamides a) tert-Butyl 4-(4-amino-3-4-[(tert-butoxycarbonyl)amino]-3-fluorophenyl-1H-pyrazolo[3,4-d]pyrimidin-1-yl)-1-piperidinecarboxylate A mixture of tert-butyl 4-(4-amino-3-iodo-1H-pyrazolo[3,4-d]pyrimidin-1-yl)-1-piperidinecarboxylate (8.756 g, 20.26 mmol), tert-butyl N-[2-fluoro-4-(4,4,5,5-tetramethyl-1,3,2-dioxaborolan-2-yl)phenyl]carbamate (10.25 g, 30.38 mmol), tetrakistriphenylphosphine palladium (940 mg, 0.81 mmol) and sodium carbonate (4.20 g, 50.64 mmol) was suspended in degassed water (57 mL) and DME (323 mL) and heated at 80° C. for 18 h. The solvent was removed in vacuo and the residue was partitioned between ethyl acetate (200 mL) and 10% aqueous sodium carbonate solution (200 mL). The organic layer was further washed with 10% aqueous sodium carbonate solution (2×200 mL), dried over anhydrous sodium sulfate and concentrated under reduced pressure. Purification via column chromatography over silica gel using 1:1 ethyl acetate heptane followed by neat ethyl acetate as the eluents gave an impure fraction. This fraction was further purified by crystallization from ethyl acetate to give tert-butyl 4-(4-amino-3-4-[(tert-butoxycarbonyl)amino]-3-fluorophenyl-1H-pyrazolo[3,4-d]pyrimidin-1-yl)-1-piperidinecarboxylate (7.256 g, 68%); $^1$H NMR (DMSO-$d_6$, 400 MHz) δ 1.43 (9H, s), 1.49 (9H, s), 1.93 (2H, m), 2.01 (2H, m), 3.00 (2H, br m), 4.04 (2H, br d), 4.90 (1H, m), 7.42 (2H, m), 7.83 (1H, t), 8.24 (1H, s) and 9.17 (1H, br s).

b) 3-(4-Amino-3-fluorophenyl)-1-(4-piperidyl)-1H-pyrazolo[3,4-d]pyrimidin-4-amine A mixture of tert-butyl 4-(4-amino-3-{4-[(tert-butoxycarbonyl)amino]-3-fluorophenyl}-1H-pyrazolo[3,4-d]pyrimidin-1-yl)-1-piperidinecarboxylate (6.26 g, 11.9 mmol), 5M HCl (95 mL) and acetone (390 mL) was stirred at ambient temperature for 16 h. The reaction was basified with sodium carbonate and concentrated under reduced pressure. The residues were partitioned between $CH_2Cl_2$ (200 mL) and water (200 mL) and the aqueous phase was extracted with additional $CH_2Cl_2$ (2×200 mL). The combined organic layers were dried over anhydrous sodium sulfate and evaporated to dryness to afford 3-(4-amino-3-fluorophenyl)-1-(4-piperidyl)-1H-pyrazolo[3,4-d]pyrimidin-4-amine (3.427 g, 88%); $^1$H NMR (DMSO-$d_6$, 400 MHz) δ 1.85 (2H, br t), 2.06 (2H, m), 2.65 (2H, m), 3.10 (2H, m), 4.72 (1H, m), 5.45 (2H, br s), 6.89 (1H, m), 7.22 (2H, m) and 8.19 (1H, s).

c) N1-4-(4-Amino-1-{4-[1-(1-methylpiperid-4-yl)piperidyl]}-1H-pyrazolo[3,4-d]pyrimidin-3-yl)-2-fluorophenylaniline To a solution of 3-(4-amino-3-fluorophenyl)-1-(4-piperidyl)-1H-pyrazolo[3,4-d]pyrimidin-4-amine (2.0 g, 6.11 mmol), N-methylpiperid-4-one (0.69 g, 6.11 mmol, 0.8 mL) and glacial acetic acid (1.25 mL) in N-methylpyrrolidinone (100 mL) under nitrogen was added sodium triacetoxyborohydride (1.5 equiv., 1.94 g, 9.16 mmol). The solution was stirred for 18 h then additional sodium triacetoxyborohydride (0.6 equiv., 0.78 g) and N-methylpiperid-4-one (0.4 equiv., 0.32 mL) were added and the reaction continued for a further 18 h. The reaction was concentrated in vacuo, partitioned between dichloromethane (100 mL) and saturated aqueous $NaHCO_3$ (100 mL). The aqueous layer was further extracted with dichloromethane (4×100 mL) and the combined organic layers were dried over anhydrous magnesium sulfate and evaporated to dryness to give a yellow foam (0.95 g). Purification by column chromatography over silica gel using dichloromethane:methanol (4:1) as the eluent gave N1-4-(4-amino-1-{4-[1-(1-methylpiperid-4-yl)piperidyl]}-1H-pyrazolo[3,4-d]pyrimidin-3-yl)-2-fluorophenylaniline (1.67 g, 72%); $^1$H NMR (DMSO-$d_6$, 400 MHz) δ 1.44 (2H, m), 1.69 (3H, m), 1.83 (4H, m), 2.13 (3H, s), 2.28 (4H, m), 2.78 (2H, br d), 2.98 (2H, br d), 4.58 (1H, m), 5.25 (2H, br s), 6.89 (1H, t), 7.18 (1H, d), 7.24 (1H, d) and 8.19 (1H, s).

d) General Procedure for the Sulfonylation of N1-4-(4-Amino-1-{4-[1-(1-methylpiperid-4-yl)piperidyl]}-1H-pyrazolo[3,4-d]pyrimidin-3-yl)-2-fluorophenylaniline A mixture of N1-4-(4-amino-1-{4-[1-(1-methylpiperid-4-yl)piperidyl]}-1H-pyrazolo[3,4-d]pyrimidin-3-yl)-2-fluorophenylaniline (100 mg, 0.236 mmol) and aryl sulfonyl chloride (2 equivs., 0.471 mmol) in pyridine (2 mL) was heated at 40° C. for 3 days. The solvent was removed in vacuo. Purification was effected using mass actuated preparative RP-HPLC (Micromass/Gilson, Hypersil BDS C18, 5 μm, 100×21.2 mm column; 0–100% acetonitrile in 0.05M ammonium acetate buffered to pH 4.5 over 12.5 min at 25 mL/min) to afford the following compounds:

| | Structure | HPLC Rt (min) | Purity | %/zm/z (MH$^+$) |
|---|---|---|---|---|
| 174 | 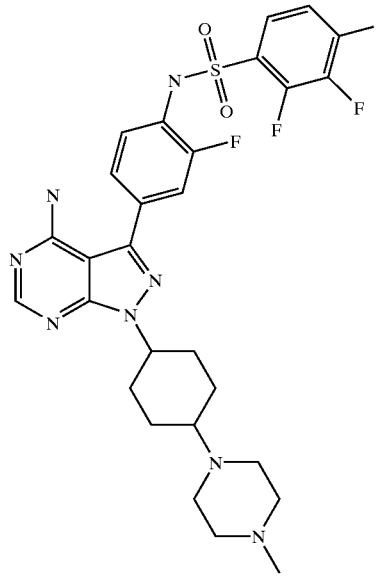 | 11.045 | 98.6 | 619.2 |

-continued
| Structure | HPLC Rt (min) | Purity | %/zm/z (MH+) |
|---|---|---|---|
| 175 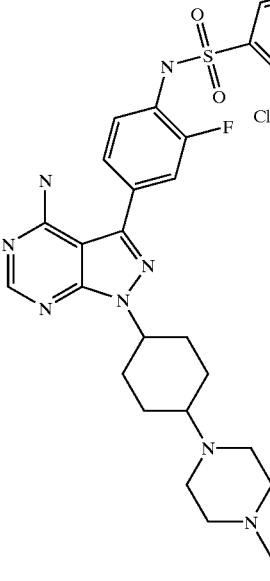 | 11.982 | 91.6 | 633.1 |
| 176 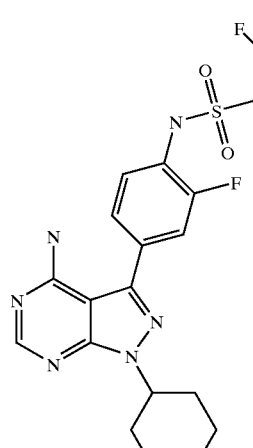 | 10.099 | 77.9 | 601.2 |

| Structure | HPLC Rt (min) | Purity % | zm/z (MH+) |
|---|---|---|---|
| 177 | 11.059 | 93.9 | 617.2 |
| 178 | 10.332 | 92.5 | 583.5 |

-continued
| | Structure | HPLC Rt (min) | Purity | %/zm/z (MH+) |
|---|---|---|---|---|
| 180 | 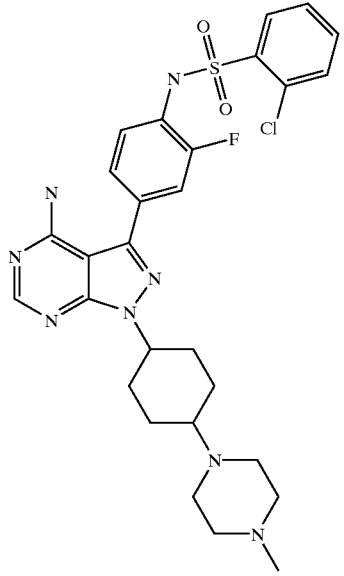 | 10.929 | 84.3 | 643.2 |
| 181 | 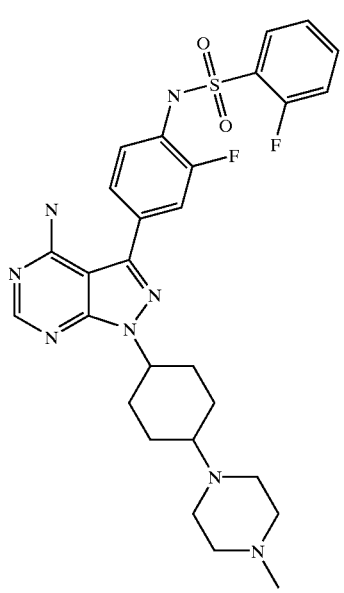 | 10.074 | 87.1 | 583.2 |

-continued
| Structure | HPLC Rt (min) | Purity | %/zm/z (MH⁺) |
|---|---|---|---|
| 182 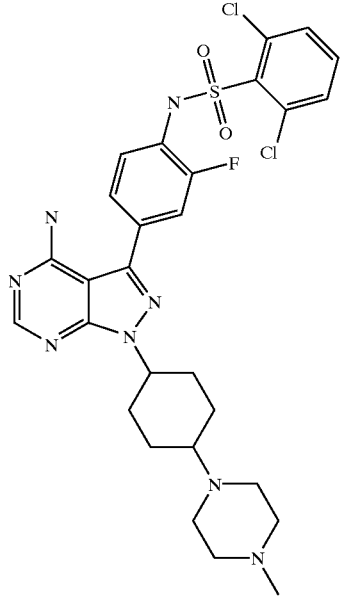 | 11.256 | 90.5 | 633.1 |
| 183 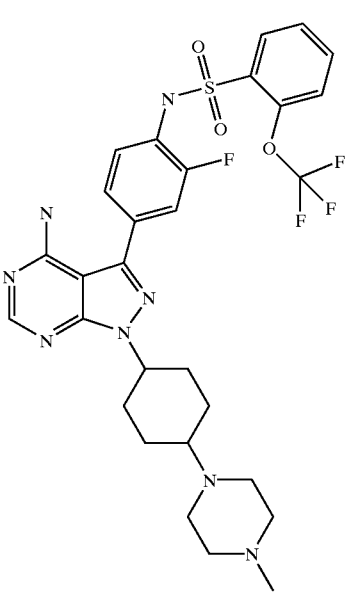 | 11.807 | 75.7 | 649.2 |

| | Structure | HPLC Rt (min) | Purity | %/zm/z (MH⁺) |
|---|---|---|---|---|
| 184 | 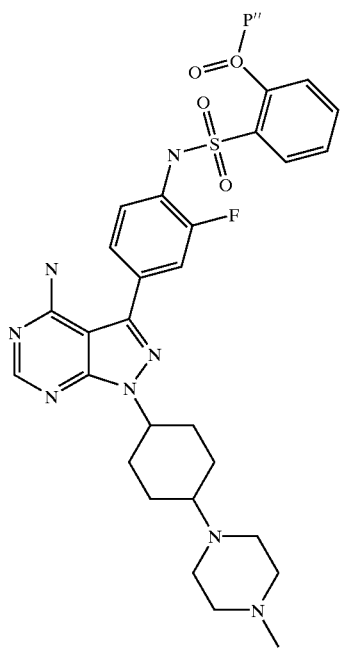 | 10.617 | 100 | 610.2 |
| 185 | 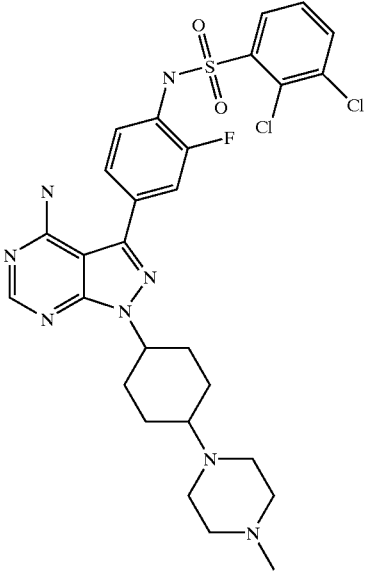 | 11.895 | 88.4 | 633.2 |

Analytical RP-HPLC conditions: 10 to 90% CH₃CN in 0.1 N aqueous ammonium acetate, buffered to pH 4.5, over 12 min at 2 mL/min using a Waters Symmetry C18, 5 μm, 250×4.6 mm column.

Example 186–189 cis-3-{4-[Amino(phenyl)methyl]phenyl}-1-[4-(4-methylpiperazino)cyclohexyl]-1H-pyrazolo[3,4-d] pyrimidin-4-amine Analogs a. General Synthetic Route to Sulfonamide and Carboxamide Derivatives A mixture of cis-3-{4-[amino(phenyl)methyl]phenyl}-1-[4-(4-methylpiperazino)cyclohexyl]-1H-pyrazolo[3,4-d] pyrimidin-4-amine (50 mg, 0.10 mmol), corresponding electrophile (sulfonyl chloride or acid chloride) (1 equiv.) and pyridine (1 mL) was heated at 40° C. for 24–72 h. (In some cases, additional electrophile (typically 1 equiv.) was necessary for the reaction to reach completion). The solvent was removed in vacuo. Purification was effected using mass actuated preparative RP-HPLC (Micromass/Gilson, Hypersil BDS C18, 5 μm, 100×21.2 mm column; 0–100% acetonitrile and 0.05M ammonium acetate, buffered to pH 4.5, over 12.5 min at 25 mL/min) to afford the following compounds:

| Ex | Structure | HPLC Rt (min) | Purity (%) | m/z (MH+) |
|---|---|---|---|---|
| 186 | 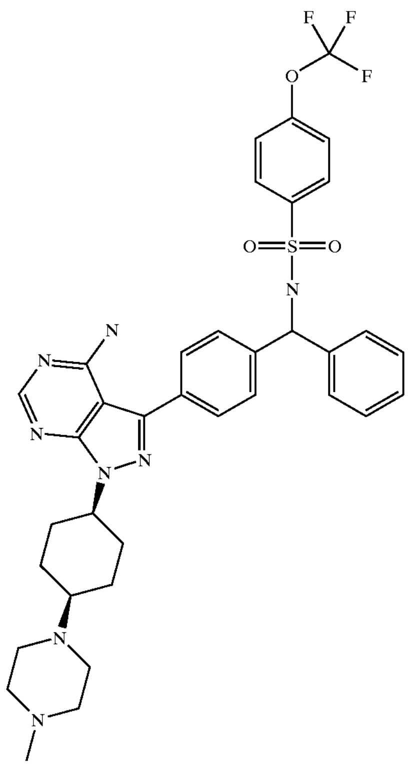 | 15.76 | 94.9 | 721.6 |
| 187 | 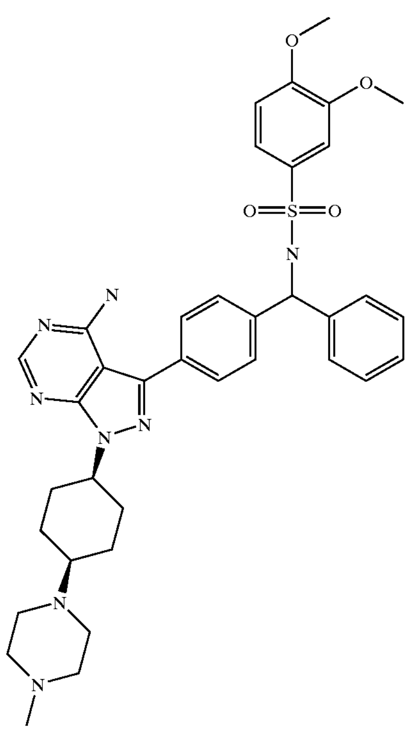 | 13.21 | 94.9 | 697.3 |

-continued

| Ex | Structure | HPLC Rt (min) | Purity (%) | m/z (MH+) |
|---|---|---|---|---|
| 188 | 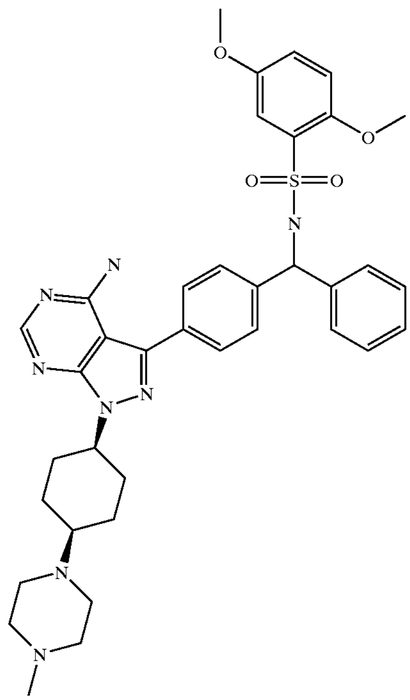 | 14.20 | 91.3 | 697.4 |
| 189 | 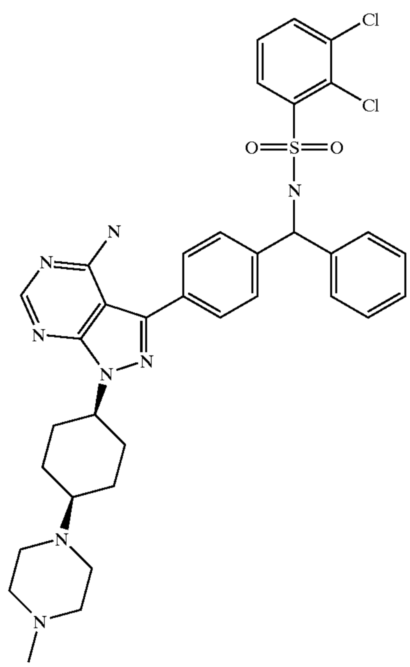 | 15.30 | 96.8 | 705.3 |

-continued
| Ex | Structure | HPLC Rt (min) | Purity (%) | m/z (MH+) |
|---|---|---|---|---|
| 190 | 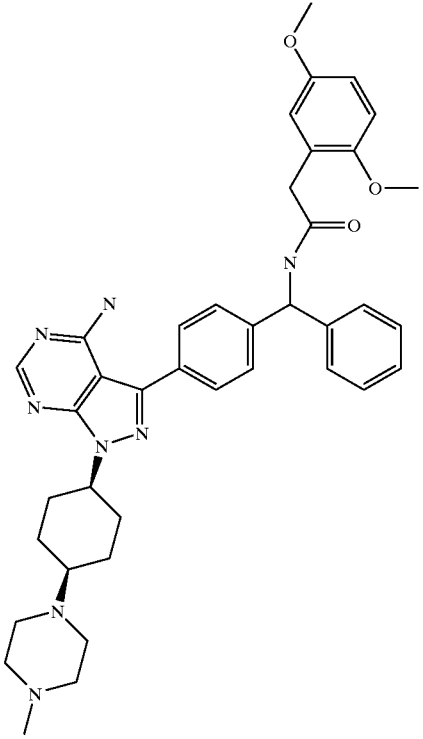 | 14.00 | 100 | 675.4 |
| 191 | 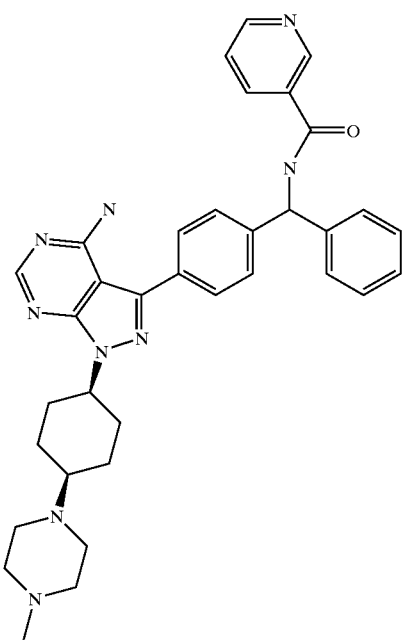 | 12.00 | 99 | 602.4 |

-continued
| Ex | Structure | HPLC Rt (min) | Purity (%) | m/z (MH+) |
|---|---|---|---|---|
| 192 | 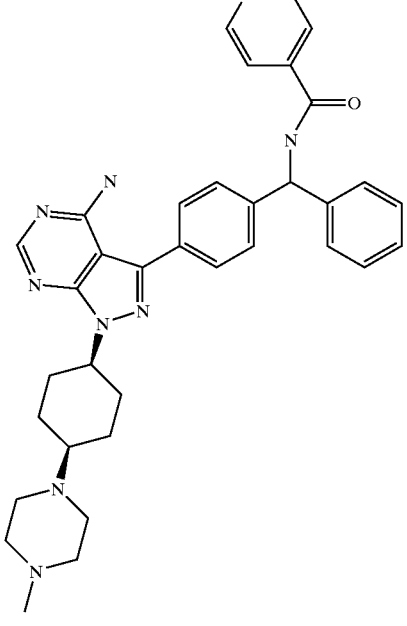 | 12.08 | 100 | 602.3 |
| 193 | 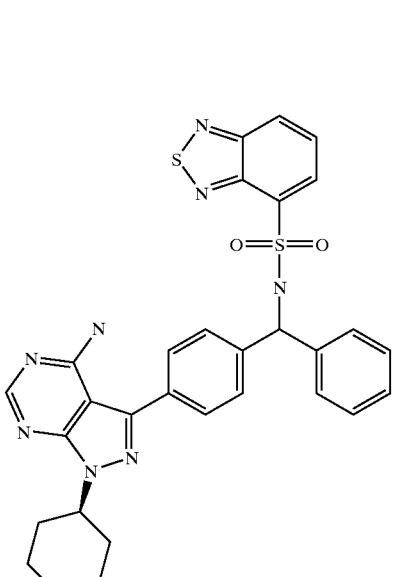 | 13.68 | 100 | 695 |

-continued

| Ex | Structure | HPLC Rt (min) | Purity (%) | m/z (MH+) |
|---|---|---|---|---|
| 194 | 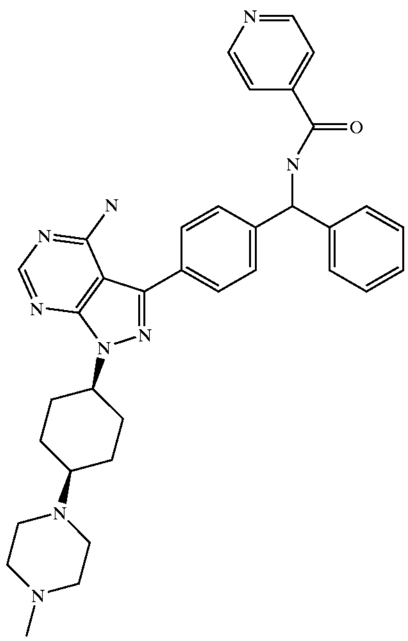 | 12.08 | 100 | 100 |

Analytical RP-HPLC conditions 10 to 90% CH$_3$CN in 0.1 N aqueous ammonium acetate, buffered to pH 4.5, over 12 min at 2 mL/min using a Waters Symmetry C18, 5 μm, 250×4.6 mm column.

Example 195

1-[4-(4-Methylpiperazino)cyclohexyl]-3-{4-[(phenethylamino)(phenyl)methyl]phenyl}-1H-pyrazolo[3,4-d]pyrimidin-4-amine To a solution of cis-3-{4-[amino(phenyl)methyl]phenyl}-1-[4-(4-methylpiperazino)cyclohexyl]-1H-pyrazolo[3,4-d]pyrimidin-4-amine (50 mg, 0.10 mmol), phenylacetaldehyde (13 mg) and glacial acetic acid (0.013 mL) in 1,2-dichloroethane (1 mL) under nitrogen was added sodium triacetoxyborohydride (2 equivs., 43 mg). The solution was stirred for 18 h then concentrated in vacuo, partitioned between dichloromethane (10 mL) and saturated aqueous NaHCO$_3$ (10 mL) and the organic layer separated. The aqueous layer was further extracted with dichloromethane (4×10 mL) and the combined organic layers were dried over anhydrous magnesium sulfate and evaporated to dryness. Purification was effected using mass actuated preparative RP-HPLC (Micromass/Gilson, Hypersil BDS C18, 5 μm, 100×21.2 mm column; 0–100% acetonitrile and 0.05M ammonium acetate, buffered to pH 4.5, over 12.5 min at 25 mL/min) to afford 1-[4-(4-methylpiperazino)cyclohexyl]-3-{4-[(phenethylamino)(phenyl)methyl]phenyl}-1H-pyrazolo[3,4-d]pyrimidin-4-amine (28 mg); RP-HPLC (10 to 90% CH$_3$CN in 0.1 N aqueous ammonium acetate, buffered to pH 4.5, over 12 min at 2 mL/min using a Waters Symmetry C18, 250×4.6 mm column) R$_t$=12.269 min, 95.2%; m/z (MH$^+$) 601.3.

Example 196

N-{4-[4-Amino-1-(4-oxocyclohexyl)-1H-pyrazolo[3,4-d]pyrimidin-3-yl]-2-fluorophenyl}-N'-(3-methylphenyl)urea m-Tolyl isocyanate (1.2 equiv., 37.7 mg, 0.283 mmol) was added to a solution of 4-[4-amino-3-(4-amino-3-fluorophenyl)-1H-pyrazolo[3,4-d]pyrimidin-1-yl]-1-cyclohexanone (80.3 mg, 0.236 mmol) in pyridine. After 16 h at 40° C., the reaction was quenched with water (2 mL) and evaporated to dryness. Purification by preparative RP-HPLC (10% to 40% CH$_3$CN in 0.1 N aqueous ammonium acetate, buffered to pH 4.5, over 60 min at 10 mL/min using a Waters Deltapak C18, 15 μm, 100×40 mm column, λ=254 nm) gave N-{4-[4-amino-1-(4-oxocyclohexyl)-1H-pyrazolo[3,4-d]pyrimidin-3-yl]-2-fluorophenyl}-N'-(3-methylphenyl)urea (91 mg, 84%); $^1$H NMR (DMSO-d$_6$, 400 MHz) δ 2.26 (2H, br t), 2.30 (3H, s), 2.43 (4H, m), 2.69 (2H, m), 5.26 (1H, m), 6.82 (1H, d), 7.18 (1H, t), 7.25 (1H, br d), 7.32 (1H, br s), 7.45 (2H, m), 8.26 (1H, s), 8.36 (1H, t), 8.72 (1H, d) and 9.05 (1H, s) and RP-HPLC (10 to 90% CH$_3$CN in 0.1 N aqueous ammonium acetate, buffered to pH 4.5, over 12 min at 2 mL/min using a Waters Symmetry C18, 5 μm, 250×4.6 mm column) R$_t$=15.433 min, 97.9%.

Example 197

Ethyl 2-[4-Amino-3-(4-[(2,3-dichlorophenyl)sulfonyl]amino-3-fluorophenyl)-1H-pyrazolo[3,4-d]pyrimidin-1-yl]acetate a) Ethyl 2-(4-Amino-3-iodo-1H-pyrazolo[3,4-d]pyrimidin-1-yl)acetate Sodium hydride (60%, 0.138 g, 3.45 mmol) was added to a suspension of 3-iodo-1H-pyrazolo[3,4-d]pyrimidin-4-amine (0.750 g, 2.87 mmol) in N,N-dimethylformamide (9 mL), and the mixture was stirred at ambient temperature for 1 hour until a homogeneous solution was obtained. Ethyl bromoacetate (0.447 mL, 4.03 mmol) was added, and the mixture was stirred at ambient temperature under an atmosphere of nitrogen for 14 hours. The solvent was removed under reduced pressure and the resulting solid was triturated sequentially with water (25 mL) and then ether/petroleum ether (4:1, 50 mL) to yield ethyl 2-(4-amino-3-iodo-1H-pyrazolo[3,4-d]pyrimidin-1-yl)acetate (0.791 g, 2.28 mmol) as a brown solid: $^1$H NMR (DMSO-$d_6$, 400 MHz) δ 8.21 (s, 1H), 5.17 (s, 2H), 4.15 (qt, 2H), 1.20 (t, 3H); RP-HPLC (25 to 100% $CH_3CN$ in 0.1 M aqueous ammonium acetate over 10 min at 1 mL/min using a Hypersil HS C18, 250×4.6 mm column) $R_t$ 6.87 min.

b) Ethyl 2-(4-Amino-3-4-[(tert-butoxycarbonyl)amino]-3-fluorophenyl-1H-pyrazolo[3,4-d]pyrimidin-1-yl)acetate A suspension of ethyl 2-(4-amino-3-iodo-1H-pyrazolo[3,4-d]pyrimidin-1-yl)acetate (0.790 g, 2.28 mmol), tert-butyl N-[2-fluoro-4-(4,4,5,5-tetramethyl-1,3,2-dioxaborolan-2-yl)phenyl]carbamate (1.08 g, 3.19 mmol), tetrakis (triphenylphosphine) palladium (0.105 g, 0.091 mmol), and sodium bicarbonate (0.478 g, 5.69 mmol) in N,N-dimethylformamide (12 mL) and water (2 mL) was heated at 90° C. for 14 hours under an atmosphere of nitrogen. The solvent was removed under reduced pressure, and the residue was partitioned between saturated aqueous sodium chloride (50 mL) and ethyl acetate (30 mL). The aqueous layer was separated and extracted further with ethyl acetate (3×30 mL). The combined organic extracts were dried over magnesium sulfate, filtered, and concentrated under reduced pressure. Purification by flash column chromatography on silica gel using ethyl acetate/heptane (9:1) as a mobile phase afforded ethyl 2-(4-amino-3-4-[(tert-butoxycarbonyl)amino]-3-fluorophenyl-1H-pyrazolo[3,4-d]pyrimidin-1-yl)acetate (0.193 g, 0.449 mmol) as a yellow oil: $^1$H NMR ($CDCl_3$, 400 MHz) δ 8.41 (s, 1H), 8.30 (m, 1H), 7.47 (m, 2H), 6.81 (s, 1H), 5.47 (br, 2H), 5.20 (s, 2H), 4.25 (qt, 2H), 1.55 (s, 9H), 1.27 (t, 3H); RP-HP (25 to 100% acetonitrile in 0.1 M aqueous ammonium acetate over 10 min at 1 mL/min using a Hypersil HS C18, 250×4.6 mm column) $R_t$ 9.47 min.

c) Ethyl 2-[4-Amino-3-(4-[(2,3-dichlorophenyl)sulfonyl]amino)-3-fluorophenyl)-1H-pyrazolo[3,4-d]pyrimidin-1-yl]acetate To a 50-mL flask containing a solution of hydrogen chloride in dioxane (4 M, 6 mL) and ethanol (6 mL) was added ethyl 2-(4-amino-3-4-[(tert-butoxycarbonyl)amino]-3-fluorophenyl-1H-pyrazolo[3,4-d]pyrimidin-1-yl)acetate (0.452 g, 1.05 mmol). An air condenser was affixed to the flask, and the mixture was stirred at 50° C. under an atmosphere of nitrogen. After 16 hours, the reaction mixture was cooled to ambient temperature, and the solvent was removed under reduced pressure. The residue was partitioned between aqueous hydrochloric acid (0.5 M, 30 mL) and ether (20 mL). The organic layer was separated and discarded. The aqueous layer was basified with saturated aqueous sodium bicarbonate (30 mL), and the resulting mixture was extracted with ethyl acetate (3×30 mL). The combined ethyl acetate extracts were dried over magnesium sulfate, filtered, and concentrated to afford a yellow solid (0.295 g)

This yellow solid was added to a solution of 2,3-dichlorobenzenesulfonyl chloride (0.263 g, 1.07 mmol) and 4-dimethylaminopyridine (0.005 g, 0.041 mmol) in pyridine (5 mL), and the resulting solution was stirred under an atmosphere of nitrogen for 3 days. Methanol/dichloromethane (1:19, 100 mL) was added and the resulting mixture was extracted with aqueous sodium bicarbonate (3×10 mL). The organic layer was dried over magnesium sulfate, filtered, and concentrated. A portion of the material was purified by preparative HPLC (25 to 100% acetonitrile in 0.1 M aqueous ammonium acetate over 20 min at 21 mL/min using an 8μ Hypersil HS C18, 250×21 mm column, $R_t$ 12.4–13.9 min) to afford ethyl 2-[4-amino-3-(4-[(2,3-dichlorophenyl)sulfonyl]amino-3-fluorophenyl)-1H-pyrazolo[3,4-d]pyrimidin 1-yl]acetate as a white solid (0.011 g, 0.020 mmol): RP-HP (25 to 100% $CH_3CN$ in 0.1 M aqueous ammonium acetate over 10 min at 1 mL/min using a Hypersil HS C18, 250×4.6 mm column) $R_t$ 9.78 min. $^1$H NMR (DMSO-$d_6$, 400 MHz) δ 10.84 (s, 1H), 8.25 (s, 1H), 7.97 (s, 1H), 7.95 (s, 1H), 7.54 (t, 1H), 7.43 (m, 3H), 5.21 (s, 2H), 4.15 (qt, 2H), 1.20 (t, 3H); MS: $MH^+$539.

Example 198

N1-4-[4-Amino-1-(2-hydroxyethyl)-1H-pyrazolo[3,4-d]pyrimidin-3-yl]-2-fluorophenyl-2,3-dichloro-1-benzenesulfonamide Ethyl 2-[4-amino-3-(4-[(2,3-dichlorophenyl)sulfonyl]amino-3-fluorophenyl)-1H-pyrazolo[3,4-d]pyrimidin-1-yl]acetate (0.120 g, 0.222 mmol) was suspended in ethylene glycol dimethyl ether (2 mL), and the suspension was cooled to 0° C. Lithium aluminum hydride (0.025 g, 0.660 mmol) was added, and the reaction mixture was warmed to ambient temperature. After 24 hours, excess hydride was quenched by the addition of aqueous hydrochloric acid (0.5 M, 10 mL). The aqueous layer was extracted with ethyl acetate (2×7 mL), and the organic extracts were discarded. The aqueous layer was basified with saturated aqueous sodium bicarbonate (10 mL), saturated with sodium chloride, and extracted with methanol/dichloromethane (1:9, 4×20 mL). The organic layers were combined, dried over magnesium sulfate, filtered, and concentrated under reduced pressure. Purification by preparative HPLC (25 to 100% acetonitrile in 0.1M aqueous ammonium acetate over 20 min at 21 mL/min using an 8μ Hypersil HS C18, 250×21 mm column, $R_t$ 8.93–9.90 min) afforded N1-4-[4-amino-1-(2-hydroxyethyl)-1H-pyrazolo[3,4-d]pyrimidin-3-yl]-2-fluorophenyl-2,3-dichloro-1-benzenesulfonamide as an off-white solid (0.004 g, 0.008 mmol): $^1$H NMR (DMSO-$d_6$, 400 MHz) δ 10.82 (s, 1H), 8.23 (s, 1H), 7.97 (s, 1H), 7.95 (s, 1H), 7.54 (t, 1H), 7.39 (m, 3H), 6.90 (br, 2H), 4.86 (t, 1H), 4.35 (t, 2H), 4.04 (t, 2H); MS: $(M-H)^-$ 495.

Example 199

N1-(4-{4-Amino-1-[2-cyano-4-(4-methylpiperazino)phenyl]-1H-pyrazolo[3,4-d]pyrimidin-3-yl}-2-fluorophenyl)-2,3-dichloro-1-benzenesulfonamide A suspension of 3-iodo-1H-pyrazolo[3,4-d]pyrimidin-4-amine (0.172 g, 0.66 mmol), sodium hydride (60%, 0.030 g, 0.75 mmol), 2,5-difluorobenzonitrile (0.105 g, 0.75 mmol), and N,N-dimethylformamide (2.5 mL) were heated for 24 hours at 100° C. The reaction mixture was cooled to ambient temperature and concentrated under reduced pressure. The residue was partitioned between dichloromethane (50 mL) and water (10 mL). The organic layer was separated, dried over magnesium sulfate, filtered, and concentrated under reduced pressure.

This material (0.045 g) and cesium carbonate (0.115 g, 0.353 mmol) were suspended in 1-methylpiperazine (1 mL), and the mixture was heated at 110° C. in a sealed tube for 20 h. The reaction mixture was cooled to ambient temperature and concentrated under reduced pressure. The residue was acidified with aqueous hydrochloric acid (1 M, 10 mL), and the aqueous phase was extracted with ether (10 mL). The organic phase was discarded, and the aqueous phase was basified with aqueous sodium carbonate (3 M, 10 mL). The aqueous phase was extracted with dichloromethane (3×15 mL), and the combined organic fractions were dried over magnesium sulfate, filtered, and concentrated under reduced pressure. This material was elaborated using the procedure in (b), and deprotected and sulfonylated using the procedure in (c). Purification of the product by preparative HPLC (25 to 100% acetonitrile in 0.1 M aqueous ammonium acetate over 20 min at 21 mL/min using an 8µ Hypersil HS C18, 250×21 mm column, $R_t$ 8.4–9.4 min) afforded N1-(4-{4-amino-1-[2-cyano-4-(4-methylpiperazino) phenyl]-1H-pyrazolo[3,4-d]pyrimidin-3-yl}-2-fluorophenyl)-2,3-dichloro-1-benzenesulfonamide as a yellow solid (0.007 g, 0.011 mmol): $^1$H NMR (DMSO-$d_6$, 400 MHz) δ 8.27 (s, 1H), 7.98 (d, 1H), 7.86 (d, 1H), 7.69 (d, 1H), 7.53 (m, 6H), 3.30 (m, 4H), 2.70 (m, 4H), 2.40 (s, 3H); MS (M−H)$^-$ 650.

Example 200 cis-N1-Phenyl-4-{4-amino-1-[4-(4-methylpiperazino)cyclohexyl]-1H-pyrazolo[3,4-d]pyrimidin-3-yl}-2-methoxybenzamide a) 4-Bromo-2-methoxybenzonitrile A suspension of potassium methoxide (4.24 g, 60.0 mmol) in tetrahydrofuran (40 mL) was added in portions to a solution of 4-Bromo-2-fluorobenzonitrile (8.0 g, 40.0 mmol) in tetrahydrofuran (50 mL) at −50° C. After one hour, the dry ice bath was removed and the reaction mixture was allowed to warm up to room temperature and stirred at room temperature for 6 hours. The reaction mixture was poured onto water (250 mL) and the solid was collected by filtration to give 4-bromo-2-methoxybenzonitrile (7.85 g, 92%). $^1$H NMR (DMSO-$d_6$) δ 3.94 (s, 3H), 7.32 (d, J=8.23 Hz, 1H), 7.15 (s, 1H), 7.69 (d, J=8.23 Hz, 1H).

b) 4-Bromo-2-methoxybenzoic Acid

4-Bromo-2-methoxybenzonitrile (7.35 g, 35 mmol) was dissolved in dioxane (400 mL). Sodium hydroxide (2.0 N, 200 mL) was added and the suspension was heated at 100° C. for 16 hours. Organic solvent was removed under reduced pressure and the aqueous mixture was filtered and washed with water. The filtrate was neutralized with hydrochloric acid (5.0N) to pH 1. The solid was collected by filtration to give 4-bromo-2-methoxybenzoic acid (3 g, 37%). $^1$H NMR (DMSO-$d_6$) δ 3.84 (s, 3H), 7.21 (d, J=8.25 Hz, 1H), 7.33 (s, 1H), 7.58 (d, J=8.23 Hz, 1H).

c) 4-Bromo-2-methoxy-1-benzenecarbonyl Chloride

4-Bromo-2-methoxybenzoic acid (2.934 g, 12.70 mmol) was mixed with sodium carbonate (2.2 g, 26.51 mmol). Thionyl chloride (20 mL) was added and the reaction mixture was heated at 80° C. for 16 hours. After distilling off excess thionyl chloride, heptane was added and the solid was collected by filtration to give 4-bromo-2-methoxy-1-benzenecarbonyl chloride (3.16 g, 100%). $^1$H NMR (CDCl$_3$) δ 3.94 (s, 3H), 7.16 (s, 1H), 7.20 (d, J=8.51 Hz, 1H), 7.95 (d, J=8.51 Hz, 1H).

d) N1-Phenyl-4-bromo-2-methoxybenzamide

Aniline(1.24 mL, 13.62 mmol) was added slowly to a mixture of 4-bromo-2-methoxy-1-benzenecarbonyl chloride (3.24 g, 12.98 mmol) and triethyl amine (2.7 mL, 19.48 mmol) in dichloromethane (130 mL). After 3 hours, solvent was removed under reduced pressure. Ethyl acetate was added and the mixture was filtered. The filtrate was concentrated under reduced pressure and the residue was re-crystallized from ethyl acetate/heptane to give N1-phenyl-4-bromo-2-methoxybenzamide (2.92 g, 74%). $^1$H NMR (DMSO-$d_6$) δ 3.92 (s, 3H), 7.09 (s, 1H), 7.27 (m, 1H), 7.33 (m, 2H), 7.39 (s, 1H), 7.55 (d, J=8.15 Hz, 1H), 7.71 (m, 2H), 10.10 (s, 1H).

e) 4-(Anilinocarbonyl)-3-methoxyphenylboronic Acid n-Butyl lithium (1.6 M in hexane solution, 5.1 ml, 8.16 mmol) was added slowly to a solution of N1-phenyl-4-bromo-2-methoxybenzamide (1.0 g, 3.26 mmol) in tetrahydrofuran (25 mL) at −78° C. After 30 minutes, triisopropyl borate (1.13 mL, 4.90 mmol) was added rapidly. The reaction mixture was allowed to warm up to room temperature after 15 minutes and stirred at room temperature for 16 hours. Hydrochloric acid (2.5N, 18 mL) was added and the mixture was stirred for 5 h hours. The layers were separated and the aqueous layer was extracted with ethyl acetate. The combined organic layer was washed with brine, dried over MgSO$_4$, filtered and concentrated. The residue was re-crystallized from ethyl acetate/heptane to give 4-(anilinocarbonyl)-3-methoxyphenylboronic acid (0.549 g, 62%). $^1$H NMR (DMSO-$d_6$) δ 3.91 (s, 3H), 7.08 (m, 1H), 7.33 (m, 2H), 7.47 (d, J=7.57 Hz, 1H), 7.59 (m, 2H), 7.73 (d, J=7.36 Hz, 2H), 8.24 (s, 2H), 10.10 (s, 1H).

f) cis-N1-Phenyl-4-{4-amino-1-[4-(4-methylpiperazino)cyclohexyl]-1H-pyrazolo[3,4-d]pyrimidin-3-yl}-2-methoxybenzamide cis-3-Iodo-1-[4-(4-methylpiperazino)cyclohexyl]-1H-pyrazolo[3,4-d]pyrimidin-4-ylamine (148 mg, 0.335 mmol), 4-(anilinocarbonyl)-3-methoxyphenylboronic acid (100 mg, 0.369 mmol), palladium tetrakistriphenyphosphine (23 mg, 0.020 mmol) and sodium carbonate (85 mg, 0.845 mmol) were mixed with ethylene glycol dimethyl ether (4 mL) and water (2 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (95:5) as mobile phase to give cis-N1-Phenyl-4-{4-amino-1-[4-(4-methylpiperazino) cyclohexyl]-1H-pyrazolo[3,4-d]pyrimidin-3-yl}-2-methoxybenzamide (125 mg, 69%). $^1$H NMR (CDCl$_3$) δ 1.69 (m, 2H), 1.86 (m, 2H), 2.17 (m, 2H), 2.31 (s, 3H), 2.44 (m, 11H), 4.15 (s, 3H), 4.96 (m, 1H), 5.69 (bs, 2H), 7.14 (m, 1H), 7.37 (m, 2H), 7.45 (m, 2H), 7.68 (m, 2H), 8.41 (m, 2H), 9.77 (s, 1H). LC/MS (Micromass-Column: Pecosphere, C18, 3 um, 33×4.6 mm. Eluents: 0% B/A to 100% B/A in 4.5 min.(B: acetonitrile, A: 50 mM ammonia acetate buffer, pH 4.5), 3.5 mL/min.): MH$^+$ =541.2, $R_t$=2.58 min.

Example 201 trans-N1-Phenyl-4-{4-amino-1-[4-(4-methylpiperazino)cyclohexyl]-1H-pyrazolo[3,4-d]pyrimidin-3-yl}-2-methoxybenzamide trans-3-Iodo-1-[4-(4-methylpiperazino)cyclohexyl]-1H-pyrazolo[3,4-d]pyrimidin-4-amine (266 mg, 0.604 mmol), 4-(anilinocarbonyl)-3-methoxyphenylboronic acid (180 mg, 0.664 mmol), palladium tetrakistriphenyphosphine (42 mg, 0.036 mmol) and sodium carbonate (154 mg, 1.449 mmol) were mixed with ethylene glycol dimethyl ether (8 mL) and water (4 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (95:5) as mobile phase to give trans-N1-phenyl-4-{4-amino-1-[4-(4-methylpiperazino)cyclohexyl]-1H-pyrazolo[3,4-d]pyrimidin-3-yl}-2-methoxybenzamide (226 mg, 69%). $^1$H NMR (CDCl$_3$) δ 1.58 (m, 4H), 2.17 (m, 7H), 2.32 (s, 3H), 2.52 (m, 2H), 2.69 (2.69, 3H), 4.16 (s, 3H), 4.78 (m, 1H), 5.49 (bs, 2H), 7.14 (m, 1H), 7.43 (m, 4H), 7.69 (m, 2H), 8.44 (m, 2H), 9.77 (s, 1H). LC/MS (Micromass-Column: Pecosphere, C18, 3 um, 33×4.6 mm. Eluents: 0% B/A to 100% B/A in 4.5 min.(B: acetonitrile, A: 50 mM ammonia acetate buffer, pH 4.5), 3.5 mL/min.): MH$^+$ =541.2, R$_t$=2.61 min.

Example 202 cis-N1-Benzyl-4-{4-amino-1-[4-(4-methylpiperazino)cyclohexyl]-1H-pyrazolo[3,4-d]pyrimidin-3-yl}-2-methoxybenzamide a) N1-Benzyl-4-bromo-2-methoxybenzamide Benzylamine (0.69 mL, 6.31 mmol) was added slowly to a mixture of 4-Bromo-2-methoxy-1-benzenecarbonyl chloride (1.5 g, 6.01 mmol) and triethylamine (1.3 mL, 9.02 mmol) in dichloromethane (60 mL). After 3 hours, solvent was removed under reduced pressure. Ethyl acetate was added and the mixture was filtered. The filtrate was concentrated under reduced pressure and the residue was re-crystallized from ethyl acetate/heptane to give N1-benzyl-4-bromo-2-methoxybenzamide (1.654 g, 86%). $^1$H NMR (DMSO-d$_6$) δ 3.92 (s, 3H), 4.67 (d, J=5.67 Hz, 32H), 7.31 (m, 7H), 8.03 (bs, 1H), 8.13 (d, J=8.41, 1H).

b) 4-[(Benzylamino)carbonyl]-3-methoxyphenylboronic Acid n-Butyl lithium(1.6 M in hexane solution, 8.0 ml, 12.88 mmol) was added slowly to a solution of N1-benzyl-4-bromo-2-methoxybenzamide (1.65 g, 5.15 mmol) in tetrahydrofuran (40 mL) at −78° C. After 30 minutes, triisopropyl borate (1.8 mL, 7.73 mmol) was added rapidly. The reaction mixture was allowed to warm up to room temperature after 13 minutes and stirred for 16 hours. Hydrochloric acid (2.5N, 36 mL) was added and the mixture was stirred overnight. Organic solvent was removed and the aqueous layer was extracted with ethyl acetate. The combined organic layer was washed with brine, dried over MgSO$_4$, filtered and concentrated. The residue was purified by flash column chromatography using dichloromethane/methanol (95:5) as mobile phase to give 4-[(benzylamino)carbonyl]-3-methoxyphenylboronic acid (0.675 g, 46%). $^1$H NMR (DMSO-d$_6$) δ 3.90 (s, 3H), 4.51 (d, J=6.18 Hz, 2H), 7.24 (m, 1H), 7.34 (m, 4H), 7.43 (d, J=7.55 Hz, 1H), 7.59 (s, 1H), 7.69 (d, J=7.55 Hz, 1H), 8.23 (s, 2H), 8.69 (m, 1H).

c) cis-N1-Benzyl-4-{4-amino-1-[4-(4-methylpiperazino)cyclohexyl]-1H-pyrazolo[3,4-d]pyrimidin-3-yl}-2-methoxybenzamide cis-3-Iodo-1-[4-(4-methylpiperazino)cyclohexyl]-1H-pyrazolo[3,4-d]pyrimidin-4-amine (141 mg, 0.319 mmol), 4-[(benzylamino)carbonyl]-3-methoxyphenylboronic acid (100 mg, 0.351 mmol), palladium tetrakistriphenyphosphine (22 mg, 0.019 mmol) and sodium carbonate (81 mg, 0.765 mmol) were mixed with ethylene glycol dimethyl ether (4 mL) and water (2 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (95:5) as mobile phase to give cis-N1-benzyl-4-{4-amino-1-[4-(4-methylpiperazino)cyclohexyl]-1H-pyrazolo[3,4-d]pyrimidin-3-yl}-2-methoxybenzamide (126 mg, 71%). $^1$H NMR (CDCl$_3$) δ 1.83 (m, 6H), 2.34 (s, 3H), 2.45 (m, 11H), 4.02 (s, 3H), 4.43 (d, J=5.66 Hz, 2H), 4.95 (m, 1H), 5.52 (bs, 2H), 7.37 (m, 7H), 8.18 (m, 1H), 8.41 (m, 1H); LC/MS (Micromass-Column: Pecosphere, C18, 3 um, 33×4.6 mm. Eluents: 0% B/A to 100% B/A in 4.5 min.(B: acetonitrile, A: 50 mM ammonia acetate buffer, pH 4.5), 3.5 mL/min.): MH$^+$ =555.5, R$_t$=2.65 min.

Example 203 cis-N1-Phenethyl-4-{4-amino-1-[4-(4-methylpiperazino)cyclohexyl]-1H-pyrazolo[3,4-d]pyrimidin-3-yl}-2-methoxybenzamide a) N1-Phenethyl-4-bromo-2-methoxybenzamide Phenethylamine (0.79 mL, 6.31 mmol) was added slowly to a mixture of 4-Bromo-2-methoxy-1-benzenecarbonyl chloride (1.5 g, 6.01 mmol) and triethylamine (1.3 mL, 9.02 mmol) in dichloromethane (60 mL). After 2 hours, solvent was removed under reduced pressure. Ethyl acetate was added and the mixture was filtered. The filtrate was concentrated under reduced pressure and the residue was purified by flash column chromatography using dichloromethane/ethyl acetate (97:3) as mobile to give N1-phenethyl-4-bromo-2-methoxybenzamide (1.81 g, 90%). $^1$H NMR (DMSO-d$_6$) δ 2.83 (m, 2H), 3.50 (m, 2H), 3.84 (s, 3H), 7.31 (m, 7H), 7.65 (d, J=8.28 Hz, 1H), 8.15 (m, 1H).

b) 4-[(Phenethylamino)carbonyl]-3-methoxyphenylboronic Acid n-Butyl lithium(1.6 M in hexane solution, 8.5 ml, 13.54 mmol) was added slowly to a solution of N1-phenethyl-4-bromo-2-methoxybenzamide (1.81 g, 5.41 mmol) in tetrahydrofuran (40 mL) at −78° C. After 30 minutes, triisopropyl borate (1.87 mL, 8.12 mmol) was added rapidly. The reaction mixture was allowed to warm up to room temperature after 13 minutes and stirred for 3 hours. Hydrochloric acid (2.5N, 40 mL) was added and the mixture was stirred overnight. The layers were separated and the aqueous layer was extracted with ethyl acetate. The combined organic layer was washed with brine, dried over MgSO$_4$, filtered and concentrated. The residue was purified by flash column chromatography using dichloromethane/methanol (95:5) as mobile to give 4-[(benzylamino)carbonyl]-3-methoxyphenylboronic acid (0.916 g, 56%). $^1$H NMR (DMSO-d$_6$) δ 2.85 (m, 2H), 3.53 (m, 2H) 3.88 (s, 3H), 7.31 (m, 7H), 7.70 (d, J=7.61 Hz, 1H), 8.19 (m, 2H), 9.10 (m, 1H).

c) cis-N1-Phenethyl-4-{4-amino-1-[4-(4-methylpiperazino)cyclohexyl]-1H-pyrazolo[3,4-d]pyrimidin-3-yl}-2-methoxybenzamide cis-3-Iodo-1-[4-(4-methylpiperazino)cyclohexyl]-1H-pyrazolo[3,4-d]pyrimidin-4-amine (154 mg, 0.349 mmol), 4-[(phenethylamino)carbonyl]-3-methoxyphenylboronic acid (115 mg, 0.384 mmol), palladium tetrakistriphenyphosphine (24 mg, 0.021 mmol) and sodium carbonate (89 mg, 0.839 mmol) were mixed with ethylene glycol dimethyl ether (4 mL) and water (2 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (95:5) as mobile phase to give cis-N1-phenethyl-4-{4-amino-1-[4-(4-methylpiperazino)cyclohexyl]-1H-pyrazolo[3,4-d]pyrimidin-3-yl}-2-methoxybenzamide (64 mg, 32%). $^1$H NMR (CDCl$_3$-d) δ 1.62 (m, 4H), 2.16 (m, 16H), 2.87 (m, 2H), 3.57 (m, 2H), 3.90 (s, 3H), 4.83 (m, 1H), 7.31 (m, 7H), 7.95 (m, 1H), 8.22 (m, 2H); LC/MS (Micromass-Column: Pecosphere, C18, 3 um, 33×4.6 mm. Eluents: 0% B/A to 100% B/A in 4.5 min. (B: acetonitrile, A: 50 mM ammonia acetate buffer, pH 4.5), 3.5 mL/min.): MH$^+$ =569.3, R$_t$=2.50 min.

Example 204 cis-N1-Phenyl-4-{4-amino-1-[4-(4-methylpiperazino)cyclohexyl]-1H-pyrazolo[3,4-d]pyrimidin-3-yl}benzamide a) N1-Phenyl-4-bromobenzamide Aniline (0.87 mL, 9.57 mmol) was added slowly to a mixture of 4-Bromo-1-benzenecarbonyl chloride (2.0 g, 9.11 mmol) and triethyl amine (1.9 mL, 13.67 mmol) in dichloromethane (95 mL). After 3 hours, solvent was removed under reduced pressure. Ethyl acetate was added and the mixture was filtered. The filtrate was concentrated under reduced pressure and the residue was re-crystallized from ethyl acetate/heptane to give N1-phenyl-4-bromobenzamide (1.00 g, 40%). $^1$H NMR (DMSO-d$_6$) δ 7.11 (m, 1H), 7.38 (m, 2H), 7.76 (m, 4H), 7.92 (m, 2H), 10.30 (s, 1H).

b) 4-(Anilinocarbonyl)phenylboronic Acid n-Butyl lithium(1.6 M in hexane solution, 5.7 ml, 9.05 mmol) was added slowly to a solution of N1-phenyl-4-bromo-2-methoxybenzamide (1.0 g, 3.62 mmol) in tetrahydrofuran (27 mL) at −78° C. After 30 minutes, triisopropyl borate (1.25 mL, 5.43 mmol) was added rapidly. The reaction mixture was allowed to warm up to room temperature after 13 minutes and stirred for 6 hours. Hydrochloric acid (2.5N, 27 mL) was added and the mixture was stirred overnight. The layers were separated and the aqueous layer was extracted with ethyl acetate. The combined organic layer was washed with brine, dried over MgSO$_4$, filtered and concentrated. The residue was recrystallized from ethyl acetate/heptane to give 4-(anilinocarbonyl)phenylboronic acid (0.354 g, 40%). $^1$H NMR (DMSO-d$_6$) δ 7.10 (m, 1H), 7.35 (m, 2H), 7.80 (m, 4H), 7.92 (m, 2H), 8.23 (s, 2H), 10.23 (s, 1H).

c) cis-N1-Phenyl-4-{4-amino-1-[4-(4-methylpiperazino)cyclohexyl]-1H-pyrazolo[3,4-d]pyrimidin-3-yl}benzamide cis-3-Iodo-1-[4-(4-methylpiperazino)cyclohexyl]-1H-pyrazolo[3,4-d]pyrimidin-4-amine (100 mg, 0.226 mmol), 4-(anilinocarbonyl)phenylboronic acid (60 mg, 0.249 mmol), palladium tetrakistriphenyphosphine(16 mg, 0.014 mmol) and sodium carbonate (58 mg, 0.544 mmol) were mixed with ethylene glycol dimethyl ether (3 mL) and water (1.5 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was by preparative thin layer column chromatography using dichloromethane/methanol/ammonium hydroxide (95:5:05) as mobile phase to give cis-N1-phenyl-4-{4-amino-1-[4-(4-methylpiperazino)cyclohexyl]-1H-pyrazolo[3,4-d]pyrimidin-3-yl}benzamide (32 mg, 27%). $^1$H NMR (DMSO-d$_6$) δ 1.60 (m, 4H), 1.73 (m, 2H), 2.08 (m, 2H), 2.19 (s, 3H), 2.28 (m, 11H), 4.84 (m, 1H), 7.12 (m, 1H), 7.38 (m, 2H), 7.81 (m, 4H), 8.16 (d, J=8.30 Hz, 2H), 8.27 (s, 1H), 10.34 (s, 1H). LC/MS (Micromass-Column: Pecosphere, C18, 3 um, 33×4.6 mm. Eluents: 0% B/A to 100% B/A in 4.5 min. (B: acetonitrile, A: 50 mM ammonia acetate buffer, pH 4.5), 3.5 mL/min.): MH$^+$ =511.2, R$_t$=2.41 min.

Example 205 cis-N1-Phenethyl-4-{4-amino-1-[4-(4-methylpiperazino)cyclohexyl]-1H-pyrazolo[3,4-d]pyrimidin-3-yl}benzamide a) N1-Phenethyl-4-bromobenzamide Phenethylamine (1.2 mL, 9.57 mmol) was added slowly to a mixture of 4-Bromo-1-benzenecarbonyl chloride (2.0 g, 9.11 mmol) and triethyl amine (1.9 mL, 13.67 mmol) in dichloromethane (95 mL). After 3 hours, solvent was removed under reduced pressure. Ethyl acetate was added and the mixture was filtered. The filtrate was concentrated under reduced pressure and the residue was re-crystallized from ethyl acetate/heptane to give N1-phenyl-4-bromobenzamide (1.925 g, 69%). $^1$H NMR (DMSO-d$_6$) δ 2.84 (m, 2H), 3.47 (m, 2H), 7.28 (m, 5H), 7.67 (d, J=8.59 Hz, 2H), 7.76 (d, J=8.59 Hz, 4H), 8.64 (m, 1H).

b) 4-[(Phenethylamino)carbonyl]phenylboronic Acid n-Butyl lithium(1.6 M in hexane solution, 10 ml, 15.78 mmol) was added slowly to a solution of N1-phenyl-4-bromo-2-methoxybenzamide (1.92 g, 6.31 mmol) in tetrahydrofuran (47 mL) at −78° C. After 30 minutes, triisopropyl borate (2.2 mL, 9.47 mmol) was added rapidly. The reaction mixture was allowed to warm up to room temperature after 13 minutes and stirred for 16 hours. Hydrochloric acid (2.5N, 47 mL) was added and the mixture was stirred for 5 h hours. The layers were separated and the aqueous layer was extracted with ethyl acetate. The combined organic layer was washed with brine, dried over MgSO$_4$, filtered and concentrated. The residue was recrystallized from ethyl acetate/heptane to give 4-[(phenethylamino)carbonyl] phenylboronic acid (0.486 g, 28%). $^1$H NMR (DMSO-d$_6$) δ 2.85 (m, 2H), 3.49 (m, 2H), 7.22 (m, 5H), 7.73 (m, 4H), 8.17 (s, 2H), 8.54 (m, 1H).

c) cis-N1-Phenethyl-4-{4-amino-1-[4-(4-methylpiperazino)cyclohexyl]-1H-pyrazolo[3,4-d]pyrimidin-3-yl}benzamide cis-3-Iodo-1-[4-(4-methylpiperazino)cyclohexyl]-1H-pyrazolo[3,4-d]pyrimidin-4-amine (100 mg, 0.226 mmol), 4-[(phenethylamino)carbonyl]phenylboronic acid (60 mg, 0.249 mmol), palladium tetrakistriphenyphosphine (16 mg, 0.014 mmol) and sodium carbonate (58 mg, 0.544 mmol) were mixed with ethylene glycol dimethyl ether (3 mL) and water (1.5 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by preparative thin layer column chromatography using dichloromethane/methanol (80:20) as mobile phase to give cis-N1-phenethyl-4-{4-amino-1-[4-(4-methylpiperazino)cyclohexyl]-1H-pyrazolo[3,4-d]pyrimidin-3-yl}benzamide (28 mg, 23%). $^1$H NMR (DMSO-d$_6$) δ 1.62 (m, 4H), 2.24 (m, 16H), 2.88 (m, 2H), 3.54 (m, 2H), 4.82 (m, 1H), 7.29 (m, 7H), 8.73 (d, J=8.10 Hz, 2H), 7.99 (d, 8.17 Hz, 1H), 8.67 (m, 1H). LC/MS (Micromass-Column: Pecosphere, C18, 3 um, 33×4.6 mm. Eluents: 0% B/A to 100% B/A in 4.5 min. (B: acetonitrile, A: 50 mM ammonia acetate buffer, pH 4.5), 3.5 mL/min.): MH$^+$ =539.3, R$_t$=2.50 min.

Example 206 trans-N2-(4-{4-Amino-1-[4-(4-methylpiperazino)cyclohexyl]-1H-pyrazolo[3,4-d]pyrimidin-3-yl}-2-methoxyphenyl)-1H-2-indolecarboxamide, Trimaleate Salt a) trans-tert-Butyl N-(4-{4-Amino-1-[4-(4-methylpiperazino)cyclohexyl]-1H-pyrazolo[3,4-d]pyrimidin-3-yl}-2-methoxyphenyl)carbamate trans-3-Iodo-1-[4-(4-methylpiperazino)cyclohexyl]-1H-pyrazolo[3,4-d]pyrimidin-4-amine (4.0 g, 9.06 mmol), tert-butyl N-[2-methoxy-4-(4,4,5,5-tetramethyl-1,3,2-dioxaborolan-2-yl)phenyl]carbamate (3.48 g, 9.97 mmol), palladium tetrakistriphenyphosphine (0.63 g, 0.64 mmol)

and sodium carbonate (2.30 g, 21.75 mmol) were mixed with ethylene glycol dimethyl ether (100 mL) and water (50 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (80:20) as mobile phase to give trans-tert-butyl N-(4-{4-amino-1-[4-(4-methylpiperazino) cyclohexyl]-1H-pyrazolo[3,4-d]pyrimidin-3-yl}-2-methoxyphenyl)carbamate (4.75 g, 98%). $^1$H NMR (DMSO-d$_6$) δ 1.48 (m, 11H), 2.02 (m, 6H), 2.15 (s, 3H), 2.35 (m, 5H), 2.53 (m, 4H), 3.87 (s, 3H), 4.64 (m, 1H), 7.20 (m, 2H), 7.90 (d, J=8.15, 1H), 8.03 (s, 1H), 8.22 (s, 1H).

b) trans-3-(4-Amino-3-methoxyphenyl)-1-[4-(4-methylpiperazino)cyclohexyl]-1H-pyrazolo[3,4-d] pyrimidin-4-amine A mixture of trifluoroacetic acid/dichloromethane (20:80, 150 mL) was added to a solution of N-(4-{4-amino-1-[4-(4-methylpiperazino)cyclohexyl]-1H-pyrazolo[3,4-d] pyrimidin-3-yl}-2-methoxyphenyl)carbamate(4.75 g, 8.85 mmol) in dichloromethane (100 mL) at 0° C. 2 hours later, the ice-bath was removed and the solvents were evaporated and the residue was dissolved in dichloromethane. Sodium hydroxide (1.0N) was added to adjust the pH to about 10. The solid formed upon removal of organic solvent was collect by filtration to give trans-3-(4-amino-3-methoxyphenyl)-1-[4-(4-methylpiperazino)cyclohexyl]-1H-pyrazolo[3,4-d]pyrimidin-4-amine (3.85 g, 100%). $^1$H NMR (DMSO-d$_6$) δ 1.44 (m, 2H), 1.96 (m, 6H), 2.21 (s, 3H), 2.33 (m, 5H), 2.53 (m, 4H), 3.83 (s, 3H), 4.60 (m, 1H), 5.03 (bs, 2H), 6.76 (d, J=7.91 Hz, 1H), 6.98 (d, J=7.89 Hz, 1H), 7.03 (m, 2H), 8.19 (s, 1H).

c) trans-N2-(4-{4-Amino-1-[4-(4-methylpiperazino) cyclohexyl]-1H-pyrazolo[3,4-d]pyrimidin-3-yl}-2-methoxyphenyl)-1H-2-indolecarboxamide To 1H-2-indolecarboxylic acid (0.738 g, 4.58 mmol) in dichloromethane (14 mL) was added oxalyl chloride (4 mL, 45.8 mmol) and DMF (1drop). The reaction mixture was stirred overnight. Solvent was evaporated and the residue was dissolved in Dichloromethane (5 mL). Half of the dichloromethane solution (2.5 mL) was added to a solution of trans-3-(4-amino-3-methoxyphenyl)-1-[4-(4-methylpiperazino)cyclohexyl]-1H-pyrazolo[3,4-d] pyrimidin-4-amine (0.50 g, 1.145 mmol) in pyridine (6 mL) at 0° C. After 30 minutes, the solid as collected by filtration. Water was then added to the solid and the pH of the solution was adjusted to 10 with sodium hydroxide (1.0N). The aqueous was extracted with dichloromethane. The combined organic layer was washed with water then brine, dried over MgSO$_4$, filtered and evaporated. The residue was purified by flash column chromatography using dichloromethane/methanol (80:20) as mobile phase to give trans-N2-(4-{4-amino-1-[4-(4-methylpiperazino)cyclohexyl]-1H-pyrazolo [3,4-d]pyrimidin-3-yl}-2-methoxyphenyl)-1H-2-indolecarboxamide (0.312 g, 47%). $^1$H NMR (DMSO-d$_6$) δ 1.49 (m, 2H), 2.05 (m, 6H), 2.15 (s, 3H), 2.32 (m, 5H), 2.51 (m, 4H), 3.97 (s, 3H), 4.66 (m, 1H), 7.10 (m, 1H), 7.22 (m, 1H), 7.30 (d, J=7.98 Hz, 1H), 8.11 (d, J=8.14 Hz, 1H), 8.24 (s, 1H), 9.44 (s, 1H).

d) trans-N2-(4-{4-Amino-1-[4-(4-methylpiperazino) cyclohexyl]-1H-pyrazolo[3,4-d]pyrimidin-3-yl}-2-methoxyphenyl)-1H-2-indolecarboxamide, Trimaleate Salt trans-N2-(4-{4-Amino-1-[4-(4-methylpiperazino) cyclohexyl]-1H-pyrazolo[3,4-d]pyrimidin-3-yl}-2-methoxyphenyl)-1H-2-indolecarboxamide (312 mg, 0.539 mmol) was dissolved in hot ethyl acetate (35 mL) and maleic acid (187 mg, 1.614 mmol) in hot ethyl acetate (5 mL) was added. The reaction mixture was stirred at room temperature for 5 hours. The solid was collected by filtration to give trans-N2-(4-{4-Amino-1-[4-(4-methylpiperazino) cyclohexyl]-1H-pyrazolo[3,4-d]pyrimidin-3-yl}-2-methoxyphenyl)-1H-2-indolecarboxamide, dimaleate salt (473 mg, 95%). $^1$H NMR (DMSO-d$_6$) δ 1.60 (m, 2H), 2.09 (m, 6H), 2.68 (s, 3H), 2.84–3.19 (bm, 9H), 3.97 (s, 3H), 4.73 (m, 1H), 6.17 (s, 6H), 7.11 (m, 1H), 7.25 (m, 1H), 7.30 (m, 1H), 7.34 (s, 1H), 7.41 (s, 1H), 7.49 (d, J=8.21, 1H), 7.68 (d, J=8.02 Hz, 1H), 8.13 (d, J=8.15 Hz, 1H), 8.26 (s, 1H), 9.44 (s, 1H), 11.38 (s, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =580.4, R$_t$=2.01 min.

Example 207 trans-N2-(4-{4-Amino-1-[4-(4-methylpiperazino) cyclohexyl]-1H-pyrazolo[3,4-d]pyrimidin-3-yl}-2-methoxyphenyl)-1-methyl-1H-2-indolecarboxamide, Trimaleate Salt a) trans-N2-(4-{4-Amino-1-[4-(4-methylpiperazino) cyclohexyl]-1H-pyrazolo[3,4-d]pyrimidin-3-yl}-2-methoxyphenyl)-1-methyl-1H-2-indolecarboxamide To 1-methyl-1H-2-indolecarboxylic acid (0.802 g, 4.58 mmol) in dichloromethane (14 mL) was added oxalyl chloride (4 mL, 45.8 mmol) and DMF (1 drop). The reaction mixture was stirred overnight. Solvent was evaporated and the residue was dissolved in Dichloromethane (5 mL). Half of the dichloromethane solution (2.5 mL) was added to a solution of trans-3-(4-amino-3-methoxyphenyl)-1-[4-(4-methylpiperazino)cyclohexyl]-1H-pyrazolo[3,4-d] pyrimidin-4-amine (0.50 g, 1.145 mmol) in pyridine (6 mL) at 0° C. After 30 minutes, the solid was collected by filtration. Water was then added to the solid and the pH of the solution was adjusted to 10 with sodium hydroxide (1.0N). The aqueous was extracted with dichloromethane. The combined organic layer was washed with water then brine, dried over MgSO$_4$, filtered and evaporated. The residue was purified by flash column chromatography using dichloromethane/methanol (80:20) as mobile phase to give trans-N2-(4-{4-amino-1-[4-(4-methylpiperazino) cyclohexyl]-1H-pyrazolo[3,4-d]pyrimidin-3-yl}-2-methoxyphenyl)-1-methyl-1H-2-indolecarboxamide (0.545 g, 80%). $^1$H NMR (DMSO-d$_6$) δ 1.49 (m, 2H), 2.02 (m, 6H), 2.17 (s, 3H), 2.36 (m, 5H), 2.55 (m, 4H), 3.96 (s, 3H), 4.04 (s, 3H), 4.66 (m, 1H), 7.15 (m, 1H), 7.28–7.35 (m, 4H), 7.58 (d, J=8.42 Hz, 1H), 7.70 (d, J=7.96 Hz, 1H), 8.11 (d, J=8.14, 1H), 8.24 (s, 1H), 9.43 (s, 1H).

b) trans-N2-(4-{4-Amino-1-[4-(4-methylpiperazino) cyclohexyl]-1H-pyrazolo[3,4-d]pyrimidin-3-yl}-2-methoxyphenyl)-1-methyl-1H-2-indolecarboxamide, Trimaleate Salt trans-N2-(4-{4-Amino-1-[4-(4-methylpiperazino) cyclohexyl]-1H-pyrazolo[3,4-d]pyrimidin-3-yl}-2-methoxyphenyl)-1-methyl-1H-2-indolecarboxamide (545 mg, 0.917 mmol) was dissolved in hot ethyl acetate (60 mL) and maleic acid (320 mg, 2.75 mmol) in hot ethyl acetate (5 mL) was added. The reaction mixture was stirred at room temperature for 5 hours. The solid was collected by filtration to trans-N2-(4-{4-amino-1-[4-(4-methylpiperazino) cyclohexyl]-1H-pyrazolo[3,4-d]pyrimidin-3-yl}-2-methoxyphenyl)-1-methyl-1H-2-indolecarboxamide, dimaleate salt (473 mg). $^1$H NMR (DMSO-d$_6$) δ 1.60 (m, 2H), 2.06 (m, 6H), 2.68 (s, 3H), 2.83–3.57 (bm, 9H), 3.96 (s, 3H), 4.04 (s, 3H), 4.72 (m, 1H), 6.18 (s, 6H), 7.16 (m, 1H), 7.28–7.36 (m, 4H), 7.59 (d, J=8.44 Hz, 1H), 7.72 (d, J=7.94 Hz, 1H), 8.13 (d, J=8.15, 1H), 8.28 (s, 1H), 9.44 (s, 1H). LC/MS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =594.4, R$_t$=2.24.

Example 208 trans-N1-(4-{4-Amino-1-[4-(4-methylpiperazino) cyclohexyl]-1H-pyrazolo[3,4-d]pyrimidin-3-yl}-2-methoxyphenyl)-4-(trifluoromethyl)benzamide, Trimaleate Salt a) trans-N1-(4-{4-Amino-1-[4-(4-methylpiperazino) cyclohexyl]-1H-pyrazolo[3,4-d]pyrimidin-3-yl}-2-methoxyphenyl)-4-(trifluoromethyl)benzamide 4-(Trifluoromethyl)-1-benzenecarbonyl chloride (262 mg, 1.256 mmol) in dichloromathane (1 mL) was added to a solution of trans-3-(4-amino-3-methoxyphenyl)-1-[4-(4-methylpiperazino)cyclohexyl]-1H-pyrazolo[3,4-d] pyrimidin-4-amine (500 mg, 1.145 mmol) in pyridine (8 mL) at 0° C. After 30 minutes, the ice bath was removed the the reaction mixture was stirred at room temperature for 1.5 hour. Solvent was evaporated and the residue was purified by flash column chromatography using dichloromethane/ methanol (80:20) as mobile phase to give trans-N1-(4-{4-amino-1-[4-(4-methylpiperazino)cyclohexyl]-1H-pyrazolo [3,4-d]pyrimidin-3-yl}-2-methoxyphenyl)-4-(trifluoromethyl)benzamide (516 mg, 74%). $^1$H NMR (CDCl$_3$-d) δ 1.55 (m, 2H), 1.74 (m, 2H), 2.10–2.27 (m, 6H), 2.30 (s, 3H), 2.51 (m, 4H), 2.66 (m, 3H), 3.96 (s, 3H), 4.04 (s, 3H), 4.78 (m, 1H), 5.57 (bs, 2H), 7.30 (m, 2H), 7.79 (d, J=8.25 Hz, 2H), 8.04 (d, J=8.05 Hz, 2H), 8.38 (s, 1H), 8.64 (s, 1H), 8.68 (d, J=8.20 Hz, 1H).

b) trans-N1-(4-{4-Amino-1-[4-(4-methylpiperazino) cyclohexyl]-1H-pyrazolo[3,4-d]pyrimidin-3-yl}-2-methoxyphenyl)-4-(trifluoromethyl)benzamide, Trimaleate Salt trans-N1-(4-{4-Amino-1-[4-(4-methylpiperazino) cyclohexyl]-1H-pyrazolo[3,4-d]pyrimidin-3-yl}-2-methoxyphenyl)-4-(trifluoromethyl)benzamide (510 mg, 0.838 mmol) was dissolved in hot ethyl acetate (55 mL) and maleic acid (292 mg, 2.513 mmol) in hot ethyl acetate (5 mL) was added. The reaction mixture was stirred at room temperature for 5 hours. The solid was collected by filtration trans-N1-(4-{4-amino-1-[4-(4-methylpiperazino) cyclohexyl]-1H-pyrazolo[3,4-d]pyrimidin-3-yl}-2-methoxyphenyl)-4-(trifluoromethyl)benzamide, dimaleate salt (802 mg, 100%). $^1$H NMR (DMSO-d$_6$) δ 1.60 (m, 2H), 2.06 (m, 6H), 2.68 (s, 3H), 2.83–3.17 (bm, 9H), 3.93 (s, 3H), 4.72 (m, 1H), 6.17 (s, 6H), 7.29 (d, J=8.12 Hz, 1H), 7.33 (s, 1H), 7.92 (d, J=8.34 Hz, 2H), 8.02 (d, J=8.12 Hz, 1H), 8.17 (d, J=8.12 Hz, 2H), 8.26 (s, 1H), 9.83 (s, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =609.4, R$_t$=2.16 min.

Example 209 trans-N1-(4-{4-Amino-1-[4-(4-methylpiperazino) cyclohexyl]-1H-pyrazolo[3,4-d]pyrimidin-3-yl}-2-methoxyphenyl)-4-(trifluoromethoxy)benzamide, Trimaleate Salt a) trans-N1-(4-{4-Amino-1-[4-(4-methylpiperazino) cyclohexyl]-1H-pyrazolo[3,4-d]pyrimidin-3-yl}-2-methoxyphenyl)-4-(trifluoromethoxy)benzamide 4-(Trifluoromethoxy)-1-benzenecarbonyl chloride (283 mg, 1.256 mmol) in dichloromethane (1 mL) was added to a solution of trans-3-(4-amino-3-methoxyphenyl)-1-[4-(4-methylpiperazino)cyclohexyl]-1H-pyrazolo[3,4-d] pyrimidin-4-amine (500 mg, 1.145 mmol) in pyridine (8 mL) at 0° C. After 30 minutes, the ice bath was removed the reaction mixture was stirred at room temperature for 1.5 hour. Solvent was evaporated and the residue was purified by flash column chromatography using dichloromethane/ methanol (80:20) as mobile phase to give trans-N1-(4-{4-amino-1-[4-(4-methylpiperazino)cyclohexyl]-1H-pyrazolo [3,4-d]pyrimidin-3-yl}-2-methoxyphenyl)-4-(trifluoromethoxy)benzamide (526 mg, 74%). $^1$H NMR (CDCl$_3$) δ 1.57 (m, 2H), 1.74 (m, 2H), 2.10–2.27 (m, 6H), 2.30 (s, 3H), 2.51 (m, 4H), 2.66 (m, 3H), 4.03 (s, 3H), 4.77 (m, 3H), 5.56 (bs, 2H), 7.26–7.37 (m, 4H), 7.99 (m, 2H), 8.38 (s, 1H), 8.59 (s, 1H), 8.67 (d, J=8.21 Hz, 1H).

b) trans-N1-(4-{4-Amino-1-[4-(4-methylpiperazino) cyclohexyl]-1H-pyrazolo[3,4-d]pyrimidin-3-yl}-2-methoxyphenyl)-4-(trifluoromethoxy)benzamide, Trimaleate Salt trans-N1-(4-{4-amino-1-[4-(4-methylpiperazino) cyclohexyl]-1H-pyrazolo[3,4-d]pyrimidin-3-yl}-2-methoxyphenyl)-4-(trifluoromethoxy)benzamide (520 mg, 0.832 mmol) was dissolved in hot ethyl acetate (55 mL) and maleic acid (290 mg, 2.497 mmol) in hot ethyl acetate (5 mL) was added. The reaction mixture was stirred at room temperature for 5 hours. The solid was collected by filtration to give trans-N1-(4-{4-amino-1-[4-(4-methylpiperazino) cyclohexyl]-1H-pyrazolo[3,4-d]pyrimidin-3-yl}-2-methoxyphenyl)-4-(trifluoromethoxy)benzamide, dimaleate salt (780 mg, 96%). $^1$H NMR (DMSO-d$_6$) δ 1.60 (m, 2H), 2.06 (m, 6H), 2.68 (s, 3H), 2.83–3.17 (bm, 9H), 3.93 (s, 3H), 4.72 (m, 1H), 6.18 (s, 6H), 7.28 (d, J=8.14 Hz, 1H), 7.33 (s, 1H), 7.54 (d, J=8.47 Hz, 2H), 8.01 (d, J=8.12 Hz, 1H), 8.10 (d, J=8.69 Hz, 2H), 8.26 (s, 1H), 9.69 (s, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =625.4, R$_t$=2.21 min.

Example 210

N1-{4-[4-Amino-1-[1-(1-methylpiperidin-4-yl) piperidin-4-yl]-1H-pyrazolo[3,4-d]pyrimidin-3-yl]-2-methoxyphenyl}-3-phenylpropanamide a) tert-Butyl 4-Hydroxy-1-piperidinecarboxylate Sodium borohydride (3.8 g, 100.4 mmol) was added in portions to a solution of tert-butyl 4-oxo-1-piperidinecarboxylate (20 g, 100.4 mmol) in methanol (600 mL) at 0° C. After 15 minutes, the ice-water bath was removed and the reaction mixture was stirred at room temperature for 3 hours. Sodium hydroxide (1.0 N, 100 mL) was added and the organic solvent was evaporated. The aqueous was extracted with ether four times. The combined organic layer was washed with water then brine, dried over MgSO$_4$, filtered and evaporated to give tert-butyl 4-hydroxy-1-piperidinecarboxylate (20.48 g, 100%). $^1$H NMR (CDCl$_3$-d) δ 1.48 (s, 9H), 1.63 (m, 2H), 1.87 (m, 2H), 3.03 (m, 2H), 3.83 (m, 3H).

b) tert-Butyl-4-(4-amino-3-iodo-1H-pyrazolo[3,4-d] pyrimidin-1-yl)-1-piperidinecarboxylate 3-Iodo-1H-pyrazolo[3,4-d]pyrimidin-4-amine (10 g, 38.3 mmol), tert-butyl 4-hydroxy-1-piperidinecarboxylate (16.96 g, 84.2 mmol) and triphenylphosphine (20.09 g, 76.0 mmol) were suspended in tetrahydrofuran (425 mL). The reaction mixture was cooled in an ice-water bath and diethyl azodicarboxylate (12.09 mL, 76.0 mmol) was added dropwise. 10 minutes later, the reaction mixture was allowed to warm up to room temperature. 5 hours later, solvent was removed under reduced pressure and dichloromethane (65 mL) was added with heating. The solid was filtered and washed with dichloromethane (20 ml). The solid was further washed with ethyl acetate (5×20 mL) to give a mixture of diethyl 1,2-hydrazinedicarboxylate and tert-butyl 4-(4-amino-3-iodo-1H-pyrazolo[3,4-d]pyrimidin-1-yl)-1-piperidinecarboxylate (1:1, 14.98 g, 63%) which was used without further purification. $^1$H NMR (CDCl$_3$) δ 1.48 (s, 9H), 1.95 (m, 2H), 2.20 (m, 2H), 2.92 (m, 2H), 4.23 (m, 2H), 4.84 (m, 1H), 8.31 (s, 1H).

c) 3-Iodo-1-(4-piperidyl)-1H-pyrazolo[3,4-d]pyrimidin-4-amine

A mixture of trifluoroacetic acid/dichloromethane (20:80, 250 mL) was added to a solution of tert-butyl 4-(4-amino-3-iodo-1H-pyrazolo[3,4-d]pyrimidin-1-yl)-1-piperidinecarboxylate (10.72 g, 24.1 mmol) in dichloromethane (100 mL) at 0° C. 15 minutes later, the ice-bath was removed and the reaction mixture was stirred at room temperature for 5 hours. The solvents were evaporated and the residue was dissolved in dichloromethane. Hydrochloric acid (5.0N) was added and the aqueous layer was washed with dichloromethane three times. Sodium hydroxide (50%) was added to adjust the pH to about 10. The suspension was lyophilized to reduce the volume to one third of the original volume. The solid was collect by filtration to give 3-iodo-1-(4-piperidyl)-1H-pyrazolo[3,4-d]pyrimidin-4-amine (8.109 g, 97%). $^1$H NMR (CDCl$_3$) δ 1.81 (m, 2H), 1.99 (m, 2H), 2.65 (m, 2H), 3.07 (m, 2H), 4.68 (m, 1H), 8.19 (s, 1H).

d) 3-Iodo-1-[1-(1-methylpiperidin-4-yl)]-piperidin-4-yl]-1H-pyrazolo[3,4-d]pyrimidin-4-amine 3-Iodo-1-(4-piperidyl)-1H-pyrazolo[3,4-d]pyrimidin-4-amine (2.00 g, 5.81 mmol), 1-methyl-4-piperidone (2.14 mL, 17.42 mmol), sodium triacetoxyborohydride (2.45 g, 11.62 mmol) and glacial acetic acid (1.05 g, 17.42 mmol) were mixed with 1,2-dichloroethane (75 mL). The reaction mixture was stirred at room temperature for 6 hours and saturated sodium bicarbonate solution was added to adjust the PH to about 8. The solid was collected by filtration to give 3-Iodo-1-[1-(1-methylpiperidin-4-yl)]-piperidin-4-yl]-1H-pyrazolo[3,4-d]pyrimidin-4-amine (2.39 g, 93%). $^1$H NMR (DMSO-d$_6$) δ 1.52 (m, 2H), 1.75 (m, 2H), 1.87 (m, 2H), 2.05 (m, 4H), 2.24 (s, 3H), 2.28 (m, 3H), 2.91 (m, 2H), 3.00 (m, 2H), 4.55 (m, 1H), 8.18 (s, 1H).

e) tert-Butyl N-{4-[4-amino-1-[1-(1-methylpiperidin-4-yl)-piperidin-4-yl]-1H-pyrazolo[3,4-d]pyrimidin-3-yl]-2-methoxyphenyl}carbamate 3-Iodo-1-[1-(1-methylpiperidin-4-yl)]-piperidin-4-yl]-1H-pyrazolo[3,4-d]pyrimidin-4-amine (2.39 g, 5.41 mmol), tert-butyl N-[2-methoxy-4-(4,4,5,5-tetramethyl-1,3,2-dioxaborolan-2-yl)phenyl]carbamate (2.08 g, 5.96 mmol), palladium tetrakistriphenyphosphine (0.375 g, 0.32 mmol) and sodium carbonate (1.38 g, 13.00 mmol) were mixed with ethylene glycol dimethyl ether (80 mL) and water (40 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol/ammonium hydroxide (95:5:0.5) as mobile phase to give tert-butyl N-{4-[4-amino-1-[1-(1-methylpiperidin-4-yl)-piperidin-4-yl]-1H-pyrazolo[3,4-d]pyrimidin-3-yl]-2-methoxyphenyl}carbamate (1.67 g, 57%). $^1$H NMR (DMSO-d$_6$) δ 1.48 (m, 11H), 1.71 (m, 2H) 1.86 (m, 4H), 2.14 (s, 3H), 2.18 (m, 3H), 2.32 (m, 2H), 2.80 (m, 2H), 3.89 (s, 3H), 4.64 (m, 1H), 7.22 (m, 2H), 7.91 (d, J=8.12, 1H), 8.03 (s, 1H), 8.21 (s, 1H).

f) N1-{4-[4-Amino-1-[1-(1-methylpiperidin-4-yl)piperidin-4-yl]-1H-pyrazolo[3,4-d]pyrimidin-3-yl]-2-methoxyphenyl}-3-phenylpropanamide 3-Phenylpropanoyl chloride (77 mg, 0.458 mmol) was added to a solution of 3-(4-amino-3-methoxyphenyl)-1-[1-(1-methylpiperidin-4-yl)-piperidin-4-yl]-1H-pyrazolo[3,4-d]pyrimidin-4-amine (100 mg, 0.229 mmol) in pyridine (1.2 mL). After 5 hours, the solvent was evaporated and the residue was purified by flash column chromatography to give N1-{4-[4-amino-1-[1-(1-methylpiperidin-4-yl)piperidin-4-yl]-1H-pyrazolo[3,4-d]pyrimidin-3-yl]-2-methoxyphenyl}-3-phenylpropanamide (24 mg, 18%). $^1$H NMR (CDCl$_3$-d) δ 1.70 (m, 2H), 1.85 (m, 2H), 2.04 (m, 4H), 2.30 (s, 3H), 2.41 (m, 5H), 2.75 (m, 2H), 2.97 (m, 2H), 3.08 (m, 4H), 3.90 (s, 3H), 4.75 (m, 1H), 5.71 (bs, 2H), 7.24 (m, 8H), 7.76 (s, 1H), 8.34 (s, 1H), 8.52 (d, J=8.12, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, PH 4.5), 3.0 mL/min.): MH$^+$ =569.5, R$_t$=1.65 min.

Example 211

N1-{4-[4-Amino-1-[1-(1-methylpiperidin-yl) piperidin-4-yl]-1H-pyrazolo[3,4-d]pyrimidin-3-yl]-2-methoxyphenyl}-4-(trifluoromethoxy)benzamide 4-(Trifluoromethoxy)-1-benzenecarbonyl chloride (103 mg, 0.458 mmol) was added to a solution of 3-(4-amino-3-methoxyphenyl)-1-[1-(1-methylpiperidin-4-yl)-piperidin-4-yl]-1H-pyrazolo[3,4-d]pyrimidin-4-amine (100 mg, 0.229 mmol) in pyridine (1.0 mL). After 5 hours, the solvent was evaporated and the residue was purified by flash column chromatography to give N1-{4-[4-Amino-1-[1-(1-methylpiperidin-yl)piperidin-4-yl]-1H-pyrazolo[3,4-d]pyrimidin-3-yl]-2-methoxyphenyl}-4-(trifluoromethoxy)benzamide (40 mg, 28%). $^1$H NMR (CDCl$_3$-d) δ 1.67 (m, 2H), 1.84 (m, 2H), 1.97 (m, 2H), 2.06 (m, 2H), 2.28 (s, 3H), 2.45 (m, 5H), 2.94 (m, 2H), 3.10 (m, 2H), 4.03 (s, 3H), 4.77 (m, 1H), 5.53 (bs, 2H), 7.34 (m, 4H), 7.98 (d, J=8.73 Hz, 2H), 8.38 (s, 1H), 8.59 (s, 1H), 8.66 (d, J=8.73 Hz, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, PH 4.5), 3.0 mL/min.): MH$^+$ =625.5, R$_t$=2.00 min.

Example 212

N1-{4-[4-Amino-1-(1-methyl-4-piperidyl)-1H-pyrazolo[3,4-d]pyrimidin-3-yl]-2-methoxyphenyl}-4-(trifluoromethyl)benzamide, Trimaleate Salt a) N1-{4-[4-Amino-1-(1-methyl-4-piperidyl)-1H-pyrazolo[3,4-d]pyrimidin-3-yl]-2-methoxyphenyl}-4-(trifluoromethyl)benzamide 4-(Trifluoromethyl)-1-benzenecarbonyl chloride (48 mg, 0.231 mmol) was added to a solution of 3-(4-amino-3-methoxyphenyl)-1-[1-(1-methylpiperidin-4-yl)-piperidin-4-yl]-1H-pyrazolo[3,4-d]pyrimidin-4-amine (101 mg, 0.231 mmol) in pyridine (1.0 mL). After 5 hours, the solvent was evaporated and the residue was purified by flash column chromatography to give N1-{4-[4-amino-1-(1-methyl-4-piperidyl)-1H-pyrazolo[3,4-d]pyrimidin-3-yl]-2-methoxyphenyl}-4-(trifluoromethyl)benzamide (83 mg, 59%). $^1$H NMR (CDCl$_3$-d) δ 1.68 (m, 2H), 1.82 (m, 4H), 2.01 (m, 4H), 2.29 (s, 3H), 2.44 (m, 3H), 2.93 (m, 2H), 3.30 (m, 2H), 4.03 (s, 3H), 4.77 (m, 1H), 5.60 s, 2H), 7.33 (m, 2H), 1.79 d, J=8.19 Hz, 2H), 8.04 (d, J=8.04 Hz, 2H), 8.37 (s, 1H), 8.66 (m, 2H). LCMS (Micromass-Column: Pecosphere, C18, 3 um, 33×4.6 mm. Eluents: 0% B/A to 100% B/A in 4.5 min.(B: acetonitrile, A: 50 mM ammonia acetate buffer, PH 4.5), 3.5 mL/min.): MH$^+$ =609.4, R$_t$=2.50 min.

b) N1-{4-[4-Amino-1-(1-methyl-4-piperidyl)-1H-pyrazolo [3,4-d]pyrimidin-3-yl]-2-methoxyphenyl}-4-(trifluoromethyl)benzamide, Triimaleate Salt N1-{4-[4-Amino-1-(1-methyl-4-piperidyl)-1H-pyrazolo[3,4-d]pyrimidin-3-yl]-2-methoxyphenyl}-4-(trifluoromethyl)benzamide (78 mg, 0.128 mmol) was dissolved in hot ethyl acetate (10 mL) and maleic acid (45 mg, 0.387 mmol) in hot ethyl acetate (1 mL) was added. The reaction mixture was stirred at room temperature for 5 hours. The solvent was removed and ethyl acetate was added and the solid was collected by filtration to give N1-{4-[4-amino-1-(1-methyl-4-piperidyl)-1H-pyrazolo[3,4-d]pyrimidin-3-yl]-2-methoxyphenyl}-4-(trifluoromethyl)benzamide, trimaleate salt (115 mg, 94% ). $^1$H NMR (DMSO-d$_6$) δ 1.87 (m, 2H), 2.24 (m, 4H), 2.79 (s, 3H), 3.01–3.57 (bm, 11H), 3.93 (s, 3H), 5.09 (m, 1H), 6.12 (s, 6H), 7.32 (m, 2H), 7.93 (d, J=8.37 Hz, 2H), 8.04 (d, J=8.11 Hz, 1H), 8.16 (d, J=8.18 Hz, 2H), 8.29 (s, 1H), 9.84 (s, 1H). LCMS (Micromass-Column: Pecosphere, C18, 3 um, 33×4.6 mm. Eluents: 0% B/A to 100% B/A in 4.5 min. (B: acetonitrile, A: 50 mM ammonia acetate buffer, PH 4.5), 3.5 mL/min.): MH$^+$ =609.4, R$_t$=2.50 min.

Example 213

1-[1-(1H-2-Imidazolylmethyl)tetrahydro-1H-3-pyrrolyl]-3-(4-phenoxyphenyl)-1H-pyrazolo[3,4-d]pyrimidin-4-amine a) tert-Butyl 3-[4-Amino-3-(4-phenoxyphenyl)-1H-pyrazolo[3,4-d]pyrimidin-1-yl]-1-pyrrolidinecarboxylate 3-(4-Phenoxyphenyl)-1H-pyrazolo[3,4-d]pyrimidin-4-amine (0.5 g, 1.648 mmol), tert-butyl 3-{[(4-methylphenyl)sulfonyl]oxy}-1-pyrrolidinecarboxylate (1.12 g, 3.30 mmol) and cesium carbonate (1.07 g, 3.30 mmol) in N,N-dimethyl formamide (12 mL) was heated at 75° C. overnight. The reaction mixture was poured on to ice-water (100 mL). The aqueous layer was extracted with ethyl acetate. The combined organic layer was washed with water then brine, dried over MgSO$_4$, filtered and evaporated. The residue was purified by flash column chromatography using ethyl acetate as mobile phase to give tert-butyl 3-[4-amino-3-(4-phenoxyphenyl)-1H-pyrazolo[3,4-d]pyrimidin-1-yl]-1-pyrrolidinecarboxylate (0.20 g, 28%). $^1$H NMR (DMSO-d$_6$) δ 1.38 (m, 9H), 2.37 (m 2H), 3.32 (s, 3H), 3.44 (m, 1H), 3.59 (m, 1H), 3.65 (m, 1H), 3.75 (m, 1H), 5.44 (m, 1H), 7.16 (m, 5H), 7.43 (m, 2H), 7.65 (m, 2H), 8.26 (s, 1H).

b) 3-(4-Phenoxyphenyl)-1-tetrahydro-1H-3-pyrrolyl-1H-pyrazolo[3,4-d]pyrimidin-4-amine A mixture of trifluoroacetic acid/dichloromethane (20:80, 8 mL) was added to a solution of tert-butyl 3-[4-amino-3-(4-phenoxyphenyl)-1H-pyrazolo[3,4-d]pyrimidin-1-yl]-1-pyrrolidinecarboxylate (240 mg, 0.508 mmol) in dichloromethane (1 mL) at 0° C. After 15 minutes, the ice-bath was removed and the reaction mixture was stirred at room temperature for 5 hours. Solvents were then evaporated and the residue was dissolved in ethyl acetate. Saturated sodium bicarbonate was added to adjust the pH to about 8. The layers were separated and the aqueous layer was extracted with ethyl acetate. The combined organic layer was washed with brine, dried over MgSO$_4$, filtered and evaporated give 3-(4-phenoxyphenyl)-1-tetrahydro-1H-3-pyrrolyl-1H-pyrazolo[3,4-d]pyrimidin-4-amine (0.157 mg, 91%). $^1$H NMR (DMSO-d$_6$) δ 1.99–2.21 (m, 2H), 2.94 (m, 1H), 3.04–3.23 (m, 3H), 5.31 (m, 1H), 7.14 (m, 5H), 7.44 (m, 2H), 7.67 (m, 2H), 8.24 (s, 1H).

c) 1-[1-(1H-2-Imidazolylmethyl)tetrahydro-1H-3-pyrrolyl]-3-(4-phenoxyphenyl)-1H-pyrazolo[3,4-d]pyrimidin-4-amine 3-(4-Phenoxyphenyl)-1-tetrahydro-1H-3-pyrrolyl-1H-pyrazolo[3,4-d]pyrimidin-4-amine (100 mg, 5.81 mmol), 1H-2-imidazolecarbaldehyde (77 mg, 0.806 mmol), sodium triacetoxyborohydride (113 mg, 0.537 mmol) and glacial acetic acid (48 mg, 0.806 mmol) were mixed with 1,2-dichloroethane (4 mL). The reaction mixture was stirred at room temperature for 6 hours and saturated sodium bicarbonate solution was added to adjust the pH to about 9. The aqueous layer was extracted with dichloromethane. The combined organic layer was washed with brine, dried over MgSO$_4$, filtered and evaporated. The residue was purified by flash column chromatography using dichloromethane/methanol (90:10) as mobile phase to give 1-[1-(1H-2-imidazolylmethyl)tetrahydro-1H-3-pyrrolyl]-3-(4-phenoxyphenyl)-1H-pyrazolo[3,4-d]pyrimidin-4-amine (100 mg, 83%). $^1$H NMR (DMSO-d$_6$) δ 2.33 (m, 2H), 2.81 (m, 4H), 3.15 (m, 1H), 3.69 (s, 2H), 5.38 (m, 1H), 6.90 (s, 2H), 7.15 (m, 5H), 7.44 (m, 2H), 7.66 (m, 2H), 8.24 (s, 1H). LCMS (Micromass-Column: Pecosphere, C18, 3 um, 33×4.6 mm. Eluents: 0% B/A to 100% B/A in 4.5 min. (B: acetonitrile, A: 50 mM ammonia acetate buffer, PH 4.5), 3.5 mL/min.): MH$^+$453.4, R$_t$=2.17 min.

Example 214

1-[1-(1-Methyl-4-piperidyl)tetrahydro-1H-3-pyrrolyl]-3-(4-phenoxyphenyl)-1H-pyrazolo[3,4-d]pyrimidin-4-amine, Trimaleate Salt a) 1-[1-(1-Methyl-4-piperidyl)tetrahydro-1H-3-pyrrolyl]-3-(4-phenoxyphenyl)-1H-pyrazolo[3,4-d]pyrimidin-4-amine 3-(4-Phenoxyphenyl)-1-tetrahydro-1H-3-pyrrolyl-1H-pyrazolo[3,4-d]pyrimidin-4-amine (150 mg, 0.403 mmol), 1-methyl-4-piperidone (0.099 mL, 0.806 mmol), sodium triacetoxyborohydride (113 mg, 0.537 mmol) and glacial acetic acid (48 mg, 0.806 mmol) were mixed with 1,2-dichloroethane (4 mL). The reaction mixture was stirred at room temperature for 6 hours and saturated sodium bicarbonate solution was added to adjust the pH to about 9. The aqueous layer was extracted with dichloromethane. The combined organic layer was washed with brine, dried over MgSO$_4$, filtered and evaporated. The residue was purified by flash column chromatography using dichloromethane/methanol (85:15) as mobile phase to give 1-[1-(1-methyl-4-piperidyl)tetrahydro-1H-3-pyrrolyl]-3-(4-phenoxyphenyl)-1H-pyrazolo[3,4-d]pyrimidin-4-amine (148 mg, 78%). $^1$H NMR (DMSO-d$_6$) δ 1.42 (m, 2H), 1.81 (m, 2H), 1.92 (m, 2H), 2.15 (m, 1H), 2.26 (m, 2, 3H), 2.28 (m, 2H), 2.75 (m, 4H), 2.86 (m, 1H), 3.22 (m, 1H), 5.36 (m, 1H), 7.16 (m, 5H), 7.44 (m, 2H), 7.67 (m, 2H), 8.24 (s, 1H). LCMS (Micromass-Column: Pecosphere, C18, 3 um, 33×4.6 mm. Eluents: 0% B/A to 100% B/A in 4.5 min.(B: acetonitrile, A: 50 mM ammonia acetate buffer, PH 4.5), 3.5 mL/min.): MH$^+$ =470.4, Rt=2.01.

b) 1-[1-(1-Methyl-4-piperidyl)tetrahydro-1H-3-pyrrolyl]-3-(4-phenoxyphenyl)-1H-pyrazolo[3,4-d]pyrimidin-4-amine, Trimaleate Salt 1-[1-(1-Methyl-4-piperidyl)tetrahydro-1H-3-pyrrolyl]-3-(4-phenoxyphenyl)-1H-pyrazolo[3,4-d]pyrimidin-4-amine (148 mg, 0.315 mmol) was dissolved in hot ethyl acetate (20 mL) and maleic acid (110 mg, 0.946 mmol) in hot ethyl acetate (1 mL) was added. The reaction mixture was stirred at room temperature for 5 hours. The solid was collected by filtration to give 1-[1-(1-methyl-4-piperidyl)tetrahydro-1H-3-pyrrolyl]-3-(4-phenoxyphenyl)-1H-pyrazolo[3,4-d]pyrimidin-4-amine, trimaleate salt (230 mg, 90%). $^1$H NMR (DMSO-d$_6$) δ 1.81 (m, 2H), 2.27 (m, 2H), 2.78 (s, 3H), 2.97–3.84 (bm, 1H), 5.63 (m, 1H), 6.12 (s, 6H), 7.17 (m, 5H), 7.45 (m, 2H), 7.68 (m, 2H), 8.29 (s, 1H). LCMS (Micromass-Column: Pecosphere, C18, 3 um, 33×4.6 mm. Eluents: 0% B/A to 100% B/A in 4.5 min. (B: acetonitrile, A: 50 mM ammonia acetate buffer, PH 4.5), 3.5 mL/min.): MH$^+$ =470.4, R$_t$=2.01.

Example 215

N1-(4-{4-Amino-1-[1-(1H-2-imidazolylmethyl)-4-piperidyl]-1H-pyrazolo[3,4-d]pyrimidin-3-yl}-2-methoxyphenyl)-3-phenylpropanamide a) 1-[-(1H-2-Imidazolylmethyl)-4-piperidyl]-3-iodo-1H-pyrazolo[3,4-d]pyrimidin-4-amine 3-Iodo-1-(4-piperidyl)-1H-pyrazolo[3,4-d]pyrimidin-4-amine (0.5 g, 1.45 mmol), 1H-2-imidazolecarbaldehyde (0.42 g, 4.34 mmol), sodium triacetoxyborohydride (0.61 g, 2.90 mmol) and glacial acetic acid (0.26 g, 4.36 mmol) were mixed with 1,2-dichloroethane (20 mL). The reaction mixture was stirred at room temperature for 6 hours and saturated sodium bicarbonate solution was added to adjust the pH to about 9. The aqueous layer was extracted with dichloromethane. The combined organic layer was washed with brine, dried over MgSO$_4$, filtered and evaporated to give 1-[1-(1H-2-imidazolylmethyl)-4-piperidyl]-3-iodo-1H-pyrazolo[3,4-d]pyrimidin-4-amine (0.57 g, 92%). $^1$H NMR (DMSO-d$_6$) δ 1.85 (m, 2H), 2.17 (m, 4H), 2.92 (m, 2H), 3.55 (s, 2H), 4.57 (m, 1H), 6.92 (s, 2H), 8.14 (s, 1H).

b) tert-Butyl N-(4-{4-amino-1-[1-(1H-2-imidazolylmethyl)-4-piperidyl]-1H-pyrazolo[3,4-d]pyrimidin-3-yl}-2-methoxyphenyl)carbamate 1-[1-(H-2-Imidazolylmethyl)-4-piperidyl]-3-iodo-1H-pyrazolo[3,4-d]pyrimidin-4-amine (127 mg, 0.299 mmol), tert-butyl N-[2-methoxy-4-(4,4,5,5-tetramethyl-1,3,2-dioxaborolan-2-yl)phenyl]carbamate (115 mg, 0.329 mmol), palladium tetrakistriphenyphosphine (21 mg, 0.018 mmol) and sodium carbonate (76 mg, 0.718 mmol) were mixed with ethylene glycol dimethyl ether (3 mL) and water (1.5 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (95:5) as mobile phase to give tert-butyl N-(4-{4-amino-1-[1-(1H-2-imidazolylmethyl)-4-piperidyl]-1H-pyrazolo[3,4-d]pyrimidin-3-yl}-2-methoxyphenyl)carbamate (64 mg, 41%). $^1$H NMR (DMSO-d$_6$) δ 1.48 (m, 9H), 1.87 (m, 2H), 2.23 (m, 4H), 2.94 (m, 2H), 3.56 (s, 2H), 3.88 (s, 3H), 4.66 (m, 1H), 6.92 (s, 2H), 7.21 (m, 2H), 7.90 (d, J=8.14, 1H), 8.04 (s, 1H), 8.22 (s, 1H).

c) 3-(4-Amino-3-methoxyphenyl)-1-[1-(1H-2-imidazolylmethyl)-4-piperidyl]-1H-pyrazolo[3,4-d]pyrimidin-4-amine A mixture of trifluoroacetic acid/dichloromethane (20:80, 2 mL) was added to a solution of tert-butyl N-(4-{4-amino-1-[1-(1H-2-imidazolylmethyl)-4-piperidyl]-1H-pyrazolo[3,4-d]pyrimidin-3-yl}-2-methoxyphenyl)carbamate (55 mg, 0.106 mmol) in dichloromethane (0.5 mL) at 0° C. After 15 minutes, the ice-bath was removed and the reaction mixture was stirred at room temperature for 5 hours. Solvents were then evaporated and the residue was dissolved in dichloromethane. Saturated sodium bicarbonate was added to adjust the PH to about 8. The layers were separated and the aqueous layer was extracted with dichloromethane. The combined organic layer was washed with brine, dried over MgSO$_4$, filtered and evaporated give 3-(4-amino-3-methoxyphenyl)-1-[1-(1H-2-imidazolylmethyl)-4-piperidyl]-1H-pyrazolo[3,4-d]pyrimidin-4-amine (30 mg, 68%). $^1$H NMR (CDCl$_3$-d) δ 2.20 (m, 2H), 2.44 (m, 2H), 3.04 (m, 2H), 3.75 (s, 2H), 3.93 (s, 3H), 4.01 (s, 2H), 4.80 (m, 1H), 5.58 (bs, 2H), 6.82 (m, 1H), 7.01 (m, 4H), 8.34 (s, 1H).

e) N1-(4-{4-Amino-1-[1-(1H-2-imidazolylmethyl)-4-piperidyl]-1H-pyrazolo[3,4-d]pyrimidin-3-yl}-2-methoxyphenyl)-3-phenylpropanamide 3-Phenylpropanoyl chloride (0.011 mL, 0.0715 mmol) was added to a solution of 3-(4-amino-3-methoxyphenyl)-1-[1-(1H-2-imidazolylmethyl)-4-piperidyl]-1H-pyrazolo[3,4-d]pyrimidin-4-amine (30 mg, 0.0715 mmol) in pyridine (1.2 mL) at 0° C. After 2 hours, the solvent was evaporated and the residue was purified by flash column chromatography to give N1-(4-{4-amino-1-[1-(1H-2-imidazolylmethyl)-4-piperidyl]-1H-pyrazolo[3,4-d]pyrimidin-3-yl}-2-methoxyphenyl)-3-phenylpropanamide (20 mg, 51%). $^1$H NMR (CDCl$_3$) δ 2.27 (m, 2H), 2.61 (m, 2H), 2.76 (m, 4H), 3.09 (m, 2H), 3.93 (s, 3H), 4.07 (s, 2H), 4.96 (m, 1H), 5.61 (bs, 2H), 7.06–7.33 (m, 10H), 7.78 (s, 1H), 8.35 (s, 1H), 8.55 (d, J=8.15 Hz, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =552.5, R$_t$=1.83 min.

Examples 216–221

Amides Derived From cis-3-(4-Amino-3-methoxyphenyl)-1-[4-(4-methylpiperazino)cyclohexyl]-7H-pyrazolo[3,4-d]pyrimidin-4-amine Representative Procedure:

To the appropriate carboxylic acid (0.46 mmol) in dichloromethane (1.4 mL) was added oxalyl chloride (0.4 mL, 4.6 mmol) and DMF (1 drop). The vials were septum capped and a small bore needle inserted in each cap to relieve pressure. The vials were shaken overnight on a J-Kem shaker. 50% of the solution was separated and the excess oxalyl chloride and dichloromethane was then removed on a 12-port Supelco manifold under vacuum with nitrogen bleed. The crude acid chloride (0.23 mmol) was added to cis-3-(4-amino-3-methoxyphenyl)-1-[4-(4-methylpiperazino)cyclohexyl]-1H-pyrazolo[3,4-d]pyrimidin-4-amine (50 mg, 0.11 mmol) in dry pyridine (0.6 mL) and stirred at room temperature overnight. The resulting solutions were submitted directly to purification by preparative HPLC (Hypersil BSD C18, 5 um, 100×21 mm, 0%–100% acetonitrile/0.05M ammonium acetate over 10 min, 25.0 mL/min). The resulting products were further purified by partioning between dichloromethane (4 ml) and 1.0 N sodium hydroxide (2 ml) and passing through an Empore™ high performance extraction disk cartridge (C18-SD octadecyl) to give the corresponding products. The compounds are detailed overleaf with corresponding LCMS (Micromass-Column: Pecosphere, C18, 3 um, 33×4.6 mm. Eluents: 0% B/A to 100% B/A in 4.5 min.(B: acetonitrile, A: 50 mM ammonia acetate buffer, PH 4.5), 3.5 mL/min.) data.

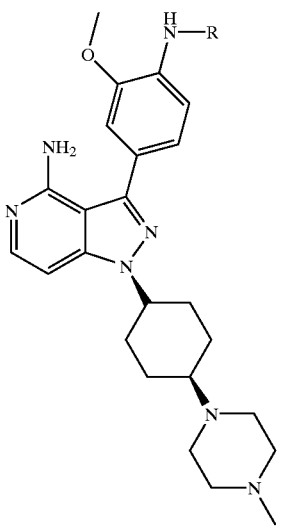

| Compound Name | R | Ex | Qt. (mg) | MH+ | R$_t$ (mins) |
|---|---|---|---|---|---|
| N1-(4-{4-amino-1-[4-(4-methylpiperazino)cyclohexyl]-1H-pyrazolo[3,4-d]pyrimidin-3-yl}-2-methoxyphenyl)-3-(2-methoxyphenyl)propanamide | | 216 | 29 | 599.4 | 2.72 |
| N1-(4-{4-amino-1-[4-(4-methylpiperazino)cyclohexyl]-1H-pyrazolo[3,4-d]pyrimidin-3-yl}-2-methoxyphenyl)-3-(4-methoxyphenyl)propanamide | | 217 | 31 | 599.4 | 2.58 |
| N1-(4-{4-amino-1-[4-(4-methylpiperazino)cyclohexyl]-1H-pyrazolo[3,4-d]pyrimidin-3-yl}-2-methoxyphenyl)-3-(3-methoxyphenyl)propanamide | | 218 | 30 | 599.4 | 2.61 |
| N1-(4-{4-amino-1-[4-(4-methylpiperazino)cyclohexyl]-1H-pyrazolo[3,4-d]pyrimidin-3-yl}-2-methoxyphenyl)-3-(4-methylphenyl)propanamide | | 219 | 33 | 583.4 | 2.70 |
| N1-(4-{4-amino-1-[4-(4-methylpiperazino)cyclohexyl]-1H-pyrazolo[3,4-d]pyrimidin-3-yl}-2-methoxyphenyl)-3-(4-fluorophenyl)propanamide | | 220 | 27 | 587.3 | 2.72 |
| N1-(4-{4-amino-1-[4-(4-methylpiperazino)cyclohexyl]-1H-pyrazolo[3,4-d]pyrimidin-3-yl}-2-methoxyphenyl)-3-(3,4-difluorophenyl)propanamide | | 221 | 34 | 605.3 | 2.80 |

Example 221 cis-3-[4-(Benzyloxy)phenyl]-1-[4-(4-methylpiperazino)cyclohexyl]-1H-pyrazolo[3,4-d]pyrimidin-4-amine A mixture of cis-3-iodo-1-[4-(4-methylpiperazino) cyclohexyl]-1H-pyrazolo[3,4-d]pyrimidin-4-amine (3.41 g, 7.74 mmol) in ethylene glycol dimethyl ether (50 mL) was treated with 4-(benzyloxy)phenylboronic acid (1.94 g, 8.51 mmol), tetrakis(triphenylphosphine)palladium (0.537 g, 0.464 mmol), and a solution of sodium carbonate (1.97 g, 18.58 mmol) in water (25 mL). The reaction mixture was stirred over night at 85° C. under a nitrogen atmosphere. The organic solvent was removed under reduced pressure. Ethyl acetate (300 mL) was added to the aqueous layer. The layers were partitioned, and the aqueous layer was extracted with ethyl acetate (200 mL). The combined organic layers were washed with water and brine (1 L each), dried over magnesium sulfate, filtered and evaporated under reduced pressure. Ethyl acetate was added to the solid. A significant amount of the solid was not soluble in ethyl acetate, and was subsequently filtered to give 2.95 g (77%) of cis-3-[4-(benzyloxy)phenyl]-1-[4-(4-methylpiperazino)cyclohexyl]-1H-pyrazolo[3,4-d]pyrimidin-4-amine. $^1$H NMR (DMSO-$d_6$, 400 MHz) δ 8.217 (s, 1H), 7.592–7.570 (m, 2H), 7.504–7.483 (m, 2H), 7.440–7.369 (m, 3H), 7.206–7.184 (m, 2H), 5.186 (s, 2H), 4.802–4.755 (m, 1H), 2.497–2.354 (m, 7H), 2.256–2.228 (m, 4H), 2.151 (s, 3H), 2.076–1.989 (m, 2H), 1.694–1.673 (m, 2H), 1.607–1.545 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.128 min (100%).

Example 222 cis-2-(4-{4-Amino-1-[4-(4-methylpiperazino) cyclohexyl]-1H-pyrazolo[3,4-d]pyrimidin-3-yl}phenoxy)-6-[(3-methoxypropyl)amino] benzonitrile cis-4-{4-Amino-1-[4-(4-methylpiperazino)cyclohexyl]-1H-pyrazolo[3,4-d]pyrimidin-3-yl}phenol A solution of cis-3-[4-(benzyloxy)phenyl]-1-[4-(4-methylpiperazino)cyclohexyl]-1H-pyrazolo[3,4-d] pyrimidin-4-amine (0.500 g, 1.005 mmol) in absolute ethanol (25 mL) was treated with palladium 10 wt. % on activated carbon (0.100 g, 0.201 mmol) and ammonium formate (0.317 g, 5.03 mmol). The reaction mixture was stirred at 80° C. for 2 h; no starting material was seen by thin layer chromatography. The reaction mixture was filtered through a pad of celite, which was washed with ethanol (500 mL). The organic layer was removed under reduced pressure. The resulting solid was dried over night under high vacuum to give 0.406 g (99%) of cis-4-{4-amino-1-[4-(4-methylpiperazino)cyclohexyl]-1H-pyrazolo[3,4-d] pyrimidin-3-yl}phenol. $^1$H NMR (DMSO-$d_6$, 400 MHz) δ 8.204–8.194 (m, 2H), 7.472–7.437 (m, 2H), 6.947–6.912 (m, 2H), 4.791–4.744 (m, 1H), 2.418 (m, 9H), 2.249–2.243 (m, 2H), 2.193 (s, 3H), 2.077–2.050 (m, 2H), 1.688–1.666 (m, 2H), 1.656–1.578 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 3.47 min (99%).

2-Fluoro-6-[(2-methoxyethyl)amino]benzonitrile

A solution of 2,6 difluorobenzonitrile (3.5 g, 25.16 mmol) in dimethylformamide (50 mL) was treated with 3-methoxypropylamine (2.24 g, 25.16 mmol) and potassium carbonate (6.94 g, 50.32 mmol). The reaction mixture was stirred over night under a nitrogen atmosphere. Water (100 mL) was added to the reaction solution. The layers were partitioned, and the aqueous layer was extracted with ethyl acetate (1.2 L). The combined organic layers were washed with water (1.5 L), dried over magnesium sulfate, filtered, and evaporated under reduced pressure. The crude product was purified by flash chromatography on silica gel using 7:1 heptane:ethyl acetate as the eluent. The column afforded 3.5 g (68%) of 2-fluoro-6-[(2-methoxyethyl)amino] benzonitrile. $^1$H NMR (DMSO-$d_6$, 400 MHz) δ 7.48–7.39 (m, 1H), 6.64–6.48 (m, 2H), 3.45–3.31 (m, 2H), 3.30–3.20 (m, 5H), 1.85–1.75 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 6.57 min (97%).

cis-2-(4-{4-Amino-1-[4-(4-methylpiperazino)cyclohexyl]-1H-pyrazolo[3,4-d]pyrimidin-3-yl}phenoxy)-6-[(3-methoxypropyl)amino]benzonitrile A solution of cis-4-{4-amino-1-[4-(4-methylpiperazino) cyclohexyl]-1H-pyrazolo[3,4-d]pyrimidin-3-yl}phenol (0.200 g, 0.491 mmol) in dimethylformamide (25 mL), was treated with 2-fluoro-6-[(2-methoxyethyl)amino] benzonitrile (0.124 g, 0.589 mmol) and potassium carbonate (0.136, 0.982 mmol). The reaction mixture was stirred at 120° C. over night under a nitrogen atmosphere. The reaction was not complete after 18 h, therefore additional 2-fluoro-6-[(2-methoxyethyl)amino]benzonitrile (0.12 g, 0.574 mmol) was added to the reaction mixture and was stirred over night. Ethyl acetate was added to the reaction mixture, and was washed with 1 N sodium hydroxide solution (300 mL). The organic layer was washed with water and brine (300 mL each), dried over magnesium sulfate, filtered and evaporated under reduced pressure. The product was purified by flash chromatography on a silica gel Supelco column using 20% methanol in dichloromethane as eluent. The column afforded 0.050 g of product that contained some starting material. The crude product was purified by preparative HPLC (Hypersil C18, 100×21 mm column, 5 μm, 15–100% Acetonitrile gradient over 8min, total run time—10 min, buffer—50 mM Ammonium Acetate, 25 ml/min). The product from the HPLC column was dissolved in dichloromethane, washed with saturated sodium bicarbonate aqueous solution to remove residual ammonium acetate. The layers were partitioned using an Empore extraction disk cartridge to give 0.010 g (3%) cis-2-(4-{4-amino-1-[4-(4-methylpiperazino)cyclohexyl]-1H-pyrazolo[3,4-d] pyrimidin-3-yl}phenoxy)-6-[(3-methoxypropyl)amino] benzonitrile. $^1$H NMR (CDCl$_3$, 400 MHz) δ 8.328 (s, 1H), 7.706–7.678 (m, 2H), 7.305–7.211 (m, 4H), 6.433–6.411 (d, 1H, J=8.8 Hz), 4.925–4.904 (m, 1H), 3.574–3.547 (m, 2H), 3.400 (s, 3H), 3.389–3.343 (m, 2H), 2.441–2.418 (m, 3H), 2.382 (s, 3H), 2.25–2.10 (m, 2H), 2.031 (s, 3H), 1.973–1.944 (m, 2H), 1.851–1.829 (m, 2H), 1.700–1.679 (m, 3H), 1.355–1.200 (m, 5H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.185 min (100%).

Example 223 cis-2-(4-{4-Amino-1-[4-(4-methylpiperazino) cyclohexyl]-1H-pyrazolo[3,4-d]pyrimidin-3-yl}phenoxy)-6-[(4-methylphenyl)sulfanyl] benzonitrile tris-Maleate 2-Fluoro-6-[(4-methylphenyl)sulfanyl]benzonitrile A solution of 2,6-difluorobenzonitrile (5.18 g, 37.26 mmol) in dimethylformamide (100 mL) was treated with p-thiocresol (4.628 g, 37.26 mmol) and potassium carbonate (10.28 g, 74.52 mmol). The reaction mixture was stirred for 24 h under a nitrogen atmosphere. Water (150 mL) and ethyl acetate (250 mL) were added to the reaction mixture. The layers were partitioned and the aqueous layer was extracted with ethyl acetate (500 mL). The combined organic layers were washed with water (1 L), dried over magnesium sulfate, filtered and evaporated under reduced pressure. The crude product was purified by flash chromatography on silica gel, eluting 7:1 heptane:ethyl acetate. The column afforded 3.341 g (37%) of 2-fluoro-6-[(4-methylphenyl)sulfanyl]benzonitrile. $^1$H NMR (DMSO-d$_6$, 400 MHz) δ 7.66–7.61 (m, 1H), 7.47–7.45 (m, 2H), 7.36–7.32 (m, 3H), 6.83–6.79 (m, 1H), 2.36 (s, 3H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 8.04 min (93%).

cis-2-(4-{4-Amino-1-[4-(4-methylpiperazino)cyclohexyl]-1H-pyrazolo[3,4-d]pyrimidin-3-yl}phenoxy)-6-[(4-methylphenyl)sulfanyl]benzonitrile tris-Maleate A solution of cis-4-{4-amino-1-[4-(4-methylpiperazino)cyclohexyl]-1H-pyrazolo[3,4-d]pyrimidin-3-yl}phenol (0.300 g, 0.736 mmol) in dimethylformamide (20 mL), was treated with 2-fluoro-6-[(4-methylphenyl)sulfanyl]benzonitrile (0.447 g, 1.84 mmol) and potassium carbonate (0.203, 1.47 mmol). The reaction mixture was stirred at 120° C. over night under a nitrogen atmosphere. Ethyl acetate (150 mL) and 1 N sodium hydroxide solution were added to the reaction solution. The layers were partitioned, and the organic layer was washed with 1 N sodium hydroxide solution (300 mL). The organic layer was washed with water and brine (400 mL each), dried over magnesium sulfate, filtered, and evaporated under reduced pressure. The crude product was purified by flash silica gel column chromatography using 10% methanol in dichloromethane as the mobile phase. The light brown solid was triturated with ethyl acetate and filtered to give 0.050 g (11%) cis-2-(4-{4-amino-1-[4-(4-methylpiperazino)cyclohexyl]-1H-pyrazolo[3,4-d]pyrimidin-3-yl}phenoxy)-6-[(4-methylphenyl)sulfanyl]benzonitrile. A warm solution of cis-2-(4-{4-amino-1-[4-(4-methylpiperazino)cyclohexyl]-1H-pyrazolo[3,4-d]pyrimidin-3-yl}phenoxy)-6-[(4-methylphenyl)sulfanyl]benzonitrile (0.050 g, 0.079 mmol) in ethyl acetate/methanol was treated with a warm solution of maleic acid (0.028 g, 0.240 mmol) in ethyl acetate. A precipitate immediately formed and was filtered under a nitrogen atmosphere to give 0.028 g of cis-2-(4-{4-amino-1-[4-(4-methylpiperazino)cyclohexyl]-1H-pyrazolo[3,4-d]pyrimidin-3-yl}phenoxy)-6-[(4-methylphenyl)sulfanyl]benzonitrile tris-maleate. $^1$H NMR (DMSO-d$_6$, 400 MHz) δ 8.251 (s, 1H), 7.72–7.70 (d, 2H, J=8 Hz), 7.55–7.48 (m, 3H), 7.37–7.33 (m, 4H), 6.96–6.93 (d, 1H, J=12 Hz), 6.74–6.72 (d, 1H, J=8 Hz), 6.18 (s, 6H), 4.85 (m, 1H), 3.15–2.90 (m, 4H), 2.85–2.75 (m, 3H), 2.38 (s, 3H), 2.05–1.99 (m, 2H), 1.90–1.60 (m, 5H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 6.359 min (100%).

Example 224 cis-2-(4-{4-Amino-1-[4-(4-methylpiperazino)cyclohexyl]-1H-pyrazolo[3,4-d]pyrimidin-3-yl}phenoxy)-6-(2-pyridylsulfanyl)benzonitrile bis-Maleate cis-2-(4-{4-Amino-1-[4-(4-methylpiperazino)cyclohexyl]-1H-pyrazolo[3,4-d]pyrimidin-3-yl}phenoxy)-6-(2-pyridylsulfanyl)benzonitrile bis-Maleate A solution of cis-4-{4-amino-1-[4-(4-methylpiperazino)cyclohexyl]-1H-pyrazolo[3,4-d]pyrimidin-3-yl}phenol (0.300 g, 0.736 mmol) in dimethylformamide (20 mL), was treated with 2-fluoro-6-(2-pyridylsulfanyl)benzonitrile (0.424 g, 1.84 mmol) and potassium carbonate (0.203, 1.47 mmol). The reaction mixture was stirred at 120° C. for 2 h under a nitrogen atmosphere. Ethyl acetate (125 mL) and 1 N sodium hydroxide solution (50 mL) were added to the reaction mixture. The layers were partitioned and the organic layer was washed with 1 N sodium hydroxide solution (300 mL). The organic layer was washed with water and brine (250 mL each), dried over magnesium sulfate, filtered and evaporated under reduced pressure. The solid was triturated with ethyl acetate to yield 0.310 g (68%) of cis-2-(4-{4-amino-1-[4-(4-methylpiperazino)cyclohexyl]-1H-pyrazolo[3,4-d]pyrimidin-3-yl}phenoxy)-6-(2-pyridylsulfanyl)benzonitrile. A warm solution of cis-2-(4-{4-amino-1-[4-(4-methylpiperazino)cyclohexyl]-1H-pyrazolo[3,4-d]pyrimidin-3-yl}phenoxy)-6-(2-pyridylsulfanyl)benzonitrile (0.310 g, 0.502 mmol) in ethanol was treated with a warm solution maleic acid (0.175 g, 1.503 mmol) in ethanol. A precipitate formed upon cooling and was filtered under a nitrogen atmosphere to give 0.356 g of cis-2-(4-{4-amino-1-[4-(4-methylpiperazino)cyclohexyl]-1H-pyrazolo[3,4-d]pyrimidin-3-yl}phenoxy)-6-(2-pyridylsulfanyl)benzonitrile bis-maleate. $^1$H NMR (DMSO-d$_6$, 400 MHz) δ 8.47–8.46 (d, 1H, J=4 Hz), 8.26 (s, 1H), 7.79–7.72 (m, 4H), 7.53–7.51 (d, 1H, J=8 Hz), 7.38–7.34 (m, 3H), 7.28–7.24 (m, 2H), 6.14 (s, 4H), 4.85 (m, 1H), 3.60–3.10 (m, 7H), 3.1–2.85 (m, 2H), 2.71–2.67 (m, 2H), 2.32–2.27 (m, 3H), 2.05–1.99 (m, 2H), 1.78–1.71 (m, 4H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.196 min (98%).

Example 225 trans-3-[4-(Benzyloxy)phenyl]-1-[4-(4-methylpiperazino)cyclohexyl]-1H-pyrazolo[3,4-d]pyrimidin-4-amine A mixture of trans-3-iodo-1-[4-(4-methylpiperazino)cyclohexyl]-1H-pyrazolo[3,4-d]pyrimidin-4-amine (1.50 g, 3.4 mmol) in ethylene glycol dimethyl ether (100 mL) was treated with 4-(benzyloxy)phenylboronic acid (0.853 g, 3.74 mmol), tetrakis(triphenylphosphine)palladium (0.236 g, 0.204 mmol), and a solution of sodium carbonate (0.864 g, 8.16 mmol) in water (35 mL). The reaction mixture was stirred over night at 85° C. under a nitrogen atmosphere. The organic solvent was removed under reduced pressure. Ethyl acetate (100 mL) was added to the aqueous layer. The layers were partitioned and the aqueous layer was extracted with ethyl acetate (300 mL). The combined organic layers were washed with water and brine (500 mL each), dried over magnesium sulfate, filtered, and evaporated under reduced pressure. The crude product was purified by flash chromatography on silica gel eluting with 5% methanol in dichloromethane, 10% methanol in dichloromethane, 20% methanol in dichloromethane, then 30% methanol in dichloromethane. The column afforded 0.817 g (49%) of trans-3-[4-(benzyloxy)phenyl]-1-[4-(4-methylpiperazino)cyclohexyl]-1H-pyrazolo[3,4-d]pyrimidin-4-amine. $^1$H NMR (DMSO-d$_6$, 400 MHz) δ 8.22 (s, 1H), 7.59–7.57 (m, 2H), 7.53–7.50 (m, 2H), 7.48–7.21 (m, 3H), 7.19–7.17 (d, 2H, J=8 Hz), 5.18 (s, 2H), 4.65–4.60 (m, 1H), 2.5 (s, 3H), 2.45–2.25 (m, 5H), 2.15 (s, 3H), 2.04–1.92 (m, 7H), 1.50–1.44 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.021 min (95%).

Example 226 trans-2-(4-{4-Amino-1-[4-(4-methylpiperazino)
cyclohexyl]-1H-pyrazolo[3,4-d]pyrimidin-3-
yl}phenoxy)-6-[(3-methoxypropyl)amino]
benzonitrile tris-Maleate trans-4-{4-Amino-1-[4-(4-methylpiperazino)cyclohexyl]-
1H-pyrazolo[3,4-d]pyrimidin-3-yl}phenol A solution of trans-3-[4-(benzyloxy)phenyl]-1-[4-(4-methylpiperazino)cyclohexyl]-1H-pyrazolo[3,4-d]pyrimidin-4-amine (0.806 g, 1.62 mmol) in absolute ethanol (40 mL) was treated with palladium 10 wt. % on activated carbon (0.161 g, 0.324 mmol) and ammonium formate (0.511 g, 8.1 mmol). The reaction mixture was stirred at 80° C. for 3 h, very little product was seen by thin layer chromatography. Palladium 10 wt. % on activated carbon (0.161 g, 0.324 mmol) was added and stirred for an additional hour, still very little product detected. Ammonium formate (0.204 g, 3.24 mmol) was added and stirred over night. The reaction mixture was filtered through a pad of celite, which was washed with ethanol (500 mL). The organic layer was removed under reduced pressure. The resulting solid was triturated with ethyl acetate, and dried over night under high vacuum to give 0.491 g (75%) of trans-4-{4-amino-1-[4-(4-methylpiperazino)cyclohexyl]-1H-pyrazolo[3,4-d]pyrimidin-3-yl}phenol. $^1$H NMR (DMSO-$d_6$, 400 MHz) δ 9.74 (s, 1H), 8.2 (s, 1H), 7.46–7.44 (d, 2H, J=8 Hz), 6.92–6.90 (d, 2H, J=8 Hz), 4.64–4.58 (m, 1H), 2.67–2.50 (m, 5H), 2.39–2.34 (m, 4H), 2.17 (s, 3H), 2.06–1.92 (m, 6H), 1.50–1.42 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 3.337 min (96%).

trans-2-(4-{4-Amino-1-[4-(4-methylpiperazino)cyclohexyl]-1H-pyrazolo[3,4-d]pyrimidin-3-yl}phenoxy)-6-[(3-methoxypropyl)amino]benzonitrile tris-Maleate A solution of trans-4-{4-amino-1-[4-(4-methylpiperazino)cyclohexyl]-1H-pyrazolo[3,4-d]pyrimidin-3-yl}phenol (0.100 g, 0.245 mmol) in dimethylformamide (25 mL), was treated with 2-fluoro-6-[(2-methoxyethyl)amino]benzonitrile (0.128 g, 0.613 mmol) and potassium carbonate (0.068, 0.49 mmol). The reaction mixture was stirred at 120° C. over night under a nitrogen atmosphere. Ethyl acetate and 1 N sodium hydroxide solution were added to the reaction mixture. The organic layer was washed with 1 N sodium hydroxide solution (1 L). The layers were partitioned and the organic layer was washed with water and brine (500 mL each), dried over magnesium sulfate, filtered and evaporated under reduced pressure. The crude product was purified by flash chromatography on silica gel using 10% methanol in dichloromethane as eluent, to afford 71 mg (48%) of trans-2-(4-{4-amino-1-[4-(4-methylpiperazino)cyclohexyl]-1H-pyrazolo[3,4-d]pyrimidin-3-yl}phenoxy)-6-[(3-methoxypropyl)amino]benzonitrile. A warm solution of trans-2-(4-{4-amino-1-[4-(4-methylpiperazino)cyclohexyl]-1H-pyrazolo[3,4-d]pyrimidin-3-yl}phenoxy)-6-[(3-methoxypropyl)amino]benzonitrile (0.071 g, 0.119 mmol) in ethyl acetate was treated with a warm solution of maleic acid (0.042 g, 0.358 mmol) in ethyl acetate. The precipitate was filtered under nitrogen and dried under high vacuum to give trans-2-(4-{4-amino-1-[4-(4-methylpiperazino)cyclohexyl]-1H-pyrazolo[3,4-d]pyrimidin-3-yl}phenoxy)-6-[(3-methoxypropyl)amino]benzonitrile tris-maleate. $^1$H NMR (DMSO-$d_6$, 400 MHz) δ 8.23 (s, 1H), 7.69–7.67 (d, 2H, J=8 Hz), 7.37–7.33 (m, 1H), 7.25–7.23 (d, 2H, J=8 Hz), 6.53–6.51 (d, 1H, J=8 Hz), 6.30–6.29 (m, 1H), 6.19–6.17 (d, 1H, J=8 Hz), 6.17 (s, 6H), 4.65–4.64 (m, 1H), 3.45–3.42 (m, 2H), 3.27 (s, 3H), 2.55–2.50 (m, 4H), 2.50–2.30 (m, 5H), 2.33 (br, s, 3H), 2.01–1.96 (m, 8 Hz), 1.84–1.80 (m, 2H), 1.49–1.46 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.181 min (95%).

Example 227 trans-N1-(4-{4-Amino-1-[4-(4-methylpiperazino)
cyclohexyl]-1H-pyrazolo[3,4-d]pyrimidin-3-yl}-2-
methoxyphenyl)-3-phenylpropanamide tris-Maleate 4-Bromo-2-methoxyaniline A solution of o-Anisidine (5.46 g, 44.3 mmol) in dichloromethane (100 mL) was treated with 2,4,4,6-tetrabromo-2,5-cyclohexadiene-1-one (18.16 g, 44.3 mmol) portionwise over 1 h at −5° C. Following the addition of the brominating agent, the dry ice/acetone bath was removed and the reaction mixture stirred over night at room temperature. Sodium hydroxide solution (1N) was added to the reaction mixture, and the layers were partitioned. The organic layer was washed with 1 N sodium hydroxide solution (1 L), washed with water (750 mL), dried over magnesium sulfate, filtered, and evaporated under reduced pressure, to give 8.096 g (89%) of 4-bromo-2-methoxyaniline. $^1$H NMR (DMSO-$d_6$, 400 MHz) δ 6.90 (s, 1H), 6.83–6.76 (m, 1H), 6.57–6.55 (m, 1H), 4.86 (s, 2H), 3.76 (s, 3H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.635 min (89%).

N1-(4-Bromo-2-methoxyphenyl)-3-phenylpropanamide

A solution of 4-bromo-2-methoxyaniline (8.096 g, 40.04 mmol) in dichloromethane (100 mL) was treated with triethylamine (6.06 g, 60.06 mmol), then hydrocinnamoyl chloride (7.08 g, 42.04 mmol). The reaction mixture was stirred for 48 h under a nitrogen atmosphere. The solvent was removed under reduced pressure, and ethyl acetate was added. The precipitate was filtered, and the filtrate was evaporated to a solid under reduced pressure. The solid was dissolved in ethyl acetate, and washed with 5 N hydrochloric acid solution, 5 N sodium hydroxide solution, water and brine. The crude material (two spots by thin layer chromatography) was triturated with methanol. The un-dissolved solid was filtered to give 6 g (50%) of N1-(4-bromo-2-methoxyphenyl)-3-phenylpropanamide. $^1$H NMR (DMSO-$d_6$, 400 MHz) δ 9.17 (s, 1H), 7.92–7.90 (m, 1H), 7.30–7.24 (m, 4H), 7.20–7.18 (m, 2H), 7.09–7.07 (m, 1H), 3.83 (s, 3H), 2.90–2.86 (m, 2H), 2.72–2.69 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 7.491 min (97%).

3-Methoxy-4-[(3-phenylpropanoyl)amino]phenylboronic Acid

A solution of N1-(4-bromo-2-methoxyphenyl)-3-phenylpropanamide (1.004 g, 3 mmol) in anhydrous tetrahydrofuran (30 mL) at −78° C. was treated with a solution of 1.6 M n-butyl lithium in hexane (4.7 mL, 7.5 mmol). The reaction mixture was stirred at −78° C. for 40 min. Triisopropyl borate(1.05 mL, 4.5 mmol) was added to this reaction mixture, and stirred at −78° C. for 20 min. The acetone/dry ice bath was removed. The reaction mixture was stirred for 4 h at room temperature. The reaction mixture was quenched with 2.5 N hydrochloric acid solution (30 mL). The organic layer was removed under reduced pressure. Ethyl acetate was added to the acidic aqueous layer. The layers were partitioned, and the aqueous layer was extracted with ethyl acetate (250 mL). The combined organic layer was washed with water and brine, dried over magnesium sulfate, filtered and evaporated under reduced pressure. The crude product was purified by flash chromatography on silica gel, using 1:1 dichloromethane:ethyl acetate as eluent. The gradient was changed to 15% methanol in dichloromethane to remove the baseline product to give 0.209 g (23%) of 3-methoxy-4-[(3-phenylpropanoyl)amino] phenylboronic acid. $^1$H NMR (DMSO-$d_6$, 400 MHz) δ 9.08 (s, 1H), 7.89–7.95 (m, 3H), 7.45–7.42 (s, 1H), 7.35–7.16 (m, 5H), 3.82 (s, 3H), 2.91–2.81 (m, 2H), 2.74–2.70 (s, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.389 min (95%).

trans-N1-(4-{4-Amino-1-[4-(4-methylpiperazino) cyclohexyl]-1H-pyrazolo[3,4-d]pyrimidin-3-yl}-2-methoxyphenyl)-3-phenylpropanamide tris-Maleate A solution of trans-3-iodo-1-[4-(4-methylpiperazino) cyclohexyl]-1H-pyrazolo[3,4-d]pyrimidin-4-amine (0.268 g, 0.607 mmol) in ethylene glycol dimethyl ether (20 mL) was treated with 3-methoxy-4-[(3-phenylpropanoyl)amino] phenylboronic acid (0.200 g, 0.669 mmol), tetrakis (triphenylphosphine)palladium (0.042 g, 0.036 mmol), and a solution of sodium carbonate (0.154, 1.46 mmol) in water (10 mL). The reaction mixture was stirred for 9 h at 85° C. under a nitrogen atmosphere. Tetrakis(triphenylphosphine) palladium (0.035 g, 0.03 mmol) was added and the mixture stirred over night (15 h). The organic layer was removed under reduced pressure, and ethyl acetate was added. The layers were partitioned, and the aqueous layer was extracted with ethyl acetate (300 mL). The combined organic layers were washed with water and brine, dried over magnesium sulfate, filtered and evaporated under reduced pressure. The crude material was purified by flash chromatography on silica gel, using 10% methanol in dichloromethane (6 L) as eluent. A second purification on a Supelco flash chromatography column was required, using 20% methanol in dichloromethane as eluent. The second column afforded 0.132 g (38%) of trans-N1-(4-{4-amino-1-[4-(4-methylpiperazino) cyclohexyl]-1H-pyrazolo[3,4-d]pyrimidin-3-yl}-2-methoxyphenyl)-3-phenylpropanamide. The product was sent for preparative HPLC purification (Hypersil C18, 100× 21 mm column, 5 μm, 15–100% Acetonitrile gradient over 8min, total run time—10 min, buffer—50 mM Ammonium Acetate, 25 m/min), and afforded 0.026 g of trans-N1-(4-{4-amino-1-[4-(4-methylpiperazino)cyclohexyl]-1H-pyrazolo[3,4-d]pyrimidin-3-yl}-2-methoxyphenyl)-3-phenylpropanamide. A warm solution of trans-N1-(4-{4-amino-1-[4-(4-methylpiperazino)cyclohexyl]-1H-pyrazolo[3,4-d]pyrimidin-3-yl}-2-methoxyphenyl)-3-phenylpropanamide (0.026 g, 0.046 mmol) in ethyl acetate was treated with a warm solution of maleic acid (0.016 g, 0.137 mmol) in ethyl acetate. The precipitate was filtered under nitrogen atmosphere and dried under high vacuum to give trans-N1-(4-{4-amino-1-[4-(4-methylpiperazino) cyclohexyl]-1H-pyrazolo[3,4-d]pyrimidin-3-yl}-2-methoxyphenyl)-3-phenylpropanamide tris-maleate.

$^1$H NMR (DMSO-$d_6$, 400 MHz) δ 9.25 (s, 1H), 8.23–8.19 (m, 2H), 7.33–7.27 (m, 5H), 7.23–7.18 (m, 2H), 6.17 (s, 6H), 4.72–4.69 (m, 1H), 3.87 (s, 3H), 2.94–2.90 (m, 4H), 2.79–2.75 (m, 5H), 2.67 (s, 4H), 2.10–1.99 (m, 8H), 1.59–1.56 (m, 3H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 4.844 min (90%).

Example 228 cis-N1-(4-{4-Amino-1-[4-(4-methylpiperazino) cyclohexyl]-1H-pyrazolo[3,4-d]pyrimidin-3-yl}-2-methoxyphenyl)-N1-methyl-3-phenylpropanamide N1-(4-Bromo-2-methoxyphenyl)-N1-methyl-3-phenylpropanamide A solution of N1-(4-bromo-2-methoxyphenyl)-3-phenylpropanamide (1.0 g, 3 mmol) in dimethylformamide (20 mL) at 0° C. was treated with pre-washed (3 times with heptane) sodium hydride (0.158 g, 6.6 mmol). The reaction mixture was stirred for 1 h at 0° C. Methyl iodide (0.511 g, 3.6 mmol) was added drop-wise, and the solution stirred for 15 min at 0° C. The ice bath was removed and the reaction mixture was stirred overnight at room temperature. The reaction did not go to completion over night; additional methyl iodide (0.511 g, 3.6 mmol) was added and the reaction mixture stirred over night. The reaction mixture was quenched with water (30 mL). Ethyl acetate was added, and the layers were partitioned. The aqueous layer was extracted with ethyl acetate. The combined organic layers were washed with water and brine, dried over magnesium sulfate, filtered and evaporated under reduced pressure. The crude product was purified by flash chromatography on silica gel eluting 3:1 heptane:ethyl acetate, and afforded 0.729 g (70%) of N1-(4-bromo-2-methoxyphenyl)-N1-methyl-3-phenylpropanamide. $^1$H NMR (DMSO-$d_6$, 400 MHz) δ 7.330–7.326 (s, 1H), 7.235–7.178 (m, 2H), 7.161–7.116 (m, 3H), 7.058–7.040 (m, 2H), 3.811 (s, 3H), 3.002 (s, 3H), 2.753–2.708 (m, 2H), 2.282–2.204 (m, 1H), 2.138–2.061 (m, 1H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 7.366 min (96%).

N1-[2-methoxy-4-(4,4,5,5-tetramethyl-1,3,2-dioxaborolan-2-yl)phenyl]-N1-methyl-3-phenylpropanamide A solution of N1-(4-bromo-2-methoxyphenyl)-N1-methyl-3-phenylpropanamide (0.729 g, 2.09 mmol) in dimethylformamide (10 mL) was treated with diboron pinacol ester (0.637 g, 2.51 mmol), potassium acetate (0.615 g, 6.27 mmol), and then [1,1'-Bis(diphenylphosphinoferrocene] dichloropalladium(II), complex with dichloromethane (1:1) (0.052 g, 0.063 mmol). The reaction mixture was stirred at 80° C. for 26 h, then additional diboron pinacol ester (0.318 g, 1.254 mmol), potassium acetate (0.312 g, 3.135 mmol), and 1,1'-Bis(diphenylphosphinoferrocene] dichloropalladium(II), complex with dichloromethane (1:1) (0.025 g, 0.031 mmol) were added. The reaction mixture was stirred for 48 h. The solvent was removed under reduced pressure, and dried under high vacuum. Dichloromethane was added to the black solid, and then filtered through a celite pad and a silica gel pad. The crude product was purified by flash chromatography on silica gel using 1:1 ethyl acetate:heptane as eluent. The column afforded 0.290 g (35%) N1-[2-methoxy-4-(4,4,5,5-tetramethyl-1,3,2-dioxaborolan-2-yl)phenyl]-N1-methyl-3-phenylpropanamide, and 0.148 g (18%) of a homocoupled bi-product. N1-[2-methoxy-4-(4,4,5,5-tetramethyl-1,3,2-dioxaborolan-2-yl)phenyl]-N1-methyl-3-phenylpropanamide: $^1$H NMR (DMSO-$d_6$, 400 MHz) δ 7.33 (s, 1H), 7.29–7.27 (m, 2H), 7.22–7.13 (m, 5H), 7.06–7.03 (m, 1H), 3.81 (s, 3H), 3.03–3.00 (m, 3H), 2.75–2.71 (m, 4H), 2.30–2.15 (m, 2H), 2.15–2.05 (m, 2H), 1.30 (s, 12H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.296 min (100%). Homocoupled bi-product: $^1$H NMR (DMSO, 400 MHz) δ 7.374 (s, 2H), 7.293–7.276 (m, 4H), 7.258–7.188 (m, 4H), 7.142–7.107 (m, 2H), 7.067–7.049 (m, 4H), 3.921 (s, 6H), 2.992 (s, 6H), 2.756–2.741 (m, 4H), 2.339–2.263 (m, 2H), 2.196–2.070 (m, 2H); HPLC Waters 2690 Alliance HPLC (Symmetry Shield $RP_{18}$ 3.5 μm, 2.1×50 mm; 5%–95% acetonitrile-0.1 M ammonium acetate over 15 min, 0.5 mL/min) $R_t$ 7.910 min (100%).

cis-N1-(4-{4-Amino-1-[4-(4-methylpiperazino) cyclohexyl]-1H-pyrazolo[3,4-d]pyrimidin-3-yl}-2-methoxyphenyl)-N1-methyl-3-phenylpropanamide A solution of cis-3-iodo-1-[4-(4-methylpiperazino) cyclohexyl]-1H-pyrazolo[3,4-d]pyrimidin-4-amine (0.293 g, 0.664 mmol) in ethylene glycol dimethyl ether (10 mL) was treated with 3-methoxy-4-[methyl(3-phenylpropanoyl) amino]phenylboronic acid (0.290 g, 0.730 mmol), tetrakis (triphenylphosphine)palladium (0.046 g, 0.040 mmol), and a solution of sodium carbonate (0.169 g, 1.59 mmol) in water (5 mL). The reaction mixture was stirred over night at 85° C. under a nitrogen atmosphere. The solvent was removed under reduced pressure, and ethyl acetate was added to the aqueous layer. The layers were partitioned, and the aqueous layer was extracted with ethyl acetate (150 mL). The combined organic layers were washed with water and brine, dried over magnesium sulfate, filtered, and evaporated under reduced pressure. The crude product was purified by flash chromatography on silica gel using 4% methanol in dichloromethane, 8% methanol in dichloromethane, and then 12% methanol in dichloromethane as eluent. A second column using a Supelco flash chromatography silica gel column using 30% methanol in dichloromethane afforded 0.037 g (10%) of cis-N1-(4-{4-amino-1-[4-(4-methylpiperazino)cyclohexyl]-1H-pyrazolo[3,4-d] pyrimidin-3-yl}-2-methoxyphenyl)-N1-methyl-3-phenylpropanamide. $^1$H NMR ($CDCl_3$, 400 MHz) δ 8.374 (s, 1H), 7.315–7.312 (m, 1H), 7.285–7.213 (m, 3H), 7.174–7.087 (m, 4H), 5.795 (br, s, 2H), 4.965–4.922 (m, 1H), 3.892 (s, 3H), 3.213 (s, 3H), 2.948–2.918 (m, 2H), 2.667 (m, 6H), 2.455–2.349 (m, 10H), 2.25–2.15 (m, 2H), 1.867–1.845 (m, 2H), 1.718–1.710 (m, 2H); HPLC Waters 2690 Alliance HPLC (Symmetry Shield $RP_{18}$ 3.5 μm, 2.1× 50 mm; 5%–95% acetonitrile-0.1 M ammonium acetate over 15 min, 0.5 mL/min) $R_t$ 4.947 min (98%).

Example 229

N1-(4-{4-Amino-1-[1-(1-methylpiperidin-4-yl) piperidin-4-yl]-1H-pyrazolo[3,4-d]pyrimidin-3-yl}-2-methoxyphenyl)-4-(trifluoromethoxy)benzamide tris-Maleate tert-Butyl N-[1-(1-Methylpiperidin-4-yl)piperidin-4-yl]-1H-pyrazolo[3,4-d]pyrimidin-3-yl-2-methoxyphenyl) carbamate A solution of 3-iodo-1-[1-(1-methylpiperidin-4-yl) piperidin-4-yl]-1H-pyrazolo[3,4-d]pyrimidin-4-amine (2.667 g, 6.04 mmol) in ethylene glycol dimethyl ether (95 mL) was treated with tert-butyl N-[2-methoxy-4-(4,4,5,5-tetramethyl-1,3,2-dioxaborolan-2-yl)phenyl]carbamate (2.32 g, 6.64 mmol), tetrakis(triphenylphosphine)palladium (0.419 g, 0.362 mmol) and a solution of sodium carbonate (1.54 g, 14.5 mmol) in water (40 mL). The reaction mixture was stirred for 18 h at 85° C. under a nitrogen atmosphere. The organic layer was removed under reduced pressure. Ethyl acetate was added (100 mL), and the layers were separated. The aqueous layer was extracted with ethyl acetate (1 L). The combined organic layers were washed with water (1 L) and brine (500 mL), dried over magnesium sulfate, filtered and evaporated under reduced pressure to give 3.71 g of crude material. The crude material was purified by flash chromatography on silica gel using 20% methanol in dichloromethane (4 L), 30% methanol in dichloromethane (1 L), and 1:1 methanol in dichloromethane (1 L) as eluent to give 2.305 g (71%) tert-butyl N-[1-(1-methylpiperidin-4-yl)piperidin-4-yl]-1H-pyrazolo [3,4-d]pyrimidin-3-yl-2-methoxyphenyl)carbamate. $^1$H NMR (DMSO-$d_6$, 400 MHz) δ 8.221 (s, 1H), 8.030 (s, 1H), 7.921–7.901 (m, 1H), 7.239–7.195 (m, 2H), 4.652–4.594 (m, 1H), 3.890 (s, 3H), 2.988–2.804 (m, 2H), 2.776–2.507 (m, 2H), 2.40–2.21 (m, 5H), 2.190 (s, 3H), 1.898–1.815 (m, 4H), 1.716–1.686 (m, 2H), 1.482–1.446 (m, 11H); HPLC Waters 2690 Alliance HPLC (Symmetry Shield $RP_{18}$ 3.5 μm, 2.1×50 mm; 5%–95% acetonitrile-0.1 M ammonium acetate over 15 min, 0.5 mL/min) $R_t$ 4.541 min (98%); TLC (20% methanol in dichloromethane) $R_t$=0.4.

3-(4-Amino-3-methoxyphenyl)-1-[1-(1-methylpiperidin-4-yl)piperidin-4-yl]-1H-pyrazolo[3,4-d]pyrimidin-4-amine A solution of tert-butyl N-[1-(1-methylpiperidin-4-yl) piperidin-4-yl]-1H-pyrazolo[3,4-d]pyrimidin-3-yl-2-methoxyphenyl)carbamate (2.298 g, 4.28 mmol) in dichloromethane (26 mL) at 0° C. was treated with a solution of trifluoroacetic acid (9.2 mL) in dichloromethane (20 mL). The reaction solution was stirred for 20 min at 0° C., after which the ice bath was removed and then stirred for a further 2 h at room temperature. Solvent was removed under reduced pressure, and the residue dried under high vacuum. Ethyl acetate (150 mL) and 5 N hydrochloric acid solution (100 mL) were added to the oil. The layers were separated, and the organic layer was extracted with 5 N hydrochloric acid solution (400 mL). The combined aqueous layers were cooled to 0° C. on an ice bath, and neutralized with 50% sodium hydroxide solution to pH 10. The neutralized layer was extracted with dichloromethane (700 mL). The organic layer was dried over magnesium sulfate, filtered and evaporated under reduced pressure to give 1.769 g (95%) of 3-(4-amino-3-methoxyphenyl)-1-[1-(1-methylpiperidin-4-yl)piperidin-4-yl]-1H-pyrazolo[3,4-d]pyrimidin-4-amine. $^1$H NMR (DMSO-$d_6$, 400 MHz) δ 8.189 (s, 1H), 7.048–7.043 (s, 1H), 7.004–6.980 (d.d., 1H, J=1 Hz, J=4 Hz), 6.775–6.755 (m, 1H), 5.039 (s, 2H), 4.605–4.565 (m, 1H), 3.831 (s, 3H), 2.992–2.882 (m, 2H), 2.882–2.794 (m, 2H), 2.40–2.15 (m, 5H), 2.149 (s, 3H), 1.876–1.849 (m, 4H), 1.727–1.698 (m, 2H), 1.486–1.448 (m, 2H); HPLC Waters 2690 Alliance HPLC (Symmetry Shield $RP_{18}$ 3.5 μm, 2.1× 50 mm; 5%–95% acetonitrile-0.1 M ammonium acetate over 15 min, 0.5 mL/min) $R_t$ 2.83 min (99%).

N1-(4-{4-Amino-1-[1-(1-methylpiperidin-4-yl)piperidin-4-yl]-1H-pyrazolo[3,4-d]pyrimidin-3-yl}-2-methoxyphenyl)-4-(trifluoromethoxy)benzamide tris-Maleate A solution of 3-(4-amino-3-methoxyphenyl)-1-[1-(1-methylpiperidin-4-yl)piperidin-4-yl]-1H-pyrazolo[3,4-d] pyrimidin-4-amine (0.450 g, 1.03 mmol) in pyridine (8 mL) at –5° C. was treated with a solution of 4-(trifluoromethoxy)-1-benzenecarbonyl chloride (0.231 g, 1.03 mmol) in dichloromethane (2.5 mL) drop-wise. The reaction mixture was stirred at –5° C. for 30 min. The ice bath was removed and the reaction mixture was stirred at room temperature for 3 h. 1 N sodium hydroxide solution (10 mL) was added, and stirred for 1 h. The organic solvent was removed under reduced pressure. Dichloromethane (10 mL) was added and the layers were separated using an Empore extraction cartridge. The organic solvent was removed under reduced pressure and the crude compound was purified by flash chromatography on silica gel using 10% methanol in dichloromethane as eluent to give 0.430 g (67%) N1-(4-{4-amino-1-[1-(1-methylpiperidin-4-yl) piperidin-4-yl]-1H-pyrazolo[3,4-d]pyrimidin-3-yl}-2-methoxyphenyl)-4-(trifluoromethoxy)benzamide. A hot solution of N1-(4-{4-amino-1-[1-(1-methylpiperidin-4-yl) piperidin-4-yl]-1H-pyrazolo[3,4-d]pyrimidin-3-yl}-2-methoxyphenyl)-4-(trifluoromethoxy)benzamide (0.430 g, 0.688 mmol) in ethyl acetate (15 mL) was treated with a hot solution of maleic acid (0.240 g, 2.07 mmol) in ethyl acetate. A precipitate was formed, filtered under nitrogen, and dried under high vacuum to give N1-(4-{4-amino-1-[1-(1-methylpiperidin-4-yl)piperidin-4-yl]-1H-pyrazolo[3,4-d]pyrimidin-3-yl}-2-methoxyphenyl)-4-(trifluoromethoxy)benzamide tris-maleate salt.

$^1$H NMR (DMSO-d$_6$, 400 MHz) δ 9.70 (s, 1H), 8.28 (s, 1H), 8.11–8.08 (m, 2H), 8.05–8.03 (m, 1H), 7.56–7.54 (m, 2H), 7.34 (m, 1H), 7.31–7.29 (m, 1H), 6.11 (s, 6H), 5.10–5.00 (m, 1H), 3.93 (s, 3H), 3.54 (m, 4H), 2.99 (m, 2H), 2.79 (s, 3H), 2.22–2.19 (m, 4H), 1.84 (m, 2H); HPLC Waters 2690 Alliance HPLC (Symmetry Shield RP$_{18}$ 3.5 μm, 2.1× 50 mm; 5%–95% acetonitrile-0.1 M ammonium acetate over 15 min, 0.5 mL/min) R$_t$ 4.999 min (100%).

Example 230

4-[4-Amino-3-(4-phenoxyphenyl)-1H-pyrazolo[3,4-d]pyrimidin-1-yl]piperidino(4-methylpiperazino)methanone bis-Maleate A solution of 3-(4-phenoxyphenyl)-1-(4-piperidyl)-1H-pyrazolo[3,4-d]pyrimidin-4-amine (0.300 g, 0.780 mmol) in pyridine (5 mL) at 0° C. was treated with 4-methyl-1-piperazinecarbonyl chloride hydrochloride (0.127 g, 0.780 mmol). The reaction mixture was stirred for 5 min at 0° C., after which the ice bath was removed, and the reaction stirred at room temperature over night. An additional equivalent of 4-methyl-1-piperazinecarbonyl chloride hydrochloride (0.127 g, 0.780 mmol) was added and stirred for 2 h. Solvent was removed under reduced pressure. Dichloromethane (10 mL) and sodium bicarbonate (5 mL) saturated aqueous solution were added to the solid. The layers were separated using an Empore extraction cartridge. The organic layer was removed under reduced pressure to give 0.417 g of crude material. The crude product was purified by flash chromatography on silica gel eluting 8% methanol in dichloromethane, 15% methanol in dichloromethane, and then 20% methanol in dichloromethane as eluent to give 0.178 g (45%) of 4-[4-amino-3-(4-phenoxyphenyl)-1H-pyrazolo[3,4-d]pyrimidin-1-yl]piperidino(4-methylpiperazino)methanone. A hot solution of 4-[4-amino-3-(4-phenoxyphenyl)-1H-pyrazolo[3,4-d]pyrimidin-1-yl]piperidino(4-methylpiperazino)methanone (0.178 g, 0.347 mmol) in ethyl acetate was treated with a hot solution of maleic acid (0.081 g, 0.693 mmol) in ethyl acetate. Upon cooling of the solvent a precipitate formed, was filtered under nitrogen, and dried under high vacuum to give 0.124 g of 4-[4-amino-3-(4-phenoxyphenyl)-1H-pyrazolo[3,4-d]pyrimidin-1-yl]piperidino(4-methylpiperazino)methanone bis-maleate.

$^1$H NMR (DMSO-d$_6$, 400 MHz) δ 8.257 (s, 1H), 7.661–7.639 (d, 2H, J=8.8 Hz), 7.441–7.42 (m, 2H), 7.210–7.112 (m, 5H), 6.142 (s, 4H), 4.963–4.908 (m, 1H), 3.784–3.754 (d, 2H, J=12 Hz), 3.7–3.2 (br s, 11H), 3.15–3.05 (m, 2H), 2.922 (s, 3H), 2.161–2.138 (m, 2H), 1.989–1.93 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 5.159 min (97%).

Example 231

N1-(4-{4-Amino-1-[1-(1-methylpiperidin-4-yl)piperidin-4-yl]-1H-pyrazolo[3,4-d]pyrimidin-3-yl}-2-methoxyphenyl)-4-(dimethylamino)benzamide tris-Maleate A suspension of 3-(4-Amino-3-methoxyphenyl)-1-[1-(1-methylpiperidin-4-yl)piperidin-4-yl]-1H-pyrazolo[3,4-d]pyrimidin-4-amine (0.398 g, 0.912 mmol) in pyridine (7 mL) at −5° C. was treated with a solution of 4-(dimethylamino)-1-benzenecarbonyl chloride (0.167 g, 0.912 mmol) in dichloromethane (3 mL). The reaction mixture was stirred at −5° C. for 2.5 h, and the ice bath was removed. 1 N sodium hydroxide solution (10 mL) was added to the reaction mixture and stirred for 1 h. The organic layer was removed under reduced pressure, and dichloromethane (15 mL) was added. The layers were separated using an Empore extraction cartridge. The organic layer was removed under reduced pressure. The crude solid was purified two times by flash chromatography on silica gel using 12% (methanol with 5% ammonium hydroxide) in dichloromethane as eluent to give 0.284 g (53%) of N1-(4-{4-amino-1-[1-(1-methylpiperidin-4-yl)piperidin-4-yl]-1H-pyrazolo[3,4-d]pyrimidin-3-yl}-2-methoxyphenyl)-4-(dimethylamino)benzamide. A hot solution of N1-(4-{4-amino-1-[1-(1-methylpiperidin-4-yl)piperidin-4-yl]-1H-pyrazolo[3,4-d]pyrimidin-3-yl}-2-methoxyphenyl)-4-(dimethylamino)benzamide (0.284 g, 0.487 mmol) in ethyl acetate and a few drops of ethanol was treated with a hot solution of maleic acid (0.169 g, 1.46 mmol) in ethyl acetate. The precipitate formed was filtered under nitrogen and dried under high vacuum to give 0.409 g N1-(4-{4-amino-1-[1-(1-methylpiperidin-4-yl)piperidin-4-yl]-1H-pyrazolo[3,4-d]pyrimidin-3-yl}-2-methoxyphenyl)-4-(dimethylamino)benzamide tris-maleate. $^1$H NMR (DMSO-d$_6$, 400 MHz) δ 9.054 (s, 1H), 8.278 (s, 1H), 8.215–8.194 (m, 1H), 7.851–7.828 (m, 2H), 7.312–7.308 (m, 1H), 7.288–7.263 (m, 1H), 6.794–6.772 (m, 2H), 6.096 (s, 6H), 5.10–5.00 (m, 1H), 3.951 (s, 3H), 3.538 (s, 4H), 3.061 (s, 8H), 2.215–2.183 (m, 4H), 1.90–1.81 (m, 2H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) R$_t$ 4.496 min (98%).

Examples 232–237 cis-N1-(4-{4-Amino-1-[4-(4-methylpiperazino)cyclohexyl]-1H-pyrazolo[3,4-d]pyrimidin-3-yl}-2-methoxyphenyl)-2-(trifluoromethyl)benzamide cis-N1-(4-{4-amino-1-[4-(4-methylpiperazino)cyclohexyl]-1H-pyrazolo[3,4-d]pyrimidin-3-yl}-2-methoxyphenyl)-2-(trifluoromethoxy)benzamide cis-N1-(4-{4-amino-1-[4-(4-methylpiperazino)cyclohexyl]-1H-pyrazolo[3,4-d]pyrimidin-3-yl}-2-methoxyphenyl)-3-(trifluoromethoxy)benzamide cis-N1-(4-{4-amino-1-[4-(4-methylpiperazino)cyclohexyl]-1H-pyrazolo[3,4-d]pyrimidin-3-yl}-2-methoxyphenyl)-2-fluoro-4-(trifluoromethyl)benzamide cis-N1-(4-{4-amino-1-[4-(4-methylpiperazino)cyclohexyl]-1H-pyrazolo[3,4-d]pyrimidin-3-yl}-2-methoxyphenyl)-3-(trifluoromethyl)benzamide Amides Derived From cis-3-(4-Amino-3-methoxyphenyl)-1-[4-(4-methylpiperazino)cyclohexyl]-7H-pyrazolo[3,4-d]pyrimidin-4-amine The commercially available acid chlorides (0.23 mmol) in dichloromethane (100 μL) were added to cis-3-(4-amino-3-methoxyphenyl)-1-[4-(4-methylpiperazino)cyclohexyl]-7H-pyrazolo[3,4-d]pyrimidin-4-amine (0.050 g, 0.115 mmol) in pyridine (800 μL). The reaction mixtures were stirred over night. The reaction mixtures were quenched with 1 N sodium hydroxide solution. Solvent was removed on a Supelco-manifold under vacuum and nitrogen purge. The remaining solids were submitted for preparative HPLC (Hypersil C18, 100×21 mm column, 5 µm, 15–100% Acetonitrile gradient over 8 min, total run time—10 min, buffer—50 mM Ammonium Acetate, 25 ml/min). Dichloromethane and 1 N sodium hydroxide solution were added to the solids. The layers were partitioned using an Empore extraction cartridge to give corresponding products. HPLC Perkin Elmer Pecosphere C18, 3 µM, 33×4.6, 3.5 ml/min 100–100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min)

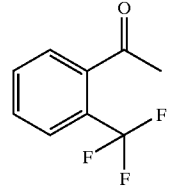

| Compound Name | R | Ex | Qty. (mg) | MH+ | Rt (mins) |
|---|---|---|---|---|---|
| cis-N1-(4-{4-amino-1-[4-(4-methylpiperazino)cyclohexyl]-1H-pyrazolo[3,4-d]pyrimidin-3-yl}-2-methoxyphenyl)-2-(trifluoromethyl)benzamide | 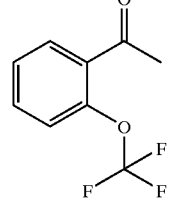 | 232 | 44 (63%) | 609.1 | 2.957 |
| cis-N1-(4-{4-amino-1-[4-(4-methylpiperazino)cyclohexyl]-1H-pyrazolo[3,4-d]pyrimidin-3-yl}-2-methoxyphenyl)-2-(trifluoromethoxy)benzamide | | 233 | 10 (14%) | 625.5 | 3.464 |
| cis-N1-(4-{4-amino-1-[4-(4-methylpiperazino)cyclohexyl]-1H-pyrazolo[3,4-d]pyrimidin-3-yl}-2-methoxyphenyl)-3-(trifluoromethoxy)benzamide | 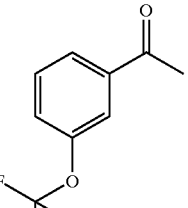 | 234 | 40 (56%) | 625.1 | 3.405 |
| cis-N1-(4-{4-amino-1-[4-(4-methylpiperazino)cyclohexyl]-1H-pyrazolo[3,4-d]pyrimidin-3-yl}-2-methoxyphenyl)-2-fluoro-4-(trifluoromethyl)benzamide | 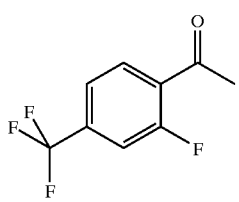 | 235 | 47 (65%) | 627.5 | 3.405 |

-continued

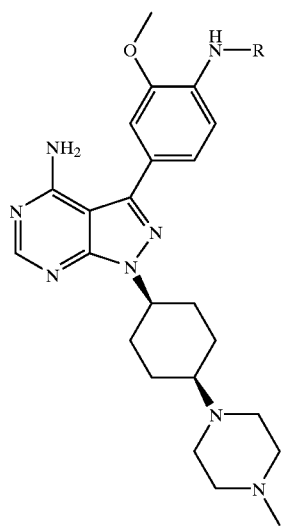

| Compound Name | R | Ex | Qty. (mg) | MH+ | $R_t$ (mins) |
|---|---|---|---|---|---|
| cis-N1-(4-{4-amino-1-[4-(4-methylpiperazino)cyclohexyl]-1H-pyrazolo[3,4-d]pyrimidin-3-yl}-2-methoxyphenyl)-3-(trifluoromethyl)benzamide | *3-(trifluoromethyl)benzoyl group* | 236 | 41 (59%) | 609.3 | 3.223 |
| cis-N1-(4-{4-amino-1-[4-(4-methylpiperazino)cyclohexyl]-1H-pyrazolo[3,4-d]pyrimidin-3-yl}-2-methoxyphenyl)-3-fluoro-4-(trifluoromethyl)benzamide | *3-fluoro-4-(trifluoromethyl)benzoyl group* | 237 | 48 (67%) | 627.4 | 3.613 |

Example 238 cis-2-(4-{4-Amino-1-[4-(4-methylpiperazino)cyclohexyl]-1H-pyrazolo[3,4-d]pyrimidin-3-yl}-2-methoxyanilino)-2-phenyl-1-ethanol Cis-3-(4-amino-3-methoxyphenyl)-1-[4-(4-methylpiperazino)cyclohexyl]-1H-pyrazolo[3,4-d]pyrimidin-4-amine (0.075 g, 0.000172 mol) and styrene oxide (0.029 g, 0.000172 mol) were dissolved in isopropanol (3 mL) and the resulting mixture was heated at reflux for 24 hours. The solvent was removed and the residue purified by preparative HPLC (Hypersil C18, 8 μm, 25 cm; 10–60% acetonitrile-0.1M ammonium acetate over 25 min, 21 mL/min) to yield cis-2-(4-{4-amino-1-[4-(4-methylpiperazino)cyclohexyl]-1H-pyrazolo[3,4-d]pyrimidin-3-yl}-2-methoxyanilino)-2-phenyl-1-ethanol (0.005 g, 0.0000089 mol) as an off-white solid.

$^1$H NMR (DMSO-$d_6$, 400 MHz) δ 8.18 (s, 1H), 7.36 (m, 5H), 7.06 (s, 1H), 6.91 (d, 1H), 6.36 (d, 1H), 5.55 (d, 1H), 5.20 (s, 1H) 4.78 (m, 1H), 4.43 (d, 2H), 3.88 (s, 3H), 3.74 (m, 1H), 3.58 (m, 1H), 2.5–2.1 (br, 13H), 2.17 (s, 3H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 11.97 min. MS: MH+ 557.

Intermediates:

cis-3-(4-amino-3-methoxyphenyl)-1-[4-(4-methylpiperazino)cyclohexyl]-1H-pyrazolo[3,4-d]pyrimidin-4-amine trans-3-(4-amino-3-methoxyphenyl)-1-[4-(4-methylpiperazino)cyclohexyl]-1H-pyrazolo[3,4-d]pyrimidin-4-amine General procedure for reductive alkylation of cis-or trans-3-(4-amino-3-methoxyphenyl)-1-[4-(4-methylpiperazino)cyclohexyl]-1H-pyrazolo[3,4-d]pyrimidin-4-amine:

Protocol A:

A mixture of the cis-or trans-3-(4-amino-3-methoxyphenyl)-1-[4-(4-methylpiperazino)cyclohexyl]-1H-pyrazolo[3,4-d]pyrimidin-4-amine (or cis or trans alone) (1 eq.), aldehyde (1 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10–60% acetonitrile-0.1M ammonium acetate over 25 min, 21 mL/min) to yield the desired products.

Protocol B:

After synthesis and purification (protocol A) the residue was digested with dichloromethane (1 mL), loaded onto Trikonex column (7 cm) and eluted with dichloromethane (5 mL). The desired band (UV-detection) was cut and the compound was extracted with the mixture of dichloromethane:methanol:triethylamine=90:5:5 (10 mL), filtered and the filtrate was concentrated under reduced pressure. The residue was suspended in diethyl ether (4 mL) and the precipitate was collected by filtration and dried.

Example 239 cis-3-{4-[(2-Furylmethyl)amino]-3-methoxyphenyl}-1-[4-(4-methylpiperazino)cyclohexyl]-1H-pyrazolo[3,4-d]pyrimidin-4-amine Acetate Protocol A $^1$H NMR (DMSO-d$_6$, 400 MHz) δ 8.18 (s, 1H), 7.57 (s, 1H), 7.06 (br, 2H), 6.77 (d, 1H), 6.38 (d, 1H), 6.32 (d, 1H), 5.65 (t, 1H), 4.78 (m, 1H), 4.38 (d, 2H), 3.88 (s, 3H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 12.65 min. MS: MH$^+$ 517.

Example 240 cis-5-[(4-{4-Amino-1-[4-(4-methylpiperazino)cyclohexyl]-1H-pyrazolo[3,4-d]pyrimidin-3-yl}-2-methoxyanilino)methyl]-2-furylmethanol Acetate Protocol A $^1$H NMR (DMSO-d$_6$, 400 MHz) δ 8.18 (s, 1H), 7.06 (br, 2H), 6.77 (d, 1H), 6.23 (d, 1H), 6.19 (d, 1H), 5.63 (t, 1H), 5.18 (t, 1H), 4.78 (m, 1H), 4.35 (d, 4H), 3.88 (s, 3H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 10.91 min. MS: MH$^+$ 547.

Example 241 trans-3-{4-[(2-Furylmethyl)amino]-3-methoxyphenyl-1-[4-(4-methylpiperazino)cyclohexyl]-1H-pyrazolo[3,4-d]pyrimidin-4-amine Dimaleate Trans-3-{4-[(2-furylmethyl)amino]-3-methoxyphenyl-1-[4-(4-methylpiperazino)cyclohexyl]-1H-pyrazolo[3,4-d]pyrimidin-4-amine was prepared according to protocol A. Trans-3-{4-[(2-furylmethyl)amino]-3-methoxyphenyl-1-[4-(4-methylpiperazino)cyclohexyl]-1H-pyrazolo[3,4-d]pyrimidin-4-amine (1 equiv.) was dissolved in ethanol (20 mL) and the solution was heated at reflux. The solution of maleic 3 equiv.) was added at once and the reflux was continued for an additional 10 min. The reaction mixture was cooled to ambient temperature, the precipitate was collected by filtration and dried.

trans-3-{4-[(2-Furylmethyl)amino]-3-methoxyphenyl-1-[4-(4-methylpiperazino)cyclohexyl]-1H-pyrazolo[3,4-d]pyrimidin-4-amine Dimaleate $^1$H NMR (DMSO-d$_6$, 400 MHz) δ 8.18 (s, 1H), 7.57 (s, 1H), 7.06 (br, 2H), 6.77 (d, 1H), 6.38 (d, 1H), 6.32 (d, 1H), 6.16 (s, 4H), 5.65 (t, 1H), 4.67 (m, 1H), 4.38 (d, 2H), 3.88 (s, 3H), 3.1 (br, 9H), 2.67 (s, 3H), 2.05 (m, 6H), 1.57 (m, 2H); RP-HPLC (Delta Pak C18, 5 μm, 300 A, 15 cm; 5%–85% acetonitrile-0.1M ammonium acetate over 20 min, 1 mL/min) R$_t$ 12.62 min. MS: MH$^+$ 517.

Example 242 trans-3-(3-Methoxy-4-[(5-methyl-2-furyl)methyl]aminophenyl)-1-[4-(4-methylpiperazino)cyclohexyl]-1H-pyrazolo[3,4-d]pyrimidin-4-amine Dimaleate It was prepared the same way as trans-3-{4-[(2-furylmethyl)amino]-3-methoxyphenyl-1-[4-(4-methylpiperazino)cyclohexyl]-1H-pyrazolo[3,4-d]pyrimidin-4-amine dimaleate described above.

$^1$H NMR (DMSO-d$_6$, 400 MHz) δ 8.18 (s, 1H), 7.08 (d, 2H), 6.77 (d, 1H), 6.16 (m, 5H), 5.95 (d, 1H), 5.65 (t, 1H), 4.67 (m, 1H), 4.32 (d, 2H), 3.88 (s, 3H), 3.1 (br, 9H), 2.67 (s, 3H), 2.22 (s, 3H), 2.05 (m, 6H), 1.57 (m, 2H); RP-HPLC (Delta Pak C18, 5 μm, 300 A, 15 cm; 5%–85% acetonitrile-0.1M ammonium acetate over 20 min, 1 mL/min) Rt 13.73 min. MS: MH$^+$ 531.

General procedure for reductive alkylation of cis-or trans-3-(4-amino-phenyl)-1-[4-(4-methylpiperazino)cyclohexyl]-1H-pyrazolo[3,4-d]pyrimidin-4-ami:

Protocol C:

A mixture of the cis-or trans-3-(4-amino-phenyl)-1-[4-(4-methylpiperazino)cyclohexyl]-1H-pyrazolo[3,4-d]pyrimidin-4-amine (either intermediate . . . or . . . ) (1 eq.), aldehyde (1 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10–60% acetonitrile-0.1M ammonium acetate over 25 min, 21 mL/min) to yield the desired products.

Example 243 cis-2-[2-(4-{4-Amino-1-[4-(4-methylpiperazino)cyclohexyl]-1H-pyrazolo[3,4-d]pyrimidin-3-yl}anilino)methyl]phenoxyacetic Acid Diacetate Protocol C $^1$H NMR (DMSO-d$_6$, 400 MHz) δ 8.18 (s, 1H), 7.33 (m, 3H), 7.17 (t, 1H), 6.83 (m, 4H), 4.76 (m, 1H), 4.46 (s, 2H), 4.29 (s, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 10.78 min. MS: MH$^+$ 571.

Example 244 cis-3-{4-[(2-Furylmethyl)amino]phenyl}-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.58 (s, 1H), 7.36 (d, 2H), 6.81 (d, 2H), 6.46 (t, 1H), 6.41 (d, 1H), 6.34 (d, 1H), 4.78 (m, 1H), 4.31 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 11.29 min. MS: MH$^+$ 487.

Example 245 cis-3-(4-[(5-Methyl-2-furyl)methyl]aminophenyl)-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.36 (d, 2H), 6.79 (d, 2H), 6.43 (t, 1H), 6.21 (d, 1H), 5.98 (d, 1H), 4.78 (m, 1H), 4.24 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 12.86 min. MS: MH$^+$ 501.

Example 246 cis-3-{4-[(3-Furylmethyl)amino]phenyl}-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.64 (d, 2H), 7.37 (d, 2H), 6.79 (d, 2H), 6.52 (s, 1H), 6.29 (t, 1H), 4.76 (m, 1H), 4.18 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 12.17 min. MS: MH$^+$ 488.

Example 247 cis-3-{4-[(Benzo[b]furan-2-ylmethyl)amino]phenyl}-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.58 (d, 1H), 7.53 (d, 1H), 7.38 (d, 2H), 7.23 (m, 2H), 6.86 (d, 2H), 6.80 (s, 1H), 6.66 (t, 1H), 4.78 (m, 1H), 4.52 (d, 2H), 2.5–2.1 (br, 13H), 2.17 (s, 3H), 1.91 (s, 6H), 1.65 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) $R_t$ 14.00 min. MS: MH$^+$ 537.

Example 248 trans-3-{4-[(2-Furylmethyl)amino]phenyl}-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.59 (s, 1H), 7.35 (d, 2H), 6.79 (d, 2H), 6.45 (t, 1H), 6.39 (d, 1H), 6.33 (d, 1H), 4.60 (m, 1H), 4.30 (d, 2H), 3.1 (br, 9H), 2.67 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 11.96 min. MS: MH$^+$ 487.

General procedure for reductive alkylation of 3-(4-amino-phenyl)-1-[1-(1-methylpiperid-4-yl)piperid-4-yl]-1H-pyrazolo[3,4-d]pyrimidin-4-amine:

Protocol D:

A mixture of 3-(4-amino-phenyl)-1-[1-(1-methylpiperid-4-yl)piperid-4-yl]-1H-pyrazolo[3,4-d]pyrimidin-4-amine (1 eq.), aldehyde (1 eq.), sodium triacetoxyborohydride (3.4 eq.) and acetic acid (3.4 eq) was stirred in anhydrous 1,2-dichloroethane for 16 hours. The reaction mixture was concentrated under reduced pressure, quenched with saturated solution of sodium bicarbonate in water and concentrated again. The residue was purified by preparative HPLC (Hypersil C18, 8 μm, 25 cm; 10–60% acetonitrile-0.1M ammonium acetate over 25 min, 21 mL/min) to yield the desired products.

Example 249

3-(4-[(5-Methyl-2-furyl)methyl]aminophenyl)-1-[1-(1-methylpiperid-4-yl)piperid-4-yl]-1H-pyrazolo[3,4-d]pyrimidin-4-amine Acetate Protocol D $^1$H NMR (DMSO-d$_6$, 400 MHz) δ 8.18 (s, 1H), 7.07 (br, 2H), 6.76 (d, 1H), 6.17 (d, 1H), 5.97 (d, 1H), 5.57 (t, 1H), 4.60 (m, 1H), 4.30 (d, 2H), 3.86 (s, 3H), 2.98 (d, 2H), 2.79 (d, 2H), 2.27 (s, 3H), 2.25 (br, 5H), 2.15 (s, 3H), 1.91 (m, 7H), 1.69 (d, 2H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 8.97 min. MS: MH$^+$ 531.

Example 250 cis-1-[4-(4-Methylpiperazino)cyclohexyl]-3-{4-[(1-phenylethyl)amino]phenyl}-1H-pyrazolo[3,4-d]pyrimidin-4-amine Diacetate a) N-(4-Bromophenyl)-N-(1-phenylethyl)amine To a solution of N-(4-bromophenyl)-N-(1-phenylmethylidene)amine (1.0 g, 0.00385 mol) in toluene (30 mL) cooled to −78° C., a 1.4M solution of methyl lithium in diethyl ether (5.5 mL) was added dropwise keeping the temperature below −75° C. The solution was warmed up to −40° C. and stirred at this temperature under an atmosphere of nitrogen for 3 hours. The reaction mixture was quenched by a dropwise addition of water and the layers were separated. The organic phase was washed with brine (50 mL), dried with magnesium sulfate and concentrated under reduced pressure to yield N-(4-bromophenyl)-N-(1-phenylethyl)amine (1.03 g, 0.00373 mol) as an off-white solid.

$^1$H NMR (DMSO-d$_6$, 400 MHz) δ 7.30 (m, 4H), 7.18 (t, 1H), 7.09 (d, 2H), 6.43 (d, 2H), 6.38 (d, 1H), 4.43 (m, 1H), 1.40 (d, 3H); TLC (ethyl acetate/heptane 5.95) $R_f$ 0.27.

b) N-(1-Phenylethyl)-N-[4-(4,4,5,5-tetramethyl-1,3,2-dioxaborolan-2-yl)phenyl]amine A mixture of N-(4-bromophenyl)-N-(1-phenylethyl)amine (0.87 g, 0.00315 mol), diboron pinacol ester (0.96 g, 0.00378 mol), [1.1'-bis(diphenylphosphino)ferrocene]-dichloropalladium (II) complex with dichloromethane (1:1) (0.077 g, 0.0000945 mol) and potassium acetate (0.93 g, 0.00945 mol) in N,N-dimethylformamide (20 mL) was heated at 80°0 C. under an atmosphere of nitrogen for sixteen hours. The mixture was allowed to cool to ambient temperature and the solvent removed under reduced pressure. Dichloromethane (60 mL) was added to the residue and the resulting solid was removed by filtration through a pad of Celite. The filtrate was concentrated to leave a yellow oil which was purified by flash chromatography on silica using ethyl acetate/n-heptane (7:93) as mobile phase. The resulting fractions were concentrated, the residue was triturated in n-heptane and the precipitate collected by filtration to yield N-(1-phenylethyl)-N-[4-(4,4,5,5-tetramethyl-1,3,2-dioxaborolan-2-yl)phenyl]amine (0.3 g, 0.00093 mol) as a white solid.

$^1$H NMR (DMSO-d$_6$, 400 MHz) δ 7.30 (m, 6H), 7.18 (t, 1H), 6.58 (d, 1H), 6.46 (d, 2H), 4.51 (m, 1H), 1.40 (d, 3H), 1.27 (s, 12H); TLC (ethyl acetate/heptane 5.95) $R_f$ 0.17.

c) cis-1-[4-(4-Methylpiperazino)cyclohexyl]-3-{4-[(1-phenylethyl)amino]phenyl}-1H-pyrazolo[3,4-d]pyrimidin-4-amine Diacetate A mixture of N-(1-phenylethyl)-N-[4-(4,4,5,5-tetramethyl-1,3,2-dioxaborolan-2-yl)phenyl]amine (0.070 g, 0.000235 mol), cis-3-iodo-1-[4-(4-methylpiperazino)-cyclohexyl]-1H-pyrazolo[3,4-d]pyrimidin-4-amine (0.080 g, 0.000181 mol), tetrakis-(triphenylphosphine)palladium (0.012 g, 0.000011 mol) and sodium carbonate monohydrate (0.056 g, 0.00045 mol) was heated in a mixture of ethylene glycol dimethyl ether (5 mL) and water (3 mL) at 80° C. for sixteen hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield Cis-1-[4-(4-methylpiperazino) cyclohexyl]-3-{4-[(1-phenylethyl)amino]phenyl}-1H-pyrazolo[3,4-d]pyrimidin-4-amine diacetate (0.062 g, 0.0000984 mol) as a white solid.

$^1$H NMR (DMSO-$d_6$, 400 MHz) δ 8.19 (s, 1H), 7.42 (d, 2H), 7.30 (m, 4H), 7.19 (t, 1H), 6.68 (d, 2H), 6.52 (d, 1H), 4.78 (m, 1H), 4.53 (m, 1H), 2.5–2.1 (br, 13H), 2.17 (s, 3H), 1.91 (s, 6H), 1.68 (m, 2H), 1.58 (m, 2H), 1.44 (d, 3H); RP-HPLC (Delta Pak C18, 5 μm, 300 A, 15 cm; 5%–85% acetonitrile-0.1M ammonium acetate over 20 min, 1 mL/min) $R_t$ 13.96 min. MS: MH$^+$ 511.

Example 251 and Example 252 cis-3-[4-(2,3-Dihydrobenzo[b]furan-3-ylamino) phenyl]-1-[4-(4-methylpiperazino)cyclohexyl]-1H-pyrazolo[3,4-d]pyrimidin-4-amine trans-3-[4-(2,3-Dihydrobenzo[b]furan-3-ylamino)phenyl]-1-[4-(4-methylpiperazino)cyclohexyl]-1H-pyrazolo[3,4-d] pyrimidin-4-amine Diacetate a) N-(4-Bromophenyl)-N-(2,3-dihydrobenzo[b]furan-3-yl) amine A 60% dispersion of sodium hydride in mineral oil (0.145 g, 0.00362 mol) was added to a solution of trimethylsulfoxonium iodide (0.8 g, 0.00362 mol) in anhydrous dimethylsulfoxide (10 mL) and the resulting mixture was stirred under an atmosphere of nitrogen for 10 min. A solution of 2-{[(4-bromophenyl)imino]methyl}phenol (0.4 g, 0.00145 mol) in anhydrous dimethylsulfoxide (5 mL) was added dropwise and the resulting mixture was stirred at ambient temperature for 2.5 hours. It was poured into ice-cold water (100 mL) and extracted with diethyl ether (2×50 mL). The combined organic extracts were dried with magnesium sulfate and concentrated under reduced pressure to yield N-(4-bromophenyl)-N-(2,3-dihydrobenzo[b]furan-3-yl) amine (0.321 g, 0.0011 mol) as an off-white solid.

$^1$H NMR (DMSO-$d_6$, 400 MHz) δ 7.34 (d, 1H), 7.23 (m, 3H), 6.90 (m, 2H), 6.67 (d, 2H), 6.34 (d, 1H), 5.23 (m, 1H), 4.72 (dd, 1H), 4.19 (dd, 1H). TLC (ethyl acetate/heptane 1:5) $R_f$ 0.52.

b) N-(2,3-Dihydrobenzo[b]furan-3-yl)-N-[4-(4,4,5,5-tetramethyl-1,3,2-dioxaborolan-2-yl)phenyl]amine A mixture of N-(4-bromophenyl)-N-(2,3-dihydrobenzo [b]furan-3-yl)amine (1.65 g, 0.00569 mol), diboron pinacol ester (1.73 g, 0.00683 mol), [1.1'-bis(diphenylphosphino) ferrocene]-dichloropalladium (II) complex with dichloromethane (1:1) (0.139 g, 0.000171 mol) and potassium acetate (0.81 g, 0.0171 mol) in N,N-dimethylformamide (35 mL) was heated at 80° C. under an atmosphere of nitrogen for 16 hours. The mixture was allowed to cool to ambient temperature and the solvent removed under reduced pressure. Dichloromethane (100 mL) was added to the residue and the resulting solid was removed by filtration through a pad of Celite. The filtrate was concentrated to leave a yellow oil which was purified by flash chromatography on silica using ethyl acetate/n-heptane (5:95) as mobile phase. The resulting fractions were concentrated, the residue was triturated in n-heptane and the precipitate collected by filtration to yield N-(2,3-dihydrobenzo[b]furan-3-yl)-N-[4-(4,4,5,5-tetramethyl-1,3,2-dioxaborolan-2-yl)phenyl]amine (0.59 g, 0.00176 mol) as a white solid.

$^1$H NMR (DMSO-$d_6$, 400 MHz) δ 7.42 (d, 2H), 7.34 (d, 1H), 7.23 (t, 1H), 6.89 (m, 2H), 6.68 (d, 2H), 6.52 (d, 1H), 5.23 (m, 1H), 4.74 (dd, 1H), 4.20 (dd, 1H). TLC (ethyl acetate/heptane 1:5) $R_f$ 0.37.

c) cis-3-[4-(2,3-dihydrobenzo[b]furan-3-ylamino)phenyl]-1-[4-(4-methylpiperazino)cyclohexyl]-1H-pyrazolo[3,4-d] pyrimidin-4-amine A mixture of N-(2,3-dihydrobenzo[b]furan-3-yl)-N-[4-(4, 4,5,5-tetramethyl-1,3,2-dioxaborolan-2-yl)phenyl]amine (0.080 g, 0.000237 mol), cis-3-iodo-1-[4-(4-methylpiperazino)-cyclohexyl]-1H-pyrazolo[3,4-d] pyrimidin-4-amine (0.087 g, 0.000198 mol), tetrakis-(triphenylphosphine)palladium (0.014 g, 0.000012 mol) and sodium carbonate monohydrate (0.061 g, 0.000495 mol) was heated in a mixture of ethylene glycol dimethyl ether (5 mL) and water (3 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1 M ammonium acetate over 25 min, 21 mL/min). Subsequently, the crude product was dissolved in dichloromethane, loaded onto Trikonex column (7 cm) and eluted with dichloromethane (5 mL). The desired band was cut, the product was extracted with a mixture of dichloromethane/methanol/triethylamine in a ratio of 90:5:5 (10 mL) and the solvents were removed under reduced pressure. The residue was triturated in diethyl ether and the precipitate was collected by filtration and dried to yield cis-3-[4-(2,3-dihydrobenzo[b]furan-3-ylamino)phenyl]-1-[4-(4-methylpiperazino)cyclohexyl]-1H-pyrazolo[3,4-d] pyrimidin-4-amine (0.021 g, 0.00004 mol) as a white solid.

$^1$H NMR (DMSO-$d_6$, 400 MHz) δ 8.23 (s, 1H), 7.40 (m, 3H), 7.25 (t, 1H), 6.90 (m, 4H), 6.50 (d, 1H), 5.35 (m, 1H), 4.80 (m, 2H), 4.28 (dd, 1H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) $R_t$ 13.39 min. MS: MH$^+$ 525.

trans-3-[4-(2,3-Dihydrobenzo[b]furan-3-ylamino)phenyl]-1-[4-(4-methylpiperazino)cyclohexyl]-1H-pyrazolo[3,4-d] pyrimidin-4-amine Diacetate A mixture of N-(2,3-dihydrobenzo[b]furan-3-yl)-N-[4-(4, 4,5,5-tetramethyl-1,3,2-dioxaborolan-2-yl)phenyl]amine (0.089 g, 0.000265 mol), trans-3-iodo-1-[4-(4-methylpiperazino)-cyclohexyl]-1H-pyrazolo[3,4-d] pyrimidin-4-amine (0.090 g, 0.000204 mol), tetrakis-(triphenylphosphine)palladium (0.014 g, 0.000012 mol) and sodium carbonate monohydrate (0.063 g, 0.00051 mol) was heated in a mixture of ethylene glycol dimethyl ether (5 mL) and water (3 mL) at 80° C. for sixteen hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield trans-3-[4-(2,3-dihydrobenzo[b]furan-3-ylamino)phenyl]-1-[4-(4-methylpiperazino)cyclohexyl]-1H-pyrazolo[3,4-d] pyrimidin-4-amine diacetate (0.078 g, 0.000121 mol) as a white solid.

$^1$H NMR (DMSO-$d_6$, 400 MHz) δ 8.23 (s, 1H), 7.40 (m, 3H), 7.25 (t, 1H), 6.90 (m, 4H), 6.50 (d, 1H), 5.33 (m, 1H), 4.79 (dd, 1H), 4.60 (m, 1H), 4.28 (dd, 1H), 3.1 (br, 9H), 2.17 (s, 3H), 2.05 (m, 6H), 1.91 (s, 6H), 1.49 (m, 2H); RP-HPLC (Delta Pak C18, 5 μm, 300 A, 15 cm; 5%–85% acetonitrile-0.1 M ammonium acetate over 20 min, 1 mL/min) $R_t$ 13.05 min. MS: MH$^+$ 525.

Example 253 cis-2-(4-{4-Amino-1-[4-(4-methylpiperazino) cyclohexyl]-1H-pyrazolo[3,4-d]pyrimidin-3-yl}anilino)-1-phenyl-1-ethanone Diacetate Cis-3-(4-aminophenyl)-1-[4-(4-methylpiperazino) cyclohexyl]-1H-pyrazolo[3,4-d]pyrimidin-4-amine (0.6 g, 0.00148 mol) and bromoacetophenone (0.295 g, 0.00148 mol) were dissolved in anhydrous N,N-dimethylformamide (30 mL) and the resulting mixture was stirred at ambient temperature under an atmosphere of nitrogen for 5 min. N,N-diisopropylethylamine (0.095 g, 0.00074 mol) was added dropwise and stirring under an atmosphere of nitrogen was continued for sixteen hours. The reaction mixture was concentrated under reduced pressure and the residue was purified by preparative HPLC (Hypersil C18, 8 μm, 25 cm; 10–60% acetonitrile-0.1 M ammonium acetate over 25 min, 21 mL/min) to yield cis-2-(4-{4-amino-1-[4-(4-methylpiperazino)cyclohexyl]-1H-pyrazolo[3,4-d]pyrimidin-3-yl}anilino)-1-phenyl-1-ethanone diacetate (0.410 g, 0.00064 mol) as a white solid.

$^1$H NMR (DMSO-d$_6$, 400 MHz) δ 8.20 (s, 1H), 7.99 (d, 2H), 7.75 (t, 1H), 7.61 (t, 2H), 7.29 (d, 2H), 6.69 (d, 2H), 5.41 (br, 3H), 4.78 (m, 1H), 2.5–2.1 (br, 13H), 2.17 (s, 3H), 1.91 (s, 6H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 12.16 min. MS: MH$^+$ 525.

Example 254 cis-2-(4-{4-Amino-1-[4-(4-methylpiperazino) cyclohexyl]-1H-pyrazolo[3,4-d]pyrimidin-3-yl}anilino)-1-phenyl-1-ethanol Diacetate A solution of cis-2-(4-{4-amino-1-[4-(4-methylpiperazino)cyclohexyl]-1H-pyrazolo[3,4-d]pyrimidin-3-yl}anilino)-1-phenyl-1-ethanone diacetate (0.050 g, 0.000077 mol) in anhydrous methanol (5 mL) was cooled to 0° C. and sodium borohydride (0.018 g, 0.0000477 mol) was added at once. The mixture was allowed to warm up to ambient temperature while stirring under an atmosphere of nitrogen for three hours. The reaction was quenched by dropwise addition of acetic acid, the reaction mixture was concentrated under reduced pressure and the residue purified by preparative HPLC (Hypersil C18, 8 μm, 25 cm; 10–60% acetonitrile-0.1 M ammonium acetate over 25 min, 21 mL/min) to yield cis-2-(4-{4-amino-1-[4-(4-methylpiperazino)cyclohexyl]-1H-pyrazolo[3,4-d]pyrimidin-3-yl}anilino)-1-phenyl-1-ethanol diacetate (0.035 g, 0.000054 mol) as a white solid.

$^1$H NMR (DMSO-d$_6$, 400 MHz) δ 8.20 (s, 1H), 7.31 (m, 7H), 6.69 (d, 2H), 5.41 (br, 2H), 5.31 (d, 1H), 4.78 (m, 1H), 2.5–2.1 (br, 14H), 2.17 (s, 3H), 1.91 (s, 6H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 11.34 min. MS: MH$^+$ 527.

Example 255 cis-N-[(4-{4-Amino-1-[4-(4-methylpiperazino) cyclohexyl]-1H-pyrazolo[3,4-d]pyrimidin-3-yl}phenyl)(phenyl)methyl]-N'-benzylurea Acetate Cis-3-{4-[amino(phenyl)methyl]phenyl}-1-[4-(4-methylpiperazino)cyclohexyl]-1H-pyrazolo[3,4-d]pyrimidin-4-amine (0.05 g, 0.0001 mol) was dissolved in anhydrous pyridine (1 mL), benzyl isocyanate (0.013 g, 0.0001 mol) was added and the resulting solution was stirred at ambient temperature for 20 hours. The solvent was removed under reduced pressure and the resulting residue purified by preparative HPLC (Hypersil C18, 8 μm, 25 cm; 10–60% acetonitrile-0.1M ammonium acetate over 25 min, 21 mL/min) to yield cis-N-[(4-{4-amino-1-[4-(4-methylpiperazino)cyclohexyl]-1H-pyrazolo[3,4-d]pyrimidin-3-yl}phenyl)(phenyl)methyl]-N'-benzylurea acetate (0.015 g, 0.000022 mol) as a white solid.

$^1$H NMR (DMSO-d$_6$, 400 MHz) δ 8.23 (s, 1H), 7.62 (d, 2H), 7.45 (d, 2H), 7.57–7.27 (br, 10H), 7.04 (d, 1H), 6.41 (t, 1H), 6.03 (d, 1H), 4.78 (m, 1H), 4.25 (d, 2H), 2.70 (s, 3H), 2.5–2.1 (br, 13H), 2.17 (s, 3H), 1.90 (s, 3H), 1.68 (m, 2H), 1.56 (m, 2H); RP-HPLC (Delta Pak C18, 5 μm, 300 A, 15 cm; 5%–85% acetonitrile-0.1M ammonium acetate over 20 min, 1 mL/min) R$_t$ 13.39 min. MS: MH$^+$ 630.

Example 256 cis-N1-[4-(4-{4-Amino-1-[4-(4-methylpiperazino) cyclohexyl]-1H-pyrazolo[3,4-d]pyrimidin-3-yl}phenoxy)benzyl]benzamide Acetate Cis-3-{4-[4-(aminomethyl)phenoxy]phenyl}-1-[4-(4-methylpiperazino)cyclohexyl]-1H-pyrazolo[3,4-d]pyrimidin-4-amine (0.051 g, 0.0001 mol) was dissolved in anhydrous pyridine (1 mL), benzoyl chloride (0.014 g, 0.0001 mol) was added and the resulting solution was stirred at ambient temperature for 20 hours. The solvent was removed under reduced pressure and the resulting residue purified by preparative HPLC (Hypersil C18, 8 μm, 25 cm; 10–60% acetonitrile-0.1M ammonium acetate over 25 min, 21 mL/min) to yield cis-N1-[4-(4-{4-amino-1-[4-(4-methylpiperazino)cyclohexyl]-1H-pyrazolo[3,4-d]pyrimidin-3-yl}phenoxy)benzyl]benzamide acetate (0.042 g, 0.000062 mol) as a white solid.

$^1$H NMR (DMSO-d$_6$, 400 MHz) δ 9.07 (t, 1H), 8.23 (s, 1H), 7.91 (d, 2H), 7.63 (d, 2H), 7.49 (m, 3H), 7.38 (t, 2H), 7.12 (d, 2H), 7.08 (d, 2H), 4.78 (m, 1H), 4.49 (d, 2H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 13.62 min. MS: MH$^+$ 617.

Example 257 cis-N1-[4-(4-{4-Amino-1-[4-(4-methylpiperazino) cyclohexyl]-1H-pyrazolo[3,4-d]pyrimidin-3-yl}phenoxy)benzyl]-1-benzenesulfonamide Acetate Cis-3-{4-[4-(aminomethyl)phenoxy]phenyl}-1-[4-(4-methylpiperazino)cyclohexyl]-1H-pyrazolo[3,4-d]pyrimidin-4-amine (0.051 g, 0.0001 mol) was dissolved in anhydrous pyridine (1 mL), benzenesulfonyl chloride (0.018 g, 0.0001 mol) was added and the resulting solution was stirred at ambient temperature for twenty hours. The solvent was removed under reduced pressure and the resulting residue purified by preparative HPLC (Hypersil C18, 8 μm, 25 cm; 10–60% acetonitrile-0.1M ammonium acetate over 25 min, 21 mL/min) to yield cis-N1-[4-(4-{4-amino-1-[4-(4-methylpiperazino)cyclohexyl]-1H-pyrazolo[3,4-d]pyrimidin-3-yl}phenoxy)benzyl]-1-benzenesulfonamide acetate (0.042 g, 0.000048 mol) as a white solid.

$^1$H NMR (DMSO-d$_6$, 400 MHz) δ 8.23 (s, 1H), 8.18 (t, 1H), 7.79 (d, 2H), 7.63 (m, 3H), 7.58 (t, 2H), 7.26 (d, 2H), 7.09 (d, 2H), 7.01 (d, 2H), 4.78 (m, 1H), 4.01 (d, 2H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 14.31 min. MS: MH$^+$ 653.

Example 258 cis-N-[4-(4-{4-Amino-1-[4-(4-methylpiperazino) cyclohexyl]-1H-pyrazolo[3,4-d]pyrimidin-3-yl}phenoxy)benzyl]-N'-benzylurea Acetate Cis-3-{4-[4-(aminomethyl)phenoxy]phenyl}-1-[4-(4-methylpiperazino)cyclohexyl]-1H-pyrazolo[3,4-d]

pyrimidin-4-amine (0.051 g, 0.0001 mol) was dissolved in anhydrous pyridine (1 mL), benzyl isocyanate (0.013 g, 0.0001 mol) was added and the resulting solution was stirred at ambient temperature for twenty hours. The solvent was removed under reduced pressure and the resulting residue purified by preparative HPLC (Hypersil C 18, 8 μm, 25 cm; 10–60% acetonitrile-0.1M ammonium acetate over 25 min, 21 mL/min) to yield cis-N-[4-(4-{4-amino-1-[4-(4-methylpiperazino)cyclohexyl]-1H-pyrazolo[3,4-d]pyrimidin-3-yl}phenoxy)benzyl]-N'-benzylurea acetate (0.019 g, 0.000027 mol) as a white solid.

$^1$H NMR (DMSO-d$_6$, 400 MHz) δ 8.23 (s, 1H), 7.63 (d, 2H), 7.27 (m, 7H), 7.13 (d, 2H), 7.09 (d, 2H), 6.46 (m, 2H), 4.78 (m, 1H), 4.24 (d, 4H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 13.49 min. MS: MH$^+$ 646.

The protocols to prepare cis-3-{4-[3-(aminomethyl)phenoxy]phenyl}-1-[4-(4-methylpiperazino)cyclohexyl]-1H-pyrazolo[3,4-d]pyrimidin-4-amine and its derivatives are identical to the ones for cis-3-{4-[4-(aminomethyl)phenoxy]phenyl}-1-[4-(4-methylpiperazino)cyclohexyl]-1H-pyrazolo[3,4-d]pyrimidin-4-amine and its derivatives.

Example 259 cis-N1-[3-(4-{4-Amino-1-[4-(4-methylpiperazino)cyclohexyl]-1H-pyrazolo[3,4-d]pyrimidin-3-yl}phenoxy)benzyl]benzamide Diacetate a) cis-3-{4-[3-(Aminomethyl)phenoxy]phenyl}-1-[4-(4-methylpiperazino)cyclohexyl]-1H-pyrazolo[3,4-d]pyrimidin-4-amine $^1$H NMR (DMSO-d$_6$, 400 MHz) δ 8.23 (s, 1H), 7.63 (d, 2H), 7.38 (m, 1H), 7.15 (m, 4H), 6.96 (d, 1H), 4.78 (m, 1H), 3.73 (s, 2H), 2.5–2.1 (br, 13H), 2.17 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 9.32 min.

b) cis-N1-[3-(4-{4-Amino-1-[4-(4-methylpiperazino)cyclohexyl]-1H-pyrazolo[3,4-d]pyrimidin-3-yl}phenoxy)benzyl]benzamide Diacetate $^1$H NMR (DMSO-d$_6$, 400 MHz) δ 9.07 (t, 1H), 8.23 (s, 1H), 7.86 (d, 2H), 7.63 (d, 2H), 7.48 (m, 4H), 7.10 (m, 5H), 4.78 (m, 1H), 4.49 (d, 2H), 2.5–2.1 (br, 13H), 2.17 (s, 3H), 1.91 (s, 6H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 13.58 min. MS: MH$^+$ 617.

Example 260 cis-N1-[3-(4-{4-Amino-1-[4-(4-methylpiperazino)cyclohexyl]-1H-pyrazolo[3,4-d]pyrimidin-3-yl}phenoxy)benzyl]-1-benzenesulfonamide Acetate $^1$H NMR (DMSO-d$_6$, 400 MHz) δ 8.23 (m, 2H), 7.78 (d, 2H), 7.62 (m, 5H), 7.31 (m, 1H), 7.04 (m, 5H), 4.78 (m, 1H), 4.03 (d, 2H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 14.36 min. MS: MH$^+$ 653.

Example 261 cis-N-[3-(4-{4-Amino-1-[4-(4-methylpiperazino)cyclohexyl]-1H-pyrazolo[3,4-d]pyrimidin-3-yl}phenoxy)benzyl]-N'-benzylurea Acetate $^1$H NMR (DMSO-d$_6$, 400 MHz) δ 8.23 (s, 1H), 7.63 (d, 2H), 7.35 (t, 1H), 7.27–7.04 (m, 10H), 6.46 (m, 2H), 4.78 (m, 1H), 4.25 (d, 2H), 4.22 (d, 2H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 13.44 min. MS: MH$^+$ 646.

Example 262 and Example 263 cis-3-(4-{4-Amino-1-[4-(4-methylpiperazino)cyclohexyl]-1H-pyrazolo[3,4-d]pyrimidin-3-yl}phenyl)-5-phenyl-1,3-oxazolan-2-one Acetate
trans-3-(4-{4-Amino-1-[4-(4-methylpiperazino)cyclohexyl]-1H-pyrazolo[3,4-d]pyrimidin-3-yl}phenyl)-5-phenyl-1,3-oxazolan-2-one a) 2-(4-Bromoanilino)-1-phenyl-1-ethanone To a solution containing 4-bromoaniline (7.42 g, 0.0431 mol) and 2-bromoacetophenone (8.58 g, 0.0431 mol) in N,N-dimethylformamide (200 mL) N,N-diisopropylethylamine was added dropwise and the reaction mixture was stirred at ambient temperature for five hours. The solvent was removed under reduced pressure and the residue partitioned between dichloromethane (150 mL) and water (100 mL). The organic phase was dried with magnesium sulfate and concentrated under reduced pressure. The residue was suspended in diethyl ether and the precipitate was collected by filtration and dried to yield 2-(4-bromoanilino)-1-phenyl-1-ethanone (10.03 g, 0.0346 mol) as an off-white solid.

$^1$H NMR (DMSO-d$_6$, 400 MHz) δ 8.06 (d, 2H), 7.69 (t, 1H), 7.58 (m, 2H), 7.20 (d, 2H), 6.66 (d, 2H), 6.11 (t, 1H), 4.68 (d, 2H). TLC (ethyl acetate/heptane 1:2) R$_f$ 0.39.

b) 2-(4-Bromoanilino)-1-phenyl-1-ethanol

A solution of 2-(4-bromoanilino)-1-phenyl-1-ethanone (3.50 g, 0.0121 mol) in anhydrous methanol (200 mL) was cooled to 0° C. and sodium borohydride (2.28 g, 0.0603 mol) was added at once. The mixture was allowed to warm up to ambient temperature while stirring under an atmosphere of nitrogen for three hours. The reaction was quenched by dropwise addition of acetic acid, the reaction mixture was concentrated under reduced pressure and the residue was partitioned between dichloromethane (120 mL) and water (85 mL). The organic phase was dried with magnesium sulfate and concentrated under reduced pressure to yield 2-(4-bromoanilino)-1-phenyl-1-ethanol (3.49 g, 0.0117 mol) as a yellow oil.

$^1$H NMR (DMSO-d$_6$, 400 MHz) δ 7.39 (d, 2H), 7.33 (m, 2H), 7.24 (t, 1H), 7.17 (d, 2H), 5.81 (t, 1H), 5.47 (d, 1H), 4.71 (m, 1H), 3.18 (m, 1H), 3.07 (m, 1H). TLC (ethyl acetate/heptane 1:2) R$_f$ 0.22.

c) 3-(4-Bromophenyl)-5-phenyl-1,3-oxazolan-2-one

A solution containing 2-(4-bromoanilino)-1-phenyl-1-ethanol (0.74 g, 0.00253 mol), N,N-diisopropylethylamine (1.01 g, 0.00786 mol) and N,N-dimethylaminopyridine (0.092 g, 0.00076 mol) in anhydrous dichloromethane (32 mL) was cooled to 0° C. and a solution of triphosgene (0.38 g, 0.00127 mol) in anhydrous dichloromethane (8 mL) was added dropwise. The reaction mixture was slowly warmed up to ambient temperature while stirring under an atmosphere of nitrogen for eighteen hours. The organic phase was washed with a saturated solution of sodium bicarbonate in water (40 mL), brine (30 mL) and dried with magnesium sulfate. The solvent was removed under reduced pressure and the residue purified by flash chromatography on silica using ethyl acetate/n-heptane (1:5) as mobile phase to yield 3-(4-bromophenyl)-5-phenyl-1,3-oxazolan-2-one (0.62 g, 0.00192 mol) as a white solid.

$^1$H NMR (DMSO-d$_6$, 400 MHz) δ 7.58 (s, 4H), 7.47 (m, 5H), 5.77 (m, 1H), 4.46 (t, 1H), 4.01 (t, 1H). TLC (ethyl acetate/heptane 1:2) R$_f$ 0.28.

d) 5-Phenyl-3-[4-(4,4,5,5-tetramethyl-1,3,2-dioxaborolan-2-yl)phenyl]-1,3-oxazolan-2-one A mixture of 3-(4-bromophenyl)-5-phenyl-1,3-oxazolan-2-one (0.6 g, 0.00189 mol), diboron pinacol ester (0.58 g, 0.00226 mol), [1.1'-bis(diphenylphosphino)ferrocene]-dichloropalladium (II) complex with dichloromethane (1:1) (0.046 g, 0.000057 mol) and potassium acetate (0.56 g, 0.0057 mol) in N,N-dimethylformamide (20 mL) was heated at 80° C. under an atmosphere of nitrogen for sixteen hours. The mixture was allowed to cool to ambient temperature and the solvent removed under reduced pressure. Dichloromethane (100 mL) was added to the residue and the resulting solid was removed by filtration through a pad of Celite. The filtrate was concentrated to leave a yellow oil which was purified by flash chromatography on silica using ethyl acetate/n-heptane (1:5) as mobile phase. The resulting fractions were concentrated, the residue was triturated in n-heptane and the precipitate collected by filtration to yield 5-phenyl-3-[4-(4,4,5,5-tetramethyl-1,3,2-dioxaborolan-2-yl)phenyl]-1,3-oxazolan-2-one (0.19 g, 0.00052 mol) as a white solid.

$^1$H NMR (DMSO-$d_6$, 400 MHz) δ 7.69 (d, 2H), 7.62 (d, 2H), 7.47 (m, 5H), 5.77 (m, 1H), 4.46 (t, 1H), 4.01 (t, 1H), 1.27 (s, 12H). TLC (ethyl acetate/heptane 1:2) $R_f$ 0.19.

e) cis-3-(4-{4-Amino-1-[4-(4-methylpiperazino)cyclohexyl]-1H-pyrazolo[3,4-d]pyrimidin-3-yl}phenyl)-5-phenyl-1,3-oxazolan-2-one Acetate A mixture of 5-phenyl-3-[4-(4,4,5,5-tetramethyl-1,3,2-dioxaborolan-2-yl)phenyl]-1,3-oxazolan-2-one (0.085 g, 0.000233 mol), cis-3-iodo-1-[4-(4-methylpiperazino)-cyclohexyl]-1H-pyrazolo[3,4-d]pyrimidin-4-amine (0.086 g, 0.000194 mol), tetrakis-(triphenylphosphine)palladium (0.013 g, 0.000012 mol) and sodium carbonate monohydrate (0.060 g, 0.000485 mol) was heated in a mixture of ethylene glycol dimethyl ether (5 mL) and water (3 mL) at 80° C. for sixteen hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1 M ammonium acetate over 25 min, 21 mL/min) to yield cis-3-(4-{4-amino-1-[4-(4-methylpiperazino)cyclohexyl]-1H-pyrazolo[3,4-d]pyrimidin-3-yl}phenyl)-5-phenyl-1,3-oxazolan-2-one acetate (0.074 g, 0.000121 mol) as a white solid.

$^1$H NMR (DMSO-$d_6$, 400 MHz) δ 8.23 (s, 1H), 7.79 (d, 2H), 7.68 (d, 2H), 7.47 (m, 5H), 5.82 (t, 1H), 4.78 (m, 1H), 4.57 (t, 1H), 4.09 (t, 1H), 2.5–2.1 (br, 13H), 2.17 (s, 3H), 1.91 (s, 3H), 1.68 (m, 2H), 1.58 (m, 2H), RP-HPLC (Delta Pak C18, 5 μm, 300 A, 15 cm; 5%–85% acetonitrile-0.1 M ammonium acetate over 20 min, 1 mL/min) $R_t$ 12.84 min. MS: MH$^+$ 553.

f) trans-3-(4-{4-Amino-1-[4-(4-methylpiperazino)cyclohexyl]-1H-pyrazolo[3,4-d]pyrimidin-3-yl}phenyl)-5-phenyl-1,3-oxazolan-2-one The compound was prepared via synthetic route similar to the one for the preparation of cis-3-(4-{4-amino-1-[4-(4-methylpiperazino)cyclohexyl]-1H-pyrazolo[3,4-d]pyrimidin-3-yl}phenyl)-5-phenyl-1,3-oxazolan-2-one acetate.

$^1$H NMR (DMSO-$d_6$, 400 MHz) δ 8.23 (s, 1H), 7.79 (d, 2H), 7.68 (d, 2H), 7.47 (m, 5H), 5.82 (t, 1H), 4.64 (m, 1H), 4.57 (t, 1H), 4.09 (t, 1H), 3.1 (br, 9H), 2.17 (s, 3H), 2.05 (m, 6H), 1.49 (m, 2H); RP-HPLC (Delta Pak C18, 5 μm, 300 A, 15 cm; 5%–85% acetonitrile-0.1M ammonium acetate over 20 min, 1 mL/min) $R_t$ 12.72 min. MS: MH$^+$ 553.

Example 264 trans-3-(4-{4-Amino-1-[4-(4-methylpiperazino)cyclohexyl]-1H-pyrazolo[3,4-d]pyrimidin-3-yl}phenyl)-5-benzyl-1,3-oxazolan-2-one Diacetate a) 1-(4-Bromoanilino)-3-phenyl-2-propanol A mixture of 4-bromoaniline (1.75 g, 0.0102 mol) and 2,3-epoxy-propylbenzene (1.77 g, 0.0132 mol) in methanol (40 mL) was heated at reflux for 16 hours. The mixture was cooled to ambient temperature and concentrated under reduced pressure. The residue was purified by flash chromatography on silica using ethyl acetate/n-heptane (1:5) as mobile phase to yield 1-(4-bromoanilino)-3-phenyl-2-propanol (2.2 g, 0.00719 mol) as a colorless oil.

$^1$H NMR (DMSO-$d_6$, 400 MHz) δ 7.33 (m, 7H), 6.50 (d, 2H), 5.76 (t, 1H), 4.83 (d, 1H), 3.82 (m, 1H), 2.98 (m, 1H), 2.90 (m, 1H), 2.78 (dd, 1H), 2.67 (dd, 1H). TLC (ethyl acetate/heptane 1:3) $R_f$ 0.29.

b) 5-Benzyl-3-(4-bromophenyl)-1,3-oxazolan-2-one

A solution containing 1-(4-bromoanilino)-3-phenyl-2-propanol (1.90 g, 0.00621 mol), N,N-diisopropylethylamine (2.48 g, 0.0193 mol) and N,N-dimethylaminopyridine (0.152 g, 0.00124 mol) in anhydrous dichloromethane (64 mL) was cooled to 0° C. and the solution of triphosgene (0.92 g, 0.0031 mol) in anhydrous dichloromethane (16 mL) was added dropwise. The reaction mixture was slowly warmed up to ambient temperature while stirring under an atmosphere of nitrogen for 18 hours. The organic phase was washed with saturated solution of sodium bicarbonate in water (70 mL), brine (60 mL) and dried with magnesium sulfate. The solvent was removed under reduced pressure and the residue purified by flash chromatography on silica using ethyl acetate/n-heptane (1:5) as mobile phase to yield 5-benzyl-3-(4-bromophenyl)-1,3-oxazolan-2-one (1.25 g, 0.00377 mol) as a white solid.

$^1$H NMR (DMSO-$d_6$, 400 MHz) δ 7.54 (d, 2H), 7.47 (d, 2H), 7.27 (m, 5H), 4.95 (m, 1H), 4.12 (t, 1H), 3.78 (t, 1H), 3.07 (d, 2H). TLC (ethyl acetate/heptane 1:3) $R_f$ 0.37.

c) 5-Benzyl-3-[4-(4,4,5,5-tetramethyl-1,3,2-dioxaborolan-2-yl)phenyl]-1,3-oxazolan-2-one A mixture of 5-benzyl-3-(4-bromophenyl)-1,3-oxazolan-2-one (1.25 g, 0.00377 mol), diboron pinacol ester (1.15 g, 0.00452 mol), [1.1'-bis(diphenylphosphino)ferrocene]-dichloropalladium (II) complex with dichloromethane (1:1) (0.092 g, 0.000114 mol) and potassium acetate (1.12 g, 0.0113 mol) in N,N-dimethylformamide (30 mL) was heated at 80° C. under an atmosphere of nitrogen for 16 hours. The mixture was allowed to cool to ambient temperature and the solvent removed under reduced pressure. Dichloromethane (100 mL) was added to the residue and the resulting solid was removed by filtration through a pad of Celite. The filtrate was concentrated to leave a yellow oil which was purified by flash chromatography on silica using ethyl acetate/n-heptane (1:5) as mobile phase. The resulting fractions were concentrated, the residue was triturated in n-heptane and the precipitate collected by filtration to yield 5-benzyl-3-[4-(4,4,5,5-tetramethyl-1,3,2-dioxaborolan-2-yl)phenyl]-1,3-oxazolan-2-one (1.03 g, 0.0027 mol) as a white solid.

$^1$H NMR (DMSO-$d_6$, 400 MHz) δ 7.65 (d, 2H), 7.54 (d, 2H), 7.27 (m, 5H), 4.95 (m, 1H), 4.12 (t, 1H), 3.78 (t, 1H), 3.07 (d, 2H), 1.28 (s, 12H). TLC (ethyl acetate/heptane 1:3) $R_f$ 0.25.

d) trans-3-(4-{4-Amino-1-[4-(4-methylpiperazino)cyclohexyl]-1H-pyrazolo[3,4-d]pyrimidin-3-yl}phenyl)-5-benzyl-1,3-oxazolan-2-one Diacetate A mixture of 5-benzyl-3-[4-(4,4,5,5-tetramethyl-1,3,2-dioxaborolan-2-yl)phenyl]-1,3-oxazolan-2-one (0.110 g, 0.00029 mol), trans-3-iodo-1-[4-(4-methylpiperazino)-cyclohexyl]-1H-pyrazolo[3,4-d]pyrimidin-4-amine (0.080 g, 0.000181 mol), tetrakis-(triphenylphosphine)palladium (0.012 g, 0.000011 mol) and sodium carbonate monohydrate (0.056 g, 0.00045 mol) was heated in a mixture of ethylene glycol dimethyl ether (5 mL) and water (3 mL) at 80° C. for sixteen hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield trans-3-(4-{4-amino-1-[4-(4-methylpiperazino)cyclohexyl]-1H-pyrazolo[3,4-d]pyrimidin-3-yl}phenyl)-5-benzyl-1,3-oxazolan-2-one diacetate (0.049 g, 0.000072 mol) as a white solid.

$^1$H NMR (DMSO-d$_6$, 400 MHz) δ 8.23 (s, 1H), 7.65 (m, 4H), 7.32 (m, 5H), 5.02 (m, 1H), 4.64 (m, 1H), 4.19 (t, 1H), 3.85 (t, 1H), 3.11 (d, 2H), 3.1 (br, 9H), 2.17 (s, 6H), 2.05 (m, 6H), 1.91 (s, 6H), 1.49 (m, 2H); RP-HPLC (Delta Pak C18, 5 μm, 300 A, 15 cm; 5%–85% acetonitrile-0.1 M ammonium acetate over 20 min, 1 mL/min) R$_t$ 13.13 min. MS: MH$^+$ 567.

Example 265 cis-N1-(4-{4-Amino-1-[4-(4-methylpiperazino)cyclohexyl]-1H-pyrazolo[3,4-d]pyrimidin-3-yl}phenyl)-2-methyl-2-phenylpropanamide Diacetate A solution containing cis-3-(4-aminophenyl)-1-[4-(4-methylpiperazino)cyclohexyl]-1H-pyrazolo[3,4-d]pyrimidin-4-amine (0.1 g, 0.000246 mol), α,α-dimethylphenylacetic acid (0.045 g, 0.000271 mol), 1-(3-dimethylaminopropyl)-3-ethylcarbodiimide hydrochloride (0.071 g, 0.000369 mol) and 1-hydroxy-7-azabenzotriazole (0.0037 g, 0.000271 mol) in anhydrous N,N-Dimethylformamide (5 mL) was stirred for 5 min., N,N-diisopropylethylamine (0.098 g, 0.00076 mol) was added dropwise and stirring under an atmosphere of nitrogen was continued for 16 hours. The reaction mixture was concentrated under reduced pressure and the residue was purified by preparative HPLC (Hypersil C18, 8 μm, 25 cm; 10–60% acetonitrile-0.1M ammonium acetate over 25 min, 21 mL/min) to yield cis-N1-(4-{4-amino-1-[4-(4-methylpiperazino)cyclohexyl]-1H-pyrazolo[3,4-d]pyrimidin-3-yl}phenyl)-2-methyl-2-phenylpropanamide diacetate (0.014 g, 0.000021 mol) as a white solid.

$^1$H NMR (DMSO-d$_6$, 400 MHz) δ 9.29 (s, 1H), 8.20 (s, 1H), 7.82 (d, 2H), 7.55 (d, 2H), 7.38 (m, 4H), 7.27 (m, 1H), 4.78 (m, 1H), 2.5–2.1 (br, 13H), 2.17 (s, 3H), 1.91 (s, 6H), 1.68 (m, 2H), 1.59 (s, 6H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 13.59 min. MS: MH$^+$ 553.

Example 266 and Example 267 cis-4-(4-{4-Amino-1-[4-(4-methylpiperazino)cyclohexyl]-1H-pyrazolo[3,4-d]pyrimidin-3-yl}anilino)-4-oxo-2-phenylbutanoic Acid Acetate
cis-4-(4-{4-Amino-1-[4-(4-methylpiperazino)cyclohexyl]-1H-pyrazolo[3,4-d]pyrimidin-3-yl}anilino)-4-oxo-3-phenylbutanoic Acid Acetate a) 1-(4-Bromophenyl)-3-phenyl-2,5-pyrrolidinedione A solution of 4-bromoaniline (5.48 g, 0.0318 mol) and phenylsuccinic anhydride (5.89 g, 0.0334 mol) in anhydrous benzene (80 mL) was heated at reflux for one and a half hours. The mixture was cooled to ambient temperature and concentrated under reduced pressure. To the residue, acetyl chloride (60 mL) was added and the solution was heated at reflux for one and a half hours. The reaction mixture was cooled to ambient temperature and the precipitate collected by filtration, washed with diethyl ether and dried to yield 1-(4-bromophenyl)-3-phenyl-2,5-pyrrolidinedione (8.7 g, 0.0264 mol) as an off-white solid.

$^1$H NMR (DMSO-d$_6$, 400 MHz) δ 7.72 (d, 2H), 7.40 (m, 7H), 4.33 (dd, 1H), 3.33 (dd, 1H), 2.94 (dd, 1H); TLC (ethyl acetate/heptane 1:4) R$_f$ 0.34.

b) 3-Phenyl-1-[4-(4,4,5,5-tetramethyl-1,3,2-dioxaborolan-2-yl)phenyl]-2,5-pyrrolidinedione A mixture of 1-(4-bromophenyl)-3-phenyl-2,5-pyrrolidinedione (2.00 g, 0.00602 mol), diboron pinacol ester (1.85 g, 0.00727 mol), [1.1'-bis(diphenylphosphino)ferrocene]-dichloropalladium (II) complex with dichloromethane (1:1) (0.148 g, 0.000182 mol) and potassium acetate (1.784 g, 0.0182 mol) in N,N-dimethylformamide (40 mL) was heated at 80° C. under an atmosphere of nitrogen for sixteen hours. The mixture was allowed to cool to ambient temperature and the solvent removed under reduced pressure. Dichloromethane (100 mL) was added to the residue and the resulting solid was removed by filtration through a pad of Celite. The filtrate was concentrated to leave a yellow oil which was purified by flash chromatography on silica using ethyl acetate/n-heptane (1:4) as mobile phase. The resulting fractions were concentrated, the residue was triturated in n-heptane and the precipitate collected by filtration to yield 3-phenyl-1-[4-(4,4,5,5-tetramethyl-1,3,2-dioxaborolan-2-yl)phenyl]-2,5-pyrrolidinedione (0.78 g, 0.00207 mol) as a white solid.

$^1$H NMR (DMSO-d$_6$, 400 MHz) δ 7.79 (d, 2H), 7.40 (m, 7H), 4.33 (dd, 1H), 3.33 (dd, 1H), 2.97 (dd, 1H), 1.31 (s, 12H); TLC (ethyl acetate/heptane 1:4) R$_f$ 0.21.

c) cis-4-(4-(4-Amino-1-[4-(4-methylpiperazino)cyclohexyl]-1H-pyrazolo[3,4-d]pyrimidin-3-yl}anilino)-4-oxo-2-phenylbutanoic Acid Acetate and cis-4-(4-{4-Amino-1-[4-(4-methylpiperazino)cyclohexyl]-1H-pyrazolo[3,4-d]pyrimidin-3-yl}anilino)-4-oxo-3-phenylbutanoic Acid Acetate A mixture of 3-phenyl-1-[4-(4,4,5,5-tetramethyl-1,3,2-dioxaborolan-2-yl)phenyl]-2,5-pyrrolidinedione (0.35 g, 0.00093 mol), cis-3-iodo-1-[4-(4-methylpiperazino)-cyclohexyl]-1H-pyrazolo[3,4-d]pyrimidin-4-amine (0.34 g, 0.000773 mol), tetrakis-(triphenylphosphine)palladium (0.053 g, 0.000046 mol) and sodium carbonate monohydrate (0.24 g, 0.00193 mol) was heated in a mixture of ethylene glycol dimethyl ether (14 mL) and water (7 mL) at 80° C. for sixteen hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield cis-4-(4-{4-amino-1-[4-(4-methylpiperazino)cyclohexyl]-1H-pyrazolo[3,4-d]pyrimidin-3-yl}anilino)-4-oxo-2-phenylbutanoic acid acetate (0.150 g, 0.000233 mol) and cis-4-(4-{4-amino-1-[4-(4-methylpiperazino)cyclohexyl]-1H-pyrazolo[3,4-d]pyrimidin-3-yl}anilino)-4-oxo-3-phenylbutanoic acid acetate (0.11 g, 0.000171 mol) both as white solids.

cis-4-(4-{4-Amino-1-[4-(4-methylpiperazino)cyclohexyl]-1H-pyrazolo[3,4-d]pyrimidin-3-yl}anilino)-4-oxo-2-phenylbutanoic Acid Acetate $^1$H NMR (DMSO-d$_6$, 400 MHz) δ 10.37 (s, 1H), 8.21 (s, 1H), 7.73 (d, 2H), 7.55 (d, 2H), 7.25 (m, 5H), 4.76 (m, 1H), 4.00 (m, 1H), 3.12 (dd, 1H), 2.71 (dd, 1H), 2.5–2.1 (br, 13H), 2.17 (s, 3H), 1.91 (s, 3H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 10.54 min. MS: MH$^+$ 583.

cis-4-(4-{4-Amino-1-[4-(4-methylpiperazino)cyclohexyl]-1H-pyrazolo[3,4-d]pyrimidin-3-yl}anilino)-4-oxo-3-phenylbutanoic Acid Acetate $^1$H NMR (DMSO-d$_6$, 400 MHz) δ 10.46 (s, 1H), 8.21 (s, 1H), 7.78 (d, 2H), 7.54 (d, 2H), 7.41 (d, 5H), 7.31 (t, 2H), 7.24 (t, 1H), 4.76 (m, 1H), 4.16 (m, 1H), 3.08 (dd, 1H), 2.51 (dd, 1H), 2.5–2.1 (br, 13H), 2.17 (s, 3H), 1.91 (s, 3H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 11.11 min. MS: MH$^+$ 583.

Example 268 cis-(4-{4-Amino-1-[4-(4-methylpiperazino)cyclohexyl]-1H-pyrazolo[3,4-d]pyrimidin-3-yl}phenyl)(phenyl)methyl Cyanide a) 2-Phenyl-2-[4-(4,4,5,5-Tetramethyl-1,3,2-dioxaborolan-2-yl)phenyl]acetonitrile A mixture of (4-bromophenyl)(phenyl)methyl cyanide (0.604 g, 0.00222 mol), diboron pinacol ester (0.677 g, 0.00266 mol), [1.1'-bis(diphenylphosphino)ferrocene]-dichloropalladium (II) complex with dichloromethane (1:1) (0.054 g, 0.000067 mol) and potassium acetate (0.52 g, 0.00666 mol) in N,N-dimethylformamide (30 mL) was heated at 80° C. under an atmosphere of nitrogen for 16 hours. The mixture was allowed to cool to ambient temperature and the solvent removed under reduced pressure. Dichloromethane (80 mL) was added to the residue and the resulting solid was removed by filtration through a pad of Celite. The filtrate was concentrated to leave a yellow oil which was purified by flash chromatography on silica using ethyl acetate/n-heptane (1:9) as mobile phase. The resulting fractions were concentrated, the residue was triturated in n-heptane and the precipitate collected by filtration to yield 2-phenyl-2-[4-(4,4,5,5-tetramethyl-1,3,2-dioxaborolan-2-yl)phenyl]acetonitrile (0.110 g, 0.000345 mol) as a white solid.

$^1$H NMR (DMSO-d$_6$, 400 MHz) δ 7.67 (d, 2H), 7.40 (m, 7H), 5.87 (s, 1H), 1.31 (s, 12H); TLC (ethyl acetate/heptane 1:9) R$_f$ 0.18.

b) cis-(4-{4-Amino-1-[4-(4-methylpiperazino)cyclohexyl]-1H-pyrazolo[3,4-d]pyrimidin-3-yl}phenyl)(phenyl)methyl Cyanide A mixture of 2-phenyl-2-[4-(4,4,5,5-tetramethyl-1,3,2-dioxaborolan-2-yl)phenyl]acetonitrile (0.120 g, 0.000376 mol), cis-3-iodo-1-[4-(4-methylpiperazino)-cyclohexyl]-1H-pyrazolo[3,4-d]pyrimidin-4-amine (0.083 g, 0.000188 mol), tetrakis-(triphenylphosphine)palladium (0.013 g, 0.000011 mol) and sodium carbonate monohydrate (0.058 g, 0.00047 mol) was heated in a mixture of ethylene glycol dimethyl ether (5 mL) and water (3 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield cis-(4-{4-amino-1-[4-(4-methylpiperazino)cyclohexyl]-1H-pyrazolo[3,4-d]pyrimidin-3-yl}phenyl)(phenyl)methyl cyanide (0.025 g, 0.0000494 mol) as an off-white solid.

$^1$H NMR (DMSO-d$_6$, 400 MHz) δ 8.23 (s, 1H), 7.70 (d, 2H), 7.58 (d, 2H), 7.47 (m, 4H), 7.38 (t, 1H), 5.93 (s, 1H), 4.76 (m, 1H), 2.5–2.1 (br, 13H), 2.17 (s, 3H), 1.68 (m, 2H), 1.58 (m, 2H); RP-HPLC (Delta Pak C18, 5 μm, 300 A, 15 cm; 5%–85% acetonitrile-0.1M ammonium acetate over 20 min, 1 mL/min) R$_t$ 12.95 min. MS: MH$^+$ 507.

Example 269 cis-N2-(4-{4-Amino-1-[4-(4-methylpiperazino)cyclohexyl]-1H-pyrazolo[3,4-d]pyrimidin-3-yl}phenyl)-1,3-benzoxazol-2-amine Diacetate a) N-(1,3-Benzoxazol-2-yl)-N-(4-bromophenyl)amine 4-Bromoaniline (3.9 g, 0.0227 mol) was added to a solution of 2-chlorobenzoxazole (1.16 g, 0.00755 mol) in xylenes and the reaction mixture was heated at 100° C. for 2 hours. It was cooled to ambient temperature and concentrated under reduced pressure. The residue was partitioned between ethyl acetate (50 mL) and water (50 mL), the organic phase was dried with magnesium sulfate and concentrated under reduced pressure. The residue was triturated in n-heptane and the precipitate collected by filtration and dried to yield N-(1,3-benzoxazol-2-yl)-N-(4-bromophenyl)amine (1.48 g, 0.00512 mol) as a white solid.

$^1$H NMR (DMSO-d$_6$, 400 MHz) δ 10.78 (s, 1H), 7.74 (d, 2H), 7.57 (d, 2H), 7.50 (m, 2H), 7.23 (t, 1H), 7.16 (t, 1H). TLC (ethyl acetate/heptane 1:3) R$_f$ 0.34.

b) N-(1,3-Benzoxazol-2-yl)-N-[4-(4,4,5,5-tetramethyl-1,3,2-dioxaborolan-2-yl)phenyl]amine A mixture of N-(1,3-benzoxazol-2-yl)-N-(4-bromophenyl)amine (0.800 g, 0.00277 mol), diboron pinacol ester (0.84 g, 0.00332 mol), [1.1'-bis(diphenylphosphino)ferrocene]-dichloropalladium (II) complex with dichloromethane (1:1) (0.068 g, 0.000083 mol) and potassium acetate (0.81 g, 0.0083 mol) in N,N-dimethylformamide (20 mL) was heated at 80° C. under an atmosphere of nitrogen for sixteen hours. The mixture was allowed to cool to ambient temperature and the solvent removed under reduced pressure. Dichloromethane (100 mL) was added to the residue and the resulting solid was removed by filtration through a pad of Celite. The filtrate was concentrated to leave a yellow oil which was purified by flash chromatography on silica using ethyl acetate/n-heptane (1:5) as mobile phase. The resulting fractions were concentrated, the residue was triturated in n-heptane and the precipitate collected by filtration to yield N-(1,3-benzoxazol-2-yl)-N-[4-(4,4,5,5-tetramethyl-1,3,2-dioxaborolan-2-yl)phenyl]amine (0.59 g, 0.00176 mol) as a white solid.

$^1$H NMR (DMSO-d$_6$, 400 MHz) δ 10.80 (s, 1H), 7.78 (d, 2H), 7.68 (d, 2H), 7.50 (d, 2H), 7.23 (t, 1H), 7.16 (t, 1H), 1.26 (s, 12H) TLC (ethyl acetate/heptane 1:3) R$_f$ 0.29.

c) cis-N2-(4-{4-Amino-1-[4-(4-methylpiperazino)cyclohexyl]-1H-pyrazolo[3,4-d]pyrimidin-3-yl}phenyl)-1,3-benzoxazol-2-amine Diacetate A mixture of N-(1,3-benzoxazol-2-yl)-N-[4-(4,4,5,5-tetramethyl-1,3,2-dioxaborolan-2-yl)phenyl]amine (0.073 g, 0.000217 mol), cis-3-iodo-1-[4-(4-methylpiperazino)-cyclohexyl]-1H-pyrazolo[3,4-d]pyrimidin-4-amine (0.080 g, 0.000181 mol), tetrakis-(triphenylphosphine)palladium (0.012 g, 0.000011 mol) and sodium carbonate monohydrate (0.056 g, 0.000453 mol) was heated in a mixture of ethylene glycol dimethyl ether (5 mL) and water (3 mL) at 80° C. for sixteen hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1 M ammonium acetate over 25 min, 21 mL/min) to yield cis-N2-(4-4-amino-1-[4-(4-methylpiperazino)cyclohexyl]-1H-pyrazolo[3,4-d]pyrimidin-3-ylphenyl)-1,3-benzoxazol-2-amine diacetate (0.082 g, 0.000128 mol) as a white solid.

$^1$H NMR (DMSO-d$_6$, 400 MHz) δ 8.23 (s, 1H), 7.95 (d, 2H), 7.66 (d, 2H), 7.51 (m, 2H), 7.25 (t, 1H), 7.15 (t, 1H), 4.78 (m, 1H), 2.5–2.1 (br, 13H), 2.17 (s, 3H), 1.91 (s, 6H), 1.68 (m, 2H), 1.58 (m, 2H), RP-HPLC (Delta Pak C18, 5 μm, 300 A, 15 cm; 5%–85% acetonitrile-0.1M ammonium acetate over 20 min, 1 mL/min) R$_t$ 12.80 min. MS: MH$^+$ 524.

Intermediate A: 2-[4-(4,4,5,5-Tetramethyl-1,3,2-dioxaborolan-2-yl)phenoxy]benzaldehyde A mixture of 2-(4-iodophenoxy)benzaldehyde (1.31 g, 4.03 mmol, 1 equiv), PdCl$_2$(dppf)$_2$ (0.092 g, 0.13 mmol, 0.03 equiv), diboronpinacol ester (1.23 g, 4.84 mmol, 1.2 equiv), and potassium acetate (1.19 g, 12.1 mmol, 3.0 equiv) in DMF (15 mL) was heated at 80° C. for 5.5 h. The reaction mixture was allowed to cool to ambient temperature and the solvent was removed under reduced pressure. The residue was dissolved in CH$_2$Cl$_2$ (50 mL) and the resulting solid was removed by filtration through a pad of Celite with the aid of CH$_2$Cl$_2$ (100 mL) and Et$_2$O (100 mL). The filtrate was concentrated to afford a brown oil which was purified by column chromatography on silica gel (elution with 500 mL of 5% MeOH/CH$_2$Cl$_2$) to afford 2-[4-(4,4,5,5-tetramethyl-1,3,2-dioxaborolan-2-yl)phenoxy]benzaldehyde as a red-brown oil (0.875 g, 2.70 mmol): $^1$H NMR (d$_6$ DMSO, 400 MHz): δ H 10.30 (1H, s), 7.87–7.89 (1H, m), 7.69–7.75 (3H, m), 7.36–7.38 (1H, m), 7.05–7.22 (3H, m), and 1.29 (12H, s).

Example 270

2-[4-(4-Amino-1-cyclopentyl-1H-pyrazolo[3,4-d]pyrimidin-3-yl)phenoxy]acetamide

A mixture of 4-(4-amino-1-cyclopentyl-1H-pyrazolo[3,4-d]pyrimidin-3-yl)phenol (0.050 g, 0.17 mmol, 1.0 equiv), dioxane (1.7 mL), and sodium hydride (60%, 0.010 g, 0.17 mmol, 1.0 equiv) was stirred at ambient temperature for 10 minutes. Iodoacetamine (0.031 g, 0.17 mmol, 1.0 equiv) was added. The reaction mixture was stirred at ambient temperature for 30 minutes and then heated at 110° C. for 3.5 h. The mixture was allowed to cool to ambient temperature and the resulting solid was removed by filtration with the aid of CH$_2$Cl$_2$ (5 mL) and EtOAc (5 mL). The solvent was removed under reduced pressure to afford a yellow solid which was triturated from EtOAc to afford 2-[(4-amino-1-cyclopentyl-1H-pyrazolo[3,4-d]pyrimidin-3-yl)oxy]acetamide as a beige solid (0.045 g, 0.13 mmol): $^1$H NMR (d$_6$ DMSO, 400 MHz): δ H 8.22 (1H, s), 7.60 (2H, d), 7.12 (2H, d), 5.20–5.25 (1H, m), 4.50 (2H, s), 2.02–2.10 (4H, m), 1.87–1.90 (2H, m), 1.68–1.71 (2H, m); RP-HPLC (Delta Pak C18, 5 μm, 300 Å Å, 15 cm; 5%–85% acetonitrile-0.1M ammonium acetate over 20 min, 1 mL/min) R$_t$ 12.38 min. MS: MH$^+$ 353.

Example 271

Methyl 5-[4-(4-Amino-1-cyclopentyl-1H-pyrazolo[3,4-d]pyrimidin-3-yl)phenoxy]-2-furoate A mixture of 4-(4-amino-1-cyclopentyl-1H-pyrazolo[3,4-d]pyrimidin-3-yl)phenol (0.107 g, 0.362 mmol, 1.0 equiv), DMSO (0.5 mL), sodium hydride (60%, 0.030 g, 0.72 mmol, 2.0 equiv), and methyl-5-nitro-2-furoate (0.062 g, 0.36 mmol, 1.0 equiv) was heated at 90° C. for 3 h. The reaction mixture was allowed to cool to room temperature, poured into ice water (10 mL), and extracted with three portions of CH$_2$Cl$_2$ (50 mL each). The combined organic extracts were washed with 5% aqueous KOH (50 mL) and the organic layer was dried over MgSO$_4$, filtered, and concentrated to afford a red oil which was purified by column chromatography on silica gel (elution with 300 mL of 5% MeOH/CH$_2$Cl$_2$) to afford methyl 5-[4-(4-amino-1-cyclopentyl-1H-pyrazolo[3,4-d]pyrimidin-3-yl)phenoxy]-2-furoate as a red solid (0.070 g, 0.17 mmol):
$^1$H NMR (d$_6$ DMSO, 400 MHz): δ H 8.24 (1H, s), 7.70–7.74 (2H, m), 7.35–7.39 (3H, m), 6.9 (2H, bs), 6.02 (1H, s), 5.22–5.26 (1H, m), 3.79 (3H, s), 2.01–2.11 (4H, m), 1.88–1.91 (2H, m), 1.67–1.71 (2H, m). RP-HPLC (Delta Pak C18, 5 μm, 300 Å, 15 cm; 5%–85% acetonitrile-0.1M ammonium acetate over 20 min, 1 mL/min) R$_t$ 18.17 min. MS: MH$^+$ 420.

Example 272

5-[4-(4-Amino-1-cyclopentyl-1H-pyrazolo[3,4-d]pyrimidin-3-yl)phenoxy]-2-furoic Acid A mixture of methyl 5-[4-(4-amino-1-cyclopentyl-1H-pyrazolo[3,4-d]pyrimidin-3-yl)phenoxy]-2-furoate (0.030 g, 0.072 mmol, 1 equiv) and sodium hydroxide (0.020 g, 0.50 mmol, 7 equiv) in 50% EtOH:water (1 mL) was heated at 80° C. for 6 h. The reaction mixture was allowed to cool to ambient temperature and diluted with water (10 mL). The mixture was neutralized by the addition of 1 M HCl and extracted with two portions of CH$_2$Cl$_2$ (20 mL each) and two portions of EtOAc (20 mL each). The combined organic extracts were dried over MgSO$_4$, filtered, and concentrated to afford a yellow oil which was purified by preparative RP-HPLC (Rainin C18, 8 μm, 300 Å, 25 cm; 50%–100% acetonitrile-0.1M ammonium acetate over 20 min, 21 mL/min). The acetonitrile was removed in vacuo and the aqueous mixture was lyopholyzed to give a light brown solid (0.009 g, 0.022 mmol): $^1$H NMR (d$_6$ DMSO, 400 MHz): δ H 13.0 (1H, bs), 8.23 (1H, s), 7.74 (2H, d), 7.35 (2H, d), 7.29 (1H, s), 6.03 (1H, s), 5.21–5.28 (1H, m), 2.01–2.11 (4H, m), 1.89–1.90 (2H, m), 1.68–1.71 (2H, m). RP-HPLC (Hypercil C18, 5 μm, 100 Å, 15 cm; 5%–100% acetonitrile-0.1M ammonium acetate over 15 min, 1 mL/min) R$_t$ 6.45 min. MS: MH$^+$ 406.

Example 273

1-Cyclopentyl-3-[4-(3-thienyloxy)phenyl]-1H-pyrazolo[3,4-d]pyrimidin-4-amine

A mixture of 4-(4-amino-1-cyclopentyl-1H-pyrazolo[3,4-d]pyrimidin-3-yl)phenol (0.212 g, 0.718 mmol, 1 equiv), potassium carbonate (0.060 g, 0.43 mmol, 0.6 equiv), copper powder (0.015 g, 0.24 mmol, 0.33 equiv), and 3-bromothiophene (0.09 mL, 0.9 mmol, 1.3 equiv) in DMF (7.2 mL) was heated at 153° C. for 24 hr. The reaction mixture was allowed to cool to ambient temperature, concentrated, and the residue was purified by preparative RP-HPLC (Rainin C18, 8 μm, 300 Å, 25 cm; 10%–60% acetonitrile-0.1M ammonium acetate over 20 min, 21 mL/min). The acetonitrile was removed in vacuo and the aqueous mixture was lyopholyzed to give 1-cyclopentyl-3-[4-(3-thienyloxy)phenyl]-1H-pyrazolo[3,4-d]pyrimidin-4-amine as a light brown solid (0.060 g, 0.16 mmol): $^1$H NMR (d$_6$ DMSO, 400 MHz): δ H 9.77 (1H, s), 8.46 (1H, s), 8.41 (1H, s), 7.73–7.74 (1H, m), 7.57 (2H, d, J=4.5 Hz), 7.46–7.48 (1H, m), 7.15 (1H, d, J=5.2 Hz), 6.96 (2H, d, J=8.6 Hz), 5.24–5.30 (1H, m), 2.03–2.05 (4H, m), 1.89–1.93 (2H, m), 1.70–1.72 (2H, m). RP-HPLC (Delta Pak C18, 5 μm, 300 Å, 15 cm; 5%–85% acetonitrile-0.1M ammonium acetate over 20 min, 1 mL/min) R$_t$ 18.76 min. MS: MH$^+$ 378.

Example 274 cis-3-{3-[(Benzo[b]furan-2-ylmethyl)amino]phenyl}-1-[4-(4-methylpiperazino)cyclohexyl]-1H-pyrazolo[3,4-d]pyrimidin-4-amine Monoacetate Salt A mixture of cis-3-(3-aminophenyl)-1-[4-(4-methylpiperazino)cyclohexyl]-1H-pyrazolo[3,4-d]

pyrimidin-4-amine (0.107 g, 0.263 mmol, 1 equiv), glacial acetic acid (0.06 mL, 1.0 mmol, 3.8 equiv), benzo[B]furan-2-carboxaldehyde (0.1 g, 0.3 mmol, 1 equiv), sodium triacetoxyborohydride (0.212 g, 1.0 mmol, 3.8 equiv), and dichloroethane (2 mL) was stirred at ambient temperature for 4.5 h. Aqueous sodium bicarbonate was added, the organic layer was separated, and the aqueous layer was extracted with two portions of $CH_2Cl_2$ (10 mL each). The combined organic extracts were dried over $MgSO_4$, filtered, and concentrated to afford a yellow oil which was purified by preparative RP-HPLC (Rainin C18, 8 µm, 300 Å, 25 cm; 10%–60% acetonitrile-0.1M ammonium acetate over 20 min, 21 mL/min). The acetonitrile was removed in vacuo and the aqueous mixture was lyopholyzed to give cis-3-{3-[(benzo[b]furan-2-ylmethyl)amino]phenyl}-1-[4-(4-methylpiperazino)cyclohexyl]-1H-pyrazolo[3,4-d]pyrimidin-4-amine monoacetate salt as a white solid (0.017 g, 0.031 mmol): $^1$H NMR ($d_6$ DMSO, 400 MHz): δ H 8.22 (1H, s), 7.51–7.58 (2H, m), 7.22–7.28 (2H, m), 6.98 (1H, s), 6.79–6.84 (2H, m), 6.59–6.62 (1H, m), 4.76–4.81 (1H, m), 4.50 (2H, d, J=5.6 Hz), 2.19–2.24 (14H, m), 2.05–2.07 (2H, m), 1.91 (3H, s), 1.60–1.75 (4H, m); RP-HPLC (Delta Pak C18, 5 µm, 300 Å, 15 cm; 5%–85% acetonitrile-0.1M ammonium acetate over 20 min, 1 mL/min) $R_t$ 13.99 min. MS: $MH^+$ 537.

Example 275 cis-3-{3-[di(2-Furylmethyl)amino]phenyl}-1-[4-(4-methylpiperazino)cyclohexyl]-1H-pyrazolo[3,4-d]pyrimidin-4-amine A mixture of cis-3-(3-aminophenyl)-1-[4-(4-methylpiperazino)cyclohexyl]-1H-pyrazolo[3,4-d]pyrimidin-4-amine (0.120 g, 0.296 mmol, 1 equiv), furfural (0.03 mL, 0.3 mmol, 1.1 equiv), glacial acetic acid (0.07 mL, 1.1 mmol, 3.8 equiv), and sodium triacetoxyborohydride (0.314 g, 1.48 mmol, 5.0 equiv) in dichloroethane (2 mL) was stirred at ambient temperature for 60 h. Saturated aqueous sodium bicarbonate solution (5 mL) was added, the organic layer was separated, and the aqueous layer was extracted with two portions of $CH_2Cl_2$ (10 mL each). The organic extracts were dried over $MgSO_4$, filtered, and concentrated to afford a yellow oil. Purification by column chromatography on silica gel (elution with 200 mL of 5% MeOH/$CH_2Cl_2$, 100 mL of 10% MeOH/$CH_2Cl_2$, and 300 mL of 10:20:70% MeOH/$Et_3$N/$CH_2Cl_2$) afforded cis-3-{3-[di(2-furylmethyl)amino]phenyl}-1-[4-(4-methylpiperazino)cyclohexyl]-1H-pyrazolo[3,4-d]pyrimidin-4-amine as a white solid (0.051 g, 0.10 mmol): $^1$H NMR ($d_6$ DMSO, 400 MHz): δ H 8.22 (1H, s), 7.60 (2H, s), 7.31–7.35 (1H, m), 7.19 (1H, s), 7.00 (1H, d, J=8.4 Hz), 6.93 (1H, d, J=7.6 Hz), 6.39 (2H, s), 6.32 (2H, s), 4.77–4.80 (1H, m), 4.60 (4H, s), 2.23–2.39 (11H, m), 2.16 (3H, s), 2.05–2.07 (2H, m), 1.59–1.71 (4H, m); RP-HPLC (Delta Pak C18, 5 µm, 300 Å, 15 cm; 5%–85% acetonitrile-0.1M ammonium acetate over 20 min, 1 mL/min) $R_t$ 14.52 min. MS: $MH^+$ 567.

Example 276 cis-N-[2-(3-{4-Amino-1-[4-(4-methylpiperazino)cyclohexyl]-1H-pyrazolo[3,4-d]pyrimidin-3-yl}phenoxy)benzyl]trifluoromethanesulfonamide Diacetate Salt To a mixture of cis-3-4-[2-(aminomethyl)phenoxy]phenyl-1-[4-(4-methylpiperazino)cyclohexyl]-1H-pyrazolo[3,4-d]pyrimidin-4-amine (0.018 g, 0.035 mmol, 1 equiv) and pyridine (0.4 mL) at 0° C. was added $CF_3SO_2Cl$ (0.05 mL, 0.04 mmol, 1.2 equiv) dropwise over 20 sec. The reaction mixture was allowed to warm slowly to ambient temperature and stirred for 3 h. The solvent was evaporated under reduced pressure and the oily yellow residue was purified by preparative RP-HPLC (Rainin C18, 8 µm, 300 Å, 25 cm; 10%–60% acetonitrile-0.1M ammonium acetate over 20 min, 21 mL/min). The acetonitrile was removed in vacuo and the aqueous mixture was lyopholyzed to give cis-N-[2-(3-{4-amino-1-[4-(4-methylpiperazino)cyclohexyl]-1H-pyrazolo[3,4-d]pyrimidin-3-yl}phenoxy)benzyl]trifluoromethanesulfonamide diacetate salt (0.004 g, 0.006 mmol): $^1$H NMR ($d_6$ DMSO, 400 MHz): δ H 8.22 (1H, s), 7.61–7.67 (3H, m), 7.25–7.30 (2H, m), 7.19–7.23 (2H, m), 6.96–6.98 (1H, m), 4.77–4.81 (1H, m), 4.25 (2H, s), 2.09–2.54 (14H, m), 2.05–2.08 (2H, m), 1.91 (6H, s), 1.57–1.74 (4H, m); RP-HPLC (Delta Pak C18, 5 µm, 300 Å, 15 cm; 5%–85% acetonitrile-0.1M ammonium acetate over 20 min, 1 mL/min) $R_t$ 15.15 min. MS: $MH^+$ 645.

Example 277 cis-2-(3-{4-Amino-1-[4-(4-methylpiperazino)cyclohexyl]-1H-pyrazolo[3,4-d]pyrimidin-3-yl}phenoxy)benzaldehyde A mixture of cis-3-iodo-1-[4-(4-methylpiperazino)cyclohexyl]-1H-pyrazolo[3,4-d]pyrimidin-4-amine (0.970 g, 2.20 mmol, 1 equiv), 2-[4-(4,4,5,5-tetramethyl-1,3,2-dioxaborolan-2-yl)phenoxy]benzaldehyde (0.842 g, 2.60 mmol, 1.2 equiv), tetrakis(triphenylphosphine)palladium (0.186 g, 0.180 mmol, 0.08 equiv), DME (9 mL), and sodium carbonate monohydrate (0.655 g, 5.30 mmol, 2.4 equiv) in water (7 mL) was heated at 85° C. for 7 h then allowed to cool to ambient temperature. Saturated aqueous sodium bicarbonate solution (50 mL) was added, and the solution was extracted with EtOAc (25 mL). The organic extract was dried over $MgSO_4$, filtered, and concentrated to afford a light brown solid. Trituration from $Et_2O$ (35 mL) afforded cis-2-(3-{4-amino-1-[4-(4-methylpiperazino)cyclohexyl]-1H-pyrazolo[3,4-d]pyrimidin-3-yl}phenoxy)benzaldehyde as an off-white solid (0.830 g, 1.62 mmol): $^1$H NMR ($d_6$ DMSO, 400 MHz): δ H 10.42 (1H, s), 8.24 (1H, s), 7.89 (1H, d, J=7.7 Hz), 7.69–7.71 (3H, m), 7.30–7.36 (1H, m), 7.29 (2H, d, J=6.3 Hz), 7.16 (1H, d, J=8.2 Hz), 4.79–4.81 (1H, m), 2.18–2.55 (11H, m), 2.17 (3H, s), 2.05–2.09 (2H, m), 1.56–1.71 (4H, m); RP-HPLC (Delta Pak C18, 5 µm, 300 Å, 15 cm; 5%–85% acetonitrile-0.1M ammonium acetate over 20 min, 1 mL/min) $R_t$ 12.56 min. MS: $MH^+$ 512.

Example 278 cis-3-{3-[2-(1H-2-Imidazolyl)phenoxy]phenyl}-1-[4-(4-methylpiperazino)cyclohexyl]-1H-pyrazolo[3,4-d]pyrimidin-4-amine A mixture of cis-2-(3-{4-amino-1-[4-(4-methylpiperazino)cyclohexyl]-1H-pyrazolo[3,4-d]pyrimidin-3-yl}phenoxy)benzaldehyde (0.102 g, 0.199 mmol, 1 equiv), glyoxal (0.12 mL, 0.99 mmol, 5 equiv), and ammonium carbonate (0.078 g, 0.99 mmol, 5 equiv) in methanol (1 mL) was stirred at ambient temperature for 16 h. Additional glyoxal (0.20 mL, 1.6 mmol, 8.3 equiv) and ammonium carbonate (0.130 g, 1.66 mmol, 8.4 equiv) were added and the reaction mixture was stirred at ambient temperature for 24 h. The crude reaction mixture was purified by preparative RP-HPLC (Rainin C18, 8 µm, 300 Å, 25 cm; 10%–60% acetonitrile-0.1M ammonium acetate over 20 min, 21 mL/min). The acetonitrile was removed in vacuo and the aqueous mixture was lyopholyzed to give cis-3-{3-[2-(1H-2-imidazolyl)phenoxy]phenyl}-1-[4-(4-methylpiperazino)cyclohexyl]-1H-pyrazolo[3,4-d]pyrimidin-4-amine as a brown solid (0.010 g, 0.018 mmol): $^1$H NMR (d$_6$ DMSO, 400 MHz): 6H 8.23 (1H, s), 8.11–8.13 (1H, dd, J=7.7, 1.9 Hz), 7.95 (1H, s), 7.66 (2H, d, J=8.5 Hz), 7.34–7.39 (1H, m), 7.23–7.27 (3H, m), 7.07–7.19 (3H, m), 4.77–4.82 (1H, m), 2.16–2.56 (11H, m), 2.14 (3H, s), 2.05–2.11 (2H, m), 1.55–1.71 (4H, m); RP-HPLC (Delta Pak C18, 5 µm, 300 Å, 15 cm; 5%–85% acetonitrile-0.1M ammonium acetate over 20 min, 1 mL/min) R$_t$ 10.43 min. MS: MH$^+$ 550.

Example 279 cis-N1-(4-{4-Amino-1-[4-(4-methylpiperazino)cyclohexyl]-1H-pyrazolo[3,4-d]pyrimidin-3-yl}-2-methoxyphenyl)-2-anilinoacetamide A mixture of 3-(4-amino-3-methoxyphenyl)-1-[4-(4-methylpiperazino)cyclohexyl]-1H-pyrazolo[3,4-d]pyrimidin-4-amine (0.151 g, 0.356 mmol, 1 equiv), potassium carbonate (0.098 g, 0.711 mmol, 2 equiv), and chloroacetylchloride (0.04 mL, 0.5 mmol, 1.5 equiv) in DMF (1.5 mL) was stirred at ambient temperature for 20 minutes and then aniline (0.32 mL, 3.5 mmol, 10 equiv) was added. The reaction mixture was stirred at ambient temperature for 72 h. The solvent was removed under reduced pressure and the residue was purified by preparative RP-HPLC (Rainin C18, 8 µm, 300 Å, 25 cm; 10%–60% acetonitrile-0.1M ammonium acetate over 20 min, 21 mL/min). The acetonitrile was removed in vacuo and the aqueous mixture was washed with saturated aqueous sodium bicarbonate (10 mL) and then extracted with CH$_2$Cl$_2$ (25 mL). The organic extract was dried over MgSO$_4$, filtered, and concentrated to give cis-N1-(4-{4-amino-1-[4-(4-methylpiperazino)cyclohexyl]-1H-pyrazolo[3,4-d]pyrimidin-3-yl}-2-methoxyphenyl)-2-anilinoacetamide as a yellow solid (0.010 g, 0.017 mmol): $^1$H NMR (d$_6$ DMSO, 400 MHz): δ H 9.30 (1H, s), 8.35–8.38 (1H, m), 8.21 (1H, s), 7.21–7.23 (2H, m), 7.12–7.16 (2H, m), 6.64–6.66 (3H, m), 6.31–6.34 (1H, m), 4.77–4.81 (1H, m), 3.90 (2H, d, J=6.0 Hz), 3.82 (3H, s), 2.21–2.51 (11H, m), 2.16 (3H, s), 2.06–2.08 (2H, m), 1.55–1.70 (4H, m); RP-HPLC (Delta Pak C18, 5 µm, 300 Å, 15 cm; 5%–85% acetonitrile-0.1M ammonium acetate over 20 min, 1 mL/min) R$_t$ 12.37 min. MS: MH$^+$ 570.

Example 280

(2S)-3-{3-[4-Amino-3-(4-phenoxyphenyl)-1H-pyrazolo[3,4-d]pyrimidin-1-yl]-1-azetanyl}propane-1,2-diol To a solution of 1-(3-azetanyl)-3-(4-phenoxyphenyl)-1H-pyrazolo[3,4-d]pyrimidin-4-amine (0.05 g, 0.00014 mol) was added (R)-(+)-glycidol (0.05 M in isopropanol, 2.8 mL, 0.00014 mol) at room temperature under an atmosphere of nitrogen. The mixture was stirred at 80° C. for three hours. The solvent was removed under reduced pressure. The residue was purified by flash chromatography on silica gel using ammonium hydroxide/methanol/dichloromethane (2:7:91) followed by ammonium hydroxide/methanol/dichloromethane (2:10:88) as mobile phase to yield (2S)-3-{3-[4-amino-3-(4-phenoxyphenyl)-1H-pyrazolo[3,4-d]pyrimidin-1-yl]-1-azetanyl}propane-1,2-diol (0.023 g, 0.000053 mol).

$^1$H NMR (Chloroform-d, 400 MHz) δ 8.31 (s, 1H), 7.64 (d, 2H), 7.38 (m, 2H), 7.15 (m, 5H), 5.90 (br, 2H), 5.60 (m, 1H), 3.97 (m, 3H), 3.88 (m, 1H), 3.75 (m, 2H), 3.61 (m, 1H), 2.80 (m, 2H). RP-HPLC (Hypersil C18, 5 µm, 250×4.6 mm; 25%–100% over 10 min with 0.1 M ammonium acetate, 1 mL/min) R$_t$ 8.6 min. MS: MH$^+$ 433.

Example 281

(2R)-3-{3-[4-Amino-3-(4-phenoxyphenyl)-1H-pyrazolo[3,4-d]pyrimidin-1-yl]-1-azetanyl}propane-1,2-diol The experimental procedure is similar to the synthesis of (2S)-3-3-[4-amino-3-(4-phenoxyphenyl)-1H-pyrazolo[3,4-d]pyrimidin-1-yl]-1-azetanylpropane-1,2-diol using (S)-(–)-glycidol $^1$H NMR (Chloroform-d, 400 MHz) δ 8.36 (s, 1H), 7.67 (d, 2H), 7.39 (m, 2H), 7.15 (m, 5H), 5.65 (br, 3H), 4.00 (m, 3H), 3.90 (m, 1H), 3.75 (m, 2H), 3.62 (m, 1H), 2.85 (m, 2H). RP-HPLC (Hypersil C18, 5 µm, 250×4.6 mm; 25%–100% over 10 min with 0.1 M ammonium acetate, 1 mL/min) R$_t$ 8.76 min. MS: MH$^+$ 433.

Example 282 tert-Butyl 4-(3-[4-Amino-3-(4-phenoxyphenyl)-1H-pyrazolo[3,4-d]pyrimidin-1-yl]-1-azetanylmethyl)-4-hydroxy-1-piperidinecarboxylate a) tert-Butyl 1-oxa-6-Azaspiro[2.5]octane-6-carboxylate A mixture of trimethylsulfoxonium iodide (2.62 g, 0.012 mol) and sodium hydride (0.44 g, 0.011 mol) in anhydrous dimethylsulfoxide (30 mL) was stirred at room temperature under an atmosphere of nitrogen for thirty minutes. The reaction mixture was cooled to 10° C. and tert-butyl 4-oxo-1-piperidinecarboxylate (2.0 g, 0.010 mol) in anhydrous dimethylsulfoxide (10 mL) was added. The reaction mixture was warmed to room temperature and stirred for one and a half hours. The mixture was poured into an aqueous saturated ammonium chloride solution (60 mL). The water phase was extracted with ethyl acetate (2×100 mL). The combined organic extracts were washed with water (1×60 mL) and brine (1×50 mL) and dried over sodium sulfate. The solvent was removed under reduced pressure to yield tert-butyl 1-oxa-6-azaspiro[2.5]octane-6-carboxylate (2.12 g, 0.0099 mol).

$^1$H NMR (Chloroform-d, 400 MHz) δ 3.74 (br, 2H), 3.44 (m, 2H), 2.69 (s, 2H), 1.80 (m, 2H), 1.47 (s, 9H), 1.46 (m, 2H); TLC (ethyl acetate/dichloromethane=20: 80) R$_f$ 0.57.

tert-Butyl 4-(3-[4-Amino-3-(4-phenoxyphenyl)-1H-pyrazolo[3,4-d]pyrimidin-1-yl]-1-azetanylmethyl)-4-hydroxy-1-piperidinecarboxylate To a mixture of 1-(3-azetanyl)-3-(4-phenoxyphenyl)-1H-pyrazolo[3,4-d]pyrimidin-4-amine (0.4 g, 0.0011 mol) in isopropanol (40 mL) was added tert-butyl 1-oxa-6-azaspiro [2.5]octane-6-carboxylate (0.27 g, 0.0013 mol) at room temperature under an atmosphere of nitrogen. The mixture was stirred at 80° C. for three and a half hours. Additional tert-butyl 1-oxa-6-azaspiro[2.5]octane-6-carboxylate (0.13 g, 0.00061 mol) was added and the mixture was stirred at 80° C. for seven hours. Furthermore, tert-butyl 1-oxa-6-azaspiro[2.5]octane-6-carboxylate (0.13 g, 0.00061 mol) was added and the mixture was stirred at 60° C. for 18 hours, then 80° C. for eight hours. The solvent was removed under reduced pressure. The residue was suspended in water (50 mL) and the aqueous phase was extracted with ethyl acetate (2×50 mL). The combined organic extracts were washed with water (1×50 mL) and brine (1×50 mL) and dried over magnesium sulfate. The solvent was removed under reduced pressure. The residue was purified by flash chromatography on silica gel using methanol/dichloromethane (5:95) followed by methanol/dichloromethane (10:90) as mobile phase to yield tert-butyl 4-(3-[4-amino-3-(4-phenoxyphenyl)-1H-pyrazolo[3,4-d]pyrimidin-1-yl]-1-azetanylmethyl)-4-hydroxy-1-piperidinecarboxylate (0.243 g, 0.000425 mol).

$^1$H NMR (Chloroform-d, 400 MHz) δ 8.38 (s, 1H), 7.67 (d, 2H), 7.43 (t, 2H), 7.17 (m, 3H), 7.10 (d, 2H), 5.78 (m, 1H), 5.48 (br, 2H), 4.34 (br, 2H), 4.20 (br, 2H), 3.89 (br, 2H), 3.18 (br, 2H), 2.91 (br, 2H), 1.60 (br, 2H), (s, 9H). RP-HPLC (Hypersil C18, 5 μm, 250×4.6 mm; 25%–100% over 10 min with 0.1 M ammonium acetate, 1 mL/min) $R_t$ 10.7 min. MS: MH$^+$ 572.

Example 283

4-(3-[4-Amino-3-(4-phenoxyphenyl)-1H-pyrazolo[3,4-d]pyrimidin-1-yl]-1-azetanylmethyl)-4-piperidinol To a solution of tert-butyl 4-(3-[4-amino-3-(4-phenoxyphenyl)-1H-pyrazolo[3,4-d]pyrimidin-1-yl]-1-azetanylmethyl)-4-hydroxy-1-piperidinecarboxylate (0.090 g, 0.00016 mol) in dichloromethane (2 mL) was slowly added a 20% solution of trifluoroacetic acid in dichloromethane (10 mL) at 0° C. under an atmosphere of nitrogen. The mixture was warmed to room temperature and stirred for four hours. The solvent was removed under reduced pressure. An aqueous solution of 5 N sodium hydroxide was added to pH 11 at 0° C. The water phase was extracted with dichloromethane (2×30 mL). The combined organic extracts were washed with water (1×60 mL) and brine (1×60 mL) and dried over sodium sulfate. The solvent was removed under reduced pressure to yield 4-(3-[4-amino-3-(4-phenoxyphenyl)-1H-pyrazolo[3,4-d]pyrimidin-1-yl]-1-azetanylmethyl)-4-piperidinol (0.045 g, 0.000096 mol).

$^1$H NMR (Chloroform-d, 400 MHz) δ 8.37 (s, 1H), 7.68 (d, 2H), 7.42 (t, 2H), 7.11 (m, 3H), 7.00 (d, 2H), 5.64 (m, 1H), 5.43 (br, 2H), 4.02 (m, 4H), 3.28 (br, 1H), 3.10 (m, 4H), 2.67 (s, 2H), 1.67 (m, 4H). RP-HPLC (Delta Pak C18, 5 μm, 300 A, 15 cm; 5%–85% acetonitrile-0.1M ammonium acetate over 10 min, 1 mL/min) Rt 8.5 min. MS: MH$^+$ 472.

Example 284

4-(3-[4-Amino-3-(4-phenoxyphenyl)-1H-pyrazolo[3,4-d]pyrimidin-1-yl]-1-azetanylmethyl)-1-methyl-4-piperidinol A mixture of 4-(3-[4-amino-3-(4-phenoxyphenyl)-1H-pyrazolo[3,4-d]pyrimidin-1-yl]-1-azetanylmethyl)-4-piperidinol (0.035 g, 0.000074 mol) and formaldehyde (0.006 mL, 37% in water, 0.000082 mol) in dichloroethane (4 mL) was stirred at room temperature under an atmosphere of nitrogen for one hr. Sodium triacetoxyborohydride (0.022 g, 0.000104 mol) was added into the mixture and stirred at ambient temperature under an atmosphere of nitrogen for eighteen hours. Molecular sieves (0.05 g, 3A, 4–8 mesh) and additional formaldehyde (0.006 mL, 37% in water, 0.000082 mol) was added and the reaction mixture was stirred at room temperature for eighteen hours. The solvent was removed under reduced pressure, and the residue was purified by RP-HPLC (Hypersil HS C18, 8 μm, 250×21.1 mm; 5%–100% over 25 min with 0.1 M ammonium acetate, 21 mL/min) to yield 4-(3-[4-amino-3-(4-phenoxyphenyl)-1H-pyrazolo[3,4-d]pyrimidin-1-yl]-1-azetanylmethyl)-1-methyl-4-piperidinol (0.020 g, 0.000041 mol).

$^1$H NMR (DMSO-d$_6$, 400 MHz) δ 8.63 (s, 1H), 7.69 (d, 2H), 7.42 (t, 2H), 7.17 (m, 5H), 5.42 (m, 1H), 3.88 (m, 2H), 3.67 (m, 2H), 2.37 (m, 2H), 2.25 (m, 2H), 2.14 (s, 3H), 1.90 (s, 2H), 1.50 (m, 4H). RP-HPLC (Delta Pak C18, 5 μm, 300 A, 15 cm; 5%–85% acetonitrile-0.1M ammonium acetate over 10 min, 1 mL/min) Rt 8.5 min. MS: MH$^+$ 486.

General Procedure:

A mixture of 1-(3-azetanyl)-3-(4-phenoxyphenyl)-1H-pyrazolo[3,4-d]pyrimidin-4-amine (0.06 g, 0.00017 mol, 1 eq.), the corresponding chloroacetamide (0.0005 mol, 3 eq.), and N,N-diisopropylethylamine (0.033 g, 0.00026 mol, 1.5 eq.) in acetonitrile (2.5 mL) was stirred at 75° C. under an atmosphere of nitrogen for three hours. The mixture was poured into water (10 mL), and the water phase was extracted with ethyl acetate (2×10 mL). The combined organic extracts were washed with water (1×10 mL) and brine (1×10 mL) and dried over sodium sulfate. The solvent was removed under reduced pressure. The residue was purified by RP-HPLC (Hypersilprep HS C18, 8 μm, 250× 21.1 mm; 5%–100% over 25 min with 0.1 M ammonium acetate, 21 mL/min) to yield the corresponding amide.

Example 285

N-Methyl-2-{3-[4-amino-3-(4-phenoxyphenyl)-1H-pyrazolo[3,4-d]pyrimidin-1-yl]-1-azetanyl}acetamide a) Chloroacetamide: N-Methyl-2-chloroacetamide $^1$H NMR (Chloroform-d, 400 MHz) δ 8.35 (s, 1H), 7.67 (d, 2H), 7.42 (m, 2H), 7.18 (m, 3H), 7.08 (d, 2H), 5.80 (br, 2H), 5.60 (m, 1H), 4.00 (m, 4H), 3.37 (s, 2H), 2.85 (s, 3H). RP-HPLC (Delta Pak C18, 5 μm, 300 A, 15 cm; 5%–85% acetonitrile-0.1M ammonium acetate over 10 min, 1 mL/min) Rt 9.2 min. MS: MH$^+$ 430.

Example 286

N,N-Dimethyl-2-{3-[4-amino-3-(4-phenoxyphenyl)-1H-pyrazolo[3,4-d]pyrimidin-1-yl]-1-azetanyl}acetamide b) Chloroacetamide: N,N-Dimethyl-2-chloroacetamide $^1$H NMR (Chloroform-d, 400 MHz) δ 8.33 (s, 1H), 7.65 (d, 2H), 7.41 (m, 2H), 7.16 (m, 3H), 7.08 (d, 2H), 5.86 (br, 2H), 5.67 (m, 1H), 4.15 (m, 2H), 3.90 (m, 2H), 3.57 (s, 2H), 3.00 (s, 3H), 2.90 (s, 3H). RP-HPLC (Delta Pak C18, 5 μm, 300 A, 15 cm; 5%–85% acetonitrile-0.1M ammonium acetate over 10 min, 1 mL/min) Rt 9.3 min. MS: MH$^+$ 444.

Example 287

N-Isopropyl-2-{3-[4-amino-3-(4-phenoxyphenyl)-1H-pyrazolo[3,4-d]pyrimidin-1-yl]-1-azetanyl}acetamide c) Chloroacetamide: N-Isopropyl-2-chloroacetamide $^1$H NMR (Chloroform-d, 400 MHz) δ 8.36 (s, 1H), 7.67 (d, 2H), 7.40 (m, 2H), 7.18 (m, 3H), 7.09 (d, 2H), 6.90 (br, 1H), 5.66 (m, 3H), 4.11 (m, 1H), 3.99 (m, 4H), 3.39 (s, 2H), 1.19 (d, 6H). RP-HPLC (Delta Pak C18, 5 μm, 300 A, 15 cm; 5%–85% acetonitrile-0.1M ammonium acetate over 10 min, 1 mL/min) Rt 9.8 min. MS: MH$^+$ 458.

Example 288

N-(3-Hydroxypropyl)-2-{3-[4-amino-3-(4-phenoxyphenyl)-1H-pyrazolo[3,4-d]pyrimidin-1-yl]-1-azetanyl}acetamide d) Chloroacetamide: N-(3-Hydroxypropyl)-2-chloroacetamide $^1$H NMR (Chloroform-d, 400 MHz) δ 8.31 (s, 1H), 7.67 (d, 2H), 7.40 (m, 2H), 7.18 (m, 3H), 7.10 (d, 2H), 5.99 (br, 2H), 5.62 (m, 1H), 3.95 (m, 4H), 3.78 (m, 2H), 3.63 (m, 2H), 3.40 (s, 2H), 1.71 (m, 2H). RP-HPLC (Delta Pak C18, 5 μm, 300 A, 15 cm; 5%–85% acetonitrile-0.1M ammonium acetate over 10 min, 1 mL/min) Rt 8.9 min. MS: MH$^+$ 474.

Example 289

Ethyl 2-[(2-{3-[4-Amino-3-(4-phenoxyphenyl)-1H-pyrazolo[3,4-d]pyrimidin-1-yl]-1-azetanyl}acetyl)amino]acetate (4037150)

e) Chloroacetamide: Ethyl 2-[(2-Chloroacetyl)amino]acetate $^1$H NMR (Chloroform-d, 400 MHz) δ 8.37 (s, 1H), 7.66 (d, 2H), 7.65 (br, 1H), 7.40 (m, 2H), 7.18 (m, 3H), 7.09 (d, 2H), 5.67 (m, 1H), 5.56 (br, 2H), 4.23 (m, 2H), 4.10 (m, 4H), 4.00 (m, 2H), 3.47 (s, 2H), 1.29 (t, 3H). RP-HPLC (Delta Pak C18, 5 μm, 300 A, 15 cm; 5%–85% acetonitrile-0.1M ammonium acetate over 10 min, 1 mL/min) Rt 9.9 min. MS: MH$^+$ 502.

Example 290

N-Benzyl-2-{3-[4-amino-3-(4-phenoxyphenyl)-1H-pyrazolo[3,4-d]pyrimidin-1-yl]-1-azetanyl}acetamide f) Chloroacetamide: N-Benzyl-2-chloroacetamide $^1$H NMR (Chloroform-d, 400 MHz) δ 8.25 (s, 1H), 7.63 (d, 2H), 7.40 (m, 2H), 7.33 (m, 5H), 7.16 (m, 5H), 5.72 (m, 1H), 4.49 (d, 2H), 3.97 (m, 4H), 3.44 (s, 2H). RP-HPLC (Delta Pak C18, 5 μm, 300 A, 15 cm; 5%–85% acetonitrile-0.1M ammonium acetate over 10 min, 1 mL/min) Rt 10.7 min. MS: MH$^+$ 506.

Example 291

N,N-Methoxymethyl-2-{3-[4-amino-3-(4-phenoxyphenyl)-1H-pyrazolo[3,4-d]pyrimidin-1-yl]-1-azetanyl}acetamide g) Chloroacetamide: N,N-Methoxymethyl-2-chloroacetamide $^1$H NMR (Chloroform-d, 400 MHz) δ 8.37 (s, 1H), 7.67 (d, 2H), 7.42 (m, 2H), 7.18 (m, 3H), 7.08 (d, 2H), 5.71 (m, 1H), 5.48 (br, 2H), 4.16 (m, 2H), 3.92 (m, 2H), 3.72 (s, 3H), 3.69 (s, 2H), 3.18 (s, 3H). RP-HPLC (Delta Pak C18, 5 μm, 300 A, 15 cm; 5%–85% acetonitrile-0.1M ammonium acetate over 10 min, 1 mL/min) Rt 9.5 min. MS: MH$^+$ 460.

Example 292

2-{3-[4-Amino-3-(4-phenoxyphenyl)-1H-pyrazolo[3,4-d]pyrimidin-1-yl]-1-azetanyl}-1-morpholino-1-ethanone h) Chloroacetamide: 2-Chloro-1-morpholino-1-ethanone $^1$H NMR (Chloroform-d, 400 MHz) δ 8.36 (s, 1H), 7.67 (d, 2H), 7.42 (m, 2H), 7.18 (m, 3H), 7.08 (d, 2H), 5.71 (m, 3H), 4.13 (m, 2H), 3.93 (m, 2H), 3.69 (br, 4H), 3.60 (br, 4H), 3.51 (s, 2H). RP-HPLC (Delta Pak C18, 5 μm, 300 A, 15 cm; 5%–85% acetonitrile-0.1M ammonium acetate over 10 min, 1 mL/min) Rt 9.3 min. MS: MH$^+$ 486.

Example 293

N-(3-Methyl-5-isoxazolyl)-2-{3-[4-amino-3-(4-phenoxyphenyl)-1H-pyrazolo[3,4-d]pyrimidin-1-yl]-1-azetanyl}acetamide i) Chloroacetamide: N-(3-Methyl-5-isoxazolyl)-2-chloroacetamide $^1$H NMR (Chloroform-d, 400 MHz) δ 10.10 (br, 1H), 8.37 (s, 1H), 7.66 (d, 2H), 7.40 (m, 2H), 7.19 (m, 3H), 7.09 (d, 2H), 6.26 (s, 1H), 5.65 (m, 1H), 4.07 (m, 4H), 3.54 (s, 2H), 2.28 (s, 3H). RP-HPLC (Delta Pak C18, 5 μm, 300 A, 15 cm; 5%–85% acetonitrile-0.1M ammonium acetate over 10 min, 1 mL/min) Rt 10.3 min. MS: MH$^+$ 497.

Example 294

1-{3-[4-Amino-3-(4-phenoxyphenyl)-1H-pyrazolo[3,4-d]pyrimidin-1-yl]-1-azetanyl}-2-(1H-4-imidazolyl)-1-ethanone A mixture of 1-(3-azetanyl)-3-(4-phenoxyphenyl)-1H-pyrazolo[3,4-d]pyrimidin-4-amine (0.05 g, 0.00014 mol), sodium 2-(1H-4-imidazolyl)acetate (0.0026 g, 0.000175 mol), 1-(3-dimethylaminopropyl)-3-ethylcarbodiimide hydrochloride (0.0034 g, 0.000175 mol), N,N-diisopropylethylamine (0.033 g, 0.00026 mol) and 1-hydroxy-7-azabenzotriazole (0.019 g, 0.00014 mol) in anhydrous N,N-dimethylformamide (6 mL) was stirred for eighteen hours at room temperature. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield 1-{3-[4-amino-3-(4-phenoxyphenyl)-1H-pyrazolo[3,4-d]pyrimidin-1-yl]-1-azetanyl}-2-(1H-4-imidazolyl)-1-ethanone (0.018 g, 0.00004 mol).

$^1$H NMR (DMSO-d$_6$, 400 MHz) δ 11.90 (br, 1H), 8.27 (s, 1H), 7.71 (d, 2H), 7.53 (s, 1H), 7.42 (m, 2H), 7.19 (m, 5H), 6.92 (br, 1H), 5.73 (m, 1H), 4.74 (m, 1H), 4.61 (m, 1H), 4.42 (m, 2H), 3.42 (s, 2H). RP-HPLC (DeltaPak C18, 5 μm, 300 A, 15 cm; 5%–85% acetonitrile-0.1M ammonium acetate over 10 min, 1 mL/min) Rt 9.0 min. MS: MH$^+$ 467.

Example 295

1-{3-[4-Amino-3-(4-phenoxyphenyl)-1H-pyrazolo[3,4-d]pyrimidin-1-yl]-1-azetanyl}-3-(1H-4-imidazolyl)-1-propanone A mixture of 1-(3-azetanyl)-3-(4-phenoxyphenyl)-1H-pyrazolo[3,4-d]pyrimidin-4-amine (0.10 g, 0.00028 mol), 3-(1H-4-imidazolyl)propanoic acid (0.050 g, 0.00035 mol), 1-(3-dimethylaminopropyl)-3-ethylcarbodiimide hydrochloride (0.0068 g, 0.00035 mol), N,N-diisopropylethylamine (0.068 g, 0.00053 mol) and 1-hydroxy-7-azabenzotriazole (0.038 g, 0.00028 mol) in anhydrous N,N-dimethylformamide (13 mL) was stirred for eighteen hours at room temperature. The solvent was removed under reduced pressure. The residue was dissolved in dichloromethane (5 mL) and washed with water (2 mL). The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield 1-{3-[4-amino-3-(4-phenoxyphenyl)-1H-pyrazolo[3,4-d]pyrimidin-1-yl]-1-azetanyl}-3-(1H-4-imidazolyl)-1-propanone (0.040 g, 0.00008 mol).

$^1$H NMR (Chloroform-d, 400 MHz) δ 8.96 (s, 1H), 7.77 (br, 1H), 7.64 (d, 2H), 7.40 (m, 2H), 7.17 (m, 3H), 7.08 (m, 2H), 6.90 (br, 1H), 5.78 (m, 1H), 5.56 (br, 2H), 4.76 (m, 1H), 4.57 (m, 3H), 2.98 (m, 2H), 2.55 (m, 2H). RP-HPLC (Delta Pak C18, 5 μm, 300 A, 15 cm; 5%–85% acetonitrile-0.1M ammonium acetate over 10 min, 1 mL/min) Rt 9.0 min. MS: MH$^+$ 481.

General Procedure

To a mixture of 1-(3-azetanyl)-3-(4-phenoxyphenyl)-1H-pyrazolo[3,4-d]pyrimidin-4-amine (0.05 g, 0.00014 mol, 1 eq.) and potassium carbonate (0.039 g, 0.00028 mol, 2 eq.) in anhydrous N,N-dimethylformamide was added chloroacetylchloride (0.031 g, 0.00028 mol, 2 eq.) at room temperature. The mixture was stirred for ten minutes before the amine (0.0014 mol, 10 eq.) was added. The mixture was stirred at room temperature from one and a half hours to two days depending on the amine. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield the corresponding acetamides.

Example 296

1-{3-[4-Amino-3-(4-phenoxyphenyl)-1H-pyrazolo[3,4-d]pyrimidin-1-yl]-1-azetanyl}-2-[(2-hydroxyethyl)amino]-1-ethanone a) Amine: 2-Amino-1-ethanol $^1$H NMR (Chloroform-d, 400 MHz) δ 8.37 (s, 1H), 7.67 (d, 2H), 7.41 (m, 2H), 7.15 (m, 3H), 7.08 (m, 2H), 5.83 (m, 1H), 5.57 (br, 2H), 4.82 (m, 1H), 4.65 (m, 3H), 3.71 (m, 2H), 3.45 (m, 2H), 2.92 (m, 2H). RP-HPLC (Delta Pak C18, 5 μm, 300 A, 15 cm; 5%–85% acetonitrile-0.1M ammonium acetate over 10 min, 1 mL/min) Rt 8.7 min. MS: MH$^+$ 460.

Example 297

1-{3-[4-Amino-3-(4-phenoxyphenyl)-1H-pyrazolo[3,4-d]pyrimidin-1-yl]-1-azetanyl}-2-[(2-methoxyethyl)amino]-1-ethanone b) Amine: 2-Methoxy-1-ethanamine $^1$H NMR (Chloroform-d, 400 MHz) δ 8.38 (s, 1H), 7.67 (d, 2H), 7.41 (m, 2H), 7.18 (m, 3H), 7.10 (m, 2H), 5.83 (m, 1H), 5.54 (br, 2H), 4.81 (m, 1H), 4.64 (m, 2H), 4.56 (m, 1H), 3.55 (t, 2H), 3.41 (s, 2H), 3.37 (s, 3H), 2.88 (t, 2H). RP-HPLC (Delta Pak C18, 5 μm, 300 A, 15 cm; 5%–85% acetonitrile-0.1M ammonium acetate over 10 min, 1 mL/min) Rt 9.0 min. MS: MH$^+$ 474.

Example 298

1-{3-[4-Amino-3-(4-phenoxyphenyl)-1H-pyrazolo[3,4-d]pyrimidin-1-yl]-1-azetanyl}-2-[(3-hydroxypropyl)amino]-1-ethanone c) Amine: 3-Amino-1-propanol $^1$H NMR (Chloroform-d, 400 MHz) δ 8.37 (s, 1H), 7.67 (d, 2H), 7.41 (m, 2H), 7.18 (m, 3H), 7.10 (m, 2H), 5.86 (m, 1H), 5.54 (br, 2H), 4.81 (m, 1H), 4.64 (m, 3H), 3.87 (m, 2H), 3.48 (m, 2H), 3.01 (m, 2H), 1.83 (m, 2H). RP-HPLC (Delta Pak C18, 5 μm, 300 A, 15 cm; 5%–85% acetonitrile-0.1M ammonium acetate over 10 min, 1 mL/min) Rt 8.7 min. MS: MH$^+$ 474.

Example 299

1-{3-[4-Amino-3-(4-phenoxyphenyl)-1H-pyrazolo[3,4-d]pyrimidin-1-yl]-1-azetanyl}-2-[(2,3-dihydroxypropyl)amino]-1-ethanone d) Amine: 3-Amino-1,2-propanediol $^1$H NMR (DMSO-d$_6$, 400 MHz) δ 8.27 (s, 1H), 7.72 (d, 2H), 7.46 (m, 2H), 7.16 (m, 5H), 5.73 (m, 1H), 4.67 (m, 1H), 4.59 (m, 2H), 4.37 (m, 2H), 3.53 (m, 1H), 3.30 (m, 1H), 3.22 (m, 2H), 2.59 (m, 1H), 2.45 (m, 1H). RP-HPLC (Delta Pak C18, 5 μm, 300 A, 15 cm; 5%–85% acetonitrile-0.1M ammonium acetate over 10 min, 1 mL/min) Rt 8.6 min. MS: MH$^+$ 490.

Example 300

1-{3-[4-Amino-3-(4-phenoxyphenyl)-1H-pyrazolo[3,4-d]pyrimidin-1-yl]-1-azetanyl}-2-[(tetrahydro-2-furanylmethyl)amino]-1-ethanone e) Amine: Tetrahydro-2-furanylmethanamine $^1$H NMR (Chloroform-d, 400 MHz) δ 8.38 (s, 1H), 7.67 (d, 2H), 7.41 (m, 2H), 7.18 (m, 3H), 7.10 (m, 2H), 5.81 (m, 1H), 5.54 (br, 2H), 4.80 (m, 1H), 4.64 (m, 2H), 4.57 (m, 1H), 4.05 (m, 1H), 3.87 (m, 1H), 3.76 (m, 1H), 3.42 (m, 2H), 2.83 (m, 1H), 2.74 (m, 1H), 2.00 (m, 1H), 1.89 (m, 2H), 1.57 (m, 1H). RP-HPLC (Delta Pak C18, 5 μm, 300 A, 15 cm; 5%–85% acetonitrile-0.1M ammonium acetate over 10 min, 1 mL/min) Rt 9.3 min. MS: MH$^+$ 500.

Example 301 f) Amine: 2-Piperidino-1-ethanamine 1-{3-[4-Amino-3-(4-phenoxyphenyl)-1H-pyrazolo[3,4-d]pyrimidin-1-yl]-1-azetanyl}-2-[(2-piperidinoethyl)amino]-1-ethanone $^1$H NMR (DMSO-d$_6$, 400 MHz) δ 8.27 (s, 1H), 7.70 (d, 2H), 7.42 (m, 2H), 7.18 (m, 5H), 5.73 (m, 1H), 4.60 (m, 2H), 4.36 (m, 2H), 3.24 (d, 2H), 2.60 (m, 2H), 2.36 (m, 6H), 1.49 (m, 4H), 1.36 (m, 2H). RP-HPLC (Delta Pak C18, 5 μm, 300 A, 15 cm; 5%–85% acetonitrile-0.1M ammonium acetate over 10 min, 1 mL/min) Rt 9.4 min. MS: MH$^+$ 527.

Example 302 g) Amine: N,N,N-Trimethyl-1,2-ethanediamine 1-{3-[4-Amino-3-(4-phenoxyphenyl)-1H-pyrazolo[3,4-d]pyrimidin-1-yl]-1-azetanyl}-2-[[2-(dimethylamino)ethyl](methyl)amino]-1-ethanone $^1$H NMR (DMSO-d$_6$, 400 MHz) δ 8.27 (s, 1H), 7.70 (d, 2H), 7.44 (m, 2H), 7.17 (m, 5H), 5.75 (m, 1H), 4.70 (m, 2H), 4.40 (m, 2H), 3.22 (d, 2H), 2.75 (br, 2H), 2.61 (m, 2H), 2.47 (s, 6H), 2.29 (s, 3H). RP-HPLC (Delta Pak C18, 5 μm, 300 A, 15 cm; 5%–85% acetonitrile-0.1M ammonium acetate over 10 min, 1 mL/min) Rt 9.4 min. MS: MH$^+$ 501.

Example 303 h) Amine: N,N-Dimethyl-1,2-ethanediamine 1-{3-[4-Amino-3-(4-phenoxyphenyl)-1H-pyrazolo[3,4-d]pyrimidin-1-yl]-1-azetanyl}-2-{[2-(dimethylamino)ethyl]amino}-1-ethanone Acetate $^1$H NMR (Chloroform-d, 400 MHz) δ 8.33 (s, 1H), 7.67 (d, 2H), 7.42 (m, 2H), 7.15 (m, 3H), 7.11 (m, 2H), 5.81 (br, 3H), 4.81 (m, 1H), 4.59 (m, 3H), 3.38 (s, 2H), 2.89 (t, 2H), 2.68 (t, 2H), 2.43 (s, 6H), 2.05 (s, 3H). RP-HPLC (Delta Pak C18, 5 μm, 300 A, 15 cm; 5%–85% acetonitrile-0.1M ammonium acetate over 10 min, 1 mL/min) Rt 9.0 min. MS: MH$^+$ 487.

Example 304 i) Amine: N-Methyl-N-(1-methyl-4-piperidyl)amine 1-{3-[4-Amino-3-(4-phenoxyphenyl)-1H-pyrazolo[3,4-d]pyrimidin-1-yl]-1-azetanyl}-2-[methyl(1-methyl-4-piperidyl)amino]-1-ethanone $^1$H NMR (Chloroform-d, 400 MHz) δ 8.36 (s, 1H), 7.67 (d, 2H), 7.41 (m, 2H), 7.18 (m, 3H), 7.10 (m, 2H), 5.76 (m, 1H), 5.58 (br, 2H), 4.87 (m, 1H), 4.79 (m, 1H), 4.62 (m, 1H), 4.55 (m, 1H), 3.27 (m, 2H), 2.97 (br, 2H), 2.51 (br, 1H), 2.35 (s, 3H), 2.31 (s, 3H), 2.04 (br, 2H), 1.79 (br, 2H), 1.65 (br, 2H). RP-HPLC (Delta Pak C18, 5 μm, 300 A, 15 cm; 5%–85% acetonitrile-0.1M ammonium acetate over 10 min, 1 mL/min) Rt 9.1 min. MS: MH$^+$ 527.

Example 305 j) Amine: 2-Morpholino-1-ethanamine 1-{3-[4-Amino-3-(4-phenoxyphenyl)-1H-pyrazolo[3,4-d]pyrimidin-1-yl]-1-azetanyl}-2-[(2-morpholinoethyl)amino]-1-ethanone $^1$H NMR (Chloroform-d, 400 MHz) δ 8.38 (s, 1H), 7.67 (d, 2H), 7.40 (m, 2H), 7.19 (m, 3H), 7.09 (m, 2H), 5.86 (m, 1H), 5.50 (br, 2H), 4.82 (m, 1H), 4.67 (m, 3H), 3.77 (m, 4H), 3.50 (s, 2H), 2.92 (t, 2H), 2.66 (t, 2H), 2.57 (br, 4H). RP-HPLC (Delta Pak C18, 5 μm, 300 A, 15 cm; 5%–85% acetonitrile-0.1M ammonium acetate over 10 min, 1 mL/min) Rt 9.1 min. MS: MH$^+$ 529.

Example 306 k) Amine: 3-Morpholino-1-propanamine 1-{3-[4-Amino-3-(4-phenoxyphenyl)-1H-pyrazolo[3,4-d]pyrimidin-1-yl]-1-azetanyl}-2-[(3-morpholinopropyl)amino]-1-ethanone $^1$H NMR (Chloroform-d, 400 MHz) δ 8.38 (s, 1H), 7.68 (d, 2H), 7.41 (m, 2H), 7.18 (m, 3H), 7.10 (m, 2H), 5.85 (m, 1H), 5.54 (br, 2H), 4.81 (m, 1H), 4.64 (m, 3H), 3.74 (m, 4H), 3.40 (s, 2H), 2.83 (br, 2H), 2.52 (br, 6H), 1.80 (br, 2H). RP-HPLC (Delta Pak C18, 5 μm, 300 A, 15 cm; 5%–85% acetonitrile-0.1M ammonium acetate over 10 min, 1 mL/min) Rt 8.9 min. MS: MH$^+$ 543.

Example 307 l) Amine: 3-(1H-1-Imidazolyl)-1-propanamine 1-{3-[4-Amino-3-(4-phenoxyphenyl)-1H-pyrazolo[3,4-d]pyrimidin-1-yl]-1-azetanyl}-2-{[3-(1H-1-imidazolyl)propyl]amino}-1-ethanone $^1$H NMR (Chloroform-d, 400 MHz) δ 8.37 (s, 1H), 7.65 (d, 2H), 7.40 (m, 3H), 7.15 (m, 3H), 7.08 (m, 3H), 6.93 (s, 1H), 5.82 (m, 1H), 5.62 (br, 2H), 4.75 (m, 1H), 4.62 (m, 3H), 4.07 (t, 2H), 3.27 (s, 2H), 2.58 (t, 2H), 1.97 (m, 2H). RP-HPLC (Delta Pak C18, 5 μm, 300 A, 15 cm; 5%–85% acetonitrile-0.1M ammonium acetate over 10 min, 1 mL/min) Rt 8.7 min. MS: MH$^+$ 524.

Example 308 m) Amine: 1-(3-Aminopropyl)-2-pyrrolidinone 1-{3-[(2-{3-[4-Amino-3-(4-phenoxyphenyl)-1H-pyrazolo[3,4-d]pyrimidin-1-yl]-1-azetanyl}-2-oxoethyl)amino]propyl}-2-pyrrolidinone $^1$H NMR (Chloroform-d, 400 MHz) δ 8.38 (s, 1H), 7.67 (d, 2H), 7.41 (m, 2H), 7.18 (m, 3H), 7.10 (m, 2H), 5.82 (m, 1H), 5.54 (br, 2H), 4.81 (m, 1H), 4.64 (m, 3H), 3.42 (m, 6H), 2.79 (t, 2H), 2.42 (t, 2H), 2.07 (m, 2H), 1.86 (br, 2H). RP-HPLC (Delta Pak C18, 5 μm, 300 A, 15 cm; 5%–85% acetonitrile-0.1M ammonium acetate over 10 min, 1 mL/min) Rt 9.0 min. MS: MH$^+$ 541.

Example 309 n) Amine: 4-Piperidinol 1-{3-[4-Amino-3-(4-phenoxyphenyl)-1H-pyrazolo[3,4-d]pyrimidin-1-yl]-1-azetanyl}-2-(4-hydroxypiperidino)-1-ethanone $^1$H NMR (Chloroform-d, 400 MHz) δ 8.38 (s, 1H), 7.67 (d, 2H), 7.38 (m, 2H), 7.18 (m, 3H), 7.09 (m, 2H), 5.77 (m, 1H), 5.57 (br, 2H), 4.90 (m, 1H), 4.78 (m, 1H), 4.63 (m, 1H), 4.56 (m, 1H), 3.73 (br, 1H), 3.18 (s, 2H), 2.91 (br, 2H), 2.38 (br, 2H), 1.95 (br, 2H), 1.62 (br, 2H). RP-HPLC (Delta Pak C18, 5 μm, 300 A, 15 cm; 5%–85% acetonitrile-0.1M ammonium acetate over 10 min, 1 mL/min) Rt 8.9 min. MS: MH$^+$ 500.

Example 310 o) Amine: 4-Piperidylmethanol 1-{3-[4-Amino-3-(4-phenoxyphenyl)-1H-pyrazolo[3,4-d]pyrimidin-1-yl]-1-azetanyl}-2-[4-(hydroxymethyl)piperidino]-1-ethanone $^1$H NMR (Chloroform-d, 400 MHz) δ 8.36 (s, 1H), 7.67 (d, 2H), 7.41 (m, 2H), 7.18 (m, 3H), 7.10 (m, 2H), 5.78 (m, 1H), 5.64 (br, 2H), 4.89 (m, 1H), 4.81 (m, 1H), 4.62 (m, 1H), 4.55 (m, 1H), 3.49 (m, 2H), 3.13 (s, 2H), 2.97 (m, 2H), 2.10 (m, 2H), 1.74 (m, 2H), 1.49 (br, 1H), 1.30 (m, 2H). RP-HPLC (Delta Pak C18, 5 μm, 300 A, 15 cm; 5%–85% acetonitrile-0.1M ammonium acetate over 10 min, 1 mL/min) Rt 9.0 min. MS: MH$^+$ 514.

Example 311 p) Amine: 1-(2-Methoxyethyl)piperazine 1-{3-[4-Amino-3-(4-phenoxyphenyl)-1H-pyrazolo[3,4-d]pyrimidin-1-yl]-1-azetanyl}-2-[4-(2-methoxyethyl)piperidino]-1-ethanone $^1$H NMR (DMSO-d$_6$, 400 MHz) δ 8.26 (s, 1H), 7.71 (d, 2H), 7.42 (m, 2H), 7.18 (m, 5H), 5.69 (m, 1H), 4.73 (m, 2H), 4.38 (m, 2H), 3.39 (t, 2H), 3.30 (s, 2H), 3.21 (s, 3H), 3.05 (m, 2H), 2.43 (br, 8H). RP-HPLC (Delta Pak C18, 5 μm, 300 A, 15 cm; 5%–85% acetonitrile-0.1M ammonium acetate over 10 min, 1 mL/min) Rt 9.0 min. MS: MH$^+$ 543.

Example 312 q) Amine: Morpholine 1-{3-[4-Amino-3-(4-phenoxyphenyl)-1H-pyrazolo[3,4-d]pyrimidin-1-yl]-1-azetanyl}-2-morpholino-1-ethanone $^1$H NMR (DMSO-d$_6$, 400 MHz) δ 8.26 (s, 1H), 7.70 (d, 2H), 7.42 (m, 2H), 7.18 (m, 5H), 5.70 (m, 1H), 4.73 (m, 2H), 4.40 (m, 2H), 3.57 (m, 4H), 3.08 (m, 2H), 2.44 (m, 4H). RP-HPLC (Delta Pak C18, 5 μm, 300 A, 15 cm; 5%–85% acetonitrile-0.1M ammonium acetate over 10 min, 1 mL/min) Rt 9.6 min. MS: MH$^+$ 486.

Example 313 r) Amine: 1-Methylpiperazine 1-{3-[4-Amino-3-(4-phenoxyphenyl)-1H-pyrazolo[3,4-d]pyrimidin-1-yl]-1-azetanyl}-2-(4-methylpiperazino)-1-ethanone $^1$H NMR (DMSO-d$_6$, 400 MHz) δ 8.26 (s, 1H), 7.70 (d, 2H), 7.44 (m, 2H), 7.16 (m, 5H), 5.70 (m, 1H), 4.70 (m, 2H), 4.35 (m, 2H), 3.29 (s, 2H), 3.06 (m, 2H), 2.45 (br, 6H), 2.16 (s, 3H). RP-HPLC (Delta Pak C18, 5 μm, 300 A, 15 cm; 5%–85% acetonitrile-0.1M ammonium acetate over 10 min, 1 mL/min) Rt 9.0 min. MS: MH$^+$ 499.

Example 314 s) Amine: 4-Piperidinopiperidine 1-{3-[4-Amino-3-(4-phenoxyphenyl)-1H-pyrazolo[3,4-d]pyrimidin-1-yl]-1-azetanyl}-2-[4-(piperid-1-yl)piperidino]-1-ethanone $^1$H NMR (DMSO-d$_6$, 400 MHz) δ 8.26 (s, 1H), 7.70 (d, 2H), 7.44 (m, 2H), 7.18 (m, 5H), 5.70 (m, 1H), 4.73 (m, 2H), 4.40 (m, 1H), 4.30 (m, 1H), 2.88 (m, 4H), 2.38 (br, 4H), 2.13 (m, 1H), 2.00 (m, 2H), 1.61 (br, 2H), 1.43 (br, 6H), 1.34 (br, 2H). RP-HPLC (Delta Pak C18, 5 μm, 300 A, 15 cm; 5%–85% acetonitrile-0.1M ammonium acetate over 10 min, 1 mL/min) Rt 9.2 min. MS: MH$^+$ 567.

Example 315 t) Amine: 1H-Imidazole 1-{3-[4-Amino-3-(4-phenoxyphenyl)-1H-pyrazolo[3,4-d]pyrimidin-1-yl]-1-azetanyl}-2-(1H-1-imidazolyl)-1-ethanone $^1$H NMR (Chloroform-d, 400 MHz) δ 8.31 (s, 1H), 7.87 (br, 1H), 7.65 (d, 2H), 7.41 (m, 2H), 7.18 (m, 4H), 7.10 (m, 3H), 5.90 (br, 2H), 5.80 (m, 1H), 4.82 (m, 1H), 4.72 (m, 3H), 4.59 (m, 1H), 4.47 (m, 1H). RP-HPLC (Delta Pak C18, 5 μm, 300 A, 15 cm; 5%–85% acetonitrile-0.1M ammonium acetate over 10 min, 1 mL/min) Rt 9.2 min. MS: MH$^+$ 467.

Example 316

1-{3-[4-Amino-3-(4-phenoxyphenyl)-1H-pyrazolo[3,4-d]pyrimidin-1-yl]-1-azetanyl}-2-(methylamino)-1-ethanone Acetate A mixture of 1-(3-azetanyl)-3-(4-phenoxyphenyl)-1H-pyrazolo[3,4-d]pyrimidin-4-amine (0.05 g, 0.00014 mol), 2-[(tert-butoxycarbonyl)(methyl)amino]acetic acid (0.0033 g, 0.000175 mol), 1-(3-dimethylaminopropyl)-3-ethylcarbodiimide hydrochloride (0.0034 g, 0.000175 mol), N,N'-diisopropylethylamine (0.033 g, 0.00026 mol) and 1-hydroxy-7-azabenzotriazole (0.019 g, 0.00014 mol) in anhydrous N,N-dimethylformamide (6 mL) was stirred for eighteen hours at room temperature. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield tert-butyl N-(2-{3-[4-amino-3-(4-phenoxyphenyl)-1H-pyrazolo[3,4-d]pyrimidin-1-yl]-1-azetanyl}-2-oxoethyl)-N-methylcarbamate. The solid was dissolved in dichloromethane (2 mL) and a 25% solution of trifluoroacetic acid in dichloromethane (4 mL) was slowly added to the reaction at 0° C. The reaction mixture was stirred for 5 hours at room temperature. The solvent was removed under reduced pressure. A 5 N aqueous solution of sodium hydroxide was added to pH 11 at 0° C. The water phase was extracted with dichloromethane (2×30 mL). The combined organic extracts were washed with water (1×60 mL) and brine (1×60 mL) and dried over sodium sulfate. The solvent was removed under reduced pressure to yield 1-{3-[4-amino-3-(4-phenoxyphenyl)-1H-pyrazolo[3,4-d]pyrimidin-1-yl]-1-azetanyl}-2-(dimethylamino)-1-ethanone acetate (0.022 g, 0.00004 mol).

$^1$H NMR (DMSO-d$_6$, 400 MHz) δ 8.27 (s, 1H), 7.69 (d, 2H), 7.42 (m, 2H), 7.15 (m, 5H), 5.75 (m, 1H), 4.70 (m, 1H), 4.60 (m, 1H), 4.40 (m, 1H), 4.35 (m, 1H), 3.18 (s, 2H), 2.25 (s, 3H), 1.90 (s, 3H). RP-HPLC (Delta Pak C18, 5 µm, 300 A, 15 cm; 5%–85% acetonitrile-0.1M ammonium acetate over 10 min, 1 mL/min) Rt 8.9 min. MS: MH$^+$ 430.

Example 317

1-{3-[4-Amino-3-(4-phenoxyphenyl)-1H-pyrazolo[3,4-d]pyrimidin-1-yl]-1-azetanyl}-2-(dimethylamino)-1-ethanone Acetate A mixture of 1-(3-azetanyl)-3-(4-phenoxyphenyl)-1H-pyrazolo[3,4-d]pyrimidin-4-amine (0.05 g, 0.00014 mol), 2-(dimethylamino)acetic acid (0.0018 g, 0.000175 mol), 1-(3-dimethylaminopropyl)-3-ethylcarbodiimide hydrochloride (0.0034 g, 0.000175 mol), N,N'-diisopropylethylamine (0.033 g, 0.00026 mol) and 1-hydroxy-7-azabenzotriazole (0.019 g, 0.00014 mol) in anhydrous N,N-dimethylformamide (6 mL) was stirred for eighteen hours at room temperature. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield 1-{3-[4-amino-3-(4-phenoxyphenyl)-1H-pyrazolo[3,4-d]pyrimidin-1-yl]-1-azetanyl}-2-(dimethylamino)-1-ethanone acetate (0.022 g, 0.00004 mol).

$^1$H NMR (DMSO-d$_6$, 400 MHz) δ 8.27 (s, 1H), 7.69 (d, 2H), 7.42 (m, 2H), 7.15 (m, 5H), 5.69 (m, 1H), 4.70 (m, 2H), 4.40 (m, 2H), 2.97 (m, 2H), 2.20 (s, 6H), 1.89 (s, 3H). RP-HPLC (Delta Pak C18, 5 µm, 300 A, 15 cm; 5%–85% acetonitrile-0.1M ammonium acetate over 10 min, 1 mL/min) Rt 9.6 min. MS: MH$^+$ 444.

Example 318

1-{3-[4-Amino-3-(4-phenoxyphenyl)-1H-pyrazolo[3,4-d]pyrimidin-1-yl]-1-azetanyl}-3-(diethylamino)-1-propanone A mixture of 1-(3-azetanyl)-3-(4-phenoxyphenyl)-1H-pyrazolo[3,4-d]pyrimidin-4-amine (0.05 g, 0.00014 mol), 3-(diethylamino)propionic acid hydrochloride (0.0032 g, 0.000175 mol), 1-(3-dimethylaminopropyl)-3-ethylcarbodiimide hydrochloride (0.0034 g, 0.000175 mol), N,N'-diisopropylethylamine (0.068 g, 0.00053 mol) and 1-hydroxy-7-azabenzotriazole (0.019 g, 0.00014 mol) in anhydrous N,N-dimethylformamide (6 mL) was stirred for 18 hours at room temperature. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield 1-{3-[4-amino-3-(4-phenoxyphenyl)-1H-pyrazolo[3,4-d]pyrimidin-1-yl]-1-azetanyl}-3-(diethylamino)-1-propanone (0.025 g, 0.00005 mol).

$^1$H NMR (DMSO-d$_6$, 400 MHz) δ 8.26 (s, 1H), 7.69 (d, 2H), 7.44 (m, 2H), 7.14 (m, 5H), 5.70 (m, 1H), 4.67 (m, 2H), 4.37 (m, 2H), 2.66 (m, 2H), 2.45 (m, 4H), 2.21 (m, 2H), 0.95 (m, 6H). RP-HPLC (Delta Pak C18, 5 µm, 300 A, 15 cm; 5%–85% acetonitrile-0.1M ammonium acetate over 10 min, 1 mL/min) Rt 9.3 min. MS: MH$^+$ 486.

Example 319

1-{4-[4-Amino-3-(4-phenoxyphenyl)-1H-pyrazolo[3,4-d]pyrimidin-1-yl]piperidino}-2-(methylamino)-1-ethanone Acetate A mixture of 3-(4-phenoxyphenyl)-1-(4-piperidyl)-1H-pyrazolo[3,4-d]pyrimidin-4-amine (0.054 g, 0.00014 mol), 2-[(tert-butoxycarbonyl)(methyl)amino]acetic acid (0.0033 g, 0.000175 mol), 1-(3-dimethylaminopropyl)-3-ethylcarbodiimide hydrochloride (0.0034 g, 0.000175 mol), N,N'-diisopropylethylamine (0.033 g, 0.00026 mol) and 1-hydroxy-7-azabenzotriazole (0.019 g, 0.00014 mol) in anhydrous N,N-dimethylformamide (6 mL) was stirred for eighteen hours at room temperature. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield tert-butyl N-(2-{4-[4-amino-3-(4-phenoxyphenyl)-1H-pyrazolo[3,4-d]pyrimidin-1-yl]piperidino}-2-oxoethyl)-N-methylcarbamate. The solid was dissolved in dichloromethane (2 mL) and 25% trifluoroaceticacid in dichloromethane (4 mL) was slowly added into the reaction at 0° C. The reaction mixture was stirred for 5 hours at room temperature. The solvent was removed under reduced pressure. To the residue a 5 N aqueous solution of sodium hydroxide was addded to pH 11 at 0° C. The water phase was extracted with dichloromethane (2×30 mL). The combined organic extracts were washed with water (1×60 mL) and brine (1×60 mL) and dried over sodium sulfate. The solvent was removed under reduced pressure to yield 1-{4-[4-amino-3-(4-phenoxyphenyl)-1H-pyrazolo[3,4-d]pyrimidin-1-yl]piperidino}-2-(methylamino)-1-ethanone acetate (0.010 g, 0.00002 mol).

$^1$H NMR (DMSO-d$_6$, 400 MHz) δ 8.25 (s, 1H), 7.67 (d, 2H), 7.45 (m, 2H), 7.13 (m, 5H), 4.94 (br, 1H), 4.53 (br, 1H), 3.99 (br, 1H), 3.36 (m, 2H), 3.21 (br, 1H), 2.85 (br, 1H), 2.26 (s, 3H), 2.10 (br, 1H), 1.96 (br, 3H), 1.85 (s, 3H). RP-HPLC (Delta Pak C18, 5 µm, 300 A, 15 cm; 5%–85% acetonitrile-0.1M ammonium acetate over 10 min, 1 mL/min) Rt 9.1 min. MS: MH$^+$ 458.

Example 320

1-{4-[4-Amino-3-(4-phenoxyphenyl)-1H-pyrazolo[3,4-d]pyrimidin-1-yl]piperidino}-2-(dimethylamino)-1-ethanone A mixture of 3-(4-phenoxyphenyl)-1-(4-piperidyl)-1H-pyrazolo[3,4-d]pyrimidin-4-amine (0.054 g, 0.00014 mol), 2-(dimethylamino)acetic acid (0.0018 g, 0.000175 mol), 1-(3-dimethylaminopropyl)-3-ethylcarbodiimide hydrochloride (0.0034 g, 0.000175 mol), N,N'-diisopropylethylamine (0.033 g, 0.00026 mol) and 1-hydroxy-7-azabenzotriazole (0.019 g, 0.00014 mol) in anhydrous N,N-dimethylformamide (6 mL) was stirred for eighteen hours at room temperature. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield 1-{4-[4-amino-3-(4-phenoxyphenyl)-1H-pyrazolo[3,4-d]pyrimidin-1-yl]piperidino}-2-(dimethylamino)-1-ethanone (0.031 g, 0.00007 mol).

$^1$H NMR (DMSO-d$_6$, 400 MHz) δ 8.25 (s, 1H), 7.67 (d, 2H), 7.42 (m, 2H), 7.15 (m, 5H), 4.97 (br, 1H), 4.50 (br, 1H), 4.22 (br, 1H), 3.25 (br, 1H), 3.12 (m, 2H), 2.83 (br, 1H), 2.21 (s, 6H), 2.16 (br, 1H), 1.90 (br, 3H). RP-HPLC (Delta Pak C18, 5 μm, 300 A, 15 cm; 5%–85% acetonitrile-0.1M ammonium acetate over 10 min, 1 mL/min) Rt 9.3 min. MS: MH$^+$ 472.

Example 321

1-{4-[4-Amino-3-(4-phenoxyphenyl)-1H-pyrazolo[3,4-d]pyrimidin-1-yl]piperidino}-3-(diethylamino)-1-propanone Acetate A mixture of 3-(4-phenoxyphenyl)-1-(4-piperidyl)-1H-pyrazolo[3,4-d]pyrimidin-4-amine (0.054 g, 0.00014 mol), 3-(diethylamino)propionic acid hydrochloride (0.0032 g, 0.000175 mol), 1-(3-dimethylaminopropyl)-3-ethylcarbodiimide hydrochloride (0.0034 g, 0.000175 mol), N,N'-diisopropylethylamine (0.068 g, 0.00053 mol) and 1-hydroxy-7-azabenzotriazole (0.019 g, 0.00014 mol) in anhydrous N,N-dimethylformamide (6 mL) was stirred for eighteen hours at room temperature. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield 1-{4-[4-amino-3-(4-phenoxyphenyl)-1H-pyrazolo[3,4-d]pyrimidin-1-yl]piperidino}-3-(diethylamino)-1-propanone acetate (0.038 g, 0.00006 mol).

$^1$H NMR (DMSO-d$_6$, 400 MHz) δ 8.25 (s, 1H), 7.67 (d, 2H), 7.42 (m, 2H), 7.15 (m, 5H), 4.97 (br, 1H), 4.52 (br, 1H), 4.03 (br, 1H), 3.27 (br, 1H), 2.80 (br, 1H), 2.66 (m, 2H), 2.49 (m, 8H), 2.11 (br, 1H), 1.95 (br, 3H), 1.87 (s, 3H), 0.93 (m, 6H). RP-HPLC (Delta Pak C18, 5 μm, 300 A, 15 cm; 5%–85% acetonitrile-0.1M ammonium acetate over 10 min, 1 mL/min) Rt 9.7 min. MS: MH$^+$ 514.

General Procedure

To a mixture of 3-(4-phenoxyphenyl)-1-(4-piperidyl)-1H-pyrazolo[3,4-d]pyrimidin-4-amine (0.05 g, 0.00013 mol, 1 eq.) and potassium carbonate (0.036 g, 0.00026 mol, 2 eq.) in anhydrous N,N-dimethylformamide (3 mL) was added chloroacetylchloride (0.028 g, 0.00026 mol, 2 eq.) at room temperature. The mixture was stirred for ten min. before the amine (0.0013 mol, 10 eq.) was added. The mixture was stirred at room temperature from three hours. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 μm, 250×21.1 mm; 5%–100% over 35 min with 0.1M ammonium acetate, 21 mL/min) to yield the corresponding acetamides.

Example 322 a) Amine: Morpholine 1-{4-[4-Amino-3-(4-phenoxyphenyl)-1H-pyrazolo[3,4-d]pyrimidin-1-yl]piperidino}-2-morpholino-1-ethanone Acetate $^1$H NMR (DMSO-d$_6$, 400 MHz) δ 8.24 (s, 1H), 7.65 (d, 2H), 7.44 (m, 2H), 7.16 (m, 5H), 4.99 (m, 1H), 4.47 (br, 1H), 4.19 (br, 1H), 3.58 (m, 4H), 3.25 (m, 2H), 3.11 (m, 1H), 2.83 (br, 1H), 2.43 (m, 4H), 2.25 (br, 1H), 1.99 (br, 3H), 1.89 (s, 3H). RP-HPLC (Delta Pak C18, 51m, 300 A, 15 cm; 5%–85% acetonitrile-0.1M ammonium acetate over 10 min, 1 mL/min) Rt 9.7 min. MS: MH$^+$ 514.

Example 323 b) Amine: 1-Methylpiperazine 1-{4-[4-Amino-3-(4-phenoxyphenyl)-1H-pyrazolo[3,4-d]pyrimidin-1-yl]piperidino}-2-(4-methylpiperazino)-1-ethanone Acetate $^1$H NMR (DMSO-d$_6$, 400 MHz) δ 8.24 (s, 1H), 7.65 (d, 2H), 7.44 (m, 2H), 7.16 (m, 5H), 4.99 (m, 1H), 4.47 (br, 1H), 4.19 (br, 1H), 3.29 (m, 2H), 3.22 (m, 2H), 3.05 (m, 1H), 2.80 (br, 1H), 2.33 (br, 6H), 2.22 (br, 1H), 2.13 (s, 3H), 1.94 (br, 3H), 1.89 (s, 3H). RP-HPLC (Delta Pak C18, 5 μm, 300 A, 15 cm; 5%–85% acetonitrile-0.1M ammonium acetate over 10 min, 1 mL/min) Rt 9.3 min. MS: MH$^+$ 527.

Example 324 and Example 325 cis and trans 2-{4-[4-Amino-3-(4-phenoxyphenyl)-1H-pyrazolo[3,4-d]pyrimidin-1-yl]-1-hydroxycyclohexyl}acetic Acid a) cis and trans tert-Butyl 2-{4-[4-Amino-3-(4-phenoxyphenyl)-1H-pyrazolo[3,4-d]pyrimidin-1-yl]-1-hydroxycyclohexyl}acetate A suspension of acid washed zinc dust (0.350 g, 0.00535 mol) and cuprous chloride (0.053 g, 0.000535 mol) in anhydrous tetrahydrofuran (10 mL) was heated at reflux for thirty minutes. The heat was discontinued and a portion (1 mL) of a solution of tert-butyl 2-bromoacetate (0.261 g, 0.00134 mol) in tetrahydrofuran (10 mL) was added immediately. The mixture was stirred five minutes, and then the remainder of the mixture was added dropwise. The mixture was heated at reflux for thirty minutes. The mixture was cooled to room temperature and a solution of 4-(4-amino-3-(4-phenoxyphenyl)-1H-pyrazolo[3,4-d]pyrimidin-1-yl)-1-cyclohexanone (0.200 g, 0.00053 mol) in anhydrous tetrahydrofuran (5 mL) was added dropwise over five minutes. The mixture was stirred at room temperature four hours. The unreacted zinc was removed by filtration, washing with ether (3×5 mL). The filtrate was washed with water (3×5 mL) and brine (10 mL). The organic layer was dried over magnesium sulfate, and the solvent was removed in vacuo. The crude material had a cis:trans ratio of 1:1. The isomers were separated by flash column chromatography on silica using dichloromethane/methanol (98:2). The solvent was removed in vacuo to give the less polar trans tert-butyl 2-{4-[4-amino-3-(4-phenoxyphenyl)-1H-pyrazolo[3,4-d]pyrimidin-1-yl]-1-hydroxycyclohexyl}acetate as a white solid (0.092 g, 0.00018 mol) and the more polar cis tert-butyl 2-{4-[4-amino-3-(4-phenoxyphenyl)-1H-pyrazolo[3,4-d]pyrimidin-1-yl]-1-hydroxycyclohexyl}acetate as a white solid (0.049 g, 0.000096 mol).

cis tert-Butyl 2-{4-[4-Amino-3-(4-phenoxyphenyl)-1H-pyrazolo[3,4-d]pyrimidin-1-yl]-1-hydroxycyclohexyl}acetate $^1$H NMR (DMSO-d$_6$, 400 MHz) δ 8.23 (s, 1H), 7.66 (d, 2H), 7.43 (t, 2H), 7.11–7.20 (m, 5H), 4.70–4.84 (m, 1H), 2.36 (s, 2H), 1.89–2.12 (m, 4H), 1.51–1.67 (m, 2H), 1.43 (s, 9H), 1.37–1.42 (m, 4H). RP-HPLC (Delta Pak C18, 5 μm, 300 A, 15 cm; 5%–85% acetonitrile-0.1M ammonium acetate over 20 min, 1 mL/min) $R_t$ 19.31 min.; MS: $MH^+$ 516.

trans tert-Butyl 2-{4-[4-Amino-3-(4-phenoxyphenyl)-1H-pyrazolo[3,4-d]pyrimidin-1-yl]-1-hydroxycyclohexyl}acetate $^1$H NMR (DMSO-$d_6$, 400 MHz) δ 8.23 (s, 1H), 7.66 (d, 2H), 7.43 (t, 2H), 7.11–7.20 (m, 5H), 4.45–4.61 (m, 1H), 2.36 (s, 2H), 1.78–1.85 (m, 2H), 1.64–1.71 (m, 2H), 1.43 (s, 9H), 1.36–1.45 (m, 4H). RP-HPLC (Delta Pak C18, 5 μm, 300 A, 15 cm; 5%–85% acetonitrile-0.1M ammonium acetate over 20 min, 1 mL/min) $R_t$ 19.64 min.; MS: $MH^+$ 516.

cis 2-{4-[4-Amino-3-(4-phenoxyphenyl)-1H-pyrazolo[3,4-d]pyrimidin-1-yl]-1-hydroxycyclohexyl}acetic Acid Cis tert-butyl 2-{4-[4-amino-3-(4-phenoxyphenyl)-1H-pyrazolo[3,4-d]pyrimidin-1-yl]-1-hydroxycyclohexyl}acetate (0.092 g, 0.000178 mol) was reacted with a solution of 20% trifluoroacetic acid in dichloromethane (10 mL) at room temperature under a nitrogen atmosphere for forty-five minutes. The solvent was removed in vacuo and the residue was dissolved in ethyl acetate (25 mL) and washed with water (3×10 mL). The solution was dried over magnesium sulfate and the solvent was removed in vacuo. The residue was suspended in water (25 mL) and lyopholyzed to give cis 2-{4-[4-amino-3-(4-phenoxyphenyl)-1H-pyrazolo[3,4-d]pyrimidin-1-yl]-1-hydroxycyclohexyl}acetic acid as a white powder (0.078 g, 0.000170 mol).

$^1$H NMR (DMSO-$d_6$, 400 MHz) δ 8.32 (s, 1H), 7.66 (d, 2H), 7.44 (t, 2H), 7.11–7.22 (m, 5H), 4.62–4.67 (m, 1H), 2.39 (s, 2H), 2.27–2.43 (m, 2H), 1.55–1.90 (m, 6H). RP-HPLC (Delta Pak C18, 51m, 300 A, 15 cm; 5%–85% acetonitrile-0.1M ammonium acetate over 20 min, 1 mL/min) $R_t$ 13.65 min. MS: $MH^+$ 460.

trans 2-{4-[4-Amino-3-(4-phenoxyphenyl)-1H-pyrazolo[3,4-d]pyrimidin-1-yl]-1-hydroxycyclohexyl}acetic Acid Trans tert-butyl 2-(4-[4-amino-3-(4-phenoxyphenyl)-1H-pyrazolo[3,4-d]pyrimidin-1-yl]-1-hydroxycyclohexyl}acetate (0.049 g, 0.000096 mol) was reacted with a solution of 20% trifluoroacetic acid in dichloromethane (10 mL) at room temperature under a nitrogen atmosphere for forty-five minutes. The solvent was removed in vacuo and the residue was dissolved in ethyl acetate (25 mL) and washed with water (3×10 mL). The solution was dried over magnesium sulfate and the solvent was removed in vacuo. The residue was suspended in water (25 mL) and lyopholyzed to give trans 2-{4-[4-amino-3-(4-phenoxyphenyl)-1H-pyrazolo[3,4-d]pyrimidin-1-yl]-1-hydroxycyclohexyl}acetic acid as a white powder (0.038 g, 0.000083 mol).

$^1$H NMR (DMSO-$d_6$, 400 MHz) δ 8.36 (s, 1H), 7.67 (d, 2H), 7.44 (t, 2H), 7.11–7.22 (m, 5H), 4.72–4.79 (m, 1H), 1.99 (s, 2H), 1.91–2.09 (m, 6H), 1.61–1.65 (m, 2H). RP-HPLC (Delta Pak C18, 5 μm, 300 A, 15 cm; 5%–85% acetonitrile-0.1M ammonium acetate over 20 min, 1 mL/min) $R_t$ 13.46 min. MS: $MH^+$ 460.

Example 326 trans 1-{3-[(Benzyloxy)methyl]cyclobutyl}-3-(4-phenoxyphenyl)-1H-pyrazolo[3,4-d]pyrimidin-4-amine $^1$H NMR (DMSO-$d_6$, 400 Hz) δ 8.23 (s, 1H), 7.69 (d, 2H), 7.44 (t, 2H), 7.37–7.39 (m, 4H), 7.29–7.31 (m, 1H), 7.11–7.21 (m, 5H), 5.42–5.47 (m, 1H), 4.57 (s, 1H), 3.63 (d, 2H), 2.76–2.81 (m, 2H), 2.60–2.70 (m, 1H), 2.28–2.34 (m, 2H). RP-HPLC (Delta Pak C18, 5 μm, 300 A, 15 cm; 5%–85% acetonitrile-0.1M ammonium acetate over 20 min, 1 mL/min) $R_t$ 21.92 min. MS: $MH^+$ 478.

Example 327

[3-[4-Amino-3-(4-phenoxyphenyl)-1H-pyrazolo[3,4-d]pyrimidin-1-yl]-1-(hydroxymethyl)cyclobutyl]methanol a) Diethyl 3-[(Methylsulfonyl)oxy]-1,1-cyclobutanedicarboxylate.

A solution of diethyl 3-hydroxy-1,1-cyclobutanedicarboxylate (0.268 g, 0.00116 mol) in pyridine (7 mL) was cooled to 0° C. Methanesulfonyl chloride (0.11 mL, 0.160 g, 0.00140 mol) was added dropwise, keeping the temperature below 2° C. The mixture was stirred for four hours, and then poured into ice water (20 mL) and extracted with ethyl ether (2×10 mL). The combined organic layers were washed with water (3×10 mL) and brine (10 mL). The organic layer was dried over magnesium sulfate and the solvent was removed in vacuo to give diethyl 3-[(methylsulfonyl)oxy]-1,1-cyclobutanedicarboxylate (0.302 g, 0.00102 mol) as a yellow oil.:

$^1$H NMR (CDCl$_3$, 400 MHz) 5.08–5.11 (m, 1H), 4.23 (q, 4H), 3.01 (s, 3H), 2.98–3.03 (m, 2H), 2.81–2.86 (m, 2H), 1.27 (t, 6H).

b) Diethyl 3-[4-Amino-3-(4-phenoxyphenyl)-1H-pyrazolo[3,4-d]pyrimidin-1-yl]-1,1-cyclobutanedicarboxylate A solution of 3-(4-phenoxyphenyl)-1H-pyrazolo[3,4-d]pyrimidin-4-amine (0.129 g, 0.00042 mmol) in N,N-dimethylformamide (5 mL) was reacted with diethyl 3-[(methylsulfonyl)oxy]-1,1-cyclobutanedicarboxylate (0.150 g, 0.00051 mmol) and cesium carbonate (0.166 g, 0.00051 mmol) at 70° C. for five days. The reaction mixture was poured into water (20 mL) and extracted with ethyl acetate (3×10 mL). The combined organic layers were washed with water (2×10 mL) and brine (10 mL). The organic layer was dried over magnesium sulfate and the solvent was removed in vacuo. The residue was purified by flash column chromatography on silica using dichloromethane/methanol (98:2). The solvent was removed in vacuo to give diethyl 3-[4-amino-3-(4-phenoxy-phenyl)-1H-pyrazolo[3,4-d]pyrimidin-1-yl]-1,1-cyclobutanedicarboxylate (0.060 g, 0.00012 mol) as a tan solid.

$^1$H NMR (DMSO-$d_6$, 400 MHz) δ 8.24 (s, 1H), 7.67 (d, 2H), 7.44 (t, 2H), 7.12–7.21 (m, 5H), 5.38–5.42 (m, 1H), 4.16–4.28 (m, 4H), 3.14–3.17 (m, 2H), 2.96–3.00 (m, 2H), 1.17–1.28 (m, 6H).

c) [3-[4-Amino-3-(4-phenoxyphenyl)-1H-pyrazolo[3,4-d]pyrimidin-1-yl]-1-(hydroxymethyl)cyclobutyl]methanol To a solution of diethyl 3-[4-amino-3-(4-phenoxyphenyl)-1H-pyrazolo[3,4-d]pyrimidin-1-yl]-1,1-cyclobutanedicarboxylate (0.045 g, 0.000089 mol) in tetrahydrofuran (10 mL) lithium aluminum hydride (0.010 g, 0.000270 mol) was added. The reaction mixture was stirred six hours at ambient temperature, after which time water (1.0 mL) was added. The mixture was filtered through a pad of Celite® 521. The solvent was removed from the filtrate in vacuo. The residue was partitioned between water (15 mL) and ethyl acetate (15 mL). The aqueous layer was extracted with ethyl acetate (3×10 mL). The combined organic layers were dried over magnesium sulfate and the solvent was removed in vacuo. The residue was purified by preparative RP-HPLC (Rainin C18, 8 μm, 300 A, 25 cm; 40% isocratic for five minutes, then 40%–100% acetonitrile-0.1M ammonium acetate over 30 min, 21 ml/min). The acetonitrile was removed in vacuo and the aqueous mixture was lyopholyzed to [3-[4-amino-3-(4-phenoxyphenyl)-1H-pyrazolo[3,4-d]pyrimidin-1-yl]-1-(hydroxymethyl)cyclobutyl]methanol as a white solid (0.007 g, 0.000017 mol):

$^1$H NMR (DMSO-d$_6$, 400 MHz) δ 8.22 (s, 1H), 7.68 (d, 2H), 7.44 (t, 2H), 7.11–7.20 (m, 5H), 5.28–5.34 (m, 1H), 4.76 (t, 1H), 4.58 (t, 1H), 3.55 (d, 2H) 3.47 (d, 2H), 2.46–2.55 (m, 2H), 2.24–2.31 (m, 2H). RP-HPLC (Delta Pak C18, 5 μm, 300 A, 15 cm; 5%–85% acetonitrile-0.1M ammonium acetate over 20 min, 1 mL/min) R$_t$ 13.81 min. MS: MH$^+$ 418.

Examples 328–334

General Procedure for the Synthesis of Aryl Alkyl cis-3-(4-Amino-3-fluorophenyl)-1-[4-(4-methylpiperazino)cyclohexyl]-1H-pyrazolo[3,4-d]pyrimidin-4-amine Analogs These compounds were synthesized using the procedure previously described for the synthesis of aryl alkyl cis-3-(4-Amino-3-fluorophenyl)-1-[4-(4-methylpiperazino)cyclohexyl]-1H-pyrazolo[3,4-d]pyrimidin-4-amine analogs.

| Ex | Structure | m/z (MH$^+$) | HPLC Rt (min) |
|---|---|---|---|
| 329 | 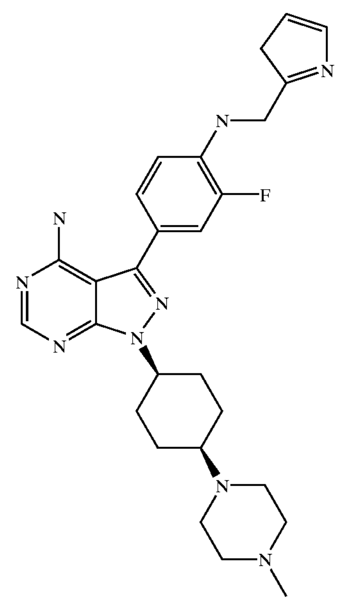 | 505.3 | 12.05 |
| 330 | 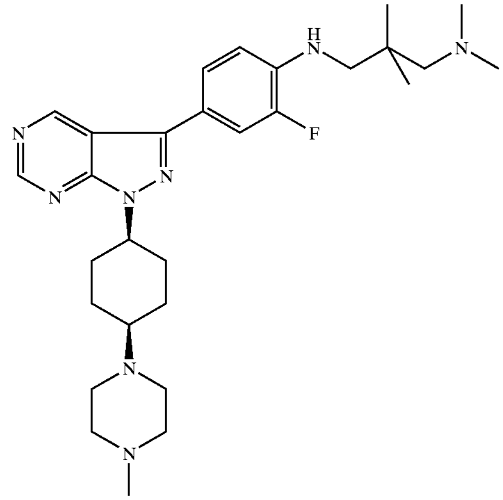 | 538.4 | 9.27 |

-continued

| Ex | Structure | m/z (MH+) | HPLC Rt (min) |
|---|---|---|---|
| 331 | 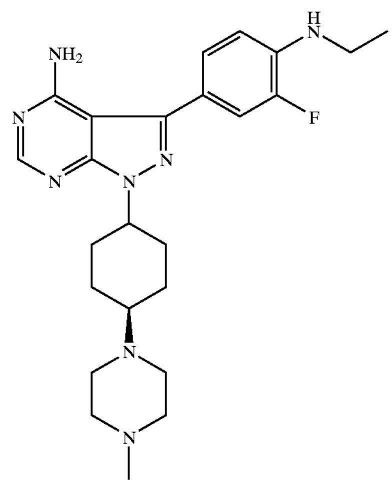 | 453.2 | 11.16 |
| 332 | 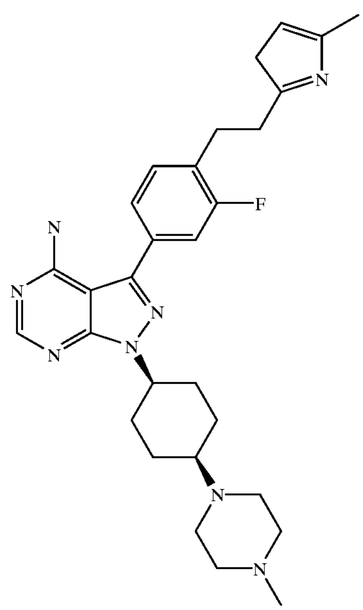 | 519.1 | 12.95 |

| Ex | Structure | m/z (MH⁺) | HPLC Rt (min) |
|---|---|---|---|
| 333 | 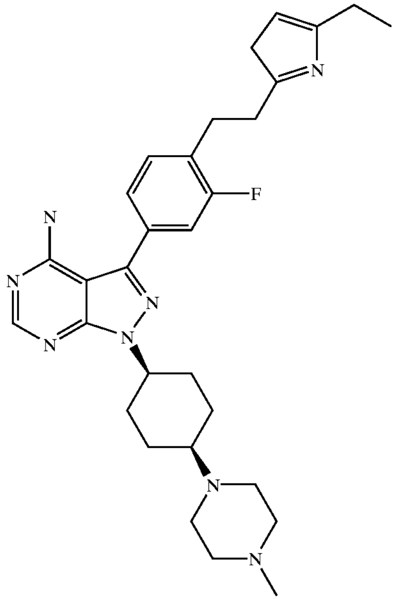 | 535.3 | 10.57 |
| 334 | 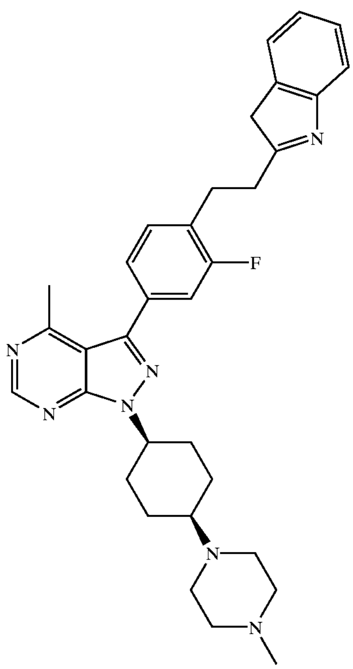 | 555.3 | 14.08 |

Example 335

N2-(4-{4-Amino-1-[4-(4-methylpiperazino)cyclohexyl]-1H-pyrazolo[3,4-d]pyrimidin-3-yl}-2-fluorophenyl)-5-chloro-2-thiophenesulfonamide Maleate Salt This compound was synthesized as the maleate salt using the procedure previously described for cis and trans-3-(4-Amino-3-fluorophenyl)-1-[4-(4-methylpiperazino)cyclohexyl]-1H-pyrazolo[3,4-d]pyrimidin-4-amine HPLC-RT: 12.39 min. (flow rate: 1 mL/min, λ=254 nm Gradient: 5% to 85% acetonitrile/0.1M aqueous ammonium acetate gradient over 20 min.; Deltapak C18, 300 Å, 5 μm, 150×3.9 mm column); m/z (MH⁺)=606.1.

Example 336

1-(4-{4-Amino-3-[4-(1,3-benzoxazol-2-ylamino)-3-fluorophenyl]-1H-pyrazolo[3,4-d]pyrimidin-1-yl}piperidino)-2-(dimethylamino)-1-ethanone a). tert-Butyl 4-Hydroxy-1-piperidinecarboxylate tert-Butyl 4-oxo-1-piperidinecarboxylate (20 g, 100.4 mmol) was dissolved in methanol (250 mL) then cooled to 0° C. and sodium borohydride (3.8 g, 100.4 mmol) was added over 10 min. The reaction mixture was warmed from 0° C. to room temperature. After 4 hours, the reaction was concentrated under reduced pressure and the remaining syrup was dissolved in 3:1 dichloromethane/isopropanol (400 mL). The organic layer was washed with aqueous 1N sodium hydroxide (200 mL). The aqueous layer was then extracted with 3:1 dichloromethane/isopropanol (3×150 mL). The organic layers were washed with brine (400 mL) then dried over anhydrous sodium sulfate and concentrated under reduced pressure to yield tert-butyl 4-hydroxy-1-piperidinecarboxylate as a light yellow syrup (20 g, 100.4 mmol). $^1$H NMR ($d_6$-DMSO): δ 1.21–1.28 (m, 2H), 1.38 (s, 9H), 1.65–1.69 (m, 2H), 2.94–2.96 (m, 2H), 3.59–3.68 (m, 3H), 4.68 (d, 1H).

b). tert-Butyl 4-(4-Amino-3-iodo-1H-pyrazolo[3,4-d]pyrimidin-1-yl)-1-piperidinecarboxylate.

3-Iodo-1H-pyrazolo[3,4-d]pyrimidin-4-amine (17.3 g, 66.33 mmol) was suspended in tetrahydrofuran (800 mL) and a solution of tert-butyl 4-hydroxy-1-piperidinecarboxylate (20 g, 99.5 mmol) in tetrahydrofuran (300 mL) and triphenylphosphine (34.8 g, 132.66 mmol) were added The reaction mixture was cooled to 0° C. and diethyl azodicarboxylate (23.1 g, 132.66 mmol) was added dropwise. After 2 hours at room temperature, the reaction was concentrated under reduced pressure to yield crude tert-butyl 4-(4-amino-3-iodo-1H-pyrazolo[3,4-d]pyrimidin-1-yl)-1-piperidinecarboxylate as an orange oil (69.44 g). HPLC-RT: 14.29 min., 19%, (flow rate: 1 mL/min λ=254 nm Gradient: 5% to 85% acetonitrile/0.1M aqueous ammonium acetate gradient over 20 min.; Deltapak C18, 300 Å, 5μm, 150×3.9 mm column).

c). 3-Iodo-1-(4-piperidyl)-1H-pyrazolo[3,4-d]pyrimidin-4-amine Dihydrochloride Salt.

The crude tert-butyl 4-(4-amino-3-iodo-1H-pyrazolo[3,4-d]pyrimidin-1-yl)-1-piperidinecarboxylate (69.4 g, 156.30 mmol) was dissolved in acetone (900 mL) and 6N aqueous hydrochloric acid (300 mL) was slowly added dropwise. The reaction was then heated at 45° C. which yielded a precipitate. After 1.5 hours, the precipitate was collected by vacuum filtration, washed with minimal acetone and dried on the lyophilizer to yield 3-iodo-1-(4-piperidyl)-1H-pyrazolo[3,4-d]pyrimidin-4-amine dihydrochloride salt as a yellow solid (16.61 g, 39.8 mmol). HPLC-RT: 6.16 min. (flow rate: 1 mL/min λ=254 nm Gradient: 5% to 85% acetonitrile/0.1M aqueous ammonium acetate gradient over 20 min.; Deltapak C18, 300A, 5 μm, 150×3.9 mm column); m/z (MH$^+$)=345.0.

d). 1-[4-(4-Amino-3-iodo-1H-pyrazolo[3,4-d]pyrimidin-1-yl)piperidino]-2-(dimethylamino)-1-ethanone.

3-Iodo-1-(4-piperidyl)-1H-pyrazolo[3,4-d]pyrimidin-4-amine dihydrochloride salt (3 g, 7.19 mmol) was suspended in dichloromethane (350 mL) then N,N-dimethyl glycine (1.02 g, 9.88 mmol), 1-hydroxy-7-azabenzotriazole (1.08 g, 7.91 mmol), 1-(3-dimethylaminopropyl)-3-ethylcarbodiimide hydrochloride (1.89 g, 9.89 mmol), and N-ethyl-N-isopropylamine (5.06 g, 39.2 mmol) were added over 4 days. The reaction was diluted with dichloromethane (300 mL) then washed with water (150 mL) and brine (150 mL). The organic layer was dried over anhydrous sodium sulfate and concentrated under reduced pressure to afford 1-[4-(4-amino-3-iodo-1H-pyrazolo[3,4-d]pyrimidin-1-yl)piperidino]-2-(dimethylamino)-1-ethanone as a tan solid (2.74 g, 6.39 mmol). HPLC-RT: 7.40 min. (flow rate: 1 mL/min λ=254 nm Gradient: 5% to 85% acetonitrile/0.1M aqueous ammonium acetate gradient over 20 min.; Deltapak C18, 300 Å, 5 μm, 150×3.9 mm column); m/z (MH$^+$)=430.3.

e). 1-(4-{4-Amino-3-[4-(1,3-benzoxazol-2-ylamino)-3-fluorophenyl]-1H-pyrazolo[3,4-d]pyrimidin-1-yl}piperidino)-2-(dimethylamino)-1-ethanone.

1-[4-(4-Amino-3-iodo-1H-pyrazolo[3,4-d]pyrimidin-1-yl)piperidino]-2-(dimethylamino)-1-ethanone (100 mg, 0.233 mmol) was dissolved in ethylene glycol dimethylether (10 mL) and water (1.5 mL). N-(1,3-benzoxazol-2-yl)-N-[2-fluoro-4-(4,4,5,5-tetramethyl-1,3,2-dioxaborolan-2-yl)phenyl]amine (103 mg, 0.291 mmol), palladium tetrakistriphenylphosphine (13 mg, 0.051 mmol) and sodium carbonate (62 mg, 0.583 mmol) were added and the reaction was heated at 80° C. for 24 hours. The reaction was concentrated under reduced pressure. The remaining residue was partitioned between dichloromethane (100 mL) and minimal water. The organic layer was concentrated under reduced pressure and triturated with diethylether (25 mL) to yield a yellow-brown solid (172 mg). Purification by RP-HPLC (Waters PrepLC 4000, flow rate: 10 mL/min. λ=254 nm Gradient: 15% to 35% acetonitrile/0.1M aqueous ammonium acetate gradient over 40 minutes; Deltapak C18, 300 Å, 15 μm, 40×100 mm column) afforded 1-(4-{4-amino-3-[4-(1,3-benzoxazol-2-ylamino)-3-fluorophenyl]-1H-pyrazolo[3,4-d]pyrimidin-1-yl}piperidino)-2-(dimethylamino)-1-ethanone as an off-white solid (64 mg, 0.121 mmol). HPLC-RT: 7.27 min. (flow rate: 1 mL/min λ=254 nm Gradient: 5% to 95% acetonitrile/0.1M aqueous ammonium acetate gradient over 20 min.; Waters Symmetry Shield C18, 3.5 μm, 50×2.1 mm column); m/z (MH$^+$)= 530.2.

Example 337

1-(4-{4-Amino-3-[4-(1,3-benzothiazol-2-ylamino)-3-fluorophenyl]-1H-pyrazolo[3,4-d]pyrimidin-1-yl}piperidino)-2-(dimethylamino)-1-ethanone HPLC-RT: 10.09 min. (flow rate: 1 mL/min λ=254 nm Gradient: 5% to 85% acetonitrile/0.1M aqueous ammonium acetate gradient over 20 min.; Deltapak C18, 300 Å, 5 μm, 150×3.9 mm column); m/z (MH$^+$)=546.2.

Examples 338–364 a) Representative procedure for alkylation: Sodium hydride (60%, 0.138 g, 3.45 mmol) was added to a suspension of 3-iodo-1H-pyrazolo[3,4-d]pyrimidin-4-amine (0.750 g, 2.87 mmol) in DMF (9 mL), and the mixture was stirred at ambient temperature for 1 hour until a homogeneous solution was obtained. The alkyl bromide (4.03 mmol) was added, and the mixture was stirred at ambient temperature under an atmosphere of nitrogen for 14 h. The solvent was removed under reduced pressure and the resulting solid was triturated sequentially with water (25 mL) and then ether/petroleum ether (4:1, 50 mL) to yield the product.

b) Representative procedure for Suzuki coupling: A suspension of the aryl iodide (2.28 mmol), tert-butyl N-[2-fluoro-4-(4,4,5,5-tetramethyl-1,3,2-dioxaborolan-2-yl)phenyl]carbamate (1.08 g, 3.19 mmol), tetrakis (triphenylphosphine) palladium (0.1 05 g, 0.091 mmol), sodium bicarbonate (0.478 g, 5.69 mmol) in N,N-dimethylformamide(12 mL) and water (2 mL) was heated at 90° C. for 14 hours under an atmosphere of nitrogen. The solvent was removed under reduced pressure, and the residue was partitioned between saturated aqueous sodium chloride (50 mL) and ethyl acetate (30 mL). The aqueous layer was separated and extracted further with ethyl acetate (3×30 mL). The combined organic extracts were dried over magnesium sulfate, filtered, and concentrated under reduced pressure. Purification by flash column chromatography on silica gel using ethyl acetate/heptane (9:1) as a mobile phase afforded the protected aniline product.

c) Representative procedure for deprotection: To a 50 mL flask containing a solution of hydrogen chloride in dioxane (4 M, 6 mL) and ethanol (6 mL) was added the protected aniline (1.05 mmol). An air condenser was affixed to the flask, and the mixture was stirred at 50° C. under an atmosphere of nitrogen. After 16 hours, the reaction mixture was cooled to ambient temperature, and the solvent was removed under reduced pressure. The residue was partitioned between aqueous hydrochloric acid (0.5 M, 30 mL) and ether (20 mL). The organic layer was separated and discarded. The aqueous layer was basified with saturated aqueous sodium bicarbonate (30 mL), and the resulting mixture was extracted with ethyl acetate (3×30 mL). The combined ethyl acetate extracts were dried over magnesium sulfate, filtered, and concentrated to afford the aniline product.

d) Representative procedure for sulfonylation: The aniline (1.0 mmol) was added to a solution of 2,3-dichlorobenzenesulfonyl chloride (0.263 g, 1.07 mmol) and 4-dimethylaminopyridine (0.005 g, 0.041 mmol) in pyridine (5 mL), and the resulting solution was stirred under an atmosphere of nitrogen for 3 days. MethanoU-dichloromethane (1:19, 100 mL) was added and the resulting mixture was extracted with half-saturated aqueous sodium bicarbonate (3×10 mL). The organic layer was dried over magnesium sulfate, filtered, and concentrated to afford the sulfonamide product.

e) Representative procedure for transesterification: The ethyl ester (2.76 mmol) was added to a solution of triethylamine (3.8 mL, 28 mmol) and methanol (30 mL). A reflux condenser was affixed to the reaction vessel, and the reaction mixture was heated at 75° C. under an atmosphere of nitrogen. After 24 h, the reaction was allowed to cool to ambient temperature, and the solvent was removed under reduced pressure to afford the methyl ester product.

f) Alternate procedure for transesterification: A solution of the ethyl ester (0.279 mmol) and sodium methoxide (0.015 g, 0.279 mmol) in methanol (2 mL) was heated in a sealed tube at 75° C. for 2 h. The reaction was cooled to ambient temperature. Methanol/dichloromethane (1:19, 100 mL) was added and the resulting mixture was extracted with half-saturated aqueous sodium bicarbonate (3×10 mL). The organic layer was dried over magnesium sulfate, filtered, and concentrated to afford the methyl ester product.

g) Representative procedure for amide formation: In a resealable Schlenk flask, the ester (0.056 mmol) was suspended in an amine solvent (1 mL). The flask was sealed with a teflon screwcap and heated at 80° C. for 2 days. The reaction was cooled to ambient temperature to afford the amide product.

h) Representative procedure for primary amide formation: A sealable Schlenk flask was charged with the methyl ester (0.086 mmol). A solution of methanol saturated with ammonia (1 mL) was added, and the Schlenk flask was sealed and heated at 90° C. for 24 h. The reaction was cooled to ambient temperature, and the solvent was removed under reduced pressure to afford the primary amide product.

i) Representative procedure for urea formation: The aniline (0.152 mmol) was dissolved in pyridine (1 mL) and the solution was cooled to −20° C. m-Tolyl isocyanate (0.143 mmol) was added, and the solution was allowed to warm naturally to ambient temperature. After 6 h, the product was concentrated under reduced pressure to afford the urea product.

Example 338

Ethyl 2-[4-Amino-3-(4-{[(2,3-dichlorophenyl)sulfonyl]amino}-3-fluorophenyl)-1H-pyrazolo[3,4-d]pyrimidin-1-yl]acetate The representative procedures for alkylation (using ethyl bromoacetate as the alkyl bromide), Suzuki coupling, deprotection, and sulfonylation were conducted in sequence. Purification by preparative HPLC (25 to 100% acetonitrile in 0.1 M aqueous ammonium acetate over 20 min at 21 mL/min using an 8$\mu$ Hypersil HS C18, 250×21 mm column, Rt 12.4–13.9 min) afforded ethyl 2-[4-amino-3-(4-{[(2,3-dichlorophenyl)sulfonyl]amino}-3-fluorophenyl)-1H-pyrazolo[3,4-d]pyrimidin-1-yl]acetate as a white solid (0.011 g, 0.020 mmol): RP-HP (25 to 100% acetonitrile in 0.1 M aqueous ammonium acetate over 10 min at 1 mL/min using a Hypersil HS C18, 250×4.6 mm column) $R_t$ 9.78 min. 1H NMR (DMSO-$d_6$, 400 MHz) δ 10.84 (s, 1H), 8.25 (s, 1H), 7.97 (s, 1H), 7.95 (s, 1H), 7.54 (t, 1H), 7.43 (m, 3H), 5.21 (s, 2H), 4.15 (qt, 2H), 1.20 (t, 3H); MS: MH$^+$ 539.

Example 339

N1-{4-[4-Amino-1-(2-morpholino-2-oxoethyl)-1H-pyrazolo[3,4-d]pyrimidin-3-yl]-2-fluorophenyl}-2,3-dichloro-1-benzenesulfonamide Ethyl 2-[4-amino-3-(4-{[(2,3-dichlorophenyl)sulfonyl]amino}-3-fluorophenyl)-1H-pyrazolo[3,4-d]pyrimidin-1-yl]acetate was treated with morpholine using the representative procedure for amide formation. Purification by preparative HPLC (25 to 100% CH$_3$CN in 0.1 M aqueous ammonium acetate over 20 min at 21 mL/min using an 8$\mu$ Hypersil HS C18, 250×21 mm column, $R_t$ 9.3–9.8 min) afforded N1-{4-[4-amino-1-(2-morpholino-2-oxoethyl)-1H-pyrazolo[3,4-d]pyrimidin-3-yl]-2-fluorophenyl}-2,3-dichloro-1-benzenesulfonamide as a white solid (0.005 g, 0.009 mmol): RP-HP (25 to 100% acetonitrile in 0.1 M aqueous ammonium acetate over 10 min at 1 mL/min using a Hypersil HS C18, 250×4.6 mm column) $R_t$ 8.22 min. $^1$H NMR (DMSO-$d_6$, 400 MHz) δ 10.82 (s, 1H), 8.21 (s, 1H), 7.96 (d, 1H), 7.94 (m, 1H), 7.53 (t, 1H), 7.39 (m, 3H), 6.97 (br, 2H), 5.32 (s, 2H), 3.5 (m, 8H); MS: MH$^+$ 580.

Example 340

N1-(4-{4-Amino-1-[2-(4-methylpiperazino)-2-oxoethyl]-1H-pyrazolo[3,4-d]pyrimidin-3-yl}-2-fluorophenyl)-2,3-dichloro-1-benzenesulfonamide Ethyl 2-[4-amino-3-(4-{[(2,3-dichlorophenyl)sulfonyl]amino}-3-fluorophenyl)-1H-pyrazolo[3,4-d]pyrimidin-1-yl]acetate was treated with 1-methylpiperazine using the representative procedure for amide formation. Purification by preparative HPLC (25 to 100% CH$_3$CN in 0.1 M aqueous ammonium acetate over 20 min at 21 mL/min using an 8Hypersil HS C18, 250×21 mm column, $R_t$ 6.4–7.0 min) afforded N1-(4-{4-amino-1-[2-(4-methylpiperazino)-2-oxoethyl]-1H-pyrazolo[3,4-d]pyrimidin-3-yl}-2-fluorophenyl)-2,3-dichloro-1-benzenesulfonamide as a white solid (0.005 g, 0.009 mmol): RP-HP (25 to 100% acetonitrile in 0.1 M aqueous ammonium acetate over 10 min at 1 mL/min using a Hypersil HS C18, 250×4.6 mm column) $R_t$ 6.83 min. $^1$H NMR (DMSO-$d_6$, 400 MHz) δ 8.20 (s, 1H), 7.96 (d, 1H), 7.88 (d, 1H), 7.50 (t, 1H), 7.36 (m, 3H), 5.31 (s, 2H), 3.45 (m, 4H), 2.50 (m, 4H), 2.30 (s, 3H), MS: MH$^+$ 593.

Example 341

N1-[(1R,2S)-2-Hydroxy-1-methyl-2-phenylethyl]-N1-methyl-2-[4-amino-3-(4-{[(2,3-dichlorophenyl)sulfonyl]amino}-3-fluorophenyl)-1H-pyrazolo[3,4-d]pyrimidin-1-yl]acetamide A solution of (+)-pseudoephedrine (0.037 g, 0.224 mmol) in ethylene glycol dimethyl ether (0.75 mL) was treated with a solution of n-butyllithium (2.5 M in hexanes, 0.060 mL, 0.150 mmol). After 20 min, this solution was transferred via cannula into a solution of ethyl 2-[4-amino-3-(4-{[(2,3-dichlorophenyl)sulfonyl]amino}-3-fluorophenyl)-1H-pyrazolo[3,4-d]pyrimidin-1-yl]acetate (0.040 g, 0.074 mmol) in N,N-dimethylfornamide (0.75 mL). The resulting solution was stirred at 50° C. for 15 h. It was then cooled to ambient temperature and partitioned between methanol/dichloromethane (1:9, 50 mL), and water (15 mL). The organic layer was separated, dried over magnesium sulfate, filtered, and concentrated under reduced pressure. Purification by preparative HPLC (25 to 100% acetonitrile in 0.1 M aqueous ammonium acetate over 20 min at 21 mL/min using an 8$\mu$ Hypersil HS C18, 250×21 mm column, $R_t$ 11.88–12.65 min) afforded N1-[(1R,2S)-2-hydroxy-1-methyl-2-phenylethyl]-N1-methyl-2-[4-amino-3-(4-{[(2,3-dichlorophenyl)sulfonyl]amino}-3-fluorophenyl)-1H-pyrazolo[3,4-d]pyrimidin-1-yl]acetamide as an off-white solid (0.010 g, 0.015 mmol): RP-HPLC (25 to 100% acetonitrile in 0.1 M aqueous ammonium acetate over 10 min at 1 mL/min using a HypersilHS C18, 250×4.6 mm column) $R_t$ 9.63 min; MS: (MH)$^+$ 658.

Example 342

N1-[(1S,2S)-2-Hydroxy-1-methyl-2-phenylethyl]-N1-methyl-2-[4-amino-3-(4-{[(2,3-dichlorophenyl)sulfonyl]amino}-3-fluorophenyl)-1H-pyrazolo[3,4-d]pyrimidin-1-yl]acetamide Using a procedure similar to that above, (+)-ephedrine hydrochloride (0.061 g, 0.302 mmol) and ethyl 2-[4-amino-3-(4-{[(2,3-dichlorophenyl)sulfonyl]amino}-3-fluorophenyl)-1H-pyrazolo[3,4-d]pyrimidin-1-yl]acetate (0.054 g, 0.10 mmol) were combined. Purification by preparative HPLC (25 to 100% acetonitrile in 0.1 M aqueous ammonium acetate over 20 min at 21 mL/min using an 8$\mu$ Hypersil HS C18, 250×21 mm column, $R_t$ 11.4–11.9 min) afforded N1-[(1S,2S)-2-hydroxy-1-methyl-2-phenylethyl]-N1-methyl-2-[4-amino-3-(4-{[(2,3-dichlorophenyl)sulfonyl]amino}-3-fluorophenyl)-1H-pyrazolo[3,4-d]pyrimidin-1-yl]acetamide as an off-white solid (0.010 g, 0.015 mmol): RP-HPLC (25 to 100% CH$_3$CN in 0.1 M aqueous ammonium acetate over 10 min at 1 mL/min using a Hypersil HS C18, 250×4.6 mm column) $R_t$ 9.36 min; MS: (M–H)$^-$ 656.

Example 343

N-[4-(4-Amino-1-{2-[(2S)-2-(hydroxymethyl) tetrahydro-1H-1-pyrrolyl]-2-oxoethyl}-1H-pyrazolo [3,4-d]pyrimidin-3-yl)-2-fluorophenyl]-2,3-dichloro-1-benzenesulfonamide Using a procedure similar to that above, (R)-pyrrolidinemethanol (0.038 mL, 0.385 mmol) and ethyl 2-[4-amino-3-(4-{[(2,3-dichlorophenyl)sulfonyl]amino}-3-fluorophenyl)-1H-pyrazolo[3,4-d]pyrimidin-1-yl]acetate (0.060 g, 0.111 mmol) were combined. Purification by preparative HPLC (25 to 100% acetonitrile in 0.1 M aqueous ammonium acetate over 20 min at 21 mL/min using an 8$\mu$ Hypersil HS C18, 250×21 mm column, $R_t$ 8.45–9.90 min) afforded N1-[4-(4-amino-1-{2-[(2S)-2-(hydroxymethyl) tetrahydro-1H-1-pyrrolyl]-2-oxoethyl}-1H-pyrazolo[3,4-d] pyrimidin-3-yl)-2-fluorophenyl]-2,3-dichloro-1-benzenesulfonamide as an off-white solid (0.024 g, 0.040 mmol): RP-HPLC (25 to 100% CH$_3$CN in 0.1 M aqueous ammonium acetate over 10 min at 1 mL/min using a Hypersil HS C18, 250×4.6 mm column) $R_t$ 8.05 min; MS: (M–H)$^-$ 592.

Example 344

N1-[4-(4-Amino-1-{2-[(2R)-2-(hydroxymethyl) tetrahydro-1H-1-pyrrolyl]-2-oxoethyl}-1H-pyrazolo [3,4-d]pyrimidin-3-yl)-2-fluorophenyl]-2,3-dichloro-1-benzenesulfonamide Using a procedure similar to that above, (S)-pyrrolidinemethanol (0.038 mL, 0.385 mmol) and ethyl 2-[4-amino-3-(4-{[(2,3-dichlorophenyl)sulfonyl]amino}-3-fluorophenyl)-1H-pyrazolo[3,4-d]pyrimidin-1-yl]acetate (0.060 g, 0.111 mmol) were combined. Purification by preparative HPLC (25 to 100% acetonitrile in 0.1 M aqueous ammonium acetate over 20 min at 21 mL/min using an 8$\mu$ Hypersil HS C18, 250×21 mm column, $R_t$ 8.15–9.70 min) afforded N1-[4-(4-amino-1-{2-[(2R)-2-(hydroxymethyl) tetrahydro-1H-1-pyrrolyl]-2-oxoethyl}-1H-pyrazolo[3,4-d] pyrimidin-3-yl)-2-fluorophenyl]-2,3-dichloro-1-benzenesulfonamide as an off-white solid (0.022 g, 0.037 mmol): RP-HPLC (25 to 100% CH$_3$CN in 0.1 M aqueous ammonium acetate over 10 min at 1 mL/min using a Hypersil HS C18, 250×4.6 mm column) $R_t$ 7.98 min; MS: (M–H)$^-$ 592.

Example 345

Methyl 2-[4-Amino-3-(4-{[(2,3-dichlorophenyl) sulfonyl]amino}-3-fluorophenyl)-1H-pyrazolo[3,4-d]pyrimidin-1-yl]acetate Using the representative procedure for transesterification, ethyl 2-[4-amino-3-(4-{[(2,3-dichlorophenyl)sulfonyl] amino}-3-fluorophenyl)-1H-pyrazolo[3,4-d]pyrimidin-1-yl] acetate (1.49 g, 2.76 mmol) was converted to the corresponding methyl ester. A portion of the crude material was purified by preparative HPLC (25 to 100% acetonitrile in 0.1 M aqueous ammonium acetate over 20 min at 21 mL/min using an 8$\mu$ Hypersil HS C18, 250×21 mm column, $R_t$ 11.0–12.3 min) to afford methyl 2-[4-amino-3-(4-{[(2,3-dichlorophenyl)sulfonyl]amino}-3-fluorophenyl)-1H-pyrazolo[3,4-d]pyrimidin-1-yl]acetate as a white solid (0.016 g, 0.030 mmol): RP-HP (25 to 100% CH$_3$CN in 0.1 M aqueous ammonium acetate over 10 min at 1 mL/min using a Hypersil HS C18, 250×4.6 mm column) $R_t$ 9.22 min. $^1$H NMR (DMSO-d$_6$, 400 MHz) δ 10.84 (s, 1H), 8.25 (s, 1H), 7.96 (m, 2H), 7.60 (m, 1H), 7.56 (m, 3H), 5.23 (s, 2H), 3.68 (s, 3H); MS: MH$^+$ 525.

Example 346

2-[4-Amino-3-(4-{[(2,3-dichlorophenyl)sulfonyl] amino}-3-fluorophenyl)-1H-pyrazolo[3,4-d] pyrimidin-1-yl]acetic Acid In a resealable Schlenk flask, methyl 2-[4-amino-3-(4-{[(2,3-dichlorophenyl)sulfonyl]amino}-3-fluorophenyl)-1H-pyrazolo[3,4-d]pyrimidin-1-yl]acetate (0.030 g, 0.057 mmol) was dissolved in methanol/water (1:1, 1 mL). The flask was sealed with a teflon screwcap and heated at 90° C. After 2 days, the reaction was cooled to ambient temperature. Purification by preparative HPLC (25 to 100% CH$_3$CN in 0.1 M aqueous ammonium acetate over 20 min at 21 mL/min using an 8$\mu$ Hypersil HS C18, 250×21 mm column, $R_t$ 6.3–6.7 min) afforded 2-[4-amino-3-(4-{[(2,3-dichlorophenyl)sulfonyl]amino}-3-fluorophenyl)-1H-pyrazolo[3,4-d]pyrimidin-1-yl]acetic acid as a white solid (0.006 g, 0.030 mmol): RP-HP (25 to 100% acetonitrile in 0.1 M aqueous ammonium acetate over 10 min at 1 mL/min using a Hypersil HS C18, 250×4.6 mm column) $R_t$ 6.42 min.

$^1$H NMR (DMSO-d$_6$, 400 MHz) δ 8.13 (s, 1H), 7.97 (d, 1H), 7.62 (d, 1H), 7.36 (t, 1H), 7.19 (m, 3H), 7.15 (d, 1H), 4.59 (s, 2H); MS: (M–H)$^-$ 509.

Example 347

N1-[2-(Dimethylamino)ethyl]-2-[4-amino-3-(4-{[(2,3-dichlorophenyl)sulfonyl]amino}-3-fluorophenyl)-1H-pyrazolo[3,4-d]pyrimidin-1-yl]acetamide The representative procedure for amide formation was used in the reaction of methyl 2-[4-amino-3-(4-{[(2,3-dichlorophenyl)sulfonyl]amino}-3-fluorophenyl)-1H-pyrazolo[3,4-d]pyrimidin-1-yl]acetate (0.035 g, 0.067 mmol) with N,N-dimethylethylenediamine (1 mL). Purification by preparative HPLC (25 to 100% acetonitrile in 0.1 M aqueous ammonium acetate over 20 min at 21 mL/min using an 8μ Hypersil HS C18, 250×21 mm column, R$_t$ 6.85–7.45 min) afforded N1-[2-(dimethylamino)ethyl]-2-[4-amino-3-(4-{[(2,3-dichlorophenyl)sulfonyl]amino}-3-fluorophenyl)-1H-pyrazolo[3,4-d]pyrimidin-1-yl]acetamide as an off-white solid (0.008 g, 0.014 mmol): $^1$H NMR (DMSO-d$_6$, 400 MHz) δ 10.20 (br, 1H), 8.22 (m, 2H), 7.96 (d, 1H), 7.80 (d, 1H), 7.45 (t, 1H), 7.31 (m, 3H), 6.90 (br, 2H), 4.96 (s, 2H), 3.40 (m, 2H), 2.75 (m, 2H), 2.07 (s, 6H); MS: (M–H)$^-$ 579.

Example 348

N1-[2-(Diethylamino)ethyl]-2-[4-amino-3-(4-{[(2,3-dichlorophenyl)sulfonyl]amino}-3-fluorophenyl)-1H-pyrazolo[3,4-d]pyrimidin-1-yl]acetamide The representative procedure for amide formation was used in the reaction of methyl 2-[4-amino-3-(4-{[(2,3-dichlorophenyl)sulfonyl]amino}-3-fluorophenyl)-1H-pyrazolo[3,4-d]pyrimidin-1-yl]acetate (0.035 g, 0.067 mmol) with N,N-diethylethylenediamine (1 mL). Purification by preparative HPLC (25 to 100% acetonitrile in 0.1 M aqueous ammonium acetate over 20 min at 21 mL/min using an 8μ Hypersil HS C18, 250×21 mm column, R$_t$ 7.12–7.98 min) afforded N1-[2-(diethylamino)ethyl]-2-[4-amino-3-(4-{[(2,3-dichlorophenyl)sulfonyl]amino}-3-fluorophenyl)-1H-pyrazolo[3,4-d]pyrimidin-1-yl]acetamide as an off-white solid (0.017 g, 0.028 mmol): $^1$H NMR (DMSO-d$_6$, 400 MHz) δ 8.22 (s, 1H), 8.12 (br, 1H), 7.96 (d, 1H), 7.78 (d, 1H), 7.44 (t, 1H), 7.31 (m, 3H); 6.95 (br, 2H), 4.96 (s, 2H), 3.35 (m, 2H), 2.82 (m, 2H), 2.50 (m, 4H), 1.05 (t, 6H); MS: (M–H)$^-$ 607.

Example 349

2-(Dimethylamino)ethyl 2-[4-Amino-3-(4-{[(2,3-dichlorophenyl)sulfonyl]amino}-3-fluorophenyl)-1H-pyrazolo[3,4-d]pyrimidin-1-yl]acetate The representative procedure for amide formation was used in the reaction of methyl 2-[4-amino-3-(4-{[(2,3-dichlorophenyl)sulfonyl]amino}-3-fluorophenyl)-1H-pyrazolo[3,4-d]pyrimidin-1-yl]acetate (0.035 g, 0.067 mmol) with N,N-dimethylethanolamine (1 mL). Purification by preparative HPLC (25 to 100% acetonitrile in 0.1 M aqueous ammonium acetate over 20 min at 21 mL/min using an 8μ Hypersil HS C18, 250×21 mm column, R$_t$ 7.50–8.07 min) afforded 2-(dimethylamino)ethyl 2-[4-amino-3-(4-{[(2,3-dichlorophenyl)sulfonyl]amino}-3-fluorophenyl)-1H-pyrazolo[3,4-d]pyrimidin-1-yl]acetate as an off-white solid (0.008 g, 0.014 mmol): $^1$H NMR (DMSO-d$_6$, 400 MHz) δ 8.24 (s, 1H), 7.96 (d, 1H), 7.83 (d, 1H), 7.48 (t, 1H), 7.32 (m, 3H), 5.23 (s, 2H), 4.29 (t, 2H), 2.86 (m, 2H), 2.39 (s, 6H); MS: (M–H)$^-$ 580.

Example 350

N1-[3-(Dimethylamino)propyl]-2-[4-amino-3-(4-{[(2,3-dichlorophenyl)sulfonyl]amino}-3-fluorophenyl)-1H-pyrazolo[3,4-d]pyrimidin-1-yl]acetamide The representative procedure for amide formation was used in the reaction of methyl 2-[4-amino-3-(4-{[(2,3-dichlorophenyl)sulfonyl]amino}-3-fluorophenyl)-1H-pyrazolo[3,4-d]pyrimidin-1-yl]acetate (0.025 g, 0.048 mmol) with 3-(dimethylamino)propylamine (1 mL). Purification by preparative HPLC (25 to 100% acetonitrile in 0.1 M aqueous ammonium acetate over 20 min at 21 mL/min using an 8μ Hypersil HS C18, 250×21 mm column, R$_t$ 6.7–7.3 min) afforded N1-[3-(dimethylamino)propyl]-2-[4-amino-3-(4-{[(2,3-dichlorophenyl)sulfonyl]amino}-3-fluorophenyl)-1H-pyrazolo[3,4-d]pyrimidin-1-yl]acetamide as an off-white powder (0.015 g, 0.025 mmol): $^1$H NMR (DMSO-d$_6$, 400 MHz) δ 8.20 (m, 1H), 7.96 (m, 1H), 7.76 (m, 1H), 7.43 (t, 1H), 7.30 (m, 2H), 4.93 (s, 2H), 3.12 (m, 2H), 2.82 (m, 2H), 2.50 (s, 6H), 1.73 (m, 2H); MS (M–H) 593.

Example 351

2-[4-Amino-3-(4-{[(2,3-dichlorophenyl)sulfonyl]amino}-3-fluorophenyl)-1H-pyrazolo[3,4-d]pyrimidin-1-yl]acetamide The representative procedure for primary amide formation was used to convert methyl 2-[4-amino-3-(4-{[(2,3-dichlorophenyl)sulfonyl]amino}-3-fluorophenyl)-1H-pyrazolo[3,4-d]pyrimidin-1-yl]acetate (0.045 g, 0.086 mmol) to the corresponding primary amide. Purification by preparative HPLC (25 to 100% acetonitrile in 0.1 M aqueous ammonium acetate over 20 min at 21 mL/min using an 8μ Hypersil HS C18, 250×21 mm column, R$_t$ 6.9–8.5 min) afforded 2-[4-amino-3-(4-{[(2,3-dichlorophenyl)sulfonyl]amino}-3-fluorophenyl)-1H-pyrazolo[3,4-d]pyrimidin-1-yl]acetamide as an off-white powder (0.015 g, 0.029 mmol): $^1$H NMR (DMSO-d$_6$, 400 MHz) δ 9.83 (br, 2H), 8.84 (br, 1H), 7.93 (s, 1H), 7.82 (s, 1H), 7.80 (s, 1H), 7.62 (s, 1H), 7.50 (m, 2H), 7.36 (m, 1H); 3.87 (s, 2H); MS (M–H)$^-$ 508.

Example 352

Ethyl 2-(4-Amino-3-{3-fluoro-4-[(3-toluidinocarbonyl)amino]phenyl}-1H-pyrazolo[3,4-d]pyrimidin-1-yl)acetate The representative procedures for alkylation (using ethyl bromoacetate as the alkyl bromide), Suzuki coupling, deprotection, and urea formation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, R$_t$ 12.1–13.5 min) afforded ethyl 2-(4-amino-3-{3-fluoro-4-[(3-toluidinocarbonyl)amino]phenyl}-1H-pyrazolo[3,4-d]pyrimidin-1-yl)acetate as a yellow powder (0.015 g, 0.032 mmol): $^1$H NMR (DMSO-d$_6$, 400 MHz) δ 9.07 (br, 1H), 8.73 (br, 1H), 8.38 (t, 1H), 8.26 (s, 1H), 7.48 (m, 2H), 7.32 (s, 1H), 7.25 (d, 1H), 7.19 (t, 1H), 6.82 (d, 1H), 5.23 (s, 2H), 4.17 (qt, 2H), 2.30 (s, 3H), 1.21 (t, 3H); MS: (M–H)$^-$ 462.

Example 353

N-{4-[4-Amino-1-(2-morpholino-2-oxoethyl)-1H-pyrazolo[3,4-d]pyrimidin-3-yl]-2-fluorophenyl}-N"-(3-methylphenyl)urea Ethyl 2-(4-amino-3-{3-fluoro-4-[(3-toluidinocarbonyl)amino]phenyl}-1H-pyrazolo[3,4-d]pyrimidin-1-yl)acetate (0.025 g, 0.054 mmol) was converted to the corresponding methyl ester using the representative procedure for transesterification. This product was dissolved in morpholine (1 mL) and the solution was heated at 50° C. in a sealed tube for 2 days. The reaction was cooled to ambient temperature, concentrated, and purified by preparative HPLC (25 to 100% acetonitrile in 0.1 M aqueous ammonium acetate over 20 min at 21 mL/min using an 8μ Hypersil HS C18, 250×21 mm column, $R_t$ 9.3–10.2 min) to afford N-{4-[4-amino-1-(2-morpholino-2-oxoethyl)-1H-pyrazolo[3,4-d]pyrimidin-3-yl]-2-fluorophenyl}-N"-(3-methylphenyl)urea as a yellow solid (0.009 g, 0.018 mmol): $^1$H NMR (DMSO-$d_6$, 400 MHz) δ 9.07 (s, 1H), 8.72 (s, 1H), 8.37 (t, 1H), 8.23 (s, 1H), 7.45 (m, 2H), 7.33 (t, 1H), 7.27 (m, 1H), 7.19 (t, 1H), 6.83 (d, 1H), 5.34 (s, 2H), 3.5 (m, 8H), 2.30 (s, 3H); MS (M–H)$^-$ 503.

Example 354

N-(4-{4-Amino-1-[2-(4-methylpiperazino)-2-oxoethyl]-1H-pyrazolo[3,4-d]pyrimidin-3-yl}-2-fluorophenyl)-N"-(3-methylphenyl)urea A procedure similar to that above, except using 1-methylpiperazine (1 mL) instead of morpholine as solvent, followed by purification by preparative HPLC (25 to 100% acetonitrile in 0.1 M aqueous ammonium acetate over 20 min at 21 mL/min using an 8μ Hypersil HS C18, 250×21 mm column, $R_t$ 7.1–7.8 min) afforded N-(4-{4-amino-1-[2-(4-methylpiperazino)-2-oxoethyl]-1H-pyrazolo[3,4-d]pyrimidin-3-yl}-2-fluorophenyl)-N"-(3-methylphenyl)urea as an off-white solid (0.008 g, 0.015 mmol): $^1$H NMR (DMSO-$d_6$, 400 MHz) δ 9.07 (s, 1H), 8.72 (s, 1H), 8.37 (t, 1H), 8.22 (s, 1H), 7.45 (m, 2H), 7.32 (s, 1H), 7.25 (m, 1H), 7.19 (t, 1H), 6.90 (br, 2H), 6.83 (d, 1H), 5.33 (s, 2H), 3.39 (m, 4H), 2.40 (m, 4H), 2.30 s, 3H); MS (M–H)$^-$ 516.

Example 355

Ethyl 2-[4-Amino-3-(4-{[(2,3-dichlorophenyl)sulfonyl]amino}-3-fluorophenyl)-1H-pyrazolo[3,4-d]pyrimidin-1-yl]propanoate The representative procedures for alkylation (using ethyl 2-bromopropionate as the alkyl bromide), Suzuki coupling, deprotection, and sulfonylation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, $R_t$ 10.1–11.0 min) afforded ethyl 2-[4-amino-3-(4-{[(2,3-dichlorophenyl)sulfonyl]amino}-3-fluorophenyl)-1H-pyrazolo[3,4-d]pyrimidin-1-yl]propanoate (0.016 g, 0.029 mmol) as a gray solid: $^1$H NMR (DMSO-$d_6$, 400 MHz) δ 10.84 (br, 1H), 8.24 (s, 1H), 7.97 (s, 1H), 7.95 (s, 1H), 7.54 (t, 1H); 7.41 (m, 3H), 7.0 (br, 1H), 5.61 (qt, 1H), 4.10 (qt, 2H), 1.73 (d, 3H), 1.11 (t, 3H); MS (M–H)$^-$ 551.

Example 356

Methyl 2-[4-Amino-3-(4-{[(2,3-dichlorophenyl)sulfonyl]amino}-3-fluorophenyl)-1H-pyrazolo[3,4-d]pyrimidin-1-yl]propanoate (4032811)

The representative procedure for transesterification was used to convert ethyl 2-[4-amino-3-(4-{[(2,3-dichlorophenyl)sulfonyl]amino}-3-fluorophenyl)-1H-pyrazolo[3,4-d]pyrimidin-1-yl]propanoate (0.400 g, 0.723 mmol) to the corresponding methyl ester. Purification of a portion of the material by preparative HPLC (25 to 100% acetonitrile in 0.1 M aqueous ammonium acetate over 20 min at 21 mL/min using an 8μ Hypersil HS C18, 250×21 mm column, $R_t$ 12.4–12.9 min) afforded methyl 2-[4-amino-3-(4-{[(2,3-dichlorophenyl)sulfonyl]amino}-3-fluorophenyl)-1H-pyrazolo[3,4-d]pyrimidin-1-yl]propanoate (0.008 g, 0.015 mmol) as a gray solid: $^1$H NMR (DMSO-$d_6$, 400 MHz) δ 10.84 (s, 1H), 8.24 (s, 1H), 7.97 (s, 1H), 7.95 (s, 1H), 7.54 (t, 1H), 7.40 (m, 3H), 4.10 (m, 1H), 3.62 (s, 3H), 1.73 (d, 3H); MS (MH)$^+$ 539.

Example 357

2-[4-Amino-3-(4-{[(2,3-dichlorophenyl)sulfonyl]amino}-3-fluorophenyl)-1H-pyrazolo[3,4-d]pyrimidin-1-yl]propanamide The representative procedure for primary amide formation was used to convert methyl 2-[4-amino-3-(4-{[(2,3-dichlorophenyl)sulfonyl]amino}-3-fluorophenyl)-1H-pyrazolo[3,4-d]pyrimidin-1-yl]propanoate (0.040 g, 0.074 mmol) to the corresponding primary amide. Purification by preparative HPLC (25 to 100% acetonitrile in 0.1 M aqueous ammonium acetate over 20 min at 21 mL/min using an 8μ Hypersil HS C18, 250×21 mm column, $R_t$ 8.1–9.6 min) afforded 2-[4-amino-3-(4-{[(2,3-dichlorophenyl)sulfonyl]amino}-3-fluorophenyl)-1H-pyrazolo[3,4-d]pyrimidin-1-yl]propanamide (0.015 g, 0.029 mmol) as a white powder: $^1$H NMR (DMSO-$d_6$, 400 MHz) δ 10.82 (s, 1H), 8.22 (s, 1H), 7.98 (s, 1H), 7.96 (s, 1H), 7.56 (t, 1H), 7.42 (m, 3H), 7.31 (br, 1H), 7.21 (br, 1H), 5.34 (qt, 1H), 1.71 (d, 3H); MS (MH)$^+$ 524.

Example 358

Ethyl 2-(4-Amino-3-{3-fluoro-4-[(3-toluidinocarbonyl)amino]phenyl}-1H-pyrazolo[3,4-d]pyrimidin-1-yl)propanoate The representative procedures for alkylation (using ethyl 2-bromopropionate as the alkyl bromide), Suzuki coupling, deprotection, and urea formation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, $R_t$ 13.3–14.3 min) afforded ethyl 2-(4-amino-3-{3-fluoro-4-[(3-toluidinocarbonyl)amino]phenyl}-1H-pyrazolo[3,4-d]pyrimidin-1-yl)propanoate as a white solid (0.022 g, 0.046 mmol): $^1$H NMR (DMSO-$d_6$, 400 MHz) δ 9.06 (s, 1H), 8.73 (s, 1H), 8.37 (t, 1H), 8.25 (s, 1H), 7.46 (m, 2H), 7.32 (s, 1H), 7.25 (m, 1H), 7.19 (t, 1H), 6.83 (d, 1H), 5.63 (qt, 1H), 4.12 (qt, 2H), 2.30 (s, 3H), 1.76 (d, 3H), 1.15 (t, 3H); MS (M–H)$^-$ 476.

Example 359

2-(4-Amino-3-{3-fluoro-4-[(3-toluidinocarbonyl)amino]phenyl}-1H-pyrazolo[3,4-d]pyrimidin-1-yl)propanamide The representative procedures for alkylation (using ethyl 2-bromopropionate as the alkyl bromide), Suzuki coupling, deprotection, the alternate procedure for transesterification, and the representative procedures for primary amide formation and urea formation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, $R_t$ 9.1–10.1 min) afforded 2-(4-amino-3-{3-fluoro-4-[(3-toluidinocarbonyl)amino]phenyl}-1H-pyrazolo[3,4-d]

pyrimidin-1-yl)propanamide as a gray solid (0.010 g, 0.022 mmol): $^1$H NMR (DMSO-d$_6$, 400 MHz) δ 9.08 (s, 1H), 8.38 (s, 1H), 8.37 (t, 1H), 8.23 (s, 1H), 7.46 (m, 2H), 7.33 (m, 2H), 7.24 (m, 2H), 7.12 (d, 1H), 6.97 (br, 2H), 6.82 (d, 1H), 5.35 (qt, 1H), 2.30 (s, 3H), 1.75 (d, 3H); MS (MH)$^+$ 449.

Example 360

Ethyl 4-[4-Amino-3-(4-{[(2,3-dichlorophenyl) sulfonyl]amino}-3-fluorophenyl)-1H-pyrazolo[3,4-d]pyrimidin-1-yl]butanoate The representative procedures for alkylation (using ethyl 4-bromobutyrate as the alkyl bromide), Suzuki coupling, deprotection, and sulfonylation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, R$_t$ 12.8–13.8 min) afforded ethyl 4-[4-amino-3-(4-{[(2,3-dichlorophenyl)sulfonyl]amino}-3-fluorophenyl)-1H-pyrazolo[3,4-d]pyrimidin-1-yl]butanoate (0.010 g, 0.018 mmol) as an off-white solid: $^1$H NMR (DMSO-d$_6$, 400 MHz) δ 10.83 (s, 1H), 8.23 (s, 1H), 7.97 (s, 1H), 7.95 (s, 1H), 7.54 (t, 1H), 7.40 (m, 3H), 6.95 (m, 2H), 4.35 (t, 2H), 3.97 (qt, 2H), 2.30 (t, 2H), 2.08 (m, 2H), 1.12 (t, 3H); MS (M–H)$^-$ 565.

Example 361

Methyl 4-[4-Amino-3-(4-{[(2,3-dichlorophenyl) sulfonyl]amino}-3-fluorophenyl)-1H-pyrazolo[3,4-d]pyrimidin-1-yl]butanoate The representative procedures for alkylation (using ethyl 4-bromobutyrate as the alkyl bromide), Suzuki coupling, deprotection, the alternate procedure for transesterification, and the representative procedure for sulfonylation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, R$_t$ 11.7–12.2 min) afforded methyl 4-[4-amino-3-(4-t[(2,3-dichlorophenyl)sulfonyl] amino}-3-fluorophenyl)-1H-pyrazolo[3,4-d]pyrimidin-1-yl] butanoate as a yellow solid (0.015 g, 0.027 mmol): $^1$H NMR (DMSO-d$_6$, 400 MHz) δ 10.84 (br, 1H), 8.23 (s, 1H), 7.95 (m, 2H), 7.52 (m, 1H), 7.40 (m, 3H), 4.35 (t, 2H), 3.52 (s, 3H), 2.32 (t, 2H), 2.09 (m, 2H); MS (MH)$^+$ 553.

Example 362

4-[4-Amino-3-(4-{[(2,3-dichlorophenyl)sulfonyl] amino}-3-fluorophenyl)-1H-pyrazolo[3,4-d] pyrimidin-1-yl]butanamide The representative procedure for primary amide formation was used to convert methyl 4-[4-amino-3-(4-{[(2,3-dichlorophenyl)sulfonyl]amino}-3-fluorophenyl)-1H-pyrazolo[3,4-d]pyrimidin-1-yl]butanoate (0.026 g, 0.047 mmol) to the corresponding primary amide. Purification by preparative HPLC (25 to 100% acetonitrile in 0.1 M aqueous ammonium acetate over 20 min at 21 mL/min using an 8μ Hypersil HS C18, 250×21 mm column, R$_t$ 8.0–9.0 min) afforded 4-[4-amino-3-(4-{[(2,3-dichlorophenyl)sulfonyl] amino}-3-fluorophenyl)-1H-pyrazolo[3,4-d]pyrimidin-1-yl] butanamide as a white solid (0.007 g, 0.013 mmol): $^1$H NMR (DMSO-d$_6$, 400 MHz) δ 10.82 (s, 1H), 8.24 (s, 1H), 7.97 (s, 1H), 7.95 (s, 1H), 7.54 (t, 1H), 7.45 (m, 3H), 7.24 (br, 1H), 6.93 (br, 2H), 6.73 (br, 1H), 4.31 (t, 2H), 2.05 (m, 4H); MS (M–H)$^-$ 536.

Example 363

Ethyl 4-(4-Amino-3-{3-fluoro-4-[(3-toluidinocarbonyl)amino]phenyl}-1H-pyrazolo[3,4-d]pyrimidin-1-yl)butanoate (4032812)

The representative procedures for alkylation (using ethyl 4-bromobutyrate as the alkyl bromide), Suzuki coupling, deprotection, and urea formation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, R$_t$ 12.6–13.6 min) afforded ethyl 4-(4-amino-3-{3-fluoro-4-[(3-toluidinocarbonyl)amino]phenyl}-1H-pyrazolo[3,4-d]pyrimidin-1-yl)butanoate as an off-white powder (0.015 g, 0.030 mmol): $^1$H NMR (DMSO-d$_6$, 400 MHz) δ 9.06 (s, 1H), 8.72 (s, 1H), 8.36 (t, 1H), 8.24 (s, 1H), 7.47 (m, 2H), 7.32 (s, 1H), 7.22 (m, 1H), 7.19 (t, 1H), 6.82 (d, 1H), 4.37 (t, 3H), 3.99 (qt, 3H), 2.34 (t, 2H), 2.30 (s, 3H), 2.11 (m, 2H), 1.13 (t, 3H); RP-HPLC (25 to 100% CH$_3$CN in 0.1 M aqueous ammonium acetate over 10 min at 1 mL/min using a Hypersil HS C18, 250×4.6 mm column) R$_t$ 10.00 min.

Example 364

4-(4-Amino-3-{3-fluoro-4-[(3-toluidinocarbonyl) amino]phenyl}-1H-pyrazolo[3,4-d]pyrimidin-1-yl) butanamide The representative procedures for alkylation (using ethyl 4-bromobutyrate as the alkyl bromide), Suzuki coupling, deprotection, the alternate procedure for transesterification, and the representative procedures for primary amide formation and urea formation were conducted in sequence. Purification by preparative HPLC (25 to 100% acetonitrile in 0.1 M aqueous ammonium acetate over 20 min at 21 mL/min using an 8μ Hypersil HS C18, 250×21 mm column, R$_t$ 8.4–9.1 min) afforded 4-(4-amino-3-{3-fluoro-4-[(3-toluidinocarbonyl)amino]phenyl}-1H-pyrazolo[3,4-d] pyrimidin-1-yl)butanamide as a white solid (0.010 g, 0.022 mmol): $^1$H NMR (DMSO-d$_6$, 400 MHz) δ 9.08 (s, 1H), 8.73 (s, 1H), 8.38 (t, 1H), 8.25 (s, 1H), 7.47 (m, 2H), 7.32 (s, 1H), 7.25 (m, 2H), 7.19 (m, 1H), 6.83 (d, 1H), 6.75 (s, 1H), 4.34 (t, 2H), 2.30 (s, 3H), 2.05 (m, 4H); MS (MH)$^+$ 463.

Example 365

2-{4-Amino-3-[4-(1,3-benzoxazol-2-ylamino) phenyl]-1H-pyrazolo[3,4-d]pyrimidin-1-yl}-5-(4-methylpiperazino)benzonitrile A suspension of 3-iodo-1H-pyrazolo[3,4-d]pyrimidin-4-amine (0.172 g, 0.66 mmol), sodium hydride (60%, 0.030 g, 0.75 mmol), 2,5-difluorobenzonitrile (0.105 g, 0.75 mmol), and N,N-dimethylformamide (2.5 mL) was heated for 24 h at 100° C. The reaction mixture was cooled to ambient temperature and concentrated under reduced pressure. The residue was partitioned between dichloromethane (50 mL) and water (10 mL). The organic layer was separated, dried over magnesium sulfate, filtered, and concentrated under reduced pressure.

A portion of the material (0.045 g, 0.118 mmol) and cesium carbonate (0.115 g, 0.353 mmol) were suspended in 1-methylpiperazine (1 mL), and the mixture was heated at 110° C. in a sealed tube for 20 h. The reaction mixture was cooled to ambient temperature and concentrated under reduced pressure. The residue was acidified with aqueous hydrochloric acid (1 M, 10 mL), and the aqueous phase was extracted with ether (10 mL). The organic phase was discarded, and the aqueous phase was basified with aqueous sodium carbonate (3 M, 10 mL). The aqueous phase was extracted with dichloromethane (3×15 mL), and the combined organic fractions were dried over magnesium sulfate, filtered, and concentrated under reduced pressure.

This material was subjected to a Suzuki coupling using the representative procedure, except that N-(1,3-benzoxazol-2-yl)-N-[4-(4,4,5,5-tetramethyl-1,3,2-dioxaborolan-2-yl)phenyl]amine was used in lieu of tert-butyl N-[2-fluoro-4-(4,4,5,5-tetramethyl-1,3,2-dioxaborolan-2-yl)phenyl]carbamate. Purification by preparative HPLC (25 to 100% acetonitrile in 0.1M aqueous ammonium acetate over 20 min at 21 mL/min using an 8$\mu$ Hypersil HS C18, 250×21 mm column, $R_t$ 7.0–8.6 min) afforded 2-{4-amino-3-[4-(1,3-benzoxazol-2-ylamino) phenyl]-1H-pyrazolo[3,4-d]pyrimidin-1-yl}-5-(4-methylpiperazino)benzonitrile as a gray solid (0.009 g, 0.017 mmol): $^1$H NMR (DMSO-$d_6$, 400 MHz) δ 10.93 (s, 1H), 8.29 (s, 1H), 7.98 (d, 2H), 7.78 (d, 2H), 7.73 (d, 1H), 7.52 (m, 3H), 7.44 (m, 1H), 7.26 (t, 1H), 7.17 (t, 1H), 3.24 (m, 4H), 2.45 (m, 4H), 2.28 (s, 3H); MS (MH)$^+$ 543.

Example 366

Ethyl 2-{4-Amino-3-[4-(1,3-benzothiazol-2-ylamino)-3-fluorophenyl]-1H-pyrazolo[3,4-d]pyrimidin-1-yl}propanoate The representative procedure for alkylation (using ethyl 2-bromopropionate as the alkyl bromide) and the representative procedure for Suzuki coupling (except using N-(1,3-benzothiazol-2-yl)-N-[2-fluoro-4-(4,4,5,5-tetramethyl-1,3,2-dioxaborolan-2-yl)phenyl]amine in lieu of tert-butyl N-[2-fluoro-4-(4,4,5,5-tetramethyl-1,3,2-dioxaborolan-2-yl) phenyl]carbamate) were conducted in sequence. Purification by preparative HPLC (25 to 100% acetonitrile in 0.1 M aqueous ammonium acetate over 20 min at 21 mL/min using an 8$\mu$ Hypersil HS C18, 250×21 mm column, $R_t$ 14.4–14.9 min) afforded ethyl 2-{4-amino-3-[4-(1,3-benzothiazol-2-ylamino)-3-fluorophenyl]-1H-pyrazolo[3,4-d]pyrimidin-1-yl}propanoate as an off-white solid (0.022 g, 0.046 mmol):

$^1$H NMR (DMSO-$d_6$, 400 MHz) δ 10.52 (s, 1H), 8.82 (t, 1H), 8.26 (s, 1H), 7.85 (d, 1H), 7.66 (d, 1H), 7.55 (m, 2H), 7.36 (t, 1H), 7.22 (t, 1H), 5.65 (qt, 1H), 4.14 (qt, 2H), 1.77 (d, 3H), 1.14 (t, 3H); MS (MH)$^+$ 478.

Example 367 cis-N2-(4-{4-Amino-1-[4-(4-methylpiperazino) cyclohexyl]-1H-pyrazolo[3,4-d]pyrimidin-3-yl}-2-fluorophenyl)-1,3-benzoxazol-2-amine N2-(4-Bromo-2-fluorophenyl)-1,3-benzoxazol-2-amine To a solution of 4-bromo-2-fluoroaniline (1.00 g, 5.26 mmol) in toluene (25 mL) was added 2-chlorobenzoxazole (0.66 mL, 5.79 mmol). The purple solution was heated at reflux for 30 min and then at 100° C. for 17 h. The resulting white suspension/purple solution was cooled to room temperature and the precipitate was filtered. The filter cake was washed with five 2-mL portions of heptane to afford N2-(4-bromo-2-fluorophenyl)-1,3-benzoxazol-2-amine (1.480 g, 92%) as a light purple powder. RP-HPLC (25 to 100% CH$_3$CN in 0.1 N aqueous ammonium acetate over 10 min at 1 mL/min using a Hypersil HS C18, 250×4.6 mm column) tr=12.87 min, 97%; m/z 307 (MH$^+$).

N2-(4-Bromo-2-fluorophenyl)-1,3-benzothiazol-2-amine

To a solution of 4-bromo-2-fluoroaniline (1.00 g, 5.26 mmol) in toluene (25 mL) was added 2-chlorobenzothiazole (0.75 mL, 5.79 mmol). The purple solution was heated at 110–150° C. in a resealable tube for 66 h and then cooled to room temperature. The resulting brown solution was concentrated to give a purple solid which was triturated with heptane to afford N2-(4-bromo-2-fluorophenyl)-1,3-benzothiazol-2-amine (1.699 g, 99%) as a light purple powder. RP-HPLC (25 to 100% CH$_3$CN in 0.1 N aqueous ammonium acetate over 10 min at 1 mL/min using a Hypersil HS C18, 250×4.6 mm column) tr=13.82 min, 95%; m/z 325 (MH$^+$).

N2-(4-Bromophenyl)-1,3-benzothiazol-2-amine

N2-(4-bromophenyl)-1,3-benzothiazol-2-amine was prepared from 4-bromoaniline (1.00 g, 5.81 mmol) in a manner similar to that used for N2-(4-bromo-2-fluorophenyl)-1,3-benzothiazol-2-amine. The compound was formed as a light purple powder (0.867 g, 49%). RP-HPLC (25 to 100% CH$_3$CN in 0.1 N aqueous ammonium acetate over 10 min at 1 mL/min using a Hypersil HS C18, 250×4.6 mm column) tr=13.32 min, 100%; m/z 307 (MH$^+$).

N2-[2-Fluoro-4-(4,4,5,5-tetramethyl-1,3,2-dioxaborolan-2-yl)phenyl]-1,3-benzoxazol-2-amine To a solution of N2-(4-bromo-2-fluorophenyl)-1,3-benzoxazol-2-amine (1.480 g, 4.819 mmol) in dimethylformamide (15 mL) under nitrogen was added bis(pinacolato) diboron (1.468 g, 5.781 mmol), potassium acetate (1.419 g, 14.45 mmol), and [1,1'-bis(diphenylphosphino)ferrocene] dichloropalladium (II) complexed with dichloromethane (1:1) (0.119 g, 0.146 mmol). The violet solution was stirred at 80° C. for 18 h and then cooled to room temperature. The resulting dark brown mixture was concentrated in vacuo to give a dark brown solid. This material was triturated with dichloromethane, filtered, and the filtrate was concentrated to give a dark brown oil. Purification via flash chromatography on silica gel (eluting with 30% ethyl acetate/heptane) afforded 2.28 g of a yellow solid. This material was triturated with heptane and the solid was collected to afford N2-[2-fluoro-4-(4,4,5,5-tetramethyl-1,3,2-dioxaborolan-2-yl)phenyl]-1,3-benzoxazol-2-amine (0.961 g, 56%) as a white powder. RP-HPLC (25 to 100% CH$_3$CN in 0.1 N aqueous ammonium acetate over 10 min at 1 mL/min using a Hypersil HS C18, 250×4.6 mm column) tr=13.80 in, 88%; m/z 355 (MH$^+$).

N2-[2-Fluoro-4-(4,4,5,5-tetramethyl-1,3,2-dioxaborolan-2-yl)phenyl]-1,3-benzothiazol-2-amine N2-[2-fluoro-4-(4,4,5,5-tetramethyl-1,3,2-dioxaborolan-2-yl)phenyl]-1,3-benzothiazol-2-amine was prepared from N2-(4-bromo-2-fluorophenyl)-1,3-benzothiazol-2-amine (1.699 g, 5.258 mmol) in a manner similar to that used for N2-[2-fluoro-4-(4,4,5,5-tetramethyl-1,3,2-dioxaborolan-2-yl)phenyl]-1,3-benzoxazol-2-amine. The compound was formed as an off-white powder (0.825 g, 42%). RP-HPLC (25 to 100% CH$_3$CN in 0.1 N aqueous ammonium acetate over 10 min at 1 mL/min using a Hypersil HS C18, 250×4.6 mm column) tr=14.48 min, 90%; m/z 371 (MH$^+$).

N2-[4-(4,4,5,5-Tetramethyl-1,3,2-dioxaborolan-2-yl) phenyl]-1,3-benzothiazol-2-amine N2-[4-(4,4,5,5-tetramethyl-1,3,2-dioxaborolan-2-yl) phenyl]-1,3-benzothiazol-2-amine was prepared from N2-(4-bromophenyl)-1,3-benzothiazol-2-amine (0.909 g, 2.98 mmol) in a manner similar to that used for N2-[2-fluoro-4-(4,4,5,5-tetramethyl-1,3,2-dioxaborolan-2-yl)phenyl]-1,3-benzoxazol-2-amine. The compound was formed as an off-white powder (0.321 g, 31%). RP-HPLC (25 to 100% CH$_3$CN in 0.1 N aqueous ammonium acetate over 10 min at 1 mL/min using a Hypersil HS C18, 250×4.6 mm column) tr=13.82 min., 92%; m/z 351 (MH$^+$).

Example 367 cis-N2-(4-{4-Amino-1-[4-(4-methylpiperazino) cyclohexyl]-1H-pyrazolo[3,4-d]pyrimidin-3-yl}-2-fluorophenyl)-1,3-benzoxazol-2-amine To a solution of cis-3-iodo-1-[4-(4-methylpiperazino) cyclohexyl]-1H-pyrazolo[3,4-d]pyrimidin-4-amine (0.150 g, 0.340 mmol) in ethylene glycol dimethyl ether (3 mL) and water (1.5 mL) under nitrogen was added N2-[2-fluoro-4-(4,4,5,5-tetramethyl-1,3,2-dioxaborolan-2-yl)phenyl]-1,3-benzoxazol-2-amine (0.151 g, 0.425 mmol), tetrakis (triphenylphosphine) palladium (0) (0.020 mg, 0.017 mmol), and sodium carbonate monohydrate (0.105 mg, 0.850 mmol). The solution was stirred at 83° C. for 19 h. The resulting yellow mixture was concentrated in vacuo to give a yellow oil. Purification by preparative RP-HPLC (25 to 100% CH$_3$CN in 0.1 N aqueous ammonium acetate over 20 min at 21 mL/min using a 8 m Hypersil HS C18, 250×21 mm column, tr=5.7–8.1 min.) afforded cis-N2-(4-{4-amino-1-[4-(4-methylpiperazino)-cyclohexyl]-1H-pyrazolo[3,4-d]pyrimidin-3-yl}-2-fluorophenyl)-1,3-benzoxazol-2-amine as an off-white solid (0.046 g, 25%): $^1$H NMR (DMSO-d$_6$, 400 MHz) δ 10.65 (s, 1H), 8.49 (m, 1H), 8.25 (s, 1H), 7.53 (d, 2H), 7.48 (d, 2H), 7.26 (t, 1H), 7.20 (t, 1H), 4.80 (m, 1H), 3.51–2.50 (m, 11H), 2.33–2.32 (m, 4H), 2.09–2.06 (m, 2H), 1.80–1.40 (m, 3H); RP-HPLC (25 to 100% CH$_3$CN in 0.1 N aqueous ammonium acetate over 10 min at 1 mL/min using a Hypersil HS C18, 250×4.6 mm column) tr=6.95 min., 99%; m/z 542 (MH$^+$).

Example 368 cis-N2-(4-{4-Amino-1-[4-(4-methylpiperazino) cyclohexyl]-1H-pyrazolo[3,4-d]pyrimidin-3-yl}-2-fluorophenyl)-1,3-benzothiazol-2-amine Cis-N2-(4-{4-amino-1-[4-(4-methylpiperazino) cyclohexyl]-1H-pyrazolo[3,4-d]pyrimidin-3-yl}-2-fluorophenyl)-1,3-benzothiazol-2-amine was prepared from cis-3-iodo-1-[4-(4-methylpiperazino)cyclohexyl]-1H-pyrazolo[3,4-d]pyrimidin-4-amine (0.100 g, 0.227 mmol) and N2-[2-fluoro-4-(4,4,5,5-tetramethyl-1,3,2-dioxaborolan-2-yl)phenyl]-1,3-benzothiazol-2-amine (0.105 g, 0.283 mmol) in a manner similar to that used for cis-N2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as an off-white powder (0.051 g, 41%): $^1$H NMR (DMSO-d$_6$, 400 MHz) δ 10.51 (s, 1H), 8.80 (m, 1H), 8.24 (s, 1H), 7.85 (d, 1H), 7.65 (d, 1H), 7.51 (m, 2H), 7.36 (t, 1H), 7.20 (t, 1H), 4.82 (m, 1H), 3.51–2.25 (m, 14H), 2.15–2.10 (m, 2H), 1.80–1.50 (m, 4H); RP-HPLC (25 to 100% CH$_3$CN in 0.1 N aqueous ammonium acetate over 10 min at 1 mL/min using a Hypersil HS C18, 250×4.6 mm column) tr=7.63 min., 100%; m/z 558 (MH$^+$).

Example 369 cis-N2-(4-{4-Amino-1-[4-(4-methylpiperazino) cyclohexyl]-1H-pyrazolo[3,4-d]pyrimidin-3-yl}phenyl)-1,3-benzothiazol-2-amine Cis-N2-(4-{4-amino-1-[4-(4-methylpiperazino) cyclohexyl]-1H-pyrazolo[3,4-d]pyrimidin-3-yl}phenyl)-1,3-benzothiazol-2-amine was prepared from cis-3-iodo-1-[4-(4-methylpiperazino)cyclohexyl]-1H-pyrazolo[3,4-d]pyrimidin-4-amine (0.100 g, 0.227 mmol) and N2-[4-(4,4,5,5-tetramethyl-1,3,2-dioxaborolan-2-yl)phenyl]-1,3-benzothiazol-2-amine (0.100 g, 0.283 mmol) in a manner similar to that used for cis-N2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as an off-white powder (0.035 g, 28%): $^1$H NMR (DMSO-d$_6$, 400 MHz) δ 10.71 (s, 1H), 8.23 (s, 1H), 7.98 (d, 2H), 7.84 (d, 1H), 7.65 (d, 3H), 7.35 (t, 1H), 7.19 (t, 1H), 4.80 (m, 1H), 3.50 (m, 1H), 2.67–2.09 (m, 15H), 1.71–1.57 (m, 4H); RP-HPLC (25 to 100% CH$_3$CN in 0.1 N aqueous ammonium acetate over 10 min at 1 mL/min using a Hypersil HS C18, 250×4.6 mm column) tr=7.47 min., 100%; m/z 540 (MH$^+$).

Example 370 trans-N2-(4-{4-Amino-1-[4-(4-methylpiperazino) cyclohexyl]-1H-pyrazolo[3,4-d]pyrimidin-3-yl}phenyl)-1,3-benzoxazol-2-amine Trans-N2-(4-{4-amino-1-[4-(4-methylpiperazino) cyclohexyl]-1H-pyrazolo[3,4-d]pyrimidin-3-yl}phenyl)-1,3-benzoxazol-2-amine was prepared from trans-3-iodo-1-[4-(4-methylpiperazino)cyclohexyl]-1H-pyrazolo[3,4-d]pyrimidin-4-amine (0.036 g, 0.082 mmol) and N2-[4-(4,4,5,5-tetramethyl-1,3,2-dioxaborolan-2-yl)phenyl]-1,3-benzoxazol-2-amine (0.034 g, 0.10 mmol) in a manner similar to that used for cis-N2-(4-{4-amino-1-[4-(4-methylpiperazino)cyclohexyl]-1H-pyrazolo[3,4-d]pyrimidin-3-yl}-2-fluorophenyl)-1,3-benzoxazol-2-amine. The compound was formed as an off-white powder (0.021 g, 50%): $^1$H NMR (DMSO-d$_6$, 400 MHz) δ 10.86 (s, 1H), 8.23 (s, 1H), 7.93 (d, 2H), 7.66 (d, 2H), 7.51 (t, 1H), 7.25 (t, 1H), 7.16 (t, 1H), 4.65 (m, 1H), 3.51 (m, 1H), 2.67–1.91 (m, 17H), 1.49–1.46 (m, 2H); RP-HPLC (25 to 100% CH$_3$CN in 0.1 N aqueous ammonium acetate over 10 min at 1 mL/min using a Hypersil HS C18, 250×4.6 mm column) tr=7.17 min., 100%; m/z 524 (MH$^+$).

Example 371 trans-N2-(4-{4-Amino-1-[4-(4-methylpiperazino) cyclohexyl]-1H-pyrazolo[3,4-d]pyrimidin-3-yl}-2-fluorophenyl)-1,3-benzoxazol-2-amine Trans-N2-(4-{4-amino-1-[4-(4-methylpiperazino) cyclohexyl]-1H-pyrazolo[3,4-d]pyrimidin-3-yl}-2-fluorophenyl)-1,3-benzoxazol-2-amine was prepared from trans-3-iodo-1-[4-(4-methylpiperazino)cyclohexyl]-1H-pyrazolo[3,4-d]pyrimidin-4-amine (0.100 g, 0.227 mmol) and N2-[2-fluoro-4-(4,4,5,5-tetramethyl-1,3,2-dioxaborolan-2-yl)phenyl]-1,3-benzoxazol-2-amine (0.151 g, 0.425 mmol) in a manner similar to that used for the cis-isomer. The compound was formed as a white powder (0.053 g, 43%).

$^1$H NMR (DMSO-d$_6$, 400 MHz) δ 10.63 (s, 1H), 8.45 (m, 1H), 8.24 (s, 1H), 7.55–7.48 (m, 4H), 7.25 (t, 1H), 7.17 (t, 1H), 4.65 (m, 1H), 3.36 (m, 1H), 3.31–1.93 (m, 16H), 1.46–1.23 (m, 3H); RP-HPLC (25 to 100% CH$_3$CN in 0.1 N aqueous ammonium acetate over 10 min at 1 mL/min using a Hypersil HS C18, 250×4.6 mm column) tr=6.73 min., 99%; m/z 542 (MH$^+$).

Example 372 trans-N2-(4-{4-Amino-1-[4-(4-methylpiperazino) cyclohexyl]-1H-pyrazolo[3,4-d]pyrimidin-3-yl}-2-fluorophenyl)-1,3-benzothiazol-2-amine Trans-N2-(4-{4-amino-1-[4-(4-methylpiperazino) cyclohexyl]-1H-pyrazolo[3,4-d]pyrimidin-3-yl}-2-fluorophenyl)-1,3-benzothiazol-2-amine was prepared from trans-3-iodo-1-[4-(4-methylpiperazino)cyclohexyl]-1H-pyrazolo[3,4-d]pyrimidin-4-amine (0.100 g, 0.227 mmol) and N2-[2-fluoro-4-(4,4,5,5-tetramethyl-1,3,2-dioxaborolan-2-yl)phenyl]-1,3-benzothiazol-2-amine (0.105 g, 0.283 mmol) in a manner similar to that used for the cis-isomer. The compound was formed as a white powder (0.052 g, 41%):

$^1$H NMR (DMSO-d$_6$, 400 MHz) δ 10.51 (s, 1H), 8.79 (m, 1H), 8.24 (s, 1H), 7.85 (d, 1 H), 7.66 (d, 1H), 7.51 (m, 2H), 7.36 (t, 1H), 7.20 (t, 1H), 4.66 (m, 1H), 3.69 (m, 1H), 2.89–1.94 (m, 17H), 1.50–1.47 (m, 2H); RP-HPLC (25 to 100% CH$_3$CN in 0.1 N aqueous ammonium acetate over 10 min at 1 mL/min using a Hypersil HS C18, 250×4.6 mm column) tr=6.30 min., 99%; m/z 558 (MH$^+$).

Example 373 cis-N2-(4-{4-Amino-1-[4-(4-methylpiperazino) cyclohexyl]-1H-pyrazolo[3,4-d]pyrimidin-3-yl}phenyl)-4-methyl-1,3-benzoxazol-2-amine 1,1'-Thiocarbonyldi-2(1H)-pyridone (0.086 g, 0.369 mmol) was added to a solution of cis-3-(4-aminophenyl) 1-[4-(4-methylpiperazino)cyclohexyl]-1H-pyrazolo[3,4-d] pyrimidin-4-amine (0.150 g, 0.369 mmol) in pyridine (7 mL) at 0° C., and the mixture was stirred for 1 h at 0° C. The resulting orange solution was partitioned between dichloromethane (10 mL) and water (10 mL). The organic layer was separated and washed with 0.5 N HCl (10 mL), dried over anhydrous magnesium sulfate, filtered, and concentrated. 2-Amino-m-cresol (0.045 g, 0.369 mmol) was added to a suspension of the resulting orange solid and toluene (10 mL), and the mixture was heated at 80° C. for 1 h. 1,3-Dicyclohexylcarbodiimide (0.114 g, 0.554 mmol) was added and the reaction mixture was heated at 80 C for an additional 18 h. The resulting orange brown solution was cooled to room temperature and concentrated to afford a light brown glassy solid. Purification by preparative HPLC (25 to 100% CH$_3$CN in 0.1 N aqueous ammonium acetate over 20 min at 21 mL/min using a 8μ Hypersil HS C18, 250×21 mm column, tr=8.1–10.3 min.) afforded cis-N2-(4-{4-amino-1-[4-(4-methylpiperazino)cyclohexyl]-1H-pyrazolo[3,4-d]pyrimidin-3-yl}phenyl)-4-methyl-1,3-benzoxazol-2-amine as an off-white solid (0.024 g, 12%): $^1$H NMR (DMSO-d$_6$, 400 MHz) δ 10.81 (s, 1H), 8.24 (s, 1H), 7.96 (d, 2H), 7.66 (d, 2H), 7.33 (d, 1H), 7.06 (m, 2H), 4.80 (m, 1H), 3.391 (m, 1H), 2.67–2.10 (m, 18H), 1.71–1.60 (m, 4H); RP-HPLC (25 to 100% CH$_3$CN in 0.1 N aqueous ammonium acetate over 10 min at 1 mL/min using a Hypersil HS C18, 250×4.6 mm column) tr=7.57 min., 99%; m/z 538 (MH$^+$).

Example 374 cis-N2-(4-{4-Amino-1-[4-(4-methylpiperazino) cyclohexyl]-1H-pyrazolo[3,4-d]pyrimidin-3-yl}phenyl)-5-chloro-1,3-benzoxazol-2-amine Cis-N2-(4-{4-amino-1-[4-(4-methylpiperazino) cyclohexyl]-1H-pyrazolo[3,4-d]pyrimidin-3-yl}phenyl)-5-chloro-1,3-benzoxazol-2-amine was prepared from cis-3-(4-aminophenyl)-1-[4-(4-methylpiperazino)cyclohexyl]-1H-pyrazolo[3,4-d]pyrimidin-4-amine (0.100 g, 0.246 mmol) and 2-amino-4-chlorophenol (0.035 g, 0.246 mmol) in a manner similar to that used for cis-N2-(4-{4-amino-1-[4-(4-methylpiperazino)cyclohexyl]-1H-pyrazolo[3,4-d] pyrimidin-3-yl}phenyl)-4-methyl-1,3-benzoxazol-2-amine. The compound was formed as a pale yellow solid (0.020 g, 15%):

$^1$H NMR (DMSO-d$_6$, 400 MHz) δ 11.03 (s, 1H), 8.24 (s, 1H), 7.92 (d, 2H), 7.67 (d, 2H), 7.56 (m, 2H), 7.20 (m, 1H), 7.16 (t, 1H), 4.81 (m, 1H), 3.41–1.60 (m, 20H); RP-HPLC (25 to 100% CH$_3$CN in 0.1 N aqueous ammonium acetate over 10 min at 1 mL/min using a Hypersil HS C18, 250×4.6 mm column) tr=7.83 min., 99%; m/z 558

Example 375 cis-N2-(4-{4-Amino-1-[4-(4-methylpiperazino) cyclohexyl]-1H-pyrazolo[3,4-d]pyrimidin-3-yl}phenyl)-5-methyl-1,3-benzoxazol-2-amine Cis-N2-(4-{4-Amino-1-[4-(4-methylpiperazino) cyclohexyl]-1H-pyrazolo[3,4-d]pyrimidin-3-yl}phenyl)-5-methyl-1,3-benzoxazol-2-amine was prepared from cis-3-(4-aminophenyl)-1-[4-(4-methylpiperazino)cyclohexyl]-1H-pyrazolo[3,4-d]pyrimidin-4-amine (0.057 g, 0.140 mmol) and 2-amino-p-cresol (0.017 g, 0.140 mmol) in a manner similar to that used for cis-N2-(4-{4-amino-1-[4-(4-methylpiperazino)cyclohexyl]-1H-pyrazolo[3,4-d] pyrimidin-3-yl)phenyl)-4-methyl-1,3-benzoxazol-2-amine. The compound was formed as an off-white solid (0.010 g, 13%): $^1$H NMR (DMSO-d$_6$, 400 MHz) δ 10.81 (s, 1H), 8.23 (s, 1H), 7.93 (d, 2H), 7.66 (d, 2H), 7.38 (d, 1H), 7.30 (s, 1H), 6.96 (d, 1H), 4.80 (m, 1H), 2.60–2.07 (m, 12H), 2.39 (s, 3H), 2.15 (s, 3H), 1.71–1.59 (m, 5H); RP-HPLC (25 to 100% CH$_3$CN in 0.1 N aqueous ammonium acetate over 10 min at 1 mL/min using a Hypersil HS C18, 250×4.6 mm column) tr=7.48 min., 90%; m/z 538 (MH$^+$).

Example 376 cis-N2-(4-{4-Amino-1-[4-(4-methylpiperazino) cyclohexyl]-1H-pyrazolo[3,4-d]pyrimidin-3-yl}phenyl)-5,7-dimethyl-1,3-benzoxazol-2-amine Cis-N2-(4-{4-amino-1-[4-(4-methylpiperazino) cyclohexyl]-1H-pyrazolo[3,4-d]pyrimidin-3-yl}phenyl)-5,7-dimethyl-1,3-benzoxazol-2-amine was prepared from cis-3-(4-aminophenyl)-1-[4-(4-methylpiperazino)cyclohexyl]-1H-pyrazolo[3,4-d]pyrimidin-4-amine (0.100 g, 0.246 mmol) and 6-amino-2,4-xylenol (0.034 g, 0.246 mmol) in a manner similar to that used for cis-N2-(4-{4-amino-1-[4-(4-methylpiperazino)cyclohexyl]-1H-pyrazolo[3,4-d] pyrimidin-3-yl}phenyl)-4-methyl-1,3-benzoxazol-2-amine. The compound was formed as an off-white solid (0.031 g, 23%): $^1$H NMR (DMSO-d$_6$, 400 MHz) δ 10.85 (s, 1H), 8.23 (s, 1H), 7.93 (d, 2H), 7.65 (d, 2H), 7.11 (s, 1H), 6.80 (s, 1H), 4.80 (m, 1H), 2.60–2.17 (m, 12H), 2.41 (s, 3H), 2.37 (s, 3H), 2.22 (s, 3H), 1.71–1.59 (m, 5H); RP-HPLC (25 to 100% CH$_3$CN in 0.1 N aqueous ammonium acetate over 10 min at 1 mL/min using a Hypersil HS C18, 250×4.6 mm column) tr=8.00 min., 93%; m/z 552 (MH$^+$).

Example 377

N2-[4-(4-Amino-1-{4-[1-(1-methylpiperid-4-yl) piperidyl]}-1H-pyrazolo[3,4-d]pyrimidin-3-yl)-2-fluorophenyl]-5-chloro-2-thiophenesulfonamide This compound was prepared from N1-4-(4-amino-1-{4-[1-(1-methylpiperid-4-yl)piperidyl]}-1H-pyrazolo[3,4-d] pyrimidin-3-yl)-2-fluorophenylaniline (100 mg, 0.236 mmol) using the method described hereinabove, to afford N2-[4-(4-amino-1-{4-[1-(1-methylpiperid-4-yl)piperidyl]}-1H-pyrazolo[3,4-d]pyrimidin-3-yl)-2-fluorophenyl]-5-chloro-2-thiophenesulfonamide (51 mg); RP-HPLC conditions: 10 to 90% CH$_3$CN in 0.1 N aqueous ammonium acetate, buffered to pH 4.5, over 20 min at 2 mL/min using a Waters Symmetry C18, 300 Å, 5 μm, 250×4.6 mm column R$_t$ 11.219 min., 98.5% and m/z (MH$^+$) 605.2.

Examples 378–383

General Synthesis of Urea and Sulfonamide Analogs of cis-3-{4-[Amino(phenyl)methyl]phenyl}-1-[4-(4-methylpiperazino)cyclohexyl]-1H-pyrazolo[3,4-d]pyrimidin-4-amine These anaologs were prepared from cis-3-{4-[amino(phenyl)methyl]phenyl}-1-[4-(4-methylpiperazino)cyclohexyl]-1H-pyrazolo[3,4-d]pyrimidin-4-amine (50 mg, 0.10 mmol) using the method described hereinabove, to afford the following examples:

| Structure | HPLC Rt (min) | Purity % | m/z (MH+) | Example |
|---|---|---|---|---|
| 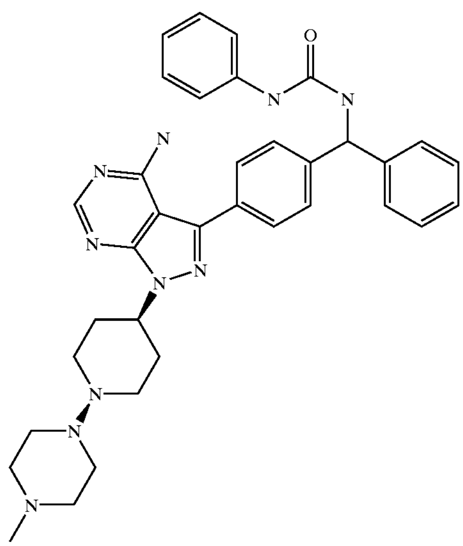 | 13.815 | 100 | 616.3 | 378 |
| 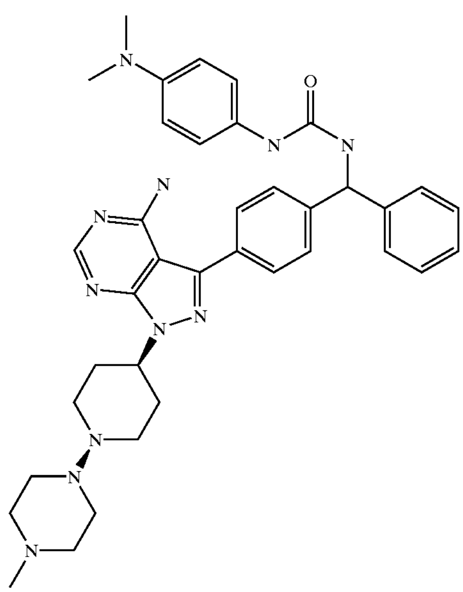 | 13.122 | 100 | 659.5 | 379 |

-continued
| Structure | HPLC Rt (min) | Purity % | m/z (MH+) | Example |
|---|---|---|---|---|
| 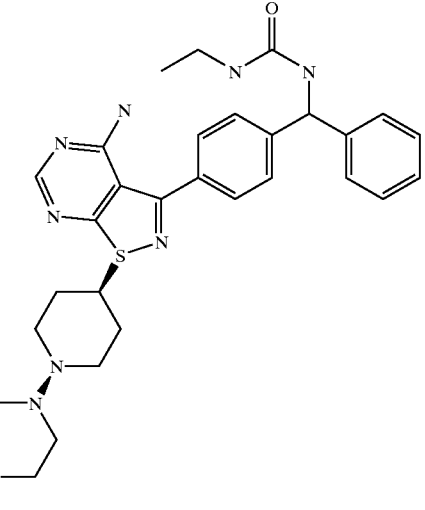 | 11.64 | 100 | 568.3 | 380 |
| 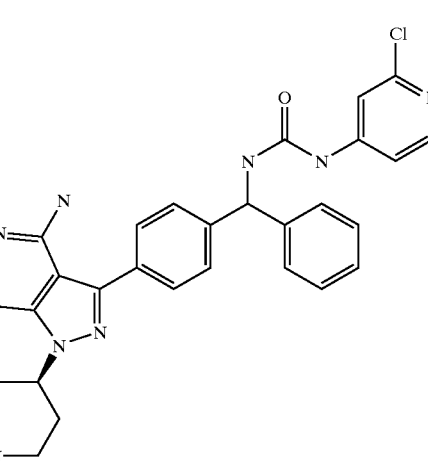 | 14.99 | 97.8 | 685.5 | 381 |

-continued

| Structure | HPLC Rt (min) | Purity % | m/z (MH⁺) | Example |
|---|---|---|---|---|
| 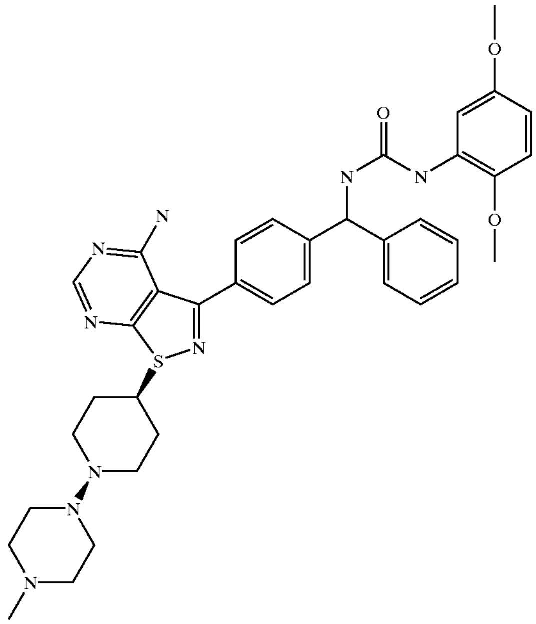 | 14.43 | 100 | 676.6 | 382 |
| 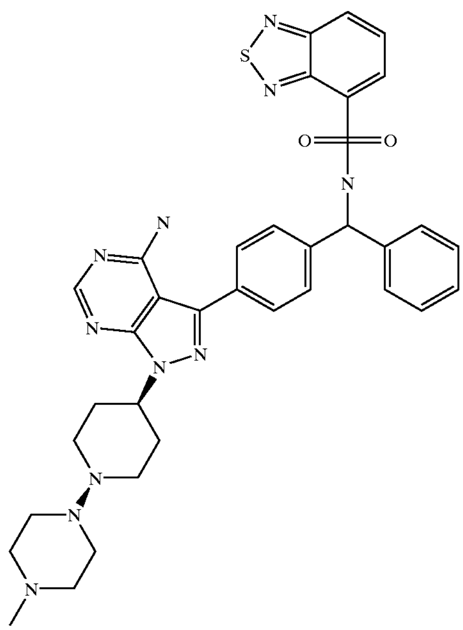 | 13.68 | 100 | 695 | 383 |

Analytical RP-HPLC conditions: 10 to 90% CH$_3$CN in 0.1 N aqueous ammonium acetate, buffered to pH 4.5, over 20 min at 2 mL/min using a Waters Symmetry C18, 5 μm, 300 Å, 250×4.6 mm column.

Example 384 trans-N-(4-{4-Amino-1-[4-(4-methylpiperazino)cyclohexyl]-1H-pyrazolo[3,4-d]pyrimidin-3-yl}benzyl)-N'-(3-methylphenyl)

A mixture containing trans-3-iodo-1-[4-(4-methylpiperazino)cyclohexyl]-1H-pyrazolo[3,4-d]pyrimidin-4-amine (850 mg, 1.93 mmol), tert-butyl N-[4-(4,4,5,5-tetramethyl-1,3,2-dioxaborolan-2-yl)benzyl]carbamate (1.25 equiv., 812 mg, 2.41 mmol), tetrakis-(triphenylphosphine)palladium (135 mg) and sodium carbonate (2.5 equiv., 511 mg, 4.83 mmol) in degassed water (10 mL) and DME (30 mL) was heated and stirred at 85° C. for 16 h. The solvent was removed under reduced pressure to give a brown foam which was purified by column chromatography over silica gel using 10% methanol and 1% ammonium hydroxide in dichloromethane as the eluent. Trans-tert-butyl N-(4-{4-amino-1-[4-(4-methylpiperazino)cyclohexyl]-1H-pyrazolo[3,4-d]pyrimidin-3-yl}benzyl)carbamate was formed as an off white foam (800 mg, 80%). A solution of tert-butyl N-(4-

{4-amino-1-[4-(4-methylpiperazino)cyclohexyl]-1H-pyrazolo[3,4-d]pyrimidin-3-yl}benzyl)carbamate (800 mg) in TFA (4 mL) and dichloromethane (4 mL) was stirred at ambient temperature for 2 h. The solvent was removed in vacuo and the oily residue was basified with saturated aqueous sodium hydrogen carbonate solution and the aqueous layer washed with dichloromethane (3×20 mL). The aqueous layer was concentrated and DMF added (20 mL). The salts were removed by filtration and the DMF was removed in vacuo. The residue was purified by column chromatography over silica gel using 10% methanol in dichloromethane as the eluent to afford 3-[4-(aminomethyl)phenyl]-1-[4-(4-methylpiperazino)cyclohexyl]-1H-pyrazolo[3,4-d]pyrimidin-4-amine as a yellow solid (70 mg, 11%). m-Tolyl isocyanate (1.1 equiv., 13.7 mg, 0.1 mmol) was added to a solution of 3-[4-(aminomethyl)phenyl]-1-[4-(4-methylpiperazino)cyclohexyl]-1H-pyrazolo[3,4-d]pyrimidin-4-amine (35 mg, 0.083 mmol) in pyridine (0.5 mL) and then stirred for 2 days. The reaction mixture was purified using mass actuated preparative RP-HPLC (Micromass/Gilson, Hypersil BDS C18, 5 μm, 100×21.2 mm column; 0–100% acetonitrile and 0.05M ammonium acetate, buffered to pH 4.5, over 12.5 min at 25 mL/min) to give trans-N-(4-{4-amino-1-[4-(4-methylpiperazino)cyclohexyl]-1H-pyrazolo[3,4-d]pyrimidin-3-yl}benzyl)-N'-(3-methylphenyl)urea (17 mg, 37%); $^1$H NMR (DMSO-d$_6$, 400 MHz) δ 1.46 (2H, m), 2.05 (4H, m), 2.18 (2H, m), 2.25 (3H, s), 2.33 (4H, m), 2.45–2.53 (8H, m), 4.38 (2H, br d), 4.65 (1H, m), 6.52 (1H, t), 6.66 (1H, d), 7.10 (1H, t), 7.19 (1H, brd), 7.26(1H, br s), 7.46(2H, d), 7.63 (2H, d), 8.23 (1H, s) and 8.51 (1H, s) and m/z (MH$^+$) 554.2.

Example 385 trans-N-(4-{04-Amino-1-[4-(4-methylpiperazino)cyclohexyl]-1H-pyrazolo[3,4-d]pyrimidin-3-yl}benzyl)-N'-(3-methoxyphenyl)urea The same method, and scale, as described in Example 240 was used to prepare trans-N-(4-{4-amino-1-[4-(4-methylpiperazino)cyclohexyl]-1H-pyrazolo[3,4-d]pyrimidin-3-yl}benzyl)-N'-(3-methoxyphenyl)urea (17 mg, 36%); $^1$H NMR (DMSO-d$_6$, 400 MHz) δ 1.46 (2H, m), 2.05 (4H, m), 2.18 (2H, m), 2.35 (4H, m), 2.45–2.53 (8H, m), 3.70 (3H, s), 4.38 (2H, br d), 4.65 (1H, m), 6.49 (1H, m), 6.67 (1H, m), 6.90 (1H, br d), 7.12 (1H, t), 7.17 (1H, m), 7.46 (2H, d), 7.63 (2H, d), 8.23 (1H, s) and 8.62 (1H, s) and m/z (MH$^+$) 570.2.

Example 386 cis-N1-(4-{4-Amino-1-[4-(4-methylpiperazino)cyclohexyl]-1H-pyrazolo[3,4-d]pyrimidin-3-yl}-2-methoxyphenyl)-2,2-dimethyl-3-phenylpropanamide 2,2-Dimethyl-3-phenylpropanenitrile A solution of N-isopropylcyclohexyl amine (2.8 g, 19.72 mmol) in anhydrous tetrahydrofuran (25 mL) at −78° C. was treated with 1.6 M n-butyl lithium in hexane (12.23 mL, 19.72 mmol) drop-wise over 15 minutes. The reaction solution was stirred for 10 min at −78° C. The solution turned yellow from colorless. Isobutyronitrile (1.36 g, 19.72 mmol) was added to the reaction solution, and the reaction mixture was stirred for a further 10 min at −78° C. This solution was syringed into a solution of benzyl chloride (2.62 g, 20.71 mmol) in anhydrous tetrahydrofuran at −78° C. under a nitrogen atmosphere. The reddish/brown reaction was solution stirred for 1 h at −78° C. The dry ice/acetone bath was then removed, and the solution stirred at room temperature for 5 h. The reaction solution was quenched with saturated aqueous ammonium chloride solution (10 mL). Ethyl acetate (25 mL) was added to the quenched reaction solution. The layers were partitioned and the aqueous layer was extracted with ethyl acetate (150 mL). The combined organic layers were washed with water and brine, dried over magnesium sulfate, filtered and evaporated under reduced pressure to yield 3.18 g of crude material. The crude material was partitioned between 2 N hydrochloric acid solution and ethyl acetate. The organic layer was washed with water and brine, dried over magnesium sulfate, filtered and evaporated to give 2.18 g (69%) 2,2-dimethyl-3-phenylpropanenitrile. $^1$H NMR (DMSO-d$_6$, 400 MHz) δ 7.369–7.333 (m, 2H), 7.309–7.270 (m, 3H), 2.832 (s, 2H), 1.294 (s, 6H). This compound was used in subsequent reaction with out further analysis.

2,2-Dimethyl-3-phenylpropanoic Acid

A solution of 2,2-dimethyl-3-phenylpropanenitrile (1.0 g, 6.28 mmol) in ethylene glycol (5 mL) was treated with solid potassium hydroxide (1.06 g, 18.84 mmol). The reaction mixture was stirred for 48 h at 196° C. under a nitrogen atmosphere. Ethylene glycol was removed under vacuum distillation. 1 N Sodium hydroxide solution (25 mL) and ethyl acetate (15 mL) were added to the brown residue. The layers were separated, and the aqueous layer was extracted with ethyl acetate (375 mL). The combined organic layers were washed with water and brine, dried over magnesium sulfate, filtered, and evaporated under reduced pressure to give 0.856 g (76%) of 2,2-dimethyl-3-phenylpropanoic acid. $^1$H NMR (DMSO-d$_6$, 400 MHz) δ 12.20 (s, 1H), 7.28–7.24 (m, 2H), 7.22–7.20 (m, 1H), 7.15–7.13 (m, 2H), 2.78 (s, 2H), 1.07 (s, 6H). This compound was used in subsequent reaction with out further analysis.

2,2-Dimethyl-3-phenylpropanoyl Chloride

A solution of 2,2-dimethyl-3-phenylpropanoic acid (0.856 g, 4.8 mmol) in chloroform (6 mL) at 0° C. was treated with oxalyl chloride (3.05 g, 24 mmol) and 1 drop of dimethylformamide. The reaction solution was stirred for 1 h at 0° C. The ice bath was removed and the reaction mixture stirred at room temperature over night. The solvent was removed under reduced pressure and dried under high vacuum to afford a quantitative amount of 2,2-dimethyl-3-phenylpropanoyl chloride. The oil was directly used in the following reaction.

cis-N1-(4-{4-Amino-1-[4-(4-methylpiperazino)cyclohexyl]-1H-pyrazolo[3,4-d]pyrimidin-3-yl}-2-methoxyphenyl)-2,2-dimethyl-3-phenylpropanamide A solution of cis-3-(4-amino-3-methoxyphenyl)-1-[4-(4-methylpiperazino)cyclohexyl]-1H-pyrazolo[3,4-d]pyrimidin-4-amine (0.100 g, 0.23 mmol) in pyridine (2.5 mL) was treated with 2,2-dimethyl-3-phenylpropanoyl chloride (0.120 g, 0.61 mmol). The reaction mixture was stirred for 2 h at room temperature under a nitrogen atmosphere. Saturated sodium bicarbonate solution (10 mL) was added, and the reaction mixture was stirred for 20 min. Solvent was removed under reduced pressure. Dichloromethane and saturated sodium bicarbonate solution was added to the residue. The layers were separated using an Empore extraction cartridge. The organic solvent was removed under reduced pressure. The crude compound was purified by flash chromatography on silica gel, using 10% methanol in dichloromethane as eluent to give 0.085 g (62%) cis-N1-(4-{4-amino-1-[4-(4-methylpiperazino)cyclohexyl]-1H-pyrazolo[3,4-d]pyrimidin-3-yl}-2-methoxyphenyl)-2,2-dimethyl-3-phenylpropanamide. $^1$H NMR (CDCl$_3$, 400

MHz) δ 8.595–8.574 (m, 1H), 8.372 (s, 1H), 7.985 (s, 1H), 7.292–7.158 (m, 7H), 4.923 (m, 1H), 3.891 (s, 3H), 3.050–3.013 (m, 1H), 2.965 (s, 2H), 2.65–2.55 (m, 5H), 2.440–2.346 (m, 4H), 2.244–2.166 (m, 4H), 1.854–1.823 (m, 3H), 1.688 (m, 3H), 1.334 (s, 6H); HPLC Waters 2690 Alliance HPLC (Symmetry Shield $RP_{18}$ 3.5 μm, 2.1×50 mm; 5%–95% acetonitrile-0.1 M ammonium acetate over 15 min, 0.5 mL/min) $R_t$ 5.517 min (100%).

Example 387 trans-N1-(4-{4-Amino-1-[4-(4-methylpiperazino)cyclohexyl]-1H-pyrazolo[3,4-d]pyrimidin-3-yl}-2-methoxyphenyl)-2,2-dimethyl-3-phenylpropanamide tris-Maleate A solution of trans-3-(4-amino-3-methoxyphenyl)-1-[4-(4-methylpiperazino)cyclohexyl]-1H-pyrazolo[3,4-d]pyrimidin-4-amine (0.250 g, 0.573 mmol) in pyridine (3 mL) at 0° C. was treated with 2,2-dimethyl-3-phenylpropanoyl chloride (0.304 g, 1.55 mmol). The reaction mixture was stirred for 10 min at 0° C. The ice bath was removed and the reaction mixture was stirred at room temperature for 5 h. Solvent was removed under reduced pressure to dryness. Dichloromethane (15 mL) and saturated sodium bicarbonate solution (5 mL) were added to the solid. The layers were separated using an Empore extraction cartridge. The organic solvent was removed under reduced pressure. The crude solid was purified by flash chromatography using 10% methanol in dichloromethane, then 15% (methanol with 5% ammonium hydroxide) in dichloromethane as eluent. The crude solid from the previous purification was recrystallized using ethyl acetate and heptane. The precipitate was filtered to give 0.201 g (59%) of trans-N1-(4-{4-amino-1-[4-(4-methylpiperazino)cyclohexyl]-1H-pyrazolo[3,4-d]pyrimidin-3-yl}-2-methoxyphenyl)-2,2-dimethyl-3-phenylpropanamide. A hot solution of trans-N1-(4-{4-amino-1-[4-(4-methylpiperazino)cyclohexyl]-1H-pyrazolo[3,4-d]pyrimidin-3-yl}-2-methoxyphenyl)-2,2-dimethyl-3-phenylpropanamide (0.201, 0.337 mmol) in ethyl acetate was treated with a hot solution of maleic acid (0.117 g, 1.011 mmol) in ethyl acetate. The precipitate was filtered under nitrogen, and dried under high vacuum to give 0.265 g of trans-N1-(4-{4-amino-1-[4-(4-methylpiperazino)cyclohexyl]-1H-pyrazolo[3,4-d]pyrimidin-3-yl}-2-methoxyphenyl)-2,2-dimethyl-3-phenylpropanamide tri-maleate. $^1$H NMR (DMSO-$d_6$, 400 MHz) δ 8.46 (s, 1H), 8.241 (s, 1H), 8.107–8.086 (d, 1H, J=8.4 Hz), 7.248–7.183 (m, 7H), 6.170 (s, 6H), 4.697 (m, 1H), 3.883 (s, 3H), 2.931 (s, 3H), 2.9–2.75 (br, s, 4H), 2.671 (s, 3H), 2.104–1.990 (m, 7H), 1.588–1.5632 (m, 2H), 1.226 (s, 7H); HPLC Waters 2690 Alliance HPLC (Symmetry Shield $RP_{18}$ 3.5 μm, 2.1×50 mm; 5%–95% acetonitrile-0.1 M ammonium acetate over 15 min, 0.5 mL/min) $R_t$ 5.413 min (95%).

Example 388 trans-N1-(4-{4-Amino-1-[4-(4-methylpiperazino)cyclohexyl]-1H-pyrazolo[3,4-d]pyrimidin-3-yl}-2-methoxyphenyl)-(1S,2S)-2-phenylcyclopropane-1-carboxamide tris-Maleate A solution of trans-3-(4-amino-3-methoxyphenyl)-1-[4-(4-methylpiperazino)cyclohexyl]-1H-pyrazolo[3,4-d]pyrimidin-4-amine (0.162 g, 0.371 mmol) in pyridine (2 mL) at 0° C. was treated with trans-2-phenyl-1-cyclopropylcarbonyl chloride (0.134 g, 0.742 mmol) under a nitrogen atmosphere. The reaction mixture was stirred for 20 min at 0° C., the ice bath was removed and the reaction mixture stirred at room temperature for 5 h. Additional trans-2-phenyl-1-cyclopropylcarbonyl chloride (0.034 g, 0.186 mmol) was added and the reaction mixture stirred for 1 h. The organic layer was removed under reduced pressure, and dichloromethane (15 mL) was then added. The layers were separated using an Empore extraction cartridge. The organic layer was removed under reduced pressure. The crude product was purified by flash chromatography on silica gel using 15% methanol in dichloromethane then 20% methanol in dichloromethane as eluent. The column afforded 0.150 g (70%) of trans-N1-(4-{4-amino-1-[4-(4-methylpiperazino)cyclohexyl]-1H-pyrazolo[3,4-d]pyrimidin-3-yl}-2-methoxyphenyl)-(1S,2S)-2-phenylcyclopropane-1-carboxamide. A hot solution of trans-N1-(4-{4-amino-1-[4-(4-methylpiperazino)cyclohexyl]-1H-pyrazolo[3,4-d]pyrimidin-3-yl}-2-methoxyphenyl)-(1S,2S)-2-phenylcyclopropane-1-carboxamide (0.147, 0.253 mmol) in ethyl acetate was treated with a hot solution of maleic acid (0.088 g, 0.759 mmol) in ethyl acetate. The precipitate formed was filtered under nitrogen and dried under high vacuum to give 0.204 g of trans-N1-(4-{4-amino-1-[4-(4-methylpiperazino)cyclohexyl]-1H-pyrazolo[3,4-d]pyrimidin-3-yl}-2-methoxyphenyl)-(1S,2S)-2-phenylcyclopropane-1-carboxamide tris-maleate. $^1$H NMR (DMSO-$d_6$, 400 MHz) δ 9.64 (s, 1H), 8.23–8.21 (m, 2H), 7.33–7.29 (m, 2H), 7.24–7.17 (m, 4H), 6.16 (s, 6H), 4.69–4.66 (m, 1H), 3.90 (s, 3H), 2.90–2.60 (m, 7H), 2.37–2.35 (m, 2H), 2.10–1.99 (m, 8H), 1.70–1.50 (m, 3H), 1.32 (m, 1H); HPLC Waters 2690 Alliance HPLC (Symmetry Shield $RP_{18}$ 3.5 μm, 2.1×50 mm; 5%–95% acetonitrile-0.1 M ammonium acetate over 15 min, 0.5 mL/min) $R_t$ 5.346 min (97%).

Examples 389 cis-N2-(4-{4-Amino-1-[4-(4-methylpiperazino)cyclohexyl]-1H-pyrazolo[3,4-d]pyrimidin-3-yl}-2-methoxyphenyl)benzo[b]thiophene-2-carboxamide Example 390 cis-N2-(4-{4-Amino-1-[4-(4-methylpiperazino)cyclohexyl]-1H-pyrazolo[3,4-d]pyrimidin-3-yl}-2-methoxyphenyl)-2-thiophenecarboxamide Example 391 cis-N2-(4-{4-Amino-1-[4-(4-methylpiperazino)cyclohexyl]-1H-pyrazolo[3,4-d]pyrimidin-3-yl}-2-methoxyphenyl)-2-furamide Amides Derived From cis-3-(4-Amino-3-methoxyphenyl)-1-[4-(4-methylpiperazino)cyclohexyl]-7H-pyrazolo[3,4-d]pyrimidin-4-amine The commercially available acid chlorides (0.23 mmol) in dichloromethane (100 μL) were added to cis-3-(4-amino-3-methoxyphenyl)-1-[4-(4-methylpiperazino)cyclohexyl]-7H-pyrazolo[3,4-d]pyrimidin-4-amine (0.050 g, 0.115 mmol) in pyridine (800 μL). The reaction mixtures were stirred overnight. The reaction mixtures were quenched with 1 N sodium hydroxide solution. Solvent was removed on a Supelco-manifold under vacuum and nitrogen purge. The remaining solids were submitted for preparative HPLC (Hypersil C18, 100×21 mm column, 5 μm, 15–100% Acetonitrile gradient over 8 min, total run time—10 min, buffer—50 mM Ammonium Acetate, 25 ml/min). Dichloromethane and 1 N sodium hydroxide solution were added to the solids. The layers were partitioned using an Empore extraction cartridge to give corresponding products. HPLC Perkin Elmer Pecosphere C18, 3 μM, 33×4.6, 3.5 ml/min 100–100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min)

trans-N1-(4-{4-Amino-1-[4-(4-methylpiperazino) cyclohexyl]-1H-pyrazolo[3,4-d]pyrimidin-3-yl}-2-methoxyphenyl)-3-methyl-3-phenylbutanamide tris-Maleate A solution of trans-3-(4-amino-3-methoxyphenyl)-1-[4-(4-methylpiperazino)cyclohexyl]-7H-pyrazolo[3,4-d]pyrimidin-4-amine (0.200 g, 0.458 mmol) in pyridine (4

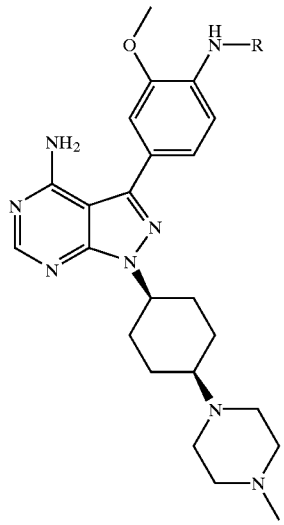

| Compound Name | R | Qty. (mg) | MH+ | $R_t$ (mins) |
|---|---|---|---|---|
| cis-N2-(4-{4-amino-1-[4-(4-methylpiperazino)cyclohexyl]-1H-pyrazolo[3,4-d pyrimidin-3-yl}-2-methoxyphenyl)benzo[b]thiophene-2-carboxamide Ex 389 | benzo[b]thiophen-2-yl carbonyl | 45 (66%) | 596.8 | 3.464 |
| cis-N2-(4-{4-amino-1-[4-(4-methylpiperazino)cyclohexyl]-1H-pyrazolo[3,4-d]pyrimidin-3-yl}-2-methoxyphenyl)-2-thiophenecarboxamide Ex 390 | thiophen-2-yl carbonyl | 47 (75%) | 547.1 | 2.746 |
| cis-N2-(4-{4-amino-1-[4-(4-methylpiperazino)cyclohexyl]-1H-pyrazolo [3,4-d]pyrimidin-3-yl}-2-methoxyphenyl)-2-furamide Ex 391 | furan-2-yl carbonyl | 36 (59%) | 531.3 | 2.626 |

Example 392 trans-N1-(4-{4-Amino-1-[4-(4-methylpiperazino) cyclohexyl]-1H-pyrazolo[3,4-d]pyrimidin-3-yl}-2-methoxyphenyl)-3-methyl-3-phenylbutanamide tris-Maleate 3-Methyl-3-phenylbutanoyl Chloride A solution of 3-methyl-3-phenylbutyric acid (0.508 g, 2.85 mmol) in dichloromethane (10 mL) at −78° C. was treated with oxalyl chloride (3.62, 28.5 mmol) and 1 drop of dimethylformamide. The reaction mixture was stirred at −78° C. for 10 min, and dry ice/acetone bath was removed to stir at room temperature over night. Solvent was removed under reduced pressure, and dried under high vacuum. The product was used directly for subsequent reaction without analysis.

mL) at −5° C. was treated with a solution of 3-methyl-3-phenylbutanoyl chloride (0.101 g, 0.514 mmol) in dichloromethane (1 mL) drop-wise. The reaction mixture was stirred for 20 min at −5° C., then the dry ice/acetone bath was removed and the reaction mixture stirred at room temperature for 4 h. 1 N sodium hydroxide solution (5 mL) was added and the mixture stirred over night. Solvent was removed under reduced pressure. The crude solid was dried under high vacuum. Dichloromethane (10 mL) and 1 N sodium hydroxide solution (10 mL) were added. The layers were separated using an Empore extraction cartridge. The organic solvent was removed by blowing nitrogen over the top, to give 0.240 g (88%) of trans-N1-(4-{4-amino-1-[4-(4-methylpiperazino)cyclohexyl]-1H-pyrazolo[3,4-d] pyrimidin-3-yl}-2-methoxyphenyl)-3-methyl-3-phenylbutanamide. A hot solution of trans-N1-(4-{4-amino-1-[4-(4-methylpiperazino)cyclohexyl]-1H-pyrazolo[3,4-d]

pyrimidin-3-yl}-2-methoxyphenyl)-3-methyl-3-phenylbutanamide (0.240 g, 0.402 mmol) in ethyl acetate and a few drops of ethanol was treated with a hot solution of maleic acid (0.140 g, 1.206 mmol) in ethyl acetate. The precipitated formed was filtered under nitrogen atmosphere, and dried on a lyophilizer to give 0.323 g trans-N1-(4-{4-amino-1-[4-(4-methylpiperazino)cyclohexyl]-1H-pyrazolo[3,4-d]pyrimidin-3-yl}-2-methoxyphenyl)-3-methyl-3-phenylbutanamide tris-maleate. $^1$H NMR (DMSO-d$_6$, 400 MHz) δ 8.807 (s, 1H), 8.226 (s, 1H), 8.109–8.088 (d, 1H, J=8.4 Hz), 7.489–7.470 (d, 2H, J=7.6 Hz), 7.345–7.306 (m, 2H), 7.213–7.134 (m, 3H), 6.151 (s, 5H), 4.680 (m, 1H), 3.836 (s, 3H), 3.3 (br, s, 7H), 2.655 (s, 3H), 2.541 (s, 4H), 2.085–1.989 (m, 6H), 1.574–1.551 (m, 2H), 1.431 (s, 6H); HPLC Waters 2690 Alliance HPLC (Symmetry Shield RP$_{18}$ 3.5 μm, 2.1×50 mm; 5%–95% acetonitrile-0.1M ammonium acetate over 15 min, 0.5 mL/min) R$_t$ 5.407 min (99%).

Examples 393–397

Amides Derived From cis-3-(4-Amino-3-methoxyphenyl)-1-[4-(4-methylpiperazino)cyclohexyl]-7H-pyrazolo[3,4-d]pyrimidin-4-amine Representative Procedure:

To the appropriate carboxylic acid (0.46 mmol) in dichloromethane (1.4 mL) was added oxalyl chloride (0.4 mL, 4.6 mmol) and DMF (1 drop). The vials were septum capped and a small bore needle inserted in each cap to relieve pressure. The vials were shaken overnight on a J-Kem shaker. 50% of the solution was separated and the excess oxalyl chloride and dichloromethane was then removed on a 12-port Supelco manifold under vacuum with nitrogen bleed. The crude acid chloride (0.23 mmol) was added to cis-3-(4-amino-3-methoxyphenyl)-1-[4-(4-methylpiperazino)cyclohexyl]-1H-pyrazolo[3,4-d]pyrimidin-4-amine (50 mg, 0.11 mmol) in dry pyridine (0.6 mL) and stirred at room temperature overnight. The resulting solutions were submitted directly to purification by preparative HPLC (Hypersil BSD C18, 5 um, 100×21 mm, 0%–100% acetonitrile/0.05M ammonium acetate over 10 min, 25.0 mL/min). The resulting products were further purified by partioning between dichloromethane (4 ml) and 1.0 N sodium hydroxide (2 ml) and passing through an Empore™ high performance extraction disk cartridge (C18-SD octadecyl) to give the corresponding products. The compounds are detailed overleaf with corresponding LCMS (Micromass-Column: Pecosphere, C18, 3 um, 33×4.6 mm. Eluents: 0% B/A to 100% B/A in 4.5 min. (B: acetonitrile, A: 50 mM ammonia acetate buffer, pH 4.5), 3.5 mL/min.) data.

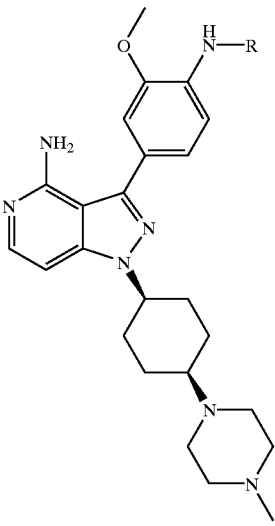

| Compound Name | R | Qty. (mg) | MH$^+$ | R$_t$ (mins) |
|---|---|---|---|---|
| N1-(4-{4-amino-1-[4-(4-methylpiperazino)cyclohexyl]-1H-pyrazolo[3,4-d]pyrimidin-3-yl}-2-methoxyphenyl)-3-phenylbutanamide Ex 393 | | 25 | 583.4 | 2.76 |
| N1-(4-{4-amino-1-[4-(4-methylpiperazino)cyclohexyl]-1H-pyrazolo[3,4-d]pyrimidin-3-yl}-2-methoxyphenyl)-2-methyl-3-phenylpropanamide Ex 394 | | 20 | 583.4 | 2.76 |

-continued

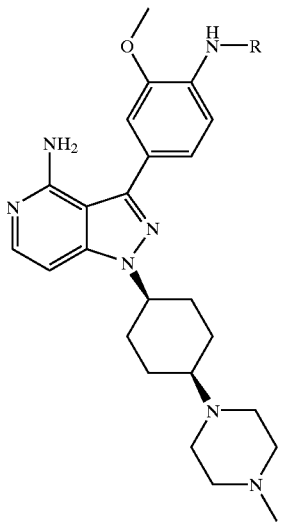

| Compound Name | R | Qty. (mg) | MH⁺ | R_t (mins) |
|---|---|---|---|---|
| N2-(4-{4-amino-1-[4-(4-methylpiperazino)cyclohexyl]-1H-pyrazolo[3,4-d]pyrimidin-3-yl}-2-methoxyphenyl)-1,2,3,4-tetrahydro-2-naphthalenecarboxamide Ex 395 | | 30 | 595.4 | 2.97 |
| N1-(4-{4-amino-1-[4-(4-methylpiperazino)cyclohexyl]-1H-pyrazolo[3,4-d]pyrimidin-3-yl}-2-methoxyphenyl)-(3R)-3-phenylbutanamide Ex 396 | | 14 | 583.4 | 2.85 |
| N1-(4-{4-amino-1-[4-(4-methylpiperazino)cyclohexyl]-1H-pyrazolo[3,4-d]pyrimidin-3-yl}-2-methoxyphenyl)-(3S)-3-phenylbutanamide Ex 397 | | 13 | 583.4 | 2.78 |

Example 398 cis-N4-(4-{4-Amino-1-[4-(4-methylpiperazino)cyclohexyl]-1H-pyrazolo[3,4-d]pyrimidin-3-yl}-2-methoxyphenyl)-3,5-dimethyl-4-isoxazolecarboxamide a) cis-tert-Butyl N-(4-{4-Amino-1-[4-(4-methylpiperazino)cyclohexyl]-1H-pyrazolo[3,4-d]pyrimidin-3-yl}-2-methoxyphenyl)carbamate cis-3-Iodo-1-[4-(4-methylpiperazino)cyclohexyl]-1H-pyrazolo[3,4-d]pyrimidin-4-amine (10 g, 22.66 mmol), tert-butyl N-[2-methoxy-4-(4,4,5,5-tetramethyl-1,3,2-dioxaborolan-2-yl)phenyl]carbamate (9.49 g, 27.17 mmol), palladium tetrakistriphenyphosphine (1.57 g, 1.36 mmol) and sodium carbonate (5.76 g, 54.38 mmol) were mixed with ethylene glycol dimethyl ether (180 mL) and water (90 mL). The reaction mixture was heated at reflux overnight. Organic solvent was removed under reduced pressure and the aqueous layer was extracted with dichloromethane. The combined organic layer was washed with water then brine, dried over MgSO₄, filtered and evaporated. The residue was purified by preparative thin layer column chromatography using dichloromethane/methanol (80:20) as mobile phase to give cis-tert-butyl N-(4-{4-amino-1-[4-(4-methylpiperazino)cyclohexyl]-1H-pyrazolo[3,4-d]pyrimidin-3-yl}-2-methoxyphenyl)carbamate (10.859 g, 89%). ¹H NMR (DMSO-d₆) δ 1.49 (s, 9H), 1.58 (m, 2H), 1.71 (m, 2H), 2.08 (m, 2H), 2.17 (s, 3H), 2.45 (m, 4H), 2.38 (m, 4H), 2.45 (m, 3H), 3.87 (s, 3H), 4.80 (m, 1H), 7.22 (m, 2H), 7.91 (d, J=8.14, 1H), 8.04 (s, 1H), 8.22 (s, 1H).

b) cis-3-(4-Amino-3-methoxyphenyl)-1-[4-(4-methylpiperazino)cyclohexyl]-1H-pyrazolo[3,4-d]pyrimidin-4-amine A mixture of trifluoroacetic acid/dichloromethane (20:80, 200 mL) was added to a solution of N-(4-{4-amino-1-[4-(4-methylpiperazino)cyclohexyl]-1H-pyrazolo[3,4-d]pyrimidin-3-yl}-2-methoxyphenyl)carbamate(10.85 g, 20.24 mmol) in dichloromethane (100 mL) at 0° C. 2 hours later, the ice-bath was removed and the solvents were evaporated and the residue was dissolved in dichloromethane. Sodium hydroxide (1.0N) was added to adjust the pH to about 10. The solid formed upon removal of organic solvent was collect by filtration to give cis-3-(4-amino-3-methoxyphenyl)-1-[4-(4-methylpiperazino)

cyclohexyl]-1H-pyrazolo[3,4-d]pyrimidin-4-amine (8.84 g, 100%). $^1$H NMR (CDCl$_3$) δ 1.65 (m, 2H), 1.83 (m, 2H), 2.18 (m, 2H), 2.31 (s, 3H), 2.35–2.60 (m, 11H), 3.90 (s, 3H), 4.00 (bs, 2H), 4.89 (m, 1H), 5.61 (bs, 2H), 6.83 (d, J=7.78 Hz, 1H), 7.12 (m, 2H), 8.35 (s, 1H).

c) cis-N4-(4-(4-Amino-1-[4-(4-methylpiperazino) cyclohexyl]-1H-pyrazolo[3,4-d]pyrimidin-3-yl}-2-methoxyphenyl)-3,5-dimethyl-4-isoxazolecarboxamide 3,5-Dimethyl-4-isoxazolecarbonyl chloride (22 mg, 0.137 mmol) was added to a solution of cis-3-(4-amino-3-methoxyphenyl)-1-[4-(4-methylpiperazino)cyclohexyl]-1H-pyrazolo[3,4-d]pyrimidin-4-amine (30 mg, 0.067 mmol) in pyridine (0.5 mL). After 5 hours, the solvent was evaporated and the residue was re-crystallized from DMSO to give cis-N4-(4-{4-amino-1-[4-(4-methylpiperazino)cyclohexyl]-1H-pyrazolo[3,4-d]pyrimidin-3-yl}-2-methoxyphenyl)-3,5-dimethyl-4-isoxazolecarboxamide (33 mg, 87%). $^1$H NMR (DMSO-d$_6$) δ 1.91 (m, 2H), 2.24 (m, 2H), 2.36 (m, 2H), 2.41 (s, 3H), 2.63 (s, 3H), 2.77 (m, 3H), 3.17 (s, 3H), 3.37 (bm, 8H), 3.95 (s, 3H), 4.95 (m, 1H), 7.37 (m, 2H), 8.17 (d, J=8.17, 1H), 8.30 (s, 1H), 9.26 (s, 1H). LC/MS (Micromass-Column: Pecosphere, C18, 3 um, 33×4.6 mm. Eluents: 0% B/A to 100% B/A in 4.5 min. (B: acetonitrile, A: 50 mM ammonia acetate buffer, pH 4.5), 3.5 mL/min.), MH$^+$ =560.2, R$_f$=2.44 min.

Example 399 cis-N3-(4-{4-Amino-1-[4-(4-methylpiperazino) cyclohexyl]-1H-pyrazolo[3,4-d]pyrimidin-3-yl}-2-methoxyphenyl)-5-methyl-3-isoxazolecarboxamide 5-Methyl-3-isoxazolecarbonyl chloride (20 mg, 0.137 mmol) was added to a solution of cis-3-(4-amino-3-methoxyphenyl)-1-[4-(4-methylpiperazino)cyclohexyl]-1H-pyrazolo[3,4-d]pyrimidin-4-amine (30 mg, 0.067 mmol) in pyridine (0.5 mL). After 5 hours, the solvent was evaporated and the residue was purified by preparative HPLC (Hypersil BSD C18, 5 um, 100×21 mm, 0%–100% acetonitrile/0.05M ammonium acetate over 10 min, 25.0 mL/min). The resulting products were further purified by partitioning between dichloromethane (4 ml) and 1.0 N sodium hydroxide (2 ml) and passing through an Empore™ high performance extraction disk cartridge (C 18-SD octadecyl) to give cis-N3-(4-{4-amino-1-[4-(4-methylpiperazino)cyclohexyl]-1H-pyrazolo[3,4-d]pyrimidin-3-yl}-2-methoxyphenyl)-5-methyl-3-isoxazolecarboxamide (14 mg, 38%). $^1$H NMR (DMSO-d$_6$) δ 1.81 (m, 2H), 2.14 (m, 2H), 2.35 (m, 2H), 2.53 (s, 3H), 2.76 (m, 3H), 3.37 (bm, 8H), 3.99 (s, 3H), 4.93 (m, 1H), 6.74 (s, 1H), 7.36 (m, 2H), 8.26 (m, 1H), 9.48 (s, 1H); LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =546.4, R$_f$=1.82 min.

Example 400 cis-N1-[(2R)-2-Phenylpropyl]-4-{4-amino-1-[4-(4-methylpiperazino)cyclohexyl]-1H-pyrazolo[3,4-d] pyrimidin-3-yl}-2-methoxybenzamide, Dimaleate Salt cis-N1-[(2R)-2-Phenylpropyl]-4-{4-amino-1-[4-(4-methylpiperazino)cyclohexyl]-1H-pyrazolo[3,4-d] pyrimidin-3-yl}-2-methoxybenzamide (100 mg, 0.172 mmol) was dissolved in hot ethyl acetate (12 mL) and maleic acid (60 mg, 0.515 mmol) in hot ethyl acetate (3 mL) was added. The reaction mixture was stirred at room temperature for 5 hours. The solid was collected by filtration to give cis-N1-[(2R)-2-phenylpropyl]-4-{4-amino-1-[4-(4-methylpiperazino)cyclohexyl]-1H-pyrazolo[3,4-d] pyrimidin-3-yl}-2-methoxybenzamide, dimaleate salt (117 mg, 87%). $^1$H NMR (DMSO-d$_6$) δ 1.25 (d, J=6.96, 3H), 1.73 (m, 42H), 2.09 (m, 2H), 2.26 (m, 2H), 2.71 (s, 3H), 2.74 (m, 2H), 2.85–3.70 (bm, 7H), 3.89 (s, 3H), 4.85 (m, 1H), 6.14 (s, 4H), 7.20 (m, 3H), 7.31 (d, J=4.33, 4H), 8.12 (d, J=8.17 Hz, 1H), 8.24 (s, 1H), 9.20 (s, 1H). LC/MS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =583.4 R$_f$=2.14 min.

Example 401 trans-N2-(4-{4-Amino-1-[4-(4-methylpiperazino) cyclohexyl]-1H-pyrazolo[3,4-d]pyrimidin-3-yl}-2-methoxyphenyl)benzo[b]furan-2-carboxamide, Trimaleate Salt a) trans-N2-(4-{4-Amino-1-[4-(4-methylpiperazino) cyclohexyl]-1H-pyrazolo[3,4-d]pyrimidin-3-yl}-2-methoxyphenyl)benzo[b]furan-2-carboxamide To benzo[b]furan-2-carboxylic acid (0.743 g, 4.58 mmol) in dichloromethane (14 mL) was added oxalyl chloride (4 mL, 45.8 mmol) and DMF (1 drop). The reaction mixture was stirred overnight. Solvent was evaporated and the residue was dissolved in Dichloromethane (5 mL). Half of the dichloromethane solution (2.5 mL) was added to a solution of trans-3-(4-amino-3-methoxyphenyl)-1-[4-(4-methylpiperazino)cyclohexyl]-1H-pyrazolo[3,4-d] pyrimidin-4-amine (0.50 g, 1.145 mmol) in pyridine (6 mL) at 0° C. After 30 minutes, the solid as collected by filtration. Water was then added to the solid and the pH of the solution was adjusted to 10 with sodium hydroxide (1.0N). The aqueous was extracted with dichloromethane. The combined organic layer was washed with water then brine, dried over MgSO$_4$, filtered and evaporated. The residue was purified by flash column chromatography using dichloromethane/methanol (80:20) as mobile phase to give trans-N2-(4-{4-Amino-1-[4-(4-methylpiperazino)cyclohexyl]-1H-pyrazolo [3,4-d]pyrimidin-3-yl}-2-methoxyphenyl)benzo[b]furan-2-carboxamide (0.497 g, 75%). $^1$H NMR (DMSO-d$_6$) δ 1.49 (m, 2H), 2.01 (m, 6H), 2.15 (s, 3H), 2.40 (m, 3H), 2.51 (m, 4H), 4.00 (s, 3H), 4.66 (m, 1H), 7.31 (m, 1H), 7.39 (m, 2H), 7.54 (m, 1H), 7.81 (m, 3H), 8.24 (m, 1H), 9.50 (s, 1H).

b) trans-N2-(4-{4-Amino-1-[4-(4-methylpiperazino) cyclohexyl]-1H-pyrazolo[3,4-d]pyrimidin-3-yl}-2-methoxyphenyl)benzo[b]furan-2-carboxamide, Trimaleate Salt trans-N2-(4-{4-Amino-1-[4-(4-methylpiperazino) cyclohexyl]-1H-pyrazolo[3,4-d]pyrimidin-3-yl}-2-methoxyphenyl)benzo[b]furan-2-carboxamide (497 mg, 0.855 mmol) was dissolved in hot ethyl acetate (56 mL) and maleic acid (298mg, 2.566 mmol) in hot ethyl acetate (5 mL) was added. The reaction mixture was stirred at room temperature for 5 hours. The solid was collected by filtration to give trans-N2-(4-{4-Amino-1-[4-(4-methylpiperazino) cyclohexyl]-1H-pyrazolo[3,4-d]pyrimidin-3-yl}-2-methoxyphenyl)benzo[b]furan-2-carboxamide, trimaleate salt (117 mg, 92%). ¹H NMR (DMSO-d₆) δ 1.60 (m, 2H), 2.09 (m, 6H), 2.68 (s, 3H), 2.82–3.17 (bm, 9H), 4.00 (s, 3H), 4.69 (m, 1H), 6.16 (s, 6H), 7.30–7.42 (m, 3H), 7.54 (m, 1H), 7.76–7.85 (m, 3H), 8.25 (m, 2H), 9.51 (s, 1H); LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH⁺ =581.4, $R_t$=2.12 min.

Example 402 trans-N1-[(2R)-2-Phenylpropyl]-4-{4-amino-1-[4-(4-methylpiperazino)cyclohexyl]-1H-pyrazolo[3,4-d]pyrimidin-3-yl}-2-methoxybenzamide, Trimaleate Salt a) trans-N1-[(2R)-2-Phenylpropyl]-4-{4-amino-1-[4-(4-methylpiperazino)cyclohexyl]-1H-pyrazolo[3,4-d]pyrimidin-3-yl}-2-methoxybenzamide To (3R)-3-phenylbutanoic acid (376 mg, 2.29 mmol) in dichloromethane (7 mL) was added oxalyl chloride (2 mL, 22.9 mmol) and DMF (1 drop). The reaction mixture was stirred overnight. Solvent was evaporated and the residue was dissolved in dichloromethane (3 mL). The dichloromethane solution was added to a solution of trans-3-(4-amino-3-methoxyphenyl)-1-[4-(4-methylpiperazino)cyclohexyl]-1H-pyrazolo[3,4-d]pyrimidin-4-amine (448 mg, 1.026 mmol) in pyridine (6 mL) at 0° C. After 2 hours, the reaction mixture was poured to ethyl acetate (60 ml) and the solid as collected by filtration. Water was then added to the solid and the pH of the solution was adjusted to 10 with sodium hydroxide (1.0N). The aqueous was extracted with dichloromethane. The combined organic layer was washed with water then brine, dried over MgSO₄, filtered and evaporated. The residue was purified by flash column chromatography using dichloromethane/methanol (80:20) as mobile phase to give trans-N1-[(2R)-2-phenylpropyl]-4-{4-amino-1-[4-(4-methylpiperazino)cyclohexyl]-1H-pyrazolo[3,4-d]pyrimidin-3-yl}-2-methoxybenzamide (383 mg, 64%). ¹H NMR (CDCl₃) δ 1.40 (d, J=6.96, 3H), 1.57 (m, 2H), 2.08–2.21 (m, 6H), 2.30 (s, 3H), 2.50 (m, 5H), 2.63–2.74 (m, 6H), 3.40 (m, 1H), 3.88 (s, 3H), 4.74 (m, 1H), 5.69 (bs, 2H), 7.16–7.34 (m, 7H), 7.66 (s, 1H), 8.34 (s, 1H), 8.49 (d, J=8.21, 1H).

b) trans-N1-[(2R)-2-Phenylpropyl]-4-{4-amino-1-[4-(4-methylpiperazino)cyclohexyl]-1H-pyrazolo[3,4-d]pyrimidin-3-yl}-2-methoxybenzamide, Trimaleate Salt trans-N1-[(2R)-2-Phenylpropyl]-4-{4-amino-1-[4-(4-methylpiperazino)cyclohexyl]-1H-pyrazolo[3,4-d]pyrimidin-3-yl}-2-methoxybenzamide (383 mg, 0.657 mmol) was dissolved in hot ethyl acetate (42 mL) and maleic acid (229 mg, 1.971 mmol) in hot ethyl acetate (5 mL) was added. The reaction mixture was stirred at room temperature for 5 hours. The solid was collected by filtration to give trans-N1-[(2R)-2-phenylpropyl]-4-{4-amino-1-[4-(4-methylpiperazino)cyclohexyl]-1H-pyrazolo[3,4-d]pyrimidin-3-yl}-2-methoxybenzamide (571 mg, 93%). ¹H NMR (DMSO-d₆) δ 1.25 (d, J=6.95, 3H), 1.57 (m, 2H), 2.03 (m, 6H), 2.60–3.40 (bm, 18H), 3.89 (s, 3H), 4.67 (m, 1H), 6.16 (s, 6H), 7.20 (m, 3H), 7.31 (d, J=4.37 Hz, 4H), 8.14 (d, J=8.22 Hz, 1H), 8.23 (s, 1H), 9.18 (s, 1H). LC/MS (Micromass-Column: Pecosphere, C18, 3 um, 33×4.6 mm. Eluents: 0% B/A to 100% B/A in 4.5 min. (B: acetonitrile, A: 50 mM ammonia acetate buffer, pH 4.5), 3.5 mL/min.): MH⁺ =583.2, $R_t$=2.89 min.

Example 403 tert-Butyl N-{4-[4-Amino-1-(1-(1-methylpiperidin-4-yl)-piperidin-4-yl)-1H-pyrazolo[3,4-d]pyrimidin-3-yl]-2-methoxyphenyl}carbamate a) tert-Butyl 4-Hydroxy-1-piperidinecarboxylate Sodium borohydride (3.8 g, 100.4 mmol) was added in portions to a solution of tert-butyl 4-oxo-1-piperidinecarboxylate (20 g, 100.4 mmol) in methanol (600 mL) at 0° C. After 15 minutes, the ice-water bath was removed and the reaction mixture was stirred at room temperature for 3 hours. Sodium hydroxide (1.0 N, 100 mL) was added and the organic solvent was evaporated. The aqueous was extracted with ether four times. The combined organic layer was washed with water then brine, dried over MgSO₄, filtered and evaporated to give tert-butyl 4-hydroxy-1-piperidinecarboxylate (20.48 g, 100%). ¹H NMR (CDCl₃) δ 1.48 (s, 9H), 1.63 (m, 2H), 1.87 (m, 2H), 3.03 (m, 2H), 3.83 (m, 3H).

b) tert-Butyl-4-(4-amino-3-iodo-1H-pyrazolo[3,4-d]pyrimidin-1-yl)-1-piperidinecarboxylate 3-Iodo-1H-pyrazolo[3,4-d]pyrimidin-4-amine (10 g, 38.3 mmol), tert-butyl 4-hydroxy-1-piperidinecarboxylate (16.96 g, 84.2 mmol) and triphenylphosphine (20.09 g, 76.0 mmol) were suspended in tetrahydrofuran (425 mL). The reaction mixture was cooled in an ice-water bath and diethyl azodicarboxylate (12.09 mL, 76.0 mmol) was added dropwise. 10 minutes later, the reaction mixture was allowed to warm up to room temperature. 5 hours later, solvent was removed under reduced pressure and dichloromethane (65 mL) was added with heating. The solid was filtered and washed with dichloromethane (20 ml). The solid was further washed with ethyl acetate (5×20 mL) to give a mixture of diethyl 1,2-hydrazinedicarboxylate and tert-butyl 4-(4-amino-3-iodo-1H-pyrazolo[3,4-d]pyrimidin-1-yl)-1-piperidinecarboxylate (1:1, 14.98 g, 63%) which was used without further purification. ¹H NMR (CDCl₃) δ 1.48 (s, 9H), 1.95 (m, 2H), 2.20 (m, 2H), 2.92 (m, 2H), 4.23 (m, 2H), 4.84 (m, 1H), 8.31 (s, 1H).

c) 3-Iodo-1-(4-piperidyl)-1H-pyrazolo[3,4-d]pyrimidin-4-amine

A mixture of trifluoroacetic acid/dichloromethane (20:80, 250 mL) was added to a solution of tert-butyl 4-(4-amino-3-iodo-1H-pyrazolo[3,4-d]pyrimidin-1-yl)-1-piperidinecarboxylate (10.72 g, 24.1 mmol) in dichloromethane (100 mL) at 0° C. 15 minutes later, the ice-bath was removed and the reaction mixture was stirred at room temperature for 5 hours. The solvents were evaporated and the residue was dissolved in dichloromethane. Hydrochloric acid (5.0N) was added and the aqueous layer was washed with dichloromethane three times. Sodium hydroxide (50%) was added to adjust the pH to about 10. The suspension was lyophilized to reduce the volume to one third of the original volume. The solid was collect by filtration to give 3-iodo-1-(4-piperidyl)-1H-pyrazolo[3,4-d]pyrimidin-4-amine (8.109 g, 97%). ¹H NMR (CDCl₃) δ 1.81 (m, 2H), 1.99 (m, 2H), 2.65 (m, 2H), 3.07 (m, 2H), 4.68 (m, 1H), 8.19 (s, 1H).

d) 3-Iodo-1-[1-(1-methylpiperidin-4-yl)]-piperidin-4-yl]-1H-pyrazolo[3,4-d]pyrimidin-4-amine 3-Iodo-1-(4-piperidyl)-1H-pyrazolo[3,4-d]pyrimidin-4-amine (2.00 g, 5.81 mmol), 1-methyl-4-piperidone (2.14 mL, 17.42 mmol), sodium triacetoxyborohydride (2.45 g, 11.62 mmol) and glacial acetic acid (1.05 g, 17.42 mmol)

were mixed with 1,2-dichloroethane (75 mL). The reaction mixture was stirred at room temperature for 6 hours and saturated sodium bicarbonate solution was added to adjust the pH to about 9. The solid was collected by filtration to give 3-Iodo-1-[1-(1-methylpiperidin-4-yl)]-piperidin-4-yl]-1H-pyrazolo[3,4-d]pyrimidin-4-amine (2.39 g, 93%). $^1$H NMR (DMSO-$d_6$) δ 1.52 (m, 2H), 1.75 (m, 2H), 1.87 (m, 2H), 2.05 (m, 4H), 2.24 (s, 3H), 2.28 (m, 3H), 2.91 (m, 2H), 3.00 (m, 2H), 4.55 (m, 1H), 8.18 (s, 1H).

e) tert-Butyl N-{4-[4-Amino-1-[1-(1-methylpiperidin-4-yl)-piperidin-4-yl]-1H-pyrazolo[3,4-d]pyrimidin-3-yl]-2-methoxyphenyl}carbamate 3-Iodo-1-[1-(1-methylpiperidin-4-yl)]-piperidin-4-yl]-1H-pyrazolo[3,4-d]pyrimidin-4-amine (2.39 g, 5.41 mmol), tert-butyl N-[2-methoxy-4-(4,4,5,5-tetramethyl-1,3,2-dioxaborolan-2-yl)phenyl]carbamate (2.08 g, 5.96 mmol), palladium tetrakistriphenyphosphine (0.375 g, 0.32 mmol) and sodium carbonate (1.38 g, 13.00 mmol) were mixed with ethylene glycol dimethyl ether (80 mL) and water (40 mL). The reaction mixture was heated at reflux overnight. Organic solvent was removed under reduced pressure and the aqueous layer was extracted with dichloromethane. The combined organic layer was washed with water then brine, dried over $MgSO_4$, filtered and evaporated. The residue was purified by flash column chromatography using dichloromethane/methanol/ammonium hydroxide (95:5:0.5) as mobile phase to give tert-butyl N-{4-[4-amino-1-[1-(1-methylpiperidin-4-yl)-piperidin-4-yl]-1H-pyrazolo[3,4-d]pyrimidin-3-yl]-2-methoxyphenyl}carbamate (1.67 g, 57%). $^1$H NMR (DMSO-$d_6$) δ 1.48 (m, 11H), 1.71 (m, 2H) 1.86 (m, 4H), 2.14 (s, 3H), 2.18 (m, 3H), 2.32 (m, 2H), 2.80 (m, 2H), 3.89 (s, 3H), 4.64 (m, 1H), 7.22 (m, 2H), 7.91 (d, J=8.12, 1H), 8.03 (s, 1H), 8.21 (s, 1H).

Example 404

3-{4-[(2-Furylmethyl)amino]-3-methoxyphenyl}-1-[1-(1-methylpiperidin-4-yl)piperidin-4-yl]-1H-pyrazolo[3,4-d]pyrimidin-4-amine a) 3-(4-Amino-3-methoxyphenyl)-1-[1-(1-methylpiperidin-4-yl)-piperidin-4-yl]-1H-pyrazolo[3,4-d]pyrimidin-4-amine A mixture of trifluoroacetic acid/dichloromethane (20:80, 28 mL) was added to a solution of tert-butyl N-{4-[4-amino-1-[1-(1-methylpiperidin-4-yl)-piperidin-4-yl]-1H-pyrazolo[3,4-d]pyrimidin-3-yl]-2-methoxyphenyl}carbamate (0.914 g, 1.70 mmol) in dichloromethane (5 mL) at 0° C. After 15 minutes, the ice-bath was removed and the reaction mixture was stirred at room temperature for 5 hours. Solvents were then evaporated and the residue was dissolved in dichloromethane. Saturated sodium bicarbonate was added to adjust the pH to about 8. The layers were separated and the aqueous layer was extracted with dichloromethane. The combined organic layer was washed with brine, dried over $MgSO_4$, filtered and evaporated give 3-(4-amino-3-methoxyphenyl)-1-[1-(1-methylpiperidin-4-yl)-piperidin-4-yl]-1H-pyrazolo[3,4-d]pyrimidin-4-amine (0.726 g, 97%). $^1$H NMR (CDCl$_3$) δ 1.67 (m, 2H) 1.83 (m, 4H), 2.00 (m, 2H), 2.27 (s, 3H), 2.39 (m, 5H), 2.91 (m, 2H), 3.08 (m, 2H), 3.92 (s, 3H), 3.99 (m, 2 h), 4.73 (m, 1H), 5.56 (bs, 2H), 6.82 (d, J=7.87, 1H), 7.08 (d, J=7.84, 1H), 7.13 (s, 1H), 8.34 (s, 1H).

b) 3-{4-[(2-Furylmethyl)amino]-3-methoxyphenyl}-1-[1-(1-methylpiperidin-4-yl)piperidin-4-yl]-1H-pyrazolo[3,4-d]pyrimidin-4-amine 3-(4-Amino-3-methoxyphenyl)-1-[1-(1-methylpiperidin-4-yl)-piperidin-4-yl]-1H-pyrazolo[3,4-d]pyrimidin-4-amine (100 mg, 0.229 mmol), 2-furaldehyde (0.027 mL, 0.321 mmol), sodium triacetoxyborohydride (193 mg, 0.916 mmol) and glacial acetic acid (55 mg, 0.916 mmol) were mixed with 1,2-dichloroethane (5 mL). The reaction mixture was stirred at room temperature overnight. Saturated sodium bicarbonate solution was added to adjust the pH to about 8. The layers were separated and the aqueous layer was extracted with dichloromethane. The combined organic layer was washed with brine, dried over $MgSO_4$, filtered and evaporated. The residue was purified by flash column chromatography using dichloromethane/methanol/ammonium hydroxide (95:5:0.2) as mobile phase to give 3-{4-[(2-furylmethyl)amino]-3-methoxyphenyl}-1-[1-(1-methylpiperidin-4-yl)piperidin-4-yl]-1H-pyrazolo[3,4-d]pyrimidin-4-amine (57 mg, 48%). $^1$H NMR (DMSO-$d_6$) 6 1.45 (m, 2H), 1.71 (m, 2H), 1.87 (m, 4H), 2.14 (s, 3H), 2.28 (m, 5H), 2.80 (m, 2H), 3.01 (m, 2H), 3.86 (s, 1H), 4.37 (d, J=3.13, 1H), 6.76 (d, J=8.62, 1H), 7.07 (m, 2H), 7.57 (s, 1H), 8.19 (s, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ 517.3, R$_t$=2.28 min.

Example 405

N1-{4-[4-Amino-1-[1-(1-methylpiperidin-4-yl) piperidin-4-yl]-1H-pyrazolo[3,4-d]pyrimidin-3-yl]-2-methoxyphenyl}-trans-2-phenylcyclopropane-1-carboxamide, Dimaleate Salt a) N1-{4-[4-Amino-1-[1-(1-methylpiperidin-4-yl)piperidin-4-yl]-1H-pyrazolo[3,4-d]pyrimidin-3-yl]-2-methoxyphenyl}-trans-2-phenylcyclopropane-1-carboxamide trans-2-Phenyl-1-cyclopropanecarbonyl chloride (42 mg, 0.231 mmol) was added to a solution of 3-(4-amino-3-methoxyphenyl)-1-[1-(1-methylpiperidin-4-yl)-piperidin-4-yl]-1H-pyrazolo[3,4-d]pyrimidin-4-amine (100 mg, 0.229 mmol) in pyridine (1.0 mL). After 5 hours, the solvent was evaporated and the residue was purified by flash column chromatography to give N1-{4-[4-amino-1-[1-(1-methylpiperidin-4-yl)piperidin-4-yl]-1H-pyrazolo[3,4-d]pyrimidin-3-yl]-2-methoxyphenyl}-trans-2-phenylcyclopropane-1-carboxamide (80 mg, 60%). $^1$H NMR (CDCl$_3$) δ 1.42 (m, 1H), 1.77 (m, 2H), 1.85 (m, 2H), 2.06 (m, 3H), 2.36–2.45 (m, 8H), 2.62 (m, 1H), 3.00 (m, 2H), 3.10 (m, 2H), 3.96 (s, 3H), 4.75 (m, 1H), 5.54 (bs, 2H), 7.14–7.33 (m, 7H), 8.10 (s, 1H), 8.36 (s, 1H), 8.54 (d, J=8.50, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =581.4, R$_t$=1.77 min.

b) N1-{4-[4-Amino-1-[1-(1-methylpiperidin-4-yl)piperidin-4-yl]-1H-pyrazolo[3,4-d]pyrimidin-3-yl]-2-methoxyphenyl}-trans-2-phenylcyclopropane-1-carboxamide, Dimaleate Salt N1-{4-[4-Amino-1-[1-(1-methylpiperidin-4-yl)piperidin-4-yl]-1H-pyrazolo[3,4-d]pyrimidin-3-yl]-2-methoxyphenyl}-trans-2-phenylcyclopropane-1-carboxamide (75 mg, 0.129 mmol) was dissolved in ethanol (2 mL) and maleic acid (45 mg, 0.387 mmol) in ethanol (1 mL) was added. The reaction mixture was stirred at room temperature for 5 hours. The solvent was removed and ethyl acetate was added and the solid was collected by filtration to give N1-{4-[4-amino-1-[1-(1-methylpiperidin-4-yl)piperidin-4-yl]-1H-pyrazolo[3,4-d]pyrimidin-3-yl]-2-methoxyphenyl}-trans-2-phenylcyclopropane-1-carboxamide, dimaleate salt (75 mg). $^1$H NMR (DMSO-d$_6$) δ 1.17 (m, 1H), 1.32 (m, 2H), 1.48 (m, 2H), 1.48, (m, 2H), 2.19 (m, 4H), 2.37 (M, 1H), 2.46 (m, 1H), 2.59 (m, 1H), 2.78 (s, 3H), 2.98–3.52 (bm, 9H), 3.90 (s, 3H), 5.02 (m, 1H), 6.08 (s, 4H), 7.17–7.33 (m, 7H), 8.25 (m, 2H), 9.65 (s, 1H). LCMS (Finigan-Column: Pecosphere, C18, 3 um, 33×4.6 mm. Eluents: 0% B/A to 100% B/A in 4 min. (B: acetonitrile, A: 50 mM ammonia acetate buffer, pH 4.5), 3.0 mL/min.): MH$^+$ =581.4, R$_t$=1.77 min.

Examples 406 and 407

Amides Derived From cis-3-(4-Amino-3-methoxyphenyl)-1-[4-(4-methylpiperazino)cyclohexyl]-7H-pyrazolo[3,4-d]pyrimidin-4-amine Representative Procedure:

To the appropriate carboxylic acid (0.46 mmol) in dichloromethane (1.5 ml) was added oxalyl chloride (400 μl, 0.2 mmol) and DMF (1 drop). The vials were septum capped and a small bore needle inserted in each cap to relieve pressure. The vials were shaken overnight on a J-Kem shaker. 50% of the solution was separated and the excess oxalyl chloride and dichloromethane was then removed on a 12-port Supelco manifold under vacuum with nitrogen bleed. The crude acid chloride (0.23 mmol) was added to cis-3-(4-amino-3-methoxyphenyl)-1-[4-(4-methylpiperazino)cyclohexyl]-1H-pyrazolo[3,4-d]pyrimidin-4-amine (40 mg, 0.09 mmol) in dry pyridine (800 μl) and stirred at room temperature. The resulting solutions were submitted directly to purification by preparative HPLC (Hypersil BSD C18, 5 um, 100×21 mm, 0%–100% acetonitrile/0.05M ammonium acetate over 10 min, 25.0 mL/min). The resulting products were further purified by partioning between dichloromethane (4 ml) and 1.0 N sodium hydroxide (2 ml) and passing through an Empore™ high performance extraction disk cartridge (C18-SD octadecyl) to give the corresponding products. The compounds are detailed overleaf with corresponding LCMS (Micromass-Column: Pecosphere, C18, 3 um, 33×4.6 mm. Eluents: 0% B/A to 100% B/A in 4.5 min.(B: acetonitrile, A: 50 mM ammonia acetate buffer, PH 4.5), 3.5 mL/min.) data.

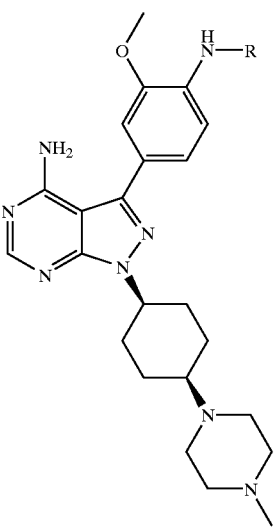

| Compound Name | R | Qty. (mg) | MH$^+$ | R$_t$ (mins) |
|---|---|---|---|---|
| N1-(4-{4-amino-1-[4-(4-methylpiperazino)cyclohexyl]-1H-pyrazolo[3,4-d]pyrimidin-3-y}-2-methoxyphenyl)-3-cyclohexylpropanamide Ex 406 | | 11 | 575.3 | 3.3 |
| N2-(4-{4-amino-1-[4-(4-methylpiperazino)cyclohexyl]-1H-pyrazolo[3,4-d]pyrimidin-3-yl}-2-methoxyphenyl)-1-methyl-1H-2-indolecarboxamide Ex 407 | | 20 | 581.3 | 2.98 |

Example 408

N2-{4-[4-Amino-1-(4-piperidyl)-1H-pyrazolo[3,4-d]pyrimidin-3-yl]phenyl}-5,7-dimethyl-1,3-benzoxazol-2-amine Dihydrochloride

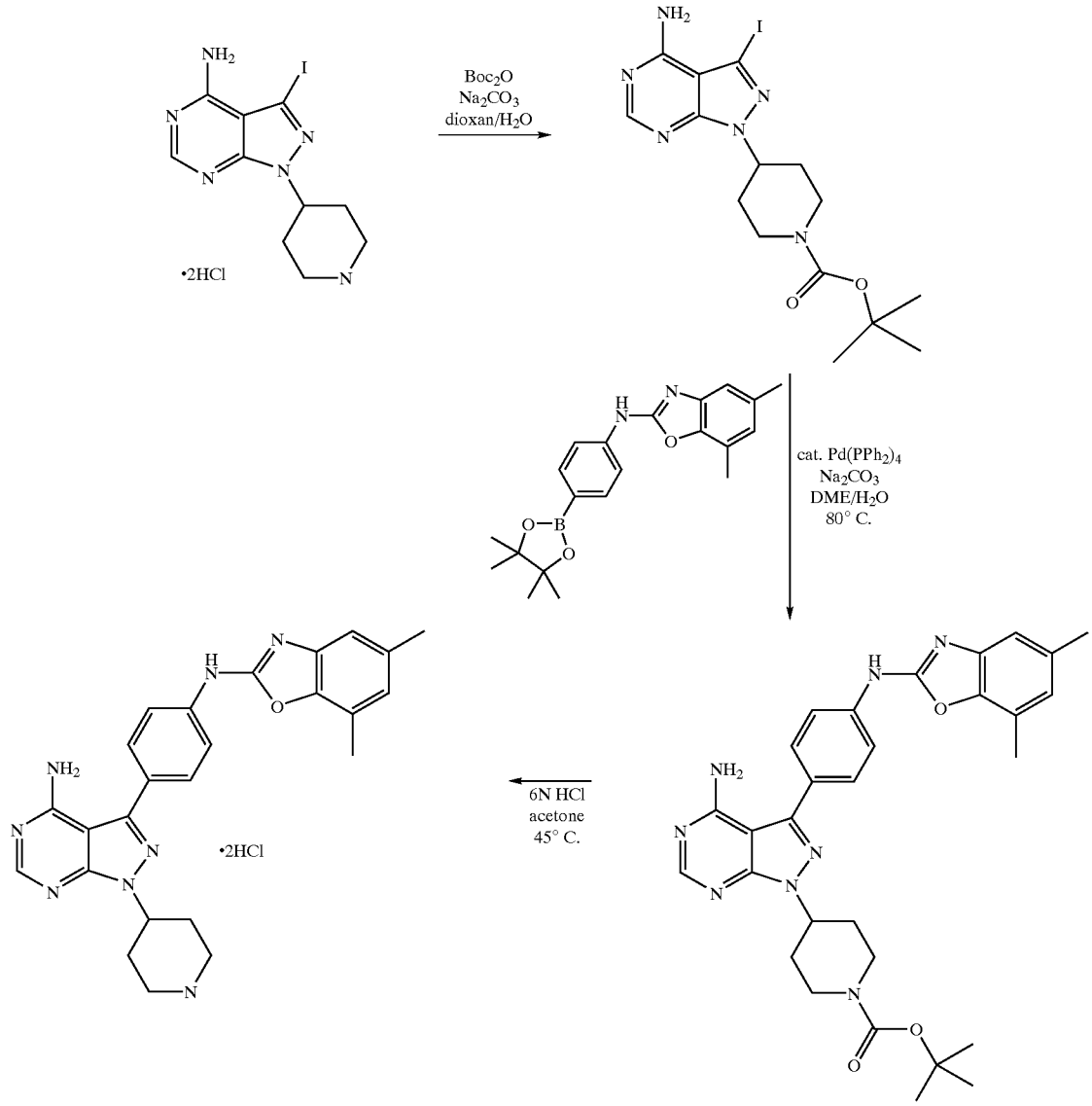

a) tert-Butyl 4-(4-Amino-3-iodo-1H-pyrazolo[3,4-d]pyrimidin-1-yl)-1-piperidinecarboxylate Di-tert-butyl dicarbonate (0.287 g, 1.32 mmol) was added to a mixture of 3-iodo-1-(4-piperidyl)-1H-pyrazolo[3,4-d]pyrimidin-4-amine dihydrochloride (0.50 g, 1.20 mmol) and sodium carbonate (0.445 g, 4.20 mmol) in dioxane (10 mL) and water (10 mL) and the reaction was stirred for 18 h. Dichloromethane (100 mL) was added and the organic layer was washed with water (30 mL) and brine (30 mL), dried (Na2SO4) and concentrated in vacuo to afford tert-butyl 4-(4-amino-3-iodo-1H-pyrazolo[3,4-d]pyrimidin-1-yl)-1-piperidinecarboxylate as a light yellow solid (0.524 g, 98%); RP-HPLC 12.227 min, 100% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z (MH+)=445.1.

b) tert-Butyl 4-(4-Amino-3-{4-[(5,7-dimethyl-1,3-benzoxazol-2-yl)amino]phenyl}-1H-pyrazolo[3,4-d]pyrimidin-1-yl)-1-piperidinecarboxylate tert-Butyl 4-(4-amino-3-iodo-1H-pyrazolo[3,4-d]pyrimidin-1-yl)-1-piperidinecarboxylate (524 mg, 1.18 mmol) was dissolved in ethylene glycol dimethylether (50 mL) and water (10 mL). N-(1,3-benzoxazol-2-yl)-N-[2-fluoro-4-(4,4,5,5-tetramethyl-1,3,2-dioxaborolan-2-yl)phenyl]amine (537 mg, 1.47 mmol), palladium tetrakistriphenylphosphine (68 mg, 0.059 mmol) and sodium carbonate (313 mg, 2.95 mmol) were added and the reaction was heated at 80° C. for 19 hours. Additional boronate (188 mg, 0.515 mmol) and palladium tetrakistriphenylphosphine (27 mg, 0.024 mmol) were added and the reaction was heated at 80° C. for a further 23 hours. The reaction was concentrated under reduced pressure. The remaining residue was partitioned between dichloromethane (100 mL) and water (100 mL). The organic layer was dried (Na2SO4) then concentrated under reduced pressure to yield an orange oil (1.4 g). Purification by chromatography over silica gel using a 2:1 to 9:1 ethyl acetate:heptane gradient followed by a 2% to 5% methanol in dichloromethane gradient afforded tert-butyl 4-(4-amino-3-{4-[(5,7-dimethyl-1,3-benzoxazol-2-yl)amino]phenyl}-1H-pyrazolo[3,4-d]pyrimidin-1-yl)-1-piperidinecarboxylate as an tan solid (577 mg, 85%); RP-HPLC 17.090 min, 98% purity (5% to 85% acetonitrile/ 0.1M aqueous ammonium acetate, buffered to pH 4.5, over 20 min at 1 mL/min; λ=254 nm; Deltapak C18, 300 Å, 5 µm, 150×3.9 mm column); m/z (MH+)=555.2.

c). N2-{4-[4-Amino-1-(4-piperidyl)-1H-pyrazolo[3,4-d]pyrimidin-3-yl]phenyl}-5,7-dimethyl-1,3-benzoxazol-2-amine Dihydrochloride tert-Butyl 4-(4-amino-3-{4-[(5,7-dimethyl-1,3-benzoxazol-2-yl)amino]phenyl}-1H-pyrazolo[3,4-d]pyrimidin-1-yl)-1-piperidinecarboxylate (142 mg, 0.256 mmol) was dissolved in acetone (7 mL) and 6N aqueous hydrochloric acid (1.4 mL). The reaction was then heated at 45° C. which yielded a precipitate. After 2.5 hours, the precipitate was collected by vacuum filtration, washed with a minimal amount of acetone and dried on the lyophilizer to N2-{4-[4-amino-1-(4-piperidyl)-1H-pyrazolo[3,4-d]pyrimidin-3-yl]phenyl}-5,7-dimethyl-1,3-benzoxazol-2-amine dihydrochloride as an orange solid (130 mg, 96%); -HPLC 10.436 min, 96% purity (5% to 85% acetonitrile/ 0.1M aqueous ammonium acetate, buffered to pH 4.5, over 20 min at 1 mL/min; λ=254 nm; Deltapak C18, 300 Å, 5 µm, 150×3.9 mm column); m/z (MH+)=455.3.

Examples 409–416

General Synthesis of Piperidine Amide Analogs of N2-{4-[4-Amino-1-(4-piperidyl)-1H-pyrazolo[3,4-d]pyrimidin-3-yl]phenyl}-5,7-dimethyl-1,3-benzoxazol-2-amine

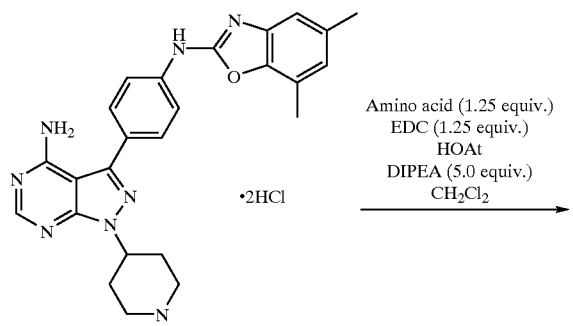

-continued

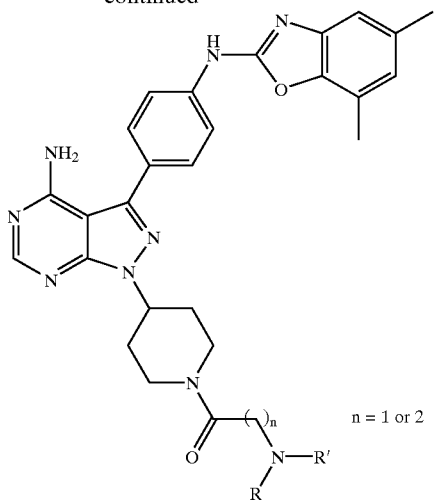

Each 20 mL scintillation vial was charged with N2-{4-[4-amino-1-(4-piperidyl)-1H-pyrazolo[3,4-d]pyrimidin-3-yl]phenyl}-5,7-dimethyl-1,3-benzoxazol-2-amine dihydrochloride (45 mg, 0.085 mmol), the N-unprotected or N-protected amino acid (1.25 equivalents), 1-hydroxy-7-azabenzotriazole (12 mg, 0.085 mmol), 1-(3-dimethylaminopropyl)-3-ethylcarbodiimide hydrochloride (20 mg, 1.06 mmol), N-ethyl-N,N-diisopropylamine (74 µL, 0.425 mmol) and dichloromethane (5 mL). The reaction was oscillated at ambient temperature for 2.5 days. For the reactions which did not reached completion, additional N-ethyl-N,N-diisopropylamine (15 µL, 0.085 mmol) and) and 1-(3-dimethylaminopropyl)-3-ethylcarbodiimide hydrochloride (8 mg, 0.0425 mmol) were added. In addition for the reactions which had low solubility, DMF (1 mL) was also added. The reactions were concentrated in vacuo, dissolved in dichloromethane (2 mL), washed with brine (2 mL) and the layers were separated by passing through an Empore cartridge (6 mL). The organic layer was concentrated under reduced pressure. For products with less than 80% purity, the samples were purified by RP-HPLC (Waters PrepLC 4000, flow rate: 10 mL/min. λ=254 nm Gradient: 15% to 35% acetonitrile/0.1M aqueous ammonium acetate gradient over 40 minutes; Deltapak C18, 300 Å, 15 µm, 40×100 mm column).

The N-tert-butoxycarbonyl protected products (0.11 mmol) were deprotected by subjecting to 6N HCl (0.7 mL) and acetone (3.5 mL) at 45° C. for 4.5 h. The acetone was removed under reduced pressure and the products were purified by RP-HPLC (Waters PrepLC 4000, flow rate: 10 mL/min. λ=254 nm Gradient: 15% to 35% acetonitrile/0.1M aqueous ammonium acetate gradient over 40 minutes; Deltapak C18, 300 Å, 15 µm, 40×100 mm column).

The N-(9-fluorenylmethoxycarbonyl) protected products (0.126 mmol) were deprotected by subjecting them to piperidine (0.4 mL) in DMF (1.6 ml) at room temperature for 3.5 h. The products were then purified by RP-HPLC (Waters PrepLC 4000, flow rate: 10 mL/min. λ=254 nm Gradient: 15% to 35% acetonitrile/0.1M aqueous ammonium acetate gradient over 40 minutes; Deltapak C18, 300 Å, 5 µm, 40×100 mm column).

The products were analyzed by RP-HPLC (5% to 85% acetonitrile/0.1M aqueous ammonium acetate, buffered to pH 4.5, over 20 min at 1 mL/min; λ=254 nm; Deltapak C18, 300 Å, 5 µm, 150×3.9 mm column) and mass spectrometry to characterize the following compounds:

| Example No. | Structure | Starting amino acid | m/z (MH+) | HPLC Rt (min) | Purity |
|---|---|---|---|---|---|
| 409 | 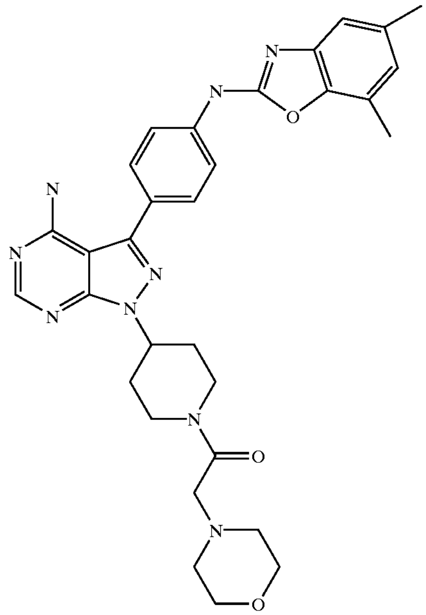 | | 582.2 | 11.394 | 96% |
| 410 | 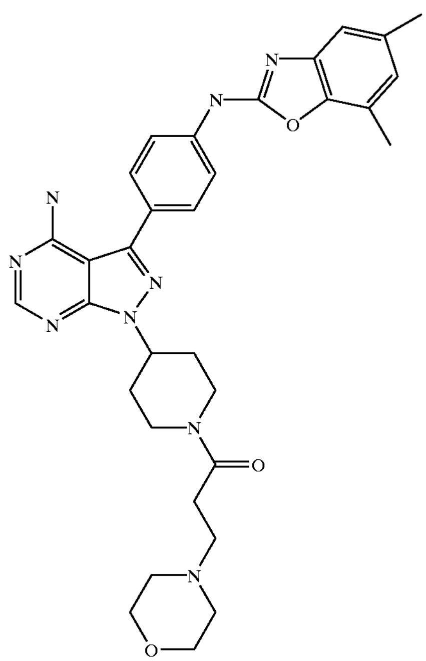 | | 596.3 | 11.104 | 91% |

-continued
| Example No. | Structure | Starting amino acid | m/z (MH+) | HPLC Rt (min) | Purity |
|---|---|---|---|---|---|
| 411 | 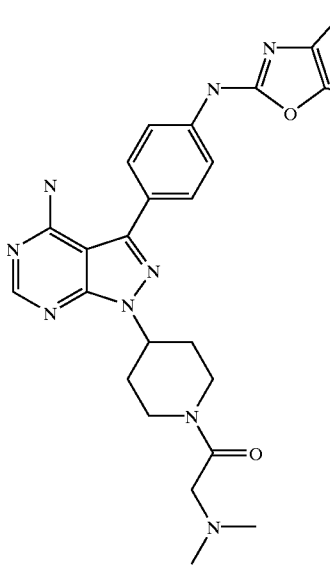 | 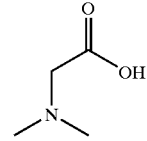 | 540.2 | 9.287 | 93% |
| 412 | 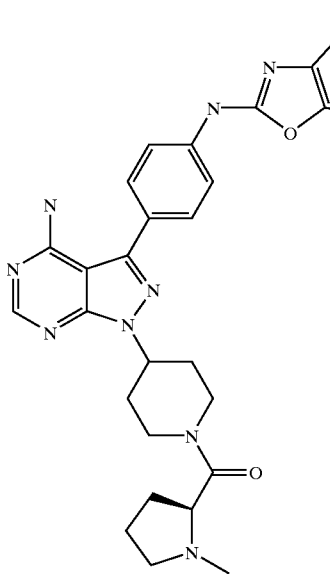 | 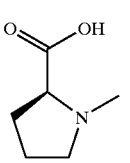 | 566.2 | 11.160 | 100% |

-continued

| Example No. | Structure | Starting amino acid | m/z (MH+) | HPLC Rt (min) | Purity |
|---|---|---|---|---|---|
| 413 | 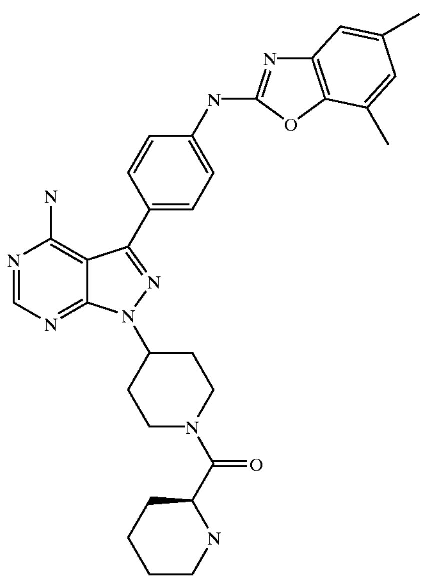 | | 566.2 | 11.139 | 100% |
| 414 | 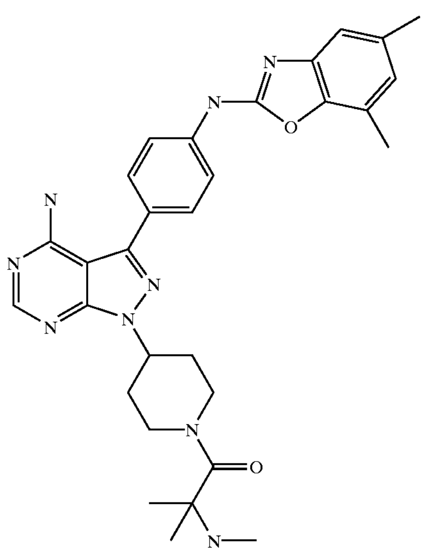 | | 554.3 | 11.035 | 93% |

-continued

| Example No. | Structure | Starting amino acid | m/z (MH+) | HPLC Rt (min) | Purity |
|---|---|---|---|---|---|
| 415 | 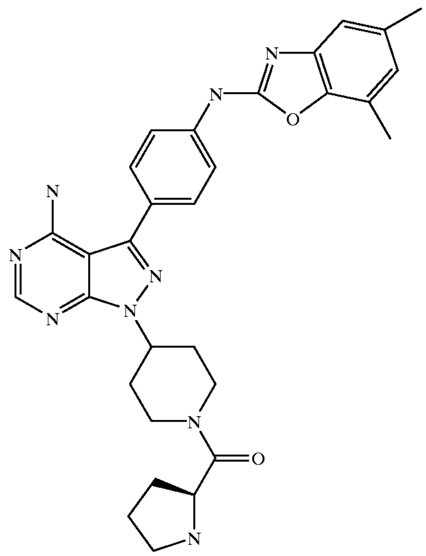 | | 552.2 | 11.051 | 100% |
| 416 | 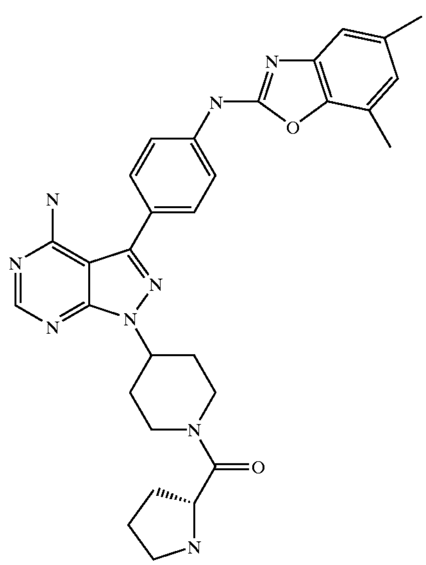 | | 551.9 | 11.027 | 100% |

Example 417 cis-4-{4-Amino-1-[4-(4-methylpiperazino)cyclohexyl]-1H-pyrazolo[3,4-d]pyrimidin-3-yl}phenyl 2,3-Dichloro-1-benzenesulfonate A solution containing cis-4-{4-amino-1-[4-(4-methylpiperazino)cyclohexyl]-1H-pyrazolo[3,4-d]pyrimidin-3-yl}phenol (100 mg, 0.245 mmol), 2,3-dichlorobenzenesulfonyl chloride (180 mg, 0.735 mmol) and triethylamine (0.34 mL, 2.45 mmol) in dichloromethane (8 mL) was stirred at ambient temperature for 17 h. Additional dichloromethane was added (20 mL) and the reaction was washed with brine (10 mL), saturated aqueous NaHCO$_3$ (10 mL), dried (Na$_2$SO$_4$) and concentrated under reduced pressure to afford cis-4-{4-amino-1-[4-(4-methylpiperazino)cyclohexyl]-1H-pyrazolo[3,4-d]pyrimidin-3-yl}phenyl 2,3-dichloro-1-benzenesulfonate as a white solid (135 mg, 90%); RP-HPLC 11.787 min, 97% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z (MH$^+$)=616.2.

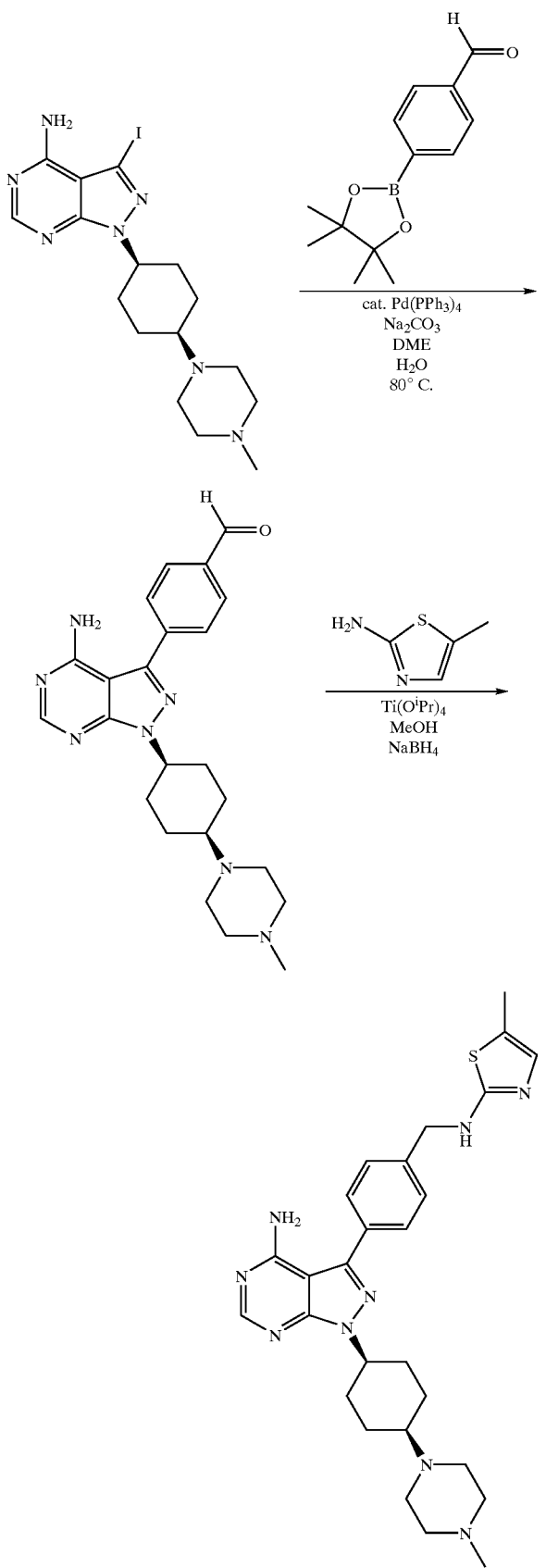

Example 418

N2-(4-{4-Amino-1-[4-(4-methylpiperazino)cyclohexyl]-1H-pyrazolo[3,4-d]pyrimidin-3-yl}benzyl)-5-methyl-1,3-thiazol-2-amine (a) cis-4-{4-Amino-1-[4-(4-methylpiperazino)cyclohexyl]-1H-pyrazolo[3,4-d]pyrimidin-3-yl}benzaldehyde.

A mixture of cis-3-iodo-1-[4-(4-methylpiperazino)cyclohexyl]-1H-pyrazolo[3,4-d]pyrimidin-4-ylamine (5.0 g, 11.33 mmol), 4-formylphenyl boronic acid (2.55 g, 16.98 mmol), palladium tetrakistriphenylphosphine (0.47 g, 0.4 mmol), and sodium carbonate (3.002 g, 28.32 mmol) in ethylene glycol dimethylether (170 mL) and water (30 mL) was heated at 80° C. for 18 h. Additional boronate (1.567 equiv.) and catalyst (0.0135 equiv.) were added and the reaction continued for a further 40 h. The reaction was cooled to ambient temperature and concentrated in vacuo. The residues were partitioned between ethyl acetate (300 mL) and water (200 mL). The resulting precipitate was collected by filtration and dried on the lyophiliser to afford cis-4-{4-Amino-1-[4-(4-methylpiperazino)cyclohexyl]-1H-pyrazolo[3,4-d]pyrimidin-3-yl}benzaldehyde as a light brown solid (2.1 g, 43%); RP-HPLC 7.003 min, 98% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); $^1$H NMR (DMSO-$d_6$, 400 MHz) δ 1.60 (2H, br t), 1.72 (2H, m), 2.06 (2H, m), 2.17 (3H, s), 2.27 (3H, m), 2.35–2.50 (6H, m), 3.39 (2H, m), 4.84 (1H, m), 7.88 (2H, d), 8.07 (2H, d), 8.26 (1H, s), and 10.11 (1H, s)

b) N2-(4-{4-Amino-1-[4-(4-methylpiperazino)cyclohexyl]-1H-pyrazolo[3,4-d]pyrimidin-3-yl}benzyl)-5-methyl-1,3-thiazol-2-amine A slurry containing cis-4-{4-Amino-1-[4-(4-methylpiperazino)cyclohexyl]-1H-pyrazolo[3,4-d]pyrimidin-3-yl}benzaldehyde (100 mg, 0.24 mmol) and 2-amino-5-methylthiazole (33 mg, 0.29 mmol) in titanium isopropoxide (0.48 mL) was stirred at room temperature for 4 h. Methanol (2 mL) was added followed by careful addition of sodium borohydride (1 3.5 mg, 0.36 mmol). After 10 min. the effervescence subsided and the reaction was quenched with aqueous sodium hydroxide (0.1 N, 10 mL). The resulting mixture was allowed to stand overnight then filtered through a celite pad using additional methanol (approx. 10 mL). The filtrate was evaporated to dryness then dissolved in dichloromethane (50 mL) and washed with brine (50 mL). The aqueous layer was extracted further with dichloromethane (3×50 mL) and the combined organic layers were dried (MgSO4) and concentrated in vacuo. Purification by RP-HPLC (Pecosphere, C18, 3 μm, 33×4.6 mm column, 0% to 100% acetonitrile in 50 mM ammonium acetate, buffered to pH 4.5, at 3.5 mL/min) afforded 2 fractions. The first fraction contained (4-{4-amino-7-[4-(4-methylpiperazino)cyclohexyl]-7H-cyclopenta[d]pyrimidin-5-yl}phenyl)methanol (5 mg, 5%); RP-HPLC 6.261 min, 82% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); m/z (MH$^+$)=422.1.

The second fraction afforded N2-(4-{4-Amino-1-[4-(4-methylpiperazino)cyclohexyl]-1H-pyrazolo[3,4-d]pyrimidin-3-yl}benzyl)-5-methyl-1,3-thiazol-2-amine (4 mg, 3%); RP-HPLC 8.344 min, 100% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); $^1$H NMR (DMSO-$d_6$, 400 MHz) δ 1.59 (2H, br t), 1.70 (2H, m), 2.07 (2H, m), 2.10–2.50 (9H, m), 2.16 (3H, s), 2.54 (3H, s), 3.29 (2H, m), 4.47 (2H, d), 4.80 (1H, m), 6.66 (1H, s), 7.49 (2H, d), 7.61 (2H, d), 7.88 (1H, m), and 8.23 (1H, s).

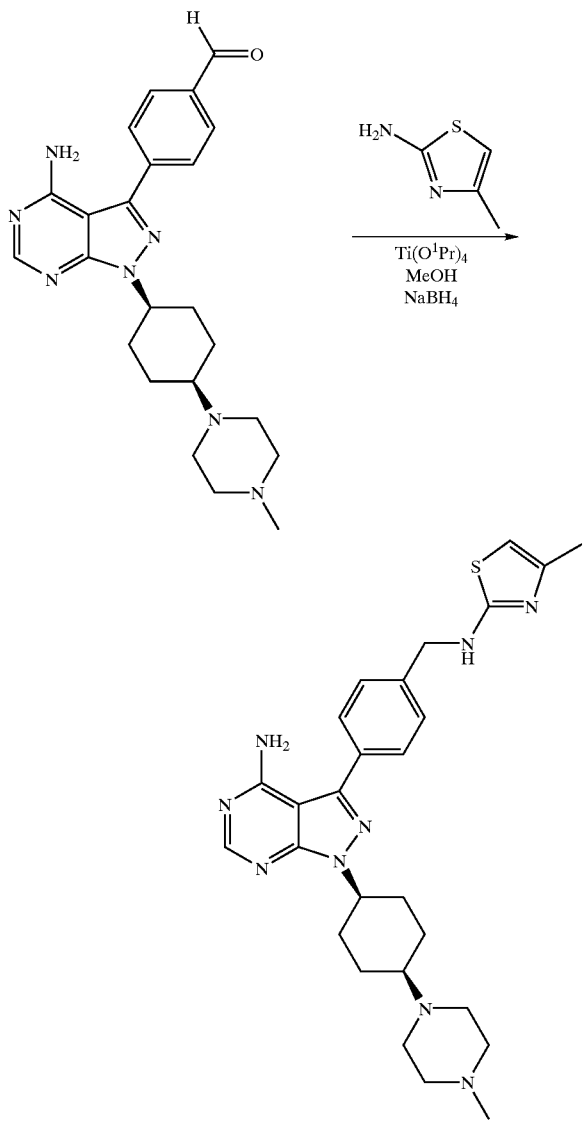

Example 419

N2-(4-{4-Amino-1-[4-(4-methylpiperazino) cyclohexyl]-1H-pyrazolo[3,4-d]pyrimidin-3-yl}benzyl)-4-methyl-1,3-thiazol-2-amine N2-(4-{4-Amino-1-[4-(4-methylpiperazino)cyclohexyl]-1H-pyrazolo[3,4-d]pyrimidin-3-yl}benzyl)-4-methyl-1,3-thiazol-2-amine was prepared using the same procedure and scale as detailed for the 5-methyl analog (see above) (11 mg, 8%); RP-HPLC 8.177 min, 97% purity (5% to 85% acetonitrile/0.1M aqueous ammonium acetate, buffered to pH 4.5, over 20 min at 1 mL/min; λ=254 nm; Deltapak C18, 300 Å, 5 μm, 150×3.9 mm column); $^1$H NMR (DMSO-$d_6$, 400 MHz) δ 1.57 (2H, br t), 1.67 (2H, m), 2.07 (2H, m), 2.10–2.50 (9H, m), 2.19 (3H, s), 2.54 (3H, s), 3.29 (2H, m), 4.50 (2H, br s), 4.79 (1H, m), 6.17 (1H, s), 7.50 (2H, d), 7.62 (2H, d), 7.99 (1H, m), and 8.23 (1H, s).

Example 420 cis-N2-(4-{4-Amino-1-[4-(4-methylpiperazino) cyclohexyl]-1H-pyrazolo[3,4-d]pyrimidin-3-yl}phenyl)-5,7-dichloro-1,3-benzoxazol-2-amine a) 2-Amino-6-chlorophenol A solution of 2-chloro-6-nitrophenol (1.210 g, 6.972 mmol) in ethanol (50 mL) was treated with iron powder (1.947 g, 34.86 mmol) and concentrated HCl (3 mL). The yellow mixture was heated to reflux for 18 h and then cooled to room temperature. The reaction mixture was filtered through a pad of Celite, and the filtrate was neutralized with satd aq NaHCO$_3$ solution. The resulting gray suspension was filtered through a pad of Celite, and the filtrate was extracted with ethyl acetate (3×20 mL). The combined organic layers were washed with brine, dried over anhydrous magnesium sulfate, filtered, and concentrated to give a black solid. Trituration with heptane afforded 2-amino-6-chlorophenol (0.577 g, 58%) as a dark brown solid. RP-HPLC (25 to 100% CH$_3$CN in 0.1 N aqueous ammonium acetate over 10 min at 1 mL/min using a Hypersil HS C18, 100 Å, 5 μm, 250×4.6 mm column) tr=7.30 min., 91%; m/z 143 (MH$^+$).

b) cis-N2-(4-{4-Amino-1-[4-(4-methylpiperazino) cyclohexyl]-1H-pyrazolo[3,4-d]pyrimidin-3-yl}phenyl)-5,7-dichloro-1,3-benzoxazol-2-amine was prepared from cis-3-(4-aminophenyl)-1-[4-(4-methylpiperazino)cyclohexyl]-1H-pyrazolo[3,4-d]pyrimidin-4-amine (0.100 g, 0.245 mmol) and 2-amino-4,6-dichlorophenol (0.044 g, 0.245 mmol) in a manner similar to that used in the synthesis of cis-N2-(4-{4-amino-1-[4-(4-methylpiperazino)cyclohexyl]-1H-pyrazolo[3,4-d]pyrimidin-3-yl}phenyl)-4-methyl-1,3-benzoxazol-2-amine (PH4042235). The compound was formed as an off-white solid (0.008 g, 6%): RP-HPLC (25 to 100% CH$_3$CN in 0.1 N aqueous ammonium acetate over 10 min at 1 mL/min using a Hypersil HS C18, 100 Å, 5 μm, 250×4.6 mm column) tr=8.93 min., 95%; m/z 594 (MH$^+$).

Example 421 cis-N2-(4-{4-Amino-1-[4-(4-methylpiperazino) cyclohexyl]-1H-pyrazolo[3,4-d]pyrimidin-3-yl}phenyl)-7-methyl-1,3-benzoxazol-2-amine a) 2-Amino-4,6-dichlorophenol 2-Amino-4,6-dichlorophenol was prepared from 2,4-dichloro-6-nitrophenol (0.625 g, 2.40 mmol) in a manner similar to that described for 2-amino-6-chlorophenol. The compound was formed as a black solid (0.044 g, 10%). RP-HPLC (25 to 100% CH$_3$CN in 0.1 N aqueous ammonium acetate over 10 min at 1 mL/min using a Hypersil HS C18, 100 Å, 5 μm, 250×4.6 mm column) tr=9.033 min., 74%; m/z 177 (MH$^+$).

b) Cis-N2-(4-{4-amino-1-[4-(4-methylpiperazino) cyclohexyl]-1H-pyrazolo[3,4-d]pyrimidin-3-yl}phenyl)-7-methyl-1,3-benzoxazol-2-amine was prepared from cis-3-(4-aminophenyl)-1-[4-(4-methylpiperazino)cyclohexyl]-1H-pyrazolo[3,4-d]pyrimidin-4-amine (0.100 g, 0.245 mmol) and 2-amino-6-methylphenol (0.030 g, 0.245 mmol) in a manner similar to that used in the synthesis of cis-N2-(4-{4-amino-1-[4-(4-methylpiperazino)cyclohexyl]-1H-pyrazolo[3,4-d]pyrimidin-3-yl}phenyl)-4-methyl-1,3-benzoxazol-2-amine (PH4052419F). The compound was formed as an off-white solid (0.018 g, 14%): RP-HPLC (25 to 100% CH$_3$CN in 0.1 N aqueous ammonium acetate over 10 min at 1 mL/min using a Hypersil HS C18, 100 Å, 5 μm, 250×4.6 mm column) tr=7.37 min., 85%; m/z 539 (MH$^+$).

Example 422 cis-N2-(4-{4-Amino-1-[4-(4-methylpiperazino)
cyclohexyl]-1H-pyrazolo[3,4-d]pyrimidin-3-
yl}phenyl)-7-chloro-1,3-benzoxazol-2-amine a) 2-Amino-6-methylphenol 2-Amino-6-methylphenol was prepared from 2-methyl-6-nitrophenol (0.500 g, 3.26 mmol) in a manner similar to that described for 2-amino-6-chlorophenol. The compound was formed as a black solid (0.030 g, 8%). RP-HPLC (25 to 100% CH$_3$CN in 0.1 N aqueous ammonium acetate over 10 min at 1 mL/min using a Hypersil HS C18, 100 Å, 5 µm, 250×4.6 mm column) tr=5.78 min., 86%; m/z 123 (MH$^+$).

b) Cis-N2-(4-{4-Amino-1-[4-(4-methylpiperazino)cyclohexyl]-1H-pyrazolo[3,4-d]pyrimidin-3-yl}phenyl)-7-chloro-1,3-benzoxazol-2-amine was prepared from cis-3-(4-aminophenyl)-1-[4-(4-methylpiperazino)cyclohexyl]-1H-pyrazolo[3,4-d]pyrimidin-4-amine (0.100 g, 0.245 mmol) and 2-amino-6-chlorophenol (0.053 g, 0.367 mmol) in a manner similar to that used in the synthesis of cis-N2-(4-{4-amino-1-[4-(4-methylpiperazino)cyclohexyl]-1H-pyrazolo[3,4-d]pyrimidin-3-yl}phenyl)-4-methyl-1,3-benzoxazol-2-amine (PH4052419F). The compound was formed as an off-white solid (0.018 g, 13%): RP-HPLC (25 to 100% CH$_3$CN in 0.1 N aqueous ammonium acetate over 10 min at 1 mL/min using a Hypersil HS C18, 100 Å, 5 µm, 250×4.6 mm column) tr=7.78 min., 94%; m/z 558 (MH$^+$).

Example 423

2-{4-Amino-3-[4-(1,3-benzoxazol-2-ylamino)
phenyl]-1H-pyrazolo[3,4-d]pyrimidin-1-yl}-3-
pyridyl Cyanide The procedure for Suzuki coupling, used in the preparation of ethyl 2-[4-amino-3-(4-{[(2,3-dichlorophenyl)sulfonyl]amino}-3-fluorophenyl)-1H-pyrazolo[3,4-d]pyrimidin-1-yl]acetate, was used to couple N-(1,3-benzoxazol-2-yl)-N-[4-(4,4,5,5-tetramethyl-1,3,2-dioxaborolan-2-yl)phenyl]amine (0.052 g, 0.155 mmol) with 2-(4-amino-3-iodo-1H-pyrazolo[3,4-d]pyrimidin-1-yl)-3-pyridyl cyanide (0.045 g, 0.124 mmol). Purification by preparative HPLC (25 to 100% acetonitrile in 0.1 M aqueous ammonium acetate over 20 min at 21 mL/min using an 8µ Hypersil HS C18, 250×21 mm column, R$_t$ 10.1–11.2 min) afforded 2-{4-amino-3-[4-(1,3-benzoxazol-2-ylamino)phenyl]-1H-pyrazolo[3,4-d]pyrimidin-1-yl}-3-pyridyl cyanide as a yellow powder (0.004 g, 0.009 mmol): RP-HPLC (25 to 100% acetonitrile in 0.1 M aqueous ammonium acetate over 10 min at 1 mL/min using a 5µ Hypersil HS C18, 250×4.6 mm column) R$_t$ 8.55 min; MS (MH)$^+$ 446.

Example 424

N1-[2-(Dimethylamino)ethyl]-2-(4-amino-3-{4-[(5,
7-dimethyl-1,3-benzoxazol-2-yl)amino]phenyl}-1H-
pyrazolo[3,4-d]pyrimidin-1-yl)propanamide Ethyl 2-(4-amino-3-iodo-1H-pyrazolo[3,4-d]pyrimidin-1-yl)propanoate (2.03 g, 5.62 mmol), an intermediate described in the preparation of ethyl 2-[4-amino-3-(4-{[(2,3-dichlorophenyl)sulfonyl]amino}-3-fluorophenyl)-1H-pyrazolo[3,4-d]pyrimidin-1-yl]propanoate, was converted to the corresponding methyl ester (1.90 g, 5.47 mmol) using the esterification procedure described in the preparation of methyl 4-[4-amino-3-(4-{[(2,3-dichlorophenyl)sulfonyl]amino}-3-fluorophenyl)-1H-pyrazolo[3,4-d]pyrimidin-1-yl]butanoate: RP-HPLC (25 to 100% acetonitrile in 0.1 M aqueous ammonium acetate over 10 min at 1 mL/min using a 5µ Hypersil HS C18, 250×4.6 mm column) R$_t$ 6.88 min.

A portion of this methyl ester (0.110 g, 0.32 mmol) was then converted to the secondary amide with N,N-dimethylethylenediamine using the procedure for amide formation used to prepare N1-{4-[4-amino-1-(2-morpholino-2-oxoethyl)-1H-pyrazolo[3,4-d]pyrimidin-3-yl]-2-fluorophenyl}-2,3-dichloro-1-benzenesulfonamide: RP-HPLC (25 to 100% acetonitrile in 0.1 M aqueous ammonium acetate over 10 min at 1 mL/min using a 5µ Hypersil HS C18, 250×4.6 mm column) R$_t$ 3.47 min The secondary amide (0.12 g, 0.30 mmol) was coupled with N-(5,7-dimethyl-1,3-benzoxazol-2-yl)-N-[4-(4,4,5,5-tetramethyl-1,3,2-dioxaborolan-2-yl)phenyl]amine (0.100 g, 0.275 mmol) using the procedure for Suzuki coupling used in the preparation of ethyl 2-[4-amino-3-(4-{[(2,3-dichlorophenyl)sulfonyl]amino}-3-fluorophenyl)-1H-pyrazolo[3,4-d]pyrimidin-1-yl]acetate. Purification of the product by preparative HPLC (25 to 100% acetonitrile in 0.1 M aqueous ammonium acetate over 20 min at 21 mL/min using an 8µ Hypersil HS C18, 250×21 mm column, R$_t$ 6.3–8.3 min) afforded N1-[2-(dimethylamino)ethyl]-2-(4-amino-3-{4-[(5,7-dimethyl-1,3-benzoxazol-2-yl)amino]phenyl}-1H-pyrazolo[3,4-d]pyrimidin-1-yl)propanamide as a yellow powder (0.0015 g, 0.003 mmol); RP-HPLC (25 to 100% acetonitrile in 0.1 M aqueous ammonium acetate over 10 min at 1 mL/min using a 5µ Hypersil HS C18, 250×4.6 mm column) R$_t$ 7.60 min; MS (MH)$^+$ 514.

Example 425

N-(4-{4-Amino-1-[2-cyano-4-(4-methylpiperazino)
phenyl]-1H-pyrazolo[3,4-d]pyrimidin-3-yl}-2-
fluorophenyl)-N'-(3-methylphenyl)urea The same procedure used to prepare N1-(4-{4-Amino-1-[2-cyano-4-(4-methylpiperazino)phenyl]-1H-pyrazolo[3,4-d]pyrimidin-3-yl}-2-fluorophenyl)-2,3-dichloro-1-benzenesulfonamide was employed, except that the final step employed the procedure for urea formation used to prepare ethyl 2-(4-amino-3-{3-fluoro-4-[(3-toluidinocarbonyl)amino]phenyl}-1H-pyrazolo[3,4-d]pyrimidin-1-yl)acetate, entailing the reaction of 2-[4-amino-3-(4-amino-3-fluorophenyl)-1H-pyrazolo[3,4-d]pyrimidin-1-yl]-5-(4-methylpiperazino)benzonitrile (0.018 g, 0.041 mmol) with m-tolyl isocyanate (0.005 mL, 0.040 mmol). Purification of the product by preparative HPLC (25 to 100% acetonitrile in 0.1 M aqueous ammonium acetate over 20 min at 21 mL/min using an 8µ Hypersil HS C18, 250×21 mm column, R$_t$ 9.3–10.3 min) afforded N-(4-{4-amino-1-[2-cyano-4-(4-methylpiperazino)phenyl]-1H-pyrazolo[3,4-d]pyrimidin-3-yl}-2-fluorophenyl)-N'-(3-methylphenyl)urea as a yellow powder (0.008 g, 0.014 mmol); RP-HPLC (25 to 100% acetonitrile in 0.1 M aqueous ammonium acetate over 10 min at 1 mL/min using a 5µ Hypersil HS C18, 250×4.6 mm column) R$_t$ 8.03 min; MS (MH)$^+$ 577.

Example 426 cis-N2-(4-{4-Amino-1-[4-(4-methylpiperazino)
cyclohexyl]-1H-pyrazolo[3,4-d]pyrimidin-3-
yl}phenyl)-6-chloro-1,3-benzothiazol-2-amine Solid 4-Bromoaniline (1.00 g, 5.81 mmol) and 2,6-dichlorobenzothiazole (1.18 g, 5.81 mmol) were heated at 140° C. for 3 days in a flask equipped with an air condenser (fusion occurred within a few minutes to give a clear liquid which solidified over the course of 3 days). The reaction mixture was allowed to cooled to ambient temperature to give N-(4-bromophenyl)-N-(6-chloro-1,3-benzothiazol-2- yl)amine (1.97 g, 5.81 mmol): RP-HPLC (25 to 100% acetonitrile in 0.1 M aqueous ammonium acetate over 10 min at 1 mL/min using a 5µ Hypersil HS C18, 250×4.6 mm column) $R_t$ 14.65 min.

Procedure for boronate formation: Crude N-(4-bromophenyl)-N-(6-chloro-1,3-benzothiazol-2-yl)amine (0.178 g, 0.525 mmol), bis(pinacolato)diboron (0.180 g, 0.709 mmol), potassium acetate (0.154 g, 1.57 mmol), and [1,1'-bis(diphenylphosphino)ferrocene]dichloropalladium (II) (0.043 g, 0.053 mmol. [1:1 complex with dichloromethane]) in N,N-dimethylformamide (3 mL) in a resealable Schlenk flask were heated at 90° C. for 24 hr. The mixture was cooled to ambient temperature, filtered through Celite and the crude product purified by flash column chromatography on silica gel using ethyl acetate/heptane (1:3) to afford the boronate intermediate N-(6-chloro-1,3-benzothiazol-2-yl)-N-[4-(4,4,5,5-tetramethyl-1,3,2-dioxaborolan-2-yl)phenyl]amine as a white powder (0.116 g, 0.30 mmol): RP-HPLC (25 to 100% acetonitrile in 0.1 M aqueous ammonium acetate over 10 min at 1 mL/min using a 5µ Hypersil HS C18, 250×4.6 mm column) $R_t$ 15.15 min.

Procedure for Suzuki coupling: A mixture of N-(6-chloro-1,3-benzothiazol-2-yl)-N-[4-(4,4,5,5-tetramethyl-1,3,2-dioxaborolan-2-yl)phenyl]amine (0.116 g, 0.30 mmol), cis-3-iodo-1-[4-(4-methylpiperazino)cyclohexyl]-1H-pyrazolo[3,4-d]pyrimidin-4-amine (0.106 g, 0.24 mmol) and tetrakis(triphenylphosphine)palladium (0) (0.014 g, 0.012 mmol) in ethylene glycol dimethyl ether (3.0 mL), sodium carbonate (0.064 g, 0.60 mmol), and water (1.5 mL) in a sealed Schlenk flask were heated at 90° C. for 24 h. The mixture was cooled, diluted with water (10 mL) and extracted with methanol/dichloromethane (1:19, 3×20 mL). The combined organic fractions were dried (magnesium sulfate), filtered, concentrated and purified by preparative HPLC (25 to 100% acetonitrile in 0.1 M aqueous ammonium acetate over 20 min at 21 mL/min using an 8µ Hypersil HS C18, 250×21 mm column, $R_t$ 7.8–10.0 min) to afford cis-N2-(4-{4-amino-1-[4-(4-methylpiperazino)cyclohexyl]-1H-pyrazolo[3,4-d]pyrimidin-3-yl}phenyl)-6-chloro-1,3-benzothiazol-2-amine as a yellow powder (0.036 g, 0.062 mmol); RP-HPLC (25 to 100% acetonitrile in 0.1 M aqueous ammonium acetate over 10 min at 1 mL/min using a 5µ Hypersil HS C18, 250×4.6 mm column) $R_t$ 8.42 min; MS (MH)$^+$ 574.

Example 427 cis-N2-(4-{4-Amino-1-[4-(4-methylpiperazino)cyclohexyl]-1H-pyrazolo[3,4-d]pyrimidin-3-yl}phenyl)-6-methoxy-1,3-benzothiazol-2-amine Using a procedure similar to that used to prepare cis-N2-(4-4-amino-1-[4-(4-methylpiperazino)cyclohexyl]-1H-pyrazolo[3,4-d]pyrimidin-3-ylphenyl)-6-chloro-1,3-benzothiazol-2-amine, except using 2-chloro-6-methoxybenzothiazole (0.352 g, 2.05 mmol), purification of the product by preparative HPLC (25 to 100% acetonitrile in 0.1 M aqueous ammonium acetate over 20 min at 21 mL/min using an 8µ Hypersil HS C18, 250×21 mm column, $R_t$ 6.3–8.3 min) afforded cis-N2-(4-{4-amino-1-[4-(4-methylpiperazino)cyclohexyl]-1H-pyrazolo[3,4-d]pyrimidin-3-yl}phenyl)-6-methoxy-1,3-benzothiazol-2-amine as a white powder (0.046 g, 0.080 mmol); RP-HPLC (25 to 100% acetonitrile in 0.1 M aqueous ammonium acetate over 10 min at 1 mL/min using a 5µ Hypersil HS C18, 250×4.6 mm column) $R_t$ 7.40 min; MS (MH)$^+$ 570.

Example 428 cis-N2-(4-{4-Amino-1-[4-(4-methylpiperazino)cyclohexyl]-1H-pyrazolo[3,4-d]pyrimidin-3-yl}phenyl)-4-ethyl-1,3-thiazol-2-amine A solution of fluorenylmethyloxycarbonyl isothiocyanate (1.36 g, 4.84 mmol, Kearney, P. C.; Fernandez, M.; Flygare, J. A. J. Org. Chem. 1998, 63, 196–200) in dichloromethane (40 mL) was added via a pipet to a solution of 4-Bromoaniline (0.86 g, 5.00 mmol) in dichloromethane (10 mL) maintained at 0° C. and the resulting mixture stirred at ambient temperature for 14 h. The reaction was diluted with dichloromethane (60 mL) and washed with aqueous hydrochloric acid (0.5 M, 2×10 mL). The organic layer was dried (magnesium sulfate), filtered, and concentrated to afford the 9H-9-fluorenyl-methyl-N-[(4-bromoanilino)carbothioyl]carbamate (2.25 g, 4.97 mmol): RP-HPLC (25 to 100% acetonitrile in 0.1 M aqueous ammonium acetate over 10 min at 1 mL/min using a 5µ Hypersil HS C18, 250×4.6 mm column) $R_t$ 14.25 min.

Procedure for thiazole synthesis: 9H-9-fluorenyl-methyl-N-[(4-bromoanilino)carbothioyl]carbamate (0.25 g, 0.55 mmol) was dissolved in piperidine/N,N-dimethylformamide (1:6, 3.5 mL) and the mixture stirred at ambient temperature for 2 h. The solvent was removed under reduced pressure and the residue dissolved in a mixture of acetic acid (1 mL), ethanol (2 mL), and dioxane (2 mL). 1-Bromo-2-butanone (90%, 0.11 mL, 1.10 mmol) was added and the mixture was stirred for 14 h at ambient temperature. The reaction mixture was diluted with half saturated aqueous sodium carbonate (15 mL) and extracted with methanol/dichloromethane (1:19, 3×20 mL). The combined organic layers were dried (magnesium sulfate), filtered, concentrated and purified by flash column chromatography on silica gel using ethyl acetate/heptane (1:4) to afford the bromothiazole N-(4-bromophenyl)-N-(4-ethyl-1,3-thiazol-2-yl)amine (0.15 g, 0.53 mmol): RP-HPLC (25 to 100% acetonitrile in 0.1 M aqueous ammonium acetate over 10 min at 1 mL/min using a 5µ Hypersil HS C18, 250×4.6 mm column) $R_t$ 13.15 min.

The above bromothiazole intermediate was converted into the boronate using the procedure described for the preparation of N2-(4-{4-amino-1-[4-(4-methylpiperazino)cyclohexyl]-1H-pyrazolo[3,4-d]pyrimidin-3-yl}phenyl)-6-chloro-1,3-benzothiazol-2-amine to afford the boronate intermediate N-(4-ethyl-1,3-thiazol-2-yl)-N-[4-(4,4,5,5-tetramethyl-1,3,2-dioxaborolan-2-yl)phenyl]amine (0.158 g, 0.48 mmol): RP-HPLC (25 to 100% acetonitrile in 0.1 M aqueous ammonium acetate over 10 min at 1 mL/min using a 5µ Hypersil HS C18, 250×4.6 mm column) $R_t$ 13.60 min.

The boronate intermediate (0.15 g, 0.45 mmol) was coupled with cis-3-iodo-1-[4-(4-methylpiperazino)cyclohexyl]-1H-pyrazolo[3,4-d]pyrimidin-4-amine (0.182 g, 0.41 mmol) using the procedure for Suzuki coupling described in the preparation of N2-(4-{4-amino-1-[4-(4-methylpiperazino)cyclohexyl]-1H-pyrazolo[3,4-d]pyrimidin-3-yl}phenyl)-6-chloro-1,3-benzothiazol-2-amine. Purification of the product by preparative HPLC (25 to 100% acetonitrile in 0.1 M aqueous ammonium acetate over 20 min at 21 mL/min using an 8µ Hypersil HS C18, 250×21 mm column, $R_t$ 7.0–8.0 min) afforded cis-N2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine as an off-white powder (0.069 g, 0.133 mmol); RP-HPLC (25 to 100% acetonitrile in 0.1 M aqueous ammonium acetate over 10 min at 1 mL/min using a 5µ Hypersil HS C18, 250×4.6 mm column) $R_t$ 7.05 min; MS (MH)$^+$ 518.

Example 429 cis-N2-(4-{4-Amino-1-[4-(4-methylpiperazino)cyclohexyl]-1H-pyrazolo[3,4-d]pyrimidin-3-yl}phenyl)-4,5-dimethyl-1,3-thiazol-2-amine The procedure for thiazole synthesis, described in the preparation of cis-N2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine, was employed with the exception that 3-bromo-2-butanone (0.183 g, 1.21 mmol) was used as the alkylating agent, and the alkylation reaction was conducted at 40° C. for 24 h. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 6.7–7.7 min) afforded cis-N2-(4-{4-amino-1-[4-(4-methylpiperazino)cyclohexyl]-1H-pyrazolo[3,4-d]pyrimidin-3-yl}phenyl)-4,5-dimethyl-1,3-thiazol-2-amine as an off-white powder (0.069 g, 0.133 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 6.83 min; MS (MH)$^+$ 518.

Example 430 cis-N2-(4-{4-Amino-1-[4-(4-methylpiperazino) cyclohexyl]-1H-pyrazolo[3,4-d]pyrimidin-3-yl}phenyl)-4-phenyl-1,3-thiazol-2-amine The procedure for thiazole synthesis, described in the preparation of cis-N2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine, was employed with the exception that 2-bromoacetophenone (0.131 g, 0.66 mmol) was used as the alkylating agent. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 8.7–9.8 min) afforded cis-N2-(4-{4-amino-1-[4-(4-methylpiperazino)cyclohexyl]-1H-pyrazolo[3,4-d]pyrimidin-3-yl}phenyl)-4-phenyl-1,3-thiazol-2-amine as a yellow powder (0.036 g, 0.064 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 8.22 min; MS (MH)$^+$ 566.

Example 431 cis-N2-(4-{4-Amino-1-[4-(4-methylpiperazino) cyclohexyl]-1H-pyrazolo[3,4-d]pyrimidin-3-yl}phenyl)-4-(4-methylphenyl)-1,3-thiazol-2-amine The procedure for thiazole synthesis, described in the preparation of cis-N2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine, was employed with the exception that 2-bromo-4'-methylacetophenone (0.118 g, 0.554 mmol) was used as the alkylating agent. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 9.1–10.7 min) afforded cis-N2-(4-{4-amino-1-[4-(4-methylpiperazino)cyclohexyl]-1H-pyrazolo[3,4-d]pyrimidin-3-yl}phenyl)-4-(4-methylphenyl)-1,3-thiazol-2-amine as an off-white powder (0.022 g, 0.038 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 8.88 min; MS (MH)$^+$ 580.

Example 432 cis-N2-(4-{4-Amino-1-[4-(4-methylpiperazino) cyclohexyl]-1H-pyrazolo[3,4-d]pyrimidin-3-yl}phenyl)-5-methyl-4-phenyl-1,3-thiazol-2-amine The procedure for thiazole synthesis, described in the preparation of cis-N2-(4-{4-amino-1-[4-(4-methylpiperazino)cyclohexyl]-1H-pyrazolo[3,4-d]pyrimidin-3-yl}phenyl)-4-ethyl-1,3-thiazol-2-amine, was employed with the exception that 2-bromopropiophenone (0.081 mL, 0.532 mmol) was used as the alkylating agent, and the alkylation reaction was conducted at 50° C. for 24 h. Purification of the product by preparative HPLC (25 to 100% acetonitrile in 0.1 M aqueous ammonium acetate over 20 min at 21 mL/min using an 8μ Hypersil HS C18, 250×21 mm column, $R_t$ 9.1–10.3 min) afforded cis-N2-(4-{4-amino-1-[4-(4-methylpiperazino)cyclohexyl]-1H-pyrazolo[3,4-d]pyrimidin-3-yl}phenyl)-5-methyl-4-phenyl-1,3-thiazol-2-amine as a white powder (0.015 g, 0.026 mmol); RP-HPLC (25 to 100% acetonitrile in 0.1 M aqueous ammonium acetate over 10 min at 1 mL/min using a 5μ Hypersil HS C18, 250×4.6 mm column) $R_t$ 8.67 min; MS (MH)$^+$ 580.

Example 433

N1-(4-{4-Amino-1-[1-(1-methylpiperidin-4-yl) piperidin-4-yl]-1H-pyrazolo[3,4-d]pyrimidin-3-yl}-2-methoxyphenyl)-(3R)-3-phenylbutanamide tri-Maleate (3R)-3-Phenylbutanoyl Chloride A solution of R-3-phenylbutyric acid (0.755 g, 4.6 mmol) in dichloromethane (3 mL) was treated with oxalyl chloride (0.700 g, 5.52 mmol) and one drop of dimethylformamide. The reaction mixture was shaken for 15 hours at room temperature under a nitrogen atmosphere. The reaction mixture was shaken for 15 h. The solvent was removed under reduced pressure and dried under high vacuum to afford a quantitative amount of (3R)-3-phenylbutanoyl chloride. The oil was directly used in the following reaction.

N1-(4-{4-Amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide tri-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at –5° C. was treated with a solution of (3R)-3-phenylbutanoyl chloride (0.420 g, 2.3 mmol) in dichloromethane (3 mL). The reaction mixture stirred for 20 min at –5° C., then the dry ice/acetone bath was removed and was stirred at room temperature under a nitrogen atmosphere. (3R)-3-phenylbutanoyl chloride (0.210 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide was purified by flash chromatography on silica gel using 15% (methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.378 g (57%) pure N1-(4-{4-amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide. A warmed solution of N1-(4-{4-amino-1-[1-(1-methylpiperidin-4-yl) piperidin-4-yl]-1H-pyrazolo[3,4-d]pyrimidin-3-yl}-2-methoxyphenyl)-(3R)-3-phenylbutanamide (0.378 g, 0.649 mmol) in ethyl acetate was treated with a warmed solution of maleic acid (0.226 g, 1.95 mmol) in ethyl acetate. The precipitate was filtered under nitrogen and dried on lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide tri-maleate. $^1$H NMR (DMSO-d$_6$, 400 MHz) δ 9.200 (s, 1H), 8.263 (s, 1H0, 8.1747–8.1543 (d, 1H, J=8.16 Hz), 7.312–7.282 (m, 4H), 7.235–7.232 (s, 1H), 7.211–7.168 (m, 2H), 6.114 (s, 6H), 5.061 (m, 1H), 3.890 (s, 3H), 3.301 (m, 4H), 2.997 (m, 2H), 2.783–2.741 (m, 6H), 2.541 (m, 8H), 2.261–2.185 (m, 4H), 1.879 (m, 2H); HPLC Perkin Elmer Pecosphere C18, 3 μM, 33×4.6, 3.5 ml/min 100-100% 50 mM ammonium acetate to acetonitrile in 4.5 minutes, C$_{36}$H$_{44}$N$_6$O$_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) R$_t$ 2.64 min (100%).

Example 434

N1-(4-{4-Amino-1-[1-(1-methylpiperidin-4-yl)piperidin-4-yl]-1H-pyrazolo[3,4-d]pyrimidin-3-yl}-2-methoxyphenyl)-benzo[b]furan-2-carboxamide tri-Maleate Benzo[b]furan-2-carbonyl Chloride A suspension of 2-benzofurancarboxylic acid (0.746 g, 4.6 mmol) in dichloromethane (3 mL) was treated with oxalyl chloride (0.700 g, 5.52 mmol) and one drop of dimethylformamide. The reaction mixture was shaken for 15 h. The solvent was removed under reduced pressure and dried under high vacuum to afford a quantitative amount of benzo[b]furan-2-carbonyl chloride. The oil was directly used in the following reaction.

N1-(4-{4-Amino-1-[1-(1-methylpiperidin-4-yl)piperidin-4-yl]-1H-pyrazolo[3,4-d]pyrimidin-3-yl}-2-methoxyphenyl)-benzo[b]furan-2-carboxamide tri-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of benzo[b]furan-2-carbonyl chloride (0.415 g, 2.3 mmol) in dichloromethane (3 mL). The reaction mixture stirred for 20 min at −5° C., then the dry ice/acetone bath was removed and was stirred at room temperature under a nitrogen atmosphere. Benzo[b]furan-2-carbonyl chloride (0.207 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl))-benzo[b]furan-2-carboxamide was purified by flash chromatography on silica gel using 15% (methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.143 g (21%) pure N1-(4-{4-amino-1-[1-(1-methylpiperidin-4-yl)piperidin-4-yl]-1H-pyrazolo[3,4-d]pyrimidin-3-yl}-2-methoxyphenyl))-benzo[b]furan-2-carboxamide. A warmed solution of N1-(4-{4-amino-1-[1-(1-methylpiperidin-4-yl)piperidin-4-yl]-1H-pyrazolo[3,4-d]pyrimidin-3-yl}-2-methoxyphenyl))-benzo[b]furan-2-carboxamide (0.143 g, 0.246 mmol) in ethyl acetate was treated with a warmed solution of maleic acid (0.086 g, 0.739) in ethyl acetate. The precipitate was filtered under nitrogen and dried on lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl)-benzo[b]furan-2-carboxamide tri-maleate. $^1$H NMR (DMSO-d$_6$, 400 MHz) δ 9.518 (s, 1H), 8.282 (s, 1H), 8.2652–8.2447 (d, 1H, J=8.2 Hz), 7.849–7.814 (m, 2H), 7.7813–7.7603 (d, 1H, J=8.4 Hz), 7.562–7.523 (m, 1H), 7.418–7.369 (m, 2H), 7.338–7.313 (m, 1H), 6.088 (s, 5H), 5.10–5.00 (m, 1H), 4.003 (s, 3H), 3.529 (m, 4H), 3.314 (m, 2H), 2.971 (m, 2H), 2.778 (s, 3H), 2.497 (m, 3H), 2.209 (m, 4H), 1.909 (m, 2H); HPLC Perkin Elmer Pecosphere C18, 3 μM, 33×4.6, 3.5 ml/min 100-100% 50 mM ammonium acetate to acetonitrile in 4.5 minutes, C$_{36}$H$_{44}$N$_6$O$_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) R$_t$ 2.73 min (100%).

Example 435

N1-(4-{4-Amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide tri-Maleate (3S)-3-Phenylbutanoyl Chloride A solution of S-3-phenylbutyric acid (0.755 g, 4.6 mmol) in dichloromethane (3 mL) was treated with oxalyl chloride (0.700 g, 5.52 mmol) and one drop of dimethylformamide. The reaction mixture was shaken for 15 hours at room temperature under a nitrogen atmosphere. The reaction mixture was shaken for 15 h. The solvent was removed under reduced pressure and dried under high vacuum to afford a quantitative amount of (3S)-3-phenylbutanoyl chloride. The oil was directly used in the following reaction.

N1-(4-{4-Amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide tri-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of (3S)-3-phenylbutanoyl chloride (0.420 g, 2.3 mmol) in dichloromethane (3 mL). The reaction mixture stirred for 20 min at −5° C., then the dry ice/acetone bath was removed and was stirred at room temperature under a nitrogen atmosphere. (3S)-3-phenylbutanoyl chloride (0.210 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide was purified by flash chromatography on silica gel using 15% (methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.455 g (68%) pure N1-(4-{4-amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide. A warmed solution of N1-(4-{4-amino-1-[1-(1-methylpiperidin-4-yl)piperidin-4-yl]-1H-pyrazolo[3,4-d]pyrimidin-3-yl}-2- methoxyphenyl)-(3S)-3-phenylbutanamide (0.455 g, 0.782 mmol) in ethyl acetate was treated with a warmed solution of maleic acid (0.272 g, 2.35) in ethyl acetate. The precipitate was filtered under nitrogen and dried on lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide tri-maleate. $^1$H NMR (DMSO-d$_6$, 400 MHz) δ 9.199 (s, 1H), 8.261 (s, 1H), 8.1733–8.1528 (d, 1H, J=8.2 Hz), 7.312–7.282 (m, 4H), 7.236–7.232 (m, 1H), 7.211–7.168 (m, 2H), 6.094 (s, 6H), 5.046 (m, 1H), 3.890 (s, 3H), 3.534 (m, 4H), 2.994 (m, 2H), 2.784–2.740 (m, 6H), 2.506–2.470 (m, 8H), 2.442–2.200 (m, 4H), 1.855 (m, 2H); HPLC Perkin Elmer Pecosphere C18, 3 μM, 33×4.6, 3.5 ml/min 100-100% 50 mM ammonium acetate to acetonitrile in 4.5 minutes, C$_{36}$H$_{44}$N$_6$O$_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) R$_t$ 2.64 min (100%).

Example 436 tert-Butyl N-(4-{4-Amino-1-[4-nitrophenyl]-1H-pyrazolo[3,4-d]pyrimidin-3-yl}-2-methoxyphenyl)carbamate 4-Amino-1-[4-nitrophenyl]-3-iodo-1H-pyrazolo[3,4-d]pyrimidine A suspension of 3-iodo-1H-pyrazolo[3,4-d]pyrimidin-4-amine (2.00 g, 7.66 mmol) in dimethylformamide (40 mL) was treated with cesium carbonate (3.74 g, 11.49 mmol) and p-fluoronitrobenzene (1.08 g, 7.66 mmol). The reaction mixture stirred at 80° C. for 5 h under a nitrogen atmosphere. The reaction mixture was added to ice. The precipitate was filtered and washed with water. The product, 4-amino-1-[4-nitrophenyl]-3-iodo-1H-pyrazolo[3,4-d]pyrimidine, was dried on the lyophilizer overnight to give 2.55 g (87%). $^1$H NMR (DMSO-d$_6$, 400 MHz) δ 8.4952–8.4720 (m, 2H), 8.4142–8.3654 (m, 3H); LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) t$_R$=3.73 min (100%) M$^+$ 380.6.

tert-Butyl N-(4-{4-Amino-1-[4-nitrophenyl]-1H-pyrazolo[3,4-d]pyrimidin-3-yl}-2-methoxyphenyl)carbamate A suspension of 4-amino-1-[4-nitrophenyl]-3-iodo-1H-pyrazolo[3,4-d]pyrimidine (0.500 g, 1.31 mmol) in dimethylformamide (8 mL) was treated with tert-butyl N-[2-methoxy-4-(4,4,5,5-tetramethyl-1,3,2-dioxaborolan-2-yl)phenyl]carbamate (0.915 g, 2.62 mmol), tetrakis(triphenylphosphine)palladium (0.091 g, 0.06 mmol), and a solution of sodium carbonate (0.333 g, 3.14 mmol) in water (4 mL). The reaction mixture stirred at 85° C. for 26 h under a nitrogen atmosphere. Water was added to the reaction mixture. The precipitate was filtered and washed with water. The solid was triturated with diethyl ether to give 0.431 g, (63%) of tert-butyl N-(4-{4-amino-1-[4-nitrophenyl]-1H-pyrazolo[3,4-d]pyrimidin-3-yl}-2-methoxyphenyl)carbamate. $^1$H NMR (DMSO-d$_6$, 400 MHz) δ 8.6862–8.6634 (d, 2H, J=9.12 Hz), 8.4897–8.4423 (m, 3H), 8.1117 (s, 1H), 8.0074–7.9872 (d, 1H, J=8.08 Hz), 7.3743–7.3293 (m, 2H), 3.9189 (s, 3H), 1.4959 (s, 9H); LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) t$_R$=4.38 min M$^+$ 478.1.

Example 437

4-Amino-3-(4-amino-3-methoxyphenyl)-1-[4-nitrophenyl]-1H-pyrazolo[3,4-d]pyrimidine A suspension of tert-butyl N-(4-{4-amino-1-[4-nitrophenyl]-1H-pyrazolo[3,4-d]pyrimidin-3-yl}-2-methoxyphenyl)carbamate (0.386 g, 0.808 mmol) in dichloromethane (8 mL) at 0° C. was treated with trifluoroacetic acid (1.6 mL). The reaction mixture stirred for 20 min at 0° C., then ice bath was removed to stir at room temperature under a nitrogen atmosphere. The reaction mixture was stirred for 18 h. Solvent was removed under reduced pressure. Dichloromethane (15 mL) and sodium hydroxide 1N solution were added to the oil residue. The precipitate formed was filtered and dried over night on the lyophilizer to give 0.286 g (94%) of 4-amino-3-(4-amino-3-methoxyphenyl)-1-[4-nitrophenyl]-1H-pyrazolo[3,4-d]pyrimidine. $^1$H NMR (DMSO-d$_6$, 400 MHz) δ 8.7826–8.759 (m, 2H), 8.4892–8.4296 (m, 3H), 7.1861–7.1338 (m, 2H), 6.8320–6.8121 (d, 1H, J=7.96 Hz), 5.2225 (s, 2H), 3.8672 (s, 3H); LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) t$_R$=3.48 min M$^+$ 377.6.

Example 438

N1-(4-{4-Amino-1-[1-(1-methylpiperidin-4-yl)piperidin-4-yl]-1H-pyrazolo[3,4-d]pyrimidin-3-yl}-2-methoxyphenyl)-1-methyl-1H-2-indolecarboxamide di-Maleate 1-Methyl-1H-2-indolecarbonyl Chloride A suspension of 1-methylindole-2-carboxylic acid (0.805 g, 4.6 mmol) in dichloromethane (3 mL) was treated with oxalyl chloride (0.700 g, 5.52 mmol) and one drop of dimethylformamide. The reaction mixture was shaken for 18 h. The solvent was removed under reduced pressure and dried under high vacuum to afford a quantitative amount of 1-methyl-1H-2-indolecarbonyl chloride. The oil was directly used in the following reaction.

N1-(4-{4-Amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide di-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of 1-methyl-1H-2-indolecarbonyl chloride (0.445 g, 2.3 mmol) in dichloromethane (3 mL). The reaction mixture stirred for 20 min at −5° C., then the dry ice/acetone bath was removed and was stirred at room temperature under a nitrogen atmosphere. 1-methyl-1H-2-indolecarbonyl chloride (0.221 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide was purified by flash chromatography on silica gel using 15% (methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.463 g (68%) pure N1-(4-{4-amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide. A warmed solution of N1-(4-{4-amino-1-[1-(1-methylpiperidin-4-yl)piperidin-4-yl]-1H-pyrazolo[3,4-d]pyrimidin-3-yl}-2-methoxyphenyl))-1- methyl-1H-2-indolecarboxamide (0.463 g, 0.781 mmol) in ethyl acetate was treated with a warmed solution of maleic acid (0.272, 2.34 mmol) in ethyl acetate. The precipitate was filtered under nitrogen, and dried on the lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide di-maleate. $^1$H NMR (DMSO-d$_6$, 400 MHz) δ 9.4495 (s, 1H), 8.2848 (s, 1H), 8.1505–8.1301 (d, 1H, J=8.16 Hz), 7.7232–7.7034 (d, 1H, J=7.92 Hz), 7.6054–7.5844 (d, 1H, J=8.4 Hz), 7.3583–7.3012 (m, 4H), 7.1778–7.1406 (m, 1H), 6.0804 (s, 4H), 5.10–5.00 (m, 1H), 4.0403 (s, 3H), 3.9614 (s, 3H), 3.5336 (m, 4H), 3.1879 (m, 2H), 2.9937 (m, 2H), 2.7836 (s, 3H), 2.4979 (m, 3H), 2.2157 (m, 4H), 1.8513 (m, 2H); HPLC Perkin Elmer Pecosphere C18, 3 μM, 33×4.6, 3.5 ml/min 100-100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) $R_t$ 2.76 min (100%).

Example 439

N1-(4-{4-Amino-1-[1-(1-methylpiperidin-4-yl) piperidin-4-yl]-1H-pyrazolo[3,4-d]pyrimidin-3-yl}-2-methoxyphenyl))-1H-2-indolecarboxamide di-Maleate 1H-2-Indolecarbonyl Chloride A suspension of indole-2-carboxylic acid (0.742 g, 4.6 mmol) in dichloromethane (3 mL) was treated with oxalyl chloride (0.700 g, 5.52 mmol) and one drop of dimethyl formamide. The reaction mixture was shaken for 18 h. The solvent was removed under reduced pressure and dried under high vacuum to afford a quantitative amount of 1H-2-indolecarbonyl chloride. The oil was directly used in the following reaction.

N1-(4-{4-Amino-1-[1-(1-methylpiperidin-4-yl)piperidin-4-yl]-1H-pyrazolo[3,4-d]pyrimidin-3-yl}-2-methoxyphenyl))-1H-2-indolecarboxamide di-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of 1H-2-indolecarbonyl chloride (0.413 g, 2.3 mmol) in dichloromethane (1 mL). The reaction mixture stirred for 20 min at −5° C. The dry ice/acetone bath was removed and the reaction mixture stirred for 18 h under nitrogen atmosphere. 1H-2-indolecarbonyl chloride (0.207 g, 1.15 mmol) was added and was stirred for an additional 2 h. Sodium hydroxide (1 N) solution (10 mL) was added and was stirred for 30 min. Organic solvent was removed under reduced pressure, and dichloromethane (25 mL) was added. The layers were partitioned, and the aqueous layer was extracted with dichloromethane. The combined organic layers were washed with water and brine, dried over magnesium sulfate, filtered, and reduced under pressure to give crude N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide. N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide was purified by flash chromatography on silica gel using 15% (methanol with 2% ammonium hydroxide) in dichloromethane to still give a crude product. A second column using a gradient of 10% (methanol with 2% ammonium hydroxide) to 50% (methanol with 2% ammonium hydroxide) gave 0.139 g (21%) pure N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide. N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide (0.139 g, 0.24 mmol) in warmed ethyl acetate was treated with a warmed solution of maleic acid (0.083 g, 0.719 mmol) in ethyl acetate. The precipitate formed was filtered under nitrogen to give 0.166 g of N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide di-maleate. $^1$H NMR (DMSO-d$_6$, 400 MHz) δ 11.83 (s, 1H), 9.442 (s, 1H), 8.283 (s, 1H), 8.154–8.134 (d, 1H, J=8.12 Hz), 7.694–7.674 (d, 1H, J=8.04 Hz), 7.498–7.477 (d, 1H, J=8.20 Hz), 7.407–7.402 (m, 1H), 7.352–7.325 (m, 2H), 7.267–7.229 (m, 1H), 7.112–7.074 (m, 1H), 6.078 (s, 4H), 5.10–5.00 (m, 1H), 3.974 (s, 3H), 3.525 (m, 4H), 3.178 (m, 2H), 2.975 (m, 2H), 2.771 (s, 3H), 2.457 (s, 3H), 2.208 (m, 4H), 1.909 (m, 2H); HPLC Perkin Elmer Pecosphere C18, 3 μM, 33×4.6, 3.5 m/min 100—100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mi/min) $R_t$ 2.67 min (100%).

Example 440

3-Phenyl-1-trityl-1H-pyrazolo[3,4-d]pyrimidin-4-amine

3-Iodo-1-trityl-1H-pyrazolo[3,4-d]pyrimidin-4-amine

A suspension of 3-iodo-1H-pyrazolo[3,4-d]pyrimidin-4-amine (3.0 g, 11.5 mmol) in dimethylformamide (50 mL) was treated with cesium carbonate (5.62 g, 17.25 mmol) and triphenylmethyl chloride (3.85 g, 13.8 mmol). The reaction mixture was stirred at 70° C. for 22.5 h under a nitrogen atmosphere. Cesium carbonate (3.75 g, 11.5 mmol) and triphenylmethyl chloride (3.2 g, 11.5 mmol) were added to the reaction mixture and was stirred for 6.5 h. The reaction mixture was added to ice water. The precipitate was filtered and washed with water. The product, 3-iodo-1-trityl-1H-pyrazolo[3,4-d]pyrimidin-4-amine, was dried over night on the lyophilizer. The resulting solid was triturated with ethyl acetate to give 3.05 g (53%) of 3-iodo-1-trityl-1H-pyrazolo[3,4-d]pyrimidin-4-amine. $^1$H NMR (DMSO-d$_6$, 400 MHz) δ 7.3190–7.1106 (m, 16H); TLC (Baker Pre-coated Hard Layer Silica Gel TLC plates, Si250F$_{254}$, 30% Ethyl acetate in heptane) $R_f$=0.33.

3-Phenyl-1-trityl-1H-pyrazolo[3,4-d]pyrimidin-4-amine

A solution of 3-iodo-1-trityl-1H-pyrazolo[3,4-d]pyrimidin-4-amine (1.0 g, 1.99 mmol) in dimethylformamide (20 mL) was treated with phenylboronic acid (0.485 g, 3.8 mmol), tetrakis(triphenylphosphine)palladium (0.138 g, 0.119 mmol), and a solution of sodium carbonate (0.506 g, 4.78 mmol) in water (10 mL). The reaction mixture was stirred at 80° C. for 18.5 h under a nitrogen atmosphere. The reaction mixture was cooled to room temperature and water (15 mL) was added. The precipitate was filtered and was washed with water. The crude solid was triturated with diethyl ether (30 mL). The resulting solid was dried over night on the lyophilizer to give 0.407 g (45%) of 3-phenyl-1-trityl-1H-pyrazolo[3,4-d]pyrimidin-4-amine. $^1$H NMR (DMSO-d$_6$, 400 MHz) δ 7.9416 (s, 1H), 7.6190–7.6011 (m, 2H), 7.5369–7.4493 (m, 3H), 7.3995–7.2248 (m, 15H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) $R_f$=11.813 min (97%).

Example 441

N1-{4-[4-Amino-1-(4-oxocyclohexyl)-1H-pyrazolo[3,4-d]pyrimidin-3-yl]-2-methoxyphenyl}-(3R)-3-phenylbutanamide (3R)-3-Phenylbutanoyl chloride (2.22 g, 12.18 mmol) in dichloromethane (10 mL) was added to a solution of 4-[4- amino-3-(4-amino-3-methoxyphenyl)-1H-pyrazolo[3,4-d]pyrimidin-1-yl]-1-cyclohexanone (2.86 g, 8.12 mmol) in pyridine (50 mL) at −10° C. After 15 minutes, the ice-water bath was removed and the reaction mixture was stirred at room temperature overnight. Sodium hydroxide (1.0N, 15 mL) was added and the organic solvent was evaporated. The aqueous residue was extracted with dichloromethane. The combined organic layer was washed with brine, dried over MgSO$_4$, filtered and evaporated. The residue was purified by flash column chromatography using dichlromethane/methanol (95:5) as mobile phase to give N1-{4-[4-amino-1-(4-oxocyclohexyl)-1H-pyrazolo[3,4-d]pyrimidin-3-yl]-2-methoxyphenyl}-(3R)-3-phenylbutanamide (3.11 g, 77%). $^1$H NMR (CDCl$_3$) δ 1.40 (d, J=6.97 Hz, 3H), 2.04 (m, 1H), 2.59–2.78 (m, 9H), 3.40 (m, 1H), 3.98 (s, 3H), 5.28 (m, 1H), 5.70 (bs, 2H), 7.15–7.35 (m, 7H), 7.66 (s, 1H), 8.38 (s, 1H), 8.51 (d, J=8.18, 1H). HPLC (Waters Alliance-Column: Waters SymmetryShield, RP$_{18}$, 3.5 um, 2.1×50 mm. Eluents: 5% B/A to 95% B/A in 9.0 min.(B: acetonitrile, A: 100 mM ammonia acetate buffer, pH 4.5), 0.5 mL/min.): R$_t$=6.273 min.

Example 442

{4-[4-Amino-3-(4-phenoxyphenyl)-1H-pyrazolo[3,4-d]pyrimidin-1-yl]phenyl}methanol a) 4-[4-Amino-3-(4-phenoxyphenyl)-1H-pyrazolo[3,4-d]pyrimidin-1-yl]benzaldehyde 3-(4-Phenoxyphenyl)-1H-pyrazolo[3,4-d]pyrimidin-4-amine (2.0 g, 6.59 mmol) was mixed with 4-fluorobenzaldehyde (1.06 mL, 9.89 mmol), cesium carbonate (4.30 g, 13.19 mmol) in DMF (6 mL). The reaction mixture was heated at 86° C. overnight. After cooling to room temperature, the reaction mixture was poured onto ice water. The solid was collected by filtration to give 4-[4-amino-3-(4-phenoxyphenyl)-1H-pyrazolo[3,4-d]pyrimidin-1-yl]benzaldehyde (2.46 g, 92%). $^1$H NMR (CDCl$_3$) δ 7.19 (m, 5H), 7.46 (m, 2H), 7.78 (d, J=8.64 Hz, 2H), 8.10 (d, J=8.70 Hz, 2H), 8.44 (s, 1H), 8.59 (d, J=8.70 Hz, 2H), 10.03 (s, 1H).

b) {4-[4-Amino-3-(4-phenoxyphenyl)-1H-pyrazolo[3,4-d]pyrimidin-1-yl]phenyl}methanol Sodium borohydride (19 mg, 0.491 mmol) was added to a solution of 4-[4-amino-3-(4-phenoxyphenyl)-1H-pyrazolo[3,4-d]pyrimidin-1-yl]benzaldehyde (100 mg, 0.245 mmol) in methanol (2 mL). After 16 hours, THF (1 mL) and more sodium borohydride (19 mg, 0.491 mmol) was added. 5 hours later, the solvent was removed and water was added. The aqueous layer was extracted with dichloromathane. The combined organic layer was washed with brine, dried over MgSO$_4$, filtered and evaporated. The residue was purified by flash column chromatography using ethyl acetate/dichloromethane (80:20 to 100:0) as mobile phase to give {4-[4-amino-3-(4-phenoxyphenyl)-1H-pyrazolo[3,4-d]pyrimidin-1-yl]phenyl}methanol (36 mg, 36%). $^1$H NMR (DMSO-d$_6$) δ 4.56 (s, 2H), 5.27 (bs, 1H), 7.16 (m, 5H), 7.47 (m, 4H), 7.76 (d, J=8.64 Hz, 2H), 8.18 (d, J=8.52, 2H), 8.37 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =410.1, R$_t$=2.43 min.

Example 443

1-{4-[(4-Methylpiperazino)methyl]phenyl}-3-(4-phenoxyphenyl)-1H-pyrazolo[3,4-d]pyrimidin-4-amine Sodium triacetoxyborohydride (67 mg, 0.319 mmol) was added to a mixture of 4-[4-amino-3-(4-phenoxyphenyl)-1H-pyrazolo[3,4-d]pyrimidin-1-yl]benzaldehyde (100 mg, 0.245 mmol), 4-methylpiperazine (37 mg, 0.369 mmol), glacial acetic acid (35 mg, 0.589 mmol) in dichloroethane (4 mL). After stirring at room temperature over night, more sodium triacetoxyborohydride (67 mg, 0.319 mmol) was added and the reaction mixture was stirred over night. Water (2 mL) was added and followed by sodium bicarbonate (250 mg). After stirring vigorously for 1 hour, the layers were separated and the aqueous layer was extracted with dichloromethane. The combined organic layer was washed with brine, dried over MgSO$_4$, filtered and evaporated. The residue was purified by flash column chromatography using dichlromethane/methanol (97:3 to 80:20) as mobile phase to give 1-{4-[(4-methylpiperazino)methyl]phenyl}-3-(4-phenoxyphenyl)-1H-pyrazolo[3,4-d]pyrimidin-4-amine (25 mg, 21%). $^1$H NMR (DMSO-d$_6$) δ 2.30 (s, 3H), 2.48 (bm, 8H), 3.56 (s, 3H), 5.75 (bs, 2H), 7.11 (d, J=8.50, 2H), 7.18 (m, 3H), 7.40 (m, 2H), 7.48 (d, J=8.50 Hz, 2H), 7.29 (d, J=8.63 Hz, 2H), 8.12 (d, J=8.50 Hz, 2H), 8.47 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =492.2, R$_t$=2.97 min.

Example 444 tert-Butyl N-(4-{4-Amino-1-[4-(4-methylpiperazino)cyclohexyl]-1H-pyrazolo[3,4-d]pyrimidin-3-yl}-5-fluoro-2-methoxyphenyl)carbamate a) 1-Bromo-2-fluoro-5-methoxy-4-nitrobenzene Potassium tert-butoxide (1.0 N in THF, 38 mL, 38 mmol) was added to methanol (1.54 mL, 38.0 mmol) in THF (30 mL) at 0° C. After 30 minutes, the cloudy solution was cannulated to a solution of 1-bromo-2,5-difluoro-4-notrobenzene (9.04 g, 38.0 mmol) in THF (27 mL) at −78° C. After 30 minutes, the cooling bath was removed and the reaction mixture was allowed to warm up to 0° C. Water (250 mL) was added and 10 minutes later, the organic solvent was removed. The solid was collected by filtration to give 1-bromo-2-fluoro-5-methoxy-4-nitrobenzene (9.28 g, 98%). $^1$H NMR (CDCl$_3$) δ 3.97 (s, 3H), 7.30 (d, J=5.48 Hz, 2H), 7.71 (d, J=7.58 Hz, 2H).

b) 4-Bromo-5-fluoro-2-methoxyaniline

Sodium hydrosulfite (14.7 g, 84.4 mmol) was added to a solution of 1-bromo-2-fluoro-5-methoxy-4-nitrobenzene (9.28 g, 37.12 mmol) in ethanol (180 mL) and water (130 mL) at 80° C. in three portions. After 5 hours the organic solvent was removed and the solid in aqueous layer was collected by filtration. The solid was further washed with heptane/ethyl acetate (3:2, 400 mL). The filtrate was evaporated to give 4-bromo-5-fluoro-2-methoxyaniline (3.29 g, 40%). $^1$H NMR (DMSO-d$_6$) δ 3.75 (s, 3H), 5.22 (s, 2H), 6.56 (d, J=10.68 Hz, 2H), 6.94 (d, J=6.57 Hz, 2H).

c) tert-Butyl N-(4-Bromo-5-fluoro-2-methoxyphenyl)carbamate di-tert-Butyl dicarbonate (3.42 g, 15.70 mmol) was mixed with 4-bromo-5-fluoro-2-methoxyaniline (3.29 g, 14.95 mmol) in THF (30 mL). The reaction mixture was heated at 65° C. for 3 days with addition of di-tert-butyl dicarbonate (3.42 g, 15.70 mmol) every day. After removing solvent, the residue was purified by flash column chromatography using heptane/ethyl acetate (95:5 to 85:15) as mobile phase to give a mixture of the desired product tert-butyl N-(4-bromo-5-fluoro-2-methoxyphenyl)carbamate and di-tert-butyl dicarbonate (10.4 g). Sodium hydroxide (50% solution, 2.0 mL) was added to the mixture in methanol (30 mL) at 0° C. and the reaction mixture was stirred at room temperature overnight. After removing solvent, water was added and the aqueous layer was extracted with heptane. The combined organic layer was washed with brine, dried over $MgSO_4$, filtered and evaporated to give tert-butyl N-(4-bromo-5-fluoro-2-methoxyphenyl)carbamate (4.24 g, 89%). $^1$H NMR ($CDCl_3$) δ 1.52 (s, 9H), 3.85 (s, 3H), 6.93 (d, J=6.10 Hz, 1H), 7.06 (s, 1H), 8.01 (d, J=10.4 Hz, 1H).

d) tert-Butyl N-[5-Fluoro-2-methoxy-4-(4,4,5,5-tetramethyl-1,3,2-dioxaborolan-2-yl)phenyl]carbamate.

tert-Butyl N-(4-bromo-5-fluoro-2-methoxyphenyl) carbamate (4.24 g, 13.26 mmol), diboron pinacol ester (4.04 g, 15.91 mmol), potassium acetate (3.90 g, 39.78 mmol) and [1,1'-bis(diphenylphosphino)-ferrocene)dichloropalladium (II) complex with dichloromethane (0.32 g, 0.40 mmol) in DMF (75 mL) was heated at 85° C. overnight. Diboron pinacol ester (2.02 g, 7.96 mmol) and [1,1'-bis(diphenylphosphino)-ferrocene)dichloropalladium(II) complex with dichloromethane (0.32 g, 0.40 mmol) was added and the heating continued for another 5 hours. After removing solvent the black residue was dissolved in dichloromethane and filtered through celite. The crude mixture was purified by flash column chromatography using heptane/ethyl acetate (95:5 to 85:15) as mobile phase to give a mixture of tert-butyl N-[5-fluoro-2-methoxy-4-(4,4,5,5-tetramethyl-1,3,2-dioxaborolan-2-yl)phenyl]carbamate and diboron pinacol ester (1:1 ratio, 4.23 g) which was used in the next reaction without further purificatio e) trans-tert-Butyl N-(4-{4-Amino-1-[4-(4-methylpiperazino)cyclohexyl]-1H-pyrazolo[3,4-d]pyrimidin-3-yl}-5-fluoro-2-methoxyphenyl)carbamate trans-3-Iodo-1-[4-(4-methylpiperazino)cyclohexyl]-1H-pyrazolo[3,4-d]pyrimidin-4-amine (0.60 g, 1.36 mmol), tert-butyl N-[5-fluoro-2-methoxy-4-(4,4,5,5-tetramethyl-1,3,2-dioxaborolan-2-yl)phenyl]carbamate (1.0 g, 2.72 mmol), palladium tetrakistriphenyphosphine(0.094 g, 0.082 mmol) and sodium carbonate (0.35 g, 3.27 mmol) were mixed with ethylene glycol dimethyl ether (14 mL) and water (7 mL). The reaction mixture was heated at reflux overnight. Organic solvent was removed under reduced pressure and the aqueous layer was extracted with dichloromethane. The combined organic layer was washed with water then brine, dried over $MgSO_4$, filtered and evaporated. The residue was purified by flash column chromatography using dichloromethane/methanol (95:5 to 70:30) as mobile phase to give trans-tert-butyl N-(4-{4-amino-1-[4-(4-methylpiperazino)cyclohexyl]-1H-pyrazolo[3,4-d]pyrimidin-3-yl}-5-fluoro-2-methoxyphenyl)carbamate (0.264 g, 35%). $^1$H NMR (DMSO-$d_6$) δ 1.49 (s, 9H), 1.97 (m, 6H), 2.16 (s, 3H), 2.33 (m, 5H), 2.53 (m, 4H), 3.84 (s, 3H), 4.64 (m, 1H), 7.60 (d, J=6.78 Hz, 1H), 7.83 (d, J=11.96 Hz, 1H), 8.20 (s, 1H), 8.24 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =555.3, R$_t$=2.00 min.

Example 445 trans-3-(4-Amino-2-fluoro-5-methoxyphenyl)-1-[4-(4-methylpiperazino)cyclohexyl]-1H-pyrazolo[3,4-d]pyrimidin-4-amine A mixture of trifluoroacetic acid/dichloromethane (20:80, 7 mL) was added to a solution of trans-tert-butyl N-(4-{4-amino-1-[4-(4-methylpiperazino)cyclohexyl]-1H-pyrazolo[3,4-d]pyrimidin-3-yl}-5-fluoro-2-methoxyphenyl)carbamate (250 mg, 0.451 mmol) in dichloromethane (4.0 mL) at 0° C. After 15 minutes, the ice-bath was removed and the reaction mixture was stirred at room temperature for 4 hours. Solvent was then evaporated and the residue was dissolved in dichloromethane. Saturated sodium bicarbonate was added to adjust the pH to 8. The layers were separated and the aqueous layer was extracted with dichloromethane. The combined organic layer was washed with brine, dried over $MgSO_4$, filtered and evaporated give trans-3-(4-amino-2-fluoro-5-methoxyphenyl)-1-[4-(4-methylpiperazino) cyclohexyl]-1H-pyrazolo[3,4-d]pyrimidin-4-amine (179 mg, 87%). $^1$H NMR ($CDCl_3$) δ 1.56 (m, 2H), 2.15 (m, 7H), 2.31 (s, 3H), 2.51 (m, 4H), 2.67 (m, 4H), 3.88 (s, 3H), 4.16 (bs, 2H), 4.74 (m, 1H), 5.64 (bs, 2H), 6.56 (d, J=10.84 Hz, 1H), 6.88 (d, J=6.55 Hz, 1H), 8.33 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =455.2, R$_t$=0.63 min.

Example 446 trans-N1-(4-{4-Amino-1-[4-(4-methylpiperazino) cyclohexyl]-1H-pyrazolo[3,4-d]pyrimidin-3-yl}-5-fluoro-2-methoxyphenyl)-trans-2-phenyl-1-cyclopropanecarboxamide trans-2-Phenyl-1-cyclopropanecarbonyl chloride (32 mg, 0.176 mmol) in dichloromethane (0.3 mL) was added to a solution of trans-3-(4-amino-2-fluoro-5-methoxyphenyl)-1-[4-(4-methylpiperazino)cyclohexyl]-1H-pyrazolo[3,4-d] pyrimidin-4-amine (80 mg, 0.176 mmol) in pyridine (1.5 mL) at 0° C. After 5 minutes the ice-water bath was removed and the reaction mixture was stirred at room temperature for 3 hours. More trans-2-phenyl-1-cyclopropanecarbonyl chloride (32 mg, 0.176 mmol) was added to ensure the reaction went to completion. Solvent was evaporated and the residue was purified by flash column chromatography to give trans-N1-(4-{4-amino-1-[4-(4-methylpiperazino)cyclohexyl]-1H-pyrazolo[3,4-d]pyrimidin-3-yl}-5-fluoro-2-methoxyphenyl)-2-phenyl-1-cyclopropanecarboxamide (93 mg, 88%). $^1$H NMR (DMSO-$d_6$) δ 1.35 (m, 1H), 1.50 (m, 3H), 1.98 (m, 6H), 2.19 (s, 3H), 2.37–2.68 (m, 11H), 3.87 (s, 3H), 4.64 (m, 1H), 7.09 (m, 1H), 7.21 (m, 3H), 7.31 (m, 2H), 8.21 (m, 2H), 9.82 (m, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =599.3, R$_t$=1.97 min.

Example 447 tert-Butyl N-{4-[4-Amino-1-(1-methyl-4-piperidyl)-1H-pyrazolo[3,4-d]pyrimidin-3-yl]-2-methoxyphenyl}carbamate a) 3-Iodo-1-(1-methyl-4-piperidyl)-1H-pyrazolo[3,4-d] pyrimidin-4-amine 3-Iodo-1-(4-piperidyl)-1H-pyrazolo[3,4-d]pyrimidin-4-amine (0.5 g, 1.45 mmol), formaldehyde (30% in water, 0.16 mL, 1.60 mmol) and sodium triacetoxyborohydride (0.43 g, 2.03 mmol) was mixed in dichloroethane (5 mL). After 4 hours, saturated sodium bicarbonate was added followed by sodium hydroxide (1.0N) to bring the pH to 10. The aqueous layer was extracted with dichloromethane. The combined organic layer was washed with brine, dried over $MgSO_4$, filtered and evaporated to give 3-iodo-1-(1-methyl-4-piperidyl)-1H-pyrazolo[3,4-d]pyrimidin-4-amine (0.275 g, 53%). $^1$H NMR (DMSO-$d_6$) δ 1.85 (m, 2H), 2.09 (m, 4H), 2.22 (s, 3H), 2.88 (m, 2H), 4.75 (m, 1H), 8.19 (s, 1H), 8.32 (s, 1H).

b) tert-Butyl N-{4-[4-Amino-1-(1-methyl-4-piperidyl)-1H-pyrazolo[3,4-d]pyrimidin-3-yl]-2-methoxyphenyl}carbamate 3-Iodo-1-(1-methyl-4-piperidyl)-1H-pyrazolo[3,4-d]pyrimidin-4-amine (270 mg, 0.754 mmol), tert-butyl N-[2-methoxy-4-(4,4,5,5-tetramethyl-1,3,2-dioxaborolan-2-yl)phenyl]carbamate(290 mg, 0.829 mmol), palladium tetrakistriphenyphosphine(52 mg, 0.045 mmol) and sodium carbonate (192 mg, 1.81 mmol) were mixed with ethylene glycol dimethyl ether (8 mL) and water (4 mL). The reaction mixture was heated at reflux overnight. Organic solvent was removed under reduced pressure and the aqueous layer was extracted with dichloromethane. The combined organic layer was washed with water then brine, dried over $MgSO_4$, filtered and evaporated. The residue was purified by flash column chromatography using dichloromethane/methanol (90:10 to 70:30) as mobile phase to give tert-butyl N-{4-[4-amino-1-(1-methyl-4-piperidyl)-1H-pyrazolo[3,4-d]pyrimidin-3-yl]-2-methoxyphenyl}carbamate (250 mg, 73%). $^1$H NMR (DMSO-$d_6$) δ 1.48 (s, 9H), 1.88 (m, 2H), 2.10 (m, 2H), 2.24 (m, 5H), 2.92 (m, 2H), 3.69 (s, 3H), 4.64 (m, 1H), 7.21 (m, 2H), 7.91 (d, J=8.16 Hz, 1H), 8.04 (s, 1H), 8.23 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): $MH^+$ =454.2, $R_t$=1.67 min.

Example 448

N1-(4-{4-Amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide tri-Maleate (3R)-3-Phenylbutanoyl Chloride A solution of R-3-phenylbutyric acid (0.755 g, 4.6 mmol) in dichloromethane (3 mL) was treated with oxalyl chloride (0.700 g, 5.52 mmol) and one drop of dimethylformamide. The reaction mixture was shaken for 15 hours at room temperature under a nitrogen atmosphere. The reaction mixture was shaken for 15 h. The solvent was removed under reduced pressure and dried under high vacuum to afford a quantitative amount of (3R)-3-phenylbutanoyl chloride. The oil was directly used in the following reaction. N1-(4-{4-Amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide tri-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of (3R)-3-phenylbutanoyl chloride (0.420 g, 2.3 mmol) in dichloromethane (3 mL). The reaction mixture stirred for 20 min at −5° C., then the dry ice/acetone bath was removed and was stirred at room temperature under a nitrogen atmosphere. (3R)-3-phenylbutanoyl chloride (0.210 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide was purified by flash chromatography on silica gel using 15% (methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.378 g (57%) pure N1-(4-{4-amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide. A warmed solution of N1-(4-{4-amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide (0.378 g, 0.649 mmol) in ethyl acetate was treated with a warmed solution of maleic acid (0.226 g, 1.95 mmol) in ethyl acetate. The precipitate was filtered under nitrogen and dried on lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl)-(3R)-3-phenylbutanamide tri-maleate. $^1$H NMR (DMSO-$d_6$, 400 MHz) δ 9.200 (s, 1H), 8.263 (s, 1H0, 8.1747–8.1543 (d, 1H, J=8.16 Hz), 7.312–7.282 (m, 4H), 7.235–7.232 (s, 1H), 7.211–7.168 (m, 2H), 6.114 (s, 6H), 5.061 (m, 1H), 3.890 (s, 3H), 3.301 (m, 4H), 2.997 (m, 2H), 2.783–2.741 (m, 6H), 2.541 (m, 8H), 2.261–2.185 (m, 4H), 1.879 (m, 2H); HPLC Perkin Elmer Pecosphere C18, 3 μM, 33×4.6, 3.5 ml/min 100-100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) $R_t$ 2.64 min (100%).

Example 449

N1-(4-{4-Amino-1-[1-(1-methylpiperidin-4-yl)piperidin-4-yl]-1H-pyrazolo[3,4-d]pyrimidin-3-yl}-2-methoxyphenyl)-benzo[b]furan-2-carboxamide tri-Maleate Benzo[b]furan-2-carbonyl Chloride A suspension of 2-benzofurancarboxylic acid (0.746 g, 4.6 mmol) in dichloromethane (3 mL) was treated with oxalyl chloride (0.700 g, 5.52 mmol) and one drop of dimethylformamide. The reaction mixture was shaken for 15 h. The solvent was removed under reduced pressure and dried under high vacuum to afford a quantitative amount of benzo[b]furan-2-carbonyl chloride. The oil was directly used in the following reaction. N1-(4-{4-Amino-1-[1-(1-methylpiperidin-4-yl)piperidin-4-yl]-1H-pyrazolo[3,4-d]pyrimidin-3-yl}-2-methoxyphenyl)-benzo[b]furan-2-carboxamide tri-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of benzo[b]furan-2-carbonyl chloride (0.415 g, 2.3 mmol) in dichloromethane (3 mL). The reaction mixture stirred for 20 min at −5° C., then the dry ice/acetone bath was removed and was stirred at room temperature under a nitrogen atmosphere. Benzo[b]furan-2-carbonyl chloride (0.207 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl))-benzo[b]furan-2-carboxamide was purified by flash chromatography on silica gel using 15%

(methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.143 g (21%) pure N1-(4-{4-amino-1-[1-(1-methylpiperidin-4-yl)piperidin-4-yl]-1H-pyrazolo[3,4-d]pyrimidin-3-yl}-2-methoxyphenyl))-benzo[b]furan-2-carboxamide. A warmed solution of N1-(4-{4-amino-1-[1-(1-methylpiperidin-4-yl)piperidin-4-yl]-1H-pyrazolo[3,4-d]pyrimidin-3-yl}-2-methoxyphenyl))-benzo[b]furan-2-carboxamide (0.143 g, 0.246 mmol) in ethyl acetate was treated with a warmed solution of maleic acid (0.086 g, 0.739) in ethyl acetate. The precipitate was filtered under nitrogen and dried on lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl)-benzo[b]furan-2-carboxamide tri-maleate. $^1$H NMR (DMSO-$d_6$, 400 MHz) δ 9.518 (s, 1H), 8.282 (s, 1H), 8.2652–8.2447 (d, 1H, J=8.2 Hz), 7.849–7.814 (m, 2H), 7.7813–7.7603 (d, 1H, J=8.4 Hz), 7.562–7.523 (m, 1H), 7.418–7.369 (m, 2H), 7.338–7.313 (m, 1H), 6.088 (s, 5H), 5.10–5.00 (m, 1H), 4.003 (s, 3H), 3.529 (m, 4H), 3.314 (m, 2H), 2.971 (m, 2H), 2.778 (s, 3H), 2.497 (m, 3H), 2.209 (m, 4H), 1.909 (m, 2H); HPLC Perkin Elmer Pecosphere C18, 3 μM, 33×4.6, 3.5 ml/min 100-100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) $R_t$ 2.73 min (100%).

Example 450

N1-(4-{4-Amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide tri-Maleate (3S)-3-Phenylbutanoyl Chloride A solution of S-3-phenylbutyric acid (0.755 g, 4.6 mmol) in dichloromethane (3 mL) was treated with oxalyl chloride (0.700 g, 5.52 mmol) and one drop of dimethylformamide. The reaction mixture was shaken for 15 hours at room temperature under a nitrogen atmosphere. The reaction mixture was shaken for 15 h. The solvent was removed under reduced pressure and dried under high vacuum to afford a quantitative amount of (3S)-3-phenylbutanoyl chloride. The oil was directly used in the following reaction.

N1-(4-{4-Amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide tri-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of (3S)-3-phenylbutanoyl chloride (0.420 g, 2.3 mmol) in dichloromethane (3 mL). The reaction mixture stirred for 20 min at −5° C., then the dry ice/acetone bath was removed and was stirred at room temperature under a nitrogen atmosphere. (3S)-3-phenylbutanoyl chloride (0.210 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide was purified by flash chromatography on silica gel using 15% (methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.455 g (68%) pure N1-(4-{4-amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide. A warmed solution of N1-(4-{4-amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide (0.455 g, 0.782 mmol) in ethyl acetate was treated with a warmed solution of maleic acid (0.272 g, 2.35) in ethyl acetate. The precipitate was filtered under nitrogen and dried on lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl)-(3S)-3-phenylbutanamide tri-maleate. $^1$H NMR (DMSO-$d_6$, 400 MHz) δ 9.199 (s, 1H), 8.261 (s, 1H), 8.1733–8.1528 (d, 1H, J=8.2 Hz), 7.312–7.282 (m, 4H), 7.236–7.232 (m, 1H), 7.211–7.168 (m, 2H), 6.094 (s, 6H), 5.046 (m, 1H), 3.890 (s, 3H), 3.534 (m, 4H), 2.994 (m, 2H), 2.784–2.740 (m, 6H), 2.506–2.470 (m, 8H), 2.442–2.200 (m, 4H), 1.855 (m, 2H); HPLC Perkin Elmer Pecosphere C18, 3 μM, 33×4.6, 3.5 ml/min 100-100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) $R_t$ 2.64 min (100%).

Example 451 tert-Butyl N-(4-{4-Amino-1-[4-nitrophenyl]-1H-pyrazolo[3,4-d]pyrimidin-3-yl}-2-methoxyphenyl) carbamate 4-Amino-1-[4-nitrophenyl]-3-iodo-1H-pyrazolo[3,4-d]pyrimidine A suspension of 3-iodo-1H-pyrazolo[3,4-d]pyrimidin-4-amine (2.00 g, 7.66 mmol) in dimethylformamide (40 mL) was treated with cesium carbonate (3.74 g, 11.49 mmol) and p-fluoronitrobenzene (1.08 g, 7.66 mmol). The reaction mixture stirred at 80° C. for 5 h under a nitrogen atmosphere. The reaction mixture was added to ice. The precipitate was filtered and washed with water. The product, 4-amino-1-[4-nitrophenyl]-3-iodo-1H-pyrazolo[3,4-d]pyrimidine, was dried on the lyophilizer overnight to give 2.55 g (87%). $^1$H NMR (DMSO-$d_6$, 400 MHz) δ 8.4952–8.4720 (m, 2H), 8.4142–8.3654 (m, 3H); LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) $t_R$=3.73 min (100%) M$^+$ 380.6.

tert-Butyl N-(4-{4-Amino-1-[4-nitrophenyl]-1H-pyrazolo[3,4-d]pyrimidin-3-yl}-2-methoxyphenyl)carbamate A suspension of 4-amino-1-[4-nitrophenyl]-3-iodo-1H-pyrazolo[3,4-d]pyrimidine (0.500 g, 1.31 mmol) in dimethylformamide (8 mL) was treated with tert-butyl N-[2-methoxy-4-(4,4,5,5-tetramethyl-1,3,2-dioxaborolan-2-yl)phenyl]carbamate (0.915 g, 2.62 mmol), tetrakis (triphenylphosphine)palladium (0.091 g, 0.06 mmol), and a solution of sodium carbonate (0.333 g, 3.14 mmol) in water (4 mL). The reaction mixture stirred at 85° C. for 26 h under a nitrogen atmosphere. Water was added to the reaction mixture. The precipitate was filtered and washed with water. The solid was triturated with diethyl ether to give 0.431 g, (63%) of tert-butyl N-(4-{4-amino-1-[4-nitrophenyl]-1H-pyrazolo[3,4-d]pyrimidin-3-yl}-2-methoxyphenyl)

carbamate. $^1$H NMR (DMSO-d$_6$, 400 MHz) δ 8.6862–8.6634 (d, 2H, J=9.12 Hz), 8.4897–8.4423 (m, 3H), 8.1117 (s, 1H), 8.0074–7.9872 (d, 1H, J=8.08 Hz), 7.3743–7.3293 (m, 2H), 3.9189 (s, 3H), 1.4959 (s, 9H); LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) t$_R$=4.38 min M$^+$ 478.1.

Example 452

4-Amino-3-(4-amino-3-methoxyphenyl)-1-[4-nitrophenyl]-1H-pyrazolo[3,4-d]pyrimidine A suspension of tert-butyl N-(4-{4-amino-1-[4-nitrophenyl]-1H-pyrazolo[3,4-d]pyrimidin-3-yl}-2-methoxyphenyl)carbamate (0.386 g, 0.808 mmol) in dichloromethane (8 mL) at 0° C. was treated with trifluoroacetic acid (1.6 mL). The reaction mixture stirred for 20 min at 0° C., then ice bath was removed to stir at room temperature under a nitrogen atmosphere. The reaction mixture was stirred for 18 h. Solvent was removed under reduced pressure. Dichloromethane (15 mL) and sodium hydroxide 1N solution were added to the oil residue. The precipitate formed was filtered and dried over night on the lyophilizer to give 0.286 g (94%) of 4-amino-3-(4-amino-3-methoxyphenyl)-1-[4-nitrophenyl]-1H-pyrazolo[3,4-d]pyrimidine. $^1$H NMR (DMSO-d$_6$, 400 MHz) δ 8.7826–8.759 (m, 2H), 8.4892–8.4296 (m, 3H), 7.1861–7.1338 (m, 2H), 6.8320–6.8121 (d, 1H, J=7.96 Hz), 5.2225 (s, 2H), 3.8672 (s, 3H); LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) t$_R$=3.48 min M$^+$ 377.6.

Example 453

N1-(4-{4-Amino-1-[1-(1-methylpiperidin-4-yl)piperidin-4-yl]-1H-pyrazolo[3,4-d]pyrimidin-3-yl}-2-methoxyphenyl)-1-methyl-1H-2-indolecarboxamide di-Maleate 1-Methyl-1H-2-indolecarbonyl Chloride A suspension of 1-methylindole-2-carboxylic acid (0.805 g, 4.6 mmol) in dichloromethane (3 mL) was treated with oxalyl chloride (0.700 g, 5.52 mmol) and one drop of dimethylformamide. The reaction mixture was shaken for 18 h. The solvent was removed under reduced pressure and dried under high vacuum to afford a quantitative amount of 1-methyl-1H-2-indolecarbonyl chloride. The oil was directly used in the following reaction.
N1-(4-{4-Amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide di-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of 1-methyl-1H-2-indolecarbonyl chloride (0.445 g, 2.3 mmol) in dichloromethane (3 mL). The reaction mixture stirred for 20 min at −5° C., then the dry ice/acetone bath was removed and was stirred at room temperature under a nitrogen atmosphere. 1-methyl-1H-2-indolecarbonyl chloride (0.221 g, 1.15 mmol) was added to the reaction mixture and was stirred for 2 h. Sodium hydroxide (1 N) solution (10 mL) was added and was stirred over night. The organic solvent was removed under reduced pressure, and dichloromethane (20 mL) was added. The layers were partitioned, and the aqueous layer was extracted with dichloromethane (125 mL). The combined organic layers were washed with water, dried over magnesium sulfate, filtered and the solvent removed under reduced pressure. N1-(4-{4-amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide was purified by flash chromatography on silica gel using 15% (methanol with 2% ammonium hydroxide) in dichloromethane (10 min), 20% (methanol with 2% ammonium hydroxide) in dichloromethane (15 min), 50% (methanol with 2% ammonium hydroxide) in dichloromethane (7 min) to give 0.463 g (68%) pure N1-(4-{4-amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide. A warmed solution of N1-(4-{4-amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide (0.463 g, 0.781 mmol) in ethyl acetate was treated with a warmed solution of maleic acid (0.272, 2.34 mmol) in ethyl acetate. The precipitate was filtered under nitrogen, and dried on the lyophilizer to give N1-(4-{4-amino-1-[1-(1-methylpiperidin-4-yl)piperidin-4-yl]-1H-pyrazolo[3,4-d]pyrimidin-3-yl}-2-methoxyphenyl))-1-methyl-1H-2-indolecarboxamide di-maleate. $^1$H NMR (DMSO-d$_6$, 400 MHz) δ 9.4495 (s, 1H), 8.2848 (s, 1H), 8.1505–8.1301 (d, 1H, J=8.16 Hz), 7.7232–7.7034 (d, 1H, J=7.92 Hz), 7.6054–7.5844 (d, 1H, J=8.4 Hz), 7.3583–7.3012 (m, 4H), 7.1778–7.1406 (m, 1H), 6.0804 (s, 4H), 5.10–5.00 (m, 1H), 4.0403 (s, 3H), 3.9614 (s, 3H), 3.5336 (m, 4H), 3.1879 (m, 2H), 2.9937 (m, 2H), 2.7836 (s, 3H), 2.4979 (m, 3H), 2.2157 (m, 4H), 1.8513 (m, 2H); HPLC Perkin Elmer Pecosphere C18, 3 μM, 33×4.6, 3.5 ml/min 100–100% 50 mM ammonium acetate to acetonitrile in 4.5 minutes, C$_{36}$H$_{44}$N$_6$O$_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) R$_t$ 2.76 min (100%).

Example 454

N1-(4-{4-Amino-1-[1-(1-methylpiperidin-4-yl)piperidin-4-yl]-1H-pyrazolo[3,4-d]pyrimidin-3-yl}-2-methoxyphenyl))-1H-2-indolecarboxamide di-Maleate 1H-2-Indolecarbonyl Chloride A suspension of indole-2-carboxylic acid (0.742 g, 4.6 mmol) in dichloromethane (3 mL) was treated with oxalyl chloride (0.700 g, 5.52 mmol) and one drop of dimethyl formamide. The reaction mixture was shaken for 18 h. The solvent was removed under reduced pressure and dried under high vacuum to afford a quantitative amount of 1H-2-indolecarbonyl chloride. The oil was directly used in the following reaction.
N1-(4-{4-Amino-1-[1-(1-methylpiperidin-4-yl)piperidin-4-yl]-1H-pyrazolo[3,4-d]pyrimidin-3-yl}-2-methoxyphenyl))-1H-2-indolecarboxamide di-Maleate A solution of 3-(4-amino-3-methoxyphenyl)-1-[1-(1-methylpiperidin-4-yl)piperidin-4-yl]-1H-pyrazolo[3,4-d]pyrimidin-4-amine (0.500 g, 1.15 mmol) in pyridine (8 mL) at −5° C. was treated with a solution of 1H-2-indolecarbonyl chloride (0.413 g, 2.3 mmol) in dichloromethane (1 mL). The reaction mixture stirred for 20 min at −5° C. The dry ice/acetone bath was removed and the reaction mixture stirred for 18 h under nitrogen atmosphere. 1H-2-indolecarbonyl chloride (0.207 g, 1.15 mmol) was added and was stirred for an additional 2 h. Sodium hydroxide (1 N) solution (10 mL) was added and was stirred for 30 min. Organic solvent was removed under reduced pressure, and dichloromethane (25 mL) was added. The layers were partitioned, and the aqueous layer was extracted with dichloromethane. The combined organic layers were washed with water and brine, dried over magnesium sulfate, filtered, and reduced under pressure to give crude N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide. N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide was purified by flash chromatography on silica gel using 15% (methanol with 2% ammonium hydroxide) in dichloromethane to still give a crude product. A second column using a gradient of 10% (methanol with 2% ammonium hydroxide) to 50% (methanol with 2% ammonium hydroxide) gave 0.139 g (21%) pure N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide. N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide (0.139 g, 0.24 mmol) in warmed ethyl acetate was treated with a warmed solution of maleic acid (0.083 g, 0.719 mmol) in ethyl acetate. The precipitate formed was filtered under nitrogen to give 0.166 g of N1-(4-{4-amino-1-[1-(1-methylpiperidin-4-yl)piperidin-4-yl]-1H-pyrazolo[3,4-d]pyrimidin-3-yl}-2-methoxyphenyl))-1H-2-indolecarboxamide di-maleate. $^1$H NMR (DMSO-$d_6$, 400 MHz) δ 11.83 (s, 1H), 9.442 (s, 1H), 8.283 (s, 1H), 8.154–8.134 (d, 1H, J=8.12 Hz), 7.694–7.674 (d, 1H, J=8.04 Hz), 7.498–7.477 (d, 1H, J=8.20 Hz), 7.407–7.402 (m, 1H), 7.352–7.325 (m, 2H), 7.267–7.229 (m, 1H), 7.112–7.074 (m, 1H), 6.078 (s, 4H), 5.10–5.00 (m, 1H), 3.974 (s, 3H), 3.525 (m, 4H), 3.178 (m, 2H), 2.975 (m, 2H), 2.771 (s, 3H), 2.457 (s, 3H), 2.208 (m, 4H), 1.909 (m, 2H); HPLC Perkin Elmer Pecosphere C18, 3 μM, 33×4.6, 3.5 ml/min 100-100% 50 mM ammonium acetate to acetonitrile in 4.5 minutes, $C_{36}H_{44}N_6O_3$ (581.2), 95%. LCMS (Perkin Elmer, Pecosphere C18 column, 3 um particle size, 33×4.6 mm; 100% 50 mM ammonium Acetate in Water to 100% Acetonitrile over 5 min, 3.0 to 3.5 mil/min) $R_t$ 2.67 min (100%).

Example 455

3-Phenyl-1-trityl-1H-pyrazolo[3,4-d]pyrimidin-4-amine

3-Iodo-1-trityl-1H-pyrazolo[3,4-d]pyrimidin-4-amine

A suspension of 3-iodo-1H-pyrazolo[3,4-d]pyrimidin-4-amine (3.0 g, 11.5 mmol) in dimethylformamide (50 mL) was treated with cesium carbonate (5.62 g, 17.25 mmol) and triphenylmethyl chloride (3.85 g, 13.8 mmol). The reaction mixture was stirred at 70° C. for 22.5 h under a nitrogen atmosphere. Cesium carbonate (3.75 g, 11.5 mmol) and triphenylmethyl chloride (3.2 g, 11.5 mmol) were added to the reaction mixture and was stirred for 6.5 h. The reaction mixture was added to ice water. The precipitate was filtered and washed with water. The product, 3-iodo-1-trityl-1H-pyrazolo[3,4-d]pyrimidin-4-amine, was dried over night on the lyophilizer. The resulting solid was triturated with ethyl acetate to give 3.05 g (53%) of 3-iodo-1-trityl-1H-pyrazolo[3,4-d]pyrimidin-4-amine. $^1$H NMR (DMSO-$d_6$, 400 MHz) δ 7.3190–7.1106 (m, 16H); TLC (Baker Pre-coated Hard Layer Silica Gel TLC plates, Si250F$_{254}$, 30% Ethyl acetate in heptane) $R_f$=0.33.

3-Phenyl-1-trityl-1H-pyrazolo[3,4-d]pyrimidin-4-amine

A solution of 3-iodo-1-trityl-1H-pyrazolo[3,4-d]pyrimidin-4-amine (1.0 g, 1.99 mmol) in dimethylformamide (20 mL) was treated with phenylboronic acid (0.485 g, 3.8 mmol), tetrakis(triphenylphosphine)palladium (0.138 g, 0.119 mmol), and a solution of sodium carbonate (0.506 g, 4.78 mmol) in water (10 mL). The reaction mixture was stirred at 80° C. for 18.5 h under a nitrogen atmosphere. The reaction mixture was cooled to room temperature and water (15 mL) was added. The precipitate was filtered and was washed with water. The crude solid was triturated with diethyl ether (30 mL). The resulting solid was dried over night on the lyophilizer to give 0.407 g (45%) of 3-phenyl-1-trityl-1H-pyrazolo[3,4-d]pyrimidin-4-amine. $^1$H NMR (DMSO-$d_6$, 400 MHz) δ 7.9416 (s, 1H), 7.6190–7.6011 (m, 2H), 7.5369–7.4493 (m, 3H), 7.3995–7.2248 (m, 15H); HPLC Waters 2690 Alliance HPLC (Symmetry Shield RP$_{18}$ 3.5 μm, 2.1×50 mm; 5%–95% acetonitrile-0.1 M ammonium acetate over 15 min, 0.5 mL/min) $R_t$ =11.813 min (97%).

Example 456

N1-{4-[4-Amino-1-(4-oxocyclohexyl)-1H-pyrazolo[3,4-d]pyrimidin-3-yl]-2-methoxyphenyl}-(3R)-3-phenylbutanamide (3R)-3-Phenylbutanoyl chloride (2.22 g, 12.18 mmol) in dichloromethane (10 mL) was added to a solution of 4-[4-amino-3-(4-amino-3-methoxyphenyl)-1H-pyrazolo[3,4-d]pyrimidin-1-yl]-1-cyclohexanone (2.86 g, 8.12 mmol) in pyridine (50 mL) at −10° C. After 15 minutes, the ice-water bath was removed and the reaction mixture was stirred at room temperature overnight. Sodium hydroxide (1.0N, 15 mL) was added and the organic solvent was evaporated. The aqueous residue was extracted with dichloromethane. The combined organic layer was washed with brine, dried over MgSO$_4$, filtered and evaporated. The residue was purified by flash column chromatography using dichlromethane/methanol (95:5) as mobile phase to give N1-{4-[4-amino-1-(4-oxocyclohexyl)-1H-pyrazolo[3,4-d]pyrimidin-3-yl]-2-methoxyphenyl}-(3R)-3-phenylbutanamide (3.11 g, 77%). $^1$H NMR (CDCl$_3$) δ 1.40 (d, J=6.97 Hz, 3H), 2.04 (m, 1H), 2.59–2.78 (m, 9H), 3.40 (m, 1H), 3.98 (s, 3H), 5.28 (m, 1H), 5.70 (bs, 2H), 7.15–7.35 (m, 7H), 7.66 (s, 1H), 8.38 (s, 1H), 8.51 (d, J=8.18, 1H). HPLC (Waters Alliance-Column: Waters SymmetryShield, RP8, 3.5 um, 2.1×50 mm. Eluents: 5% B/A to 95% B/A in 9.0 min.(B: acetonitrile, A: 100 mM ammonia acetate buffer, pH 4.5), 0.5 mL/min.): $R_t$=6.273 min.

Example 457

{4-[4-Amino-3-(4-phenoxyphenyl)-1H-pyrazolo[3,4-d]pyrimidin-1-yl]phenyl}methanol 4-[4-Amino-3-(4-phenoxyphenyl)-1H-pyrazolo[3,4-d]pyrimidin-1-yl]benzaldehyde 3-(4-Phenoxyphenyl)-1H-pyrazolo[3,4-d]pyrimidin-4-amine (2.0 g, 6.59 mmol) was mixed with 4-fluorobenzaldehyde (1.06 mL, 9.89 mmol), cesium carbonate (4.30 g, 13.19 mmol) in DMF (6 mL). The reaction mixture was heated at 86° C. overnight. After cooling to room temperature, the reaction mixture was poured onto ice water. The solid was collected by filtration to give 4-[4-amino-3-(4-phenoxyphenyl)-1H-pyrazolo[3,4-d]pyrimidin-1-yl]benzaldehyde (2.46 g, 92%). $^1$H NMR (CDCl$_3$) δ 7.19 (m, 5H), 7.46 (m, 2H), 7.78 (d, J=8.64 Hz, 2H), 8.10 (d, J=8.70 Hz, 2H), 8.44 (s, 1H), 8.59 (d, J=8.70 Hz, 2H), 10.03 (s, 1H).

b) {4-[4-Amino-3-(4-phenoxyphenyl)-1H-pyrazolo[3,4-d]pyrimidin-1-yl]phenyl}methanol Sodium borohydride (19 mg, 0.491 mmol) was added to a solution of 4-[4-amino-3-(4-phenoxyphenyl)-1H-pyrazolo

[3,4-d]pyrimidin-1-yl]benzaldehyde (100 mg, 0.245 mmol) in methanol (2 mL). After 16 hours, THF (1 mL) and more sodium borohydride (19 mg, 0.491 mmol) was added. 5 hours later, the solvent was removed and water was added. The aqueous layer was extracted with dichloromathane. The combined organic layer was washed with brine, dried over MgSO$_4$, filtered and evaporated. The residue was purified by flash column chromatography using ethyl acetate/dichloromethane (80:20 to 100:0) as mobile phase to give {4-[4-amino-3-(4-phenoxyphenyl)-1H-pyrazolo[3,4-d]pyrimidin-1-yl]phenyl}methanol (36 mg, 36%). $^1$H NMR (DMSO-d$_6$) δ 4.56 (s, 2H), 5.27 (bs, 1H), 7.16 (m, 5H), 7.47 (m, 4H), 7.76 (d, J=8.64 Hz, 2H), 8.18 (d, J=8.52 Hz, 2H), 8.37 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$=410.1, R$_t$=2.43 min.

Example 458

1-{4-[(4-Methylpiperazino)methyl]phenyl}-3-(4-phenoxyphenyl)-1H-pyrazolo[3,4-d]pyrimidin-4-amine Sodium triacetoxyborohydride (67 mg, 0.319 mmol) was added to a mixture of 4-[4-amino-3-(4-phenoxyphenyl)-1H-pyrazolo[3,4-d]pyrimidin-1-yl]benzaldehyde (100 mg, 0.245 mmol), 4-methylpiperazine (37 mg, 0.369 mmol), glacial acetic acid (35 mg, 0.589 mmol) in dichloroethane (4 mL). After stirring at room temperature over night, more sodium triacetoxyborohydride (67 mg, 0.319 mmol) was added and the reaction mixture was stirred over night. Water (2 mL) was added and followed by sodium bicarbonate (250 mg). After stirring vigorously for 1 hour, the layers were separated and the aqueous layer was extracted with dichloromethane. The combined organic layer was washed with brine, dried over MgSO$_4$, filtered and evaporated. The residue was purified by flash column chromatography using dichlromethane/methanol (97:3 to 80:20) as mobile phase to give 1-{4-[(4-methylpiperazino)methyl]phenyl}-3-(4-phenoxyphenyl)-1H-pyrazolo[3,4-d]pyrimidin-4-amine (25 mg, 21%). $^1$H NMR (DMSO-d$_6$) δ 2.30 (s, 3H), 2.48 (bm, 8H), 3.56 (s, 3H), 5.75 (bs, 2H), 7.11 (d, J=8.50, 2H), 7.18 (m, 3H), 7.40 (m, 2H), 7.48 (d, J=8.50 Hz, 2H), 7.29 (d, J=8.63 Hz, 2H), 8.12 (d, J=8.50 Hz, 2H), 8.47 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$=492.2, R$_t$=2.97 min.

Example 459 tert-Butyl N-(4-{4-Amino-1-[4-(4-methylpiperazino)cyclohexyl]-1H-pyrazolo[3,4-d]pyrimidin-3-yl}-5-fluoro-2-methoxyphenyl)carbamate c) 1-Bromo-2-fluoro-5-methoxy-4-nitrobenzene Potassium tert-butoxide (1.0 N in THF, 38 mL, 38 mmol) was added to methanol (1.54 mL, 38.0 mmol) in THF (30 mL) at 0° C. After 30 minutes, the cloudy solution was cannulated to a solution of 1-bromo-2,5-difluoro-4-notrobenzene (9.04 g, 38.0 mmol) in THF (27 mL) at –78° C. After 30 minutes, the cooling bath was removed and the reaction mixture was allowed to warm up to 0° C. Water (250 mL) was added and 10 minutes later, the organic solvent was removed. The solid was collected by filtration to give 1-bromo-2-fluoro-5-methoxy-4-nitrobenzene (9.28 g, 98%). $^1$H NMR (CDCl$_3$) δ 3.97 (s, 3H), 7.30 (d, J=5.48 Hz, 2H), 7.71 (d, J=7.58 Hz, 2H).

d) 4-Bromo-5-fluoro-2-methoxyaniline

Sodium hydrosulfite (14.7 g, 84.4 mmol) was added to a solution of 1-bromo-2-fluoro-5-methoxy-4-nitrobenzene (9.28 g, 37.12 mmol) in ethanol (180 mL) and water (130 mL) at 80° C. in three portions. After 5 hours the organic solvent was removed and the solid in aqueous layer was collected by filtration. The solid was further washed with heptane/ethyl acetate (3:2, 400 mL). The filtrate was evaporated to give 4-bromo-5-fluoro-2-methoxyaniline (3.29 g, 40%). $^1$H NMR (DMSO-d$_6$) δ 3.75 (s, 3H), 5.22 (s, 2H), 6.56 (d, J=10.68 Hz, 2H), 6.94 (d, J=6.57 Hz, 2H).

c) tert-Butyl N-(4-Bromo-5-fluoro-2-methoxyphenyl)carbamate di-tert-Butyl dicarbonate (3.42 g, 15.70 mmol) was mixed with 4-bromo-5-fluoro-2-methoxyaniline (3.29 g, 14.95 mmol) in THF (30 mL). The reaction mixture was heated at 65° C. for 3 days with addition of di-tert-butyl dicarbonate (3.42 g, 15.70 mmol) every day. After removing solvent, the residue was purified by flash column chromatography using heptane/ethyl acetate (95:5 to 85:15) as mobile phase to give a mixture of the desired product tert-butyl N-(4-bromo-5-fluoro-2-methoxyphenyl)carbamate and di-tert-butyl dicarbonate (10.4 g). Sodium hydroxide (50% solution, 2.0 mL) was added to the mixture in methanol (30 mL) at 0° C. and the reaction mixture was stirred at room temperature overnight. After removing solvent, water was added and the aqueous layer was extracted with heptane. The combined organic layer was washed with brine, dried over MgSO$_4$, filtered and evaporated to give tert-butyl N-(4-bromo-5-fluoro-2-methoxyphenyl)carbamate (4.24 g, 89%). $^1$H NMR (CDCl$_3$) δ 1.52 (s, 9H), 3.85 (s, 3H), 6.93 (d, J=6.10 Hz, 1H), 7.06 (s, 1H), 8.01 (d, J=10.4 Hz, 1H).

d) tert-Butyl N-[5-Fluoro-2-methoxy-4-(4,4,5,5-tetramethyl-1,3,2-dioxaborolan-2-yl)phenyl]carbamate tert-Butyl N-(4-bromo-5-fluoro-2-methoxyphenyl)carbamate (4.24 g, 13.26 mmol), diboron pinacol ester (4.04 g, 15.91 mmol), potassium acetate (3.90 g, 39.78 mmol) and [1,1'-bis(diphenylphosphino)-ferrocene)dichloropalladium (II) complex with dichloromethane (0.32 g, 0.40 mmol) in DMF (75 mL) was heated at 85° C. overnight. Diboron pinacol ester (2.02 g, 7.96 mmol) and [1,1'-bis(diphenylphosphino)-ferrocene)dichloropalladium(II) complex with dichloromethane (0.32 g, 0.40 mmol) was added and the heating continued for another 5 hours. After removing solvent the black residue was dissolved in dichloromethane and filtered through celite. The crude mixture was purified by flash column chromatography using heptane/ethyl acetate (95:5 to 85:15) as mobile phase to give a mixture of tert-butyl N-[5-fluoro-2-methoxy-4-(4,4,5,5-tetramethyl-1,3,2-dioxaborolan-2-yl)phenyl]carbamate and diboron pinacol ester (1:1 ratio, 4.23 g) which was used in the next reaction without further purification.

e) trans-tert-Butyl N-(4-{4-Amino-1-[4-(4-methylpiperazino)cyclohexyl]-1H-pyrazolo[3,4-d]pyrimidin-3-yl}-5-fluoro-2-methoxyphenyl)carbamate trans-3-Iodo-1-[4-(4-methylpiperazino)cyclohexyl]-1H-pyrazolo[3,4-d]pyrimidin-4-amine (0.60 g, 1.36 mmol), tert-butyl N-[5-fluoro-2-methoxy-4-(4,4,5,5-tetramethyl-1,3,2-dioxaborolan-2-yl)phenyl]carbamate (1.0 g, 2.72 mmol), palladium tetrakistriphenyphosphine(0.094 g, 0.082 mmol) and sodium carbonate (0.35 g, 3.27 mmol) were mixed with ethylene glycol dimethyl ether (14 mL) and water (7 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (95:5 to 70:30) as mobile phase to give trans-tert-butyl N-(4-{4-amino-11-[4-(4-methylpiperazino)cyclohexyl]-1H-pyrazolo[3,4-d]pyrimidin-3-yl}-5-fluoro-2-methoxyphenyl)carbamate (0.264 g, 35%). $^1$H NMR (DMSO-d$_6$) δ 1.49 (s, 9H), 1.97 (m, 6H), 2.16 (s, 3H), 2.33 (m, 5H), 2.53 (m, 4H), 3.84 (s, 3H), 4.64 (m, 1H), 7.60 (d, J=6.78 Hz, 1H), 7.83 (d, J=11.96 Hz, 1H), 8.20 (s, 1H), 8.24 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =555.3, R$_t$=2.00 min.

Example 460 trans-3-(4-Amino-2-fluoro-5-methoxyphenyl)-1-[4-(4-methylpiperazino)cyclohexyl]-1H-pyrazolo[3,4-d]pyrimidin-4-amine A mixture of trifluoroacetic acid/dichloromethane (20:80, 7 mL) was added to a solution of trans-tert-butyl N-(4-{4-amino-1-[4-(4-methylpiperazino)cyclohexyl]-1H-pyrazolo[3,4-d]pyrimidin-3-yl}-5-fluoro-2-methoxyphenyl)carbamate (250 mg, 0.451 mmol) in dichloromethane (4.0 mL) at 0° C. After 15 minutes, the ice-bath was removed and the reaction mixture was stirred at room temperature for 4 hours. Solvent was then evaporated and the residue was dissolved in dichloromethane. Saturated sodium bicarbonate was added to adjust the pH to 8. The layers were separated and the aqueous layer was extracted with dichloromethane. The combined organic layer was washed with brine, dried over MgSO$_4$, filtered and evaporated give trans-3-(4-amino-2-fluoro-5-methoxyphenyl)-1-[4-(4-methylpiperazino)cyclohexyl]-1H-pyrazolo[3,4-d]pyrimidin-4-amine (179 mg, 87%). $^1$H NMR (CDCl$_3$) δ 1.56 (m, 2H), 2.15 (m, 7H), 2.31 (s, 3H), 2.51 (m, 4H), 2.67 (m, 4H), 3.88 (s, 3H), 4.16 (bs, 2H), 4.74 (m, 1H), 5.64 (bs, 2H), 6.56 (d, J=10.84 Hz, 1H), 6.88 (d, J=6.55 Hz, 1H), 8.33 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =455.2, R$_t$=0.63 min.

Example 461 trans-N1-(4-{4-Amino-1-[4-(4-methylpiperazino)cyclohexyl]-1H-pyrazolo[3,4-d]pyrimidin-3-yl}-5-fluoro-2-methoxyphenyl)-trans-2-phenyl-1-cyclopropanecarboxamide trans-2-Phenyl-1-cyclopropanecarbonyl chloride (32 mg, 0.176 mmol) in dichloromethane (0.3 mL) was added to a solution of trans-3-(4-amino-2-fluoro-5-methoxyphenyl)-1-[4-(4-methylpiperazino)cyclohexyl]-1H-pyrazolo[3,4-d]pyrimidin-4-amine (80 mg, 0.176 mmol) in pyridine (1.5 mL) at 0° C. After 5 minutes the ice-water bath was removed and the reaction mixture was stirred at room temperature for 3 hours. More trans-2-phenyl-1-cyclopropanecarbonyl chloride (32 mg, 0.176 mmol) was added to ensure the reaction went to completion. Solvent was evaporated and the residue was purified by flash column chromatography to give trans-N1-(4-{4-amino-1-[4-(4-methylpiperazino)cyclohexyl]-1H-pyrazolo[3,4-d]pyrimidin-3-yl}-5-fluoro-2-methoxyphenyl)-2-phenyl-1-cyclopropanecarboxamide (93 mg, 88%). $^1$H NMR (DMSO-d$_6$) δ 1.35 (m, 1H), 1.50 (m, 3H), 1.98 (m, 6H), 2.19 (s, 3H), 2.37–2.68 (m, 11H), 3.87 (s, 3H), 4.64 (m, 1H), 7.09 (m, 1H), 7.21 (m, 3H), 7.31 (m, 2H), 8.21 (m, 2H), 9.82 (m, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =599.3, R$_t$=1.97 min.

Example 462 tert-Butyl N-{4-[4-Amino-1-(1-methyl-4-piperidyl)-1H-pyrazolo[3,4-d]pyrimidin-3-yl]-2-methoxyphenyl}carbamate b) 3-Iodo-1-(1-methyl-4-piperidyl)-1H-pyrazolo[3,4-d]pyrimidin-4-amine 3-Iodo-1-(4-piperidyl)-1H-pyrazolo[3,4-d]pyrimidin-4-amine (0.5 g, 1.45 mmol), formaldehyde (30% in water, 0.16 mL, 1.60 mmol) and sodium triacetoxyborohydride (0.43 g, 2.03 mmol) was mixed in dichloroethane (5 mL). After 4 hours, saturated sodium bicarbonate was added followed by sodium hydroxide (1.0N) to bring the pH to 10. The aqueous layer was extracted with dichloromethane. The combined organic layer was washed with brine, dried over MgSO$_4$, filtered and evaporated to give 3-iodo-1-(1-methyl-4-piperidyl)-1H-pyrazolo[3,4-d]pyrimidin-4-amine (0.275 g, 53%). $^1$H NMR (DMSO-d$_6$) δ 1.85 (m, 2H), 2.09 (m, 4H), 2.22 (s, 3H), 2.88 (m, 2H), 4.75 (m, 1H), 8.19 (s, 1H), 8.32 (s, 1H).

b) tert-Butyl N-{4-[4-Amino-1-(1-methyl-4-piperidyl)-1H-pyrazolo[3,4-d]pyrimidin-3-yl]-2-methoxyphenyl}carbamate 3-Iodo-1-(1-methyl-4-piperidyl)-1H-pyrazolo[3,4-d]pyrimidin-4-amine (270 mg, 0.754 mmol), tert-butyl N-[2-methoxy-4-(4,4,5,5-tetramethyl-1,3,2-dioxaborolan-2-yl)phenyl]carbamate(290 mg, 0.829 mmol), palladium tetrakistriphenyphosphine(52 mg, 0.045 mmol) and sodium carbonate (192 mg, 1.81 mmol) were mixed with ethylene glycol dimethyl ether (8 mL) and water (4 mL). The reaction mixture was heated at reflux overnight. Organic solvent was removed under reduced pressure and the aqueous layer was extracted with dichloromethane. The combined organic layer was washed with water then brine, dried over MgSO$_4$, filtered and evaporated. The residue was purified by flash column chromatography using dichloromethane/methanol (90:10 to 70:30) as mobile phase to give tert-butyl N-{4-[4-amino-1-(1-methyl-4-piperidyl)-1H-pyrazolo[3,4-d]pyrimidin-3-yl]-2-methoxyphenyl}carbamate (250 mg, 73%). $^1$H NMR (DMSO-d$_6$) δ 1.48 (s, 9H),1.88 (m, 2H), 2.10 (m, 2H), 2.24 (m, 5H), 2.92 (m, 2H), 3.69 (s, 3H), 4.64 (m, 1H), 7.21 (m, 2H), 7.91 (d, J=8.16 Hz, 1H), 8.04 (s, 1H), 8.23 (s, 1H). LCMS (Thermoquest AQA single Quad MS, Finnigan HPLC-Column: Genesis, C18, 3 um, 33×4.6 mm. Eluents: 30% B/A to 95% B/A in 4.5 min. (B: acetonitrile, A: 50 mM ammonia acetate buffer, pH 4.5), 0.8 mL/min.): MH$^+$ =454.2, R$_t$=1.67 min.

Example 463 trans-3-{4-[(2-Chlorobenzyl)amino]-3-methoxyphenyl}-1-[4-(4-methylpiperazino)cyclohexyl]-1H-pyrazolo[3,4-d]pyrimidin-4-amine Diacetate Protocol A (General Procedure for Reductive Alkylation of trans-3-(4-Amino-3-methoxyphenyl)-1-[4-(4-methylpiperazino)cyclohexyl]-1H-pyrazolo[3,4-d]pyrimidin-4-amin)

$^1$H NMR (DMSO-d$_6$, 400 MHz) δ 8.18 (s, 1H), 7.46 (d, 1H), 7.30 (m, 3H), 7.08 (s, 1H), 7.01 (d, 1H), 6.42 (d, 1H), 5.96 (t, 1H), 4.59 (m, 1H), 4.45 (d, 2H), 3.90 (s, 3H), 2.6–2.2 (br, 9H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 15.22 min. MS: MH$^+$ 561.

Example 464 trans-3-{3-Methoxy-4-[(1,3-thiazol-2-ylmethyl)amino]phenyl}-1-[4-(4-methylpiperazino)cyclohexyl]-1H-pyrazolo[3,4-d]pyrimidin-4-amine Diacetate Protocol A $^1$H NMR (DMSO-d$_6$, 400 MHz) δ 8.18 (s, 1H), 7.76 (d, 1H), 7.59 (d, 1H), 7.08 (s, 1H), 7.02 (d, 1H), 6.59 (d, 1H), 6.27 (t, 1H), 4.68 (d, 2H), 4.61 (m, 1H), 3.89 (s, 3H), 2.6–2.2 (br, 9H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 11.09 min. MS: MH$^+$ 534.

Example 465 trans-3-(3-Methoxy-4-[(3-methyl-1H-4-pyrazolyl)methyl]aminophenyl)-1-[4-(4-methylpiperazino)cyclohexyl]-1H-pyrazolo[3,4-d]pyrimidin-4-amine Diacetate Protocol A $^1$H NMR (DMSO-d$_6$, 400 MHz) δ 8.19 (s, 1H), 7.47 (s, 1H), 7.06 (m, 3H), 6.74 (d, 1H), 5.08 (t, 1H), 4.61 (m, 1H), 4.13 (d, 2H), 3.84 (s, 3H), 2.6–2.2 (br, 9H), 2.25 (s, 3H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 10.65 min. MS: MH$^+$ 531.

Example 466 trans-3-{3-Methoxy-4-[(2-thienylmethyl)amino]phenyl}-1-[4-(4-methylpiperazino)cyclohexyl]-1H-pyrazolo[3,4-d]pyrimidin-4-amine Acetate Protocol A $^1$H NMR (DMSO-d$_6$, 400 MHz) δ 8.19 (s, 1H), 7.36 (d, 1H), 7.01 (m, 4H), 6.71 (d, 1H), 5.87 (t, 1H), 4.61 (m, 3H), 3.86 (s, 3H), 2.6–2.2 (br, 9H), 2.13 (s, 3H), 2.05 (m, 6H), 1.91 (s, 3H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 13.61 min. MS: MH$^+$ 533.

Example 467 trans-3-(3-Methoxy-4-[(5-methyl-2-thienyl)methyl]aminophenyl)-1-[4-(4-methylpiperazino)cyclohexyl]-1H-pyrazolo[3,4-d]pyrimidin-4-amine Acetate Protocol A $^1$H NMR (DMSO-d$_6$, 400 MHz) δ 8.19 (s, 1H), 7.04 (m, 2H), 6.84 (d, 1H), 6.70 (d, 1H), 6.62 (d, 1H), 5.77 (t, 1H), 4.61 (m, 1H), 4.47 (d, 2H), 3.86 (s, 3H), 2.6–2.2 (br, 9H), 2.37 (s, 3H), 2.13 (s, 3H), 2.05 (m, 6H), 1.91 (s, 3H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 14.66 min. MS: MH$^+$ 547.

Example 468 trans-3-(4-[(5-Chloro-2-thienyl)methyl]amino-3-methoxyphenyl)-1-[4-(4-methylpiperazino)cyclohexyl]-1H-pyrazolo[3,4-d]pyrimidin-4-amine Acetate Protocol A $^1$H NMR (DMSO-d$_6$, 400 MHz) δ 8.19 (s, 1H), 7.04 (m, 2H), 6.95 (s, 1H), 6.69 (d, 1H), 5.99 (t, 1H), 4.61 (m, 1H), 4.50 (d, 2H), 3.86 (s, 3H), 2.6–2.2 (br, 9H), 2.13 (s, 3H), 2.05 (m, 6H), 1.91 (s, 3H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 15.04 min. MS: MH$^+$ 567.

Example 469 trans-3-(3-Methoxy-4-[(2-methyl-1,3-thiazol-4-yl)methyl]aminophenyl)-1-[4-(4-methylpiperazino)cyclohexyl]-1H-pyrazolo[3,4-d]pyrimidin-4-amine Diacetate a) 2-Methyl-1,3-thiazole-4-carbaldehyde To a solution of 4-chloromethyl-2-methyl-1,3-thiazole (1.91 g, 0.0129 mol) in toluene (50 mL), N-methylmorpoline-N-oxide (4.55 g, 0.0389 mol) was added and the reaction mixture was heated at 90° C. for 4 hours. N-methylmorpoline-N-oxide (1.60 g, 0.0137 mol) was added and the heating was conitinued for another 1.5 hours. The mixture was cooled to ambient temperature, washed with water (3×50 mL) and concentrated to yield 2-methyl-1,3-thiazole-4-carbaldehyde (1.40 g, 0.011 mol) as a brown liquid.

$^1$H NMR (DMSO-d$_6$, 400 MHz) δ 9.87 (s, 1H), 8.57 (s, 1H), 2.72 (s, 3H). TLC (ethyl acetate/heptane 1:3) $R_f$ 0.26.

b) trans-3-(3-Methoxy-4-[(2-methyl-1,3-thiazol-4-yl)methyl]aminophenyl)-1-[4-(4-methylpiperazino)cyclohexyl]-1H-pyrazolo[3,4-d]pyrimidin-4-amine Diacetate Protocol A $^1$H NMR (DMSO-d$_6$, 400 MHz) δ 5 8.19 (s, 1H), 7.21 (s, 1H), 7.06 (m, 2H), 6.66 (d, 1H), 5.70 (t, 1H), 4.60 (m, 1H), 4.41 (d, 2H), 3.87 (s, 3H), 2.64 (s, 3H), 2.6–2.2 (br, 9H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 11.71 min. MS: MH$^+$ 548.

Example 470 trans-3-{4-[(1H-7-Indolylmethyl)amino]phenyl}-1-[4-(4-methylpiperazino)cyclohexyl]-1H-pyrazolo[3,4-d]pyrimidin-4-amine Diacetate Protocol C (General Procedure for Reductive Alkylation of trans-3-(4-Amino-phenyl)-1-[4-(4-methylpiperazino)cyclohexyl]-1H-pyrazolo[3,4-d]pyrimidin-4-amin)

$^1$H NMR (DMSO-d$_6$, 400 MHz) δ 11.14 (s, 1H), 8.18 (s, 1H), 7.44 (d, 1H), 7.37 (m, 3H), 7.12 (d, 1H), 6.97 (t, 1H), 6.77 (d, 2H), 6.55 (t, 1H), 6.46 (m, 1H), 4.60 (m, 3H), 2.6–2.2 (br, 9H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 13.68 min. MS: MH$^+$ 536.

Example 471 trans-3-{4-[(2-Chloro-6-fluorobenzyl)amino]phenyl}-1-[4-(4-methylpiperazino)cyclohexyl]-1H-pyrazolo[3,4-d]pyrimidin-4-amine Diacetate Protocol C $^1$H NMR (DMSO-d$_6$, 400 MHz) δ 8.18 (s, 1H), 7.41 (m, 4H), 7.29 (t, 1H), 6.83 (d, 2H), 6.26 (t, 1H), 4.61 (m, 1H), 4.37 (d, 2H), 2.6–2.2 (br, 9H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) $R_t$ 14.46 min. MS: MH$^+$ 549.

Example 472 trans-1-[4-(4-Methylpiperazino)cyclohexyl]-3-(4-[(5-methyl-1H-4-pyrazolyl)methyl]aminophenyl)-1H-pyrazolo[3,4-d]pyrimidin-4-amine Diacetate Protocol C $^1$H NMR (DMSO-d$_6$, 400 MHz) δ 8.19 (s, 1H), 7.49 (s, 1H), 7.35 (d, 2H), 6.76 (d, 2H), 6.07 (t, 1H), 4.59 (m, 1H), 4.06 (d, 2H), 2.6–2.2 (br, 9H), 2.21 (s, 3H), 2.13 (s, 3H), 2.05 (m, 6H), 1.91 (s, 6H), 1.46 (m, 2H); RP-HPLC (Delta Pak C18, 5 µm, 300 A, 15 cm; 5%–85% acetonitrile-0.1M ammonium acetate over 20 min, 1 mL/min) R$_t$ 10.15 min. MS: MH$^+$ 501.

Example 473 trans-3-{4-[(2-aminobenzyl)amino]phenyl}-1-[4-(4-methylpiperazino)cyclohexyl]-1H-pyrazolo[3,4-d]pyrimidin-4-amine diacetate a) tert-Butyl N-[2-(Hydroxymethyl)phenyl]carbamate To a solution of di-tert-butyl dicarbonate (23.04 g, 0.106 mol) in anhydrous dichloromethane (150 mL) at 0° C., a solution of 2-aminobenzyl alcohol (10.0 g, 0.0812 mol) was added and the resulting mixture was stirred under an atmosphere of nitrogen at ambient temperature for 18 hours. The organic phase was washed with saturated solution of sodium bicarbonate in water (2×250 mL), dried with magnesium sulfate and concentrated under reduced pressure. The residue was purified by flash chromatography on silica using ethyl acetate/n-heptane (1:5) as mobile phase to yield tert-butyl N-[2-(hydroxymethyl)phenyl]carbamate (17.2 g, 0.077 mol) as a colorless oil.

$^1$H NMR (DMSO-d$_6$, 400 MHz) δ 8.52 (s, 1H), 7.57 (d, 1H), 7.30 (d, 1H), 7.22 (t, 1H), 7.04 (t, 1H), 5.42 (t, 1H), 4.51 (d, 2H), 1.46 (s, 9H). TLC (ethyl acetate/heptane 1:3) R$_f$ 0.28.

b) tert-Butyl N-(2-Formylphenyl)carbamate

A 20% dispersion of pyridinium chlorochromate in basic alumina (50 g) was added to a solution of tert-butyl N-[2-(hydroxymethyl)phenyl]carbamate (11.0 g, 0.0493 mol) in anhydrous chloroform and the resulting suspension was stirred under an atmosphere of nitrogen at ambient temperature for 1 hour. Additional 16 g of a 20% dispersion of pyridinium chlorochromate in basic alumina was added and the stirring was continued for 45 min. At this point in time, additional 15 g of of 20% dispersion of pyridinium chlorochromate in basic alumina was added and the stirring was continued for 25 min. The resulting suspension was filtered through a silica gel pad, the filtrate was concentrated under reduced pressure and the residue purified by flash chromatography on silica using ethyl acetate/n-heptane (2:98) as mobile phase to yield tert-butyl N-(2-formylphenyl)carbamate (8.67 g, 0.0392 mol) as a white solid.

$^1$H NMR (DMSO-d$_6$, 400 MHz) δ 10.31 (s, 1H), 9.95 (s, 1H), 8.18 (d, 1H), 7.87 (d, 1H), 7.67 (t, 1H), 7.24 (t, 1H), 1.49 (s, 9H). TLC (ethyl acetate/heptane 1:5) R$_f$ 0.56.

c) trans-tert-Butyl N-2-[(4-{4-Amino-1-[4-(4-methylpiperazino)cyclohexyl]-1H-pyrazolo[3,4-d]pyrimidin-3-yl}anilino)methyl]phenylcarbamate Acetate Protocol C $^1$H NMR (DMSO-d$_6$, 400 MHz) δ 8.69 (s, 1H), 8.18 (s, 1H), 7.33 (m, 4H), 7.18 (t, 1H), 7.12 (t, 1H), 6.68 (d, 2H), 6.51 (t, 1H), 4.58 (m, 1H), 4.30 (d, 2H), 2.6–2.2 (br, 9H), 2.13 (s, 3H), 2.05 (m, 6H), 1.91 (s, 3H), 1.47 (s, 9H), 1.46 (m, 2H); RP-HPLC (Delta Pak C18, 5 µm, 300 A, 15 cm; 5%–85% acetonitrile-0.1M ammonium acetate over 20 min, 1 mL/min) R$_t$ 14.73 min.

d) trans-3-{4-[(2-Aminobenzyl)amino]phenyl}-1-[4-(4-methylpiperazino)cyclohexyl]-1H-pyrazolo[3,4-d]pyrimidin-4-amine Diacetate Trans-tert-butyl N-2-[(4-4-amino-1-[4-(4-methylpiperazino)cyclohexyl]-1H-pyrazolo[3,4-d]pyrimidin-3-ylanilino)methyl]phenylcarbamate acetate (0.080 g, 0.000118 mol) was dissolved in dichloromethane (4 mL) at 0° C. and trifluoroacetic acid (1 mL) was added dropwise. The mixture was stirred at ambient temperature under an atmosphere of nitrogen for 1.5 hours, concentrated under reduced pressure and the residue purified by preparative HPLC (Hypersil C18, 8 µm, 25 cm; 10–60% acetonitrile-0.1M ammonium acetate over 25 min, 21 mL/min) to yield trans-3-{4-[(2-aminobenzyl)amino]phenyl}-1-[4-(4-methylpiperazino)cyclohexyl]-1H-pyrazolo[3,4-d]pyrimidin-4-amine diacetate (0.067 g, 0.000106 mol) as a white solid.

$^1$H NMR (DMSO-d$_6$, 400 MHz) δ 8.18 (s, 1H), 7.35 (d, 2H), 7.09 (d, 1H), 6.95 (t, 1H), 6.73 (d, 2H), 6.66 (d, 1H), 6.53 (d, 1H), 6.36 (t, 1H), 4.97 (br, 1H), 4.58 (m, 1H), 4.13 (d, 2H), 2.6–2.2 (br, 9H), 2.13 (s, 3H), 2.05 (m, 6H), 1.91 (s, 6H), 1.46 (m, 2H); RP-HPLC (Delta Pak C18, 5 µm, 300 A, 15 cm; 5%–85% acetonitrile-0.1M ammonium acetate over 20 min, 1 mL/min) R$_t$ 11.87 min. MS: MH$^+$ 512.

Example 474 trans-N1-2-[(4-{4-Amino-1-[4-(4-methylpiperazino)cyclohexyl]-1H-pyrazolo[3,4-d]pyrimidin-3-yl}anilino)methyl]phenylacetamide Diacetate To a solution of trans-3-{4-[(2-aminobenzyl)amino]phenyl}-1-[4-(4-methylpiperazino)cyclohexyl]-1H-pyrazolo[3,4-d]pyrimidin-4-amine diacetate (0.050 g, 0.000079 mol) in dichloromethane (3 mL) at 0° C., N,N-diisopropylethylamine (0.041 g, 0.000316 mol) and acetic anhydride (0.011 g, 0.000103 mol) were successively added and the resulting mixture was stirred at ambient temperature under an atmosphere of nitrogen for 18 hours. The mixture was concentrated under reduced pressure and the residue purified by preparative HPLC (Hypersil C18, 8 µm, 25 cm; 10–60% acetonitrile-0.1M ammonium acetate over 25 min, 21 mL/min) to yield trans-N1-2-[(4-{4-amino-1-[4-(4-methylpiperazino)cyclohexyl]-1H-pyrazolo[3,4-d]pyrimidin-3-yl}anilino)methyl]phenylacetamide diacetate (0.010 g, 0.0000148 mol) as a white solid.

$^1$H NMR (DMSO-d$_6$, 400 MHz) δ 9.48 (s, 1H), 8.18 (s, 1H), 7.35 (m, 4H), 7.20 (m, 1H), 7.13 (m, 1H), 6.66 (d, 2H), 6.53 (t, 1H), 4.58 (m, 1H), 4.29 (d, 2H), 2.6–2.2 (br, 9H), 2.13 (s, 3H), 2.08 (s, 3H), 2.05 (m, 6H), 1.91 (s, 6H), 1.46 (m, 2H); RP-HPLC (Delta Pak C18, 5 µm, 300 A, 15 cm; 5%–85% acetonitrile-0.1M ammonium acetate over 20 min, 1 mL/min) R$_t$ 10.67 min. MS: MH$^+$ 554.

Example 475 trans-3-[3-Chloro-4-(2,3-dihydrobenzo[b]furan-3-ylamino)phenyl]-1-[4-(4-methylpiperazino)cyclohexyl]-1H-pyrazolo[3,4-d]pyrimidin-4-amine Acetate a) tert-Butyl N-(4-Bromo-2-chlorophenyl)carbamate A solution of 4-bromo-2-chloroaniline (5.00 g, 0.0242 mol) in tetrahydrofuran (50 mL) was reacted with a 1.0 M solution of sodium bis(trimethylsilyl)amide in tetrahydrofuran (53.2 mL, 0.0532 mol). The mixture was stirred 15 minutes at ambient temperature. Di-tert-butyl dicarbonate (6.34 g, 0.0290 mol) was added and the solution was stirred for 2 hours. The solvent was removed in vacuo, and the crude material was purified by flash column chromatography on silica using heptane/ethyl acetate (4:1). The solvent was removed in vacuo to give tert-butyl N-(4-bromo-2-chlorophenyl)carbamate as a white solid (4.214 g, 0.0137 mol).

¹H NMR (DMSO-d₆, 400 MHz) δ 8.75 (s, 1H), 7.71 (d, 1H), 7.54 (d, 1H), 7.50 (dd, 5H), 1.46 (s, 9H); TLC (heptane/ethylacetate 4:1) R$_f$ 0.54.

b) tert-Butyl N-[2-Chloro-4-(4,4,5,5-tetramethyl-1,3,2-dioxaborolan-2-yl)phenyl]carbamate A mixture of tert-butyl N-(4-bromo-2-chlorophenyl)carbamate (2.10 g, 0.00685 mol), diboron pinacol ester (2.09 g, 0.00822 mol), [1,1'-bis(diphenylphosphino)ferrocene]dichloropalladium(II) complex with dichloromethane (1:1) (0.17 g, 0.00021 mol) and potassium acetate (2.02 g, 0.02055 mol) in N,N-dimethylformamide (50 ml) was heated at 80° C. under a nitrogen atmosphere for 6 hours. The solvent was removed under reduced pressure. The residue was triturated with heptane (70 mL) and the resulting solids were removed by filtration through a pad of celite. The heptane was removed in vacuo to give tert-butyl N-[2-chloro-4-(4,4,5,5-tetramethyl-1,3,2-dioxaborolan-2-yl)phenyl]carbamate as a grey solid (1.93 g, 0.00546 mol).

¹H NMR (DMSO-d₆, 400 MHz) δ 8.65 (s, 1H), 7.74 (d, 1H), 7.61 (d, 1H), 7.56 (dd, 1H), 1.47 (s, 9H), 1.29 (s, 12H).

c) trans tert-Butyl N-(4-{4-Amino-1-[4-(4-methylpiperazino)cyclohexyl]-1H-pyrazolo[3,4-d]pyrimidin-3-yl}-2-chlorophenyl)carbamate A mixture of trans 3-iodo-1-[4-(4-methylpiperazino)cyclohexyl]-1H-pyrazolo[3,4-d]pyrimidin-4-amine (2.20 g, 0.00498 mol), tert-butyl N-[2-chloro-4-(4,4,5,5-tetramethyl-1,3,2-dioxaborolan-2-yl)phenyl]carbamate (1.93 g, 0.00548 mol), sodium carbonate (1.32 g, 0.01245 mol) in 1,2-dimethoxyethane (50 mL) and water (100 mL) was stirred rapidly and tetrakis(triphenylphosphine)palladium(0) (0.345 g, 0.00030 mol) was added. The reaction mixture was stirred 6 hours at 80° C., after which time additional tetrakis(triphenylphosphine)palladium(0) (0.345 g, 0.00030 mol) was added. The reaction mixture was stirred an additional 16 hours at 80° C. The solvents were removed in vacuo and the residue was partitioned between ethyl acetate (100 mL) and saturated aqueous sodium bicarbonate (200 mL). The phases were separated and the aqueous phase was extracted with ethyl acetate (3×75 mL). The combined organic phases were dried over magnesium sulfate, and the solvent was removed in vacuo. The product was purified by flash column chromatography on silica using dichloromethane/methanol/ammonium hydroxide (90:10:0.5). The solvent was removed in vacuo to give trans tert-butyl N-(4-{4-amino-1-[4-(4-methylpiperazino)cyclohexyl]-1H-pyrazolo[3,4-d]pyrimidin-3-yl}-2-chlorophenyl)carbamate as a white solid (1.993 g, 0.00368 mol):

¹H NMR (DMSO-d₆, 400 MHz) δ 8.76 (s, 2H), 8.23 (s, 1H), 7.80 (d, 1H), 7.68 (d, 1H), 7.57 (dd, 1H), 4.58–4.71 (m, 1H), 2.15 (2, 3H), 1.89–2.61 (m, 15H), 1.49 (s, 9H), 1.40–1.48 (m, 2H); TLC (dichloromethane/methanol= 90:10) R$_f$ 0.13, MS: MH⁺ 541.

d) trans 3-(4-Amino-3-chlorophenyl)-1-[4-(4-methylpiperazino)cyclohexyl]-1H-pyrazolo[3,4-d]pyrimidin-4-amine Trans tert-butyl N-(4-{4-amino-1-[4-(4-methylpiperazino)cyclohexyl]-1H-pyrazolo[3,4-d]pyrimidin-3-yl}-2-chlorophenyl)carbamate (1.993 g, 0.00368 mol) was added to a solution of 20% trifluoroacetic acid in dichloromethane. The mixture was stirred for 2 hours at ambient temperature. The solvent was removed in vacuo and the residue was dissolved in dichloromethane (50 mL) and washed with 1.0 M aqueous sodium hydroxide (2×25 mL). The organic layer was dried over magnesium sulfate and the solvent was removed in vacuo to give trans 3-(4-amino-3-chlorophenyl)-1-[4-(4-methylpiperazino)cyclohexyl]-1H-pyrazolo[3,4-d]pyrimidin-4-amine (1.564 g, 0.00355 mol) as a white solid.

¹H NMR (DMSO-d₆, 400 MHz) δ 8.20 (s, 1H), 7.45 (d, 1H), 7.31 (dd, 1H), 6.92 (d, 1H), 4.57–4.63 (m, 1H), 2.23–2.55 (m, 9H), 2.14 (s, 3H), 1.89–2.08 (m, 6H), 1.38–1.52 (m, 2H); TLC (dichloromethane/methanol= 90:10) R$_f$ 0.08, MS: MH⁺ 441.

e) trans-3-[3-Chloro-4-(2,3-dihydrobenzo[b]furan-3-ylamino)phenyl]-1-[4-(4-methylpiperazino)cyclohexyl]-1H-pyrazolo[3,4-d]pyrimidin-4-amine Acetate Salicylaldehyde (0.033 g, 0.000274 mol) and trans-3-(4-amino-3-chlorophenyl)-1-[4-(4-methylpiperazino)cyclohexyl]-1H-pyrazolo[3,4-d]pyrimidin-4-amine (0.115 g, 0.000261 mol) were combined in absolute ethanol and stirred at ambient temperature for 48 hours. The reaction mixture was concentrated under reduced pressure and the residue dried overnight to yield trans-2-[(4-{4-amino-1-[4-(4-methylpiperazino)cyclohexyl]-1H-pyrazolo[3,4-d]pyrimidin-3-yl}-2-chlorophenyl)imino]methylphenol which was used without further purification. Trimethylsulfoxonium iodide (0.110 g, 0.0005 mol) was dissolved in anhydrous dimethylsulfoxide (2 mL) and 60% dispersion of sodium hydride in paraffine (0.02 g, 0005 mol) was added at once. After 10 min., the solution of trans-2-[(4-{4-amino-1-[4-(4-methylpiperazino)cyclohexyl]-1H-pyrazolo[3,4-d]pyrimidin-3-yl}-2-chlorophenyl)imino]methylphenol in anhydrous dimethylsulfoxide (2 mL) was added and the resulting mixture was stirred at ambient temperature under an atmosphere of nitrogen for 2.5 hours. The solution was poured into ice-cold water (50 mL) and extracted with dichloromethane (2×40 mL). The combined organic extracts were dried with magnesium sulfate and concentrated under reduced pressure. The residue was purified by preparative HPLC (Hypersil C18, 8 μm, 25 cm; 10–60% acetonitrile-0.1M ammonium acetate over 25 min, 21 mL/min) to yield trans-3-[3-chloro-4-(2,3-dihydrobenzo[b]furan-3-ylamino)phenyl]-1-[4-(4-methylpiperazino)cyclohexyl]-1H-pyrazolo[3,4-d]pyrimidin-4-amine acetate (0.044 g, 0.000071 mol) as a white solid.

¹H NMR (DMSO-d₆, 400 MHz) δ 8.21 (s, 1H), 7.55 (s, 1H), 7.45 (d, 1H), 7.38 (d, 1H), 7.25 (t, 1H), 7.11 (d, 1H), 6.89 (m, 2H), 5.70 (d, 1H), 5.54 (m, 1H), 4.83 (t, 1H), 4.61 (m, 1H), 4.41 (m, 1H), 2.6–2.2 (br, 9H), 2.13 (s, 3H), 2.05 (m, 6H), 1.91 (s, 3H), 1.46 (m, 2H); RP-HPLC (Delta Pak C18, 5 μm, 300 A, 15 cm; 5%–85% acetonitrile-0.1M ammonium acetate over 20 min, 1 mL/min) R$_t$ 14.94 min. MS: MH⁺ 559.

Example 476 trans-3-[4-(2,3-Dihydrobenzo[b]furan-3-ylamino)-3-methoxyphenyl]-1-[4-(4-methylpiperazino)cyclohexyl]-1H-pyrazolo[3,4-d]pyrimidin-4-amine Diacetate Salicylaldehyde (0.034 g, 0.000282 mol) and trans-3-(4-amino-3-methoxyphenyl)-1-[4-(4-methylpiperazino)cyclohexyl]-1H-pyrazolo[3,4-d]pyrimidin-4-amine (0.117 g, 0.000268 mol) were combined in absolute ethanol and stirred at ambient temperature for 48 hours. The reaction mixture was concentrated under reduced pressure and the residue dried overnight to yield trans-2-[(4-{4-amino-1-[4-(4-methylpiperazino)cyclohexyl]-1H-pyrazolo[3,4-d]pyrimidin-3-yl}-2-methoxyphenyl)imino]methylphenol which was used without further purification. Trimethylsulfoxonium iodide (0.145 g, 0.00068 mol) was dissolved in anhydrous dimethylsulfoxide (2 mL) and a 60% dispersion of sodium hydride in parafine (0.027 g, 00068 mol) was added at once. After 10 min., the solution of trans-2-[(4-{4-amino-1-[4-(4-methylpiperazino)cyclohexyl]-1H-pyrazolo

[3,4-d]pyrimidin-3-yl}-2-methoxyphenyl) imino] methylphenol in anhydrous dimethylsulfoxide (2 mL) was added and the resulting mixture was stirred at ambient temperature under an atmosphere of nitrogen for 2.5 hours. The solution was poured into ice-cold water (50 mL) and extracted with dichloromethane (2×40 mL). The combined organic extracts were dried with magnesium sulfate and concentrated under reduced pressure. The residue was purified by preparative HPLC (Hypersil C18, 8 μm, 25 cm; 10–60% acetonitrile-0.1M ammonium acetate over 25 min, 21 mL/min) to yield trans-3-[4-(2,3-dihydrobenzo[b]furan-3-ylamino)-3-methoxyphenyl]-1-[4-(4-methylpiperazino) cyclohexyl]-1H-pyrazolo[3,4-d]pyrimidin-4-amine diacetate (0.096 g, 0.000142 mol) as a white solid.

$^1$H NMR (DMSO-d$_6$, 400 MHz) δ 8.21 (s, 1H), 7.38 (d, 1H), 7.25 (t, 1H), 7.11 (m, 2H), 6.89 (m, 3H), 5.42 (m, 1H), 5.18 (d, 1H), 4.77 (t, 1H), 4.61 (m, 1H), 4.37 (m, 1H), 3.83 (s, 3H), 2.6–2.2 (br, 9H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) R$_t$ 14.16 min. MS: MH$^+$ 555.

Example 477 trans-3-[4-(3-Methyl-5-phenyl-1H-1-pyrazolyl) phenyl]-1-[4-(4-methylpiperazino)cyclohexyl]-1H-pyrazolo[3,4-d]pyrimidin-4-amine Diacetate a) 1-(4-Bromophenyl)-3-methyl-5-phenyl-4,5-dihydro-1H-pyrazole To a solution of 1-benzoylacetone (3.63 g, 0.0224 mol) and N,N-diisopropylethylamine (2.88 g, 0.0224 mol) in anhydrous methanol (160 mL), 4-bromophenylhydrazine hydrochloride was added and the resulting mixture was stirred at ambient temperature for 20 hours. The solvent was removed under reduced pressure and the resulting mixture was partitioned between a 5% solution of citric acid solution in water (200 mL) and ethyl acetate (150 mL). The organic phase was successively washed with water (2×200 mL) and brine (150 mL), dried with magnesium sulfate and concentrated. The resulting residue was purified by flash chromatography on silica using ethyl acetate/n-heptane (5:95) as mobile phase to yield 1-(4-bromophenyl)-3-methyl-5-phenyl-4,5-dihydro-1H-pyrazole (4.05 g, 0.0129 mol) as an off-white solid.

$^1$H NMR (DMSO-d$_6$, 400 MHz) δ 7.58 (d, 2H), 7.36 (m, 3H), 7.21 (d, 2H), 7.17 (d, 2H), 6.46 (s, 1H), 2.72 (s, 3H). TLC (ethyl acetate/heptane 1:5) R$_f$ 0.41.

b) 3-Methyl-5-phenyl-1-[4-(4,4,5,5-tetramethyl-1,3,2-dioxaborolan-2-yl)phenyl]-4,5-dihydro-1H-pyrazole A mixture of 1-(4-bromophenyl)-3-methyl-5-phenyl-4,5-dihydro-1H-pyrazole (2.17 g, 0.00693 mol), diboron pinacol ester (2.11 g, 0.00832 mol), [1.1'-bis(diphenylphosphino) ferrocene]-dichloropalladium (II) complex with dichloromethane (1:1) (0.170 g, 0.000207 mol) and potassium acetate (2.03 g, 0.0207 mol) in N,N-dimethylformamide (50 mL) was heated at 80° C. under an atmosphere of nitrogen for 16 hours. The mixture was allowed to cool to ambient temperature and the solvent was removed under reduced pressure. Dichloromethane (70 mL) was added to the residue and the resulting solid was removed by filtration through a pad of Celite. The filtrate was concentrated to leave a yellow oil which was purified by flash chromatography on silica using ethyl acetate/n-heptane (7:93) as mobile phase. The resulting fractions were concentrated, the residue was triturated in n-heptane and the precipitate collected by filtration to yield 3-methyl-5-phenyl-1-[4-(4,4,5,5-tetramethyl-1,3,2-dioxaborolan-2-yl)phenyl]-4,5-dihydro-1H-pyrazole (1.00 g, 0.00278 mol) as a white solid.

$^1$H NMR (DMSO-d$_6$, 400 MHz) δ 7.65 (d, 2H), 7.36 (m, 3H), 7.21 (m, 4H), 6.46 (s, 1H), 2.79 (s, 3H), 1.29 (s, 12H). TLC (ethyl acetate/heptane 1:5) R$_f$ 0.27.

c) trans-3-[4-(3-Methyl-5-phenyl-1H-1-pyrazolyl)phenyl]-1-[4-(4-methylpiperazino)cyclohexyl]-1H-pyrazolo[3,4-d]pyrimidin-4-amine Diacetate A mixture of 3-methyl-5-phenyl-1-[4-(4,4,5,5-tetramethyl-1,3,2-dioxaborolan-2-yl)phenyl]-4,5-dihydro-1H-pyrazole (0.102 g, 0.000283 mol), trans-3-iodo-1-[4-(4-methylpiperazino)-cyclohexyl]-1H-pyrazolo[3,4-d]pyrimidin-4-amine (0.104 g, 0.000236 mol), tetrakis-(triphenylphosphine)palladium (0.016 g, 0.000014 mol) and sodium carbonate monohydrate (0.073 g, 0.00055 mol) was heated in a mixture of ethylene glycol dimethyl ether (5 mL) and water (3 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield trans-3-[4-(3-methyl-5-phenyl-1H-1-pyrazolyl)phenyl]-1-[4-(4-methylpiperazino)cyclohexyl]-1H-pyrazolo[3,4-d]pyrimidin-4-amine diacetate (0.094 g, 0.000141 mol) as a white solid. $^1$H NMR (DMSO-d$_6$, 400 MHz) δ 8.23 (s, 1H), 7.64 (d, 2H), 7.37 (m, 7H), 6.49 (s, 1H), 4.63 (m, 1H), 2.6–2.2 (br, 9H), 2.30 (s, 3H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min) R$_t$ 14.10 min. MS: MH$^+$ 548.

Example 478 trans-3-[4-(5-Ethoxy-1H-1-pyrazolyl)phenyl]-1-[4-(4-methylpiperazino)cyclohexyl]-1H-pyrazolo[3,4-d]pyrimidin-4-amine Acetate a) 1-(4-Bromophenyl)-1H-5-pyrazolyl Ethyl Ether Ethyl acetoacetate (3.49 g, 0.02684 mol) and 4-bromophenylhydrazine hydrochloride (6.00 g, 0.02684 mol) were refluxed in acetic acid (50 mL) for 4 hours. The precipitate was removed by filtration, the filtrate concentrated under reduced pressure and the residue purified by flash chromatography on silica using ethyl acetate/n-heptane (7:93) as mobile phase to yield 1-(4-bromophenyl)-1H-5-pyrazolyl ethyl ether (2.63 g, 0.00936 mol) as an off-white solid.

$^1$H NMR (CDCl$_3$-d$_6$, 400 MHz) δ 7.61 (d, 2H), 7.49 (d, 2H), 7.26 (s, 1H), 5.47 (s, 1H), 4.14 (q, 2H), 2.26 (s, 3H), 1.44 (t, 3H). TLC (ethyl acetate/heptane 1:9) R$_f$ 0.24.

b) 5-Ethoxy-3-methyl-1-[4-(4,4,5,5-tetramethyl-1,3-dioxolan-2-yl)phenyl]-1H-pyrazole A mixture of 1-(4-bromophenyl)-1H-5-pyrazolyl ethyl ether (2.22 g, 0.00791 mol), diboron pinacol ester (2.41 g, 0.00949 mol), [1.1'-bis(diphenylphosphino)ferrocene]-dichloropalladium (II) complex with dichloromethane (1:1) (0.194 g, 0.000237 mol) and potassium acetate (2.32 g, 0.0237 mol) in N,N-dimethylformamide (60 mL) was heated at 80° C. under an atmosphere of nitrogen for 16 hours. The mixture was allowed to cool to ambient temperature and the solvent removed under reduced pressure. Dichloromethane (70 mL) was added to the residue and the resulting solid was removed by filtration through a pad of Celite. The filtrate was concentrated to leave a yellow oil which was purified by flash chromatography on silica using ethyl acetate/n-heptane (7:93) as mobile phase. The resulting fractions were concentrated, the residue was triturated in n-heptane and the precipitate collected by filtration to yield 5-ethoxy-3-methyl-1-[4-(4,4,5,5-tetramethyl-1,3-dioxolan-2-yl) phenyl]-1H-pyrazole (0.604 g, 0.00184 mol) as a white solid.

¹H NMR (DMSO-d₆, 400 MHz) δ 7.72 (s, 4H), 5.72 (s, 1H), 4.18 (q, 2H), 2.16 (s, 3H), 1.37 (t, 3H), 1.29 (s, 12H). TLC (ethyl acetate/heptane 1:9) R_f 0.18.

c) trans-3-[4-(5-Ethoxy-1H-1-pyrazolyl)phenyl]-1-[4-(4-methylpiperazino)cyclohexyl]-1H-pyrazolo[3,4-d]pyrimidin-4-amine Acetate A mixture of 5-ethoxy-3-methyl-1-[4-(4,4,5,5-tetramethyl-1,3-dioxolan-2-yl)phenyl]-1H-pyrazole (0.062 g, 0.00019 mol), trans-3-iodo-1-[4-(4-methylpiperazino)cyclohexyl]-1H-pyrazolo[3,4-d]pyrimidin-4-amine (0.070 g, 0.000159 mol), tetrakis-(triphenylphosphine)palladium (0.011 g, 0.0000095 mol) and sodium carbonate monohydrate (0.049 g, 0.000398 mol) was heated in a mixture of ethylene glycol dimethyl ether (5 mL) and water (3 mL) at 80° C. for 16 hours under an atmosphere of nitrogen. The mixture was allowed to cool to ambient temperature and solvents were removed under the reduced pressure. The residue was purified by preparative HPLC (Hypersil C18, 8 μm, 25 cm; 10–60% acetonitrile-0.1M ammonium acetate over 25 min, 21 mL/min) to yield trans-3-[4-(5-ethoxy-1H-1-pyrazolyl)phenyl]-1-[4-(4-methylpiperazino)cyclohexyl]-1H-pyrazolo[3,4-d]pyrimidin-4-amine acetate (0.037 g, 0.000064 mol) as a white solid.

¹H NMR (DMSO-d₆, 400 MHz) δ 8.23 (s, 1H), 7.85 (d, 2H), 7.71 (d, 2H), 5.75 (s, 1H), 4.65 (m, 1H), 4.21 (q, 2H), 2.6–2.2 (br, 9H), 2.18 (s, 3H), 2.13 (s, 3H), 2.05 (m, 6H), 1.91 (s, 3H), 1.46 (m, 2H), 1.40 (t, 3H); RP-HPLC (Delta Pak C18, 5 μm, 300 A, 15 cm; 5%–85% acetonitrile-0.1M ammonium acetate over 20 min, 1 mL/min) R_t 12.59 min. MS: MH⁺ 516.

Example 479 trans-1-(4-{4-Amino-1-[4-(4-methylpiperazino)cyclohexyl]-1H-pyrazolo[3,4-d]pyrimidin-3-yl}phenyl)-3-methyl-4,5-dihydro-1H-5-pyrazolone Diacetate A solution of trans-3-[4-(5-ethoxy-1H-1-pyrazolyl)phenyl]-1-[4-(4-methylpiperazino)cyclohexyl]-1H-pyrazolo[3,4-d]pyrimidin-4-amine acetate (0.100 g, 0.000194 mol) in 30% hydrobromic acid in acetic acid (2.5 mL) was heated at reflux for 1.5 hours. The reaction mixture was concentrated under reduced pressure and the residue neutralized with concentrated solution of ammonium hydroxide in water. The resulting suspension was concentrated under reduced pressure and the residue was purified by preparative HPLC (Hypersil C18, 8 μm, 25 cm; 5–45% acetonitrile-0.1M ammonium acetate over 20 min, 21 mL/min) to yield trans-1-(4-{4-amino-1-[4-(4-methylpiperazino)cyclohexyl]-1H-pyrazolo[3,4-d]pyrimidin-3-yl}phenyl)-3-methyl-4,5-dihydro-1H-5-pyrazolone diacetate (0.066 g, 0.00011 mol) as a white solid.

¹H NMR (DMSO-d₆, 400 MHz) δ 8.23 (s, 1H), 8.02 (d, 2H), 7.65 (d, 2H), 4.64 (m, 1H), 2.6–2.2 (br, 9H), 2.53 (s, 2H), 2.21 (s, 3H), 2.13 (s, 3H), 2.05 (m, 6H), 1.91 (s, 6H), 1.46 (m, 2H); RP-HPLC (Delta Pak C18, 5 μm, 300 A, 15 cm; 5%–85% acetonitrile-0.1M ammonium acetate over 20 min, 1 mL/min). MS: MH⁺ 488.

Example 480

2-(2-Amino-1H-1-imidazolyl)-1-{3-[4-amino-3-(4-phenoxyphenyl)-1H-pyrazolo[3,4-d]pyrimidin-1-yl]-1-azetanyl}-1-ethanone Acetate To a mixture of 1-(3-azetanyl)-3-(4-phenoxyphenyl)-1H-pyrazolo[3,4-d]pyrimidin-4-amine (0.05 g, 0.00014 mol) and potassium carbonate (0.039 g, 0.00028 mol) in anhydrous N,N-dimethylformamide (3 mL) was added chloroacetylchloride (0.0031 g, 0.00028 mol) at room temperature. The mixture was stirred for 10 min. before 2-aminoimidazole sulfate (0.18 g, 0.0014 mol) and potassium carbonate (0.19 g, 0.0014 mol) was added. The mixture was stirred at room temperature for 2 days then warmed to 60° C. for 6 hours. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield 2-(2-amino-1H-1-imidazolyl)-1-{3-[4-amino-3-(4-phenoxyphenyl)-1H-pyrazolo[3,4-d]pyrimidin-1-yl]-1-azetanyl}-1-ethanone acetate (0.006 g, 0.00001 mol).

¹H NMR (DMSO-d₆, 400 MHz) δ 8.27 (s, 1H), 7.71 (d, 2H), 7.44 (m, 2H), 7.19 (m, 5H), 6.55 (s, 1H), 6.36 (s, 1H), 5.76 (m, 1H), 5.30 (s, 2H), 4.59 (m, 2H), 4.40 (m, 2H), 1.90 (s, 3H). RP-HPLC (Delta Pak C18, 5 μm, 300 A, 15 cm; 5%–85% acetonitrile-0.1M ammonium acetate over 10 min, 1 mL/min) R_t 9.1 min. MS: MH⁺ 482.

Example 481

1-{3-[4-Amino-3-(4-phenoxyphenyl)-1H-pyrazolo[3,4-d]pyrimidin-1-yl]-1-azetanyl}-3-[(2-hydroxyethyl)amino]-1-propanone a) tert-Butyl N-(3-{3-[4-Amino-3-(4-phenoxyphenyl)-1H-pyrazolo[3,4-d]pyrimidin-1-yl]-1-azetanyl}-3-oxopropyl)-N-(2-hydroxyethyl)carbamate A mixture of 1-(3-azetanyl)-3-(4-phenoxyphenyl)-1H-pyrazolo[3,4-d]pyrimidin-4-amine (0.05 g, 0.00014 mol), 3-[(tert-butoxycarbonyl)(2-hydroxyethyl)amino]propanoic acid (0.038 g, 0.000175 mol), 1-(3-dimethylaminopropyl)-3-ethylcarbodiimide hydrochloride (0.034 g, 0.000175 mol), N,N-diisopropylethylamine (0.034 g, 0.00026 mol) and 1-hydroxy-7-azabenzotriazole (0.019 g, 0.00014 mol) in anhydrous dichldromethane (5 mL) was stirred for 18 hours at room temperature. The solvent was removed under reduced pressure. The residue was purified by RP-HPLC (Hypersilprep HS C18, 8 μm, 250×21.1 mm; 5%–100% over 35 min with 0.1 M ammonium acetate, 21 mL/min) to yield tert-butyl N-(3-{3-[4-amino-3-(4-phenoxyphenyl)-1H-pyrazolo[3,4-d]pyrimidin-1-yl]-1-azetanyl}-3-oxopropyl)-N-(2-hydroxyethyl)carbamate (0.040 g, 0.000070 mol). RP-HPLC (Delta Pak C18, 5 μm, 300 A, 15 cm; 5%–85% acetonitrile-0.1M ammonium acetate over 10 min, 1 mL/min) R_t 10.3 min. MS: MH⁺ 574.

b) 1-{3-[4-Amino-3-(4-phenoxyphenyl)-1H-pyrazolo[3,4-d]pyrimidin-1-yl]-1-azetanyl}-3-[(2-hydroxyethyl)amino]-1-propanone 2 mL of an 6 N aqueous solution of hydrochloride were added to the mixture of tert-butyl N-(3-{3-[4-amino-3-(4-phenoxyphenyl)-1H-pyrazolo[3,4-d]pyrimidin-1-yl]-1-azetanyl}-3-oxopropyl)-N-(2-hydroxyethyl)carbamate (0.040 g, 0.000070 mol) in acetone (5 mL). The mixture was stirred at 45° C. for 1.5 hours. The solvent was removed under removed pressure. Water (10 mL) was added to the residue, the mixture was lyophilized. The residue was purified by RP-HPLC (Hypersilprep HS C18, 8 μm, 250×21.1 mm; 5%–100% over 35 min with 0.1 M ammonium acetate, 21 mL/min) to yield 1-{3-[4-amino-3-(4-phenoxyphenyl)-1H-pyrazolo[3,4-d]pyrimidin-1-yl]-1-azetanyl}-3-[(2-hydroxyethyl)amino]-1-propanone (0.003 g, 0.00001 mol).

¹H NMR (DMSO-d₆, 400 MHz) δ 8.27 (s, 1H), 7.69 (d, 2H), 7.42 (m, 2H), 7.19 (m, 5H), 5.70 (m, 1H), 4.67 (m, 1H), 4.57 (m, 1H), 4.40 (m, 1H), 4.31 (m, 1H), 3.40 (m, 2H), 2.74 (m, 2H), 2.51 (m, 2H), 2.29 (m, 2H). RP-HPLC (Delta Pak C18, 5 µm, 300 A, 15 cm; 5%–85% acetonitrile-0.1M ammonium acetate over 10 min, 1 mL/min) $R_t$ 8.7 min. MS: MH⁺ 474.

Example 482

2-(2-Amino-1H-1-imidazolyl)-1-{4-[4-amino-3-(4-phenoxyphenyl)-1H-pyrazolo[3,4-d]pyrimidin-1-yl]piperidino}-1-ethanone Acetate To a mixture of 3-(4-phenoxyphenyl)-1-(4-piperidyl)-1H-pyrazolo[3,4-d]pyrimidin-4-amine (0.05 g, 0.00013 mol) and potassium carbonate (0.036 g, 0.00026 mol) in anhydrous N,N-dimethylformamide (3 mL) was added chloroacetylchloride (0.028 g, 0.00026 mol) at room temperature. The mixture was stirred for 10 min. before 2-aminoimidazole sulfate (0.18 g, 0.0014 mol) and potassium carbonate (0.19 g, 0.0014 mol) were added. The mixture was stirred at room temperature for 18 hours then warmed to 60° C. for 6 hours. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield 2-(2-amino-1H-1-imidazolyl)-1-{4-[4-amino-3-(4-phenoxyphenyl)-1H-pyrazolo[3,4-d]pyrimidin-1-yl]piperidino}-1-ethanone acetate (0.015 g, 0.00003 mol).

¹H NMR (DMSO-d₆, 400 MHz) δ 8.26 (s, 1H), 7.67 (d, 2H), 7.44 (m, 2H), 7.17 (m, 5H), 6.52 (s, 1H), 6.38 (s, 1H), 5.49 (br, 2H), 4.99 (m, 1H), 4.76 (m, 2H), 4.59 (m, 1H), 3.99 (m, 1H), 3.30 (m, 1H), 2.80 (m, 1H), 2.20 (m, 1H), 1.99 (m, 3H), 1.90 (s, 3H). RP-HPLC (Delta Pak C18, 5 µm, 300 A, 15 cm; 5%–85% acetonitrile-0.1M ammonium acetate over 10 min, 1 mL/min) $R_t$ 9.4 min. MS: MH⁺ 510.

Example 483

1-{4-[4-Amino-3-(4-phenoxyphenyl)-1H-pyrazolo[3,4-d]pyrimidin-1-yl]piperidino}-2-[(2-hydroxyethyl)amino]-1-ethanone To a mixture of 3-(4-phenoxyphenyl)-1-(4-piperidyl)-1H-pyrazolo[3,4-d]pyrimidin-4-amine (0.05 g, 0.00013 mol) and potassium carbonate (0.036 g, 0.00026 mol) in anhydrous N,N-dimethylformamide (3 mL) was added chloroacetylchloride (0.028 g, 0.00026 mol) at room temperature. The mixture was stirred for 10 min. before ethanolamine (0.078 mL, 0.0013 mol) was added. The mixture was stirred at room temperature for 18 hours. The solvent was removed under reduced pressure. The residue was dissolved in dichloromethane (3 mL) and washed with water (2 mL). The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield 1-{4-[4-amino-3-(4-phenoxyphenyl)-1H-pyrazolo[3,4-d]pyrimidin-1-yl]piperidino}-2-[(2-hydroxyethyl)amino]-1-ethanone (0.022 g, 0.00005 mol).

¹H NMR (DMSO-d₆, 400 MHz) δ 8.26 (s, 1H), 7.67 (d, 2H), 7.44 (m, 2H), 7.17 (m, 5H), 5.03 (br, 1H), 5.00 (br, 1H), 4.52 (m, 1H), 4.05 (m, 1H), 3.87 (m, 2H), 3.64 (m, 2H), 2.96 (m, 2H), 2.92 (m, 2H), 2.17 (m, 1H), 1.90 (m, 3H). RP-HPLC (Delta Pak C18, 5 µm, 300 A, 15 cm; 5%–85% acetonitrile-0.1M ammonium acetate over 10 min, 1 mL/min) $R_t$ 9.0 min. MS: MH⁺ 488.

Example 484

Synthesis of 1-{4-[4-Amino-3-(4-phenoxyphenyl)-1H-pyrazolo[3,4-d]pyrimidin-1-yl]piperidino}-3-[(2-hydroxyethyl)amino]-1-propanone tert-Butyl N-(3-{4-[4-Amino-3-(4-phenoxyphenyl)-1H-pyrazolo[3,4-d]pyrimidin-1-yl]piperidino}-3-oxopropyl)-N-(2-hydroxyethyl)carbamate A mixture of 3-(4-phenoxyphenyl)-1-(4-piperidyl)-1H-pyrazolo[3,4-d]pyrimidin-4-amine (0.05 g, 0.00013 mol), 3-[(tert-butoxycarbonyl)(2-hydroxyethyl)amino]propanoic acid (0.038 g, 0.000163 mol), 1-(3-dimethylaminopropyl)-3-ethylcarbodiimide hydrochloride (0.031 g, 0.000163 mol), N,N-diisopropylethylamine (0.031 g, 0.00024 mol) and 1-hydroxy-7-azabenzotriazole (0.018 g, 0.00013 mol) in anhydrous dichloromethane (5 mL) was stirred for 18 hours at room temperature. The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield tert-butyl N-(3-{4-[4-amino-3-(4-phenoxyphenyl)-1H-pyrazolo[3,4-d]pyrimidin-1-yl]piperidino}-3-oxopropyl)-N-(2-hydroxyethyl)carbamate (0.050 g, 0.000083 mol). RP-HPLC (Delta Pak C18, 5 µm, 300 A, 15 cm; 5%–85% acetonitrile-0.1M ammonium acetate over 10 min, 1 mL/min) $R_t$ 10.4 min. MS: MH⁺ 602.

b) 1-{4-[4-Amino-3-(4-phenoxyphenyl)-1H-pyrazolo[3,4-d]pyrimidin-1-yl]piperidino}-3-[(2-hydroxyethyl)amino]-1-propanone 2 mL of an 6 N aqueous solution of hydrochloride were added to the mixture of tert-butyl N-(3-{4-[4-amino-3-(4-phenoxyphenyl)-1H-pyrazolo[3,4-d]pyrimidin-1-yl]piperidino}-3-oxopropyl)-N-(2-hydroxyethyl)carbamate (0.050 g, 0.000083 mol) in acetone (5 mL). The mixture was stirred at 45° C. for 1.5 hours. The solvent was removed under reduced pressure. Water (10 mL) was added to the residue, the mixture was lyophilized. The residue was purified by RP-HPLC (Hypersilprep HS C18, 8 µm, 250×21.1 mm; 5%–100% over 35 min with 0.1 M ammonium acetate, 21 mL/min) to yield 1-{4-[4-amino-3-(4-phenoxyphenyl)-1H-pyrazolo[3,4-d]pyrimidin-1-yl]piperidino}-3-[(2-hydroxyethyl)amino]-1-propanone (0.014 g, 0.00003 mol).

¹H NMR (DMSO-d₆, 400 MHz) δ 8.25 (s, 1H), 7.67 (d, 2H), 7.42 (m, 2H), 7.19 (m, 5H), 4.98 (m, 1H), 4.52 (m, 2H), 4.04 (m, 1H), 3.31 (m, 2H), 2.81 (m, 2H), 2.78 (m, 1H), 2.74 (m, 2H), 2.58 (m, 2H), 1.99 (m, 1H), 1.90 (m, 3H). RP-HPLC (Delta Pak C18, 5 µm, 300 A, 15 cm; 5%–85% acetonitrile-0.1M ammonium acetate over 10 min, 1 mL/min) $R_t$ 9.1 min. MS: MH⁺ 502.

Example 485

Synthesis of 2-{4-[4-Amino-3-(4-phenoxyphenyl)-1H-pyrazolo[3,4-d]pyrimidin-1-yl]piperidino}acetic Acid a) tert-Butyl 2-{4-[4-Amino-3-(4-phenoxyphenyl)-1H-pyrazolo[3,4-d]pyrimidin-1-yl]piperidino}acetate To a mixture of 3-(4-phenoxyphenyl)-1-(4-piperidyl)-1H-pyrazolo[3,4-d]pyrimidin-4-amine (0.10 g, 0.00026 mol, 1 eq.) and potassium carbonate (0.072 g, 0.000526 mol, 2 eq.) in anhydrous N,N-dimethylformamide (8 mL) was added tert-butyl 2-bromoacetate (0.0768 g, 0.00039 mol, 1.5 eq.) at room temperature. The mixture was stirred at room temperature for 18 hours. The solvent was removed under reduced pressure. The residue was dissolved in dichloromethane (5 mL) and washed with water (3 mL). The solvent was removed under reduced pressure. The residue was purified by flash chromatography on silica gel using methanol/dichloromethane (5:95) as mobile phase to yield tert-butyl 2-{4-[4-amino-3-(4-phenoxyphenyl)-1H-pyrazolo[3,4-d]pyrimidin-1-yl]piperidino}acetate (0.10 g, 0.0002 mol). RP-HPLC (Delta Pak C18, 5 µm, 300 A, 15 cm; 5%–85% acetonitrile-0.1M ammonium acetate over 10 min, 1 mL/min) $R_t$ 11.8 min. MS: $MH^+$ 501.

2-{4-[4-Amino-3-(4-phenoxyphenyl)-1H-pyrazolo[3,4-d]pyrimidin-1-yl]piperidino}acetic Acid 2 mL of an 6 N aqueous solution of hydrochloride were added to the mixture of tert-butyl 2-{4-[4-amino-3-(4-phenoxyphenyl)-1H-pyrazolo[3,4-d]pyrimidin-1-yl]piperidino}acetate (0.10 g, 0.0002 mol) in acetone (5 mL). The mixture was stirred at 45° C. for 2 hours. The solvent was removed under reduced pressure. Water (10 mL) was added into the residue, and the mixture was lyophilized to yield 2-{4-[4-amino-3-(4-phenoxyphenyl)-1H-pyrazolo[3,4-d]pyrimidin-1-yl]piperidino}acetic acid (0.010 g, 0.0002 mol).

$^1$H NMR (DMSO-$d_6$, 400 MHz) δ 8.50 (s, 1H), 7.69 (d, 2H), 7.43 (m, 2H), 7.19 (m, 5H), 5.07 (m, 1H), 4.02 (s, 2H), 3.50 (br, 2H), 3.42 (br, 2H), 2.53 (br, 2H), 2.25 (br, 2H). RP-HPLC (Delta Pak C18, 5 µm, 300 A, 15 cm; 5%–85% acetonitrile-0.1M ammonium acetate over 10 min, 1 mL/min) $R_t$ 8.7 min. MS: $MH^+$ 445.

Example 486

N1-(1H-2-Imidazolyl)-2-{4-[4-amino-3-(4-phenoxyphenyl)-1H-pyrazolo[3,4-d]pyrimidin-1-yl]piperidino}acetamide A mixture of 2-{4-[4-amino-3-(4-phenoxyphenyl)-1H-pyrazolo[3,4-d]pyrimidin-1-yl]piperidino}acetic acid (0.06 g, 0.00013 mol), 2-aminoimidazole sulfate (0.022 g, 0.000163 mol), 1-(3-dimethylaminopropyl)-3-ethylcarbodiimide hydrochloride (0.031 g, 0.000163 mol), N,N-diisopropylethylamine (0.047 g, 0.00036 mol) and 1-hydroxy-7-azabenzotriazole (0.018 g, 0.00013 mol) in anhydrous dichloromethane (8 mL) was stirred for 18 hours at room temperature. Additional 2-aminoimidazole sulfate (0.022 g, 0.000163 mol), 1-(3-dimethylaminopropyl)-3-ethylcarbodiimide hydrochloride (0.031 g, 0.000163 mol), N,N-diisopropylethylamine (0.047 g, 0.00036 mol) and 1-hydroxy-7-azabenzotriazole (0.018 g, 0.00013 mol), were added and the mixture was stirred for 18 hour at room temperature. The mixture was warmed to 50° C. for 6 hours, then stirred at room temperature for 2 days. The solvent was removed under reduced pressure. The residue was purified by RP-HPLC (Hypersilprep HS C18, 8 µm, 250×21.1 mm; 5%–100% over 35 min with 0.1 M ammonium acetate, 21 mL/min) to yield N1-(1H-2-imidazolyl)-2-{4-[4-amino-3-(4-phenoxyphenyl)-1H-pyrazolo[3,4-d]pyrimidin-1-yl]piperidino}acetamide (0.005 g, 0.00001 mol).

$^1$H NMR (DMSO-$d_6$, 400 MHz) δ 8.24 (s, 1H), 7.68 (d, 2H), 7.43 (m, 2H), 7.19 (m, 5H), 6.80 (br, 1H), 6.70 (br, 1H), 4.80 (b, 1H), 3.06 (s, 2H), 3.05 (m, 2H), 2.43 (m, 2H), 2.33 (m, 2H), 1.92 (m, 2H). RP-HPLC (Delta Pak C18, 5 µm, 300 A, 15 cm; 5%–85% acetonitrile-0.1M ammonium acetate over 10 min, 1 mL/min) $R_t$ 9.2 min. MS: $MH^+$ 510.

Example 487 trans N1-{4-[4-Amino-1-(4-piperidyl)-1H-pyrazolo[3,4-d]pyrimidin-3-yl]-2-methoxyphenyl}-2-phenyl-1-cyclopropanecarboxamide Maleate a) Benzyl 4-(4-Amino-3-iodo-1H-pyrazolo[3,4-d]pyrimidin-1-yl)-1-piperidinecarboxylate To a mixture of 3-iodo-1-(4-piperidyl)-1H-pyrazolo[3,4-d]pyrimidin-4-amine dihydrochloride (13.86 g, 0.0333 mol) and sodium bicarbonate (8.4 g, 0.0999 mol) in water (140 mL) was added benzylchloroformate (6.48 g, 0.0383 mol) in dioxane (120 mL) at room temperature. The mixture was stirred at room temperature under an atmosphere of nitrogen for 18 hours. The yellow solid was filtered and washed with ethyl ether to yield benzyl 4-(4-amino-3-iodo-1H-pyrazolo[3,4-d]pyrimidin-1-yl)-1-piperidinecarboxylate (12 g, 0.025 mol). RP-HPLC (Delta Pak C18, 5 µm, 300 A, 15 cm; 5%–85% acetonitrile-0.1M ammonium acetate over 10 min, 1 mL/min) $R_t$ 10.5 min. MS: $MH^+$ 479.

b) Benzyl 4-(4-Amino-3-{4-[(tert-butoxycarbonyl)amino]-3-methoxyphenyl}-1H-pyrazolo[3,4-d]pyrimidin-1-yl)-1-piperidinecarboxylate A mixture of benzyl 4-(4-amino-3-iodo-1H-pyrazolo[3,4-d]pyrimidin-1-yl)-1-piperidinecarboxylate (7.0 g, 0.0146 mol), tert-butyl N-[2-methoxy-4-(4,4,5,5-tetramethyl-1,3,2-dioxaborolan-2-yl)phenyl]carbamate (6.15 g, 0.0176 mol), tetrakis(triphenylphosphine)palladium (1.0 g, 0.000876 mol) and sodium carbonate (3.9 g, 0.0365 mol) in ethylene glycol dimethyl ether (170 mL) and water (70 mL) was heated at 75° C. for 16 hours under an atmosphere of nitrogen. After addition of tert-butyl N-[2-methoxy-4-(4,4,5,5-tetramethyl-1,3,2-dioxaborolan-2-yl)phenyl]carbamate (6.15 g, 0.0176 mol, 1.2 eq.) and tetrakis(triphenylphosphine)palladium (1.0 g, 0.000876 mol) the mixture was stirred at 85° C. for additional 16 hours. The mixture was allowed to cool to ambient temperature and ethylene glycol dimethyl ether was removed under reduced pressure. The aqueous layer was extracted with ethyl acetate (3×150 mL). The combined organic extracts were washed with water, saturated aqueous sodium bicarbonate solution, and brine, and dried over magnesium sulfate. The solvents were evaporated under the reduced pressure to leave a brownish solid which was purified by flash column chromatography on silica using 20%–40% ethyl acetate/dichloromethane followed by 2%–5% methanol/dichloromethane as a mobile phase to give benzyl 4-(4-amino-3-{4-[(tert-butoxycarbonyl)amino]-3-methoxyphenyl}-1H-pyrazolo[3,4-d]pyrimidin-1-yl)-1-piperidinecarboxylate (8.0 g, 0.014 mol). RP-HPLC (Delta Pak C18, 5 µm, 300 A, 15 cm; 5%–85% acetonitrile-0.1M ammonium acetate over 10 min, 1 mL/min) $R_t$ 12.6 min. MS: $MH^+$ 574.

c) Benzyl 4-[4-Amino-3-(4-amino-3-methoxyphenyl)-1H-pyrazolo[3,4-d]pyrimidin-1-yl]-1-piperidinecarboxylate To a mixture of benzyl 4-(4-amino-3-{4-[(tert-butoxycarbonyl)amino]-3-methoxyphenyl}-1H-pyrazolo[3,4-d]pyrimidin-1-yl)-1-piperidinecarboxylate (7.68 g, 0.0134 mol) in dichloromethane (10 mL) was added a 25% solution of trifluoroacetic acid in dichloromethane at 0° C. The mixture was stirred under an atmosphere of nitrogen at room temperature for 18 hours. The solvents were removed under reduced pressure. The residue was cooled to 0° C. and basified with an aqueous 5 N solution of sodium hydroxide. The aqueous layer was extracted with dichloromethane (3×150 mL). The combined organic layer was washed with water and brine, and dried over magnesium sulfate. The solvents were removed under reduced pressure to give benzyl 4-[4-amino-3-(4-amino-3-methoxyphenyl)-1H-pyrazolo[3,4-d]pyrimidin-1-yl]-1-piperidinecarboxylate (6.02 g, 0.0127 mol). RP-HPLC (Delta Pak C18, 5 µm, 300 A, 15 cm; 5%–85% acetonitrile-0.1M ammonium acetate over 10 min, 1 mL/min) $R_t$ 10.3 min. MS: $MH^+$ 474.

d) trans Benzyl 4-[4-Amino-3-(3-methoxy-4-{[(2-phenylcyclopropyl)carbonyl]amino}phenyl)-1H-pyrazolo[3,4-d]pyrimidin-1-yl]-1-piperidinecarboxylate To a mixture of benzyl 4-[4-amino-3-(4-amino-3-methoxyphenyl)-1H-pyrazolo[3,4-d]pyrimidin-1-yl]-1- piperidinecarboxylate (3.0 g, 0.0063 mol) in pyridine (100 mL) was added racemic trans-2-phenyl-cyclopropane carbonyl chloride (1.163 g, 0.007 mol) at −5° C. The mixture was stirred at −5° C. for 10 minutes then warmed up to room temperature and stirred for 1.5 hours. The mixture was quenched with an aqueous 1N solution of sodium hydroxide. Organic solvents were removed under reduced pressure. The residue was partitioned between water (200 mL) and ethyl acetate (200 mL). The organic layer was washed with a 5% aqueous solution of citric acid (3×100 mL), 1 N aqueous solution of hydrochloride (3×100 mL), water, saturated aqueous solution of sodium bicarbonate, and brine, and dried over magnesium sulfate. The solvents were removed under reduced pressure to give trans benzyl 4-[4-amino-3-(3-methoxy-4-{[(2-phenylcyclopropyl)carbonyl]amino}phenyl)-1H-pyrazolo[3,4-d]pyrimidin-1-yl]-1-piperidinecarboxylate (3.47 g, 0.006 mol). RP-HPLC (Delta Pak C18, 5 μm, 300 A, 15 cm; 5%–85% acetonitrile-0.1M ammonium acetate over 10 min, 1 mL/min) $R_t$ 11.5 min. MS: MH⁺ 618.

e) trans N1-{4-[4-Amino-1-(4-piperidyl)-1H-pyrazolo[3,4-d]pyrimidin-3-yl]-2-methoxyphenyl}-(1S,2S)/(1R,2R)-2-phenyl-1-cyclopropanecarboxamide Maleate The mixture of trans benzyl 4-[4-amino-3-(3-methoxy-4-{[(2-phenylcyclopropyl)carbonyl]amino}phenyl)-1H-pyrazolo[3,4-d]pyrimidin-1-yl]-1-piperidinecarboxylate (3.4 g, 0.0055 mol) and 20% palladium hydroxide on carbon (0.4 g) in ethanol (150 mL) was stirred under atmosphere of hydrogen at room temperature for 18 hours. The mixture was filtered and solvents were removed. To the residue 20% palladium hydroxide on carbon (0.4 g), acetic acid (0.25 mL) in ethanol (60 mL) and ethyl acetate (40 mL) were added. The mixture was stirred under atmosphere of hydrogen at room temperature for additional 18 hours. The mixture was filtered and the solvents were removed under reduced pressure. The residue was purified by flash column chromatography on silica using 25%–50% methanol/dichloromethane to give trans N1-{4-[4-amino-1-(4-piperidyl)-1H-pyrazolo[3,4-d]pyrimidin-3-yl]-2-methoxyphenyl}-(1S,2S)/(1R,2R)-2-phenyl-1-cyclopropanecarboxamide (1.36 g, 0.0028 mol). Trans N1-{4-[4-amino-1-(4-piperidyl)-1H-pyrazolo[3,4-d]pyrimidin-3-yl]-2-methoxyphenyl}-(1S,2S)/(1R,2R)-2-phenyl-1-cyclopropanecarboxamide (0.05 g, 0.000104 mol) in ethyl acetate (5 mL) was heated to 40° C. Maleic acid (0.00133 g, 0.000114 mol) was dissolved in warm ethyl acetate before added into the mixture. The mixture was stirred at 40° C. for 10 minutes then cooled to room temperature. The white precipitates were filtered to give trans N1-{4-[4-amino-1-(4-piperidyl)-1H-pyrazolo[3,4-d]pyrimidin-3-yl]-2-methoxyphenyl}-(1S,2S)/(1R,2R)-2-phenyl-1-cyclopropanecarboxamide maleate (0.0044 g, 0.00001 mol).

¹H NMR (DMSO-d₆, 400 MHz) δ 9.65 (s, 1H), 8.26 (m, 2H), 7.25 (m, 7H), 6.01 (d, 2H), 5.09 (br, 1H), 3.90 (s, 3H), 3.48 (m, 2H), 3.18 (m, 2H), 2.61 (br, 1H), 2.37 (m, 3H), 2.13 (m, 2H), 1.50 (br, 1H), 1.34 (br, 1H). RP-HPLC (Delta Pak C18, 5 μm, 300 A, 15 cm; 5%–95% acetonitrile-0.1M ammonium acetate over 10 min, 1 mL/min) $R_t$ 9.0 min. MS: MH⁺ 484.

Example 488

N1-(4-{4-Amino-1-[1-(1H-2-imidazolylmethyl)-4-piperidyl]-1H-pyrazolo[3,4-d]pyrimidin-3-yl}-2-methoxyphenyl)-(1S,2S)/(1R,2R)-2-phenyl-1-cyclopropanecarboxamide A mixture of N1-{4-[4-amino-1-(4-piperidyl)-1H-pyrazolo[3,4-d]pyrimidin-3-yl]-2-methoxyphenyl}-(1S,2S)/(1R,2R)-2-phenyl-1-cyclopropanecarboxamide (0.10 g, 0.00021 mol), 2-imidazole carboxaldehyde (0.022 g, 0.00023 mol), and acetic acid (0.037 g, 0.0006 mol) in dichloroethane (8 mL) was stirred at room temperature under an atmosphere of nitrogen for 1.5 hrs. Sodium triacetoxyborohydride (0.133 g, 0.00063 mol) was added into the mixture and stirred at ambient temperature under an atmosphere of nitrogen for 18 hours. Additonal acetic acid (0.037 g, 0.0006 mol), 2-imidazole carboxaldehyde (0.011 g, 0.00012 mol), and sodium triacetoxyborohydride (0.133 g, 0.00063 mol) were added to the mixture and the mixture was stirred for 18 hours. The reaction was quenched with an aqueous 5N solution of sodium hydroxide. The solvents were removed under reduced pressure, and the residue was partitioned between water and dichloromethane. The organic layer was washed with water and brine. The solvents were removed under reduced pressure. The residue was purified by RP-HPLC (Hypersilprep HS C18, 8 μm, 250× 21.1 mm; 5%–100% over 35 min with 0.1 M ammonium acetate, 21 mL/min) to yield N1-(4-{4-amino-1-[1-(1H-2-imidazolylmethyl)-4-piperidyl]-1H-pyrazolo[3,4-d]pyrimidin-3-yl}-2-methoxyphenyl)-(1S,2S)/(1R,2R)-2-phenyl-1-cyclopropanecarboxamide (0.019 g, 0.000034 mol).

¹H NMR (DMSO-d₆, 400 MHz) δ 11.8 (br, 1H), 9.63 (s, 1H), 8.22 (m, 2H), 7.25 (m, 7H), 6.99 (br, 1H), 6.83 (br, 1H), 4.68 (br, 1H), 3.90 (s, 3H), 3.56 (s, 2H), 2.93 (m, 2H), 2.58 (br, 1H), 2.37 (br, 1H), 2.22 (m, 3H), 1.90 (m, 3H), 1.50 (br, 1H), 1.30 (br, 1H). RP-HPLC (Delta Pak C18, 5 μm, 300 A, 15 cm; 5%–95% acetonitrile-0.1M ammonium acetate over 10 min, 1 mL/min) $R_t$ 9.4 min. MS: MH⁺ 564.

Example 489

N1-[4-(4-Amino-1-{1-[(1-methyl-1H-2-imidazolyl)methyl]-4-piperidyl}-1H-pyrazolo[3,4-d]pyrimidin-3-yl)-2-methoxyphenyl]-(1S,2S)/(1R,2R)-2-phenyl-1-cyclopropanecarboxamide A mixture of N1-{4-[4-amino-1-(4-piperidyl)-1H-pyrazolo[3,4-d]pyrimidin-3-yl]-2-methoxyphenyl}-(1S,2S)/(1R,2R)-2-phenyl-1-cyclopropanecarboxamide (0.10 g, 0.00021 mol), 1-methyl-2-imidazole carboxaldehyde (0.025 g, 0.00023 mol), and acetic acid (0.037 g, 0.0006 mol) in dichloroethane (8 mL) was stirred at room temperature under an atmosphere of nitrogen for 1.5 hrs. Sodium triacetoxyborohydride (0.133 g, 0.00063 mol) was added into the mixture and stirred at ambient temperature under an atmosphere of nitrogen for 18 hours. The reaction was quenched with an aqueous 5N solution of sodium hydroxide. The solvents were removed under reduced pressure, and the residue was partitioned between water and dichloromethane. The organic layer was washed with water and brine. The solvents were removed under reduced pressure. The residue was purified by flash chromatography on silica gel using 5%–50% methanol/dichloromethane as mobile phase to yield N1-[4-(4-amino-1-{1-[(1-methyl-1H-2-imidazolyl)methyl]-4-piperidyl}-1H-pyrazolo[3,4-d]pyrimidin-3-yl)-2-methoxyphenyl]-(1S,2S)/(1R,2R)-2-phenyl-1-cyclopropanecarboxamide (0.070 g, 0.00012 mol).

¹H NMR (DMSO-d₆, 400 MHz) δ 9.63 (s, 1H), 8.22 (m, 2H), 7.25 (m, 7H), 7.09 (s, 1H), 6.75 (s, 1H), 4.68 (br, 1H), 3.90 (s, 3H), 3.68 (s, 3H), 3.20 (s, 2H), 2.93 (m, 2H), 2.58 (br, 1H), 2.35 (br, 1H), 2.24 (m, 4H), 1.89 (m, 2H), 1.50 (br, 1H), 1.30 (br, 1H). RP-HPLC (Delta Pak C18, 5 μm, 300 A, 15 cm; 5%–95% acetonitrile-0.1M ammonium acetate over 10 min, 1 mL/min) $R_t$ 9.6 min. MS: MH⁺ 578.

Example 490

3-(3-Methoxy-4-{[(5-methyl-2-furyl)methyl]amino}phenyl)-1-(4-piperidyl)-1H-pyrazolo[3,4-d]pyrimidin-4-amine a) Benzyl 4-[4-Amino-3-(3-methoxy-4-{[(5-methyl-2-furyl)methyl]amino}phenyl)-1H-pyrazolo[3,4-d]pyrimidin-1-yl]-1-piperidinecarboxylate A mixture of benzyl 4-[4-amino-3-(4-amino-3-methoxyphenyl)-1H-pyrazolo[3,4-d]pyrimidin-1-yl]-1- piperidinecarboxylate (3.0 g, 0.0063 mol), 5-methylfurfural (0.77 g, 0.007 mol), and acetic acid (1.15 g, 0.019 mol) in dichloroethane (100 mL) was stirred at room temperature under an atmosphere of nitrogen for 1.5 hrs. Sodium triacetoxyborohydride (4.1 g, 0.0195 mol) was added to the mixture and the mixture was stirred at ambient temperature under an atmosphere of nitrogen for 18 hours. The reaction was quenched with an aqueous 5N solution of sodium hydroxide. The solvents were removed under reduced pressure, and the residue was partitioned between water and dichloromethane. The aqueous layer was extracted with dichloromethane (3×200 mL), and the combined organic layer was washed with water and brine, and dried over magnesium sulfate. The solvents were removed under reduced pressure. The residue was purified by flash chromatography on silica gel using 2%–5% methanol/dichloromethane as mobile phase to yield benzyl 4-[4-amino-3-(3-methoxy-4-{[(5-methyl-2-furyl)methyl]amino}phenyl)-1H-pyrazolo[3,4-d]pyrimidin-1-yl]-1-piperidinecarboxylate (2.63 g, 0.0046 mol). RP-HPLC (Delta Pak C18, 5 μm, 300 A, 15 cm; 5%–95% acetonitrile-0.1M ammonium acetate over 10 min, 1 mL/min) $R_t$ 11.59 min. MS: MH$^+$ 568.

b) 3-(3-Methoxy-4-{[(5-methyl-2-furyl)methyl]amino}phenyl)-1-(4-piperidyl)-1H-pyrazolo[3,4-d]pyrimidin-4-amine A mixture of benzyl 4-[4-amino-3-(3-methoxy-4-{[(5-methyl-2-furyl)methyl]amino}phenyl)-1H-pyrazolo[3,4-d]pyrimidin-1-yl]-1-piperidinecarboxylate (0.18 g, 0.000317 mol) and 20% palladium hydroxide on carbon (0.02 g) in ethyl acetate (10 mL) was stirred under atmosphere of hydrogen at room temperature for 18 hours. The mixture was filtered and solvents were removed. The residue was purified by flash column chromatography on silica using 5%–10% methanol/dichloromethane (2% NH$_4$OH) to give 3-(3-methoxy-4-{[(5-methyl-2-furyl)methyl]amino}phenyl)-1-(4-piperidyl)-1H-pyrazolo[3,4-d]pyrimidin-4-amine (0.02 g, 0.000046 mol).

$^1$H NMR (DMSO-d$_6$, 400 MHz) δ 8.20 (s, 1H), 7.07 (m, 2H), 6.78 (m, 1H), 6.18 (s, 1H), 5.97 (s, 1H), 5.59 (m, 1H), 4.79 (br, 1H), 4.31 (m, 2H), 3.86 (s, 3H), 3.16 (m, 2H), 2.74 (m, 2H), 2.23 (s, 3H), 2.15 (m, 2H), 1.90 (m, 2H). RP-HPLC (Delta Pak C18, 5 μm, 300 A, 15 cm; 5%–95% acetonitrile-0.1M ammonium acetate over 10 min, 1 mL/min) $R_t$ 8.7 min. MS: MH$^+$ 434.

Example 491

3-(3-Methoxy-4-{[(5-methyl-2-furyl)methyl]amino}phenyl)-1-{1-[(1-methyl-1H-2-imidazolyl)methyl]-4-piperidyl}-1H-pyrazolo[3,4-d]pyrimidin-4-amine A mixture 3-(3-methoxy-4-{[(5-methyl-2-furyl)methyl]amino}phenyl)-1-(4-piperidyl)-1H-pyrazolo[3,4-d]pyrimidin-4-amine (0.045 g, 0.0001 mol), 1-methyl-2-imidazole carboxaldehyde (0.011 g, 0.00011 mol), and acetic acid (0.018 g, 0.0003 mol) in dichloroethane (4 mL) was stirred at room temperature under an atmosphere of nitrogen for 1.5 hrs. Sodium triacetoxyborohydride (0.064 g, 0.0003 mol) was added into the mixture and the mixture was stirred at ambient temperature under an atmosphere of nitrogen for 18 hours. The reaction was quenched with an aqueous 5 N solution of sodium hydroxide. The solvents were removed under reduced pressure, and the residue was partitioned between water and dichloromethane. The organic layer was washed with water and brine. The solvents were removed under reduced pressure. The residue was purified by RP-HPLC (Hypersilprep HS C18, 8 μm, 250× 21.1 mm; 5%–100% over 35 min with 0.1 M ammonium acetate, 21 mL/min) to yield 3-(3-methoxy-4-{[(5-methyl-2-furyl)methyl]amino}phenyl)-1-{1-[(1-methyl-1H-2-imidazolyl)methyl]-4-piperidyl}-1H-pyrazolo[3,4-d]pyrimidin-4-amine (0.03 g, 0.00006 mol).

$^1$H NMR (DMSO-d$_6$, 400 MHz) δ 8.19 (s, 1H), 7.16 (s, 1H), 7.06 (m, 2H), 6.86 (s, 1H), 6.77 (d, 1H), 6.18 (s, 1H), 5.98 (s, 1H), 5.59 (m, 1H), 4.67 (br, 1H), 4.31 (m, 2H), 3.85 (s, 3H), 3.71 (s, 3H), 3.66 (s, 2H), 2.96 (m, 2H), 2.27 (m, 2H), 2.23 (s, 3H), 2.18 (m, 2H), 1.91 (m, 2H). RP-HPLC (Delta Pak C18, 5 μm, 300 A, 15 cm; 5%–95% acetonitrile-0.1M ammonium acetate over 10 min, 1 mL/min) $R_t$ 9.5 min. MS: MH$^+$ 528.

Example 492 trans N1-(4-{4-Amino-1-[(4-hydroxy-4-piperidyl)methyl]-1H-pyrazolo[3,4-d]pyrimidin-3-yl}-2-methoxyphenyl)-2-phenyl-1-cyclopropanecarboxamide a) tert-Butyl 4-[(4-Amino-3-iodo-1H-pyrazolo[3,4-d]pyrimidin-1-yl)methyl]-4-hydroxy-1-piperidinecarboxylate A mixture of 3-iodo-1H-pyrazolo[3,4-d]pyrimidin-4-amine (0.86 g, 0.0033 mol), tert-butyl 1-oxa-6-azaspiro[2.5]octane-6-carboxylate (0.7 g, 0.0033 mol) and cesium carbonate (1.1 g, 0.0033 mol) in anhydrous N,N-dimethylformamide (30 mL) was stirred at 60° C. for 18 hours. The solvent was removed under reduced pressure. The residue was partitioned between water and dichloromethane (200 mL). The organic layer was washed with water and brine, and dried over magnesium sulfate. The solvent was removed under reduced pressure. The residue was triturated with dichloromethane, and the solid was filtered to give tert-butyl 4-[(4-amino-3-iodo-1H-pyrazolo[3,4-d]pyrimidin-1-yl)methyl]-4-hydroxy-1-piperidinecarboxylate (0.66 g, 0.0014 mol). RP-HPLC (Delta Pak C18, 5 μm, 300 A, 15 cm; 5%–85% acetonitrile-0.1M ammonium acetate over 10 min, 1 mL/min) Rt 8.7 min. MS: MH$^+$ 475.

b) tert-Butyl 4-{[4-Amino-3-(4-{[(benzyloxy)carbonyl]amino}-3-methoxyphenyl)-1H-pyrazolo[3,4-d]pyrimidin-1-yl]methyl}-4-hydroxy-1-piperidinecarboxylate A mixture of tert-butyl 4-[(4-amino-3-iodo-1H-pyrazolo[3,4-d]pyrimidin-1-yl)methyl]-4-hydroxy-1-piperidinecarboxylate (0.27 g, 0.00057 mol), benzyl N-[2-methoxy-4-(4,4,5,5-tetramethyl-1,3,2-dioxaborolan-2-yl)phenyl]carbamate (0.26 g, 0.00068 mol), tetrakis(triphenylphosphine)palladium (0.039 g, 0.000034 mol) and sodium carbonate (0.15 g, 0.0014 mol) in ethylene glycol dimethyl ether (7 mL) and water (3 mL) was heated at 85° C. for 16 hours under an atmosphere of nitrogen. The mixture was allowed to cool to ambient temperature and ethylene glycol dimethyl ether was removed under the reduced pressure. The aqueous layer was extracted with dichloromethane (2×100 mL). The combined organic extracts were washed with water and brine, and dried over magnesium sulfate. The organic layer was filtered through silica gel twice to remove the catalyst, and the solvent was removed under reduced pressure. The residue was purified by RP-HPLC (Hypersilprep HS C18, 8μm, 250×21.1 mm; 5%–100% over 35 min with 0.1 M ammonium acetate, 21 mL/min) to yield tert-butyl 4-{[4-amino-3-(4-{[(benzyloxy)carbonyl]amino}-3-methoxyphenyl)-1H-pyrazolo[3,4-d]

pyrimidin-1-yl]methyl}-4-hydroxy-1-piperidinecarboxylate (0.1 g, 0.00017 mol). RP-HPLC (Delta Pak C18, 5 μm, 300 A, 15 cm; 5%–85% acetonitrile-0.1M ammonium acetate over 10 min, 1 mL/min) Rt 10.9 min. MS: MH+ 604.

c) tert-Butyl 4-{[4-Amino-3-(4-amino-3-methoxyphenyl)-1H-pyrazolo[3,4-d]pyrimidin-1-yl]methyl}-4-hydroxy-1-piperidinecarboxylate A mixture of tert-butyl 4-{[4-amino-3-(4-{[(benzyloxy)carbonyl]amino}-3-methoxyphenyl)-1H-pyrazolo[3,4-d]pyrimidin-1-yl]methyl}-4-hydroxy-1-piperidinecarboxylate (0.1 g, 0.000017 mol) and palladium on carbon (0.01 g) in ethanol (2.5 mL) and tetrahydrofuran (2.5 mL) was stirred under atmosphere of hydrogen at room temperature for 18 hours. The mixture was filtered and additional palladium on carbon (0.01 g) was added. The mixture was stirred under atmosphere of hydrogen at room temperature for 18 hours. The mixture was filtered through celite and the solvents were removed under reduced pressure to give tert-butyl 4-{[4-amino-3-(4-amino-3-methoxyphenyl)-1H-pyrazolo[3,4-d]pyrimidin-1-yl]methyl}-4-hydroxy-1-piperidinecarboxylate (0.08 g, 0.00017 mol). RP-HPLC (Delta Pak C18, 5 μm, 300 A, 15 cm; 5%–85% acetonitrile-0.1M ammonium acetate over 10 min, 1 mL/min) Rt 8.8 min. MS: MH+ 470.

d) trans tert-Butyl 4-{[4-Amino-3-(3-methoxy-4-{[(2-phenylcyclopropyl)carbonyl]amino}phenyl)-1H-pyrazolo[3,4-d]pyrimidin-1-yl]methyl}-4-hydroxy-1-piperidinecarboxylate To a mixture of tert-butyl 4-{[4-amino-3-(4-amino-3-methoxyphenyl)-1H-pyrazolo[3,4-d]pyrimidin-1-yl]methyl}-4-hydroxy-1-piperidinecarboxylate (0.08 g, 0.00017 mol) in pyridine (4 mL) was added trans-2-phenylcyclopropane carbonyl chloride (0.035g, 0.00019 mol) at −5° C. The mixture was stirred at −5° C. for 10 minutes then warmed up to room temperature to stir for 1 hours. The mixture was quenched with an aqueous 1N solution of sodium hydroxide. Pyridine was removed under reduced pressure. The residue was partitioned between water and dichloromethane (50 mL). The organic layer was washed with water. The solvents were removed under reduced and the residue was purified by RP-HPLC (Hypersilprep HS C18, 8μm, 250×21.1 mm; 5%–100% over 35 min with 0.1 M ammonium acetate, 21 mL/min) to yield trans tert-butyl 4-{[4-amino-3-(3-methoxy-4-{[(2-phenylcyclopropyl)carbonyl]amino}phenyl)-1H-pyrazolo[3,4-d]pyrimidin-1-yl]methyl}-4-hydroxy-1-piperidinecarboxylate (0.08 g, 0.00013 mol). RP-HPLC (Delta Pak C18, 5 μm, 300 A, 15 cm; 5%–85% acetonitrile-0.1M ammonium acetate over 10 min, 1 mL/min) R$_t$ 10.7 min. MS: MH+ 614.

e) Trans N1-(4-{4-amino-1-[(4-hydroxy-4-piperidyl)methyl]-1H-pyrazolo[3,4-d]pyrimidin-3-yl}-2-methoxyphenyl)-2-phenyl-1-cyclopropanecarboxamide hydrochloride salt. A mixture of trans tert-butyl 4-{[4-amino-3-(3-methoxy-4-{[(2-phenylcyclopropyl)carbonyl]amino}phenyl)-1H-pyrazolo[3,4-d]pyrimidin-1-yl]methyl}-4-hydroxy-1-piperidinecarboxylate (0.08 g, 0.00013 mol) in acetone (12 mL) and 6 N aqueous hydrochloride solution (3 mL) was stirred at 40° C. for 2 hours. Acetone was removed under reduced pressure, and the residue was lyophilized to give trans N1-(4-{4-amino-1-[(4-hydroxy-4-piperidyl)methyl]-1H-pyrazolo[3,4-d]pyrimidin-3-yl}-2-methoxyphenyl)-2-phenyl-1-cyclopropanecarboxamide hydrochloride salt (0.07 g, 0.00012 mol).

$^1$H NMR (DMSO-d$_6$, 400 MHz) δ 9.65 (s, 1H), 8.71 (br, 1H), 8.43 (s, 1H), 8.26 (m, 1H), 7.25 (m, 7H), 4.40 (s, 2H), 3.90 (s, 3H), 3.10 (m, 2H), 2.98 (m, 2H), 2.51 (m, 1H), 2.34 (m, 1H), 1.89 (m, 2H), 1.71 (m, 2H), 1.48 (m, 1H), 1.31 (m, 1H). RP-HPLC (Delta Pak C18, 5 μm, 300 A, 15 cm; 5%–95% acetonitrile-0.1M ammonium acetate over 10 min, 1 mL/min) Rt 8.7 min. MS: MH+ 514.

Example 493

N1-4-[4-Amino-1-(4-oxocyclohexyl)-1H-pyrazolo[3,4-d]pyrimidin-3-yl]-2-methoxyphenyl-(1S,2S)/(1R,2R)-2-phenylcyclopropane-1-carboxamide A suspension of 4-[4-amino-3-(4-amino-3-methoxyphenyl)-1H-pyrazolo[3,4-d]pyrimidin-1-yl]-1-cyclohexanone (2.00 g, 0.00568 mol) in pyridine (20 mL) was cooled to −10° C. A solution of racemic trans-2-benzylcyclopropane-1-carbonyl chloride (1.53 g, 0.00852 mol)) in dichloromethane (5 mL) was added dropwise, keeping the temperature less than to −5° C. The reaction mixture was allowed to come to ambient temperature over four hours. Aqueous sodium hydroxide (1.0 M, 10 mL) was added and the mixture was stirred 1 hour. The solvents were removed in vacuo and the residue was partitioned between ethyl acetate (25 mL) and water (50 mL). The phases were separated and the aqueous phase was extracted with ethyl acetate (2×25 mL). The combined organic phases were dried over magnesium sulfate, and the solvent was removed in vacuo to give N1-4-[4-amino-1-(4-oxocyclohexyl)-1H-pyrazolo[3,4-d]pyrimidin-3-yl]-2-methoxyphenyl-(1S,2S)-2-phenylcyclopropane-1-carboxamide as a white solid (1.603 g, 0.00323 mol).

$^1$H NMR (DMSO-d$_6$, 400 MHz) δ 9.64 (s, 1H), 8.27 (s, 1H), 8.23 (d, 1H), 7.14–7.35 (m, 7H), 5.24–5.27 (m, 1H), 3.90 (s, 3H), 2.65–2.78 (m, 2H), 2.56–2.63 (m, 1H), 2.34–2.37 (m, 5H), 2.20–2.30 (m, 2H), 1.45–1.53 (m, 1H), 1.28–1.35 (m, 1H); RP-HPLC (Delta Pak C18, 5 μm, 300 A, 15 cm; 5%–95% acetonitrile-0.1M ammonium acetate over 20 min, 1 mL/min) R$_t$ 15.04 min.; MS: MH+ 497.

Example 494 cis N1-(4-{4-Amino-1-[4-(ammoniomethyl)-4-hydroxycyclohexyl]-1H-pyrazolo[3,4-d]pyrimidin-3-yl}-2-methoxyphenyl-(1S,2S)/(1R,2R)-2-phenylcyclopropane-1-carboxamide acetate a) cis N1-4-[4-Amino-1-(1-oxaspiro[2.5]oct-6-yl)-1H-pyrazolo[3,4-d]pyrimidin-3-yl]-2-methoxyphenyl-(1S,2S)-2-phenylcyclopropane-1-carboxamide In a heat dried flask, trimethylsulfoxonium iodide (0.425 g, 0.00193 mol) in dimethylsulfoxide (5 ml) was reacted with 60% sodium hydride dispersion in mineral oil (0.071 g, 0.00193 mol). The mixture was stirred at room temperature for 30 minutes and then cooled to 10° C. A solution of N1-4-[4-amino-1-(4-oxocyclohexyl)-1H-pyrazolo[3,4-d]pyrimidin-3-yl]-2-methoxyphenyl-(1S,2S)/(1R,2R)-2-phenylcyclopropane-1-carboxamide (0.800 g, 0.00161 mol) in dimethylsulfoxide (5 ml) was added, and the mixture was stirred at ambient temperature for 6 hours. Water (5 mL) was added and the mixture was extracted with ethyl acetate (3×10 mL). The organic phase was washed with water (5 mL), brine (5 mL) and dried over magnesium sulfate. The solvent was removed in vacuo to give cis N1-4-[4-amino-1-(1-oxaspiro[2.5]oct-6-yl)-1H-pyrazolo[3,4-d]pyrimidin-3-yl]-2-methoxyphenyl-(1S,2S)/(1R,2R)-2-phenylcyclopropane-1-carboxamide as a white solid (0.820 g, 0.00160 mol):

$^1$H NMR (DMSO-d$_6$, 400 MHz) δ 9.64 (s, 1H), 8.24 (s, 1H), 8.22 (d,1H), 7.17–7.31 (m, 7H), 4.84–4.90 (m, 1H), 3.92 (s, 3H), 2.70 (s, 2H), 2.56–2.63 (m, 1H), 2.34–2.42 (m, 1H), 2.12–2.33 (m, 4H), 1.90–1.99 (m, 2H), 1.44–1.52 (m, 1H), 1.27–1.37 (m, 3H); MS: MH+ 413.

b) cis N1-(4-{4-Amino-1-[4-(ammoniomethyl)-4-hydroxycyclohexyl]-1H-pyrazolo[3,4-d]pyrimidin-3-yl}-2-methoxyphenyl)-(1S,2S)I(1R,2R)-2-phenylcyclopropane-1-carboxamide Acetate A mixture of cis N1-4-[4-amino-1-(1-oxaspiro[2.5]oct-6-yl)-1H-pyrazolo[3,4-d]pyrimidin-3-yl]-2-methoxyphenyl-(1S,2S)/(1R,2R)-2-phenylcyclopropane-1-carboxamide (0.200 g, 0.000391 mol) in 2-propanol (5 mL) and ammonium hydroxide (5 mL) was heated at 65° C. in a pressure tube for 18 hours. The solvent was removed in vacuo, and the residue was purified by preparative RP-HPLC (Rainin C18, 8μm, 300 A, 25 cm; 30% isocratic for five minutes, then 30%–60% acetonitrile-0.1M ammonium acetate over 15 min, 21 ml/min). The acetonitrile was removed in vacuo and the aqueous mixture was lyopholyzed to give cis N1-(4-{4-amino-1-[4-(ammoniomethyl)-4-hydroxycyclohexyl]-1H-pyrazolo[3,4-d]pyrimidin-3-yl}-2-methoxyphenyl)-(1S,2S)/(1R,2R)-2-phenylcyclopropane-1-carboxamide acetate as a white solid (0.112 g, 0.000212 mol).:
$^1$H NMR (DMSO-d$_6$, 400 MHz) δ 9.64 (s, 1H), 8.23 (d, 1H), 8.22–8.24 (m, 1H), 7.17–7.33 (m, 7H), 4.59–4.80 (m, 1H), 3.91 (s, 3H), 2.28–2.65 (m, 4H), 1.88 (s, 3H), 1.68–1.72 (m, 4H), 1.47–1.51 (m, 3H), 1.30–1.33 (m, 1H); RP-HPLC (Delta Pak C18, 5 μm, 300 A, 15 cm; 5%–85% acetonitrile-0.1M ammonium acetate over 20 min, 1 mL/min) R$_t$ 13.11 min.; MS: MH$^+$ 528.

Example 495 trans N1-Benzyl-2-{4-[4-amino-3-(4-phenoxyphenyl)-1H-pyrazolo[3,4-d]pyrimidin-1-yl]-1-hydroxycyclohexyl}acetamide A suspension of trans 2-{4-[4-amino-3-(4-phenoxyphenyl)-1H-pyrazolo[3,4-d]pyrimidin-1-yl]-1-hydroxycyclohexyl}acetic acid (0.076 g, 0.000165 mol) in dichloromethane (2 mL) was reacted with triethylamine (0.050 g, 0.000496 mol) and bis(2-oxo-3-oxazolidinyl)phosphinic chloride (0.063 g, 0.000248 mol). The mixture was stirred two hours at ambient temperature, during which time dissolution occurred. The solution was washed with water (2×2 mL). The organic layer was dried over magnesium sulfate, and the solvent was removed in vacuo. The crude material was dissolved in dichloromethane (5 mL) and reacted with benzylamine (0.052 g, 0.000489 mol) at ambient temperature for 18 hours. The crude material was purified by flash column chromatography on silica using dichloromethane/methanol (95:5), followed by preparative RP-HPLC (Rainin C18, 8 μm, 300 A, 25 cm; 60% isocratic for five minutes, then 60%–100% acetonitrile-0.1M ammonium acetate over 20 min, 21 ml/min). The acetonitrile was removed in vacuo and the aqueous mixture was lyopholyzed to give trans N1-benzyl-2-{4-[4-amino-3-(4-phenoxyphenyl)-1H-pyrazolo[3,4-d]pyrimidin-1-yl]-1-hydroxycyclohexyl}acetamide as a white solid (0.010 g, 0.000018 mol).
$^1$H NMR (DMSO-d$_6$, 400 MHz) δ 8.53 (t, 1H) 8.24 (s, 1H), 7.66 (d, 2H), 7.43 (t, 2H), 7.09–7.34 (m, 10H), 5.24 (s, 1H), 4.70–4.79 (m, 1H), 4.30 (d, 2H), 2.02–2.18 (m, 2H), 1.91 (s, 2H), 1.86–1.98 (m, 4H), 1.56–1.64 (m, 2H); RP-HPLC (Delta Pak C18, 5 μm, 300 A, 15 cm; 5%–95% acetonitrile-0.1M ammonium acetate over 20 min, 1 mL/min) R$_t$ 16.16 min.; MS: MH$^+$ 549.

Example 496

1-(Aminomethyl)-3-[4-amino-3-(4-phenoxyphenyl)-1H-pyrazolo[3,4-d]pyrimidin-1-yl]-1-cyclobutanol A solution of 3-[4-amino-3-(4-phenoxyphenyl)-1H-pyrazolo[3,4-d]pyrimidin-1-yl]-1-cyclobutanone (0.150 g, 0.000404 mol) in dichloromethane (5 mL) was reacted with 1,1,1-trimethylsilyl cyanide (0.060 g, 0.000606 mol) and anhydrous zinc iodide (0.004 g, 0.000012 mol). The mixture was stirred eight hours at reflux temperature. The mixture was partitioned between water (20 mL) and diethyl ether (10 mL). The organic layer was separated and the aqueous layer was extracted with diethyl ether (10 mL). The combined organic layers were washed with brine and dried over magnesium sulfate. The solvent was removed in vacuo, and the crude material was dissolved in anhydrous tetrahydrofuran (10 mL) and reacted with lithium aluminum hydride (0.031 g, 0.000804 mol) at ambient temperature for 18 hours. The crude material was purified by preparative RP-LC/MS (Gilson-Micromass C18, 5 μm, 130A, 21 cm, 0%–100% acetonitrile-0.1M ammonium acetate over 9 min, 25 mL/min). The acetonitrile was removed in vacuo and the aqueous mixture was lyopholyzed to give a 4:1 mixture of isomers of 1-(aminomethyl)-3-[4-amino-3-(4-phenoxyphenyl)-1H-pyrazolo[3,4-d]pyrimidin-1-yl]-1-cyclobutanol as a white solid (0.024 g, 0.000060 mol).

$^1$H NMR (DMSO-d$_6$, 400 MHz) δ 8.24 (s, 1H) minor, 8.23 (s, 1H) major, 7.66–7–70 (m, 2H), 7.41–7.46 (m, 2H), 7.11–7.21 (m, 5H), 5.45–5.50 (m, 1H) minor, 4.87–4.96 (m, 1H) major, 4.30 (d, 2H), 2.34–2.72 (m, 6H); RP-HPLC ( Delta Pak C18, 5 μm, 300 A, 15 cm; 5%–85% acetonitrile-0.1M ammonium acetate over 20 min, 1 mL/min) R$_t$ 12.07 min.(minor) and 12.36 min (major); MS: MH$^+$ 403.

We claim:
1. A compound of Formula (I)

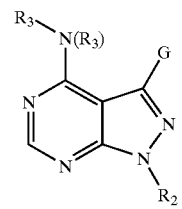

racemic-diastereomeric mixtures, optical isomers, pharmaceutically-acceptable salts or prodrugs thereof wherein:

G is

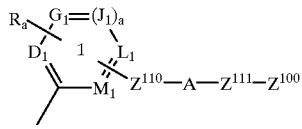

where $Z^{100}$ is

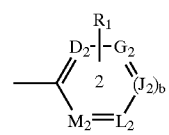

or a group optionally substituted with $R_1$ selected from the group consisting of, cycloalkyl, naphthyl, tetrahydronaphthyl,

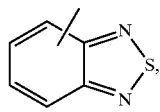

benzothienyl, furanyl, thienyl, benzoxazolyl, benzothiazolyl,

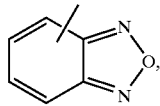

thiazolyl, benzofuranyl, 2,3-dihydrobenzofuranyl, indolyl, isoxazolyl, tetrahydropyranyl, tetrahydrofuranyl, piperidinyl, pyrazolyl, pyrrolyl, oxazolyl, isothiazolyl, oxadiazolyl, thiadiazolyl, indolinyl, indazolyl, benzoisothiazolyl, pyrido-oxazolyl, pyrido-thiazolyl, pyrimido-oxazolyl, pyrimido-thiazolyl and benzimidazolyl;

$Z^{110}$ is a covalent bond, or an optionally substituted $(C_1-C_6)$ which is optionally substituted with one or more substituents selected from the group consisting of alkyl, CN, OH, halogen, $NO_2$, COOH, substituted or unsubstituted amino and substituted or unsubstituted phenyl;

$Z^{111}$ is a covalent bond, an optionally substituted $(C_1-C_6)$ or an optionally substituted $-(CH_2)_n-$cycloalkyl-$(CH_2)_n-$; where the optionally substituted groups are optionally substituted with one or more substituents selected from the group consisting of alkyl, CN, OH, halogen, $NO_2$, COOH, substituted or unsubstituted amino and substituted or unsubstituted phenyl;

$R_a$ and $R_1$ each represent one or more substituents for each occurrence independently selected from the group consisting of hydrogen, halogen, —CN, —$NO_2$, —C(O)OH, —C(O)H, —OH, —C(O)O-alkyl, substituted or unsubstituted carboxamido, tetrazolyl, trifluoromethylcarbonylamino, trifluoromethylsulfonamido, substituted or unsubstituted alkyl, substituted or unsubstituted alkoxy, substituted or unsubstituted aryl, substituted or unsubstituted alkenyl, substituted or unsubstituted aryloxy, substituted or unsubstituted heteroaryloxy, substituted or unsubstituted arylalkyl, substituted or unsubstituted alkynyl, substituted or unsubstituted amino, substituted or unsubstituted aminoalkyl, substituted or unsubstituted amido groups, substituted or unsubstituted heteroarylthio, substituted or unsubstituted arylthio, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, $R_c$ and $CH_2OR_c$;

where $R_c$ for each occurrence is independently hydrogen, substituted or unsubstituted alkyl, substituted or unsubstituted aryl, —$CH_2$—$NR_dR_e$, —W—$(CH_2)_t$—$NR_dR_e$, —W—$(CH_2)_t$—O-alkyl, —W—$(CH_2)_t$—S-alkyl, or —W—$(CH_2)_t$—OH;

$Z^{105}$ for each occurrence is independently a covalent bond or $(C_1-C_6)$;

$Z^{200}$ for each occurrence is independently a substituted or unsubstituted $(C_1-C_6)$, substituted or unsubstituted phenyl or substituted or unsubstituted —$(C_1-C_6)$-phenyl;

$R_d$ and $R_e$ for each occurrence are independently H, alkyl, alkanoyl or $SO_2$-alkyl; or $R_d$, $R_e$ and the nitrogen atom to which they are attached together form a five- or six-membered heterocyclic ring; t for each occurrence is independently an integer from 2 to 6; W for each occurrence is independently a direct bond or O, S, S(O), S(O)$_2$, or $NR_f$, wherein $R_f$ for each occurrence is independently H or alkyl;

or $R_1$ is a substituted or unsubstituted carbocyclic or heterocyclic ring fused with ring 2;

$R_3$ is hydrogen, hydroxy, substituted or unsubstituted alkoxy;

A is -, —O—; —S—; —S(O)$_p$—; —N(R)—; —N(C(O)OR)—; —N(C(O)R)—; —N(SO$_2$R)—; —CH$_2$O—; —CH$_2$S—; —CH$_2$N(R)—; —CH(NR)—; —CH$_2$N(C(O)R))—; —CH$_2$N(C(O)OR)—; —CH$_2$N(SO$_2$R)—; —CH(NHR)—; —CH(NHC(O)R)—; —CH(NHSO$_2$R)—; —CH(NHC(O)OR)—; —CH(OC(O)R)—; —CH(OC(O)NHR)—; —CH=CH—; —C(=NOR)—; —C(O)—; —CH(OR)—; —C(O)N(R)—; —N(R)C(O)—; —N(R)S(O)$_p$—; —OC(O)N(R)—; —N(R)—C(O)—(CH$_2$)$_n$—N(R)—, —N(R)C(O)O—; —N(R)—(CH$_2$)$_{n+1}$—C(O)—, —S(O)$_p$N(R)—; —O—(CR$_2$)$_{n+1}$—C(O)—, —O—(CR$_2$)$_{n+1}$—O—, —N(C(O)R)S(O)$_p$—; —N(R)S(O)$_p$N(R)—; —N(R)—C(O)—(CH$_2$)$_n$—O—, —C(O)N(R)C(O)—; —S(O)$_p$N(R)C(O)—; —OS(O)$_p$N(R)—; —N(R)S(O)$_p$O—; —N(R)S(O)$_p$C(O)—; —SO$_p$N(C(O)R)—; —N(R)SO$_p$N(R)—; —C(O)O—; —N(R)P(OR$_b$)O—; —N(R)P(OR$_b$)—; —N(R)P(O)(OR$_b$)O—; —N(R)P(O)(OR$_b$)—; —N(C(O)R)P(OR$_b$)O—; —N(C(O)R)P(OR$_b$)—; —N(C(O)R)P(O)(OR$_b$)O—, or —N(C(O)R)P(OR$_b$)—;

where R for each occurrence is independently H, substituted or unsubstituted alkyl, substituted or unsubstituted arylalkyl or substituted or unsubstituted aryl;

$R_b$ for each occurrence is independently H, substituted or unsubstituted alkyl, substituted or unsubstituted arylalkyl, substituted or unsubstituted cycloalkyl or substituted or unsubstituted aryl;

p is 1 or 2;

or in a phosphorus containing group, the nitrogen atom, the phosphorus atom, R and $R_b$ together form a five- or six-membered heterocyclic ring; or A is NRSO$_2$ and R, $R_a$ and the nitrogen atom together form a substituted or unsubstituted five or-six-membered heterocyclic ring fused to ring 1;

$R_2$ is —$Z^{101}$-$Z^{102}$;

$Z^{101}$ is a covalent bond, —(C$_1$-C$_6$)—, —(C$_1$-C$_6$)——O—, —(C$_1$-C$_6$)—C(O)—, —(C$_1$-C$_6$)— —C(O)O—, —(C$_1$-C$_6$)—C(O)—NH—, —(C$_1$-C$_6$)—C(O)—N((C$_1$-C$_6$))— or a substituted or unsubstituted phenyl group;

$Z^{102}$ is hydrogen; a substituted or unsubstituted alkyl group; a substituted or unsubstituted cycloalkyl group; a substituted or unsubstituted, saturated or unsaturated heterocyclic group; or a substituted or unsubstituted, saturated or unsaturated heterobicyclic group; said substituted heterocyclic and substituted heterobicyclic group having one or more substituents each independently selected from the group consisting of hydroxyl, cyano, substituted or unsubstituted alkoxy, substituted or unsubstituted sulfonamido, substituted or unsubstituted ureido, substituted or unsubstituted carboxamido, substituted or unsubstituted amino, oxo, a saturated, unsaturated or aromatic, substituted or unsubstituted heterocyclic group consisting of one or more nitrogen atoms, one or more oxygen atoms or a combination thereof wherein the nitrogen atoms are independently optionally substituted or unsubstituted alkyl, substituted or unsubstituted aryl, substituted or unsubstituted arylalkyl group; or $R_2$ is a group of the formula —B—E, wherein B is a substituted or unsubstituted cycloalkyl, substituted or unsubstituted azacycloalkyl, substituted or unsubstituted amino, substituted or unsubstituted aminoalkylsulfonyl, substituted or unsubstituted alkoxyalkyl, substituted or unsubstituted alkoxy, substituted or unsubstituted aminoalkylcarbonyl, hydroxy substituted or unsubstituted alkylene, substituted or unsubstituted aminoalkyl, substituted or unsubstituted alkylenecarbonyl or substituted or unsubstituted aminoalkylcarbonyl group; and E is substituted or unsubstituted azacycloalkyl, substituted or unsubstituted azacycloalkylcarbonyl, substituted or unsubstituted azacycloalkylsulfonyl, substituted or unsubstituted azacycloalkylalkyl, substituted or unsubstituted heteroaryl-substituted or unsubstituted heteroarylcarbonyl, substituted or unsubstituted heteroarylsulfonyl, substituted or unsubstituted heteroarylalkyl, substituted or unsubstituted azacycloalkylcarbonylamino, substituted or unsubstituted heteroarylcarbonylamino s or substituted or unsubstituted aryl;

a is 1 and $D_1$, $G_1$, $J_1$, $L_1$ and $M_1$ are each independently selected from the group consisting of $CR_a$ and N, provided that at least two of $D_1$, $G_1$, $J_1$, $L_1$ and $M_1$ are $CR_a$; or a is 0, and one of $D_1$, $G_1$, $L_1$ and $M_1$ is $NR_a$, one of $D_1$, $G_1$, $L_1$ and $M_1$ is $CR_a$ and the remainder are independently selected from the group consisting of $CR_a$ and N, wherein $R_a$ is as defined above;

b is 1 and $D_2$, $G_2$, $J_2$, $L_2$ and $M_2$ are each independently selected from the group consisting of $CR_a$ and N, provided that at least two of $D_2$, $G_2$, $J_2$, $L_2$ and $M_2$ are $CR_a$; or b is 0, and one of $D_2$, $G_2$, $L_2$ and $M_2$ is $NR_a$, one of $D_2$, $G_2$, $L_2$ and $M_2$ is $CR_a$ and the remainder are independently selected from the group consisting of $CR_a$ and N, wherein $R_a$ is as defined above; and n for each occurrence is independently an integer from 0 to 6.

2. The compound of claim 1 wherein $R_3$ is H; $R_1$ for each occurrence is independently selected from the group consisting of F, Cl, Br, I, $CH_3$, $NO_2$, $OCF_3$, $OCH_3$, CN, $CO_2CH_3$, $CF_3$, —$CH_2NR_dR_e$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

3. The compound of claim 1 wherein $R_3$ is H; $R_a$ for each occurrence is independently selected from the group consisting of F, Cl, Br, I, $CH_3$, $NO_2$, $OCF_3$, $OCH_3$, CN, $CO_2CH_3$, $CF_3$, t-butyl, pyridyl, substituted or unsubstituted oxazolyl, substituted or unsubstituted benzyl, substituted or unsubstituted benzenesulfonyl, substituted or unsubstituted phenoxy, substituted or unsubstituted phenyl, substituted or unsubstituted amino, carboxyl, substituted or unsubstituted tetrazolyl, and substituted or unsubstituted styryl.

4. The compound of claim 1 wherein $R_3$ is H; $R_2$ is of the formula

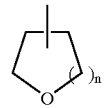

wherein n is 1, 2 or 3.

5. The compound of claim 1 wherein $R_3$ is H; $R_2$ is of the formula

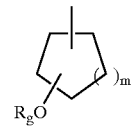

wherein m is 0, 1, 2 or 3 and $R_g$ is H or —$(CH_2)_pN(R_4)R_5$, wherein p is an integer from 2 to 6 and $R_4$ and $R_5$ are each, independently, H, azabicycloalkyl or Y—Z, wherein Y is selected from the group consisting of —C(O)—, —$(CH_2)_q$—, —$S(O)_2$—, —C(O)O—, —$SO_2NH$—, —CONH—, —$(CH2)_qO$—, —$(CH_2)_qNH$—, and —$(CH_2)_qS(O)_r$—; wherein q is an integer from 0 to 6; and r is 0, 1 or 2; and Z is a substituted or unsubstituted moiety selected from the group consisting of alkyl, alkoxy, amino, aryl, heteroaryl and heterocycloalkyl group or $R_4$, $R_5$ and the nitrogen atom to which they are attached together form a 3, 4, 5, 6 or 7-membered, substituted or unsubstituted heterocyclic or heterobicyclic group.

6. The compound of claim 1 wherein $R_3$ is H; $R_2$ is of the formula

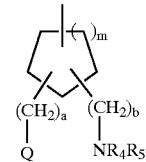

wherein m is 0, 1, 2 or 3 a and b are each, independently, an integer from 0 to 6;

Q is —$OR_6$ or —$NR_4R_5$;

each $R_4$ and $R_5$ is, independently, H, azabicycloalkyl or Y—Z, wherein Y is selected from the group consisting of —C(O)—, —$(CH_2)_q$—, —$S(O)_2$—, —C(O)O—, —$SO_2NH$—, —CONH—, $(CH_2)_qO$—, —$(CH_2)_qNH$—, and —$(CH_2)_qS(O)_r$—; wherein q is an integer from 0 to 6; and r is 0, 1 or 2; and Z is a substituted or unsubstituted alkyl, substituted or unsubstituted alkoxy, amino, aryl, heteroaryl or heterocycloalkyl group or $R_4$, $R_5$ and the nitrogen atom to which they are attached together form a 3, 4, 5, 6 or 7-membered, substituted or unsubstituted heterocyclic or heterobicyclic group; and $R_6$ is hydrogen or a substituted or unsubstituted alkyl group.

7. The compound of claim 1 wherein $R_3$ is H; $R_2$ is of the formula

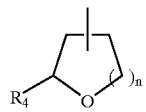

wherein n is 1, 2 or 3; and $R_4$ is H, azabicycloalkyl or Y—Z, wherein Y is selected from the group consisting of —C(O)—, —(CH$_2$)$_q$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein q is an integer 0 to 6; and r is 0, 1 or 2; and Z is a substituted or unsubstituted alkyl, substituted or unsubstituted amino, aryl, substituted or unsubstituted heteroaryl or substituted or unsubstituted heterocycloalkyl group.

8. The compound of claim 1 wherein $R_3$ is H; $R_2$ is of the formula

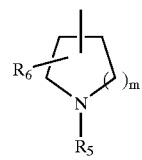

wherein m is 0, 1, 2 or 3;

$R_5$ is H, azabicycloalkyl or Y—Z, wherein Y is selected from the group consisting of a covalent bond, —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, (CH$_2$)$_q$C(O)—, —C(O)(CH$_2$)$_q$— and —(CH$_2$)$_q$S(O)$_r$—, where the alkyl portion of —(CH$_2$)$_q$O—, —(CH$_2$)$_q$O—, —(CH$_2$)$_q$NH—, —(CH$_2$)$_q$C(O)—, —C(O)(CH$_2$)$_q$— and —(CH$_2$)$_q$S(O)$_r$ is optionally substituted by a halogen, hydroxy or an alkyl group; wherein q is an integer from 0 to 6; and r is 0, 1 or 2; and Z is a substituted or unsubstituted alkyl, substituted or unsubstituted amino, substituted or unsubstituted alkoxy, substituted or unsubstituted aryl, substituted or unsubstituted heteroaryl or substituted or unsubstituted heterocycloalkyl group;

or Y and Z together are a natural or unnatural amino acid, which may be mono- or di-alkylated at the amine nitrogen; and $R_6$ represents one or more substituents each independently selected from the group consisting of hydrogen, hydroxy, oxo, substituted or unsubstituted alkyl, substituted or unsubstituted aryl, substituted or unsubstituted heterocyclyl, substituted or unsubstituted alkoxycarbonyl, substituted or unsubstituted alkoxyalkyl, substituted or unsubstituted aminocarbonyl, substituted or unsubstituted alkylcarbonyl, substituted or unsubstituted arylcarbonyl, substituted or unsubstituted heterocyclylcarbonyl, substituted or unsubstituted aminoalkyl and substituted or unsubstituted arylalkyl; provided that the carbon atoms adjacent to the nitrogen atom are not substituted by a hydroxy group.

9. The compound of claim 1 wherein $R_3$ is H; $R_2$ is of the formula

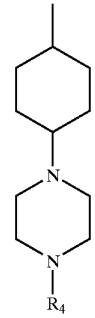

wherein $R_4$ is H, substituted or unsubstituted alkyl, substituted or unsubstituted azabicycloalkyl or Y—Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6, and r is 0, 1 or 2; and Z is hydrogen, substituted or unsubstituted alkyl, substituted or unsubstituted amino, substituted or unsubstituted aryl, substituted or unsubstituted heteroaryl or substituted or unsubstituted heterocycloalkyl.

10. The compound of claim 1 wherein $R_3$ is H; $R_2$ is of the formula

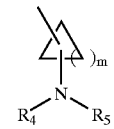

wherein m is an integer from 1 to 6; and $R_4$ and $R_5$ are each, independently, H, substituted or unsubstituted azabicycloalkyl or Y—Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; wherein q is an integer from 0 to 6; and r is 0, 1 or 2; and Z is a substituted or unsubstituted alkyl, substituted or unsubstituted amino, substituted or unsubstituted aryl, substituted or unsubstituted heteroaryl or substituted or unsubstituted heterocycloalkyl group; or $R_4$, $R_5$ and the nitrogen atom to which they are attached together form a 3, 4, 5, 6 or 7-membered, substituted or unsubstituted heterocyclic or substituted or unsubstituted heterobicyclic group.

11. The compound of claim 1 wherein $R_3$ is H; $R_2$ is of the formula

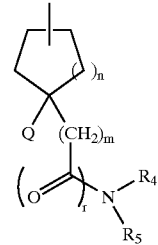

wherein n is an integer from 0 to 4;

r is 0 and m is an integer from 1 to 6; or r is 1 and m is an integer from 0 to 6;

Q is —OR$_6$ or —NR$_4$R$_5$;

each R$_4$ and R$_5$ is, independently, H, substituted or unsubstituted azabicycloalkyl or Y—Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, —(CH$_2$)$_q$NH—, and —(CH$_2$)$_q$S(O)$_r$—; q is an integer from 0 to 6; and r is 0, 1 or 2; and Z is a substituted or unsubstituted alkyl, substituted or unsubstituted alkoxy, substituted or unsubstituted amino, substituted or unsubstituted aryl, substituted or unsubstituted heteroaryl or substituted or unsubstituted heterocycloalkyl group; or R$_4$, R$_5$ and the nitrogen atom to which they are attached together form a 3, 4, 5 or 6-membered, substituted or unsubstituted heterocyclic group; and R$_6$ is hydrogen or a substituted or unsubstituted alkyl group.

12. The compound of claim 1 wherein R$_3$ is H; R$_2$ is of the formula

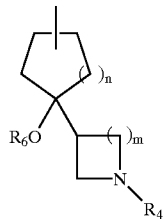

n is an integer from 0 to 4;

m is an integer from 0 to 6;

R$_4$ is H, substituted or unsubstituted azabicycloalkyl or Y—Z, wherein Y is selected from the group consisting of —C(O)—, —(CH$_2$)$_q$—, —S(O)$_2$—, —C(O)O—, —SO$_2$NH—, —CONH—, —(CH$_2$)$_q$O—, (CH$_2$)$_q$NH—, and —(CH$_2$)$_q$S(O)$_r$—; wherein q is an integer from 0 to 6; and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl; and R$_6$ is hydrogen or a substituted or unsubstituted alkyl group.

13. The compound of claim 10 wherein R$_4$, R$_5$ and the nitrogen atom together form a heterocyclic group of the formula

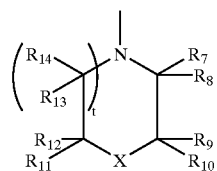

wherein

R$_7$, R$_8$, R$_9$, R$_{10}$, R$_{11}$, R$_{12}$, R$_{13}$ and R$_{14}$ are each, independently, lower alkyl or hydrogen; or at least one pair of substituents R$_7$ and R$_8$; R$_9$ and R$_{10}$; R$_{11}$ and R$_{12}$; or R$_{13}$ and R$_{14}$ together are an oxygen atom; or at least one of R$_7$ and R$_9$ is cyano, CONHR$_{15}$, COOR$_{15}$, CH$_2$OR$_{15}$ or CH$_2$NR$_{15}$(R$_{16}$), wherein R$_{15}$ and R$_{16}$ are each, independently, H, azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or R$_{15}$, R$_{16}$ and the nitrogen atom together form a 3, 4, 5, 6 or 7-membered, substituted or unsubstituted heterocyclic or a substituted or unsubstituted heterobicyclic group;

X is O, S, SO, SO$_2$, CH$_2$, CHOR$_{17}$ or NR$_{17}$, wherein R$_{17}$ is hydrogen, substituted or unsubstituted alkyl, substituted or unsubstituted aryl, substituted or unsubstituted arylalkyl, —C(NH)NH$_2$, —C(O)R$_{17}$, or —C(O)OR$_{18}$, wherein R$_{18}$ is hydrogen, substituted or unsubstituted alkyl, substituted or unsubstituted aryl or substituted or unsubstituted arylalkyl; and t is 0 o 1.

14. The compound of claim 10 wherein R$_4$, R$_5$ and the nitrogen atom together form a heterocycle of the formula

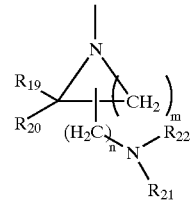

wherein

R$_{19}$ and R$_{20}$ are each, independently, hydrogen or lower alkyl; or R$_{19}$ and R$_{20}$ together are an oxygen atom;

R$_{21}$ and R$_{22}$ are each, independently, H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, (CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or R$_{21}$, R$_{22}$ and the nitrogen atom together form a 3, 4, 5 or 6-membered, substituted or unsubstituted heterocyclic group;

m is an integer from 1 to 6; and n is an integer from 0 to 6.

15. The compound of claim 10 wherein R$_4$, R$_5$ and the nitrogen atom together form a heterocyclic group of the formula

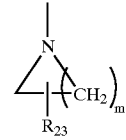

wherein m is an integer from 1 to 6; and

R$_{23}$ is CH$_2$OH, NRR', C(O)NRR' or COOR, wherein R and R' are each, independently, hydrogen or substituted or unsubstituted alkyl, substituted or unsubstituted aryl or substituted or unsubstituted arylalkyl.

16. The compound of claim 10 wherein $R_4$, $R_5$ and the nitrogen atom together form a heterocyclic group of the formula

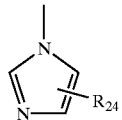

wherein $R_{24}$ is substituted or unsubstituted alkyl, substituted or unsubstituted aryl, substituted or unsubstituted arylalkyl, carboxyl, cyano, $C(O)OR_{25}$, $CH_2OR_{25}$, $CH_2NR_{26}R_{27}$ or $C(O)NHR_{26}$, wherein $R_{25}$ is substituted or unsubstituted alkyl, substituted or unsubstituted aryl, substituted or unsubstituted arylalkyl, substituted or unsubstituted heterocyclic or substituted or unsubstituted heterocycloaryl; and $R_{26}$ and $R_{27}$ are each, independently, H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or $R_{26}$, $R_{27}$ and the nitrogen atom together form a 3, 4, 5 or 6-membered, substituted or unsubstituted heterocyclic group.

17. The compound of claim 10 wherein at least one of $R_4$ and $R_5$ is of the formula Y—Z, wherein Z is of the formula

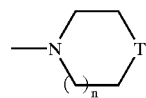

wherein

T is C(O), S, SO, SO$_2$, CHOR or NR, wherein R is hydrogen or a substituted or unsubstituted alkyl, substituted or unsubstituted aryl or substituted or unsubstituted arylalkyl group; and n is 0, 1 or 2.

18. The compound of claim 10 wherein at least one of $R_4$ and $R_5$ is of the formula Y—Z, wherein Z is of the formula —N($R_{28}$)$R_{29}$, wherein $R_{28}$ and $R_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or $R_{28}$ and $R_{29}$, together with the nitrogen atom, form a five- or six-membered substituted or unsubstituted heterocyclic group.

19. The compound of claim 11 wherein $R_4$, $R_5$ and the nitrogen atom together form a heterocycle of the formula

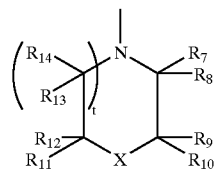

wherein $R_7$, $R_8$, $R_9$, $R_{10}$, $R_{11}$, $R_{12}$, $R_{13}$ and $R_{14}$ are each, independently, lower alkyl or hydrogen; or at least one pair of substituents $R_7$ and $R_8$; $R_9$ and $R_{10}$; $R_{11}$ and $R_{12}$; or $R_{13}$ and $R_{14}$ together are an oxygen atom; or at least one of $R_7$ and $R_9$ is cyano, CONHR$_{15}$, COOR$_{15}$, CH$_2$OR$_{15}$ or CH$_2$NR$_{15}$(R$_{16}$), wherein $R_{15}$ and $R_{16}$ are each, independently, H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl; or $R_{15}$, $R_{16}$ and the nitrogen atom together form a 3, 4, 5, 6 or 7-membered, substituted or unsubstituted heterocyclic or heterobicyclic group;

X is O, S, SO, SO$_2$, CH$_2$, CHOR$_{17}$ or NR$_{17}$, wherein $R_{17}$ is hydrogen, substituted or unsubstituted alkyl, substituted or unsubstituted aryl, substituted or unsubstituted arylalkyl, —C(NH)NH2, —C(O)R$_{18}$, or —C(O)OR$_{18}$, wherein $R_{18}$ is hydrogen, substituted or unsubstituted alkyl, substituted or unsubstituted aryl or substituted or unsubstituted arylalkyl; and t is 0 or 1.

20. The compound of claim 1 wherein $R_4$, $R_5$ and the nitrogen atom together form a heterocycle of the formula

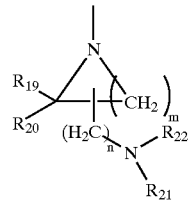

wherein $R_{19}$ and $R_{20}$ are each, independently, hydrogen or lower alkyl; or $R_{19}$ and $R_{20}$ together are an oxygen atom;

$R_{21}$ and $R_{22}$ are each, independently, H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or $R_{21}$, $R_{22}$ and the nitrogen atom together form a 3, 4, 5 or 6-membered, substituted or unsubstituted heterocyclic group;

m is an integer from 2 to 6; and n is an integer from 0 to 6.

21. The compound of claim 11 wherein $R_4$, $R_5$ and the nitrogen atom together form a heterocyclic group of the formula

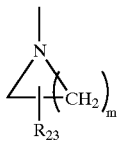

wherein m is an integer from 1 to 6; and $R_{23}$ is $CH_2OH$, NRR', C(O)NRR' or COOR, wherein R is hydrogen or a substituted or unsubstituted alkyl, substituted or unsubstituted aryl or substituted or unsubstituted arylalkyl group.

22. The compound of claim 11 wherein $R_4$, $R_5$ and the nitrogen atom together form a heterocyclic group of the formula

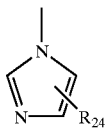

wherein $R_{24}$ is substituted or unsubstituted alkyl, substituted or unsubstituted aryl or substituted or unsubstituted arylalkyl, carboxyl, cyano, $C(O)OR_{25}$, $CH_2OR_{25}$, $CH_2NR_{26}R_{27}$ or $C(O)NHR_{26}$, wherein $R_{25}$ is substituted or unsubstituted alkyl, substituted or unsubstituted aryl, substituted or unsubstituted arylalkyl, substituted or unsubstituted heterocyclic or substituted or unsubstituted heterocycloaryl group; and $R_{26}$ and $R_{27}$ are each, independently, H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl group; or $R_{26}$, $R_{27}$ and the nitrogen atom together form a 3, 4, 5 or 6-membered, substituted or unsubstituted heterocyclic group.

23. The compound of claim 11 wherein at least one of $R_4$ and $R_5$ is of the formula Y—Z, wherein Z is of the formula

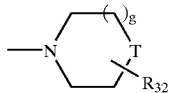

wherein g is 0 or 1;

T is C(O), O, S, SO, SO$_2$, CH$_2$, CHOR$_7$ or NR$_{17}$, wherein R$_{17}$ is hydrogen, substituted or unsubstituted alkyl, substituted or unsubstituted aryl, substituted or unsubstituted arylalkyl, —C(NH)NH$_2$, —C(O)R$_{18}$, or —C(O)OR$_{18}$, wherein R$_{18}$ is hydrogen, substituted or unsubstituted alkyl, substituted or unsubstituted aryl or substituted or unsubstituted arylalkyl; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl.

24. The compound of claim 11 wherein at least one of $R_4$ and $R_5$ is of the formula Y—Z, wherein Z is of the formula —N(R$_{28}$)R$_{29}$, wherein R$_{28}$ and R$_{29}$ are each, independently, substituted or unsubstituted carboxyalkyl, substituted or unsubstituted alkoxycarbonylalkyl, substituted or unsubstituted hydroxyalkyl, substituted or unsubstituted alkylsulfonyl, substituted or unsubstituted alkylcarbonyl or substituted or unsubstituted cyanoalkyl; or $R_{28}$ and $R_{29}$, together with the nitrogen atom, form a five- or six-membered substituted or unsubstituted heterocyclic group.

25. The compound of claim 8 wherein $R_5$ is Y—Z, wherein Z is of the formula N(R$_{30}$)R$_{31}$, wherein R$_{30}$ and R$_{31}$ are each, independently, hydrogen, alkyl, alkoxycarbonyl, alkoxyalkyl, hydroxyalkyl, aminocarbonyl, cyano, alkylcarbonyl or arylalkyl.

26. The compound of claim 8 wherein $R_5$ is Y—Z, wherein Z is of the formula

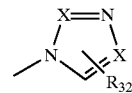

wherein each X is, independently, CH or N; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

27. The compound of claim 8 wherein $R_5$ is Y—Z, wherein Z is of the formula

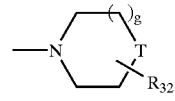

wherein g is 0 or 1;

T is O, S, SO, SO$_2$, CH$_2$, CHOR$_{17}$ or NR$_{17}$, wherein R$_{17}$ is hydrogen, substituted or unsubstituted alkyl, substituted or unsubstituted aryl, substituted or unsubstituted arylalkyl, C(O)NH$_2$, —C(NH)NH$_2$, —C(O)R$_{17}$, or —C(O)OR$_{18}$, wherein R$_{18}$ is hydrogen, substituted or unsubstituted alkyl, substituted or unsubstituted aryl or substituted or unsubstituted arylalkyl; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

28. The compound of claim 8 wherein $R_5$ is Y—Z, wherein Z is of the formula

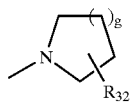

wherein g is 0, 1 or 2; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

29. The compound of claim 8 wherein $R_5$ is Y—Z, wherein Z is of the formula

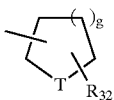

wherein

T is C(O), O, S, SO, $SO_2$, $CH_2$, $CHOR_{17}$ or $NR_{17}$, wherein $R_{17}$ is hydrogen, substituted or unsubstituted alkyl, aryl, arylalkyl, —C(NH)$NH_2$, —C(O)$R_{18}$, or —C(O)O$R_{18}$, wherein $R_{18}$ is hydrogen, substituted or unsubstituted alkyl, substituted or unsubstituted aryl or substituted or unsubstituted arylalkyl;

g is 0 or 1; and $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, substituted or unsubstituted alkylcarbonyl or substituted or unsubstituted arylalkyl group.

30. The compound of claim 8 wherein $R_5$ is Y—Z, wherein Z is of the formula

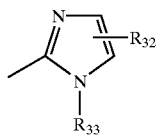

wherein $R_{32}$ is hydrogen, cyano, substituted or unsubstituted alkyl, substituted or unsubstituted alkoxycarbonyl, substituted or unsubstituted alkoxyalkyl, substituted or unsubstituted hydroxyalkyl, substituted or unsubstituted aminocarbonyl, alkylcarbonyl, substituted or unsubstituted thioalkoxy or substituted or unsubstituted arylalkyl; and $R_{33}$ is hydrogen, substituted or unsubstituted alkyl, substituted or unsubstituted alkoxycarbonyl, substituted or unsubstituted alkoxyalkyl, substituted or unsubstituted aminocarbonyl, perhaloalkyl, substituted or unsubstituted alkenyl, substituted or unsubstituted alkylcarbonyl or substituted or unsubstituted arylalkyl.

31. The compound of claim 1 wherein $R_3$ is H; $R_2$ is of the formula

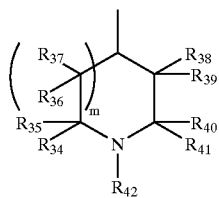

wherein m is 0 or 1;

$R_{34}$, $R_{35}$, $R_{36}$, $R_{37}$, $R_{38}$, $R_{39}$, $R_{40}$ and $R_{41}$ are each, independently, methyl or hydrogen; or at least one pair of substituents $R_{34}$ and $R_{35}$; $R_{36}$ and $R_{37}$; $R_{38}$ and $R_{39}$; or $R_{40}$ and $R_{41}$ together are an oxygen atom; and $R_{42}$ is H, substituted or unsubstituted azabicycloalkyl or Y—Z, wherein Y is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and —(CH$_2$)$_q$S(O)$_r$—; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl group; or $R_{42}$ is of the formula

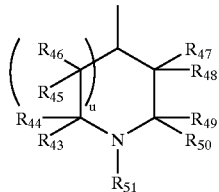

wherein u is 0 or 1;

$R_{43}$, $R_{44}$, $R_{45}$, $R_{46}$, $R_{47}$, $R_{48}$, $R_{49}$ and $R_{50}$ are each, independently, methyl or hydrogen;

or at least one pair of substituents $R_{43}$ and $R_{44}$; $R_{45}$ and $R_{46}$; $R_{47}$ and $R_{48}$; or $R_{49}$ and $R_{50}$ together are an oxygen atom; and $R_{51}$ is H, substituted or unsubstituted azabicycloalkyl or V—L, wherein V is selected from the group consisting of —C(O)—, —(CH$_2$)$_p$—, —S(O)$_2$—, —C(O)O—, —SO$_2$NH—, —CONH—, (CH$_2$)$_q$O, —(CH$_2$)$_q$NH—, and —(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl.

32. The compound of claim 1 wherein $R_3$ is H; $R_2$ is of the formula

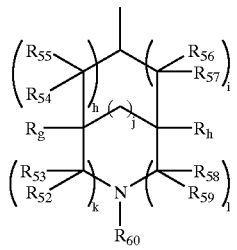

wherein h, i, j, k and l are independently 0 or 1;

$R_{52}$, $R_{53}$, $R_{54}$, $R_{55}$, $R_{56}$, R57, $R_{58}$, $R_{59}$, $R_g$ and $R_h$ are each, independently, methyl or hydrogen; or at least one pair of substituents $R_{52}$ and $R_{53}$; $R_{54}$ and $R_{55}$; $R_{56}$ and $R_{57}$; or $R_{58}$ and $R_{59}$ together are an oxygen atom; and $R_{60}$ is H, substituted or unsubstituted azabicycloalkyl or Y—Z, wherein Y is selected from the group consisting of —C(O)—, —(CH$_2$)$_p$—, —S(O)$_2$—, —C(O)O—, —SO$_2$NH—, —CONH—, —(CH$_2$)$_q$O—, (CH$_2$)$_q$NH—, and —(CH$_2$)$_q$S(O)$_r$—; wherein p is an integer from 0 to 6, q is an integer from 0 to 6, and r is 0, 1 or 2; and Z is substituted or unsubstituted alkyl, substituted or unsubstituted amino, substituted or unsubstituted aryl, substituted or unsubstituted heteroaryl or substituted or unsubstituted heterocycloalkyl; or $R_{60}$ is of the formula

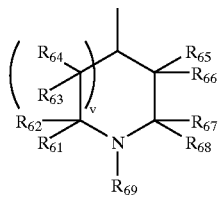

wherein v is 0 or 1;

$R_{61}$, $R_{62}$, $R_{63}$, $R_{64}$, $R_{65}$, $R_{66}$, $R_{67}$ and $R_{68}$ are each, independently, lower alkyl or hydrogen; or at least one pair of substituents $R_{61}$ and $R_{62}$; $R_{63}$ and $R_{64}$; R65 and $R_{66}$; and $R_{67}$ and $R_{68}$ together are an oxygen atom; and $R_{69}$ is H, substituted or unsubstituted azabicycloalkyl or V—l, wherein V is selected from the group consisting of —C(O)—, —(CH$_2$)$_p$—, —S(O)$_2$—, —C(O)O—, —SO$_2$NH—, —CONH—, (CH$_2$)$_q$O—, —(CH$_2$)$_q$NH—, and ≦(CH$_2$)$_q$S(O)$_r$—; wherein p is an integer from 0 to 6, q is an integer from 0 to 6, and r is 0, 1 or 2; and L is substituted or unsubstituted alkyl, substituted or unsubstituted amino, substituted or unsubstituted aryl, substituted or unsubstituted heteroaryl or substituted or unsubstituted heterocycloalkyl.

33. A method of inhibiting one or more protein kinase activity in a patient comprising administering a therapeutically effective amount of a compound of claim 1 or a physiologically acceptable salt, or prodrug thereof to said patient.

34. The method of claim 33 wherein said protein kinase is selected from the group consisting of KDR, FGFR-1, PDGFRβ, PDGFRα, IGF-1R, c-Met, Flt-1, Flt-4, TIE-2, TIE-1, Lck, Src, fyn, Lyn, Blk, hck, fgr and yes.

35. A method of affecting angiogenesis in a patient comprising administering a therapeutically effective amount of a compound of claim 1 or a physiologically acceptable salt, or prodrug thereof to said patient.

36. The method of claim 33 wherein the protein kinase is a protein serine/threonine kinase or a protein tyrosine kinase.

37. A method of treating one or more ulcers in a patient comprising administering a therapeutically effective amount of a compound of claim 1 or a physiologically acceptable salt, or prodrug thereof to said patient.

38. The method of claim 37 wherein the ulcer or ulcers are caused by a bacterial or fungal infection; or the ulcer or ulcers are Mooren ulcers; or the ulcer or ulcers are a symptom of ulcerative colitis.

39. A method of treating a condition in a patient comprising administering a therapeutically effective amount of a compound of claim 1 or a physiologically acceptable salt, prodrug or biologically active metabolites thereof to said patient, wherein said condition is Crow-Fukase (POEMS) syndrome, a diabetic condition, sickle cell anaemia, systemic lupus, glomerulonephritis, synovitis, inflammatory bowel disease, Crohn's disease, glomerulonephritis, rheumatoid arthritis, osteoarthritis, multiple sclerosis, graft rejection, Lyme disease, sepsis, von Hippel Lindau disease, pemphigoid, psoriasis, Paget's disease, polycystic kidney disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, hypoxia, ischemia, ovarian hyperstimulation syndrome, preeclampsia, menometrorrhagia, endometriosis, or infection by Herpes simplex, Herpes Zoster, human immunodeficiency virus, parapoxvirus, protozoa or toxoplasmosis.

40. The method of claim 39 wherein the ocular condition is ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy or macular degeneration.

41. The method of claim 39 wherein the cardiovascular condition is atherosclerosis, restenosis, ischemia/reperfusion injury, vascular occlusion or carotid obstructive disease.

42. The method of claim 39 wherein the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, Kaposi's sarcoma, Hodgkin's disease, lymphoma, myeloma, leukemia or malignant ascites.

43. The method of claim 39 wherein the diabetic condition is insulin-dependent diabetes mellitus glaucoma, diabetic retinopathy or microangiopathy.

44. A method of decreasing fertility in a patient, said method comprising the step of administering to the patient an effective amount of a compound of claim 1 or a physiologically acceptable salt, or prodrug thereof.

45. The method of claim 34 wherein the protein kinase is Tie-2.

46. The method of claim 35 wherein the compound of Formula I, or physiologically acceptable salt, or prodrug thereof, is administered in combination with a pro-angiogenic growth factor.

47. The method of claim 46 wherein the pro-angiogenic growth factor is selected from the group consisiting of VEGF, VEGF-B, VEGF-C, VEGF-D, VEGF-E, HGF, FGF-1, FGF-2, derivatives thereof and antiiodotypic antibodies.

48. The method of claim 35 wherein the patient is suffering from anemia, ischemia, infarct, transplant rejection, a wound, gangrene or necrosis.

49. The method of claim 33 wherein the protein kinase activity is involved in T cell activation, B cell activation, mast cell degranulation, monocyte activation, the potentiation of an inflammatory response or a combination thereof.

50. A compound according to claim 1, wherein $R_3$ is H; $R_2$ is —$Z^{101}$-$Z^{102}$ where $Z^{101}$ is a covalent bond, —($C_1$-$C_6$)—, —($C_1$-$C_6$)—O—, —($C_1$-$C_6$)—C(O)—, —($C_1$-$C_6$)—C(O)O—, —($C_1$-$C_6$)—C(O)—NH—, —($C_1$-$C_6$)—C(O)—N(($C_1$-$C_6$))— or a substituted phenyl group; and $Z^{102}$ is hydrogen, a substituted or unsubstituted alkyl group or a substituted or unsubstituted, saturated or unsaturated heterocyclic group.

51. A compound according to claim 50, wherein $Z^{101}$ is selected from the group consisting of —$CH_2$—C(O)O—, —$CH_2$—C(O)—, —$CH_2$—C(O)—NH—, —$CH_2$—C(O)—N(Me)—, —CH(Me)—C(O)O—, —($CH_2$)$_3$—C(O)O—, —CH(Me)—C(O)—NH— and —($CH_2$)$_3$—C(O)—NH—;

$Z^{102}$ is selected from the group consisting of hydrogen, methyl, ethyl, N,N-dimethylaminoethyl, N,N-diethylaminoethyl, 2-phenyl-2-hydroxyethyl, morpholino, piperazinyl, N-methylpiperazinyl and 2-hydroxymethylpyrrolidinyl.

52. A compound according to claim 51, wherein G is

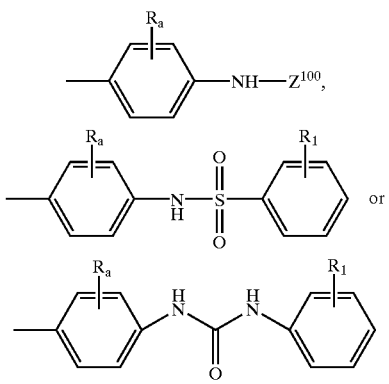

where $Z^{100}$ is a substituted or unsubstituted benzoxazolyl or a substituted or unsubstituted benzthiazolyl.

53. A compound according to claim 8, 9, 10 or 51, wherein G is

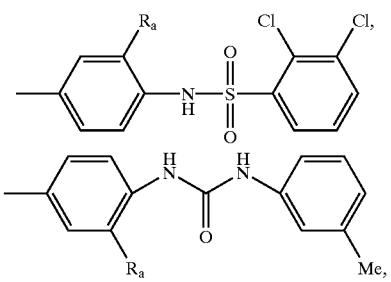

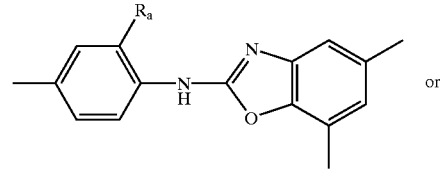

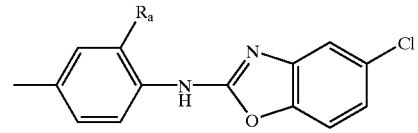

where there is only one $R_a$ and it is H or F.

54. A compound according to claim 50, wherein $Z^{101}$ is a covalent bond; and $Z^{102}$ is an optionally substituted pyridyl.

55. A compound according to claim 54, wherein G is

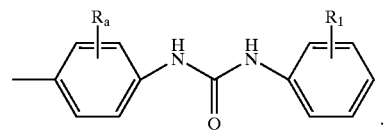

56. A compound according to claim 1, wherein $R_3$ is H; $R_2$ is cyclopentyl; and G is

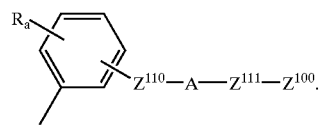

57. A compound according to claim 56, wherein $Z^{110}$ is hydrogen;
A is O; and $Z^{100}$ is optionally substituted phenyl, furanyl or thienyl, where $Z^{100}$ is optionally substituted with one or more substituents each independently selected from the group consisting of F, COOH, $NO_2$, OMe, —COOMe, $OCF_3$ and $CF_3$.

58. A compound according to claim 56, wherein $Z^{110}$ is hydrogen;
A is —O—, —O—($CR_2$)$_n$—C(O)— or —O—($CR_2$)$_n$—O—;
n for each occurrence is 0 to 3;
$Z^{100}$ is an optionally substituted group selected from the group consisting of cyclohexyl, phenyl, tetrahydropyranyl, tetrahydrofuranyl, isoxazolyl and piperidinyl; where $Z^{100}$ is optionally substituted with one or more substituents selected from the group consisting of alkyl, alkoxy, halo, hydroxy and alkoxycarbonyl.

59. A compound according to claim 56, wherein $R^2$ is an optionally substituted group selected from the group consisting of cyclobutyl and cyclohexyl.

60. A compound according to claim 59, wherein $R^2$ is optionally substituted with one or more substituents selected from the group consisting of hydroxy, alkyl, hydroxyalkyl, carboxyalkyl and phenylalkoxyalkyl.

61. A compound according to claim 60, wherein G is 4-phenoxyphenyl.

62. A compound according to claim 6 wherein m is 2; a is 0; $R_6$ is H; b is 1 or 2; and $R_4$ and $R_5$ are each hydrogen.

63. A compound according to claim 8, wherein m is 0, 1 or 2; $R_6$ is hydrogen; $R_5$ is H or Y—Z;

where Y is a covalent bond, —C(O)—, —(CH$_2$)$_q$O—, —(CH$_2$)$_q$—, —(CH$_2$)$_q$C(O)— or —C(O)(CH$_2$)$_q$—, where the alkyl portion of —(CH$_2$)$_q$O—, —(CH$_2$)$_q$—, —(CH$_2$)$_q$C(O)— and —C(O)(CH$_2$)$_q$— is optionally substituted by a halogen, hydroxy or an alkyl group; and Z is hydrogen, alkyl, optionally substituted alkyl, alkoxyalkyl, optionally substituted heterocycloalkyl, optionally substituted heteroaryl, or optionally substituted amino.

64. A compound according to claim 63, wherein

Z is hydrogen, methyl, ethyl, hydroxymethyl, methoxyethyl, N-methylpiperidinyl, (t-butoxycarbonyl)(hydroxy)-piperidinyl, hydroxypiperidinyl, (hydroxymethyl)piperdinyl, (hydroxy)(methyl)-piperidinyl, morpholino, (methoxyethyl)piperizinyl, methylpiperizinyl, 4-piperidinylpiperidinyl, imidazolyl, methylimidazolyl, N-methylamino, N,N-dimethylamino, N-isopropylamino, N,N-diethylamino, 2,3-dihydroxypropylamino, 2-hydroxyethylamino, 3-hydroxypropylamino, methoxyethylamino, ethoxycarbonylmethylamino, phenylmethylamino, N-methyl-N-methoxyamino,

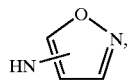

furanylmethylamino, piperidinylethylamino, N-(2-N,N-dimethylaminoethyl)-N-methylamino, 2-N,N-dimethylaminoethylamino, N-methyl-N-(N-methylpiperidin-4-yl)amino, 2-morpholino-ethylamino, 3-morpholino-propylamino, 3-imidazolylpropylamino, or 3-(2-oxopyrrolidinyl)propylamino.

65. A compound according to claim 8, wherein m is 2; R$_5$ is Y—Z; Y is —C(O)—; and Z is

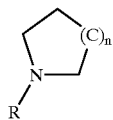

where n is 0, 1, 2 or 3.

66. A compound according to claim 9, wherein

R$_4$ is hydrogen or methyl;

G is

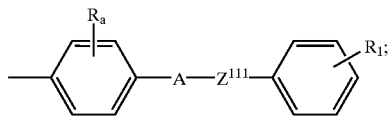

A is selected from the group consisting of O, —N(R)— and —N(R)C(O)—;

Z$^{111}$ is —(CH$_2$)$_n$-cycloalkyl-(CH$_2$)$_n$—;

R is hydrogen or alkyl;

n is 0 to 5;

R$_a$ is one or more substituents each independently selected from the group consisting of H, OH, F, Cl, methyl and methoxy; and R$_1$ is one or more substituents each independently selected from the group consisting of H, CN, F, CF$_3$, OCF$_3$, methyl, methoxy and an optionally substituted amino group;

where said amino group is optionally substituted with one or two groups each independently selected from the group consisting of alkyl, alkoxyalkyl, phenyl, substituted phenyl, and optionally substituted heteroaryl.

67. A compound according to claim 66, wherein R$_1$ is 4-methylphenylthio or 2-pyridinylthio.

68. A compound according to claim 9, wherein

G is

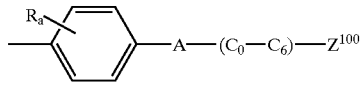

where Z$^{100}$ is selected from the group consisting of benzo[b]thiophene, furanyl and thiophene.

69. A compound according to claim 9, wherein R$_a$ is alkoxy; A is —NH—C(O)—; and there is a covalent bond between A and Z$^{100}$.

70. A compound according to claims 1, 8 or 9, wherein

G is

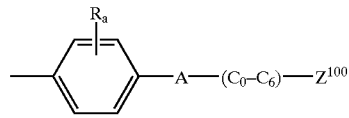

A is selected from the group consisting of —N(R)—C(O)—N(R)—, —(CH$_2$)$_n$—N(R)C(O)N(R)—, —N(R)— and —N(R)—SO$_2$—; R is hydrogen or alkyl;

Z$^{100}$ is

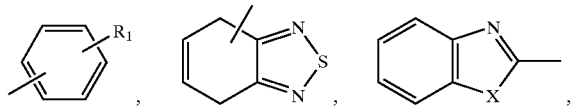

pyridinyl, thiazolyl, furanyl, benzofuranyl or oxazolyl;

X is S, O or NR$^1$ where R$^1$ for each occurrence is independently H or Me;

R$_a$ is one or more substituents each independently selected from the group consisting of H and F; and R$_1$ is one or more substituents each independently selected from the group consisting of H, F, Cl, Br, NO$_2$, CF$_3$, alkyl, alkoxy and alkoxycarbonyl.

71. A compound according to claim 70, wherein

R$_4$ is methyl; m is 1, 2 or 3; R$_5$ is Y—Z, where Y is —C(O)O—, —C(O)— or —C(O)—(CH$_2$)$_p$—; and Z is aminoalkyl, N-alkylamino, N,N-dialkylamino or hydroxyalkylaminoalkyl.

72. A compound according to claim 9, wherein

R$_4$ is methyl; G is

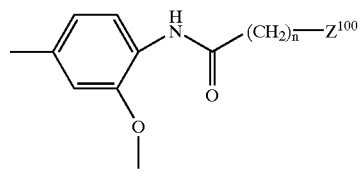

where n is 0 to 3; Z$^{100}$ is an optionally substituted group selected from the group consisting of indolyl, indenyl, methylindenyl, methylindolyl, dimethylaminophenyl, phenyl, cyclohexyl and benzofuranyl.

73. A compound according to claim 9, wherein G is

[structure: $R_a$-substituted phenyl—$Z^{110}$—A—$Z^{111}$—$Z^{100}$]

$Z^{100}$ is an optionally substituted group selected from the group consisting of phenyl, imidazolyl, indolyl, furanyl, benzofuranyl and 2,3-dihydrobenzofuranyl;
where $Z^{100}$ is optionally substituted with one or more substituents each independently selected from the group consisting of F, Cl, CN, optionally substituted alkyl, —O— (optionally substituted alkyl), —COOH, —$Z^{105}$—C(O)N(R)$_2$, —$Z^{105}$—N(R)—C(O)—$Z^{200}$, —$Z^{105}$—N(R)—S(O)$_2$—$Z^{200}$, and —$Z^{105}$—N(R)—C(O)—N(R)—$Z^{200}$;
$Z^{105}$ is a covalent bond or ($C_1$-$C_6$);
$Z^{200}$ is an optionally substituted group selected from group consisting of ($C_1$-$C_6$), phenyl and —($C_1$-$C_6$)-phenyl;
$Z^{110}$ and $Z^{111}$ are each independently a covalent bond or ($C_1$-$C_3$) group optionally substituted with alkyl, hydroxy, COOH, CN or phenyl; and
A is O, —N(R)—C(O)—N(R)—, —N(R)—C(O)—O—, —N(R)— or —N(R)—C(O)—, where R is H or alkyl.

74. A compound according to claim 73, wherein $R_4$ is methyl.

75. A compound according to claim 8, 9 or 10, wherein G is

[structure: $R_a$-substituted phenyl—A—$Z^{100}$]

where $Z^{100}$ is an optionally substituted group selected from the group consisting of benzoxazolyl, benzothiazolyl and benzimidazolyl.

76. A compound according to claim 75, wherein $R_4$ is methyl; A is —NH—; there is only one $R_a$ and it is H or F; and $Z^{100}$ is optionally substituted with one or more substituents each independently selected from the group consisting of alkyl, halo, $CF_3$, and alkoxy.

77. A compound according to claim 9, wherein G is

[structure: $R_a$-substituted phenyl—$Z^{110}$—A—$Z^{111}$—$Z^{100}$]

$Z^{100}$ is an optionally substituted group selected from the group consisting of phenyl, pyrrolyl, pyridyl, benzimidazolyl, naphthyl and

[structure: benzothiadiazole]

where $Z^{100}$ is optionally substituted with one or more substituents each independently selected from the group consisting of F, Cl, Br, $NO_2$, amino, N-alkylamino, N,N-dialkylamino, CN, optionally substituted alkyl, —O-(optionally substituted alkyl) and phenyl;
$Z^{110}$ and $Z^{111}$ for each occurrence is independently ($C_0$-$C_3$) optionally substituted with optionally substituted phenyl; and
A is —N(R)—C(O)—N(R)—, —N(R)—S(O)$_2$—, —N(R)—C(O)—, —N(R)— or —N(R)—C(O)—O—.

78. A compound according to claim 77, wherein $R_4$ is methyl and there is only one $R_a$ and it is F.

79. A compound according to claim 9 or 64, wherein G is

[structure: $R_a$-substituted phenyl—$Z^{110}$—A—$Z^{111}$—$Z^{100}$]

$Z^{100}$ is an optionally substituted group selected from the group consisting of phenyl, isoxazolyl, tetrahydronaphthyl, furanyl, benzofuranyl, pyridyl and indolyl;
where $Z^{100}$ is optionally substituted with one or more substituents each independently selected from the group consisting of F, CN,$NO_2$, —C(O)H, —$CONH_2$, —$NHSO_2CF_3$, optionally substituted alkyl, optionally substituted heteroaryl and —O-(optionally substituted alkyl);
$Z^{110}$ and $Z^{111}$ are each independently optionally substituted ($C_0$-$C_3$); and
A is O, —N(R)—C(O)—$(CH_2)_n$—N(R)—, —C(O)—N(R)—, —N(R)—C(O)—O—, —N(R)—C(O)— or —N(R)—.

80. A compound according to claim 79, wherein $R_4$ is methyl; $R_a$ is H or methoxy; and $Z^{110}$ and $Z^{111}$ are each unsubstituted.

81. A compound according to claim 9, wherein G is

[structures showing $R_a$-substituted phenyl groups with NR—C(O)—CH=CH—$Z^{100}$ linkages]

-continued

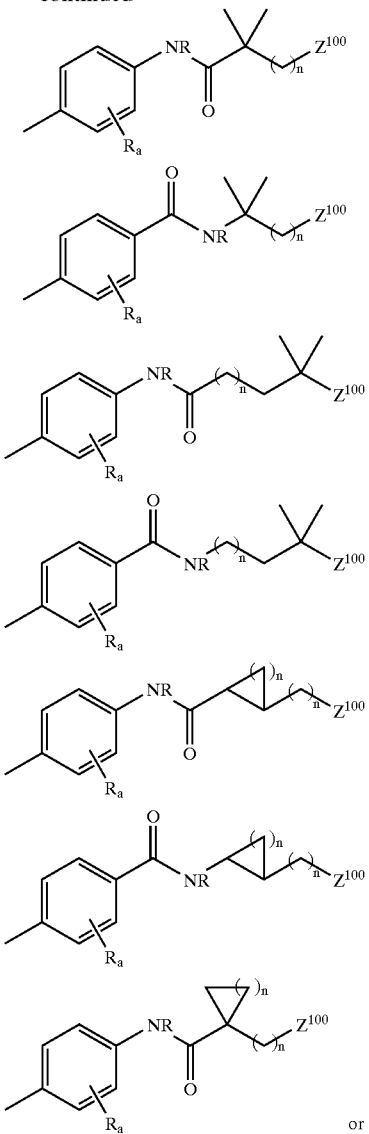

-continued

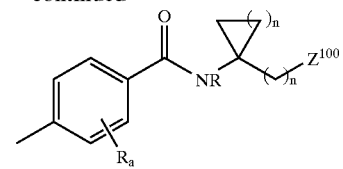

where R is H or lower alkyl and n is for each occurrence is independently 1 to 6.

82. A compound according to claim 81, wherein G is

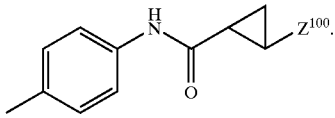

83. A compound according to claim 82, wherein $Z^{100}$ is substituted or unsubstituted phenyl.

84. A compound according to claim 8, 9 or 10, wherein G is

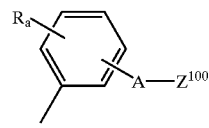

where $Z^{100}$ is an optionally substituted group selected from the group consisting of benzoxazolyl, benzothiazolyl and benzimidazolyl.

85. A compound according to claim 11 wherein n is 2; $R_6$ is H; m is 1; r is 1; and $R_4$ and $R_5$ are each hydrogen.

86. A compound according to claim 66 or 85 wherein G is 4-phenoxyphenyl.

* * * * *